US012163135B2

(12) United States Patent
Starzl et al.

(10) Patent No.: US 12,163,135 B2
(45) Date of Patent: Dec. 10, 2024

(54) METHODS AND COMPOSITIONS TO PREVENT MICROBIAL INFECTION

(71) Applicant: BioPlx, Inc., Boulder, CO (US)

(72) Inventors: Timothy W. Starzl, Boulder, CO (US); Todd D. Turner, Superior, CO (US); Ravi S. V. Starzl, Boulder, CO (US)

(73) Assignee: BioPlx, Inc., Boulder, CO (US)

( * ) Notice: Subject to any disclaimer, the term of this patent is extended or adjusted under 35 U.S.C. 154(b) by 1284 days.

(21) Appl. No.: 16/209,706

(22) Filed: Dec. 4, 2018

(65) Prior Publication Data

US 2019/0169623 A1 Jun. 6, 2019

Related U.S. Application Data

(60) Provisional application No. 62/594,943, filed on Dec. 5, 2017.

(51) Int. Cl.

| | |
|---|---|
| ***C12N 15/74*** | (2006.01) |
| ***A61K 9/00*** | (2006.01) |
| ***A61K 35/00*** | (2006.01) |
| ***A61K 35/74*** | (2015.01) |
| ***A61K 35/741*** | (2015.01) |
| ***A61K 45/06*** | (2006.01) |
| ***A61P 31/04*** | (2006.01) |
| ***C12N 1/20*** | (2006.01) |
| ***C12N 15/09*** | (2006.01) |
| ***C12N 15/63*** | (2006.01) |
| ***C12N 15/64*** | (2006.01) |
| ***C12N 15/77*** | (2006.01) |
| ***C12N 15/78*** | (2006.01) |

(52) U.S. Cl.

CPC .............. *C12N 15/74* (2013.01); *A61K 35/74* (2013.01); *A61K 35/741* (2013.01); *A61K 45/06* (2013.01); *A61P 31/04* (2018.01); *C12N 1/20* (2013.01); *C12N 15/09* (2013.01); *C12N 15/63* (2013.01); *C12N 15/64* (2013.01); *C12N 15/77* (2013.01); *C12N 15/78* (2013.01); *A61K 9/0014* (2013.01); *A61K 2035/11* (2013.01); *A61K 2035/115* (2013.01); *C12N 2820/002* (2013.01); *C12N 2820/55* (2013.01); *C12N 2830/55* (2013.01); *C12N 2840/002* (2013.01); *C12N 2840/55* (2013.01)

(58) Field of Classification Search

CPC ....... A61P 31/04; A61K 35/74; A61K 35/741; A61K 45/06; A61K 9/0014; A61K 2035/11; A61K 2035/115; C12N 1/20; C12N 15/09; C12N 15/63; C12N 15/64; C12N 15/77; C12N 15/78; C12N 15/74; C12N 2820/002; C12N 2820/55; C12N 2830/55; C12N 2840/002; C12N 2840/55; C12N 9/16; C12Y 301/21004; C07K 14/245; C07K 14/31

See application file for complete search history.

(56) References Cited

U.S. PATENT DOCUMENTS

| | | | |
|---|---|---|---|
| 4,133,875 | A | 1/1979 | Hillman |
| 4,548,807 | A | 10/1985 | Westfall et al. |
| 4,716,032 | A | 12/1987 | Westfall et al. |
| 5,525,336 | A | 6/1996 | Green et al. |
| 5,607,672 | A | 3/1997 | Hillman |
| 5,733,540 | A | 3/1998 | Lee |
| 5,853,718 | A | 12/1998 | Molin et al. |
| 6,274,567 | B1 | 8/2001 | Brown et al. |
| 6,417,002 | B1 | 7/2002 | Horlick et al. |
| 6,461,607 | B1 | 10/2002 | Farmer |
| 6,660,262 | B2 | 12/2003 | McKinney |
| 6,719,991 | B2 | 4/2004 | Darouiche et al. |
| 6,737,248 | B2 | 5/2004 | Kunsch et al. |
| 6,905,692 | B2 | 6/2005 | Farmer |
| 7,078,223 | B2 | 7/2006 | Szell et al. |
| 7,459,272 | B2 | 12/2008 | Morris et al. |
| 7,482,023 | B2 | 1/2009 | Runeman et al. |
| 7,623,971 | B2 | 11/2009 | Moriarty |
| 7,627,437 | B2 | 12/2009 | Forney et al. |
| 7,871,604 | B1 | 1/2011 | Curtiss, III et al. |
| 8,247,406 | B2 | 8/2012 | Street et al. |
| 8,460,648 | B2 | 6/2013 | Borody |
| 8,618,091 | B2 | 12/2013 | Street et al. |
| 8,682,619 | B2 | 3/2014 | Amodei et al. |
| 8,729,013 | B2 | 5/2014 | Heinrichs et al. |
| 8,741,588 | B2 | 6/2014 | Huang et al. |
| 8,852,916 | B2 | 10/2014 | Hyde et al. |
| 8,906,668 | B2 | 12/2014 | Henn et al. |
| 8,926,960 | B2 | 1/2015 | Smoragiewicz et al. |
| 8,975,061 | B2 | 3/2015 | Bielinski et al. |
| 9,011,834 | B1 | 4/2015 | McKenzie et al. |
| 9,028,841 | B2 | 5/2015 | Henn et al. |
| 9,091,689 | B2 | 7/2015 | Torres et al. |

(Continued)

FOREIGN PATENT DOCUMENTS

| | | |
|---|---|---|
| AU | 2010257855 B2 | 5/2014 |
| AU | 2016201651 B2 | 2/2018 |

(Continued)

OTHER PUBLICATIONS

Daniel I.H.Linzer and John C. Mordacq, Transcriptional Regulation of Proliferin Gene Expression in Response to Serum in Transfected Mouse Cells, 1987, The EMBO Journal, vol. 6 No. 8 pp. 2281-2288 (Year: 1987).*

(Continued)

*Primary Examiner* — Nancy J Leith
*Assistant Examiner* — Kyle T Rega
(74) *Attorney, Agent, or Firm* — Merchant & Gould, P.C.

(57) ABSTRACT

Methods and compositions are provided for durably influencing microbiological ecosystems (microbiomes) in a subject in order to prevent infection and reduce recurrence of infection by microorganisms. In some embodiments, compositions and methods are provided for the creation and use of molecularly-modified bacterial strains with the potential to prevent a variety of microorganism infections.

30 Claims, 31 Drawing Sheets

Specification includes a Sequence Listing.

(56) References Cited

U.S. PATENT DOCUMENTS

| | | | |
|---|---|---|---|
| 9,101,597 B2 | 8/2015 | Garry et al. | |
| 9,107,938 B2 | 8/2015 | Donoghue et al. | |
| 9,138,441 B2 | 9/2015 | Trachtman | |
| 9,140,698 B2 | 9/2015 | Orth et al. | |
| 9,180,147 B2 | 11/2015 | McKenzie et al. | |
| 9,265,820 B2 | 2/2016 | Shirtliff et al. | |
| 9,446,080 B2 | 9/2016 | McKenzie et al. | |
| 9,487,764 B2 | 11/2016 | Falb et al. | |
| 9,533,014 B2 | 1/2017 | Henn et al. | |
| 9,585,921 B2 | 3/2017 | McKenzie et al. | |
| 9,603,876 B2 | 3/2017 | Blaser et al. | |
| 9,636,196 B2 | 5/2017 | Hillman | |
| 9,688,967 B2 | 6/2017 | Falb et al. | |
| 9,700,611 B2 | 7/2017 | Lawrence et al. | |
| 9,701,964 B2 | 7/2017 | Clube et al. | |
| 9,760,676 B2 | 9/2017 | Apte et al. | |
| 9,855,303 B2 | 1/2018 | McKenzie et al. | |
| 9,889,165 B2 | 2/2018 | Taylor et al. | |
| 10,010,568 B2 | 7/2018 | Kovarik et al. | |
| 10,293,007 B2 | 5/2019 | Taylor et al. | |
| 11,207,357 B2 | 12/2021 | Taylor et al. | |
| 2002/0192741 A1 | 12/2002 | McKillip | |
| 2003/0095950 A1 | 5/2003 | McKinney | |
| 2003/0100083 A1 | 5/2003 | Szell et al. | |
| 2004/0043037 A1* | 3/2004 | Kunsch | C12N 15/1093 435/69.3 |
| 2004/0166094 A1 | 8/2004 | Darouiche et al. | |
| 2004/0241150 A1 | 12/2004 | Hargis et al. | |
| 2005/0118159 A1* | 6/2005 | Stinson | C12N 9/52 424/94.63 |
| 2006/0019291 A1 | 1/2006 | Clark | |
| 2006/0172330 A1 | 8/2006 | Osborn et al. | |
| 2006/0257373 A1 | 11/2006 | Tzeng et al. | |
| 2007/0173462 A1 | 7/2007 | Shue et al. | |
| 2008/0107699 A1 | 5/2008 | Spigelman et al. | |
| 2010/0074872 A1 | 3/2010 | Blaser et al. | |
| 2010/0260739 A1 | 10/2010 | Short et al. | |
| 2010/0260794 A1 | 10/2010 | De Greve et al. | |
| 2011/0008303 A1 | 1/2011 | Liu | |
| 2011/0028945 A1* | 2/2011 | Amodei | A61K 47/6901 604/890.1 |
| 2013/0011374 A1 | 1/2013 | Luquet et al. | |
| 2013/0017203 A1 | 1/2013 | Torres et al. | |
| 2013/0023035 A1 | 1/2013 | Bielinksi et al. | |
| 2013/0323218 A1 | 12/2013 | Donoghue et al. | |
| 2014/0065209 A1 | 3/2014 | Putaala et al. | |
| 2014/0068797 A1* | 3/2014 | Doudna | A61P 31/04 435/375 |
| 2014/0186386 A1 | 7/2014 | Weiser et al. | |
| 2014/0219995 A1 | 8/2014 | Moir et al. | |
| 2015/0050253 A1 | 2/2015 | Gabant | |
| 2015/0210756 A1 | 7/2015 | Torres et al. | |
| 2015/0273031 A1 | 10/2015 | Yeaman et al. | |
| 2015/0337349 A1 | 11/2015 | Kuczynski et al. | |
| 2015/0368322 A1 | 12/2015 | McAdow et al. | |
| 2016/0024510 A1 | 1/2016 | Bikard et al. | |
| 2016/0030494 A1 | 2/2016 | Henn et al. | |
| 2016/0151427 A1 | 6/2016 | Whitlock et al. | |
| 2016/0177274 A1* | 6/2016 | Falb | A61P 25/00 435/252.33 |
| 2016/0206666 A1 | 7/2016 | Falb et al. | |
| 2016/0243175 A1 | 8/2016 | Bushman et al. | |
| 2016/0333326 A1 | 11/2016 | Falb et al. | |
| 2016/0338979 A1 | 11/2016 | Huang | |
| 2016/0348120 A1 | 12/2016 | Esvelt et al. | |
| 2017/0020932 A1 | 1/2017 | Cutcliffe et al. | |
| 2017/0037363 A1 | 2/2017 | Whitlock et al. | |
| 2017/0049827 A1 | 2/2017 | Jones et al. | |
| 2017/0065647 A1 | 3/2017 | Kim et al. | |
| 2017/0081707 A1 | 3/2017 | Dillon et al. | |
| 2017/0119827 A1 | 5/2017 | Kovarik | |
| 2017/0151291 A1 | 6/2017 | Henn et al. | |
| 2017/0165302 A1 | 6/2017 | Henn et al. | |
| 2017/0216372 A1 | 8/2017 | Borody | |
| 2017/0246221 A1 | 8/2017 | Clube et al. | |
| 2017/0306321 A1 | 10/2017 | Valdivia et al. | |
| 2017/0319738 A1* | 11/2017 | Solecki | A61L 24/0015 |
| 2017/0348359 A1 | 12/2017 | Kovarik et al. | |
| 2017/0348360 A1 | 12/2017 | Borody | |
| 2018/0000876 A1 | 1/2018 | Yamamoto et al. | |
| 2018/0028576 A1 | 2/2018 | Blaser et al. | |
| 2018/0087051 A1 | 3/2018 | Apte et al. | |
| 2018/0142202 A1 | 5/2018 | Pätzold et al. | |
| 2018/0146681 A1 | 5/2018 | Clube | |
| 2018/0161380 A1 | 6/2018 | Munivar et al. | |
| 2018/0163188 A1 | 6/2018 | Xie et al. | |
| 2018/0185420 A1 | 7/2018 | Liu et al. | |
| 2018/0250222 A1 | 9/2018 | Lyle | |

FOREIGN PATENT DOCUMENTS

| | | | |
|---|---|---|---|
| EP | 2 180 050 A2 | 4/2010 | |
| EP | 2 972 371 B1 | 9/2018 | |
| EP | 3 384 918 A1 | 10/2018 | |
| KR | 10-2006-0118705 A | 11/2006 | |
| WO | 97/31114 A2 | 8/1997 | |
| WO | 99/58652 A2 | 11/1999 | |
| WO | 02/15896 A2 | 2/2002 | |
| WO | 2008/068533 A2 | 6/2008 | |
| WO | 2008/077251 A1 | 7/2008 | |
| WO | 2009/030040 A1 | 3/2009 | |
| WO | 2009/117310 A2 | 9/2009 | |
| WO | 2009/152298 A1 | 12/2009 | |
| WO | 2010/036876 A2 | 4/2010 | |
| WO | 2010/123599 A2 | 10/2010 | |
| WO | 2011/005756 A1 | 1/2011 | |
| WO | 2011/085367 A2 | 7/2011 | |
| WO | 2012/150269 A1 | 11/2012 | |
| WO | 2012/177658 A2 | 12/2012 | |
| WO | WO-2013050590 A1 * | 4/2013 | C07K 14/31 |
| WO | 2013/122932 A2 | 8/2013 | |
| WO | 2013/153358 A1 | 10/2013 | |
| WO | 2014/137906 A1 | 9/2014 | |
| WO | 2014/145958 A2 | 9/2014 | |
| WO | 2014/145958 A4 | 9/2014 | |
| WO | 2014/205127 A2 | 12/2014 | |
| WO | 2015/048364 A1 | 4/2015 | |
| WO | 2015/077794 A1 | 5/2015 | |
| WO | 2015/077794 A4 | 5/2015 | |
| WO | 2015/089073 A2 | 6/2015 | |
| WO | 2015/106175 A1 | 7/2015 | |
| WO | 2015/196299 A1 | 12/2015 | |
| WO | 2016/128414 A1 | 8/2016 | |
| WO | 2016/141108 A1 | 9/2016 | |
| WO | 2016/177682 A1 | 11/2016 | |
| WO | 2016/183531 A1 | 11/2016 | |
| WO | 2016/183532 A1 | 11/2016 | |
| WO | 2016/200614 A2 | 12/2016 | |
| WO | 2016/205749 A1 | 12/2016 | |
| WO | 2016/210373 A2 | 12/2016 | |
| WO | 2016/210384 A2 | 12/2016 | |
| WO | 2017/008018 A1 | 1/2017 | |
| WO | 2017/023818 A1 | 2/2017 | |
| WO | 2017/059245 | 4/2017 | |
| WO | 2017/091753 A1 | 6/2017 | |
| WO | 2017/099559 A1 | 6/2017 | |
| WO | 2017/103593 | 6/2017 | |
| WO | 2017/112620 A1 | 6/2017 | |
| WO | 2017/123676 | 7/2017 | |
| WO | 2017/182796 A1 | 10/2017 | |
| WO | 2017/184601 A1 | 10/2017 | |
| WO | 2017/184992 A1 | 10/2017 | |
| WO | 2017/210428 A1 | 12/2017 | |
| WO | 2017/220708 A1 | 12/2017 | |
| WO | 2018/050056 A1 | 3/2018 | |
| WO | 2018/094190 A2 | 5/2018 | |
| WO | 2018/109018 A1 | 6/2018 | |
| WO | 2018/112194 A1 | 6/2018 | |
| WO | 2018/141907 A1 | 8/2018 | |
| WO | 2018/152306 A1 | 8/2018 | |
| WO | 2018/157152 A1 | 8/2018 | |
| WO | 2018/182515 A1 | 10/2018 | |
| WO | 2018/195097 A1 | 10/2018 | |

(56) References Cited

FOREIGN PATENT DOCUMENTS

OTHER PUBLICATIONS

Jeremy M. Yarwood et al., Repression of the *Staphylococcus aureus* Accessory Gene Regulator in Serum and In Vivo, 2002, American Society for Microbiology Journal of Bacteriology, vol. 184 pp. 1095-1101 (Year: 2002).*
Gordon L. Archer and Michael W. Climo, Antimicrobial Susceptibility of Coagulase-Negative Staphylococci, 1994, Antimicrobial Agents and Chemotherapy, vol. 38, No. 10, p. 2231-2237 (Year: 1994).*
Sayed, N., Jousselin, A. & Felden, B. A cis-antisense RNA acts in trans in *Staphylococcus aureus* to control translation of a human cytolytic peptide. Nat Struct Mol Biol 19, 105-112 (2012) (Year: 2012).*
Ishii (Infection and immunity 82.4 (2014): 1500-1510) (Year: 2014).*
Malachowa (PloS one 6.4 (2011): e18617) (Year: 2011).*
McAleese (Microbiology 149.1 (2003): 99-109) (Year: 2003).*
International Search Report and Written Opinion for PCT/US2018/63880, dated Apr. 29, 2019, 16 pages total.
Linzer et al., "Transcriptional regulation of proliferin gene expression in response to serum in transfected mouse cells", The EMBO Journal, 1987, vol. 6, No. 8, pp. 2281-2288.
Active Bacterial Core Surveillance (ABCs) Report, Emerging Infections Program Network, Methicillin-Resistant *Staphylococcus aureus,* Centers for Disease Control and Prevention., https://www.cdc.gov/hai/eip/pdf/2015-mrsa-annual-summary.pdf, 3 pages (2015).
Acton et al., Intestinal carriage of *Staphylococcus aureus*: how does its frequency compare with that of nasal carriage and what is its clinical impact? Eur J Clin Microbiol Infect Dis, vol. 28, pp. 115-127 (2009).
Adherence to the Centers for Disease Control and Prevention's (CDC's) Infection Definitions and Criteria is Needed to Ensure Accuracy, Completeness, and Comparability of Infection Information, Centers for Disease Control and Prevention, https://www.cdc.gov/nhsn/cms/cms-reporting.html, 3 pages (Oct. 2015).
Albert et al., "Bullous Impetigo Due to Group II *Staphylococcus aureus,*" Amer J Dis Child, vol. 120, pp. 10-13 (Jul. 1970).
Altschul et al., "Gapped BLAST and PSI-BLAST: a new generation of protein database search programs," Nucleic Acids Research, vol. 25, No. 17, pp. 3389-3402 (1997).
Aly et al., "Bacterial Interference among Strains of *Staphylococcus aureus* in Man," The Journal of Infectious Diseases, vol. 129, No. 6, pp. 720-724 (Jun. 1974).
Anthony et al., "Bacterial Interference in Experimental Burns," The Journal of Experimental Medicine, vol. 125, pp. 319-336 (1967).
Antibiotic/Antimicrobial Resistance (AR/AMR), Biggest Threats and Data, https://www.cdc.gov/drugresistance/biggest_threats.html, 19 pages (Sep. 10, 2018).
Antibiotic Resistance (AR) Solutions Initiative: Microbiome, CDC Microbiome Fact Sheet, www.cdc.gov/drugresistance/solutions-initiative/microbiome-innovations.html, 1 page (2016).
Antibiotic Resistance Threats in the United States, https://www.cdc.gov/drugresistance/biggest_threats, pp. 1-113 (2013).
Anton et al., "Trojan Microparticles for Drug Delivery," Pharmaceutics, vol. 4, doi:10.3390/pharmaceutics4010001, pp. 1-25 (2012).
ATCC Product Sheet *Staphylococcus aureus* subsp. *aureus* (ATCC 27217), 2 pages (2014).
Bae et al., "Allelic replacement in *Staphylococcus aureus* with inducible counter-selection," Plasmid, vol. 55, pp. 58-63 (2006).
Beck et al., "Additional DNA in Methicillin-Resistant *Staphylococcus aureus* and Molecular Cloning of mec-Specific DNA," Journal of Bacteriology, vol. 165, No. 2, pp. 373-378 (Feb. 1986).
Benton et al., "Large-Scale Identification of Genes Required for Full Virulence of *Staphylococcus aureus,*" Journal of Bacteriology, vol. 186, No. 24, pp. 8478-8489 (Dec. 2004).
Bessesen et al., "MRSA colonization and the nasal microbiome in adults at high risk of colonization and infection," Journal of Infection, vol. 71, pp. 649-657 (2015).
Beylot et al., "Propionibacterium acnes: an update on its role in the pathogenesis of acne," Journal of the European Academy of Dermatology and Venereology, vol. 28, No. 3, pp. 271-278 (2014).
Blair et al., "Multiple infections among newborns resulting from colonization with *Staphylococcus aureus* 502A," The American Journal of Clinical Pathology, vol. 52, No. 1, pp. 42-49 (Jul. 1969).
Bleiziffer et al., "The Plasmin-Sensitive Protein Pls in Methicillin-Resistant *Staphylococcus aureus* (MRSA) is a Glycoprotein," PLoS Pathog 13(1): e1006110, pp. 1-36 (Jan. 12, 2017).
Blum, "Tools for Building a Better Antibiogram," Infectious Disease Special Edition, pp. 18-19 (Fall 2017).
Boers et al., "Novel micelle PCR-based method for accurate, sensitive and quantitative microbiota profiling," Scientific Reports 7:45536; doi: 10.1038/srep45536, 7 pages (2017).
Bohn et al., "Experimental discovery of small RNAs in *Staphylococcus aureus* reveals a riboregulator of central metabolism," Nucleic Acids Research, vol. 38, No. 19, pp. 6620-6636 (2010).
Boris et al., "IV. The Louisiana Epidemic," American Journal of Diseases of Children, vol. 105, pp. 674-682 (Jun. 1963).
Boris et al., "Bacterial Interference: Protection of Adults Against Nasal *Staphylococcal aureus* Infection After Colonization With a Heterologous *S aureus* Strain." American Journal of Diseases of Children, vol. 108, pp. 252-261 (Sep. 1964).
Boris et al, . "Bacterial Interference: Protection Against Recurrent Intrafamilial Staphylococcal Disease." Amer J Dis Child, vol. 115, pp. 521-529 (May 1968).
Bourgeois-Nicolaos et al., "Maternal vaginal colonisation by *Staphylococcus aureus* and newborn acquisition at delivery,". Paediatric and Perinatal Epidemiology, doi: 10.1111/j.1365-3016.2010.01139.x, vol. 24, pp. 488-491 (2010).
Buckingham, "Prevention of recurrent MRSA skin infections: What you need to know," consultant360.com/content/prevention-recurrent-mrsa-skin-infections-what-you-need-know, 8 pages (Apr. 26, 2011).
Burian et al., "Regulatory Adaptation of *Staphylococcus aureus* during Nasal Colonization of Humans," PLoS ONE, 5 (4): e10040, doi:10.1371/journal.pone.0010040, 9 pages (2010).
Burnside et al. "Vaccination with a UV-Irradiated Genetically Attenuated Mutant of *Staphylococcus aureus* Provides Protection Against Subsequent Systemic Infection," The Journal of Infectious Diseases, vol. 206, pp. 1734-1744 (Dec. 2012).
Castro-Escarpulli et al., "Identification and Typing Methods for the Study of Bacterial Infections: a Brief Review and Mycobacterial as Case of Study," Archives of Clinical Microbiology, vol. 7, No. 1:3, pp. 1-10 (2015).
CDC Press Release, "Nearly half a million Americans suffered from Clostridium difficile infections in a single year," www.cdc.gov/media/releases/2015/p0225-clostridium-difficile, 6 pages (2015).
CDC's Antibiotic Resistance (AR) Solutions Initiative: Microbiome, www.cdc.gov/drugresistance/solutions-initiative/innovations-to-slow-AR.html, 1 page (2017).
Cespedes et al., "The Clonality of *Staphylococcus aureus* Nasal Carriage," The Journal of Infectious Diseases, vol. 191, pp. 444-452 (Feb. 2005).
Chan et al., "'Deadman' and 'Passcode' microbial kill switches for bacterial containment," Nature Chemical Biology, vol. 12, pp. 82-86, DOI: 10.1038/NCHEMBIO.1979 (Feb. 2016).
Chen et al., "Impact of Traditional Hospital Strain of Methicillin-Resistant *Staphylococcus aureus* (MRSA) and Community Strain of MRSA on Mortality in Patients With Community-Onset *S aureus* Bacteremia," Medicine, vol. 89, op. 285-294 (2010).
Chen et al., "Rapid and Efficient Genome Editing in *Staphylococcus aureus* by Using an Engineered CRISPR/Cas9 System," Journal of the American Chemical Society, vol. 139, No. 10, pp. 3790-3795 (2017).
CHROMagar *Staph aureus* Data Sheet, 4 pages (2017).
CHROMagar *Staph.aureus* Instructions for Use, 2 pages (2015).
Chuah et al., "Antimicrobial Activities of Plant Extracts against Methicillin-Susceptible and Methicillin-Resistant *Staphylococcus aureus,*" Journal of Microbiology Research, vol. 4, No. 1, pp. 6-13 (2014).

(56) References Cited

OTHER PUBLICATIONS

Cohen et al., "VI. Detection of Implanted *Staphylococcus aureus* Strain. Use of Serological and Phage Typing," American Journal of Diseases of Children, vol. 105, No. 6, pp. 689-691 (1963).
Cosgrove et al., "Comparison of Mortality Associated with Methicillin-Resistant and Methicillin-Susceptible *Staphylococcus aureus* Bacteremia: A Meta-analysis," Clinical Infectious Diseases, vol. 36, pp. 53-59 (2003).
Cosgrove et al., "The Impact of Methicillin Resistance in *Staphylococcus aureus* Bacteremia on Patient Outcomes: Mortality, Length of Stay, and Hospital Charges,". Infection Control and Hospital Epidemiology, vol. 26, No. 2, pp. 166-174 (Feb. 2005).
Creech et al. "Prevention of Recurrent Staphylococcal Skin Infections," Infect Dis Clin North Am., vol. 29, No. 3 pp. 429-464 (Sep. 2015).
Dale et al, "Involvement of SirABC in Iron-Siderophore Import in *Staphylococcus aureus,*" Journal of Bacteriology, vol. 186, No. 24, pp. 8356-8362 (Dec. 2004).
Dall'Antonia et al., "Competition between methicillin-sensitive and-resistant *Staphylococcus aureus* in the anterior Nares," Journal of Hospital Infection, vol. 61, pp. 62-67 (2005).
Dantes et al., "National Burden of Invasive Methicillin-Resistant *Staphylococcus aureus* Infections, United States, 2011," JAMA Internal Medicine, vol. 173, No. 21, pp. 1970-1978 (Nov. 25, 2013).
Darouiche et al., "Pilot trial of bacterial interference for preventing urinary tract infection," Urology, vol. 58, pp. 339-344 (2001).
Das et al., "Natural mutations in a *Staphylococcus aureus* virulence regulator attenuate cytotoxicity but permit bacteremia and abscess formation," PNAS, www.pnas.org/cgi/doi/10.1073/pnas.1520255113, pp. E3101-E3110 (May 16, 2016).
Date et al., "Global Gene Expression of Methicillin-resistant *Staphylococcus aureus* USA300 During Human and Mouse Infection," The Journal of Infectious Diseases, vol. 209, pp. 1542-1550 (2014).
David et al., Community-Associated Methicillin-Resistant *Staphylococcus aureus*: Epidemiology and Clinical Consequences of an Emerging Epidemic, Clinical Microbiology Reviews, vol. 23, No. 3, pp. 616-687 (Jul. 2010).
Rasmussen et al., "Future challenges and treatment of *Staphylococcus aureus* bacteremia with emphasis on MRSA," Future Microbiol., vol. 6, No. 1, pp. 43-56 (Jan. 2011).
Reid et al., "Can bacterial interference prevent infection?," TRENDS in Microbiology, vol. 9, No. 9, pp. 424-428 (Sep. 2001).
Reisch, "The Microbiome Comes to Cosmetics," C&EN, vol. 95, Issue 19, pp. 30-34 (May 8, 2017).
Relman, "The human microbiome: ecosystem resilience and health," Nutr Rev., vol. 70, Suppl 1, pp. S2-S9 (Aug. 2012).
Ren et al., "Effects of mixed lactic acid bacteria on intestinal microbiota of mice infected with *Staphyloccus aureus,*" BMC Microbiology, 18:109, https://doi.org/10.1186/s12866-018-1245-1, 7 pages (2018).
Ribble, "A mechanism of bacterial interference in vitro," The Journal of Immunology, vol. 98, No. 4, pp. 716-723 (1967).
Ribet et al., "How bacterial pathogens colonize their hosts and invade deeper tissue," Microbes and Infection, vol. 17, No. 3, pp. 173-183 (Mar. 2015).
Rogasch et al., "Influence of the Two-Component System SaeRS on Global Gene Expression in Two Different *Staphylococcus aureus* Strains," Journal of Bacteriology, vol. 188, No. 22, pp. 7742-7758 (Nov. 2006).
Rolo et al., "Evidence for the evolutionary steps leading to mecA-mediated β-lactam resistance in staphylococci," PLoS Genetics, 13(4): e1006674. doi:10.1371/journal.pgen.1006674, 22 pages (2017).
Rovner et al., "Recoded organisms engineered to depend on synthetic amino acids," Nature, vol. 518, No. 7537, pp. 89-93 (Feb. 5, 2015).
Safdar et al., "The risk of Infection after Nasal Colonization with *Staphylococcus aureus,*" Am J Med, vol. 121, pp. 310-315 (2008).
Saiman et al., "Hospital Transmission of Community-Acquired Methicillin-Resistant *Staphylococcus aureus* among Postpartum Women," Clinical Infectious Diseases, vol. 37, pp. 1313-1319 (2003).
Sakr et al., "*Staphylococcus aureus* Nasal Colonization: An Update on Mechanisms, Epidemiology, Risk Factors, and Subsequent Infections," Frontiers in Microbiology, vol. 9, Article 2419, pp. 1-15 (Oct. 2018).
Sayed et al., "Functional and Structural Insights of a *Staphylococcus aureus* Apoptotic-like Membrane Peptide from a Toxin-Antitoxin Module," The Journal of Biological Chemistry, vol. 287, No. 52, pp. 43454-43463 (Dec. 21, 2012).
Sayed et al., "A cis-antisense RNA acts in trans in *Staphylococcus aureus* to control translation of a human cytolytic peptide," Nature Structural and Molecular Biology, vol. 19, No. 1, pp. 105-112 (2012).
Shinefield et al., "Bacterial Interference: Its Effect on Nursery-Acquired Infection with *Staphylococcus aureus* I. Preliminary Observations on Artificial Colonization of Newborns," American Journal of Diseases of Children, vol. 105, pp. 646-654 (Jun. 1963).
Shinefield et al., "II. The Ohio Epidemic," American Journal of Diseases of Children, vol. 105, pp. 655-662 (Jun. 1963).
Shinefield et al., "III. The Georgia Epidemic," American Journal of Diseases of Children, vol. 105, pp. 663-673 (Jun. 1963).
Shinefield et al., "V. An Analysis and Interpretation," American Journal of Diseases of Children, vol. 105, pp. 683-688 (Jun. 1963).
Shinefield et al., "Interactions of Staphylococcal Colonization," Amer J Dis Child, vol. 111, pp. 11-21 (Jan. 1966).
Shinefield et al., "Bacterial Interference Between Strains of *Staphylococcus aureus,* 1960 to 1970," Amer J Dis Child, vol. 121, pp. 148-152 (Feb. 1971).
Shinefield et al., "Bacterial interference between strains of *Staphylococcus aureus,*" Contributions to Microbiology and Immunology, vol. 1, pp. 541-547 (1973).
Shu et al., "Fermentation of Propionibacterium acnes, a Commensal Bacterium in the Human Skin Microbiome, as Skin Probiotics against Methicillin-Resistant *Staphylococcus aureus,*". PLoS ONE, vol. 8, Issue 2, e55380. https://doi.org/10.1371/journal.pone.0055380, 11 pages (2013).
Skovbjerg et al., "Spray bacteriotherapy decreases middle ear fluid in children with secretory otitis media," Arch. Dis. Child, vol. 94, pp. 92-98 (2009).
Smith, "Better Antibiotic Susceptibility Testing Method," Infectious Disease Special Edition, p. 16 (Sep. 19, 2017).
Smith et al., "Bacterial Substitution for Staphylococcal Infection," New Zealand Medical Journal, vol. 67, pp. 407-409 (Mar. 1968).
Song et al., "Integrating Ecological and Engineering Concepts of Resilience in Microbial Communities," Frontiers in Microbiology, vol. 6, Article 1298, doi.: 10.3389/fmicb.2015.01298, pp. 1-7 (Dec. 2015).
Speck et al., "Effect of bacterial flora on staphylococcal colonization of the newborn," Journal of Clinical Pathology, vol. 31, pp. 153-155 (1978).
Spellberg et al., "The Epidemic of Antibiotic-Resistance Infections: A Call to Action for the Medical Community from the Infectious Diseases Society of America," Clinical Infectious Diseases, vol. 46, pp. 155-164 (Jan. 15, 2008).
Sprunt et al., "Evidence Suggesting Importance of Role of Interbacterial Inhibition in Maintaining Balance of Normal Flora," Annals of Internal Medicine, vol. 68, No. 3, pp. 579-590 (Mar. 1968).
Sprunt et al., "The use of bacterial interference to prevent infection," Can. J. Microbiol. vol. 34, pp. 332-338 (1988).
Stapleton et al., "Characterization of IsaA and SceD, Two Putative Lytic Transglycosylases of *Staphylococcus aureus,*" Journal of Bacteriology, vol. 189, No. 20, pp. 7316-7325 (Oct. 2007).
Stauff et al., "Signaling and DNA-binding Activities of the *Staphylococcus aureus* HssR-HssS Two-component System Required for Heme Sensing," The Journal of Biological Chemistry, vol. 282, No. 36, pp. 26111-26121 (Sep. 7, 2007).
Strauss et al., "Purposeful Change of Staphylococcal Bacteriophage Types," JAMA, vol. 191, No. 9, pp. 759-761 (Mar. 1, 1965).

(56) References Cited

OTHER PUBLICATIONS

Strauss et al., "Bacterial Interference Treatment of Recurrent Furunculosis. 2. Demonstration of the Relationship of Strain to Pathogenicity," JAMA, vol. 208, No. 5, pp. 861-863 (May 5, 1969).
Sugimoto et al. "*Staphylococcus epidermidis* Esp Degrades Specific Proteins Associated with *Staphylococcus aureus* Biofilm Formation and Host-Pathogen Interaction," Journal of Bacteriology, vol. 195, No. 8, pp. 1645-1655 (Apr. 2013).
Surmann et al., "Comparative proteome analysis reveals conserved and specific adaptation patterns of *Staphylococcus aureus* after internalization by different types of human non-professional phagocytic host cells," Front. Microbiol., vol. 5, pp. 1-14, https://doi.org/10.3389/fmicb.2014.00392, 26 pages (Aug. 1, 2014).
Surmann et al., "A proteomic perspective of the interplay of *Staphylococcus aureus* and human alveolar epithelial cells during infection," Journal of Proteomics, vol. 128, pp. 203-217, doi: 10.1016/j.jprot.2015.07.034 (2015).
Tacconelli et al., "ESCMID guidelines for the management of the infection control measures to reduce transmission of multidrug-resistant Gram-negative bacteria in hospitalized patients," Clin Microbiol Infect, vol. 20 (Suppl. 1), pp. 1-55 (2014).
Tomita et al., "Molecular Biology of the Pore-forming Cytolysins from *Staphylococcus aureus,* α- and γ-Hemolysins and Leukocidin," Biosci. Biotech. Bioc/zem, vol. 61, No. 4, pp. 565-572 (1997).
Tong et al., "*Staphylococcus aureus* Infections: Epidemiology, Pathophysiology, Clinical Manifestations, and Management," Clinical Microbiology Reviews, vol. 28, No. 3, pp. 603-661 (Jul. 2015).
Tulinski et al., "*Staphylococcus aureus* ST398 gene expression profiling during ex vivo colonization of porcine nasal epithelium," BMC Genomics, 15:915, 10 pages (2014).
Uehara et al., "Bacterial interference among nasal inhabitants: eradication of *Staphyloccus aureus* from nasal cavities by artificial implantation of *Corynebacterium* sp." Journal of Hospital Infection, vol. 44, pp. 127-133 (2000).
Valentino et al., "Genes Contributing to *Staphylococcus aureus* Fitness in Abscess- and Infection-Related Ecologies," mBio, vol. 5, Issue 5 e01729-14 doi:10.1128/mBio.01729-14, 10 pages (2014.
Von Eiff et al., "Nasal carriage as a source of *Staphyloccus aureus* bacteremia," The New England Journal of Medicine, vol. 344, No. 1, pp. 11-16 (Jan. 4, 2001).
Votintseva, et al., "Multiple-Strain Colonization in Nasal Carriers of *Staphylococcus aureus,*" Journal of Clinical Microbiology, vol. 52, No. 4, pp. 1192-1200 (Apr. 2014).
Wang et al., "Genome-wide operon prediction in *Staphylococcus aureus,*" Nucleic Acids Research, vol. 32, No. 12, pp. 3689-3702. doi:10.1093/nar/gkh694 (2004).
Wang et al., "*Staphylococcus epidermidis* in the human skin microbiome mediates fermentation to inhibit the growth of Propionibacterium acnes: Implications of probiotics in acne vulgaris," Appl Microbiol Biotechnol, vol. 98, No. 1, pp. 411-424 (Jan. 2014).
Wertheim et al., "Risk and outcome of nosocomial *Staphylococcus aureus* bacteraemia in nasal carriers versus non-carriers," Lancet, vol. 364, No. 9435, pp. 703-705 (Aug. 21, 2004).
Wertheim et al., "The role of nasal carriage in *Staphylococcus aureus* infections," Lancet Infect Dis, vol. 5, pp. 751-762 (Dec. 2005).
Invitation to Pay Additional Fees And, Where Applicable, Protest Fee for International Application No. PCT/US2018/63880 dated Feb. 21, 2019, 3 pages total.
Wertheim et al., "Key Role for Clumping Factor B in *Staphylococcus aureus* Nasal Colonization of Humans," PLoS Med., 5(1): e17. doi: 10.1371/journal.pmed.0050017: 10.1371/journal.pmed.0050017, 16 pages (Jan. 2008).
Whitby et al., "Risk of death from methicillin-resistant *Staphylococcus aureus* bacteraemia: a meta-analysis," The Medical Journal of Australia, vol. 175, pp. 264-267 (Sep. 3, 2001.
Wiltshire et al., "Identification and Analysis of *Staphyloccus aureus* Components Expressed by a Model System of Growth in Serum," Infection and Immunity, vol. 69, No. 8, pp. 5198-5202 (Aug. 2001).
Withers et al., "Sequence-specific DNA Recognition by the Smal Endonuclease," The Journal of Biological Chemistry, vol. 270, No. 12, pp. 6496-4504 (Mar. 24, 1995).
Wright et al., "GeneGuard: A Modular Plasmid System Designed for Biosafety," ACS Synthetic Biology, vol. 4, No. 3, pp. 307-316 (2015).
Xia et al. "Staphylococcal LTA-Induced miR-143 Inhibits Propionibacterium acnes-Mediated Inflammatory Response in Skin," Journal of Investigative Dermatology, vol. 136, No. 3, pp. 621-630 (2016).
Yandell, "Controlling Synthetic Bacteria "Kill switches" ensure that genetically engineered bacteria survive only in certain environmental conditions," The Scientist Magazine, http://www.the-scientist.com/?articles.view/articleNo/44715/title/Controlling-Synthetic-B, 4 pages (Dec. 7, 2015).
Yoshida et al., "Physiological and molecular analysis of mecA-negative *Staphylococcus aureus* clinical strain that expresses heterogeneous methicillin resistance," Journal of Antimicrobial Chemotherapy, vol. 51, pp. 247-255 (2003).
Ythier et al., "Proteomic and Transcriptomic Profiling of *Staphylococcus aureus* Surface LPXTG-proteins: Correlation with agr Genotypes and Adherence Phenotypes," Molecular & Cellular Proteomics, vol. 11, No. 11, pp. 1123-1139 (2012).
Zarate et al., "Protective Effect of Vaginal Lactobacillus paracasei CRL 1289 against Urogenital Infection Produced by *Staphylococcus aureus* in a Mouse Animal Modal," Infectious Diseases in Obstetrics and Gynecology, vol. 2007, Article ID 48358, 6 pages (2007).
Zhang et al., "Structure-Based Discovery of Small Molecule Inhibitors of Cariogenic Virulence," Scientific Reports, 7: 5974 DOI:10.1038/s41598-017-06168-1 (2017).
Zhang, "Using Photosensitizers Instead of Antibiotics to Kill MRSA," GEN News Highlights, https://www.genengnews.com/topics/drug-discovery/using-photosensitizers-instead-of-antibiotics-to-kill-mrsa/, 7 pages (Aug. 20, 2018).
Popov et al., "Three-dimensional human skin models to understand *Staphylococcus aureus* skin colonization and infection," Frontiers in Immunology, vol. 5, Article 41, pp. 1-6 (Feb. 2014).
European Search Report for EP Application No. 18886851.7 mailed Nov. 9, 2021 (7 pages).
Delaney et al., "Mortality after infection with methicillin resistant *Staphylococcus aureus* (MRSA) diagnosed in the community," BMC Medicine, 6:2 doi:10.1186/1741-7015-6-2, 8 pages (2008).
Detels et al., "The Incidence and Correlates of Symptomatic and Asymptomatic Chlamydia trachomatis and Neisseria gonorrhoeae Infections in Selected Populations in Five Countries," Sex Tarnsm Dis, vol. 38, No. 6, pp. 503-509 (Jun. 2011).
Dietert et al., "The Microbiome and Sustainable Healthcare," Healthcare, vol. 3, pp. 100-129 (2015).
Dréno et al., "Cutibacterium acnes (*Propionibacterium acnes*) and acne vulgaris: a brief look at the latest updates," Journal of the European Academy of Dermatology and Venereology, vol. 32 (Suppl. 2), pp. 5-14 (2018).
Drutz et al., "Bacterial Interference in the Therapy of Recurrent Staphylococcal Infections Multiple Abscesses Due to the Implantation of the 502A Strain of *Staphylococcus,*" The New England Journal of Medicine, vol. 275, No. 21, pp. 1161-1165 (Nov. 1966).
Epstein et al., "Risk Factors for Invasive Methicillin-Resistant *Staphylococcus aureus* Infection After Recent Discharge From an Acute-Care Hospitalization," Clinical Infectious Diseases, vol. 62, pp. 45-52 (2016).
Eriksen et al., "Carriage of *Staphylococcus aureus* among 104 healthy persons during a 19-month period," Epidemiol. Infect., vol. 115, pp. 51-60 (1995).
Falkow, "Who Speaks for Microbes?," Emerging Infectious Diseases, vol. 4, No. 3, pp. 495-497 (Jul.-Sep. 1998).
Fernandez et al., "A double-blind, randomized, placebo-controlled clinical trial to evaluate the safety and efficacy of mupirocin calcium ointment for eliminating nasal carriage of *Staphylococcus aureus* among hospital personnel," Journal of Antimicrobial Chemotherapy, vol. 35, pp. 399-408 (1995).

(56) References Cited

OTHER PUBLICATIONS

Filice et al., "Excess Costs and Utilization Associated with Methicillin Resistance for Patients with *Staphylococcus aureus* Infection," Infection Control and Hospital Epidemiology, vol. 31, No. 4, pp. 365-373 (Apr. 2010).
Fine et al., "Bacterial Interference in the Treatment of Recurrent Staphylococcal Infections in a Family," The Journal of Pediatrics, vol. 70, No. 4, pp. 548-553 (Apr. 1967).
Flack et al , "Differential regulation of staphylococcal virulence by the sensor kinase SaeS in response to neutrophil-derived stimuli," PNAS, www.pnas.org/cgi/doi/10.1073/ pnas.1322125111, pp. E2037-E2045, (Apr. 29, 2014).
Forrsten et al, "*Streptococcus mutans,* Caries and Simulation Models," Nutrients, vol. 2, No. pp. 290-298 (Mar. 2, 2010).
Gallagher et al., "Multilayered genetic safeguards limit growth of microorganisms to defined environments," Nucleic Acids Research, vol. 1, doi: 10.1093/nar/gku1378, pp. 1-10 (2015).
Garg et al.,"Comprehensive review on additives of topical dosage forms for drug delivery," Drug Delivery, vol. 22, No. 8, DOI: 10.3109/10717544.2013.879355, pp. 969-987 (2015).
Garzoni et al., A global view of *Staphylococcus aureus* whole genome expression upon internalization in human epithelial cells. BMC Genomics, 8:171 doi:10.1186/1471-2164-8-171, 14 pages (2007).
Geissman et al. "A search for small noncoding RNAs in *Staphylococcus aureus* reveals a conserved sequence motif for regulation," Nucleic Acids Research, vol. 37, No. 21, pp. 7239-7257 (2009).
Gill et al., Antibiotic Adjuvants: Diverse Strategies for Controlling Drug-Resistant Pathogens, Chem Biol Drug Des, vol. 85, pp. 56-78 (2015).
Gonzalez et al., "Bacteremic Pneumonia Due to *Staphylococcus aureus:* A Comparison of Disease Caused by Methicillin-Resistant and Methicillin-Susceptible Organisms," Clinical Infectious Diseases, vol. 29, pp. 1171-1177 (Nov. 1999).
Gouaux et al., "α-Hemolysin, i-hemolysin, and leucocidin from *Staphylococcus aureus*: Distant in sequence but similar in structure," Protein Science, vol. 6, pp. 2631-2635 (1997).
Gould et al., "The evaluation of novel chromogenic substrates for the detection of lipolytic activity in clinical isolates of *Staphylococcus aureus* and MRSA from two European study groups," FEMS Microbiology Letters, vol. 297, pp. 10-16 (2009).
Grice, "The skin microbiome: potential for novel diagnostic and therapeutic approaches to cutaneous disease," Semin Cutan med Surg, vol. 33, No. 2, pp. 98-103 (Jun. 2014).
Guillet et al., "Emerging Functions for the *Staphylococcus aureus* RNome," PLOS Pathogens, vol. 9, Issue 12, e1003767-. doi:10.1371/journal.ppat.1003767, 13 pages (Dec. 2013).
Günther et al., "MRSA decolonization failure—are biofilms the missing link?" Antimicrobial Resistance and Infection Control., vol. 6, pp. 32-38 (2017).
Gupta et al., "'Use a Thorn to Draw Thorn' Replacement Therapy for Prevention of Dental Caries," International Journal of Clinical Pediatric Dentistry, vol. 3, No. 3, pp. 125-137 (Sep.-Dec. 2010).
Gurieva et al., "Cost and Effects of Different Admission Screening Strategies to Control the Spread of Methicillin-resistant *Staphylococcus aureus,*" PLoS Comput Biol 9(2): e1002874. doi:10.1371/journal.pcbi.1002874, 11 pages (2013).
Hanberger et al., "Increased mortality associated with meticillin-resistant *Staphylococcus aureus* (MRSA) infection in the Intensive Care Unit: results from the EPIC II study," 2011, International Journal of Antimicrobial Agents, vol. 38, No. 4, pp. 331-335, http://dx.doi.org/10.1016/j.ijantimicag.2011.05.013 (2011).
Hao et al., "Microflora of the Gastrointestinal Tract: A Review," Methods in Molecular Biology, vol. 268, pp. 491-502 (2004).
Hardin, "The Competitive Exclusion Principle," Science, vol. 131, No. 3409, pp. 1292-1297 (Apr. 29, 1960).
Hartman et al., "Low-Affinity Penicillin-Binding Protein Associated with β-Lactam Resistance in *Staphylococcus aureus,*" Journal of Bacteriology, vol. 158, No. 2, pp. 513-516 (May 1984).
Hassoun et al., "Incidence, prevalence, and management of MRSA bacteremia across patient populations—a review of recent developments in MRSA management and treatment," Critical Care 21:211, 10 pages (2017).
Hazenbos et al., Novel Staphyloccocal Glycosyltransfereases SdgA, SdgB Mediate Immunogenicity and Protection of Virulence-Associated Cell Wall Proteins, PLOS Pathogens, vol. 9, Issue 10, e1003653. doi: 10.1371/journal.ppat.1003653, 18 pages (Oct. 10, 2013).
Helle et al. "Vectors for improved Tet repressor-dependent gradual gene induction or silencing in *Staphylococcus aureus.*" Microbiology vol. 157, pp. 3314-3323 (2011).
Herold et al., "Community-Acquired Methicillin-Resistant *Staphylococcus aureus* in Children With No Identified Predisposing Risk," JAMA, vol. 279, No. 8, pp. 593-598 (Feb. 25, 1998).
Hillman, "Genetically modified *Streptococcus mutans* for the prevention of dental caries," Antonie van Leuwenhoek, vol. 82, pp. 361-366 (2002).
Hisano et al., "Cranberries and lower urinary tract infection prevention," Clinics, vol. 67, No. 6, pp. 661-667 (2012).
Holt, "Bringing the Hutchinsonian niche into the 21st century: ecological and evolutionary perspectives," PNAS, vol. 106, Suppl. 2, pp. 19659-19665 (Nov. 17, 2009).
Holz et al., "Novel bioactive from Lactobacillus brevis DSM17250 to stimulate the growth of *Staphylococcus epidermidis*: a pilot study," Beneficial Microbes, vol. 8, No. 1, pp. 121-131 (2017).
Honda et al., "*Staphylococcus aureus* Nasal Colonization and Subsequent Infection in Intensive Care Unit Patients: Does Methicillin Resistance Matter?," Infection Control and Hospital Epidemiology, vol. 31, No. 6, pp. 584-591 (2010).
Horgan et al., "Phage Lysin LysK Can Be Truncated to Its CHAP Domain and Retain Lytic Activity against Live Antibiotic-Resistant Staphylococci," Applied and Environmental Microbiology, vol. 75, No. 3, pp. 872-874 (Feb. 2009).
Houck et al., "Fatal Septicemia Due to *Staphylococcus aureus* 502A," Amer J Dis Child, vol. 123, pp. 45-48 (Jan. 1972).
Howell et al., "Dosage effect on uropathogenic *Escherichia coli* anti-adhesion activity in urine following consumption of cranberry powder standardized for proanthocyanidin content: a multicentric randomized double blind study," BMC Infectious Diseases, 10:94, http://www.biomedcentral.com/1471-2334/10/94, 11 pages (2010).
Huang et al., "Risk of Methicillin-Resistant *Staphylococcus aureus* Infection after Previous Infection or Colonization," Clinical Infectious Diseases, Fol. 36, No. 3, pp. 281-285 (Feb. 1, 2003).
Huang et al., "Colonization with antibiotic-susceptible srains protects against methicillin-resistant *Staphylococcus aureus* but not vancomycin-resistant enterococci acquisition: a nested case-control study," Critical Care, 15:R210, http://ccforum.com/content/15/5/R210, 10 pages (2011).
Huang et al., "Targeted versus Universal Decolonization to Prevent ICU Infection," The New England Journal of Medicine, vol. 368, No. 24, pp. 2255-2265 (Jun. 13, 2013).
Huang et al., "Probiotics in personal care products," Microbiology Discovery, vol. 3, Article 5, http://www.hoajonline.com/journals/pdf/2052-6180-3-5.pdf, 9 pages (2015).
Iwase et al., "*Staphylococcus epidermidis* Esp inhibits *Staphylococcus aureus* biofilm formation and nasal colonization," Nature, vol. 465, pp. 346-348 (May 20, 2010).
Jonas et al., "Controlling the Growth of *Staphylococcus epidermidis* by Layer-By-Layer Encapsulation," ACS Applied Materials & Interfaces, vol. 10, pp. 16250-16259 (2018).
Kali, "Antibiotics and bioactive natural products in treatment of methicillin resistant *Staphylococcus aureus*: A brief review," Pharmacognosy Review, vol. 9, No. 17, pp. 29-34 (Jan.-Jun. 2015).
Kavanagh et al., "The use of surveillance and preventative measures for methicillin-resistant *Staphyloccus aureus* infections in surgical patients," Antimicrobial Resistance and Infection Control, 3:18, http://www.aricjournal.com/content/3/1/18, 7 pages (2014).
Kim et al., "Effects of a Topical Angiotensin-Converting Enzyme Inhibitor and a Selective COX-2 Inhibitor on the Prevention of Hypertrophic Scarring in the Skin of a Rabbit Ear," Wounds, vol. 24, No. 12, pp. 356-364 (2012).

(56) References Cited

OTHER PUBLICATIONS

Klevens et al., "Invasive Methicillin-Resistant *Staphylococcus aureus* Infections in the United States," JAMA, vol. 298, No. 11, pp. 1763-1771 (Oct. 17, 2007).
Knudsen et al., "Development and Testing of Improved Suicide Functions for Biological Containment of Bacteria," Applied and Environmental Microbiology, vol. 61, No. 3, pp. 985-991 (Mar. 1995).
Kober at al., "The effect of probiotics on immune regulation, acne, and photoaging," International Journal of Women's Dermatology, vol. 1, pp. 85-89 (2015).
Laupland et al., *Staphylococcus aureus* Bloodstream Infections: Risk Factors, Outcomes, and the Influence of Methicillin Resistance in Calgary, Canada, 2000-2006, The Journal of Infectious Diseases, vol. 138, pp. 336-343 (2008).
Lei et al., "A single copy integration vector that integrates at an engineered site on the *Staphylococcus aureus* chromosome," BMC Research Notes, 5:5; http://www.biomedcentral.com/1756-0500/5/5, 8 pages (2012).
Lei et al., "Determination of essentiality and regulatory function of staphylococcal YeaZ in branched-chain amino acid biosynthesis," Virulence, vol. 6, No. 1, pp. 75-84 (2015).
Li et al., "Immunomodulation and Disease Tolerance to *Staphylococcus aureus*," Pathogens, vol. 4, pp. 793-815 (2015).
Libberton et al., "Evidence that Intraspecific Trait Variation among Nasal Bacteria Shapes the Distribution of *Staphylococcus aureus*," Infection and Immunity, vol. 82, No. 9, pp. 3811-3815 (Sep. 2014).
Light et al., "Control of a Staphylococcal Outbreak in a Nursery." JAMA, vol. 193, No. 9, pp. 699-704 (Aug. 30, 1965).
Light et al., "Use of Bacterial Interference to Control a Staphylococcal Nursery Outbreak." Amer J Dis Child, vol. 113, pp. 291-300 (Mar. 1967).
Liu et al., "Clinical Practice Guidelines by the Infectious Diseases Society of America for the Treatment of Methicillin-Resistant *Staphylococcus aureus* Infections in Adults and Children," Clinical Infectious Diseases, vol. 52, No. 3, pp. 318-e55 (2011).
Liu et al., "*Staphylococcus aureus* and the ecology of the nasal microbiome," Science Advances,:1:e1400216, DOI: 10.1126/sciadv.1400216, 8 pages (2015).
Lowy, "Antimicrobial resistance: the example of *Staphylococcus aureus*," The Journal of Clinical Investigation, vol. 111, No. 9, pp. 1265-1273 (May 2003).
Maibach et al., "Bacterial interference: Relating to chronic furunculosis in man," Br. J. Derm., vol. 8, Suppl. 1, pp. 69-76 (1969).
Malachowa et al., "Global Changes in *Staphylococcus aureus* Gene Expression in Human Blood," PLoS ONE 6(4): e18617 doi:10.1371/journal.pone.0018617, 13 pages (2011).
Mandell et al., "Biocontainment of genetically modified organisms by synthetic protein design," Nature, vol. 518, No. 7537, pp. 55-60 (Feb. 5, 2015).
Marchisio et al., "*Streptococcus salivarius* 24SMB administered by nasal spray for the prevention of acute otitis media in otitis-prone children," Eur J Clin Microbiol Infect Dis, vol. 34, pp. 2377-2383, DOI 10.1007/s10096-015-2491-x (2015).
Martin et al., "Defining Resilience Mathematically: From Attractors to Viability," Viability and Resilience of Complex Systems, Understanding Complex Systems, Deffuant G., Gilbert N. (eds). Springer, Berlin, Heidelberg, Chapter 1, pp. 15-36 (2011).
Mayo Clinic MRSA Infection; https://www.mayoclinic.org/diseases-conditions/mrsa/symptoms-causes/syc-20375336?p=1, 4 pages (Copyright 1998-2019).
McDonnell et al., "Antiseptics and Disinfectants: Activity, Action, and Resistance," Clinical Microbiology Reviews, vol. 12, No. 1, pp. 147-179 (Jan. 1999).
McLoughlin et al., "Short-chain fatty acids, prebiotics, synbiotics, and systemic inflammation: a systematic review and meta-analysis," Am J Clin Nutr, doi: https://doi.org/10.3945/ajcn.117.156265, 16 pages (2017).
Mertz et al., "Throat Swabs are Necessary to Reliably Detect Carriers of *Staphylococcus aureus*," Clinical Infectious Diseases, vol. 45, pp. 475-477 (2007).
Mitra et al., "An integrative quantifier of multistability in complex systems based on ecological resilience," Scientific Reports, 5:16196 DOI: 10.1038/srep16196, 10 pages (2015).
Moe-Behrens et al., "Preparing synthetic biology for the world," Frontiers in Microbiology, vol. 4, Article 5, pp. 1-10 (Jan. 2013).
Mole, "Widely adopted method for thwarting MRSA fails in hospital that developed it," https://arstechnica.com/science/2017/05/widely-adopted-method-for-thwarting-mrsa-fails. 4 pages (May 17, 2017).
Mondragon et al., "RNA aptamer inhibitors of a restriction endonuclease," Nucleic Acids Research, vol. 43, No. 15, pp. 7544-7555 (Jul. 15, 2015).
Mongkolrattanothai et al., "Novel Non-mecA-Containing Staphylococcal Chromosomal Cassette Composite Island Containing php4 and tagF Genes in a Commensal Staphylococcal Species: a Possible Reservoir for Antibiotic Resistance Islands in *Staphylococcus aureus*," Antimicrobial Agents and Chemotherapy, vol. 48, No. 5, pp. 1823-1836 (May 2004).
Monk et al., "Transforming the Untransformable: Application of Direct Transformation to Manipulate Genetically *Staphylococcus aureus* and *Staphylococcus epidermidis*," mBio 3(2):e00277-11. doi:10.1128/mBio.00277-11, pp. 1-11 (Mar./Apr. 2012).
Monogue et al., "Antimicrobial Efficacy," Infectious Disease Special Edition, pp. 41-47 (Fall 2017).
Moore et al., "EcoFlex: A Multifunctional MoClo Kit for *E. coli* Synthetic Biology," ACS Synthetic Biology, vol. 5, pp. 1059-1069 (2016).
Moreno-Mateos et al., "CRISPRscan: designing highly efficient sgRNAs for CRISPR/Cas9 targeting in vivo," Nature Methods, vol. 12, No. 10, pp. 982-988 (Oct. 2015).
Morrissey et al , "Molecular Cloning and Analysis of a Putative Siderophore ABC Transporter from *Staphylococcus aureus*," Infection and Immunity, vol. 68, No. 11, pp. 6281-6288 (Nov. 2000).
Narukawa et al., "Sequence-Based spa Typing as a Rapid Screening Method for the Areal and Nosocomial Outbreaks of MRSA," Tohoku J Exp Med, vol. 218, No. 3, pp. 207-213 (2009).
Nguyen, "Friendly bacteria may not be so friendly," C&EN, vol. 96, Issue 30, p. 5 (Jul. 23, 2018).
Novick et al., "Coding sequence for the Pt181 repC product: A plasmid-coded protein uniquely required for replication," Proc. Natl. Acad. Sci. USA, vol. 79, pp. 4108-4112 (Jul. 1982).
Novick et al., "Synthesis of staphyloccal virulence factors is controlled by a regulatory RNA molecule," The EMBO Journal, vol. 12, No. 10, pp. 3967-3975 (1993).
O'Flaherty et al., "The Recombinant Phage Lysin LysK has a Broad Spectrum of Lytic Activity against Clinically Relevant Staphylococci, Including Methicillin-Resistant *Staphylococcus aureus*," Journal of Bacteriology, vol. 187, No. 20, pp. 7161-7164 (Oct. 2005).
Dogai et al., "Expression of Virulence Factors by *Staphyloccus aureus* Grown in Serum," Applied and Environmental Microbiology, vol. 77, No. 22, pp. 8097-8105 (Nov. 2011).
Otto, "*Staphylococcus aureus* toxin gene hitchhikes on a tarnsferable antibiotic resistance element," Virulence, vol. 1, Issue 1, pp. 49-51 (Jan./Feb. 2010).
Otto, "*Staphylococcus* colonization of the skin and antimicrobial peptides," Expert Rev Dermatol, vol. 5, No. 2, pp. 183-195 (Apr. 2010).
Otto, "MRSA virulence and spread," Cell Microbiol., vol. 14, No. 10, pp. 1513-1521 (Oct. 2012).
Palazzolo-Ballance et al., "Neutrophil Microbicides Induce a Pathogen Survival Response in Community-Associated Methicillin-Resistant *Staphylococcus aureus*," The Journal of Immunology, vol. 180, pp. 500-509 (2008).
Parker et al., "Genome Sequence of Bacterial Interference Strain *Staphylococcus aureus* 502A," Genome Announcements, 2(2):e00284-14. doi:10.1128/genomeA.00284-14, 2 pages (Mar./Apr. 2014).
Peri, "Prevention of *Staphlococcus aureus* infections among surgical patients: Beyond traditional perioperative prophylaxis," Surgery, vol. 134, No. 5, pp. S10-S17 (Nov. 2003).

(56) References Cited

OTHER PUBLICATIONS

Peterson, "Bacterial Pathogenesis," Medical Microbiology, 4th Edition, Chapter 7, Baron S, editor, Galveston (TX): University of Texas Medical Branch at Galveston; NCBI Bookshelf. A service of the National Library of Medicine, National Institutes of Health, 21 pages (1996).

Pinel-Marie et al., "Dual Toxic-Peptide-Coding *Staphylococcus aureus* RNA under Antisense Regulation Targets Host Cells and Bacterial Rivals Unequally," Cell Reports, vol. 7, pp. 424-435 (Apr. 24, 2014).

Popoola et al., "Decolonization to prevent *Staphylococcus aureus* transmission and infections in the neonatal intensive care unit," Journal of Perinatology, vol. 34, pp. 805-810 (2014).

Press Release, "Seres Therapeutics Announces Interium Results from SER-109 Phase 2 ECOSPOR Study in Multiply Recurrent Clostridium difficile Infection," http://www.businesswire.com/news/home/20160729005385/en/Seres-Therapeutics-Anno, 4 pages (Jul. 29, 2016).

Pujol et al., "Nosocomial *Staphylococcus aureus* Bacteremia among Nasal Carriers of Methicillin-resistant and Methicillin-susceptible Strains," The American Journal of Medicine, vol. 100, pp. 509-516 (May 1996).

Japanese Office Action for Application No. 2020-550034 mailed Nov. 22, 2022 with English Translation.

Sledjeski et al., "Isolation of human plasma-inducible, growth phase- and temperature-regulated gene fusions in *Streptococcus pyogenes* using a Tn917-lacZ transposon," Journal of Microbiological Methods, vol. 46, No. 2, pp. 107-117, doi: 10.1016/s0167-7012(01)00257-3 (Aug. 2001).

Australian Examination Report for corresponding application No. 2018379996, dated Sep. 24, 2024, 7 pgs.

* cited by examiner

Table 4A. Recombinant Primers

| SEQ ID NO: | Name | Sequence | Description |
|---|---|---|---|
| 9 | TKO1 | GATGCGCATGCGAAACAGATTATCTATTC | LeuA PCR Amplification with Sph1 (upstream pr) |
| 10 | TKO2 | GATGCGCATGCCAGATTATCTATTCAAAG | LeuA PCR Amplification with Sph1 (upstream pr-alternate) |
| 11 | TKO3 | CATGATCTGCAGAGTAAATTCCCCCGTAAATT | LeuA PCR Amplification with Pst1 (downstream pr) |
| 12 | TKO4 | CACGTGATCTGCAGAGTAAATTCCCCCGTAAA | LeuA PCR Amplification with Pst1 (downstream pr-alternate) |
| 13 | TKO5 | GACTACGAATTCAGGTGATGAAAAATTTAGAA | upstream primer to amplify ClfB promoter with EcoRI |
| 14 | TKO6 | GACTACGAATTCTGATGAAAAATTTAGAACTT | backup to TKO5 |
| 15 | TKO7 | CTTAGCTGGATCCAAATATTACTCCATTTCAA | downstream primer to amplify ClfB promoter with BamHI |
| 16 | TKO8 | CTTAGCTGGATCCAAATATTACTCCATTTCAATTTC | backup to TKO7 |
| 17 | TKO9 | GATGCGCATGCTCACAAACTATTGCGAAATC | upstream primer to amplify the HLGA RR; contains Sph1 |
| 18 | TKO10 | GATGCGCATGCAAACTATTGCGAAATCCATTC | backup to TKO9 |
| 19 | TKO11 | CATGATCTGCAGATATATAATAATCCATTTGT | downstream primer to amplify HLGA RR; contains PstI |
| 20 | TKO12 | CATGATCTGCAGATATATAATAATCCATTTGTAAGCG | backup to TKO11 |
| 21 | TKO13 | GTGTTACGATAGCAAATGCA | First sense primer for sequencing constructs containing pCAD promoter |

FIG. 3A

Table 4A. Recombinant Primers (cont.)

| SEQ ID NO: | Name | Sequence | Description |
|---|---|---|---|
| 22 | TKO14 | TTATTGGCTAAGTAGACGCA | second sense sequencing primer anneals roughly in the middle of the SprA1 gene |
| 23 | TKO15 | CACATGTTCTTTCCTGCGTT | primer to anneal just upstream of the serum responsive RRs for LEUA and HLGA. Anneals in the PCN51 vector about 75 nt upstream of the Sph1 site |
| 24 | TKO16 | ACGCGGCCTTTTTACGGTTC | backup in case TKO15 produces low quality reads |
| 25 | TKO17 | GAATGGGACTTGTAAACGTC | primer to anneal near the downstream one third of the LEUA promoter/RR |
| 26 | TKO18 | GAATGGGACTTGTAAACG | backup to TKO17 |
| 27 | TKO19 | ATAAACGCCTGCGACCAATA | primer to anneal near the downstream one third of the HLGA promoter/RR |
| 28 | TKO20 | GCGACCAATAAATCTTTTAA | Backup to TKO19 in case it produces low quality reads |
| 29 | TKO21 | TTGAATAGATAATCTGTTTCGCATGCAGCGGCCGCCAGCT | pTK1 vector with leuA pro homology R |
| 30 | TKO22 | AATTTACGGGGGAATTTACTCTGCAGGGTACCGCAGAGAG | pTK1 vector with leuA pro homology F |
| 31 | TKO23 | AGCTGGCGGCCGCTGCATGCGAAACAGATTATCTATTCAAAGTTAATTG | leuA insert with pTK1 homology F |
| 32 | TKO24 | CTCTCTGCGGTACCCTGCAGAGTAAATTCCCCCGTAAATTTTAATG | leuA insert with pTK1 homology R |
| 33 | TKO25 | CATTAAAATTTACGGGGGAATTTACTCTGCAGATGAGCAGGGATGA | pTK9 vector with leuA pro homology F |

FIG. 3B

Table 4A. Recombinant Primers (cont.)

| SEQ ID NO: | Name | Sequence | Description |
|---|---|---|---|
| 34 | TKO26 | CAATTAACTTTGAATAGATAATCTGTTTCGCATGCAGCGGCCGCCAGCT | pTK9 vector with leuA pro homology R |
| 35 | TKO27 | CATTAAAATTTACGGGGGAATTTACTCTGCAGATGGTAGAGATAGC | pTK12 vector with leuA pro homology F |
| 36 | TKO28 | GCTATCTCTACCATCTGCAGAGTAAATTCCCCCGTAAATTTTAATG | leuA insert with pTK12 homology R |
| 37 | TKO29 | gcaatccatcttgttcaatcatTATAACCCTCTTTAATTTGGTTATATG | pTKvector R with kanR homology (remove ermR) |
| 38 | TKO30 | ccttcttgacgagttcttctgaGTTAAGGGATGCATAAACTGCA | pTKvector F with kanR homology (remove ermR) |
| 39 | TKO31 | CATATAACCAAATTAAAGAGGGTTATAatgattgaacaagatggattgc | pCASSA kanR F with pTK homology (add kanR) |
| 40 | TKO32 | TGCAGTTTATGCATCCCTTAACtcagaagaactcgtcaagaagg | pCASSA kanR R with pTK homology (add kanR) |
| 41 | TKO33 | GAATGGGACTTGTAAACGTCCC | leuA colony screen PCR F |
| 42 | TKO34 | GGGACGTTTACAAGTCCCATTC | leuA colony screen PCR R |

FIG. 3C

Table 4B. CRISPR Primers

| SEQ ID NO: | BPC No. | Name | Sequence | Purpose |
|---|---|---|---|---|
| 43 | 1 | BPC - T1.1 - FOR | gaaaGGAGTAATATCGATGGAGTA | gRNA insertion for pCasSA |
| 44 | 2 | BPC - T1.1 - REV | caaaTACTCCATCGATATTACTCC | gRNA insertion for pCasSA |
| 45 | 3 | BPC - T1.2 - FOR | gaaaGGAGAGGATGATGATTATAA | gRNA insertion for pCasSA |
| 46 | 4 | BPC - T1.2 - REV | caaaTTATAATCATCATCCTCTCC | gRNA insertion for pCasSA |
| 47 | 5 | BPC - T1.3 - FOR | gaaaGGGAGAGGATGATGATTATA | gRNA insertion for pCasSA |
| 48 | 6 | BPC - T1.3 - REV | caaaTATAATCATCATCCTCTCCC | gRNA insertion for pCasSA |
| 49 | 7 | BPC - T1.4 - FOR | gaaaGGGTCTAATGTTATTGCTTA | gRNA insertion for pCasSA |
| 50 | 8 | BPC - T1.4 - REV | caaaTAAGCAATAACATTAGACCC | gRNA insertion for pCasSA |
| 51 | 9 | BPC - T1.5 - FOR | gaaaGGAGAGGATGATGATTATA | gRNA insertion for pCasSA |
| 52 | 10 | BPC - T1.5 - REV | caaaTATAATCATCATCCTCTCC | gRNA insertion for pCasSA |
| 53 | 11 | BPC - T1.6 - FOR | gaaaGGTAGTATGAGTAATATCGA | gRNA insertion for pCasSA |
| 54 | 12 | BPC - T1.6 - REV | caaaTCGATATTACTCATACTACC | gRNA insertion for pCasSA |
| 55 | 13 | BPC - T1.7 - FOR | gaaaGGAATTATATAAATATAAAG | gRNA insertion for pCasSA |
| 56 | 14 | BPC - T1.7 - REV | caaaCTTTATATTTATATAATTCC | gRNA insertion for pCasSA |
| 57 | 15 | BPC - T1.8 - FOR | gaaaGGCTACCTCCATATTTTCTA | gRNA insertion for pCasSA |
| 58 | 16 | BPC - T1.8 - REV | caaaTAGAAAATATGGAGGTAGCC | gRNA insertion for pCasSA |

FIG. 4A

Table 4B. CRISPR Primers (cont.)

| SEQ ID NO: | BPC No. | Name | Sequence | Purpose |
|---|---|---|---|---|
| 59 | 17 | BPC - T1.9 - FOR | gaaaGGATAGAACTGTATTAGACT | gRNA insertion for pCasSA |
| 60 | 18 | BPC - T1.9 - REV | caaaAGTCTAATACAGTTCTATCC | gRNA insertion for pCasSA |
| 61 | 19 | BPC - T1.10 - FOR | gaaaGGTGTCTAATGTTATTGCTT | gRNA insertion for pCasSA |
| 62 | 20 | BPC - T1.10 - REV | caaaAAGCAATAACATTAGACACC | gRNA insertion for pCasSA |
| 63 | 21 | BPC - gRNA - FOR | TGTTCTTTCCTGCGTTGTCG | sequencing primers for gRNA insertion into the pCasSA vector |
| 64 | 22 | BPC - gRNA - REV | TCGCATTGACGTTAATACCTACAT | sequencing primers for gRNA insertion into the pCasSA vector |
| 65 | 23 | BPC - T1.1.2 - REV | aaacTACTCCATCGATATTACTCC | Correct reverse primers for gRNA |
| 66 | 24 | BPC - T1.2.2 - REV | aaacTTATAATCATCATCCTCTCC | Correct reverse primers for gRNA |
| 67 | 25 | BPC - T1.3.2 - REV | aaacTATAATCATCATCCTCTCCC | Correct reverse primers for gRNA |
| 68 | 26 | BPC - T1.4.2 - REV | aaacTAAGCAATAACATTAGACCC | Correct reverse primers for gRNA |
| 69 | 27 | BPC - T1.5.2 - REV | aaacTATAATCATCATCCTCTCC | Correct reverse primers for gRNA |
| 70 | 28 | BPC - T1.6.2 - REV | aaacTCGATATTACTCATACTACC | Correct reverse primers for gRNA |
| 71 | 29 | BPC - T1.7.2 - REV | aaacCTTTATATTTATATAATTCC | Correct reverse primers for gRNA |
| 72 | 30 | BPC - T1.8.2 - REV | aaacTAGAAAATATGGAGGTAGCC | Correct reverse primers for gRNA |

FIG. 4B

Table 4B. CRISPR Primers (cont.)

| SEQ ID NO: | BPC No. | Name | Sequence | Purpose |
|---|---|---|---|---|
| 73 | 31 | BPC - T1.9.2 - REV | aaacAGTCTAATACAGTTCTATCC | Correct reverse primers for gRNA |
| 74 | 32 | BPC - T1.10.2 - REV | aaacAAGCAATAACATTAGACACC | Correct reverse primers for gRNA |
| 75 | 33 | BPC - pCN51-1 - FOR | TTTGCTGGCCTTTTGCTCAC | Primers to check insertion into pCN51 |
| 76 | 34 | BPC - pCN51-1 - REV | TGCTTTTTCGATTGATGAACACCT | Primers to check insertion into pCN51 |
| 77 | 35 | BPC - pCN51-2 - FOR | CGGCCTTTTTACGGTTCCTG | Primers to check insertion into pCN51 |
| 78 | 36 | BPC - pCN51-2 - REV | ACGTTGCTTTTTCGATTGATGAAC | Primers to check insertion into pCN51 |
| 79 | 37 | BPC - mChr-1 - FOR | **cacgtgat**CTGCAGTCACATGGTGAGCAAGGGC | mCherry mRNA with Pst1 |
| 80 | 38 | BPC - mChr-1 - REV | **gactac**GAATTCAAAACTGATTTCGTTGACCCG | mCherry mRNA with EcoR1 |
| 81 | 39 | BPC - mChr-2 - REV | cttagctGGATCCAAAACTGATTTCGTTGACCCG | mCherry mRNA with BamH1 alternate to #39 |
| 82 | 40 | BPC - pCN51-hdr - REV | cttagctCCCGGGTGCTTTTTCGATTGATGAACACCT | 34BPC-REV with Xma1, use with TKO15 to add homologous arms |
| 83 | 41 | BPC - 2a - FOR | CGCCAAACGTTTCGTCAGTT | 502a Target 1 genomic incorp check |
| 84 | 42 | BPC - 2a - REV | TTCAAGCGTGACAAAGCAGC | 502a Target 1 genomic incorp check |
| 85 | 43 | BPC - 2a - FOR | TGCGCAATGGCCAAAAAGAT | 502a Target 1 genomic incorp check |
| 86 | 44 | BPC - 2a - REV | CGTGCTAACATCCGCTTCAA | 502a Target 1 genomic incorp check |

FIG. 4C

Table 4B. CRISPR Primers (cont.)

| SEQ ID | BPC No. | Name | Sequence | Purpose |
|---|---|---|---|---|
| 87 | 45 | BPC - mChr-1 - REV | **AAAACTGATTTCGTTGACCCG** | mCherry |
| 88 | 46 | BPC - mChr-1 - FOR | **cacgtgat**CTGCAGTCACATGGTTTCTAAAGGT | mCherry with Pst1 (codon opt seq in pJ204: 300995) |
| 89 | 47 | BPC - pJ204-1 - FOR | ACGTTGCTTTTTCGATTGATGA | Checking for insertion btwn HAs in pJ204 |
| 90 | 48 | BPC - pJ204-1 - REV | TCCCCATGCGAGAGTAGGG | Checking for insertion btwn HAs in pJ204 |
| 91 | 49 | BPC - pJ204-2 - FOR | GAATATTTAAGGGCGCCTGTCAC | Checking for insertion btwn HAs in pJ204 |
| 92 | 50 | BPC - pJ204-2 - REV | TATGGGGTGTCGCCCTTT | Checking for insertion btwn HAs in pJ204 |
| 93 | 51 | BPC - mChr-1 - FOR | **TCACATGGTTTCTAAAGGT** | mCherry (codon opt seq in pJ204: 300995) |
| 94 | 52 | BP - repF-1 - F | CATGCCTGCAGAACGGATTG | Checking for repF removal |
| 95 | 53 | BP - repF-1 - R | GCGCGGGAATATGATGCTAA | Checking for repF removal |
| 96 | 54 | BP - repF-2 - F | AGGTGACTGATGGCTGGTTG | Checking for repF removal |
| 97 | 55 | BP - repF-2 - R | TATGTCTTTTGCGCAGTCGG | Checking for repF removal |
| 98 | 56 | BP - srtA - F | gaaaCAAACAAATATGCTGCCACT | srtA CRISPR targeting from Dong et al. |
| 99 | 57 | BP - srtA - R | aaacAGTGGCAGCATATTTGTTTG | srtA CRISPR targeting |
| 100 | 58 | BP - hla - F | gaaaGCTTCCAATATCTGTAGTAC | hla CRISPR targeting from Dong et al. |
| 101 | 59 | BP - hla - R | aaacGTACTACAGATATTGGAAGC | hla CRISPR targeting |
| 102 | 60 | BP - coa - F | gaaaGCCATTTTTAAATCTGTACG | coa CRISPR targeting from Dong et al. |
| 103 | 61 | BP - coa - R | aaacCGTACAGATTTAAAAATGGC | coa CRISPR targeting |

FIG. 4D

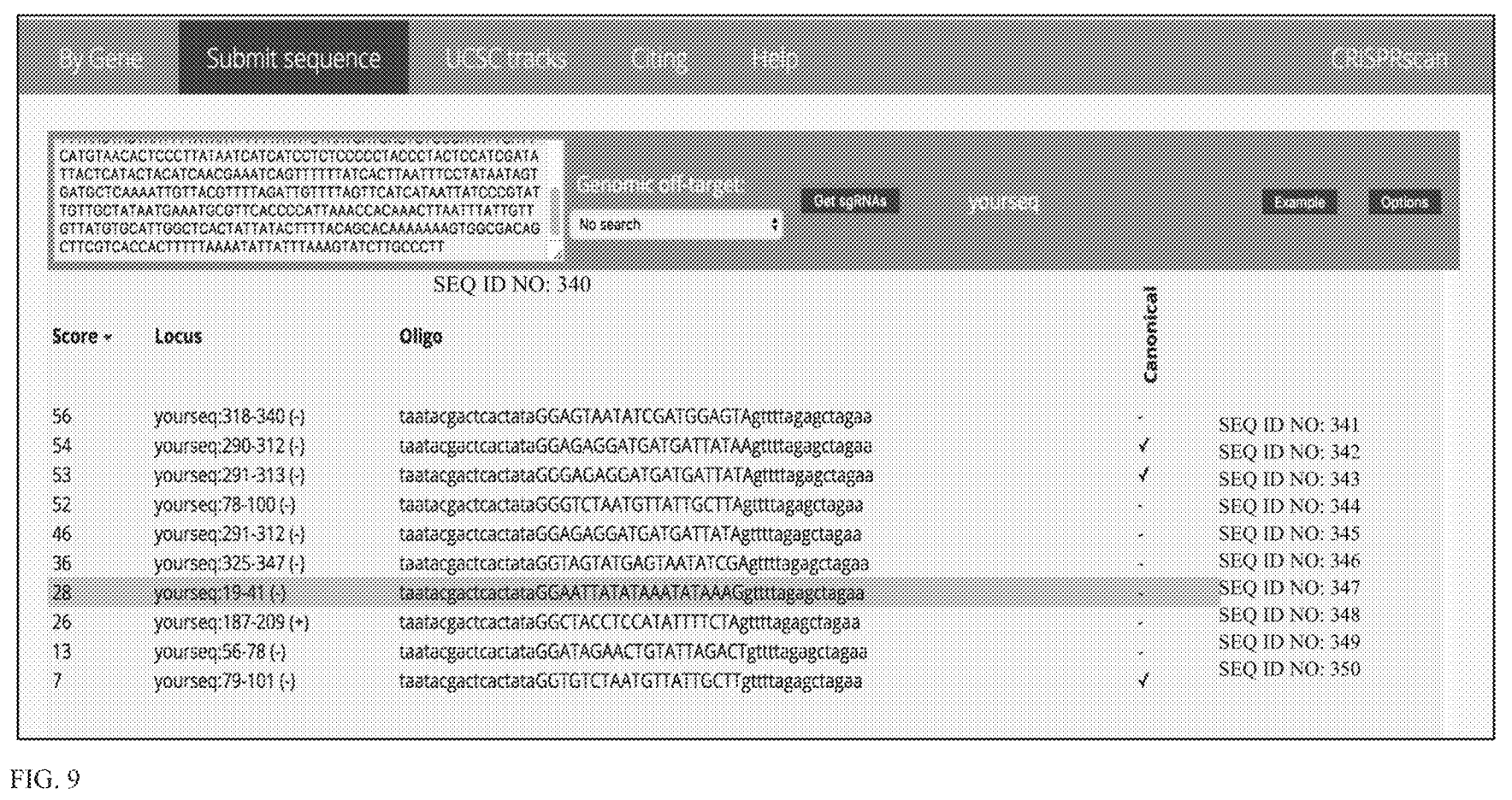

By Gene | Submit sequence | UCSC tracks | Citing | Help | CRISPRscan

CATGTAACACTCCCTTATAATCATCATCCTCTCCCCCTACCCTACTCCATCGATA
TTACTCATACTACATCAACGAAATCAGTTTTTTATCACTTAATTTCCTATAATAGT
GATGCTCAAAATTGTTACGTTTTAGATTGTTTTAGTTCATCATAATTATCCCGTAT
TGTTGCTATAATGAAATGCGTTCACCCCATTAAACCACAAACTTAATTTATTGTT
GTTATGTGCATTGGCTCACTATTATACTTTTACAGCACAAAAAAAGTGGCGACAG
CTTCGTCACCACTTTTTAAAATATTATTTAAAGTATCTTGCCCTT

Genomic off-target: No search

Get sgRNAs | yourseq | Example | Options

SEQ ID NO: 340

| Score | Locus | Oligo | Canonical | |
|---|---|---|---|---|
| 56 | yourseq:318-340 (-) | taatacgactcactataGGAGTAATATCGATGGAGTAgttttagagctagaa | - | SEQ ID NO: 341 |
| 54 | yourseq:290-312 (-) | taatacgactcactataGGAGAGGATGATGATTATAAgttttagagctagaa | ✓ | SEQ ID NO: 342 |
| 53 | yourseq:291-313 (-) | taatacgactcactataGCGAGAGGATGATGATTATAgttttagagctagaa | ✓ | SEQ ID NO: 343 |
| 52 | yourseq:78-100 (-) | taatacgactcactataGGGTCTAATGTTATTGCTTAgttttagagctagaa | - | SEQ ID NO: 344 |
| 46 | yourseq:291-312 (-) | taatacgactcactataGGAGAGGATGATGATTATAgttttagagctagaa | - | SEQ ID NO: 345 |
| 36 | yourseq:325-347 (-) | taatacgactcactataGGTAGTATGAGTAATATCGAgttttagagctagaa | - | SEQ ID NO: 346 |
| 28 | yourseq:19-41 (-) | taatacgactcactataGGAATTATATAAATATAAAGgttttagagctagaa | - | SEQ ID NO: 347 |
| 26 | yourseq:187-209 (+) | taatacgactcactataGGCTACCTCCATATTTTCTAgttttagagctagaa | - | SEQ ID NO: 348 |
| 13 | yourseq:56-78 (-) | taatacgactcactataGGATAGAACTGTATTAGACTgttttagagctagaa | - | SEQ ID NO: 349 |
| 7 | yourseq:79-101 (-) | taatacgactcactataGGTGTCTAATGTTATTGCTTgttttagagctagaa | ✓ | SEQ ID NO: 350 |

FIG. 9

Promoter Screen
A. Vector for promoter screen with fluorescence
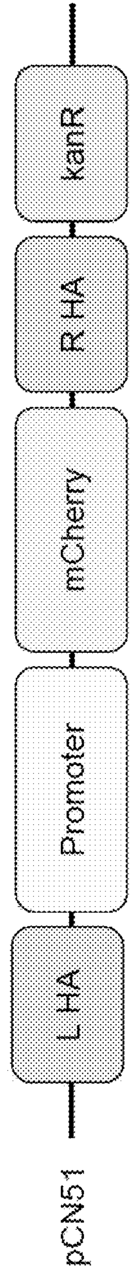
B. Vector for promoter screen with cell death
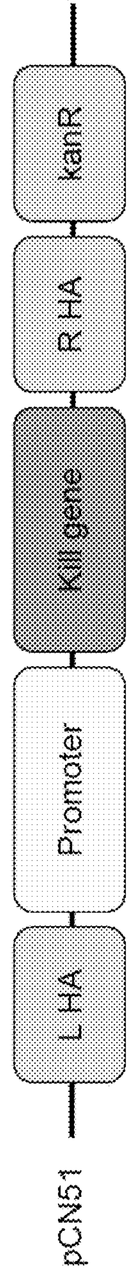
Integration
C. Vector for chromosomal integration using CRISPR
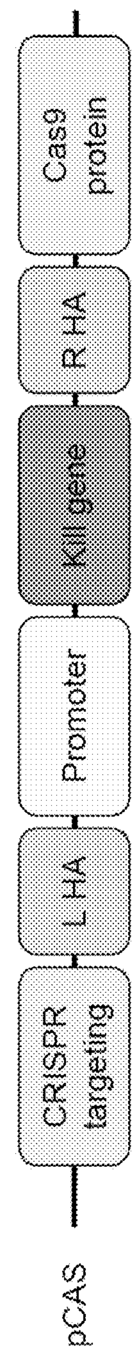
D. Vector for chromosomal integration using homologous recombination
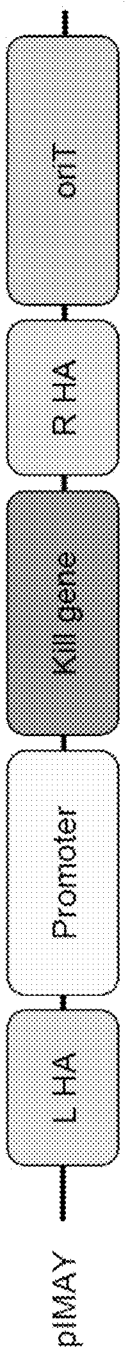
FIG. 11

```
   1 gcatgcgttt tagcgtttat ttcgtttagt tatcggcata atcgttaaaa caggcgttat
  61 cgtagcgtaa aagcccttga gcgtagcgtg gctttgcagc gaagatgttg tctgttagat
 121 tatgaaagcc gatgactgaa tgaaataata agcgcagcgc ccttctattt cggttggagg
 181 aggctcaagg gagtatgagg gaatgaaatt ccctcatggg tttgatttta aaaattgctt
 241 gcaattttgc cgagcggtag cgctggaaaa tttttgaaaa aaatttggaa tttggaaaaa
 301 aatgggggga aaggaagcga attttgcttc cgtactacga cccccatta agtgccgagt
 361 gccaattttt gtgccaaaaa cgctctatcc caactggctc aagggtttaa ggggtttttc
 421 aatcgccaac gaatcgccaa cgttttcgcc aacgtttttt ataaatctat atttaagtag
 481 ctttattgtt gtttttatga ttacaaagtg atacactaac tttataaaat tatttgattg
 541 gagtttttta aatggtgatt tcagaatcga aaaaaagagt tatgatttct ctgacaaaag
 601 agcaagataa aaaattaaca gatatggcga aacaaaaagg tttttcaaaa tctgcggttg
 661 cggcgttagc tatagaagaa tatgcaagaa aggaatcaga acaaaaaaaa taagcgaaag
 721 ctcgcgtttt tagaaggata cgagttttcg ctacttgttt ttgataaggt aattatatca
 781 tggctattaa aaatactaaa gctagaaatt ttggattttt attatatcct gactcaattc
 841 ctaatgattg gaaagaaaaa ttagagagtt tgggcgtatc tatggctgtc agtcctttac
 901 acgatatgga cgaaaaaaaa gataaagata catggaataa tagtaatatt atacaaaatg
 961 gaaagcacta taaaaaacca cactatcacg ttatatatat tgcacgaaat cctgtaacaa
1021 tagaaagcgt taggaacaag attaagcgaa aattggggaa tagttcagtt gctcatgttg
1081 agatacttga ttatatcaaa ggttcatatg aatatttgac tcatgaatca aaggacgcta
1141 ttgctaagaa taaacatata tacgacaaaa aagatatttt gaacattaat gattttgata
1201 ttgaccgcta tataacactt gatgaaagcc aaaaaagaga attgaagaat ttacttttag
1261 atatagtgga tgactataat ttggtaaata caaaagattt aatggctttt attcgcctta
1321 ggggagcgga gtttggaatt ttaaatacga atgatgtaaa agatattgtt tcaacaaact
1381 ctagcgcctt tagattatgg tttgagggca attatcagtg tggatataga gcaagttatg
1441 caaaggttct tgatgctgaa acgggggaaa taaaatgaca aacaaagaaa aagagttatt
1501 tgctgaaaat gaggaattaa aaaaagaaat taaggactta aaagagcgta ttgaaagata
1561 cagagaaatg gaagttgaat taagtacaac aatagattta ttgagaggag ggattattga
1621 ataaataaaa gccccctgac gaaagtcgaa ggggggtttt attttggttt gatgttgcga
1681 ttaatagcaa tacattctat aatagaaggt atggaggatg ttatataatg agacagaatt
1741 atgatgatca tatgtcaact aacggggcag gttagtgaca ttagaaaacc gactgtaaaa
1801 agtacagtcg gcattatctc atattataaa agccagtcat taggcctatc tgacaattcc
1861 tgaatagagt tcataaacaa tcctgcatga taaccatcac aaacagaatg atgtacctgt
1921 aaagatagcg gtaaatatat tgaattacct ttattaatga attttcctgc tgtaataatg
1981 ggtagaaggt aattactatt attattgata tttaagttaa acccagtaaa tgaagtccat
2041 ggaataatag aaagagaaaa agcattttca ggtataggtg ttttgggaaa caatttcccc
2101 gaaccattat atttctctac atcagaaagg tataaatcat aaaactcttt gaagtcattc
2161 tttacaggag tccaaatacc agagaatgtt ttagatacac catcaaaaat tgtataaagt
2221 ggctctaact tatcccaata acctaactct ccgtcgctat tgtaaccagt tctaaaagct
2281 gtatttgagt ttatcaccct tgtcactaag aaaataaatg cagggtaaaa tttatatcct
2341 tcttgtttta tgtttcggta taaaacacta atatcaattt ctgtggttat actaaaagtc
```

FIG. 12A (SEQ ID NO: 131 cont.)

```
2401 gtttgttggt tcaaataatg attaaatatc tcttttctct tccaattgtc taaatcaatt
2461 ttattaaagt tcatgggttt cactctcctt ctacattttt taacctaata atgccaaata
2521 ccgtttgcca cccctctctt tgataattat aatattggcg aaattcgctt ctaaagatga
2581 aacgcaatat tatatgcttg ctttatcggc cgtatgtgat tataccagcc ccctcactac
2641 atgtcaagaa taaactgcca aagcataatg ggataattaa ccctcactaa agggaacaaa
2701 agctgggtac cgggcccccc ctcgaggtcg acggtatcga taagcttgat atcgaattcc
2761 tgcagcccgg gggatccact agttctagag cggccgccac cgcggtggag ctccaattcg
2821 ccctatagtg agtcgtatta cgacgtccca gggcttcccg gtatcaacag ggacaccagg
2881 atttatttat tctgcgaagt gatcttccgt cacaggtatt tattcggcgc aaagtgcgtc
2941 gggtgatgct gccaacttac tgatttagtg tatgatggtg tttttgaggt gctccagtgg
3001 cttctgtttc tatcagctgt ccctcctgtt cagctactga cggggtggtg cgtaacggca
3061 aaagcaccgc cggacatcag cgctagcgga gtgtatactg gcttactatg ttggcactga
3121 tgagggtgtc agtgaagtgc ttcatgtggc aggagaaaaa aggctgcacc ggtgcgtcag
3181 cagaatatgt gatacaggat atattccgct tcctcgctca ctgactcgct acgctcggtc
3241 gttcgactgc ggcgagcgga aatggcttac gaacggggcg gagatttcct ggaagatgcc
3301 aggaagatac ttaacaggga agtgagaggg ccgcggcaaa gccgtttttc cataggctcc
3361 gcccccctga caagcatcac gaaatctgac gctcaaatca gtggtggcga aacccgacag
3421 gactataaag ataccaggcg tttccccctg gcggctccct cgtgcgctct cctgttcctg
3481 cctttcggtt taccggtgtc attccgctgt tatggccgcg tttgtctcat tccacgcctg
3541 acactcagtt ccgggtaggc agttcgctcc aagctggact gtatgcacga accccccgtt
3601 cagtccgacc gctgcgcctt atccggtaac tatcgtcttg agtccaaccc ggaaagacat
3661 gcaaaagcac cactggcagc agccactggt aattgattta gaggagttag tcttgaagtc
3721 atgcgccggt taaggctaaa ctgaaaggac aagttttggt gactgcgctc ctccaagcca
3781 gttacctcgg ttcaaagagt tggtagctca gagaaccttc gaaaaaccgc cctgcaaggc
3841 ggttttttcg ttttcagagc aagagattac gcgcagacca aaacgatctc aagaagatca
3901 tcttattaat cagataaaat atttctagat ttcagtgcaa tttatctctt caaatgtagc
3961 acctgaagtc agccccatac gatataagtt gtaattctcc gccgcttgcc ctcatctgtt
4021 acgccggcgg tagccggcca gcctcgcaga gcaggattcc cgttgagcac cgccaggtgc
4081 gaataaggga cagtgaagaa ggaacacccg ctcgcgggtg ggcctacttc acctatcctg
4141 cccggctgac gccgttggat acaccaagga aagtctacac gaaccctttg gcaaaatcct
4201 gtatatcgtg cgaaaaagga tggatatacc gaaaaaatcg ctataatgac cccgaagcag
4261 ggttatgcag cggaaaagcg ctgcttccct gctgttttgt ggaatatcta ccgactggaa
4321 acaggcaaat gcaggaaatt actgaactga ggggacaggc gagaggagat cttgatctaa
4381 tgattcaaac ccttgtgaac ttctttagaa caaaagaggt tcgtaacaag attttcttca
4441 cactagcaat gttagtaatt tttaaaatag ggacttatat accagctcca ggagtaaatc
4501 ctgcagcttt tgataatccc caaggttctc aaggtgccac tgagttatta aatacttttg
4561 gtggcggagc cttgaaacga ttttctattt ttgcaatggg tattgtaccc tacatcactg
4621 catcaatcgt aatgcaatta ttacaaatgg atattgtccc taaattctca gaatgggcaa
4681 aacaaggtga agtaggtaga agaaagttaa ataacgttac tcgttattta gcaatttctt
4741 tagcatttat ccaatctata ggtatggcat tccaatttaa taattatctc aaaggtgcgc
```

FIG. 12B (SEQ ID NO: 131 cont.)

```
4801 tgattatcaa tcagtcaatt atgagttatt tattaatagc actagttttg acagcaggaa
4861 ctgctttctt aatatggctt ggtgatcaaa tcactcagtt cggtgttggt aatggtattt
4921 ctattatcat attcccatca agcttatttt aattatactc tatcaatgat agagtgtcaa
4981 tattttttt agtttttcat gaactcgagg ggatccaaat aaaaaactag tttgacaaat
5041 aactctatca atgatagagt gtcaacaaaa aggaggaatt aatgatgtct agattagata
5101 aaagtaaagt gattaacagc gcattagagc tgcttaatga ggtcggaatc gaaggtttaa
5161 caacccgtaa actcgcccag aagctaggtg tagagcagcc tacattgtat tggcatgtaa
5221 aaaataagcg ggctttgctc gacgccttag ccattgagat gttagatagg caccatactc
5281 acttttgccc tttagaaggg gaaagctggc aagatttttt acgtaataac gctaaaagtt
5341 ttagatgtgc tttactaagt catcgcgatg gagcaaaagt acatttaggt acacggccta
5401 cagaaaaaca gtatgaaact ctcgaaaatc aattagcctt tttatgccaa caaggttttt
5461 cactagagaa tgcattatat gcactcagcg ctgtggggca ttttacttta ggttgcgtat
5521 tggaagatca agagcatcaa gtcgctaaag aagaaaggga aacacctact actgatagta
5581 tgccgccatt attacgacaa gctatcgaat tatttgatca ccaaggtgca gagccagcct
5641 tcttattcgg ccttgaattg atcatatgcg gattagaaaa acaacttaaa tgtgaaagtg
5701 ggtcttaaaa gcagcataac ctttttccgt gatggtaact tca
```

FIG. 12C (SEQ ID NO: 131 cont.)

METHODS AND COMPOSITIONS TO PREVENT MICROBIAL INFECTION

CROSS REFERENCES TO RELATED APPLICATIONS

This application claims the benefit of U.S. Provisional Application No. 62/594,943, filed 5 Dec. 2017, the entire contents of which are incorporated herein by reference.

SEQUENCE LISTING

The present application includes a Sequence Listing in ASCII electronic format as a txt file entitled "Sequence-Listing," which was created on 3 Dec. 2018 and which has a size of 128,065 bytes. The contents of txt file "Sequence-Listing" are incorporated by reference herein.

BACKGROUND OF THE DISCLOSURE

Field of the Disclosure

Methods and compositions are provided for durably influencing microbiological ecosystems (microbiomes) in a subject in order to resist infection and reduce recurrence of infection by an undesirable microorganism by decolonizing and durably replacing with a synthetic microorganism. Synthetic microorganisms are provided that may durably replace an undesirable microorganism under dermal or mucosal conditions, and that contain molecular modifications designed to enhance safety, for example, by self-destructing when exposed to systemic conditions, by reducing the potential for acquisition of virulence or antibiotic resistance genes, and/or by producing a desirable product at the site of the ecosystem in a subject.

Description of the Related Art

Health care or community associated infection often results from colonizing microorganisms that overcome patient defenses. Inappropriate use of antibiotics may lead to mismanagement of the microbiome. One critical unintended consequence of the mismanagement of the microbiome has been the emergence of antibiotic resistant microorganisms.

Each individual is host to a vast population of trillions of microorganisms, composed of perhaps 10,000 different species, types and strains. These "commensal" organisms are found both on external sites (e.g. dermal) and on internal sites (e.g. gastrointestinal), and are necessary for survival of the human species. "Colonization" happens automatically through ongoing interactions with the environment.

The menagerie of microorganisms constitutes the "biome", a dynamic, structured, living system that in many cases, and in many ways, is essential for our health and wellness. A biomic structure is created by a vast combinatorial web of relationships between the host, the environment, and the components of the biome. The human microbiome is an ecosystem. It has a dynamic but persistent structure—it is "resilient" and has a "healthy" normal base state.

Nonetheless, under some circumstances the microbiome can be invaded and occupied by pathogenic microorganisms. This type of' "colonization" may become a precursor to "infection" This kind of disruption to the microbiome can cause serious and even life-threatening disease.

One unintended consequence of the mismanagement of our biome has been the emergence of "antibiotic resistance". This happens when antibiotics and antiseptics do not fully eliminate the target microorganisms. The few survivors that show resistance to these materials then preferentially grow back ("recolonize") into an open environment (or vacated "niche") already cleared of competing organisms. The survivor organisms then dominate the space, usually retaining that resistance for their descendants. If exposed to a new killing agent they will tend to develop resistance to that as well. Over only a few generations these microorganisms can develop resistance to many or all of our known antibiotics, becoming the now famous "super-bugs", and along the way creating an enormous new global health problem.

A phenomenon called "recurrence" is at the heart of the process that creates antibiotic resistance. While methods to treat pathogenic infection exist, methods to prevent recurrence are effectively nonexistent.

Bacterial infections are the home territory of the emerging "super bug" phenomenon. The overuse and misuse of antibiotics has caused many strains of pathogenic bacteria to evolve resistance to an increasing number of antibiotic therapies, creating a massive global public health problem. As each new variation of antibiotic is applied to treat these superbugs, the inevitable process of selecting for resistant strains begins anew, and resistant variants of the pathogen quickly develop. Unfortunately, today bacteria are becoming resistant faster than new antibiotics can be developed.

Beyond cultivating antibiotic resistance, and frequently causing adverse health effects in the recipients, antibiotic treatments also have the undesirable effect of disrupting the entire microbiome, including both good and bad bacteria. This often creates new problems such as opening the microbiome to colonization by adventitious pathogens after the treatment.

Bacteria however have less leeway to adapt to different resources, as these requirements are more basic on a molecular level and are intrinsically defined in the genome. This allows the microbiome ecology to behave as more of an "ideal" system, leading to full exclusion of one of the identical strain competitors from the niche.

The community of organisms colonizing the human body is referred to as the microbiome. The microbiome is often subdivided for analysis into sections of geography (i.e. the skin microbiome versus the gastrointestinal microbiome) or of phylogeny (i.e. bacterial microbiome versus the fungal or protist microbiome).

Antibiotics are life-saving medicines, but they can also change, unbalance, and disrupt the microbiome. The microbiome is a community of naturally-occurring germs in and on the body—on skin, gut, mouth or respiratory tract, and in the urinary tracts. A healthy microbiome helps protect from infection. Antibiotics disrupt the microbiome, eliminating both "good" and "bad" bacteria. Drug-resistant bacteria—like MRSA, CRE, and *C. difficile*—can take advantage of this disruption and multiply. With this overgrowth of resistant bacteria, the body is primed for infection. Once subjects are colonized with resistant bacteria, the resistant bacteria can easily be spread to others. See "Antibiotic Resistance (AR) Solutions Initiative: Microbiome, CDC Microbiome Fact Sheet 2016". www.cdc.gov/drugresistance/solutions-initiative/innovations-to-slow-AR.html.

According to the Center for Disease Control (CDC), the top drug-resistant threats to the United States include *Neisseria gonorrhoeae*, multi-drug resistant *Acinetobacter*, drug-resistant *Campylobacter*, fluconazole-resistant *Candida*, vancomycin-resistant *Enterococcus* (VRE), multi-drug resistant *Pseudomonas Aeruginosa*, drag-resistant non-typhoidal *Salmonella*, drug-resistant *Salmonella* serotype

*typhi*, methicillin-resistant *Staphylococcus aureus* (MRSA), drug-resistant *Streptococcus pneumoniae*, drug-resistant Tuberculosis, vancomycin-resistant *Staphylococcus aureus*, erythromycin-resistant Group A *Streptococcus*, and clindamycin-resistant Group B *Streptococcus*. See "Antibiotic/Antimicrobial Resistance (AR/AMR)", https://www.cdc.gov/drugresistance/biggest_threats.html.

*Neisseria gonorrhoeae* causes gonorrhea, a sexually transmitted disease that can result in discharge and inflammation at the urethra, cervix, pharynx, or rectum. There are about 820,000 gonorrhea infections per year. Of these, there are about 246,000 drug-resistant gonorrhea infections: 188,600 tetracycline resistant, 11,489 reduced susceptibility to cefixime, 3,280 reduced susceptibility to ceftriaxone, and about 2,460 exhibit reduced susceptibility to azithromycin.

*Acinetobacter* is a type of gram-negative bacteria that is a cause of pneumonia or bloodstream infections among critically ill patients. Many of these bacteria have become very resistant to antibiotics. There are about 12,000 Actinobacter infections per year, including about 7,300 multidrug-resistant Actinobacter infections and 500 deaths.

Candidiasis is a fungal infection caused by yeasts of the genus *Candida*. There are more than 20 species of *Candida* yeasts that can cause infection in humans, the most common of which is *Candida albicans. Candida* yeasts normally live on the skin and mucous membranes without causing infection. However, overgrowth or invasion of these microorganisms can cause symptoms to develop. Symptoms of candidiasis vary depending on the area of the body that is infected. *Candida* is the fourth most common cause of healthcare-associated bloodstream infections in the United States. In some hospitals it is the most common cause. These infections tend to occur in the sickest patients. There are about 46,000 *Candida* infections per year, including about 3,400 fluconazole-resistant *Candida* infections, and 220 deaths.

*Staphylococcus aureus* is a common type of bacteria that is found on the skin. During medical procedures when patients require catheters or ventilators or undergo surgical procedures, *Staphylococcus aureus* can enter the body and cause infections. Methicillin-resistant *Staphylococcus aureus* (MRSA) causes a range of illnesses, from skin and wound infections to pneumonia and bloodstream infections that can cause sepsis and death. Staph bacteria, including MRSA, are one of the most common causes of healthcare-associated infections. There are about 80,461 severe MRSA infections per year, and about 11,285 deaths from MRSA per year. When *Staphylococcus aureus* becomes resistant to vancomycin, there are few treatment options available because vancomycin-resistant *Staphylococcus aureus* bacteria identified to date were also resistant to methicillin and other classes of antibiotics. There have been at least 13 cases of vancomycin-resistant *Staphylococcus aureus* in 4 states since 2002.

*Streptococcus pneumoniae* (*S. pneumoniae*, or pneumococcus) is the leading cause of bacterial pneumonia and meningitis in the United States. It also is a major cause of bloodstream infections and ear and sinus infections. There are about 1,200,000 drug resistant infections per year, with about 19,000 excess hospitalizations, and 7,000 deaths.

Group A *Streptococcus* (GAS) causes many illnesses, including pharyngitis (strep throat), streptococcal toxic shock syndrome, necrotizing fasciitis ("flesh-eating" disease), scarlet fever, rheumatic fever, and skin infections such as impetigo. Group A *Streptococcus* is the leading cause of necrotizing fasciitis ("flesh-eating" disease). There are about 1-2.6 million Strep throat infections peer year, including about 1,300 drug-resistant Group A Strep infections per year, and about 160 deaths.

Group B *Streptococcus* (GBS) is a type of bacteria that can cause severe illness in people of all ages, ranging from bloodstream infections (sepsis) and pneumonia to meningitis and skin infections, Group B Strep is the leading cause of serious microorganism infections in newborns. There were about 27,000 severe cases of GBS in 2011, including about 7,600 drug-resistant Group B Strep infections, and about 440 deaths.

Prior art methods of preventing infection and transmission of drug-resistant microorganisms in colonized individuals include screening and isolation, decolonization of the drug-resistant microorganism, and/or recolonization with a drug-susceptible microorganism.

Prior art methods employing suppression (decolonization) alone-such as use of antibiotics and antimicrobial agents-often fail because they are subject to high rates of recurrence. Decolonization is often insufficient when used alone to effectively prevent recurrence and/or transmission of the drug-resistant microorganism.

Among pathogenic microorganisms causing health care related infection, methicillin-resistant *Staphylococcus aureus* (MRSA) has been given priority because of its virulence and disease spectrum, multidrug resistant profile and increasing prevalence in health care settings. MRSA is the most common cause of ventilator-associated pneumonia and surgical site infection and the second most common cause of central catheter associate bloodstream infection.

Strategies involving screening of new hospital patients for MRSA, and isolating those who carry it, with or without decolonization have been shown to be somewhat effective in reducing transmission. However, this type of therapy is rather expensive requiring extra accommodations, with special containment and hygiene procedures.

Decolonization alone has been used in hospital patients in an attempt to reduce transmission and prevent disease in *Staphylococcus aureus* carriers. Decolonization may involve a multi-day regimen of antibiotic and/or antiseptic agents—for example, intranasal mupirocin and chlorhexidine bathing. Universal decolonization is a method employed by some hospitals where all intensive care unit (ICU) hospital patients are washed daily with chlorhexidine and intranasal mupirocin, but since its widespread use, MRSA infection rates in the U.S. have not significantly changed. In addition, microorganisms may develop resistance to chlorhexidine and mupirocin upon repeated exposure.

Decolonization when used alone may not be durable because the vacated niche may become recolonized with pathogenic or drug-resistant microorganisms.

For example, Shinefield et al., 1963, Amer J Dis Child 105, June 1963, 146-154, observed that colonization of newborn infants with strains of *Staphylococcus aureus* of the 52/52a/80/81 phage complex by contact with a carrier was often followed by disease in babies and their family contacts. Shinefield also observed that control measures using antiseptic or antimicrobial agents applied to the infant lead to colonization with abnormal flora, consisting primarily of highly resistant coagulase negative staphylocci and Gram-negative organisms such as *Pseudomonas* and *Proteus*. Shinefield attempted to solve the problem by artificially colonizing newborns with staphylococcal strain 502a by nasal and/or umbilical inoculation. 502a is a coagulase positive strain of *Staphylococcus aureus* of low virulence, susceptible to penicillin, and incapable of being induced to produce beta-lactamase. It was shown that presence of other staphylococci interfered with acquisition of 502a. Persistence of colonization was at best 35% after 6 months to one year.

Boris M. et al, "Bacterial Interference: Protection Against Recurrent Intrafamilial Staphylococcal Disease." Amer J Dis Child 115 (1968): 521-29, deliberately colonized ~4000 infants in first few hours of life with *Staphylococcus aureus* 502a (nares & umbilical stump). Virtually complete protection of babies from 80/81 infection was observed (babies were monitored for 1-year post inoculation). Although 5-15% of babies developed tiny treatment emergent vesicles that self-resolved in first 3 days post-treatment. Prior decolonization improves persistence of 502a up to 5-fold compared to placebo (saline) n=63. Controlled studies in recurrent furunculosis showed that decolonization with systemic antibiotics+nasal antimicrobial followed by application of 502a curtailed disease in 80% of patients.

Recolonization with a drug-susceptible strain may not be safe because the drug-susceptible strain may still cause systemic infection.

Shinefield et al., 1973, Microbiol Immunol, vol. 1, 541-547, reported using bacterial replacement including decolonization in treating patients with recurrent furanculosis. Chronic staphylococcal carriers were treated with antibiotic therapy including systemic antibiotics and application of antimicrobial cream to nasal mucosa. In an initial study, 31 patients received antibiotic therapy alone and exhibited a 74% recurrence rate of original strain. 18 patients received antibiotic treatment followed by 502a inoculation and exhibited 27% recurrence of original strain. A larger study of 587 patients resulted in 21% recurrence of original strain after 12 months. However, a high relapse rate was noted in patients with diabetes, eczema or acne. Disease associated with 502a was noted in 11 patients.

Aly et al., 1974 J Infect Dis 129(6) pp. 720-724, studied bacterial interference in carriers of *Staphylococcus aureus*. The carriers were treated with antibiotics and antibacterial soaps and challenged with strain 502a. Specifically, decolonization method involved oral dicloxacillin 8 days; neosporin in nose for 8 days, and trichlorocabanilide. It was found that full decolonization was needed to get good take. Day 7 showed 100% take, but at day 23 the take way down to 60 to 80%. The persistence data was 73% at 23 weeks for well-decolonized subjects, and only 17% persistence for partially decolonized subjects. Co-colonization was found in 5/12 subjects at day 3, 2/12 subjects at day 10, and 1/12 subjects at day 35 and at day 70.

Decolonization, followed by recolonization with a microorganism of the same genus, but a different species, may not be durable because the vacated niche is not adequately filled by the different species.

WO2009117310 A2, George Liu, assigned to Cedars-Sinai Medical Center, discloses methods for treatment and prevention of methicillin-resistant *Staphylococcus aureus* and methicillin-sensitive *Staphylococcus aureus* (MSSA) using a decolonization/recolonization method. In one example, mice are treated with antibiotics to eradicate existing flora, including MRSA, and newly cleared surface area is colonized with bacteria of the same genus, but of a different species, such as *Staphylococcus epidermidis*. No specific data regarding recurrence is provided.

Administration of probiotics in an attempt to treat infection by pathogenic microorganisms may not be effective and may not be durable because the probiotic may not permanently colonize the subject.

U.S. Pat. No. 6,660,262, Randy Mckinney, assigned to Bovine Health Products, Inc., discloses broad spectrum antimicrobial compositions comprising certain minerals, vitamins, cobalt amino acids, kelp and a *Lactobacillus* species for use in treating microbial infection in animals. Field trials in cattle and horses were performed, but the infectious bacterial strain or other infectious agent was not identified.

U.S. Pat. No. 6,905,692, Sean Farmer, assigned to Ganeden Biotech, Inc., discloses topical compositions containing certain combinations of probiotic *Bacillus* bacteria, spores and extracellular products for application to skin or mucosa of a mammal for inhibiting growth of certain bacterium, yeast, fungi, and virus. Compositions comprising *Bacillus coagulens* spores, or *Bacillus* species, culture supernatants and *Pseudomonas lindbergii* culture supernatants in a vehicle such as emu oil are provided. The disclosure states since probiotics do not permanently colonize the host, they need to be ingested or applied regularly for any health-promoting properties to persist.

U.S. Pat. No. 6,461,607, Sean Farmer, assigned to Ganeden Biotech, Inc., discloses lactic acid-producing bacteria, preferably strains of *Bacillus coagulans*, for the control of gastrointestinal tract pathogens in a mammal. Methods for selective breeding and isolation of probiotic, lactic acid-producing bacterial strains which possess resistance to an antibiotic are disclosed. Methods for treating infections with a composition comprising an antibiotic-resistant lactic acid producing bacteria and an antibiotic are disclosed.

U.S. Pat. No. 8,906,668, assigned to Seres Therapeutics, provide cytotoxic binary combinations of 2 or more bacteria of different operational taxonomic units (OTUs) to durably exclude a pathogenic bacterium. The OTUs are determined by comparing sequences between organisms, for example as sharing at least 95% sequence identity of 16S ribosomal RNA genes in at least in a hypervariable region.

Prior art methods employing replacement of the original pathogenic microorganism (recolonization) alone are subject to poor colonization rates with the new microorganism. The process may fail if the recolonization is done incorrectly. Effective recolonization is critical but not sufficient when used alone to prevent recurrence.

Prior art methods involving both suppression (decolonization) of the original pathogenic microorganism and replacement (recolonization) with a new microorganism may give variable recurrence of the pathogenic microorganism depending on the specific method.

Rather than waging an un-winnable war against commensal pathogenic or drug-resistant microorganisms, a better approach may be to manage the microbiome: to actively promote "good bugs" and their supporting system dynamics, while selectively suppressing the recurrence of specific pathogenic organisms. Improved methods to safely and durably prevent and reduce recurrence of infection by undesirable microorganisms, such as virulent, pathogenic and/or drug-resistant microorganisms, are desirable.

SUMMARY OF THE INVENTION

Methods and compositions are provided for safely and durably influencing microbiological ecosystems (microbiomes) in a subject to perform a variety of functions, for example, including reducing the risk of infection by an undesirable microorganism such as virulent, pathogenic and/or drug-resistant microorganism.

Methods are provided herein to prevent or reduce the risk of colonization, infection, recurrence of colonization, or recurrence of a pathogenic infection by an undesirable microorganism in a subject, comprising: decolonizing the undesirable microorganism on at least one site in the subject to reduce or eliminate the presence of the undesirable microorganism from the site; and durably replacing the undesirable microorganism by administering a synthetic microorganism to the at least one site in the subject, wherein the synthetic microorganism can durably integrate with a host microbiome by occupying the niche previously occupied by the undesirable microorganism; and optionally promoting colonization of the synthetic microorganism within the subject.

The disclosure provides a method for eliminating and preventing the recurrence of a undesirable microorganism in a subject hosting a microbiome, comprising (a) decolonizing the host microbiome; and (b) durably replacing the undesirable microorganism by administering to the subject a synthetic microorganism comprising at least one element imparting a non-native attribute, wherein the synthetic microorganism is capable of durably integrating to the host microbiome, and occupying the same niche in the host microbiome as the undesirable microorganism.

In some embodiments, the decolonizing is performed on at least one site in the subject to substantially reduce or eliminate the detectable presence of the undesirable microorganism from the at least one site.

In some embodiments, the detectable presence of an undesirable microorganism or a synthetic microorganism is determined by a method comprising a phenotypic method and/or a genotypic method, optionally wherein the phenotypic method is selected from the group consisting of biochemical reactions, serological reactions, susceptibility to anti-microbial agents, susceptibility to phages, susceptibility to bacteriocins, and/or profile of cell proteins. In some embodiments, the genotypic method is selected a hybridization technique, plasmids profile, analysis of plasmid polymorphism, restriction enzymes digest, reaction and separation by Pulsed-Field Gel Electrophoresis (PFGE), ribotyping, polymerase chain reaction (PCR) and its variants, Ligase Chain Reaction (LCR), and Transcription-based Amplification System (TAS).

In some embodiments, the niche is a dermal or mucosal environment that allows stable colonization of the undesirable microorganism at the at least one site in the subject.

In some embodiments, the ability to durably integrate to the host microbiome is determined by detectable presence of the synthetic microorganism at the at least one site for a period of at least two weeks, at least four weeks, at least six weeks, at least eight weeks, at least ten weeks, at least 12 weeks, at least 16 weeks, at least 26 weeks, at least 30 weeks, at least 36 weeks, at least 42 weeks, or at least 52 weeks after the administering step.

In some embodiments, the ability to durably replace the undesirable microorganism is determined by the absence of detectable presence of the undesirable microorganism at the at least one site for a period of at least two weeks, at least four weeks, at least six weeks, at least eight weeks, at least ten weeks, at least 12 weeks, at least 16 weeks, at least 26 weeks, at least 30 weeks, at least 36 weeks, at least 42 weeks, or at least 52 weeks after the administering step.

In some embodiments, the ability to occupy the same niche is determined by absence of co-colonization of the undesirable microorganism and the synthetic microorganism at the at least one site after the administering step. In some embodiments, the absence of co-colonization is determined at least two weeks, at least four weeks, at least six weeks, at least eight weeks, at least ten weeks, at least 12 weeks, at least 16 weeks, at least 26 weeks, at least 30 weeks, at least 36 weeks, at least 42 weeks, or at least 52 weeks after the administering step.

In some embodiments, the synthetic microorganism comprises at least one element imparting the non-native attribute that is durably incorporated to the synthetic microorganism. In some embodiments, the at least one element imparting the non-native attribute is durably incorporated to the host microbiome via the synthetic microorganism.

In some embodiments, the at least one element imparting the non-native attribute is a kill switch molecular modification, virulence block molecular modification, or nanofactory molecular modification. In some embodiments, the synthetic microorganism comprises molecular modification that is integrated to a chromosome of the synthetic microorganism. In some embodiments, the synthetic microorganism comprises a virulence block molecular modification that prevents horizontal gene transfer of genetic material from the undesirable microorganism.

In some embodiments, the measurable average cell death of the synthetic microorganism occurs within at least a preset period of time following induction of the first promoter after the change in state. In some embodiments, the measurable average cell death occurs within at least a preset period of time selected from the group consisting of within at least 1, 5, 15, 30, 60, 90, 120, 180, 240, 300, or 360 min minutes following the change of state. In some embodiments, the measurable average cell death is at least a 50% cfu, at least 70%, at least 80%, at least 90%, at least 95%, at least 99%, at least 99.5%, at least 99.8%, or at least 99.9% cfu count reduction following the preset period of time. In some embodiments, the change in state is selected from one or more of pH, temperature, osmotic pressure, osmolality, oxygen level, nutrient concentration, blood concentration, plasma concentration, serum concentration, metal concentration, chelated metal concentration, change in composition or concentration of one or more immune factors, mineral concentration, and electrolyte concentration. In some embodiments, the change in state is a higher concentration of and/or change in composition of blood, serum, or plasma compared to normal physiological (niche) conditions at the at least one site in the subject.

In some embodiments, the undesirable microorganism is a *Staphylococcus aureus* strain, and wherein the detectable presence is measured by a method comprising obtaining a sample from the at least one site of the subject, contacting a chromogenic agar with the sample, incubating the contacted agar and counting the positive cfus of the bacterial species after a predetermined period of time.

In some embodiments, a method is provided comprising a decolonizing step comprising topically administering a decolonizing agent to at least one site in the subject to reduce or eliminate the presence of the undesirable microorganism from the at least one site.

In some embodiments, the decolonizing step comprises topical administration of a decolonizing agent, wherein no systemic antimicrobial agent is simultaneously administered. In some embodiments, no systemic antimicrobial agent is administered prior to, concurrent with, and/or subsequent to within one week, two weeks, three weeks, one month, two months, three months, six months, or one year of the first topical administration of the decolonizing agent or administration of the synthetic microorganism. In some embodiments, the decolonizing agent is selected from the group consisting of a disinfectant, bacteriocide, antiseptic, astringent, and antimicrobial agent. In some embodiments, the decolonizing agent is selected from the group consisting of alcohols (ethyl alcohol, isopropyl alcohol), aldehydes (glutaraldehyde, formaldehyde, formaldehyde-releasing agents (noxythiolin=oxymethylenethiourea, tauroline, hexamine, dantoin), o-phthalaldehyde), anilides (triclocarban=TCC=3,4,4'-triclorocarbanilide), biguanides (chlorhexidine, alexidine, polymeric biguanides (polyhexamethylene biguanides with MW>3,000 g/mol, vantocil), diamidines (propamidine, propamidine isethionate, propamidine dihydrochloride, dibromopropamidine, dibromopropamidine isethionate), phenols (fentichlor, p-chloro-m-xylenol, chloroxylenol, hexachlorophene), bis-phenols (triclosan, hexachlorophene), chloroxylenol (PCMX), quaternary ammonium compounds (cetrimide, benzalkonium chloride, cetyl pyridinium chloride), silver compounds (silver sulfadiazine, silver nitrate), peroxy compounds (hydrogen peroxide, peracetic acid, benzoyl peroxide), iodine compounds (povidone-iodine, poloxamer-iodine, iodine), chlorine-releasing agents (sodium hypochlorite, hypochlorous acid, chlorine dioxide, sodium dichloroisocyanurate, chloramine-T), copper compounds (copper oxide), isotretinoin, sulfur compounds, botanical extracts (*Melaleuca* spp. (tea tree oil), (*Vaccinium* spp. (e.g., A-type proanthocyanidins), *Cassia fistula* Linn, Backea frutesdens L., *Melia azedarach* L., *Muntingia calabura, Vitis vinifera* L, *Terminalia avicennioides* Guill & Perr., *Phylantus discoideus* muel, Muel-Arg., *Ocimum gratissimum* Linn., *Acalypha wilkesiana* Muell-Arg., *Hypericum pruinatum* Boiss. &B al., *Hypericum olimpicum* L. and *Hypericum sabrum* L., *Hamamelis virginiana* (witch hazel), Clove oil, *Eucalyptus* spp., *Rosemarinus officinalis* spp. (rosemary), *thymus* spp. (thyme), *Lippia* spp. (oregano), *lemongrass* spp., *cinnamomum* spp., *geranium* spp., *lavendula* spp.), aminolevulonic acid, and topical antibiotic compounds (bacteriocins; mupirocin, bacitracin, neomycin, polymyxin B, gentamicin).

In some embodiments, the antimicrobial agent is selected from the group consisting of vancomycin, cefazolin, cepahalothin, cephalexin, linezolid, daptomycin, clindamycin, lincomycin, mupirocin, bacitracin, neomycin, polymyxin B, gentamicin, prulifloxacin, ulifloxacin, fidaxomicin, minocyclin, metronidazole, metronidazole, sulfamethoxazole, ampicillin, trimethoprim, ofloxacin, norfloxacin, tinidazole, norfloxacin, oridazole, levofloxacin, nalidixic acid, ceftriaxone, azithromycin, cefixime, ceftriaxone, cefalexin, ceftriaxone, rifaximin, ciprofloxacin, norfloxacin, ofloxacin, levofloxacin, gatifloxacin, gemifloxacin, prufloxacin, alifloxacin, moxifloxacin, nystatin, amphotericin B, flucytosine, ketoconazole, posaconazole, clotrimazole, voriconazole, griseofulvin, miconazole nitrate, and fluconazole.

In some embodiments, the decolonizing comprises topically administering the decolonizing agent at least one, two, three, four, five or six or more times prior to the replacing step. In some embodiments, the decolonizing step comprises administering the decolonizing agent to the at least one host site in the subject from one to six or more times or two to four times at intervals of between 0.5 to 48 hours apart, and wherein the replacing step is performed after the final decolonizing step.

In some embodiments, a method is provided comprising decolonizing an undesirable microorganism, and replacing with a synthetic microorganism comprising topical administration of a composition comprising at least $10^5$, at least $10^6$, at least $10^7$, at least $10^8$, at least $10^9$, at least $10^{10}$, or at least $10^{11}$ CFU of the synthetic strain and a pharmaceutically acceptable carrier to at least one host site in the subject. In some embodiments, the initial replacing step is performed within 12 hours, 24 hours, 36 hours, 2 days, 3 days, 4 days, 5 days, 6 days, 7 days, 8 days, 9 days or 10 days, or between 0.5-10 days, 1-7 days, or 2 to 5 days of the decolonizing step. In some embodiments, the replacing step is repeated at intervals of no more than once every two weeks to six months following the final decolonizing step. In some embodiments, the decolonizing step and the replacing step is repeated at intervals of no more than once every two weeks to six months, or three weeks to three months. In some embodiments, the replacing comprises administering the synthetic microorganism to the at least one site at least one, two, three, four, five, six, seven, eight, nine, or ten times. In some embodiments, the replacing comprises administering the synthetic microorganism to the at least one site no more than one, no more than two, no more than three times, or no more than four times per month.

In some embodiments, the method of decolonizing the undesirable microorganism and replacing with a synthetic microorganism further comprises promoting colonization of the synthetic microorganism in the subject. In some embodiments, the promoting colonization of the synthetic microorganism in the subject comprises administering to the subject a promoting agent, optionally where the promoting agent is a nutrient, prebiotic, commensal, stabilizing agent, humectant, and/or probiotic bacterial species. In some embodiments, the promoting comprises administering a probiotic species at from $10^5$ to $10^{10}$ cfu, $10^6$ to $10^9$ cfu, or $10^7$ to $10^8$ cfu to the subject after the initial decolonizing step.

In some embodiments, the nutrient is selected from sodium chloride, lithium chloride, sodium glycerophosphate, phenylethanol, mannitol, tryptone, peptide, and yeast extract. In some embodiments, the prebiotic is selected from the group consisting of short-chain fatty acids (acetic acid, propionic acid, butyric acid, isobutyric acid, valeric acid, isovaleric acid), glycerol, pectin-derived oligosaccharides from agricultural by-products, fructo-oligosaccarides (e.g., inulin-like prebiotics), galacto-oligosaccharides (e.g., raffinose), succinic acid, lactic acid, and mannan-oligosaccharides.

In some embodiments, the probiotic is selected from the group consisting of *Bifidobacterium breve, Bifidobacterium bifidum, Bifidobacterium lactis, Bifidobacterium infantis, Bifidobacterium breve, Bifidobacterium longum, Lactobacillus reuteri, Lactobacillus paracasei, Lactobacillus plantarum, Lactobacillus johnsonii, Lactobacillus rhamnosus, Lactobacillus acidophilus, Lactobacillus salivarius, Lactobacillus casei, Lactobacillus plantarum, Lactococcus lactis, Streptococcus thermophiles*, and *Enterococcus fecalis*.

In some embodiments, the commensal is selected from the group consisting of *Acinetobacter johnsonii, Acinetobacter baumannil, Staphylococcus aureus, Staphylococcus epidermidis, Staphylococcus lugdunensis, Staphylococcus warneri, Staphylococcus saprophyticus, Corynebacterium acnes, Corynebacterium striatum, Corynebacterium diphtheriae. Corynebacterium mimnissimum, Cutibacterium acnes, Propionibacterium acnes, Propionibacterium grandiosum, Streptococcus pyogenes, Streptococcus aureus, Streptococcus agalactiae, Streptococcus mitis, Streptococcus viridans. Streptococcus pneumoniae, Streptococcus anginasis, Steptococcus constellatus, Streptococcal intermedius, Streptococcus agalactiae, Pseudomonas aeruginosa, Pseudomonas oryzihabitans, Pseudomonas stutzeri, Pseudomonas putida*, and *Pseudomonas fluorescens*.

In some embodiments, the undesirable microorganism is an antimicrobial agent-resistant microorganism. In some embodiments, the antimicrobial agent-resistant microorganism is an antibiotic resistant bacteria. In some embodiments, the antibiotic-resistant bacteria is a Gram-positive bacterial species selected from the group consisting of a *Streptococcus* spp., *Cutibacterium* spp., and a *Staphylococcus* spp. In some embodiments, the *Streptococcus* spp. is selected from the group consisting of *Streptococcus pneumoniae, Steptococcus mutans, Streptococcus sobrinas, Streptococcus pyogenes*, and *Streptococcus agalactiae*. In some embodiments, the *Cutibacterium* spp. is selected from the group consisting of *Cutibacterium acnes* subsp. *acnes, Cutibacterium acnes* subsp. *defendens*, and *Cutibacterium acnes* subsp. *elongatum*. In some embodiments, the *Staphylococcus* spp. is selected from the group consisting of *Staphylococcus aureus, Staphylococcus epidermidis*, and *Staphylococcus saprophyticus*. In some embodiments, the undesirable microorganism is a methicillin-resistant *Staphylococcus aureus* (MRSA) strain that contains a staphylococcal chromosome cassette (SCCmec types I-III), which encode one (SCCmec type I) or multiple antibiotic resistance genes (SCCmec type II and III), and/or produces a toxin. In some embodiments, the toxin is selected from the group consisting of a Panton-Valentine leucocidin (PVL) toxin, toxic shock syndrome toxin-1 (TSST-1), staphylococcal alpha-hemolysin toxin, staphylococcal beta-hemolysin toxin, staphylococcal gamma-hemolysin toxin, staphylococcal delta-hemolysin toxin, enterotoxin A, enterotoxin B, enterotoxin C, enterotoxin D, enterotoxin E, and a coagulase toxin.

In some embodiments, the subject treated with a method according to the disclosure does not exhibit recurrence or colonization of the undesirable microorganism as evidenced by swabbing the subject at the at least one site for at least two weeks, at least two weeks, at least four weeks, at least six weeks, at least eight weeks, at least ten weeks, at least 12 weeks, at least 16 weeks, at least 24 weeks, at least 26 weeks, at least 30 weeks, at least 36 weeks, at least 42 weeks, or at least 52 weeks after the administering step.

The disclosure provides a synthetic microorganism for durably replacing an undesirable microorganism in a subject. The synthetic microorganism comprises a molecular modification designed to enhance safety by reducing the risk of systemic infection. In one embodiment, the molecular modification causes a significant reduction in growth or cell death of the synthetic microorganism in response to blood, serum, or plasma. The synthetic microorganism may be used in methods and compositions for preventing or reducing recurrence of dermal or mucosal colonization or recolonization of an undesirable microorganism in a subject.

The disclosure provides a synthetic microorganism for use in compositions and methods for treating or preventing, reducing the risk of, or reducing the likelihood of colonization, or recolonization, systemic infection, bacteremia, or endocarditis caused by an undesirable microorganism in a subject.

The disclosure provides a synthetic microorganism comprising a recombinant nucleotide comprising at least one kill switch molecular modification comprising a first cell death gene operatively associated with a first regulatory region comprising an inducible first promoter, wherein the first inducible promoter exhibits conditionally high level gene expression of the recombinant nucleotide in response to exposure to blood, serum, or plasma of at least three fold increase of basal productivity. In some embodiments, the inducible first promoter exhibits, comprises, is derived from, or is selected from a gene that exhibits upregulation of at least 5-fold, at least 10-fold, at least 20-fold, at least 50-fold, or at least 100-fold within at least 30 min, 60 min. 90 min, 120 min, 180 min, 240 min, 300 min, or at least 360 min following exposure to blood, serum, or plasma.

In some embodiments, the synthetic microorganism comprises a kill switch molecular modification comprising a first cell death gene operably linked to a first regulatory region comprising a inducible first promoter, wherein the first promoter is activated (induced) by a change in state in the microorganism environment in contradistinction to the normal physiological (niche) conditions at the at least one site in the subject.

In some embodiments, the synthetic microorganism further comprises an expression clamp molecular modification comprising an antitoxin gene specific for the first cell death gene or a product thereof, wherein the antitoxin gene is operably associated with a second regulatory region comprising a second promoter which is constitutive or active upon dermal or mucosal colonization or in a complete media, but is not induced, induced less than 1.5-fold, or is repressed after exposure to blood, serum or plasma for at least 30 minutes. In some embodiments, the second promoter is active upon dermal or mucosal colonization or in TSB media, but is repressed by at least 2 fold upon exposure to blood, serum or plasma after a period of time of at least 30 min, 60 min, 90 min, 120 min, 180 min, 240 min, 300 min, or at least 360 min.

In some embodiments, the synthetic microorganism exhibits measurable average cell death of at least 50% cfu reduction within at least 1, 5, 15, 30, 60, 90, 120, 180, 240, 300, or 360 minutes following exposure to blood, serum, or plasma. In some embodiments, the synthetic microorganism exhibits measurable average cell death of at least 70%, at least 80%, at least 90%, at least 95%, at least 99%, at least 99.5%, at least 99.8%, or at least 99.9% cfu count reduction within at least 1, 5, 15, 30, 60, 90, 120, 180, 240, 300, or 360 minutes following exposure to blood, serum, or plasma.

In some embodiments, the synthetic microorganism comprises a kill switch molecular modification that reduces or prevents infectious growth of the synthetic microorganism under systemic conditions in a subject.

In some embodiments, the synthetic microorganism comprises at least one molecular modification that is integrated to a chromosome of the synthetic microorganism.

In some embodiments, the synthetic microorganism is derived from a target microorganism having the same genus and species as an undesirable microorganism. In some embodiments, the target microorganism is susceptible to at least one antimicrobial agent. In some embodiments, the target microorganism is selected from a bacterial, fungal, or protozoal target microorganism. In certain embodiments, the target microorganism is capable of colonizing a dermal and/or mucosal niche.

In some embodiments, the target microorganism has the ability to biomically integrate with the decolonized host microbiome. In some embodiments, the synthetic microorganism is derived from a target microorganism isolated from the host microbiome. In some embodiments, the target microorganism is selected from a bacterial, fungal, or protozoal target microorganism.

In some embodiments, the target microorganism that is a member of a genus selected from the group consisting of *Acinetobacter, Corynebacterium, Cutibacterium, Staphylococcus, Streptococcus, Propionibacterium*, and *Pseudomonas*.

In some embodiments, the target microorganism is a bacterial species capable of colonizing a dermal and/or mucosal niche and is a member of a genus selected from the group consisting of *Acinetobacter, Corynebacterium, Cutibacterium, Staphylococcus, Streptococcus, Propionibacterium*, and *Pseudomonas*. In some embodiments, the target microorganism is selected from the group consisting of *Acinetobacter johnsonii, Acinetobacter baumannii, Staphylococcus aureus, Staphylococcus epidermidis, Staphylococcus lugdunensis, Staphylococcus warneri, Staphylococcus saprophyticus, Corynebacterium acnes, Corynebacterium striatum, Corynebacterium diphtheriae, Corynebacterium minutissinnum, Cutibacterim acnes, Propionibacterium acnes, Propionibacterium granadosum, Streptococcus pyogenes Streptococcus aureus, Streptococcus agalactiae, Streptococcus mitis, Streptococcus viridans, Streptococcus pneumoniae, Streptococcus anginosis, Steptococcus constellatus, Streptococcal intermedius, Streptococcus agalactiae, Pseudomonas aeruginosa, Pseudomonas oryzihabitans, Pseudomonas stutzeri, Pseudomonas putida*, and *Pseudomonas fluorescens*. In a particular embodiment, a synthetic microorganism is provided that is derived from a *Staphylococcus aureus* strain. In some embodiments, the target strain is a *Staphylococcus aureus* 502a strain or RN4220 strain.

In some embodiments, the synthetic microorganism comprises a kill switch molecular modification comprising a cell death gene selected from the group consisting of sprA1, sprA2, kpn1, sma1, sprG, relF, rsaE, yoeB, mazF, yefM, or lysostaphin toxin gene. In some embodiments, the cell death gene comprises a nucleotide sequence selected from the group consisting of SEQ ID NOs: 122, 124, 125, 126, 127, 128, 274, 275, 284, 286, 288, 290, 315, and 317, or a substantially identical nucleotide sequence.

In some embodiments, the inducible first promoter is a blood, serum, and/or plasma responsive promoter. In some embodiments, the first promoter is upregulated by at least 1.5 fold, at least 3-fold, at least 5-fold, at least 10-fold, at least 20-fold, at least 50-fold, or at least 100-fold within a period of time selected from the group consisting of at least 30 min, 60 min, 90 min, 120 min, 180 min, 240 min, 300 min, and at least 360 min following exposure to human blood, serum or plasma. In some embodiments, the first promoter is not induced, induced less than 1.5 fold, or is repressed in the absence of the change of state. In some embodiments, the first promoter is induced at least 1.5, 2, 3, 4, 5 or at least 6 fold within a period of time in the presence of serum, blood or plasma. In some embodiments, the first promoter is not induced, induced less than 1.5 fold, or repressed under the normal physiological (niche) conditions at the at least one site.

In some embodiments, the inducible first promoter comprises or is derived from a gene selected from the group consisting of isdA (iron-regulated surface determinant protein A), isdB (iron-regulated surface determinant protein B), RxdG (heme-degrading monooxygenase), higA (gamma-hemolysin component A), hlgA1 (gamma-hemolysin), hlgA2 (gamma-hemolysin), hlgB (gamma-hemolysin component B), hrtAB (heme-regulated transporter), sbnC (luc C family siderophore biosyntheis protein), sbnD, sbnI, shnE (lucA/lucC family siderophore biosynthesis protein), isdI, lrgA (murein hydrolase regulator A), lrgB (murein hydrolase regulator B), ear (Ear protein), fhuA (ferrichrome transport ATP-binding protein fhuA), fhuB (ferrichrome transport permease), hlb (phospholipase C), heme ABC transporter 2 gene, heme ABC transporter gene, isd ORF3, sbnF, alanine dehydrogenase gene, diaminopimelate decarboxylase gene, iron ABC transporter gene, threonine dehydratase gene, siderophore ABC transporter gene, SAM dep Metrans gene, HarA, splF (serine protease SplF), splD (serine protease SplD), dps (general stress protein 20U), SAUSA300_2617 (putative cobalt ABC transporter, ATP-binding protein), SAUSA300_2268 (sodium/bile acid symporter family protein), SAUSA300_2616 (cobalt family transport protein), srtB (Sortase B), shnA (probable siderophore biosynthesis protein sbnA), sbnB, sbnG, leuA (2-isopropylmalate synthase amino acid biosynthetic enzyme), sstA (iron transport membrane protein), sirA (iron ABC transporter substrate-binding protein), isdA (heme transporter), and spa (Staphyloccocal protein A). In some embodiments, the inducible first promoter comprises a nucleotide sequence selected from the group consisting of SEQ ID NO: 114, 115, 119, 120, 121, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, and 163, or a substantially identical nucleotide sequence thereof.

In some embodiments, the synthetic microorganism comprises an expression clamp molecular modification comprising a second promoter operatively associated with an antitoxin gene that encodes an antisense RNA sequence capable of hybridizing with at least a portion of the first cell death gene. In some embodiments, the antitoxin gene encodes an antisense RNA sequence capable of hybridizing with at least a portion of the first cell death gene. In some embodiments, the antitoxin gene is selected from the group consisting of a sprA1 antitoxin gene, sprA2 antitoxin gene, sprG antitoxin gene or sprF, holin antitoxin gene, 187-lysK antitoxin gene, yefM antitoxin gene, lysostaphin antitoxin gene, or mazE antitoxin gene, kpn1 antitoxin gene, sma1 antitoxin gene, relF antitoxin gene, rsaE antitoxin gene, or yoeB antitoxin gene, respectively. In some embodiments, the antitoxin gene comprises a nucleotide sequence selected from the group consisting of SEQ ID NOs: 273, 306, 307, 308, 309, 310, 311, 312, 314, 319, or 322, or a substantially identical nucleotide sequence.

In some embodiments, the second promoter comprises or is derived from a gene selected from the group consisting of clfB (Clumping factor B), sceD (autolysin, exoprotein D), walKR (virulence regulator), atlA (Major autolysin), outA (O-acetyltransferase A); phosphoribosylglycinamide formyltransferase gene, phosphoribosylaminoimidazole synthetase gene, amidophosphoribosyltransferase gene, phosphoribosylformylglycinamidine synthase gene, phosphoribosylformylglycinamidine synthase gene, phosphoribosylaminoimidazole-succinocarboxamide gene, trehalose permease IIC gen, DeoR family transcriptional regulator gene, phosphofructokinase gene, PTS fructose transporter subunit IIC gene, galactose-6-phosphate isomerase gene, NarZ, NarH, NarT, alkylhydroperoxidase gene, hypothetical protein gene, DeoR trans factor gene, lysophospholipase gene, protein disaggregation chaperon gene, alkylhydroperoxidase gene, phosphofructokinase gene, gyrB, sigB, and rho. In some embodiments, the second promoter is a Pam (clumping factor B) that comprises a nucleotide sequence of SEQ ID NO: 117, 118, 129 or 130, or a substantially identical nucleotide sequence thereof.

In some embodiments, the synthetic microorganism comprises a virulence block molecular modification, and/or a nanofactory molecular modification. In some embodiments, the virulence block molecular modification prevents horizontal gene transfer of genetic material from the undesirable microorganism.

In some embodiments, the nanofactory molecular modification comprises an insertion of a gene that encodes, a knock out of a gene that encodes, or a genetic modification of a gene that encodes a product selected from the group consisting of an enzyme, amino acid, metabolic intermediate, and a small molecule.

The disclosure provides a composition comprising an effective amount of a synthetic microorganism according to the disclosure and a pharmaceutically acceptable carrier, diluent, emollient, binder, excipient, lubricant, sweetening agent, flavoring agent, wetting agent, preservative, buffer, or absorbent, or a combination thereof. In some embodiments, the composition further comprises a promoting agent. In some embodiments, the promoting agent is selected from a nutrient, prebiotic, commensal, and/or probiotic bacterial species.

The disclosure provides a single dose unit comprising a composition or synthetic microorganism of the disclosure. In some embodiments, the single dose unit comprises at least at least about $10^5$, at least $10^6$, at least $10^7$, at least $10^8$, at least $10^9$, at least $10^{10}$ CFU, or at least $10^{11}$ of the synthetic strain and a pharmaceutically acceptable carrier. In some embodiments, the single dose unit is formulated for topical administration. In some embodiments, the single dose unit is formulated for dermal or mucosal administration.

The disclosure provides a synthetic microorganism, composition according to the disclosure for use in the manufacture of a medicament for use in a method eliminating, preventing, or reducing the risk of the recurrence of a undesirable microorganism in a subject.

The disclosure provides a kit for preventing or reducing recurrence of dermal or mucosal colonization or recolonization of an undesirable microorganism in a subject, the kit comprising in at least one container, comprising a synthetic microorganism, composition, or single dose of the disclosure, and optionally one or more additional components selected from a second container comprising a decolonizing agent, a sheet of instructions, at least a third container comprising a promoting agent, and/or an applicator.

BRIEF DESCRIPTION OF THE DRAWINGS

FIGS. 3A-3C shows Table 4A with primer sequences for recombinant construction of synthetic *Staphylococcus aureus* from strain BioPlx-01.

FIGS. 4A-4D shows Table 4B with primer sequences for CRISPR construction of synthetic *Staphylococcus aureus* from strain BioPlx-01.

FIG. 9 shows a representative screen shot of CRISPRScan used to find putative gRNAs for use in CRISPR methods. Submitted sequence SEQ ID NO: 340 is shown at upper left. A list of oligos SEQ ID NO: 341-350 is also shown.

FIG. 11 shows vectors for use in the present disclosure. A is a vector used for promoter screen with fluorescence using pCN51. B is a vector for promoter screen with cell death gene. C is a vector for chromosomal integration using CRISPR. D is a vector for chromosomal integration using homologous recombination. Left & Right (or upstream and downstream) HA: homology arms to genomic target locus, CRISPR targeting: RNA guide to genomic locus, mCherry: fluorescent reporter protein, Cas9 protein: CRISPR endonuclease, kanR: kanamycin resistance, oriT: origin of transfer (for integration), and smaI: representative kill gene (restriction endonuclease).

FIG. 12A-12C shows nucleotide sequence (SEQ ID NO: 131) of pIMAY Integrative Plasmid. (accession number JQ62198).

FIG. 16 shows cell growth pre- and post-induction of four synthetic strains derived from *Staphylococcus aureus* 502a having a plasmid based inducible expression system comprising four different cell death gene candidates sprA1, 187-lysK, Holin, and sprG. The candidate cell death genes had been cloned behind an tetracycline inducible promoter on pRAB11 plasmids and transformed into *Staphylococcus aureus* 502a cells. Calculated OD600 readings were taken at T=0, 30, 60, 120, and 240 min after induction of AtC induced (+) strains illustrated by dashed lines (- - - - - -) and uninduced (−) strains indicated by solid lines (−) for BP_068 (502a pRAB11-Ptet-sprA1), BP_069 (502a pRAB11-Ptet-187lysK), BP_070 (502a pRAB11-Ptet-holin), and BP_071 (502a pRAB11-Ptet-sprG1) and compared to BP_001 (502a wt) in BHI media, Each of the induced (+) strains BP_068 (sprA1), BP_069 (187lysK) and BP_070 (holin) exhibited both (i) good cell growth pre-induction and (ii) significant inhibition of cell growth post-induction. BP_068 (+) exhibited the best inhibition of cell growth at each time point T=30, T=60, T=60, T=120 and T=240 min post-induction, so the sprA1 gene was selected for initial further development of a kill switch in *Staphylococcus aureus* 502a.

FIG. 17 shows a bar graph showing difference in the colony forming units (cfu)/ml between T=0 (gray) and 240 min (black) of un-induced (−) and anhydrotetracycline induced (+) strains BP_068 (502a pRAB11-Ptet-sprA1), BP_069 (502a pRAB11-Ptet-187lysK), BP_070 (502a pRAB11-Ptet-holin), and BP_071 (502a pRAB11-Ptet-sprG1) compared to BP_001 (502a wt) in BHI media. Each of the induced (+) strains BP_068 (sprA1), BP_069 (187lysK) and BP_070 (holin) exhibited both (I) good cell growth pre-induction and (ii) significant inhibition of cell growth post-induction. BP_068 exhibited the best inhibition of cell growth 240 min post-induction, so the sprA1 gene was selected for initial further development of a kill switch in *Staphylococcus aureus* 502a.

DETAILED DESCRIPTION OF THE INVENTION

Figures 1, 2:
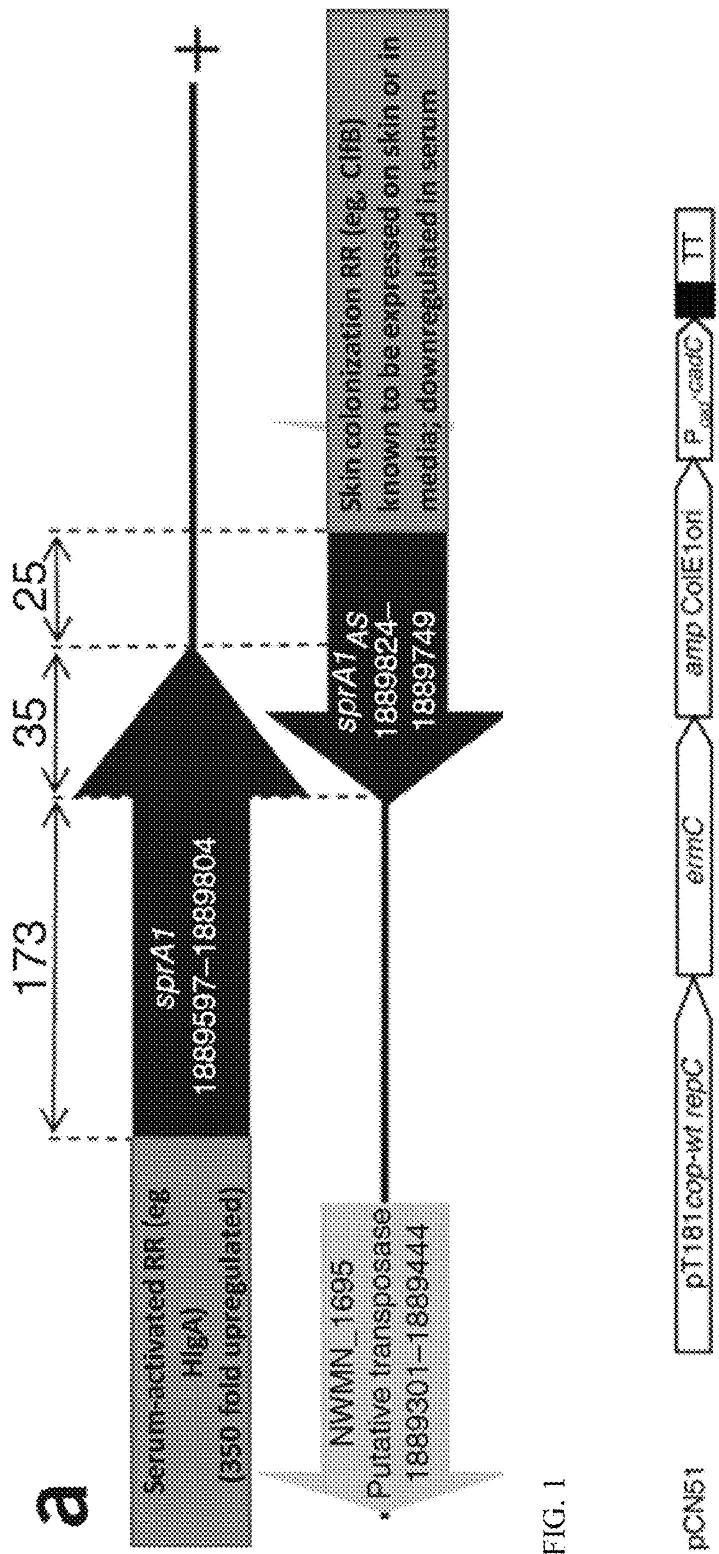
FIG. 1 shows a diagram of a representative molecular modification inserted to a *Staphylococcus aureus*, e.g., BioPlx-01, to create a synthetic microorganism BioPlx strain. A cassette comprising the molecular modification comprises a kill switch and an expression clamp, including expression clamp (e.g., CHB) promoter cloned to drive expression of the SprA1 antisense (antitoxin) RNA wherein the cassette is incorporated into the same expression module from a kill switch comprising a serum-responsive promoter (e.g., $P_{higA}$) operably associated with SprA1 toxin gene. In this strain, serum/blood exposure activates the toxin (e.g., up to 350-fold or more) but not the antitoxin, and growth in TSB or on the skin activates antitoxin bot not toxin.
FIG. 2 shows shuttle vector PCN51 used to clone genes into an *E coli-Staphylococcus aureus* pass-through strain (IMO8B) for transfection of the vector into BioPlx-01 for evaluation.

The present disclosure relies upon a principle known as “bacterial replacement”, or “niche exclusion”, where one microorganism replaces and excludes another. In the field of ecology, competitive exclusion, or Gause’s Law, states that two species that compete for the exact same resources cannot stably coexist. This is due to the fact that one of the competitors will possess some slight advantage over the other leading to extinction of the lesser competitor in the long run. In higher order organisms, this often leads to the adaptation of the lesser competitor to a slightly different ecologic niche.

Methods and compositions for durably managing the microbiome of a subject are provided. In embodiments, the microbiome is a dermal and/or mucosal microbiome (Exobiome). While methods to treat infection by a pathogenic microorganism exist, methods to prevent recurrence are effectively nonexistent.

Infectious Agent—*Staphylococcus aureus* (MSSA and MRSA)

Classified since the early twentieth century as among the deadliest of all disease-causing organisms, each year around 500,000 patients in hospitals of the United States contract a staphylococcal infection, chiefly by *Staphylococcus aureus*. Up to 50,000 deaths each year in the USA are linked with *Staphylococcus aureus* infections. *Staphylococcus aureus* exists on the skin or inside the nostrils of 40-44% of healthy people. *Staphylococcus aureus* is also sometimes found in the mouth, gastrointestinal, genitourinary, and upper respiratory tracts. Some studies indicate even higher colonization prevalence. For example, Eriksen et al maintain that there is a higher percentage of transient or intermittent carriers that increase the prevalence number; sometimes to greater than 75%.

*Staphylococcus aureus* 502a WT BioPlx-01WT® and Other Replacement and Blocking Strains A *Staphylococcus aureus* 502a WT strain called BioPlx-01WT® is employed in example 1 and is a natural “wild-type" organism known to be relatively non-infectious, and which has no known side effects. It has been shown in BioPlx clinical studies to be highly effective in this intended application (occupying and blocking the required microbiomic niche to prevent the recurrence of MRSA).

The present methods prevent infection by durably replacing the (typically virulent and antibiotic-resistant) colonizing undesirable *Staphylococcus aureus* strain with a "blocking" organism—in this study the BioPlx01-WT *Staphylococcus aureus* 502a WT strain. This phenomenon is expected to be applied in a similar manner for any other pathogen replacement organism developed by BioPix.

Other replacement strains such as synthetic strains are provided herein that are fully able to colonize the properly prepared skin and mucosal surfaces, and to occupy the ecologic niche used by this bacterial species, thereby blocking other variants from recolonizing that niche.

There are a very large number of *Staphylococcus aureus* variants (10,000+ genomes as of September/2017), as well as a wide range of genetic cassettes and virulence factors associated with this species.

Methicillin-resistant *Staphylococcus aureus* (MRSA) refers to a class of antibiotic resistant variants of this common human commensal and sometimes pathogenic bacteria. It varies from the wild-type strain (MSSA-Methicillin Sensitive *Staphylococcus aureus*) by its carriage of a mecA cassette that allows MRSA strains to produce an alternate penicillin binding protein (PBP2A) that renders them resistant to treatment with most beta lactam and many other first-line antibiotics.

Methicillin-Resistant *Staphylococcus aureus* (MRSA) and Virulent Methicillin-Susceptible *Staphylococcus aureus* (vMSSA) are virulent, invasive variants of *Staphylococcus aureus* that colonize many humans, and which can further cause both superficial soft tissue and severe systemic infections. Colonization with MRSA or vMSSA is usually a required precursor to active Staph infection. Infection is caused by the bacteria colony on the skin or mucosal membranes, penetrating the outer immunological barrier and invading tissue or the blood stream through a wound, an incision, a needle puncture, or other break in the skin. This can lead to bacteremia and other systemic infections that have high mortality rates.

The present disclosure uses a generally passive strain of *Staphylococcus aureus* to replace and exclude MRSA or vMSSA from its usual place in the dermal/mucosal microbiome. The wild type interfering *Staphylococcus aureus* used by BioPlx is known to be poor at causing systemic disease, however, regardless of the level of variance or invasiveness virtually any microorganism can become an "accidental pathogen" through natural or accidental inoculation. This is particularly true in the case of *Staphylococcus aureus*.

The decolonization and BioPlx01 strain application methods developed by BioPlx allows the strains provided herein a massive numerical and positional competitive advantage. The consequences of this method provide a much longer effect of MRSA decolonization than a simple antiseptic destruction of the virulent MRSA strain. Early studies show a greater than 6 month total exclusionary effect of the BioPlx01 MRSA decolonization/recolonization process with the BioPlx product as opposed to prior literature demonstrating 45% recurrence of *Staphylococcus aureus* nasal colonization at 4 weeks and 60% at 12 weeks with the standard decolonization method alone.

Overview of Indication

*Staphylococcus aureus* infections are a severe problem in both hospitals and community health settings. Methicillin-resistant *Staphylococcus aureus* (MRSA) is genetically different from other strains of *Staphylococcus aureus*, with genetic elements conferring resistance to the antibiotic methicillin and other (usually beta-lactam) antibiotics typically used to treat *Staphylococcus aureus* infections. MRSA strains carry a mecA expression cassette that allows MRSA strains to produce an alternate penicillin binding protein (PBP2A), and it's this mutation that confers resistance. Due to this resistance, MRSA is difficult to treat, making it a life-threatening problem in many cases. MRSA is frequently contracted in hospitals or other types of healthcare settings (Hospital Associated [HA]). These infections typically occur at the time of an invasive procedure such as surgery, intravenous catheterization, intubation, or artificial joint placement. Community-associated (CA) MRSA is typically spread by skin-to-skin contact, and the first symptoms tend to be large boils on the skin.

The BioPlx method using BioPlx strains is not a treatment for invasive MRSA disease, and therefore is not intentionally applied to a patient during the invasive disease state. The benefits of the BioPlx method can be demonstrated in a patient group that: 1) is at high risk for invasive disease. 2) has high morbidity and mortality from this increased risk to show significant clinical benefit, and has no other effective options for the prevention of invasive *Staphylococcus aureus* disease. These characteristics define the group of patients that the Centers for Disease Control have been tracking regarding the MRSA subset since 2005 who have already experienced invasive MRSA disease—72,444 according to ABC surveillance data in 2014.

The surface of the human skin and mucosal layer where *Staphylococcus aureus* resides in the colonization state has a very different level of required nutrients as well as different environmental qualities than that inside the human body. It has been widely recognized that in order for bacteria to be successfully invasive, they must be able to adjust their needs and responses between the colonization and invasive states. This is accomplished by the bacterium sensing the changes between these environments and switching on or off certain gene cassettes allowing for the production of proteins more adapted to the new invasive state.

The BioPlx method, and specifically BioPlx01 strains, take advantage of this requirement by rearranging molecular instructions leading to the death of the organism in the operons of one or more of these specific cassettes. This creates a "holding strain" of colonizing *Staphylococcus aureus* that is unable to cause disease in the patient to whom it is introduced, but also does not allow other circulating *Staphylococcus aureus* strains that may normally colonize the human population to colonize this patient. This occurs through the ecologic premise of competitive exclusion.

The current "Standard of Care" for patients colonized with MRSA is not uniform. There are no guidelines as to the management of staphylococcal colonization in patients that are at high risk of recurrent disease. The IDSA Clinical Practice Guidelines for the Treatment of MRSA Infections in Adults and Children in 2011 provide only C-III level (the lowest—no data, expert opinion) support for decolonization procedures in patients with recurrent community-acquired skin and soft tissue infections and make no mention of the role of decolonization in the prevention of invasive MRSA disease. Some hospitals have pursued a broad screening and isolation program for all admitted patients to their institution, but this has not been shown to be effective owing to (including) poor durability of effect and lower baseline risk of the average hospitalized patient (i.e. UC Irvine MRSA outbreak.) Other hospitals therefore have reduced their attention to patients admitted to the ICU and cardiothoracic surgery cases only. This strategy has been shown to reduce MRSA clinical isolates as well as bloodstream infection from any pathogen. However, these are short term situational strategies designed to reduce risk of MRSA infection over a near time frame.

MRSA disease and colonization is a complicated epidemiologic problem for both the United States and the rest of the world. The manifestations of MRSA are broad from asymptomatic colonization to invasive disease states conferring high mortality and cost to the system. It is clear that the MRSA patients that have experienced invasive disease is medically distinct. They have a higher mortality than any other MRSA subpopulation. They have a higher treatment failure rate. They have a much higher risk for another invasive MRSA incident than any other group of patients. This makes this group an appropriate orphan group toward which the BioPlx method should be directed, and which would benefit from its use.

It can be concluded that decolonization is largely ineffective in durably clearing MRSA colonization, and leads to a high rate of recurrence. We have found that only decolonization in conjunction with active recolonization provides long term conversion from one organism (variant) to another.

Recurrent Invasive MRSA as a Clinically Distinct Disease

Another indication is "prevention of recurrent invasive MRSA." Patients who have already experienced an episode of invasive MRSA infection have a greatly increased susceptibility to a subsequent invasive MRSA infection. The BioPlx technology provided herein works by occupying the niche in the microbiome that would normally have the potential to be occupied by a virulent form of MRSA.

Invasive MRSA-Caused Systemic Infection:

SA, including the variant MRSA, can exist in harmless coexistence on the surface of the skin and mucous membranes of at least 40% of all humanity, so the bacterium itself is not descriptive of disease; rather, its clinical presentation is definitional.

The whole of national and international authorities that define and monitor this condition concur that invasive MRSA infection is a separate and distinct disease from other conditions caused by this bacterium.

Simple colonization with any type of *Staphylococcus aureus* should not be considered a disease state. In fact, those humans with nutritional and environmental characteristics of their skin and mucosal biomes that are hospitable to *Staphylococcus aureus* must have some such niche occupant as part of their microbial flora to achieve a stable balanced "resting state" of their biome. The goal of any method would be to durably replace a MRSA strain on an at-risk patient with the product strain—in this case an antibiotic sensitive *Staphylococcus aureus* modified to be unable to survive within the human body in the invasive state.

To create invasive infectious disease, MRSA must abandon its passive commensal status, and breach the dermal/mucosal barrier, entering into the subdermal interstitial (interstitial fluid) or circulatory (blood, serum, plasma) areas. This "state change" initiates a new disease state, with new organism behaviors and relationships to the host.

*Staphylococcus aureus* bacteremia (SAB) is an important instance of this type of infection with an incidence rate ranging from 20 to 50 cases/100,000 population per year (ranging from 64,600 to 161,500 cases per year). Between 10% and 30% of these patients will die from SAB. Invasive systemic MRSA bacteremia has a mortality rate of around 20%. Comparatively, this accounts for a greater number of deaths than for AIDS, tuberculosis, and viral hepatitis combined.

The latest report for which there is a CDC-US national case estimate for invasive MRSA disease (2014) is 72,444 cases. The number of patients with this disease is less than 200,000 per annum, and it may permit an orphan drug designation. MRSA can impact patients at three distinct levels: 1) colonization. 2) superficial infection—skin and soft tissue, and 3) systemic invasive infection.

1) Colonization. *Staphylococcus aureus* is a normal commensal organism permanently colonizing around one third of the human population, with transient colonization occurring in about one additional third of the population. MRSA variants of this organism occupy organism the microbiome niche, and have colonized approximately 2% of the population in the US (with a high degree of variability depending on location and occupation). MRSA colonization creates a standing reservoir of potentially infectious organisms located directly on the outer layer of our immune/defense system, and this poses an ongoing risk to the patient.

2) Superficial infection—skin and soft tissue infection. Skin-associated MRSA or skin and soft tissue infection is the most common of the two major disease state categories. It typically starts as a swollen, pus or fluid filled, boil that can be painful and warm to the touch, and at times accompanied by a fever. If left untreated, these boils can turn into abscesses that require surgical intervention for draining. For MRSA that's confined to the skin, surgical draining of abscesses may be the only necessary treatment, and antibiotics are not indicated. Skin and soft tissue infections are treated by surgically draining the boil and only administering antibiotics when deemed absolutely necessary.

3) Systemic invasive infection. MRSA bacteremia (invasive MRSA) is a systemic MRSA infection that is defined as the presence of MRSA in typically sterile sites, including the bloodstream, cerebrospinal fluid, joint fluid, bone, lower respiratory tract, and other body fluids. MRSA bacteremia bas a far worse prognosis compared to MRSA infections confined to the skin, with 20% of cases resulting in death. The difference in prognosis, location of the infection, and clinical symptoms of the condition make it clinically distinct from skin and soft tissue infection MRSA infections. MRSA bacteremia causes multiple complications not seen in skin and soft tissue infections, including infective endocarditis, septic arthritis, and osteomyelitis. For invasive MRSA, daptomycin and vancomycin are recommended treatments in the U.S. Vancomycin has a relatively slow onset and poorly penetrates some tissues. Daptomycin has been shown to be effective, but treatment-emergent nonsusceptibility is an issue, in addition to the issue of vancomycin encouraging daptomycin resistance in MRSA. The difference in clinical symptoms as well as treatment methods for invasive MRSA provides clear evidence for invasive MRSA as & clinically distinct condition from MRSA Skin and soft tissue infections.

The BioPlx technology works by preventing the recurrence of an invasive MRSA infection in those who have been colonized (including those that have already experienced an invasive MRSA infection) and who have undergone a decolonization procedure. As a decolonization/recolonization microbioic method, the BioPlx technology would not be administered to "treat" a patient while they had a systemic MRSA infection. It would be applied subsequent to the clearance of a systemic MRSA infection (and a full body decolonization).

It is an established principle of medical nomenclature that a disease or condition is not simply synonymous with the causative agent. In the present case, MRSA-mediated systemic bacteremia (or other designations of invasive systemic disease) is unambiguously distinct from the other superficial skin and mucosal conditions that may be caused by, or associated with, MRSA, or by other *Staphylococcus aureus* strains. Invasive systemic MRSA-mediated disease has a clearly distinct diagnosis, pathology, treatment, and prognosis profile.

It's important to note that, based on the mechanism of action of BioPlx01 strains, patients are prevented from subsequent systemic MRSA infection, as opposed to treatment of invasive MRSA infection per se. So, "prevention of recurrent systemic MRSA infection" would be the most accurate description of the indication for BioPlx01 strains.

The target population of patients that have had invasive MRSA Infection, have been successfully cleared of the organism (typically through standard antibiotic intervention (e.g. Vancomycin), and yet have a high risk (rate) of MRSA recolonization, recurrence and the associated elevated risk of MRSA systemic reinfection.

International and US Recognition of the Disease Designation:

A clear definition of this disease is put forth by the Centers for Disease Control and Prevention (CDC) as it has been actively monitoring this condition in the United States since 2005. The agency performs this monitoring utilizing the Active Bacterial Core surveillance system via the Emerging Infections Program (EIP). A case in this context is defined by the isolation of MRSA from a normally sterile body site. Normally sterile sites included blood, cerebrospinal fluid, pleural fluid, pericardial fluid, peritoneal fluid, joint/synovial fluid, bone, internal body site (lymph node, brain, heart, liver, spleen, vitreous fluid, kidney, pancreas, or ovary), or other normally sterile sites.

The CDC also created the National Healthcare Safety Network (NHSN) as a tracking system for more than 16,000 US healthcare facilities to provide data to guide prevention efforts. The Center for Medicare Services (CMS) and other payers use this data to determine financial incentives to healthcare facilities for performance. The system tracks MRSA bloodstream infections as a marker for invasive disease for epidemiologic purposes.

The MRSA mediated invasive disease state is also codified in the ICD9 and ICD10 system by a grouping of conditions each with their own numeric code specific for the causative agent MRSA. For example, sepsis due to MRSA is coded A41.02, pneumonia due to MRSA is coded J15.212. This further exemplifies the differential characterization that invasive MRSA disease is given in juxtaposition to superficial skin and soft tissue disease due to the same agent-code L03.114 (left upper limb example) with the follow code of B95.6 MRSA as the cause of disease classified elsewhere, which is attached to a variety of other infection codes to indicate MRSA as the cause of the disease condition.

The European Center for Disease Control (ECDC), a branch of the EU also surveilles invasive *Staphylococcus aureus* isolates by similar definition to the NHSN and tracks methicillin-resistance percentages but the reporting requirements do not produce an EU estimate of total annual cases.

Differentially, unlike systemic conditions, simple MRSA colonization is not itself typically regarded as a disease. Colonization however is considered a precondition for most invasive disease, as evidenced (for example) by studies that show that nasal *Staphylococcus aureus* isolates are usually identical to strains later causing clinical infection. This persistent colonization state reflects the ecological stability of this bacteria on skin and mucosal surfaces.

This colonization state is recorded in the ICD10 system, Z22.322, under the Z subheading which is reserved for factors influencing health status and contact with health services but not an illness or injury itself.

The Target Orphan Disease Population:

The orphan disease population targeted for the BioPlx non-recurrence method is the group of people previously invasively infected (systemic infection) with MRSA (a population known to be susceptible), and who continue to suffer ongoing recolonization with MRSA. CDC monitors all U.S. cases of invasive MRSA infection. Multiple researchers have described this medically distinct population-patients who have already suffered one defined episode of invasive MRSA infection. This group is at increased risk for life threatening invasive disease as a result of their demonstrated susceptibility and their continued colonization.

In some embodiments, a method is provided for preventing recolonization, or preventing recurrence of MRSA-caused systemic invasive bacteremia, comprising prevention of (or prevention of recurrence of) a prerequisite MRSA colonization by 1) decolonization of MRSA from mucosal and dermal microbiomes, and
2) recolonization of these microbiomes with a synthetic *Staphylococcus aureus* (e.g., a BioPlx01 strain). The method is effective, through the effect of bacterial interference, operating through niche dynamics within the target dermal/mucosal microbiome ecosystem, because the synthetic *Staphylococcus aureus* (e.g., a BioPlx01 strain) serves to occupy specific niches, and thus blocks/prevents MRSA recolonization (blocks recurrence). The efficacy of this method has been demonstrated clearly in proof of principle studies provided herein.

SA is present as part of the normal microbiome of more than 40% of the total human population. The MSSA colonization state is common. The MRSA variant is found on around 1-2% of the US population, but in certain areas or demographics this level can be considerably higher. It is thought that MRSA has the ability colonize anyone within the *Staphylococcus aureus* susceptible population. *Staphylococcus aureus* lives most commonly on the surface of the skin and in the anterior nasal vestibules, but can also be found in smaller amounts in the deep oropharynx and gastrointestinal tract and in normal vaginal flora in some individuals.

In colonized individuals *Staphylococcus aureus* usually remains a non-invasive commensal bacterium simply occupying an ecologic niche and not causing disease. In a portion of those colonized however, this bacteria can cause disease either opportunistically or as a result of the increased likelihood of invasion due to some particular variant characteristics.

Approximately 23% of persistent MRSA carriers developed a discrete MRSA infection within one year after identification as a carrier.

Many *Staphylococcus aureus* variants have acquired genetic cassettes coding for virulence protein products that allow such strains to more effectively invade through the epidermal or mucosal tissue layers, and subsequently initiating deep or systemic infection. In colonization or infection the presence of the mecA cassette limits the treatment options for these patients, and a number of studies have documented the increased mortality rate associated with MRSA when compared to MSSA in bacteremia, endovascular infection and pneumonia.

It is not possible to predetermine whether an individual who is colonized with MRSA will eventually progress to invasive disease or not, so it is particularly important to identify and treat the entire population of patients who have a well-documented increased risk for invasive MRSA disease.

MRSA-Mediated Invasive Disease Statistics:

MRSA was identified by British scientists in 1961 and the first American clinical case was documented in 1968. For the next 25 years, MRSA was regarded largely as an endemic hospital-based problem that was increasing in incidence, however starting in the mid to late 19909, an increase of incidence of community-associated MRSA was seen mostly manifesting in superficial skin and soft tissue infections. Of greatest concern to the medical community has been the increase in invasive infections caused by MRSA. The increasing trend in incidence of invasive MRSA disease was seen throughout the 1990s and peaked in 2005.

The CDC tracks the incidence of invasive MRSA disease through the NHSN and the Emerging Infections Program—Active Bacterial Core surveillance system also starting in 2005. As compared to 2005, 2015 data shows that the overall incidence for invasive MRSA disease has decreased almost 50% from an incidence rate of 37.56 to 18.8. Expensive and laborious infection control interventions enacted in hospitals in response to this public health crisis has been given much of the credit for the decreased incidence, as the majority of the gain was seen in health care associated cases as opposed to community associated ones. Despite the gains that have been made over the past decade, invasive MRSA infections continue to be a prioritized public health issue. These infections can be very difficult to treat and treatment failure has been shown in nearly 25% of patients on proper therapy. Predicting which health care experienced patients are at risk for invasive MRSA is a challenging problem. Risk factors such as MRSA colonization, the presence of chronic open wounds and the presence of invasive devices have been elucidated.

The presence of these characteristics alone do not predict which patient will ultimately display invasive disease. However, one of the most predictive risk factors for a patient getting an invasive MRSA infection is having had a previous invasive MRSA infection. In the 2004-2005 data from the Active Bacterial Core Surveillance (ABCs) it was noted that almost 13% of their invasive cases went on to develop a second invasive MRSA infection during the 18 months of retrospective data evaluation. Another look at the EIP-ABC data in the calendar year 2011 found that 8% of these patients had more than one invasive MRSA infection separated by at least 30 days. The longer term risk of recurrent invasive MRSA infection is surely greater still as these estimates will miss earlier infections in these patients prior to the study time period and later ones that occur after the end date. Since Huang and Platt (2003) showed that 29% of hospitalized patients with known MRSA colonization or infection went on to develop a second MRSA infection (often severe) within an 18 month follow up, targeting this group to prevent recurrence of the invasive disease state could prevent approximately 17,500 subsequent invasive MRSA infections (using the most recent CDC data).

Invasive MRSA and skin and soft tissue infection from MRSA are both caused by the same pathogen. However, orphan designations are awarded based on the dyad of drug and disease. MRSA is a pathogen, and not a disease state. However, it can cause infection, and it's these different types of infectious disease that are being treated. Invasive MRSA comes with a far more severe prognosis as well as different clinical manifestations from MRSA confined to the skin or simply being colonized with MRSA. About 40% of the U.S. population is colonized with *Staphylococcus aureus*, typically found in the nose or on the skin. Generally, there are no signs of infection that would be considered "a disease state." However, systemic MRSA infection will manifest as high grade fever, chills, dizziness, chest pain, swelling of the affected area, headache, rash, cough, and other systemic symptoms. These two conditions are treated differently, where skin and soft tissue infections are typically treated by incising and draining the boils commonly associated with skin and soft tissue infections. Antibiotics and decolonization are only employed if there are signs of systemic or severe disease that has spread to multiple sites.

Invasive MRSA has an incidence rate of 20 to 50 cases/100,000 people per year.[6a] With a current U.S. population of 326,199,002 (accessed on Nov. 2, 2017 from www.census.gov/popclock), this means there are 163,100 cases of invasive MRSA infection in the U.S. per year conservatively, falling below the 200,000 patient criteria for FDA orphan designation. We searched for other sources of reported prevalence to confirm that we had calculated the most conservative estimate of this patient population. Hassoun et. al reported an incidence of 72,444 cases of invasive MRSA in the U.S. in 2014, which had decreased from 111,261 in 2005.[7a] Based on this, and assuming that the population will continue to decrease, we can assume that a prevalence of 163,029 patients with invasive MRSA in the U.S. in 2017 is a very conservative estimate. According to the CDC, there were more than 80,000 invasive MRSA infections and 11,285 related deaths in 2011.

To address this problem the present inventors have developed BioPlx01 strains, molecularly-altered strains of *Staphylococcus aureus* that are unable to cause disease but can reside in the microbiome niche that MRSA could take hold in. The lack of invasiveness of BioPlx01 strains is made possible by operons that are turned on upon contact with blood or plasma, triggering the death of the organism. A patient who has tested positive for MRSA and is experiencing systemic symptoms will undergo a full body decolonization before the BioPlx01 strain is administered, allowing it to occupy the niche that MRSA would have previously occupied in that patient's microbiome. By preventing virulent strains of MRSA from occupying the niche, these virulent strains cannot colonize, and subsequently invade sterile tissue sites. BioPlx01 strain is able to prevent recurrent systemic MRSA infections.

In one embodiment, a method for treatment of *Staphylococcus aureus* lung infections in patients with cystic fibrosis is provided.

In one embodiment, a method for treatment of Invasive Bacteremia is provided. Using the criteria adopted by CDC (Centers for Disease Control and Prevention), Invasive Bacteremia is indicated by the isolation of bacteria from a normally sterile body site. These may include blood, CSF, joint fluid, bone samples, lower respiratory tract samples and other sterile body fluids. This condition is related to, but is clearly distinguished from, simple bacterial colonization and bacteria mediated skin and soft tissue infection. It is accepted that the colonization state is a prerequisite for invasive disease in the vast majority of cases.

MRSA and v-MSSA Mediated Invasive (Systemic) Bacterial Infection

Mediated by *Staphylococcus aureus*, MRSA Invasive Bacterial Infection may also be referred to commonly or in the literature as: MRSA bacteremia or sepsis, Systemic MRSA infection, MRSA bloodstream infections, invasive MRSA infection. Specific MRSA induced systemic conditions range from osteomyelitis, septic arthritis, pneumonia, endocarditis, bacteremia, toxic shock syndrome, to septic shock. The development of a method to prevent or reduce the recurrence of invasive MRSA disease in high-risk populations, through the mechanism of durably interfering with colonization of undesirable strains, would be a significant advance in the prevention of conditions typically required for invasive MRSA infection, and would reduce the likelihood of these patients suffering a subsequent invasive MRSA infection.

One objective of the present disclosure is to evaluate the BioPlx-01 WT material's ability to prevent the recurrence of MRSA in active healthy adult medical workers. This population is particularly at-risk for MRSA infection and has amongst the highest rates of MRSA colonization of any demographic. Successfully demonstrating a protective effect for this group would validate BioPlx-01 WT's efficacy in being able to prevent MRSA recurrence amongst effectively all those who are at risk.

"Recurrence" simply means "the bug comes back". Recurrence is of central importance to both disease evolution and control. With recurrence, the pathogen comes back again and again, and each time it goes through a survival cycle it "learns" to be more and more resistant to the antibiotics it has seen. Without this recurrence, once the pathogen is gone, it would stay gone, and that would be that. If there were no recurrence, there would be no pressure to evolve toward antibiotic resistance.

In various embodiments, the subject may be colonized with one or more pathogenic microorganisms. In certain embodiments, the undesirable microorganism is a drug-resistant pathogenic microorganism. The drug-resistant pathogenic microorganism may be selected from a *Neisseria gonorrhoeae*, fluconazole-resistant *Candida*, MRSA, drug-resistant *Streptococcus pneumoniae*, drug-resistant Tuberculosis, vancomycin-resistant *Staphylococcus aureus*, erythromycin-resistant Group A *Streptococcus*, and clindamycin-resistant Group B *Streptococcus*. https://www.cdc.gov/drugresistance/biggest_threats.html.

In one embodiment, the undesirable microorganism may be a drug-resistant pathogenic *Staphylococcus aureus*.

Staphylococci are the most abundant skin-colonizing bacterial genus and the most important causes of nosocomial infections and community-associated skin infections. The species *Staphylococcus aureus* may cause fulminant infection, while infections by other staphylococcal species are mostly subacute. Colonization is usually a prerequisite for infection. Otto 2010, Expert Rev Dermatol 2010 April; S (2): 183-198. However, not all invasive *Staphylococcus aureus* infections are preceded by detected colonization with identical strain. The non-correlative fraction may be explained either by the "direct inoculation" or "direct wound seeding" theory such as an intraoperative event from a second carrier, or incomplete detection of all of these patient's *Staphylococcus aureus* strains in colonization or colonization with the invasive strain in the time since the initial colonization surveillance.

SA is a common human commensal organism that is present (colonizes), typically without symptoms, in 30 to 50% of the (US) population. The asymptomatic carriage of *Staphylococcus aureus* by humans is the primary natural reservoir, although domestic animals, livestock, and fomites may serve as adjunctive reservoirs.

There are many different strains of *Staphylococcus aureus*, many of which can also act as serious pathogens. Symptoms of *Staphylococcus aureus* infections can be diverse, ranging from none, to minor Skin and soft tissue infections, to invasive life-threatening systemic disease such as endovascular infections, pneumonia, septic arthritis, endocarditis, osteomyelitis, foreign-body infections, sepsis, toxic shock and endocarditis. The anterior nasal mucosa has traditionally been thought to be the most frequent site for the detection of colonization of healthy carriers with *Staphylococcus aureus*. Several sites may become asymptomatically colonized including the nares, throat, axilla, perineum, inguinal region, and rectum.

MRSA isolates were once confined largely to hospitals, other health care environments, and patients frequenting these facilities. Since the mid-1990s, however, there has been an explosion in the number of MRSA infections reported in populations lacking risk factors for exposure to the health care system. This increase in the incidence of MRSA infection has been associated with the recognition of new MRSA clones known as community-associated MRSA (CA-MRSA), CA-MRSA strains differ from the older, health care-associated MRSA strains; they infect a different group of patients, they cause different clinical syndromes, they differ in antimicrobial susceptibility patterns, they spread rapidly among healthy people in the community, and they frequently cause infections in health care environments as well. David, Michael et al., 2010, Clin Microbiol Rev 23(3): 616-687.

Why recurrent CA-MRSA Skin and soft tissue infections are common is not known. The mechanism by which recurrence occurs is unclear. Possibilities include reinfection from persistent asymptomatic CA-MRSA carriage or after acquisition from environmental MRSA or after new MRSA acquisition from close human or animal contact. Skin and soft tissue infections caused by MSSA also recur but less frequently than those caused by MRSA.

Under constant antibiotic pressure, many *Staphylococcus aureus* variants have developed antibiotic resistance. Today penicillin resistance in *Staphylococcus aureus* is virtually universal, and general beta-lactam and related multi-antibiotic (methicillin) resistance is now widespread, creating a significant new class of antibiotic-resistant "super-bugs".

The pathogenic *Staphylococcus aureus* may be a drug-resistant *Staphylococcus aureus*, such as MRSA, or a vancomycin-resistant strain, such as VISA or VRSA. Alternatively, the pathogenic *Staphylococcus aureus* may be a virulent methicillin-susceptible *Staphylococcus aureus* (v-MSSA). v-MSSA is a high-virulence cause of life-threatening invasive infections. MRSA and v-MSSA are epidemic, and have a high human cost.

MRSA has become a serious public health problem in hospitals, clinics, prisons, barracks, and even in gyms and health clubs around the world. MRSA is a common cause of hospital-acquired infections (500 k US patients/year), and increasingly, of community acquired infections which can be serious. For systemically invasive disease –20% of cases result in death. MRSA is one of the most significant of the new antibiotic-resistant "super-bugs". While methods to treat *Staphylococcus aureus* infection exist, methods to prevent recurrence are effectively nonexistent. Recurrence of MRSA skin infections is found in 31% to 45% of subjects.

One effort to prevent recurrence includes decolonization. The first (and currently only) widely practiced step for preventing recurrence is decolonization. Unfortunately, simple decolonization is poor at preventing recurrence. Doctors can initially treat the microbial colonization or infection—for example MRSA or v-MSSA colonization/infection—with topical chemicals (e.g. chlorhexidine) or antibiotics. In many cases treatment with antibiotics may "clinically" eliminate the disease. Antiseptics and astringents may be used for decolonization (i.e., suppression) including tea tree oil and chlorhexidine. Antibiotics used for suppression include topical antibiotics for nasal decolonization such as mupirocin. Systemic antibiotics most frequently used for MRSA include vancomycin, first generation antibiotics such as cefazolin, cepahalothin, or cephalexin; and new generation antibiotics such as linezolid or daptomycin. In less serious MRSA cases, clindamycin or lincomycin may be employed. Nonetheless, with this decolonization alone the MRSA and v-MSSA pathogens typically recur- or grow back-nearly ½ of the time. This level of performance has naturally led to skepticism as to the efficacy of simple decolonization in preventing recurrence.

Clinicians often prescribe topical, intranasal, or systemic antimicrobial agents to patients with recurrent skin infections caused by methicillin-resistant *Staphylococcus aureus* (MRSA) in an effort to eradicate the staphylococcal carrier state. Some agents can temporarily interrupt staphylococcal carriage, but none has been proved effective for prevention of skin infections caused by MRSA. Creech et al. *Infect Dis Clin North Am.* 2015 September; 29(3): 429-464.

In both the literature and in the hands of the present inventors, it has been found that the quality of decolonization is correlated to the recurrence rate observed, but simple decolonization rarely resulted in a durable, successful, outcome.

The present disclosure provides methods and compositions focused on preventing recurrence through the effective and durable modification of microbiome populations.

Methods for preventing or decreasing recurrence of a pathogenic microbial infection have been developed comprising suppressing a microbial infection or colonization.

A method to decrease recurrence of a pathogenic infection or decrease colonization of a undesirable microorganism in a subject is provided, comprising decolonizing the undesirable microorganism on at least one site in the subject to significantly reduce or eliminate the presence of the undesirable microorganism from the site; and replacing the undesirable microorganism by administering to the subject a synthetic second microorganism having the same genus and species as the undesirable microorganism.

The methods and compositions to prevent recurrence include replacement of the pathogenic microorganism by filling the biome niche occupied by the pathogen with a specially designed synthetic microorganism—or "good bug". By occupying the same biome niche, the "good bug" crowds out the pathogen, preventing it from recolonizing, or moving into (or back into) its preferred ecological neighborhood. One way to ensure the same biome niche is filled is by designing a synthetic microorganism starting from the same genus and species as the pathogenic microorganism.

The methods and compositions to prevent recurrence include promoting or supporting the synthetic microorganism—the "good bug"—by re-establishing key nutritional, chemical, or commensal environments that further promote the preferred organism and inhibit recolonization by the pathogen. For example, a commensal cluster may provide further layered defense in preventing the pathogen from moving back into its old ecological niche—it may help prevent recurrence.

The BioPlx method is enabled by state of the art methods/technologies including microbiomics, systems & computational biology; environment interactions (clusters & signaling); proprietary organisms (selected & modified); and variant and strain substitution strategies.

Replacement microorganisms are provided herein including (1) "BioPlx01-WT® variant"—a *Staphylococcus aureus* 502a wild-type microorganism with an established history of non-virulence and passive colonization which has been isolated, verified, and prepared for field trials using this strain cluster as described in Example 1; (2) "BioPlx01-KO® engineered variant", a synthetic *Staphylococcus aureus* strain that enhances safety by knocking out specific virulence genes; and (3) "BioPlx01-KS® engineered variant", a synthetic *Staphylococcus aureus* strain that embeds a molecular programmed cell death trigger to prevent invasive virulence. In some embodiments, the synthetic microorganism acts purely as a substitution for the pathogenic strain, without "new" infection or colonization.

An extensive proprietary library of fully characterized *Staphylococcus aureus* cultures (strains and variants) has been developed which is used for replacement organism sourcing; used for durability and competition analysis; used for Genotype/Phenotype comparative analysis; used for virulence genome/transcriptome clustering modeling; and used for signaling genome/transcriptome clustering modeling.

A Library of controlled commensal organisms is being developed for potential variant cluster co-administration with the BioPlx01-KS® variant.

Methods for Computational Microbiology are also being developed including Machine Learning: Modeling of complex dynamic microbiomic systems; Genome/Transcriptome/Proteome (Phenotypic) relationships; Virulence factor genetics and promoters; Modeling resilience and changes over time/condition; n-dimensional niche-forming relationships; and High dimensional cluster relationships.

Central to the present model anti-recurrence method is the principle of "non-co-colonization", meaning that only one species, and one variant of that species, can occupy the relevant skin or mucosal biome ecological niche at any one time. Underlying this simple and testable phenomenon are a host of deeper generative principles that combine to shape the emerging science of Microbiomics. Although widely generalizable, discussion of non-co-colonization in this section refers specifically to *Staphylococcus aureus* colonizations.

Non-Co-Colonization

The principle of non-co-colonization (also known as "bacterial replacement") states that only one variant/strain of one species can occupy any given niche within the biome at any given time.

The central empirical phenomenon of non-co-colonization represents an aggregate effect: the consequence of the interaction of a large number of forces that can be found operating in complex systems, and which are only today becoming well characterized and mathematized.

Bacterial niches within the human biome that are specific to the species level underlie the present technology. If there were no specificity to biologic niche occupation, then intentional strain exchange would not be achievable, as would the experimentally demonstrated phenomenon of bacterial replacement.

Expectations for non-co-colonization are important for durability of the present method for prevention of recurrence of pathogenic colonization or infection. Variant-to-variant non-co-colonization has been demonstrated experimentally in the literature with strain/variant substitution (e.g., the *Staphylococcus aureus* 80/81 to 502a conversions of Shinefield et al., 1963) and has been confirmed in present clinical studies, as shown in Example 1.

Sustained species-to-species niche occupation is suspect because careful reading of the literature indicates that durability is low, and in vivo evidence is rare. A transient occupation may occur, but is not considered to be an important outcome, as we are only interested in durable outcomes.

Failure of durability in species-to-species substitution serves as evidence that specific niche-filling requires a "close variant" substitution. This is significant as only durable biomes can display the functional characteristics (such as resilience) required for an effective non-recurrence technology/product.

In the case of variant-to-variant replacement, such as that seen in the present disclosure with respect to MRSA anti-recurrence materials, no direct evidence from the literature has been identified as to whether the replacement requires a "biome disruptive event" (such as accidental or intentional decolonization by antimicrobials, antibiotics, etc.) or whether it can occur via a "slow competitive replacement" (one organism out competing another for resources, growth, etc.). However, overwhelmingly in human dermal biomes, only one strain colonizes a person "in toto", indicating that slow competitive replacement occurs. Further, the 55% success rate of anti-MRSA decolonization methods show that "biome disruptive events" can also induce durable biome changes. Both of these phenomena are expressions of non-co-colonization.

Non-co-colonization occurs in nature, for example, in the vast majority of cases only one variant of *Staphylococcus aureus* is detected within a single biome (over 95% of cases, with the balance likely caused by "transient conditions").

In specifying and evaluating non-co-colonization durability (efficacy) it is necessary to recognize three distinct scales of outcomes: (1) short-term—immediately post recolonization, (2) early stable stage-after shedding excess organisms, and (3) long-term—after a stable "new" biome is established.

In the short-term—immediately post recolonization, the decolonized biome is dominated by organisms applied "in excess" during recolonization—generating a type of adventitious and transient binding (like spreading peanut butter). Testing within this period can only confirm that the biome application has occurred. Duration=a few days, with subsequent shedding of excess organisms.

In the early stable stage—after shedding excess organisms, the biome per se is reestablishing its equilibrium state, but ostensibly with the replacement organism rather than the pre-existing pathogen. Confidence in this outcome is primarily due to the overwhelmingly large ratio (probably millions to one) of new organisms to surviving post-decolonization pathogens. It is expected that this will become a stable colonization with a high level of durability. Testing at this period would confirm that MRSA or vMSSA has been eliminated, and replacement strain has been re-colonized. Duration=weeks to months.

In the long-term—after stable "new" biome established will demonstrate not only the organism's ability to occupy or "take" a niche, but its ability to "hold" that niche. In some embodiments, this stage is used to evaluate how competitive the replacement strain or synthetic microorganism is against the current generation of new biome invaders (such as USA300). This question refers to the "new" replacement organism's ability to compete over time against a slow competitive replacement as well as by external forces that could be biome disruptive over time such as antibiotic or antiseptic exposures or frequent re-exposure to the pathogen—especially if the strains are differentially sensitive to this disruptor.

It is important to characterize the phenomenon of microorganism variant non-co-colonization, variant-versus-variant niche occupation, and the empirical evidence already developed that this phenomenon exists and is a strong force in the dermal biome ecosystem.

The law of "competitive exclusion" refers to the situation where only one organism dominates one niche.

One historical error in understanding this phenomenon is assuming this is a binary system, conceptually driven by either one or two variants. In fact, a large number of different microorganisms, for example various *Staphylococcus aureus* strains may be environmentally present at any one time, and over time.

It may be concluded that without the phenomenon of non-co-colonization, virtually all "staph-capable" biomes would inherently be highly variable mixed heterologous "soups" of multiple variants. Various possibilities are shown in Table 1.

TABLE 1

*Staphylococcus aureus* (SA) niche compatibilities and expected outcomes

| case | Niche compatibility | Competitive exclusion | Expected Outcome |
|---|---|---|---|
| 1) | one *Staphylococcus aureus* niche | + | one variant dominates (except transitional) |
| 2) | one *Staphylococcus aureus* niche | – | always large number of variants (soup) |
| 3) | multi *Staphylococcus aureus* niches | + | any smaller # of variants = # of discrete niches |
| 4) | multi *Staphylococcus aureus* niches | – | always large number of variants (soup) |

In Table 1, cases 2 & 4 can be eliminated, because co-colonization occurs in under 5% (in literature), and even in these cases the vast majority of co-colonization instances observed involve only one other organism. Case 3 can be considered as possible in a low number of cases (less than 5%) potentially relating to incomplete or non-overlapping footprints of the niche vs replacement organism.

There is no direct evidence from the literature as to whether the observed replacement of one variant for another (e.g. acquisition of MRSA) is caused by a biome-disruptive event or from a slow competitive replacement. However, it is empirically clear that only one strain at a time tends to colonize any individual biome (in toto). Biogeographically distinct and distant sites within a given biome strongly tend to have the same variant, and this occurs without any observable total body decolonization and replacement process, indicating that a rule-driven competitive replacement process occurs. The observation of competitive replacement is another expression of the principle of non-co-colonization.

In hypothetical cases where the replacement variant does not fill the niche completely there may be a weak tendency to co-colonization. In these cases, a variant cluster may be used to "fill the slots" with alternatives so that the co-colonization favors a synthetic replacement microorganism rather than the original pathogen. While this may involve the use of a different replacement microorganism, this is not recurrence—this is further blocking of recurrence.

Current Evidence of Non-Co-Colonization

One large study looked at the prevalence of co-colonization in 3,197 positive *Staphylococcus aureus* samples taken from healthy patients in Oxfordshire, England followed longitudinally for up to two years; the point prevalence of having multiple strains of *Staphylococcus aureus* in nares samples was 3.4 to 5.8%. Votintseva et al., 2014 J Clin Microbiol, 52 (4): 1192-1200. Of the *Staphylococcus aureus* carriers who submitted swabs nearly every two months for two years, 11% had transient co-carriage. The study used an effective spa typing protocol that allowed for a sensitive procedure for finding even low proportion co-colonization strains. The interpretation of this data set shows that *Staphylococcus aureus* colonization is a dynamic process with low prevalence of multiple *Staphylococcus aureus* strains vying for presence in the same niche over time. A simple calculation can establish that the observed results are not simply the independent occupation of a non-specific niche. In this instance, 1000 patients were screened and 360 were found to be *Staphylococcus aureus* positive. In a non-specific niche scenario, 0.36×0.36, or 13%, (130 persons), would be expected to display co-colonization; however only 3.9% of the 360 carriers, (14 persons) at that primary point were in fact co-colonized, demonstrating the strain specificity of the microbiome niche for *Staphylococcus aureus*.

A small percentage of *Staphylococcus aureus* carriers may be transiently colonized with two different strains of *Staphylococcus aureus* at any incident time point. As discussed above, Votintseva et al, looked at all variants within MSSA and MRSA and reported point incidences of this phenomenon to be in the range of 3.4-5.8%. The paper looking only at mixtures of MRSA and MSSA (would only find species that differ at the mecA site) is predictably lower at 2.3%. If co-colonization was a stable state, mixtures of *Staphylococcus aureus* species would be expected in virtually all samples. This is not observed.

Another study looked at 680 patients presenting for any type of hospital admission. It was practice of the National Health Service at that time to screen all patients being admitted for MRSA. Dall'Antonia, M. et al., 2005, J Hospital Infect 61, 62-67. During this evaluation the protocol was refined to discover MSSA, MRSA and co-colonized MRSA and MSSA patients. MSSA alone was found in 115 patients (16.9%), MRSA alone was found in 56 patients (8.2%) and co-colonization was discovered in 4 patients (0.58%), again supporting the view of a strain-exclusive niche in the microbiome for *Staphylococcus aureus*. It supports the concept that one *Staphylococcus aureus* strain can prevent the establishment of another. The results suggested a lower percentage of co-colonized carriers as would be predicted by the null hypothesis indicating that there is a significant protective effect against one *Staphylococcus aureus* strain colonization by a previous occupying resident *Staphylococcus aureus* strain. The statistical significance was $p<0.01$. The protective effect of MSSA colonization against MRSA colonization was calculated to be 78% (CI: 29-99%).

A further study looked at non-concordant *Staphylococcus aureus* isolates in a population composed of HIV infected IV drug users in a methadone clinic. There were 121 baseline positive *Staphylococcus aureus* samples and 4 of these showed clear discordance among 3 colonies evaluated by PFGE. However, re-evaluation of these 4 samples showed that 2 of the 4 were concordant at second evaluation. No discordance was found after re-evaluating 18 samples first found to be concordant. Therefore 1.7-3.3% of this population was found to have co-colonization at a singular time point. Cespedes C. et al., J Infect Dis 2005; 191: 444-52.

Historical Evidence of decolonization/recolonization studies also show evidence of Non-Co-Colonization. This principle has been previously partially demonstrated during the 1960s and 1970s in the well-known 80/81 to 502a "bacterial interference" studies and clinical applications. Absence of co-colonization is shown in the early bacterial interference papers in the 1960s and 1970s, these papers also clearly demonstrate "competitive exclusion" in regulating co-colonization. Mixed cultures of both 80/81 as the resident strain and 502A as the donor strain were not observed, experimentally demonstrating non-co-colonization as a stable situation for the microbiome. (Shinefield et al., 1963; Shinefield at al., 1966; Shinefield et al., 1973; Aly et al., 1974; Boris et al., 1964; Light et al., 1967; Fine et al., 1967).

Without "non-equivalence" and "competitive exclusion", microbiome niches would consistently be filled with multiple strains of the same species of bacteria. The isolation in nature of a pure strain culture of *Staphylococcus aureus* from the nares would be a rare event if ever seen. The population dynamic in such a state would create a heterogeneous "soup" of many varieties of *Staphylococcus aureus*, as dictated by adventitious or random exposure from the environment. Any strain that the host has ever come in to contact with would have equal opportunity to colonize that space without competition or interference with any other strain variant (polyclonal colonization). The absence of this empirical result demonstrates "competitive exclusion".

Yet, the exclusion principle is not so rigid that once a niche is occupied no other variant can usurp its position. These observations demonstrate an exclusion principle that is robust, but that allows external species to challenge an occupying species by briefly sharing that niche while the ultimate competition for dominance in that space is being enacted. On some occasions "new" strains overcome the previous resident strain and establish a new dominant resident strain. On other occasions, the interloper is rebuffed and the resident strain repels the attempt at replacement and reestablishes singular dominance. In both of these scenarios, the co-colonized state is transient and unstable; present at a low frequency.

Microbiomic Systems

Methods and compositions are provided to durably and safely prevent recurrence of a pathogenic microbial infection in a subject, comprising suppression of a pathogenic microorganism, replacement with a synthetic microorganism capable of occupying the same niche to durably exclude the pathogenic microorganism, and promotion of the synthetic microorganism for durable residence within the niche. This method is termed the BioPlx® method, as discussed above. In some embodiments, the subject is found to be colonized with the pathogenic microorganism prior to the suppression step.

In order to successfully work within the microbiome to promote the colonization of a desired organism in such a way as to produce a durable protective outcome requires that we know the "rules" of microbiomes: as discussed in greater detail in the sections following.

A non-co-colonization model has been developed to provide context and establish target product characteristics. The rationale for the present technology rests on the Microbiomic paradigm (biome/ecosystem/niche), and on the Microbiome having certain persistent and verifiable characteristics. The key discoverable metric rests on co-colonization statistics in literature modified by specifics on decolonization, testing, and other relevant conditions, followed by direct observations from the clinical study of example 1.

The skin microbiome in the subject is an entity, a persistent identifiable thing. Over 10,000 different species of microorganisms make up the skin microbiome. The skin biome is an ecosystem which may be defined as a system, or group of interconnected elements, formed by the interaction of a community of organisms with their environment. The skin microbiome ecosystem has a "healthy", or "normal" base state. The biome can be "healthy" or "sick" (dysbiosis), and can be invaded by pathogenic organisms—in other words the Microbiome can be invaded by a "Bad Bug"—such as MRSA—it can also become infected or contaminated by undesirable organisms or variants (dysbiosis). Dysbiosis is a term for a microbial imbalance or maladaptation on or inside the body, such as an impaired microbiota.

The skin microbiome has a structure created by a vast combinatorial web of relationships between the host and all of the components of the biome. The microbiome, or biome, is a dynamically structured complex system and is an "elastically resilient" ecosystem. The skin microbiome has a dynamic but persistent structure—it is "resilient", for example, even under conditions of massive cell death (e.g. washing, using ethanol, hand sanitizer, etc.) the biome regenerates in a similar form.

Resilience

The human microbiome has the quality of resilience meaning that mild perturbations tend to re-correct toward a previous established baseline of species mixture and concentration. However, members of each niche can be successfully challenged for their place in that stable mixture either as a result of an acute external disruptive event (i.e. an antimicrobial medication or an antiseptic application) or as a slow competitive replacement.

In ecology, resilience is the capacity of an ecosystem to respond to a perturbation or disturbance by resisting damage and recovering quickly. Resilience refers to ecosystem's stability and capability of tolerating disturbance and restoring itself.

In the literature, the main mathematical definitions of resilience are based on dynamical systems theory, and more specifically on attractors and attraction basins. The human microbiome operates in many ways like a multi-basin complex system. It changes states or basins, but then resilience stabilizes that state. Martin, S. et al., 2011, in: Deffuant G., Gilbert N. (eds) Viability and Resilience of Complex Systems. Understanding Complex Systems. Springer, Berlin, Heidelberg, pp. 15-36.

The microbiome operates in many ways like a multi-attractor complex system—it can changes its states or basins, but then the resilience associated with that attractor stabilizes that state.

Ecological resilience is defined as the capacity of a system to absorb disturbance and reorganize while undergoing change so as to still retain essentially the same function, structure, identity and feedbacks. Mitra, C., et al., 2015, An integrative quantifier of multistability in complex systems based on ecological resilience, Nature, Scient. Rep., 5, 1-12.

The "competitive exclusion principle" provides that complete competitors cannot exist. The "axiom of inequality" states that no two things or processes in a real world are precisely equal. Hardin, 1960, Science, vol. 131, 1292-1297, p. 1292, Based on Hardin's 'Axiom of Inequality' and the Competitive Exclusion Principle, long-term durability should only be achieved by close variant substitution, but would not likely be available with respect to species substitution. For example, MRSA and MSSA can co-colonize briefly—just like any other variants of *Staphylococcus aureus* can co-colonize in transient fashion. See Dall'Antonia, M. et al., 2005, J Hospital Infect 61, 62-67, disclosing a study of 680 patients presenting for any type of hospital admission and screened all patients being admitted for MRSA. During this evaluation the protocol was refined to discover MSSA, MRSA and co-colonized MRSA and MSSA patients. MSSA alone was found in 115 patients (16.9%), MRSA alone was found in 56 patients (8.2%) and co-colonization was discovered in 4 patients (0.58%), again supporting the view of a strain-exclusive niche in the microbiome for *Staphylococcus aureus*. It supports the concept that one *Staphylococcus aureus* strain can prevent the establishment of another.

Resilience may create recurrence—an observed natural phenomenon—as the existing (MRSA contaminated) biome tries to preserve itself.

However, resilience can also prevent MRSA recurrence—as exhibited by methods and compositions provided herein. By suppressing a pathogenic microorganism such as MRSA ("bad bug") colonized in a subject, and replacing with a safe synthetic microorganism ("good bug") of the same species, it has been established that the "good bug" durably prevents recurrence of the "bad bug" (prevents MRSA re-invasion).

A historical example of resilience creating durable, persistent substitution is seen in *Staphylococcus aureus* carriers and replacement with strain 502a. Aly et al., 1974 J Infect Dis 129(6) pp. 720-724, studied bacterial interference in carriers of *Staphylococcus aureus*. The carriers were treated with antibiotics and antibacterial soaps and challenged with *Staphylococcus aureus* strain 502a. It was found that full decolonization was needed to get good colonization of 502a. Day 7 showed 100% take, but at day 23 the take was down to 60 to 80%. The persistence data was 73% at 23 weeks for well-decolonized subjects. Thus, long-term durability is only achieved by close variant substitution. Commensal microflora (normal microflora, indigenous microbiota) can help recolonization dynamics, but they do not fulfill close variant durability requirements. The inventors have designed a method for obtaining a "passive" version of an organism or pathogen (same species) that is to be "replaced" or "excluded".

A relative stability in the microbial ecosystem of adults in the absence of gross perturbation has been suggested, and that long-term stability of human communities is not maintained by inertia, but by the action of restoring forces within a dynamic system. Relman, D. A., 2012, Nutr Rev., 70 (Suppl 1): S2-S9.

Functional resilience is an intrinsic property of microbial communities and it has been suggested that state changes in response to environmental variation may be a key mechanism driving functional resilience in microbial communities. Song et al, 2015, *Frontiers in Microbiology*, 6, 1298. Seeking an integrated concept applicable to all microbial communities, Song et al. compared engineering and ecological resilience and reconciled them by arguing that resilience is an intrinsic property of complex adaptive systems which, after perturbation, recover their system-level functions and interactions with the environment, rather than their endogenous state.

Thus, a biome ecosystem has a dynamic but "stable elastoplastic equilibrium". Once perturbed the biome "tries" to return to equilibrium. At any given moment the biome ecosystem has an equilibrium "base state". Even under conditions of stress or massive cell death (e.g. washing, using ethanol, hand sanitizer, etc.) the biome is observed to typically regenerate in a similar form.

Microbiome ecosystems have "niches" defined by structure and internal and external interactions. One "fact" or "principal" of any biome structure is that different organisms occupy different "niches" in the biome, as defined/allowed by the structure of relationships. An ecological "niche" is the role and position a species has in its environment; how it meets its needs for food and shelter, how it survives, and how it reproduces. A species' niche includes all of its interactions with the biotic and abiotic factors of its environment. A biome "niche" has specific environmental factors and conditions including, for example, pH, temperature, osmotic pressure, osmolality, oxygen level, nutrient concentration, blood concentration, plasma concentration, serum concentration, and electrolyte concentration.

Different organisms occupy different "niches" in the biome, as defined/allowed by the relationships structure. Niches as durable features of the biome ecosystem. Each niche has boundary conditions; a virtual shape or "footprint" reflecting the shape, which is discussed in the context of the "Hutchinsonian niche".

The Hutchinsonian niche is an n-dimensional hypervolume, where the dimensions are environmental conditions and resources, that define the requirements of an individual or a species to practice "its" way of life, more particularly, for its population to persist. The "hypervolume" defines the multi-dimensional space of resources (e.g., light, nutrients, structure, etc.) available to (and specifically used by) organisms, and "all species other than those under consideration are regarded as part of the coordinate system."

A niche is a very specific segment of ecospace occupied by a single species. On the presumption that no two species are identical in all respects (i.e., Hardin's 'axiom of inequality') and the competitive exclusion principle, some resource or adaptive dimension will provide a niche specific to each species.

Niches are exclusive. Each organism competes with similar organisms for that niche, and the successful organism fills that niche. Two organisms do not/cannot fill the same niche because one will out-compete the other over time. Therefore, the coexistence of two organisms in the same biome over extended time periods means they do not fill the same niche.

Once a niche is left vacant, other organisms can fill that position. This is because one species does not have the same footprint as another species, so one species cannot fill the same niche as another species. Successful replacement requires that the same organism (e.g., same species or close variant) should be used to fill or durably replace within a niche. It is recognized that partial competition exists in the form of transient colonization/infection and is an observable phenomenon.

Partial competition for a single niche can occur. One organism can "narrow" the "niche width" of another by partial competition. This might be the case with *Staphylococcus epidermidis* vs. *Staphylococcus aureus. S. epidermidis* is a commensal bacterium that secretes a serine protease capable of disassembling preformed *Staphylococcus aureus* biofilms, when used in high enough concentrations. Sugimoto et al., J Bacteriol, 195(8) 1645-1655. However, there is an important distinction between an organism as a carrier of a toxic phenotypic expression (being temporarily massively overloaded by application at a site), vs that organism as a durable inhabitant of a niche that narrows or outcompetes the pathogen.

Interspecies co-colonization is a different phenomenon than the ability to durably fill and block an ecological niche. For example, Shu et al., 2013 demonstrate that fermentation of glycerol to form short chain fatty acids (SCFA) with *Cutibacterium acnes* (*C. acnes*), a skin commensal bacterium that can inhibit growth of USA300, the most prevalent community-acquired methicillin-resistant *Staphylococcus aureus* (CA-MRSA), Shu demonstrates that SCFAs produced by *C. acnes* under anaerobic conditions inhibits *Staphylococcus aureus* growth in high concentrations. Shu et al., 2013 PLOS ONE & (2): e55380, However, these bacteria and this fermentation capability of *C. acnes* are already present in the normal human skin biome without there being effective eradication or diminution of *Staphylococcus aureus* pathogenicity. There is not any reason to believe that a hyper-physiologic application of these substrates would accomplish the goal of reduction of *Staphylococcus aureus* colonization or incidence of disease.

Decolonization/Recolonization

A method is provided to prevent or decrease recurrence of a pathogenic infection of a undesirable microorganism in a subject, comprising the steps of (i) suppressing (decolonizing) the undesirable microorganism on at least one site in the subject to reduce or eliminate the presence of the undesirable microorganism from the site; and (ii) replacing the undesirable microorganism by administering to the subject at the at least one site a synthetic second microorganism having the same genus and species as the undesirable microorganism. Optionally, the method further comprises (iii) promoting colonization of the synthetic microorganism, for example, at the site of administration.

In some embodiments, the undesirable microorganism is a pathogenic microorganism and the term suppress(S) refers to a process of suppressing, reducing or eliminating the pathogenic microorganism at one or more, two or more, three or more, four or more sites in a subject. For example, the undesirable microorganism may be subject to nasal, mucosal, and/or dermal decolonization protocols.

The term replace (R) refers to replacing the pathogenic microorganism with a synthetic microorganism that is benign, drug-susceptible, and/or incapable of causing systemic or pathogenic infection in the subject. The replacement microorganism may be a molecularly modified synthetic microorganism of the same species as the pathogenic microorganism. The synthetic microorganism may be a molecularly modified microorganism of the same species, different strain, as the pathogenic microorganism, such that the synthetic microorganism is able to colonize the site on the subject, but is unable to cause systemic infection in the subject. By filling the vacated niche of the pathogenic microorganism, the synthetic microorganism is able to eliminate re-colonization by the pathogenic microorganism in the subject and thereby decrease or eliminate recurrence of pathogenic infection.

The term promote (P) refers to methods and compositions to promote replacement synthetic microorganism in the subject, for example, by employing prebiotics and biome management, for example, by employing a biome modulator in order to promote and support the new biome comprising the synthetic microorganism.

These methods broadly define a platform technology (SRP), with specifically designed protocols developed to address specific medical conditions (e.g. MRSA). If the processes of S, R, and P are selected properly—opening and then filling and sustaining a specific biome niche—a "durable" persistent biome is created that is capable of repelling pathogenic colonization.

A method is provided to decrease recurrence or chance of systemic infection of a pathogenic microorganism in a subject, the method comprising suppressing the pathogenic microorganism on the subject to significantly reduce or eliminate the detectable presence of the pathogenic microorganism; and replacing the pathogenic microorganism by administering a synthetic microorganism to the subject, wherein the synthetic microorganism is capable of occupying the same niche as the pathogenic microorganism as evidenced by (1) having the same genetic background, or genus and species, as the pathogenic microorganism, and/or by (2) exhibiting durable detectable presence on the subject for at least 60 days following replacement. The method may include promoting the colonization of the synthetic microorganism on at least one site in the subject. In some cases, the subject may have been found to be colonized by the pathogenic microorganism.

Frequently, systemic infection of a subject with a pathogenic microorganism is preceded by colonization of the pathogenic microorganism in the subject. For example, a substantial proportion of cases of *Staphylococcus aureus* bacteremia appear to be of endogenous origin since they may originate from colonies in the nasal mucosa. For example, in one multicenter study of *Staphylococcus aureus* bacteremia, the blood isolates were identical to those from the anterior nares in 180 of 219 patients (82.2%). In a second study, 14 of 1278 patients who had nasal colonization with *Staphylococcus aureus* subsequently had *Staphylococcus aureus* bacteremia. In 12 of these 14 patients (86%), the isolates obtained from the nares were clonally identical to the isolates obtained from blood 1 day to 14 months later. See von Eiff et al., 2001, NEJM, vol. 344. No. 1, 11-16. Another study showed the relative risk of *Staphylococcus aureus* bacteremia was increased multi-fold in nasal carriers when compared to non-carriers, reporting an 80% match between the invasive isolate and previously found colonizing strain. Wertheim et al., Lancet 2004; 364: 703~705.

In some embodiments, the subject is found to be colonized with the pathogenic strain of the microorganism prior to systemic infection. In other embodiments, the subject may have been colonized or infected by a nosocomial (hospital-acquired) strain or community-acquired strain of a pathogenic microorganism.

The pathogenic microorganism may be a wild-type microorganism, and/or a pathogenic microorganism that may be colonized or detectably present in at least one site in the subject. The site may be a dermal or mucosal site in the subject. The one or sites of colonization may include skin and soft tissue including, but are not limited to, nares, throat, perineum, inguinal region, vagina, nasal, groin, perirectal area, finger webs, forehead, pharynx, axillae, hands, chest, abdomen, head, and/or toe webs.

The pathogenic microorganism may be a drug resistant microorganism. The Centers for Disease Control (CDC) recently published a report outlining the top 18 drug-resistant threats to the United States, see www.cdc.gov/drugresistance/biggest threats. In some embodiments, the undesirable microorganism is selected from *Neisseria gonorrhocae*, fluconazole-resistant *Candida*, methicillin-resistant *Staphylococcus aureus* (MRSA), vancomycin-resistant *Staphylococcus aureus*, drag-resistant *Streptococcus pneumoniae* and drug-resistant tuberculosis, erythromycin-resistant Group A *Streptococcus*, and clindamycin-resistant Group B *Streptococcus.*

In some embodiments, the pathogenic microorganism is a MRSA.

The synthetic microorganism (a) must be able to fill the ecological niche in the at least one site in the subject so as to durably exclude the undesirable microorganism following suppression; and (b) must have at least one molecular modification comprising a first cell death gene operably linked to a first regulatory region comprising a first promoter that is activated (induced) by a change in state in the environment compared to the normal physiological conditions in at least one site in the subject.

The synthetic microorganism may be of the same genus and species as the undesirable microorganism, in order to enhance the ability to fill the niche and durably exclude the undesirable microorganism in at least one site in the subject.

In some embodiments, the disclosure provides a synthetic microorganism that is not a pathogen and cannot become an accidental pathogen because it does not have the ability to infect the subject upon change in state, e.g., upon exposure to blood or serum. The synthetic microorganism comprises at least one molecular modification comprising a first cell death gene operably linked to a first regulatory region comprising a first promoter that is activated (induced) by a change in state in the environment compared to the normal physiological conditions in at least one site in the subject. For example, if the site in the subject is a dermal or mucosal site, then exposure to blood or serum is a change in state resulting in cell death of the synthetic microorganism. For example, average cell death of the synthetic microorganism may occur within 6 hours, 5 hours, 4 hours, 2 hours, 90 minutes, 60 minutes, 45 minutes, 30 minutes, 20 minutes, 15 minutes, 10 minutes, 5 minutes, 2 minutes or 1 minute following change of state. The change in state may be a change in one or more of the following conditions: pH, temperature, osmotic pressure, osmolality, oxygen level, nutrient concentration, blood concentration, plasma concentration, serum concentration, and/or electrolyte concentration from that in at least one site in a subject. In some embodiments, the change in state is a higher concentration of blood, serum, or plasma compared to normal physiological conditions at the at least one site in the subject.

In one embodiment, the pathogenic microorganism is a MRSA. MRSA is a variant subgroup of *Staphylococcus aureus*. MRSA strains typically include a mecA cassette that allows production of an alternate penicillin binding protein that render them resistant to treatment with most beta-lactam and other first-line antibiotics. *Staphylococcus aureus* as a whole (including MRSA) is present as part of the normal microbiome of approximately 30% of the total human population. As part of the microbiome *Staphylococcus aureus* lives most commonly on the surface of the skin and in the anterior nasal vestibules, but can also be found in smaller amounts in the deep oropharynx and gastrointestinal tract and as part of the normal vaginal flora in some individuals.

In the vast majority of individuals *Staphylococcus aureus* remains a non-invasive commensal bacterium merely occupying an ecologic niche and not causing disease. The colonization state is far more common than that of invasive disease—some researchers estimate this ratio to be on the order of 1000 to one. Laupland et al., J Infect Dis (2008) 198:336, However, in a fraction of those colonized this bacterium can cause disease either opportunistically or as a result of increased tendencies toward invasion due to the acquisition of genetic cassettes coding for virulence protein products that allow such strains to more effectively invade through the epidermal or mucosal tissue layers initiating deep infection. In both above circumstances, the presence of the mecA cassette limits the treatment options for these patients and a number of studies have documented the increased mortality rate associated with MRSA when compared to MSSA in bacteremia, endovascular infection and pneumonia.

Definitions

The singular forms "a", "an" and "the" are intended to include the plural forms as well, unless the context clearly indicates otherwise.

The term "and/or" refers to and encompasses any and all possible combinations of one or more of the associated listed items.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs. In the event of conflicting terminology, the present specification is controlling.

The term "pathogen" or "pathogenic microorganism" refers to a microorganism that is capable of causing disease. A pathogenic microorganism may colonize a site on a subject and may subsequently cause systemic infection in a subject. The pathogenic microorganism may have evolved the genetic ability to breach cellular and anatomic barriers that ordinarily restrict other microorganisms. Pathogens may inherently cause damage to cells to forcefully gain access to a new, unique niche that provides them with less competition from other microorganisms, as well as with a ready new source of nutrients, Falkow, Stanley, 1998 *Emerging Infectious Diseases*, Vol. 4, No. 3, 495-497. The pathogenic microorganism may be a drug-resistant microorganism.

The term "virulent" or "virulence" is used to describe the power of a microorganism to cause disease.

The term "commensal" refers to a form of symbioses in which one organism derives food or other benefits from another organism without affecting it. Commensal bacteria are usually part of the normal flora.

The term "suppress" or "decolonize" means to substantially reduce or eliminate the original undesired pathogenic microorganism by various means (frequently referred to as "decolonization"). Substantially reduce refers to reduction of the undesirable microorganism by greater than 90%, 95%, 98%, 99%, or greater than 99.9% of original colonization by any means known in the art.

The term "replace" refers to replacing the original pathogenic microorganism by introducing a new microorganism (frequently referred to as "recolonization") that "crowds out" and occupies the niche(s) that the original microorganism would ordinarily occupy, and thus preventing the original undesired microorganism from returning to the microbiome ecosystem (frequently referred to as "interference" and "non-co-colonization").

The term "durably replace", "durably exclude", "durable exclusion", or "durable replacement", refers to detectable presence of the new synthetic microorganism for a period of at least 30 days, 60 days, 84 days, 120 days, 168 days, or 180 days after introduction of the new microorganism to a subject, for example, as detected by swabbing the subject. In some embodiments, "durably replace", "durably exclude", "durable exclusion", or "durable replacement" refers to absence of the original pathogenic microorganism for a period of at least 30 days, 60 days, 84 days, 120 days, 168 days, or 180 days after introduction of the new synthetic microorganism to the subject, for example, absence as detected over at least two consecutive plural sample periods, for example, by swabbing the subject:

The term "promote", or "promoting", refers to activities or methods to enhance the colonization and survival of the new organism, for example, in the subject. For example, promoting colonization of a synthetic bacteria in a subject may include administering a nutrient, prebiotic, and/or probiotic bacterial species.

The terms "prevention", "prevent", "preventing", "prophylaxis" and as used herein refer to a course of action (such as administering a compound or pharmaceutical composition of the present disclosure) initiated prior to the onset of a clinical manifestation of a disease state or condition so as to prevent or reduce such clinical manifestation of the disease state or condition. Such preventing and suppressing need not be absolute to be useful.

The terms "treatment", "treat" and "treating" as used herein refers a course of action (such as administering a compound or pharmaceutical composition) initiated after the onset of a clinical manifestation of a disease state or condition so as to eliminate or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method, compound or pharmaceutical composition of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method, compound or pharmaceutical composition of the disclosure.

The term "individual", "subject" or "patient" as used herein refers to any animal, including birds or mammals, such as mice, Norway rats, cotton rats, gerbils, cavies, hamsters, other rodents, rabbits, dogs, cats, swine, cattle, sheep, goat, horses, or primates, and humans. The term may specify male or female or both, or exclude male or female. In one aspect, the patient is an adult human. In another aspect, the patient is a non-neonate human infant. In another aspect, the patient is a human toddler, child, or adolescent. In some embodiments, the subject is found to be colonized with a pathogenic strain of a microorganism prior to a systemic infection, or the subject may have been colonized or infected by a nosocomial (hospital-acquired) strain or community-acquired strain of a pathogenic microorganism.

The term "neonate", or newborn, refers to an infant in the first 28 days after birth. The term "non-neonate" refers to an animal older than 28 days.

The term "effective amount" as used herein refers to an amount of an agent, either alone or as a part of a pharmaceutical composition, that is capable of having any detectable, positive effect on any symptom, aspect, or characteristics of a disease state or condition. Such effect need not be absolute to be beneficial.

The term "measurable average cell death" refers to the inverse of survival percentage for a microorganism determined at a predefined period of time after introducing a change in state compared to the same microorganism in the absence of a change in state under defined conditions. The survival percentage may be determined by any known method for quantifying live microbial cells. For example, survival percentage may be calculated by counting cfus/mL for cultured synthetic microorganism cells and counting cfus/ml of uninduced synthetic microorganism cells at the predefined period of time, then dividing cfus induced/mL by cfus/mL uninduced×100=x % survival percentage. The measurable average cell death may be determined by 100%−x % survival percentage=y % measurable average cell death. For example, wherein the survival percentage is 5%, the measurable average cell death is 100%−5=95%. Any method for counting cultured live microbial cells may be employed for calculation of survival percentage including cfu, OD600, flow cytometry, or other known techniques. Likewise, an induced synthetic strain may be compared to a wild-type target microorganism exposed to the same conditions for the same period of time, using similar calculations to determine a "survival rate" wherein 100%−survival rate=z % "reduction in viable cells".

The term "including" as used herein is non-limiting in scope, such that additional elements are contemplated as being possible in addition to those listed; this term may be read in any instance as "including, but not limited to."

The term "animal" refers to the animal kingdom definition.

The term "substantial identity" or "substantially identical," when referring to a nucleotide or fragment thereof, indicates that, when optimally aligned with appropriate nucleotide insertions or deletions with another nucleotide (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleotide molecule having substantial identity to a reference nucleotide molecule may, in certain instances, encode a polypeptide having the same or substantially similar amino acid sequence as the polypeptide encoded by the reference nucleotide molecule.

The term "derived from" when made in reference to a nucleotide or amino acid sequence refers to a modified sequence having at least 50% of the contiguous reference nucleotide or amino acid sequence respectively, wherein the modified sequence causes the synthetic microorganism to exhibit a similar desirable attribute as the reference sequence of a genetic element such as promoter, cell death gene, antitoxin gene, virulence block, or nanofactory, including upregulation or downregulation in response to a change in state, or the ability to express a toxin, antitoxin, or nanofactory product, or a substantially similar sequence, the ability to transcribe an antisence RNA antitoxin, or the ability to prevent or diminish horizontal gene transfer of genetic material from the undesirable microorganism. The term "derived from" in reference to a nucleotide sequence also includes a modified sequence that has been codon optimized for a particular microorganism to express a substantially similar amino acid sequence to that encoded by the reference nucleotide sequence. The term "derived from" when made in reference to a microorganism, refers to a target microorganism that is subjected to a molecular modification to obtain a synthetic microorganism.

The term "substantial similarity" or "substantially similar" as applied to polypeptides means that two peptide or protein sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions.

The term "conservative amino acid substitution" refers to wherein one amino acid residue is substituted by another amino acid residue having a side chain (R group) with similar chemical properties, such as charge or hydrophobicity. In general, a conservative amino acid substitution will not substantially change the functional properties of the, e.g., toxin or antitoxin protein. Examples of groups of amino acids that have side chains with similar chemical properties include (1) aliphatic side chains; glycine, alanine, valine, leucine and isoleucine: (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Polypeptide sequences may be compared using FASTA using default or recommended parameters, a program in GCG Version 6.1. FASTA (e.g., FASTA2 and FASTA3) provides alignments and percent sequence identity of the regions of the best overlap between the query and search sequences (see, e.g., Pearson, W. R., Methods Mol Biol 132: 185-219 (2000), herein incorporated by reference). Another preferred algorithm when comparing a sequence of the disclosure to a database containing a large number of sequences from different organisms is the computer program BLAST, especially BLASTP or TBLASTN, using default parameters. See, e.g., Altschul et al., J Mol Biol 215:403-410 (1990) and Altschul et al., Nucleic Acids Res 25:3389-402 (1997).

Unless otherwise indicated, nucleotide sequences provided herein are presented in the 5'-3' direction.

All pronouns are intended to be given their broadest meaning. Unless stared otherwise, female pronouns encompass the male, male pronouns encompass the female, singular pronouns encompass the plural, and plural pronouns encompass the singular.

The term "systemic administration" refers to a route of administration into the circulatory system so that the entire body is affected. Systemic administration can take place through enteral administration (absorption through the gastrointestinal tract, e.g. oral administration) or parenteral administration (e.g., injection, infusion, or implantation).

The term "topical administration" refers to application to a localized area of the body or to the surface of a body part regardless of the location of the effect. Typical sites for topical administration include sites on the skin or mucous membranes. In some embodiments, topical route of administration includes enteral administration of medications or compositions.

The term "undesirable microorganism" refers to a microorganism which may be a pathogenic microorganism, drug-resistant microorganism, antibiotic-resistant microorganism, irritation-causing microorganism, odor-causing microorganism and/or may be a microorganism comprising an undesirable virulence factor.

The term "synthetic microorganism" refers to an isolated microorganism modified by any means to comprise at least one element imparting a non-native attribute. For example, the synthetic microorganism may be engineered to include a molecular modification comprising an addition, deletion and/or modification of genetic material to incorporate a non-native attribute. In some embodiments, the synthetic microorganism is not an auxotroph.

The term "detectable presence" of a microorganism refers to a confirmed positive detection in a sample of a microorganism genus, species and/or strain by any method known in the art. Confirmation may be a positive test interpretation by a skilled practitioner and/or by repeating the method.

The term "microbiome" or "microbiomic" or "microbiota" as used herein refers to microbiological ecosystems. These ecosystems are a community of commensal, symbiotic and pathogenic microorganisms found in and on all animals and plants.

The term "microorganism" as used herein refers to an organism that can be seen only with the aid of a microscope and that typically consists of only a single cell. Microorganisms include bacteria, protozoans and fungi.

The term "niche" and "niche conditions" as used herein refers to the ecologic array of environmental and nutritional requirements that are required for a particular species of microorganism. The definitions of the values for the niche of a species defines the places in the particular biomes that can be physically occupied by that species and defines the possible microbial competitors.

The term "colonization" as used herein refers to the persistent detectable presence of a microorganism on a body surface, e.g., a dermal or mucosal surface, without causing disease in the individual.

The term "co-colonization" as used herein refers to simultaneous colonization of a niche in a site on a subject by two or more strains, or variants within the same species of microorganisms. For example, the term "co-colonization" may refer to two or more strains or variants simultaneously and non-transiently occupying the same niche. The term non-transiently refers to positive identification of a strain or variant at a site in a subject over time at two or more time subsequent points in a multiplicity of samples obtained from the subject at least two weeks apart.

The term "bacterial replacement" or "non-co-colonization" as used herein refers to the principle that only one variant/strain of one species can occupy any given niche within the biome at any given time.

The term "kill switch" or "KS" as used herein refers to an intentional molecular modification of a synthetic microorganism, the molecular modification comprising a cell death gene operably linked to a regulatory region comprising an inducible promoter, genetic element or cassette, wherein induced expression of the cell death gene in the kill switch causes cell death, arrest of growth, or inability to replicate, of the microorganism in response to a specific state change such as a change in environmental condition of the microorganism.

For example, in the synthetic microorganism comprising a kill switch, the inducible first promoter may be activated by the presence of blood, serum, plasma, and/or heme, wherein the upregulation and transcription/expression of the operably associated cell death gene results in cell death of the microorganism or arrested growth of the microorganism so as to improve the safety of the synthetic microorganism.

The term "cell death gene" refers to a gene that when induced causes a cell to enter a state where it either ceases reproduction, alters regulatory mechanisms of the cell sufficiently to permanently disrupt cell viability, induces senescence, or induces fatal changes in the genetic or proteomic systems of the cell. For example, the cell death gene may be a toxin gene encoding a toxin protein or toxin peptide.

The term "antitoxin gene" refers to a gene encoding an antitoxin RNA antisense molecule or an antitoxin protein or another antitoxin molecule specific for a cell death gene or a product encoded thereby The term "virulence block" or "V-block" refers to a molecular modification of a microorganism that results in the organism have decreased ability to accept foreign DNA from other strains or species effectively resulting in the organism having decreased ability to acquire exogenous virulence or antibiotic resistance genes.

The term "nanofactory" as used herein refers to the molecular modification of a microorganism that results in the production of a product-either primary protein, polypeptide, amino acid or nucleic acid or secondary products of these modifications to beneficial effect.

The term "toxin protein" or "toxin peptide" as used herein refers to a substance produced internally within a synthetic microorganism in an effective amount to cause deleterious effects to the microorganism without causing deleterious effects to the subject that it colonizes.

The term "molecular modification" or "molecularly engineered" as used herein refers to an intentional modification of the genes of a microorganism using any gene editing method known in the art, including but not limited to recombinant DNA techniques as described herein below, NgAgo, mini-Cas9, CRISPR-Cpf1, CRISPR-C2c2, Target-AID, Lambda Red, Integrases, Recombinases, or use of phage techniques known in the art. The DNA may be sequenced and manipulated chemically or by using molecular biology techniques, for example, to arrange one or more elements, e.g., regulatory regions, promoters, toxin genes, antitoxin genes, or other domains into a suitable configuration, or to introduce codons, delete codons, optimize codons, create cysteine residues, modify, add or delete amino acids, etc. Molecular modification may include, for example, use of plasmids, gene insertion, gene knock-out to excise or remove an undesirable gene, frameshift by adding or subtracting base pairs to break the coding frame, exogenous silencing, e.g., by using inducible promoter or constitutive promoter which may be embedded in DNA encoding, e.g. RNA antisense antitoxin, production of CRISPR-cas9 or other editing proteins to digest, e.g., incoming virulence genes using guide RNA, e.g., linked to an inducible promoter or a constitutive promoter, or a restriction modification/methylation system, e.g., to recognize and destroy incoming virulence genes to increase resistance to horizontal gene transfer. The molecular modification (e.g. kill switch, expression clamp, and/or v-block) may be durably incorporated to the synthetic microorganism by inserting the modification into the genome of the synthetic microorganism.

The synthetic microorganism may further comprise additional molecular modifications, (e.g., a nanofactory), which may be incorporated directly into the bacterial genome, or into plasmids, in order to tailor the duration of the effect of, e.g., the nanofactory production, and could range from short term (with non-replicating plasmids for the bacterial species) to medium term (with replicating plasmids without addiction dependency) to long term (with direct bacterial genomic manipulation).

The molecular modifications may confer a non-native attribute desired to be durably incorporated into the host microbiome, may provide enhanced safety or functionality to organisms in the microbiome or to the host microbiome overall, may provide enhanced safety characteristics, including kill switch(s) or other control functions. In some embodiments the safety attributes so embedded may be responsive to changes in state or condition of the microorganism or the host microbiome overall.

The molecular modification may be incorporated to the synthetic microorganism in one or more, two or more, five or more, 10 or more, 30 or more, or 100 or more copies, or no more than one, no more than three, no more than five, no more than 10, no more than 30, or in no more than 100 copies.

The term "recurrence" as used herein refers to re-colonization of the same niche by a decolonized microorganisms.

The term "pharmaceutically acceptable" refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a carrier that is physiologically acceptable to the treated subject while retaining the integrity and desired properties of the synthetic microorganism with which it is administered, Exemplary pharmaceutically acceptable carriers include physiological saline or phosphate-buffered saline. Other physiologically acceptable carriers and their formulations are provided herein or are known to one skilled in the art and described, for example, in Remington's Pharmaceutical Sciences, (20th edition), ed. A. Gennaro, 2000, Lippincott, Williams & Wilkins, Philadelphia, Pa.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described.

Vectors and Target Microorganisms

Also described herein are vectors comprising polynucleotide molecules, as well as target cells transformed with such vectors. Polynucleotide molecules described herein may be joined to a vector, which include a selectable marker and origin of replication, for the propagation host of interest. Target cells are genetically engineered to include these vectors and thereby transcribe RNA and express polypeptides. Vectors herein include polynucleotides molecules operably linked to suitable transcriptional or translational regulatory sequences, such as those for microbial target cells. Examples of regulatory sequences include transcriptional promoters, operators, or enhancers, mRNA ribosomal binding sites, and appropriate sequences which control transcription and translation. Nucleotide sequences as described herein are operably linked when the regulatory sequences herein functionally relate to, e.g., a cell death gene encoding polynucleotide.

Typical vehicles include plasmids, shuttle vectors, baculovirus, inactivated adenovirus, and the like. In certain examples described herein, the vehicle may be a modified pIMAY, pIMAYz, or pKOR integrative plasmid, as discussed herein.

A target microorganism may be selected from any microorganism having the ability to durably replace a specific undesirable microorganism after decolonization. The target microorganism may be a wild-type microorganism that is subsequently engineered to enhance safety by methods described herein. The target microorganism may be selected from a bacterial, fungal, or protozoal target microorganism. The target microorganism may be a strain capable of colonizing a dermal and/or mucosal niche in a subject. The target microorganism may be a wild-type microorganism, or a synthetic microorganism that may be subjected to further molecular modification. The target microorganism may be selected from a genus selected from the group consisting of *Acinetobacter, Corynebacterium, Cutibacterium, Staphylococcus, Streptococcus, Propionibacterium*, and *Pseudomonas*. The target microorganism may be selected from the group consisting of *Acinetobacter johnsonii, Acinetobacter baumannii, Staphylococcus aureus, Staphylococcus epidermidis, Staphylococcus lugdunensis, Staphylococcus warneri, Staphylococcus saprophyticus, Corynebacterium acnes, Corynebacterium striatum, Corynebacterium diphtheriae, Corynebacterium minutissimum, Cutibacterium acnes, Propionibacterium acnes, Propionibacterium granulosum, Escherichia coli, Streptococcus pyogenes, Streptococcus aureus, Streptococcus agalactiae, Streptococcus mitis, Streptococcus viridans, Streptococcus pneumoniae, Streptococcus anginosis, Steptococcus constellatus, Streptococcal intermedius, Streptococcus agalactiae, Streptococcus mutans, Pseudomonas aeruginosa, Pseudomonas oryzihabitans, Pseudomonas stutzeri, Pseudomonas putida*, and *Pseudomonas fluorescens.*

The target microorganism may be of the same genus and species as the undesirable microorganism, but of a different strain. For example, the undesirable microorganism may be an antibiotic-resistant *Staphylococcus aureus* strain, such as an MRSA strain. The antibiotic-resistant *Staphylococcus aureus* stain may be a pathogenic strain, which may be known to be involved in dermal infection, mucosal infection, bacteremia, and/or endocarditis. Where the undesirable microorganism is a *Staphylococcus aureus* strain, e.g., an MRSA, the target microorganism may be, e.g., a less pathogenic strain which may be an isolated strain such as *Staphylococcus aureus* target cell such as an RN4220 or 502a strain, and the like. Alternatively, the target cell may be of the same strain as the undesirable microorganism. In another example, the undesirable microorganism is an *Escherichia coli* strain, for example, a uropathogenic *E. coli* type I strain or p-fimbriated strain, for example, a strain involved in urinary tract infection, bacteremia, and/or endocarditis. In another example, the undesirable strain is a *Cutibacterium acnes* strain, for example a strain involved in *acnes* vulgaris, bacteremia, and/or endocarditis. In another example, the undesirable microorganism is a *Streptococcus mutans* strain, for example, a strain involved in *S. mutans endocarditis, dental caries.*

Model Antibiotic-Susceptible Target Microorganism

The target microorganism may be an antibiotic-susceptible microorganism of the same species as the undesirable microorganism. In one embodiment, the undesirable microorganism is an MRSA strain and the replacement target microorganism is an antibiotic susceptible *Staphylococcus aureus* strain. The antibiotic susceptible microorganism may be *Staphylococcus aureus* strain 502a ("502a"). 502a is a coagulase positive, penicillin sensitive, nonpenicillinase producing *staphylococcus*, usually lysed by phages 7, 47, 53, 54, and 77, Serologic type (b)ci. Unusual disc antibiotic sensitivity pattern is exhibited by 502a because this strain is susceptible to low concentrations of most antibiotics except tetracycline; resistant to 5 μg, but sensitive to 10 μg of tetracycline. In some embodiments, the 502a strain may be purchased commercially as *Staphylococcus aureus* subsp. *Aureus* Rosenbach ATCC®27217™.

Unfortunately, even an antimicrobial agent-susceptible target microorganism may cause systemic infection. Therefore, as provided herein, the target microorganism is subjected to molecular modification to incorporate regulatory sequences including, e.g., an inducible first promoter for expression of the cell death gene, v-block, or nanofactory, in order to enhance safety and reduce the likelihood of pathogenic infection as described herein.

The target microorganism and/or the synthetic microorganism comprises (i) the ability to durably colonize a niche in a subject following decolonization of the undesirable microorganism and administering the target or synthetic microorganism to a subject, and (ii) the ability to prevent recurrence of the undesirable microorganism in the subject for a period of at least two weeks, at least four weeks, at least six weeks, at least eight weeks, at least ten weeks, at least 12 weeks, at least 16 weeks, at least 24 weeks, at least 26 weeks, at least 30 weeks, at least 36 weeks, at least 42 weeks, or at least 52 weeks after the administering step.

Selection of a Target Microorganism for MRSA

Selection of the target microorganism may be performed by decolonizing the target microorganism and replacing with a putative target microorganism, as described herein. For example, the undesirable microorganism Methicillin-Resistant *Staphylococcus aureus* (MRSA) is the cause of a disproportionate amount of invasive bacterial infections worldwide. The colonization state for *Staphylococcus aureus* is regarded as a required precondition for most invasive infections. However, decolonization with standard antiseptic regimens has been studied as a method for reducing MRSA colonization and infections with mixed results. In one example provided herein, the feasibility and durability of a novel decolonization approach to undesirable microorganism MRSA by using intentional recolonization with a different *Staphylococcus aureus* strain as a candidate target microorganism was performed in hopes of improving duration of effect versus standard decolonization. Example 1 discloses the study in which a total of 765 healthy volunteers were screened for *Staphylococcus aureus* colonization. The overall MRSA rate for the screened population was 8.5%. A cohort of 53 MRSA colonized individuals participated in a controlled study of a decolonization/recolonization therapy using *Staphylococcus aureus* 502a WT strain BioPlx-01 vs. a control group of standard decolonization alone. Duration of MRSA absence from the colonization state as well as persistence of the intentional MSSA recolonization was monitored for 6 months. The control group (n==15) for the efficacy portion of the MRSA decolonization protocol showed MRSA recurrence of 60% at the 4 week time point. The test group employing the BioPlx-01WT protocol (n=34) showed 0% MRSA recurrence at the 8 week primary endpoint and continued to show no evidence of MRSA recurrence out to 26 weeks. Instead these participants exhibited surprising persistence of colonization with MSSA likely indicating ongoing colonization with the *Staphylococcus aureus* 502a BioPlx-01WT strain product out to 26 weeks. In addition, the components of the BioPlx-01WT in a phosphate buffered saline composition used in the decolonization/recolonization therapy showed no evidence of dermal irritation in a separate cohort of 55 participants. Therefore, target strain *Staphylococcus aureus* 502a BioPlx-01WT decolonization/recolonization protocol provides longer durability of decolonization from MRSA strains than standard decolonization and shows no observed negative dermal effects.

Methods for Determining Detectable Presence of a Microorganism

Any method known in the art may be employed for determination of the detectable presence of a microorganism genus, species and strain. An overview of methods may be found in Aguilera-Arreola MG. Identification and Typing Methods for the Study of Bacterial Infections: a Brief Review and Mycobacterial as Case of Study. Arch Clin Microbiol. 2015, 7:1, which is incorporated herein by reference.

The detectable presence of a genus, species and/or strain of a bacteria may be determined by phenotypic methods and/or genotypic methods. Phenotypic methods may include biochemical reactions, serological reactions, susceptibility to anti-microbial agents, susceptibility to phages, susceptibility to bacteriocins, and/or profile of cell proteins. One example of a biochemical reaction is the detection of extracellular enzymes. For example, staphylococci produce many different extracellular enzymes including DNAase, proteinase and lipases. Gould, Simon et al., 2009, The evaluation of novel chromogenic substrates fro detection of lipolytic activity in clinical isolates of *Staphylococcus aureus* and MRSA from two European study groups. FEMS Microbiol Let 297; 10-16. Chromogenic substrates may be employed for detection of extracellular enzymes. For example, CHROMager™ MRSA chromogenic media (CHROMagar, Paris, France) may be employed for isolation and differentiation of Methicillin Resistant *Staphylococcus aureus* (MRSA) including low level MRSA. Samples are obtained from, e.g., nasal, perineal, throat, rectal specimens are obtained with a possible enrichment step. If the agar plate has been refrigerated, it is allowed to warm to room temperature before inoculation. The sample is streaked onto plate followed by incubation in aerobic conditions at 37° C. for 18-24 hours. The appearance of the colonies is read, wherein MRSA colonies appear as rose to mauve colored, Methicillin Susceptible *Staphylococcus aureus* (MSSA) colonies are inhibited, and other bacteria appear as blue, colorless or inhibited colonies. Definite identification as MRSA requires, in addition, a final identification as *Staphylococcus aureus*. For example, CHROMagar™ Staph *aureus* chromogenic media may be employed where *S. aureus* appears as mauve, *S. saprophyticus* appears turquoise blue, *E. coli, C. albicans* and *E. faecalis* are inhibited. For detection of Group B *Streptococcus* (GBS) (*S. agalactiae*), CHROMagar™ StrepB plates may be employed, wherein *Streptococcus agalactiae* (group B) appear mauve, *Enterococcus* spp. and *E. faecalis* appear steel blue, *Lactobacilli, leuconostoc* and *lactococci* appear light pink, and other microorganisms are blue, colorless or inhibits. For detection of various *Candida* spp., CHROMager™ *Candida* chromogenic media may be employed. *Candida* species are involved in superficial oropharyngeal and urogenital infections. Although *C. albicans* remains a major species involved, other types such as *C. tropicalis, C. krusai*, or *C. glabrata* have increased as new antifungal agents have worked effectively against *C. albi-*

*cans*. Sampling and direct streaking of skin, sputum, urine, vaginal specimens samples and direct streaking or spreading onto plate, followed by incubation in aerobic conditions at 30-37° C. for 48 hours, and reading of plates for colony appearance where *C. albicans* is green, *C. tropicalis* is metallic blue, *C. krusei* is pink and fuzzy, *C. kefyr* and *C. glabrata* are mauve-brown, and other species are white to mauve.

Genotypic methods for genus and species identification may include hybridization, plasmids profile, analysis of plasmid polymorphism, restriction enzymes digest, reaction and separation by Pulsed-Field Gel Electrophoresis (PFGE), ribotyping, polymerase chain reaction (PCR) and its variants, Ligase Chain Reaction (LCR), Transcription-based Amplification System (TAS), or any of the methods described herein.

Identification of a microbe can be performed, for example, by employing Galileo™ Antimicrobial Resistance (AMR) detection software (Are Bio LLC, Menlo Park, CA and Cambridge, MA) that provides annotations for gram-negative bacterial DNA sequences.

The microbial typing method may be selected from genotypic methods including Multilocus Sequence Typing (MIST) which relies on PCR amplification of several housekeeping genes to create allele profiles; PCR-Extragenic Palindromic Repetitive Elements (rep-PCR) which involves PCR amplification of repeated sequences in the genome and comparison of banding patterns; AP-PCR which is Polymerase Chain Reaction using Arbitrary Primers; Amplified Fragment Length Polymorphism (AFLP) which involves enzyme restriction digestion of genomic DNA, binding of restriction fragments and selective amplification; Polymorphism of DNA Restriction Fragments (RFLP) which involves Genomic DNA digestion or of an amplicon with restriction enzymes producing short restriction fragments; Random Amplified Polymorphic DNA (RAPD) which employs marker DNA fragments from PCR amplification of random segments of genomic DNA with single primer of arbitrary nucleotide sequence; Multilocus Tandem Repeat Sequence Analysis (MLVA) which involves PCR amplification of loci VTR, visualizing the polymorphism to create an allele profile; or Pulsed-Fields Gel Electrophoresis (PFGE) which involves comparison of macro-restriction fragments, PFGE method of electrophoresis is capable of separating fragments of a length higher than 50 kb up to 10 Mb, which is not possible with conventional electrophoresis, which can separate only fragments of 100 bp to 50 kb. This capacity of PFGE is due to its multidirectional feature, changing continuously the direction of the electrical field, thus, permitting the re-orientation of the direction of the DNA molecules, so that these can migrate through the agarose gel, in addition to this event, the applied electrical pulses are of different duration, fostering the reorientation of the molecules and the separation of the fragments of different size. One PFGE apparatus may be the Contour Clamped Homogeneous Electric Fields (CHEF, BioRad). Pulsed-filed gel electrophoresis (PFGE) is considered a gold standard technique for MRSA typing, because of its high discriminatory power, but its procedure is complicated and time consuming. The spa gene encodes a cell wall component of *Staphylococcus aureus* protein A, and exhibits polymorphism. The sequence based-spa typing can be used as a rapid test screen. Narukawa et al 2009 Tohoku J Exp Med 2009, 218, 207-213.

Methods and compositions are provided herein for suppressing (decolonizing) and replacing an undesirable microorganism with a new synthetic microorganism in order to durably displace and replace the undesirable microorganism from the microbiological ecosystem with a new microorganism so as to prevent the recurrence of the original undesirable organism (referred to here as niche or ecological interference).

In some embodiments, methods are provided to prevent colonization, prevent infection, decrease recurrence of colonization, or decrease recurrence of a pathogenic infection of a undesirable microorganism in a subject, comprising decolonization and administering a synthetic strain comprising a molecular modification that decreases the ability of the synthetic microorganism to cause disease to the subject relative to the wild type target strain where the microorganism is selected from the group consisting of *Acinetobacter johnsonii, Acinetobacter houmaii, Staphylococcus aureus, Staphylococcus epidermidis, Staphylococcus lugdunensis, Staphylococcus warneri, Staphylococcus saprophytieus, Corynebacterium acnes. Corynebacterium striatum, Corynebacterium diphtheriae, Corynebacterium minutissimum, Cutibacterium acnes, Propionibacterium acnes, Propionibacterium granulosum, Streptococcus pyogenes, Streptococcus aureus, Streptococcus agalactiae, Streptococcus mitis, Streptococcus viridans, Streptococcus pneumoniae, Streptococcus anginosis, Streptococcus constellatus, Streptococcal intermedius, Streptococcus agalactiae, Pseudomonas aeruginosa, Pseudomonas oryzihabitans, Pseudomonas stutzeri, Pseudomonas putida*, and *Pseudomonas fluorescens*.

In some embodiments, a method is provided to prevent transmission by a subject, or recurrence of colonization or infection, of a pathogenic microorganism in a subject, comprising suppressing the pathogenic microorganism in the subject, and replacing the pathogenic microorganism by topically administering to the subject a composition comprising a benign microorganism of the same species, different strain. The method may further comprise promoting the colonization of the benign microorganism. In some embodiments, the benign microorganism is a synthetic microorganism having at least one molecular modification comprising a first cell death gene operably linked to a first regulatory region comprising a first promoter, wherein the first promoter is activated in the presence of human serum or blood. In some embodiments, the first promoter is not activated during colonization of dermal or mucous membranes in a human subject.

In some embodiments, method is provided to prevent transmission by a subject, or recurrence of colonization or infection, of a methicillin-resistant *Staphylococcus aureus* (MRSA) in a subject, comprising suppressing the MRSA in the subject, and replacing the MRSA by topically administering to the subject a methicillin susceptible *Staphylococcus aureus* (MSSA) of the same species, different strain. The method may further comprise promoting the colonization of the MSSA in the subject.

A method is provided to prevent transmission by a subject, or recurrence of colonization or infection, of a undesirable microorganism in a subject, comprising suppressing the undesirable microorganism in the subject, and replacing the undesirable microorganism by administering to the subject a second microorganism of the same species, different strain. The method may further comprise promoting the colonization of the second microorganism. In some embodiments, the undesirable microorganism is a drug-resistant pathogenic microorganism. In some embodiments, the second microorganism is a drug-susceptible microorganism. In some embodiments, the second microorganism is a synthetic microorganism.

Suppression/Decolonization

An undesirable microorganism may be supressed, or decolonized, by topically applying a disinfectant, antiseptic, or biocidal composition directly to the skin or mucosa of the subject, for example, by spraying, dipping, or coating the affected area, optionally the affected area and adjacent areas, or greater than 25%, 50%, 75%, or greater than 90% of the external or mucosal surface area of the subject with the disinfectant, antiseptic, or biocidal composition. In some embodiments, the affected area, or additional surface areas are allowed to air dry or are dried with an air dryer under gentle heat, or are exposed to ultraviolet radiation or sunlight prior to clothing or dressing the subject. In one embodiment, the suppression comprises exposing the affected area, and optionally one or more adjacent or distal areas of the subject, with ultraviolet radiation. In various embodiments, any commonly employed disinfectant, antiseptic, or biocidal composition may be employed. In one embodiment, a disinfectant comprising chlorhexidine or a pharmaceutically acceptable salt thereof is employed.

In some embodiments, the bacteriocide, antiseptic, astringent, and/or antibacterial agent is selected from the group consisting of alcohols (ethyl alcohol, isopropyl alcohol), aldehydes (glutaraldehyde, formaldehyde, formaldehyde-releasing agents (noxythiolin=oxymethylenethiourea, taurolinе, hexamine, dantoin), o-phthalaldehyde), anilides (triclocarban=TCC=3,4,4'-triclorocarbanilide), biguanides (chlorhexidine, alexidine, polymeric biguanides (polyhexamethylene biguanides with MW>3,000 g/mol, vantocil), diamidines (propamidine, propamidine isethionate, propamidine dihydrochloride, dibromopropamidine, dibromopropamidine isethionate), phenols (fentichlor, p-chloro-m-xylenol, chloroxylenol, bexachlorophene), bis-phenols (triclosan, hexachlorophene), quaternary ammonium compounds (cetrimide, benzalkonium chloride, cetyl pyridinium chloride), silver compounds (silver sulfadiazine, silver nitrate), peroxy compounds (hydrogen peroxide, peracetic acid), iodine compounds (povidone-iodine, poloxamer-iodine, iodine), chlorine-releasing agents (sodium hypochlorite, hypochlorous acid, chlorine dioxide, sodium dichloroisocyanurate, chloramine-T), copper compounds (copper oxide), botanical extracts (Malaleuca spp. (tea tree oil), *Cassia fistula Linn, Boekea frutexdens L., Melia azedarach* L., Muntingia calabura, *Vitis vinifera* L, Terminalio avicennioides Guill & Perr., Phylantus discoideus muel. Muel-Arg., *Ocimum* gratissimum Linn., *Acalypha wilkesiana* Muell-Arg., *Hypericum* pruinatum Boiss.&Bal., *Hypericum* olimpicum L. and *Hypericum* sabrum L., *Hamamelis virginiana* (witch hazel), *Eucalyptus* spp., rosemarinus *officinalis* spp. (rosemary), Thymus spp. (thyme), Lippia spp. (oregano), Cymbopogon spp. (lemongrass), *Cinnamomum* spp., Geranium spp., *Lavendula* spp.), and topical antibiotic compounds (bacteriocins; mupirocin, bacitracin, neomycin, polymyxin B, gentamicin).

Suppression of the undesirable microorganism also may be performed by using photosensitizers instead of or in addition to, e.g., topical antibiotics. For example, Peng Zhang et al., Using Photosensitizers Instead of Antibiotics to Kill MRSA, GEN News Highlights, Aug. 20, 2018; 48373, developed a technique using light to activate oxygen, which suppresses to microbial growth. Photosensitizers, such as dye molecules, become excited when illuminated with light. The photosensitizers convert oxygen into reactive oxygen species that kill the microbes, such as MRSA. In order to concentrate the photosensitizers to improve efficacy, water-dispersible, bybrid photosensitizers were developed by Zhang et al., comprising noble metal nanoparticles decorated with amphiphilie polymers to entrap molecular photosensitizers. The hybrid photosensitizers may be applied to a subject, for example, on a dermal surface or wound, in the form of a spray, lotion or cream, then illuminated with red or blue light to reduce microbial growth.

A decolonizing composition may be in the form of a topical solution, lotion, or ointment form comprising a disinfectant, biocide photosensitizer or antiseptic compound and one or more pharmaceutically acceptable carriers or excipients. In one specific example, an aerosol disinfectant spray is employed comprising chlorhexidine gluconate (0.4%), glycerin (10%), in a pharmaceutically acceptable carrier, optionally containing a dye to mark coverage of the spray. In one embodiment, the suppressing step comprises administration to one or more affected areas, and optionally one or more surrounding areas, with a spray disinfectant as disclosed in U.S. Pat. Nos. 4,548,807 and/or 4,716,032, each of which is incorporated herein by reference in its entirety. The disinfectant spray may be commercially available, for example, Fight Bac®, Deep Valley Farm, Inc., Brooklyn, CT. Other disinfectant materials may include chlorhexidine or salts thereof, such as chlorhexidine gluconate, chlorhexidine acetate, and other diguanides, ethanol, SD alcohol, isopropyl alcohol, p-chloro-o-benzylphenol, o-phenylphenol, quaternary ammonium compounds, such as n-alkyl/dimethyl ethyl benzyl ammonium chloride/n-alkyl dimethyl benzyl ammonium choride, benzalkonium chloride, cetrimide, methylbenzethonium chloride, benzethonium chloride, cetalkonium chloride, cetylpyridinium chloride, dofanium chloride, domiphen bromide, peroxides and permanganates such as hydrogen peroxide solution, potassium permanganate solution, benzoyl peroxide, antibacterial dyes such as proflavine hemisulphate, triphenylmethane, Brilliant green, Crystal violet, Gentian violet, quinolone derivatives such as hydroxyquinoline sulphate, potassium hydroxyquinoline sulphate, chlorquinaldol, dequalinium chloride, di-iodohydroxyquinoline, Burow's solution (aqueous solution of aluminum acetate), bleach solution, iodine solution, bromide solution. Various Generally Recognized As Safe (GRAS) materials may be employed in the disinfectant or biocidal composition including glycerin, and glycerides, for example but not limited to mono- and diglycerides of edible fat-forming fatty acids, diacetyl tartaric acid esters of mono- and diglycerides, triacetin, acettooleins, acetostearins, glyceryl lactopalmitate, glyceryl lactooleate, and oxystearins.

The suppression step—or decolonization—may be performed comprising administering 1-3 times daily, over a period of from 1 to 10 days; for example, on one, two, three, four, five, six, seven, eight, nine, ten, eleven, twelve, thirteen or fourteen days. In other embodiments, the suppression step may be administered from two, three, four, five, or six times, each administration from 6 to 48 hours, 8 to 40 hours, 18 to 36 hours, or about 20 to 28 hours apart. In specific embodiments, the suppression step is administered once per day from one to five, or three to four consecutive days. In some embodiments, the suppression step does not include systemic administration of antimicrobial agents. In some embodiments, the suppression step does not include systemie administration of antibiotic, antiviral, or antifungal agents. In other embodiments, the suppression step includes systemic administration of antimicrobial agents. In some embodiments, the suppression step may include systemic administration of one or more antibiotic, antiviral, or antifungal agents.

Replace

Methods are provided wherein an undesirable microorganism is durably replaced with a synthetic microorganism.

The synthetic microorganism has the ability to fill the same ecological niche and/or may be of the same species, different strain, as the pathogenic microorganism. By using same species, different strain, (or even the same strain) the environmental niche of the pathogenic microorganism may be filled, or durably replaced, with the benign synthetic microorganism.

Synthetic Microorganism

In some embodiments, the undesirable pathogenic microorganism is replaced with a synthetic microorganism. For example, the replacement strain may be a synthetic microorganism that is a molecularly modified strain of the same species as the undesirable or pathogenic microorganism or the same strain as the undesirable or pathogenic microorganism.

In some embodiments, a synthetic microorganism comprising a "kill switch" is provided exhibiting rapid and complete cell death on exposure to blood or serum, but exhibits normal metabolism and colonization function in other environments. In some embodiments, the synthetic microorganism comprises stable and immobile kill switch genes. The minimal kill switch (KS) components include a regulatory region (R.R.) containing operator, promoter and translation signals, that is strongly activated in response to blood or serum exposure, a kill switch gene expressing a toxic protein or RNA, and a means of transcription termination. Chromosomal integration of the KS is preferred. The chromosomal locus may be in a transcriptionally inactive region, for example, an intergenic region (IR) between a seryl-lRNA synthetase and an amino acid transporter. Insertions here do not affect transcription of flanking genes (Lei et al., 2012). Preferably, no known sRNAs are present in the IR. Any other inert loci may be selected.

The Synthetic Microorganism Comprising a Kill Switch

In a particular embodiment, the pathogenic microorganism is an antimicrobial-resistant microorganism, and the replacement microorganism is a synthetic microorganism of the same species as the pathogenic microorganism. The synthetic microorganism may be a molecularly-modified, antibiotic-susceptible microorganism.

The synthetic microorganism may comprise one or more, two or more, or three or more molecular modifications comprising a first cell death gene operably linked to a first regulatory region comprising an inducible first promoter. Optionally, the synthetic microorganism further comprises a second cell death gene operably linked to the first regulatory region comprising the first promoter or a second regulatory region comprising an inducible second promoter. The first promoter, and optionally the second promoter, is activated (induced) by a change in state in the microorganism environment compared to the normal physiological conditions at the at least one site in the subject. For example, the change in state may be selected from one or more changes in pH, temperature, osmotic pressure, osmolality, oxygen level, nutrient concentration, blood concentration, plasma concentration, serum concentration, and electrolyte concentration. In some embodiments, the change in state is a higher concentration of blood, serum, or plasma compared to normal physiological conditions at the at least one site in the subject.

In one specific embodiment, the pathogenic microorganism is a MRSA and the replacement microorganism is a synthetic microorganism that is a molecularly modified *Staphylococcus aureus* coagulase positive strain. The synthetic microorganism may be a molecularly modified *Staphylococcus aureus* 502a, as described herein.

The use of live *Staphylococcus aureus* as a therapeutic platform raises safety concerns because this pathogen can cause serious disease if it gains access to the circulatory system. In one embodiment, the synthetic microorganism is molecularly engineered to comprise a "kill switch" (KS) and an inducible promoter that induces rapid bacterial death upon exposure to whole blood or serum. The kill switch may be composed of DNA encoding 3 main components: i) "control region", containing a promoter and other regulatory sequences, that is strongly activated by blood or seram; ii) a toxic RNA or polypeptide, whose expression is driven by the control region, and; iii) a transcription terminator. A cassette composed of these elements maybe integrated into the *Staphylococcus aureus* chromosome at a site(s) amenable to alteration without adversely affecting bacterial function.

It is desirable that basal or "leaky" expression of the control region is minimized or avoided. For example, if significant mRNA production occurs before exposure to blood or serum, the strain could be weakened during manufacturing or skin colonization and may accumulate mutations that bypass or escape the KS. To address this, candidates are screened to find those that are strongly induced in serum, but also have very low or undetectable mRNA expression in standard growth media in vitro. Despite this effort, some leaky expression may be observed, which may be controlled by further comprising a iv) "expression clamp" to prevent untimely toxin production.

Recombinant Approach to Synthetic Microorganism

A synthetic microorganism is provided which comprises a recombinant nucleotide comprising at least one molecular modification (e.g., a kill switch) comprising (i) a cell death gene operatively associated with (ii) a first regulatory region comprising a first inducible promoter which is induced by a change in state in the environment of the synthetic microorganism. The synthetic microorganism may further comprises at least a second molecular modification (expression clamp) comprising (iii) an antitoxin gene specific for the first cell death gene, wherein the antitoxin gene is operably associated with (iv) a second regulatory region comprising a second promoter which is active (e.g., constitutive) upon dermal or mucosal colonization or in a media, and preferably is downregulated by change in state of the environment of the synthetic microorganism.

In some embodiments, a synthetic microorganism is provided comprising at least one molecular modification (e.g., a kill switch) comprising a first cell death gene operably linked to a first regulatory region comprising a first promoter, wherein the first promoter is activated (induced) by a change in state in the microorganism environment compared to the normal physiological conditions at the at least one site in the subject, optionally wherein cell death of the synthetic microorganism occurs within 30, 60, 90, 120, 180, 360 or 240 minutes following change of state. The change in state may be selected from one or more conditions of pH, temperature, osmotic pressure, osmolality, oxygen level, nutrient concentration, blood concentration, plasma concentration, serum concentration, heme concentration, sweat concentration, sebum concentration, metal concentration, chelated metal concentration, change in composition or concentration of one or more immune factors, mineral concentration, and electrolyte concentration. In some embodiments, the change in state is a higher concentration of blood, serum, or plasma compared to normal physiological conditions at the at least one site in the subject.

Inducible Promoters

A synthetic microorganism is provided which may comprise a recombinant nucleotide comprising at least one molecular modification (e.g., a kill switch) comprising (i) a cell death gene operatively associated with (ii) a first regulatory region comprising a first inducible promoter which exhibits conditionally high level gene expression of the recombinant nucleotide in response to exposure to blood, serum, or plasma, of at least two fold, at least three fold, at least 10-fold, at least 20 fold, at least 50 fold, at least 100-fold increase of basal productivity.

The inducible first promoter may be activated (induced) upon exposure to an increased concentration of blood, serum, plasma, or heme after a period of time, e.g., after 15 minutes, 30 minutes, 45 minutes, 90 minutes, 120 minutes, 180 minutes, 240 minutes, 360 minutes, or any time point in between, to increase transcription and/or expression at least 5-fold, at least 10-fold, at least 20-fold, at least 50-fold, at least 100-fold, at least 300-fold, or at least 600-fold compared to transcription and/or expression in the absence of blood, serum, plasma or heme (non-induced).

The blood or serum inducible first promoter may be selected by a process comprising selecting a target microorganism, selecting one or more first promoter candidate genes in the target microorganism, growing the microorganism in a media, obtaining samples of the microorganism at t=0 min, adding serum or blood to the media, obtaining samples at t=n minutes, where n=1-240 min or more, 15-180 min, or 30-120 min, performing RNA sequencing of the samples, and comparing RNA sequencing read numbers for candidate first promoter in samples obtained at obtained at t=0 min, and t=n minutes after exposure to blood or serum for the candidate first promoter gene. Alternatively, samples obtained after t=n minutes after exposure to blood or serum may be compared to t=n minutes in media without blood or serum for the candidate first promoter. Candidate first promoters may be selected from those that exhibit upregulation by RNA sequencing after target cell growth at t=n min in blood or serum of greater than about 10-fold, greater than about 20-fold, greater than about 50-fold, greater than about 100-fold, or greater than about 500-fold, when compared to the candidate promoter in the target cell at t=0, or when compared to the candidate promoter in the target cell at t=n in media without serum or blood.

Several serum responsive promoter candidate genes in *Staphylococcus aureus* 502a were upregulated by greater than 20-fold after exposure to serum for 30 minutes as determined by RNA sequencing as compared to t=0 including isdB gene CH52_00245 (479-fold), sbnB gene CH52_05135 (158-fold), isdC gene CH52_00235 (93-fold), sbnA gene CH52_05140 (88-fold), srtB gene CH52_00215 (73-fold), sbnE gene CH52_05120 (70-fold), sbnD gene CH52_05125 (66-fold), isdI gene CH52_00210 (65-fold), heme ABC transporter 2 gene CH52_00225 (65-fold), sbnC gene CH52_05130 (63-fold), heme ABC transporter gene CH52_00230 (60-fold), isd ORF3 gene CH52_00220 (51-fold), sbnF gene CH52_05115 (43 fold), alanine dehydrogenase gene CH52_11875 (43-fold), HarA gene CH52_10455 (43-fold), sbnG gene CH52_05110 (42-fold), diaminopimelate decarboxylase gene CH52_05105 (32-fold), iron ABC transporter gene CH52_05145 (31-fold), threonine dehydratase gene CH52_11880 (24-fold), and isdA gene CH52_00240 (21-fold).

Several serum responsive promoter candidate genes in target microorganism *Staphylococcus aureus* 502a were found to be upregulated by greater than 20-fold after exposure to serum for 30 minutes as determined by RNAseq compared to TSB at 30 minutes including isdB gene CH52_00245 (471-fold), isdC gene CH52_00235 (56-fold), isdI gene CH52_00210 (53-fold), sbnD gene CH52_05125 (52-fold), sbnC gene CH52_05130 (51-fold), sbnE gene CH52_05120 (50-fold), srtB gene CH52_00215 (47-fold), sbnB gene CH52_05135 (44-fold), sbnF gene CH52_05115 (44-fold), heme ABC transporter 2 gene CH52_00225 (43-fold), isdA gene CH52_00240 (40-fold), heme ABC transporter gene CH52_00230 (40-fold), sbnA gene CH52_05140 (37-fold), isd ORF3 gene CH52_00220 (35-fold), sbnG gene CH52_05110 (34-fold), HarA gene CH52_10455 (28-fold), diaminopimelate decarboxylase gene CH52_05105 (25-fold), sbnI gene CH52_05100 (22-fold), and alanine dehydrogenase gene CH52_11875 (20-fold). Iron ABC transporter gene CH52_05145 was upregulated (19-fold) after 30 min of exposure to serum compared to 30 min in TSB. Threonine dehydratase gene CH52_11880 was upregulated (14-fold) after 30 min of exposure to serum compared to 30 min in TSB.

Several serum responsive promoter candidate genes in target microorganism *Staphylococcus aureus* 502a were upregulated by greater than 50-fold after exposure to serum after 90 minutes as determined by RNAseq compared to t=0 including isdB gene CH52_0024S (2052-fold), sbnB gene CH52_05135 (310-fold), alanine dehydrogenase gene CH52_11875 (304-fold), sbmE gene CH52_05120 (190-fold), sbnD gene CH52_05125 (187-fold), isdC gene CH52_00235 (173-fold), sbnC gene CH52_05130 (162-fold), sbnA gene CH52_05140 (143-fold), srtB gene CH52_00215 (143-fold), sbnG gene CH52_05110 (133-fold), sbnF gene CH52_05115 (129-fold), heme ABC transporter gene CH52_00230 (125-fold), heme ABC transporter 2 gene CH52_00225 (117-fold), isdI gene CH52_00210 (115-fold), HarA gene CH52_10455 (114-fold), diaminopimelate decarboxylase gene CH52_05105 (102-fold), sbnI gene CH52_05100 (101-fold), isd ORF3 gene CH52_00220 (97-fold), SAM dep Metrans gene CH52_04385 (75-fold). Iron ABC transporter gene CH52_05145 (44-fold), isdA gene CH52_00240 (44-fold), and siderophore ABC transporter gene CH52_05150 (33-fold) were also upregulated after 90 min exposure to serum compared to t=0.

Several serum responsive promoter candidate genes in target microorganism *Staphylococcus aureus* 502a were found to be upregulated by greater than 50-fold after exposure to serum after 90 minutes as determined by RNA sequencing compared to growth in TSB at 90 minutes including isdB gene CH52_00248 (1240-fold), sbnD gene CH52_05125 (224-fold), heme ABC transporter gene CH52_00230 (196-fold), sbnE gene CH52_05120 (171-fold), srB gene CH52_00215 (170-fold), isdC gene CH52_00235 (149-fold), sbnC gene CH52_03130 (147-fold), diaminopimelate decarboxylase gene CH52_0105 (141-fold), heme ABC transporter 2 gene CH52_00225 (135-fold), sbnB gene CH52_05135 (130-fold), sbnF gene CH52_05115 (127-fold), bnG gene CH52_05110 (120-fold), isd ORF3 gene CH52_00220 (119-fold), isdI gene CH52_00210 (118-fold), HarA gene CH52_10455 (117-fold), isdA gene CH52_00240 (115-fold), sbnA gene CH52_05140 (93-fold), and soul gene CH52_05100 (89-fold). Iron ABC transporter gene CH52_05145 (47-fold), siderophore ABC transporter gene CH52_05150 (37-fold), and SAM dep Metrans gene CH52_04385 (25-fold) were also upregulated after 90 min exposure to serum compared to TSB at t=90 min.

The blood or serum inducible first promoter genes for use in a *Staphylococcus aureus* synthetic microorganism may be selected from or derived from a gene selected from isdA (iron-regulated surface determinant protein A), isdB (iron-regulated surface determinant protein B), isdG (heme-degrading monooxygenase), hlgA (gamma-hemolysin component A), hlgA1 (gamma-hemolysin), hlgA2 (gamma-hemolysin), hlgB (gamma-hemolysin component B), hrtAB (heme-regulated transporter), sbnC (luc C family siderophore biosynthesis protein), sbnE (lucA/lucC family siderophore biosynthesis protein), lrgA (morein hydrolase regulator A), lrgB (murein hydrolase regulator B), ear (Ear protein), fhuA (ferrichrome transport ATP-binding protein fhuA), fhuB (ferrichrome transport permease), hlb (phospholipase C), splF (serine protease SplF), splD (serine protease SplD), dps (general stress protein 20U), SAUSA300_2617 (putative cobalt ABC transporter, ATP-binding protein), SAUSA300_2268 (sodium/bile acid symporter family protein), SAUSA300_2616 (cobalt family transport protein), srtB (Sortase B), sbnA (probable siderophore biosynthesis protein sbnA), leuA (2-isopropylmalate synthase amino acid biosynthetic enzyme), sstA (iron transport membrane protein), sirA (iron ABC transporter substrate-binding protein), IsdA (heme transporter), and Spa (*Staphylococcal* protein A), HlgA (gamma hemolysin), leuA (amino acid biosynthetic enzyme), sstA (iron transporter), sirA (iron transport), spa (protein A), or IsdA (heme transporter), or a substantially identical gene. The first promoter genes also may be selected from the group consisting of SAUSA300_0119 (Ornithine cyclodeaminase family protein), lrgA (Murein hydrolase transporter), and bioA (Adenosylmethionine-8-amino-7-oxononanoate aminotransferase), or a substantially identical gene.

The blood or serum blood or serum inducible first promoter genes for use in a *Staphylococcus aureus* synthetic microorganism may be selected from or derived from a gene selected from isdB gene CH52_00245, sbnD gene CH52_05125, heme ABC transporter gene CH52_00230, sbnE gene CH52_05120, srtB gene CH52_00215, isdC gene CH52_00235, sbnC gene CH52_05130, diaminopimelate decarboxylase gene CH52_05105, heme ABC transporter 2 gene CH52_00225, sbnB gene CH52_05135, sbnF gene CH52_05115, bnG gene CH52_05110, isd ORF3 gene CH52_00220, isdI gene CH52_00210, HarA gene CH52_10455, isdA gene CH52_00240, sbmA gene CH52_05140, and sbnI gene CH52_05100, iron ABC transporter gene CH52_05145, siderophore ABC transporter gene CH52_05150, and SAM dep Metrans gene CH52_04385.

The blood or serum inducible first promoter gene for use in a *Staphylococcus aureus* synthetic microorganism may be derived from or comprise a nucleotide sequence selected from 114, 115, 119, 120, 121, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, and 163, or a substantially identical sequence.

In one embodiment, the synthetic microorganism is a molecularly modified *Staphylococcus aureus* 502a. Raw sequences of first ORF in the operon that follows each regulatory region, from start codon to stop codon, used for design of real time PCR probes are shown in Table 2.

TABLE 2

*Staphylococcus aureus* strain 502a, raw sequences of first ORF in the operon that follows each regulatory region used for design of real time PCR probes.

| | |
|---|---|
| *Staphylococcus aureus* strain 502a, spa ORF of 502a | ATGACTTTACAAATACATACAGGGGGTATTAATTT<br>GAAAAAGAAAAACATTTATTCAATTCGTAAACTAGGTGTAGGTATTGCAT<br>CTGTAACTTTAGGTACATTACTTATATCTGGTGGCGTAACACCTGCTGCA<br>AATGCTGCGCAACACGATGAAGCTCAACAAAATGCTTTTTATCAAGTGTT<br>AAATATGCCTAACTTAAACGCTGATCAACGTAATGGTTTTATCCAAAGCC<br>TTAAAGATGATCCAAGCCAAAGTGCTAACGTTTTAGGTGAAGCTCAAAAA<br>CTTAATGACTCTCAAGCTCCAAAAGCTGATGCGCAACAAAATAACTTCAA<br>CAAAGATCAACAAAGCGCCTTCTATGAAATCTTGAACATGCCTAACTTAA<br>ACGAAGCGCAACGTAACGGCTTCATTCAAAGTCTTAAAGACGACCCAAGC<br>CAAAGCACTAATGTTTTAGGTGAAGCTAAAAAATTAAACGAATCTCAAGC<br>ACCGAAAGCTGATAACAATTTCAACAAAGAACAACAAAATGCTTTCTATG<br>AAATCTTGAATATGCCTAACTTAAACGAAGAACAACGCAATGGTTTCATC<br>CAAAGCTTAAAAGATGACCCAAGCCAAAGTGCTAACCTATTGTCAGAAGC<br>TAAAAAGTTAAATGAATCTCAAGCACCGAAAGCGGATAACAAATTCAACA<br>AAGAACAACAAAATGCTTTCTATGAAATCTTACATTTACCTAACTTAAAC<br>GAAGAACAACGCAATGGTTTCATCCAAAGCTTAAAAGATGACCCAAGCCA<br>AAGCGCTAACCTTTTAGCAGAAGCTAAAAAGCTAAATGATGCACAAGCAC<br>CAAAAGCTGACAACAAATTCAACAAAGAACAACAAAATGCTTTCTATGAA<br>ATTTTACATTTACCTAACTTAACTGAAGAACAACGTAACGGCTTCATCCA<br>AAGCCTTAAAGACGATCCTTCAGTGAGCAAAGAAATTTTAGCAGAAGCTA<br>AAAAGCTAAACGATGCTCAAGCACCAAAAGAGGAAGACAACAAAAAACCT<br>GGTAAAGAAGACGGCAACAAGCCTGGTAAAGAAGACAACAAAAAACCTGG<br>TAAAGAAGACGGCAACAAGCCTGGTAAAGAAGACAACAACAAACCTGGCA<br>AAGAAGACGGCAACAAGCCTGGTAAAGAAGACAACAACAAGCCTGGTAAA<br>GAAGACGGCAACAAGCCTGGTAAAGAAGACGGCAACAAACCTGGTAAAGA<br>AGACGGCAACGGAGTACATGTCGTTAAACCTGGTGATACAGTAAATGACA<br>TTGCAAAAGCAAACGGCACTACTGCTGACAAAATTGCTGCAGATAACAAA<br>TTAGCTGATAAAAACATGATCAAACCTGGTCAAGAACTTGTTGTTGATAA<br>GAAGCAACCAGCAAACCATGCAGATGCTAACAAAGCTCAAGCATTACCAG<br>AAACTGGTGAAGAAAATCCATTCATCGGTACAACTGTATTTGGTGGATTA<br>TCATTAGCCTTAGGTGCAGCGTTATTAGCTGGACGTCGTCGCGAACTATA<br>A<br>SEQ ID NO: 1 |

TABLE 2-continued

| *Staphylococcus aureus* strain 502a, raw sequences of first ORF in the operon that follows each regulatory region used for design of real time PCR probes. | |
|---|---|
| *Staphylococcus aureus* strain 502a, sirA ORF of 502a | ATGAATAAAGTAATTAAAATGC TTGTTGTTACGCTTGCTTTCCTACTTGTTTTAGCAGGATGTAGTGGGAAT TCAAATAAACAATCATCTGATAACAAAGATAAGGAAACAACTTCAATTAA ACATGCAATGGGTACAACTGAAATTAAAGGGAAACCAAAGCGTGTTGTTA CGCTATATCAAGGTGCCACTGACGTCGCTGTATCTTTAGGTGTTAAACCT GTAGGTGCTGTAGAATCATGGACACAAAAACCGAAATTCGAATACATAAA AAATGATTTAAAAGATACTAAGATTGTAGGTCAAGAACCTGCACCTAACT TAGAGGAAATCTCTAAATTAAAACCGGACTTAATTGTCGCGTCAAAAGTT AGAAATGAAAAAGTTTACGATCAATTATCTAAAATCGCACCAACAGTTTC TACTGATACAGTTTTCAAATTCAAAGATACAACTAAGTTAATGGGGAAAG CTTTAGGGAAAGAAAAAGAAGCTGAAGATTTACTTAAAAAGTACGATGAT AAAGTAGCTGCATTCCAAAAAGATGCAAAAGCAAAGTATAAAGATGCATG GCCATTGAAAGCTTCAGTTGTTAACTTCCGTGCTGATCATACAAGAATTT ATGCTGGTGGATATGCTGGTGAAATCTTAAATGATTTAGGATTCAAACGT AATAAAGACTTACAAAAACAAGTTGATAATGGTAAAGATATTATCCAACT TACATCTAAAGAAAGCATTCCATTAATGAACGCTGATCATATTTTTGTAG TAAAATCAGATCCAAATGCGAAAGATGCTGCATTAGTTAAAAAGACTGAA AGCGAATGGACTTCAAGTAAAGAGTGGAAAAATTTAGACGCAGTTAAAAA CAACCAAGTATCTGATGATTTAGATGAAATCACTTGGAACTTAGCTGGCG GATATAAATCTTCATTAACTTATTGACGATTTATATGAAAAGTTAAAT ATTGAAAAACAATCAAAATAA SEQ ID NO: 2 |
| *Staphylococcus aureus* strain 502a, sstA of 502a | ATGATAATGATTATCATTAATTTAA AGGGAGAAAAATTTGTAATGAAGTATTTATTAAAGGGAAATATTTTGCTT CTATTACTAATATTGTTGACAATTATTTCGTTGTTCATAGGTGTGAGTGA ACTATCAATTAAAGATTTACTACATTTAACTGAATCACAGCGGAATATTT TATTCTCAAGCCGAATACCAAGGACGATGAGTATTTTAATTGCTGGAAGT TCGTTGGCTTTAGCAGGCTTGATAATGCAACAAATGATGCAAAATAAGTT TGTTAGTCCGACTACAGCTGGAACGATGGAATGGGCTAAACTAGGTATTT TAATTGCTTTATTGTTCTTTCCAACCGGTCATATTTTATTAAAACTAGTA TTTGCTGTTATTTGCAGTATTTGCGGTACGTTTTTATTTGTTAAAATCAT TGATTTTATAAAAGTGAAAGATGTCATTTTTGTACCGCTTTTAGGAATTA TGATGGGTGGGATTGTTGCAAGTTTCACAACCTTCATCTCATTGCGCACG AATGCTGTTCAAAGCATTGGTAACTGGCTTAACGGGAACTTTGCCATTAT CACAAGTGGACGCTATGAAATTTTATATTTAAGTATTCCTCTTTTAGCAT TGACATATCTTTTTGCTAATCATTTCACGATTGTAGGAATGGGTAAAGAC TTTACTAATAATTTAGGTTTGAGTTACGAAAAATTAATTAACATCGCATT GTTTATTACTGCAACTATTACAGCATTGGTAGTGGTGACTGTTGGAACAT TACCGTTCTTAGGACTAGTAATACCAAATATTATTTCAATTTATCGAGGT GATCATTTGAAAAATGCTATCCCTCATACGATGATGTTAGGTGCCATCTT TGTATTATTTTCTGATATAGTTGGCAGAATTGTTGTTTATCCATATGAAA TAAATATTGGTTTAACAATAGGTGTATTTGGAACAATCATTTTCCTTATC TTGCTTATGAAAGGTAGGAAAAATTATGCGCAACAATAA SEQ ID NO: 3 |
| *Staphylococcus aureus* strain 502a, hlgA ORF of 502a | ATGAACT TAAAATTAAATAGAAAGAAAGTGATTTCTATGATTAAAAATAAAATATTA ACAGCAACTTTAGCAGTTGGTTTAATAGCCCCTTTAGCCAATCCATTTAT AGAAATTTCTAAAGCAGAAAATAAGATAGAAGATATCGGTCAAGGTGCAG AAATCATCAAAAGAACACAAGACATTACTAGCAAACGATTAGCTATAACT CAAAACATTCAATTTGATTTTGTAAAAGATAAAAAATATAACAAAGATGC CCTAGTTGTTAAGATGCAAGGCTTCATCAGCTCTAGAACAACATATTCAG ACTTAAAAAAATATCCATATATTAAAAGAATGATATGGCCATTTCAATAT AATATCAGTTTGAAAACGAAAGACTCTAATGTTGATTTAATCAATTATCT TCCTAAAAATAAAATTGATTCAGCAGATGTTAGTCAGAAATTAGGCTATA ATATCGGCGGAAACTTCCAATCAGCGCCATCAATCGGAGGCAGTGGCTCA TTCAACTACTCTAAAACAATTAGTTATAATCAAAAAAACTATGTTACTGA AGTAGAAAGTCAGAACTCTAAAGGTGTTAAATGGGGAGTGAAAGCAAATT CATTTGTTACACCGAATGGTCAAGTATCTGCATATGATCAATACTTATTT GCACAAGACCCAACTGGTCCAGCAGCAAGAGACTATTTCGTCCCAGATAA TCAATTACCTCCTTTAATTCAAAGTGGCTTTAATCCATCATTTATTACAA CATTGTCACACGAAAGAGGTAAAGGTGATAAAAGCGAGTTTGAAATCACT TACGGCAGAAACATGGATGCTACATATGCTTACGTGACAAGACATCGTTT AGCCGTTGATAGAAAACATGATGCTTTTAAAAACCGAAACGTTACAGTTA AATATGAAGTGAACTGGAAAACACATGAAGTAAAAATTAAAAGCATCACA CCTAAGTAA SEQ ID NO: 4 |
| *Staphylococcus aureus* strain 502a, isdA ORF of 502a | ATGACAAAACATTATTTAAACAGTAAGTATCAATC AGAACAACGTTCATCAGCTATGAAAAAGATTACAATGGGTACAGCATCTA TCATTTTAGGTTCCCTTGTATACATAGGCGCAGACAGCCAACAAGTCAAT GCGGCAACAGAAGCTACGAACGCAACTAATAATCAAAGCACACAAGTTTC TCAAGCAACATCACAACCAATTAATTTCCAAGTGCAAAAAGATGGCTCTT CAGAGAAGTCACACATGGATGACTATATGCAACACCCTGGTAAAGTAATT AAACAAAATAATAAATATTATTTCCAAACCGTGTTAAACAATGCATCATT |

TABLE 2-continued

| *Staphylococcus aureus* strain 502a, raw sequences of first ORF in the operon that follows each regulatory region used for design of real time PCR probes. | |
|---|---|
| | CTGGAAAGAATACAAATTTTACAATGCAAACAATCAAGAATTAGCAACAA<br>CTGTTGTTAACGATAATAAAAAAGCGGATACTAGAACAATCAATGTTGCA<br>GTTGAACCTGGATATAAGAGCTTAACTACTAAAGTACATATTGTCGTGCC<br>ACAAATTAATTACAATCATAGATATACTACGCATTTGGAATTTGAAAAAG<br>CAATTCCTACATTAGCTGACGCAGCAAAACCAAACAATGTTAAACCGGTT<br>CAACCAAAACCAGCTCAACCTAAAACACCTACTGAGCAAACTAAACCAGT<br>TCAACCTAAAGTTGAAAAAGTTAAACCTACTGTAACTACAACAAGCAAAG<br>TTGAAGACAATCACTCTACTAAAGTTGTAAGTACTGACACAACAAAAGAT<br>CAAACTAAAACACAAACTGCTCATACAGTTAAAACAGCACAAACTGCTCA<br>AGAACAAAATAAAGTTCAAACACCTGTTAAAGATGTTGCAACAGCGAAAT<br>CTGAAAGCAACAATCAAGCTGTAAGTGATAATAAATCACAACAAACTAAC<br>AAAGTTACAAAACATAACGAAACGCCTAAACAAGCATCTAAAGCTAAAGA<br>ATTACCAAAAACTGGTTTAACTTCAGTTGATAACTTTATTAGCACAGTTG<br>CCTTCGCAACACTTGCCCTTTTAGGTTCATTATCTTTATTACTTTTCAAA<br>AGAAAAGAATCTAAATAA<br>SEQ ID NO: 5 |
| *Staphylococcus aureus* strain 502a, leuA of 502a | ATGAGTAGTCATATTCAAATTTTTGATACGACACTAAGAGACGGTGAACA<br>AACACCAGGAGTGAATTTTACTTTTGATGAACGCTTGCGTATTGCATTGC<br>TAATAGAAAAATGGGGTGTAGATGTTATTGAAGCTGGATTTCCTGCTTCA<br>AGTACAGGTAGCTTTAAATCTGTTCAAGCAATTGCACAAACATTAACAAC<br>AACGGCTGTATGTGGTTTAGCTAGATGTAAAAAATCTGACATCGATGCTG<br>TATATGAAGCAACAAAAGATGCAGCGAAGCCGGTCGTGCATGTTTTTATA<br>GCAACATCACCTATTCATCTTGAACATAAACTTAAAATGTCTCAAGAAGA<br>CGTTTTAGCATCTATTAAAGAACATGTCACATACGCGAAACAATTATTTG<br>ACGTTGTTCAATTTTCACCTGAAGATGCAACGCGTACTGAATTACCATTC<br>TTAGTGAAATGTGTACAAACTGCCGTTGACGCTGGAGCTACAGTTATTAA<br>TATTCCTGATACAGTCGGCTACAGTTACCATGATGAATATGCACATATTT<br>TCAAAACCTTAACAGAATCTGTAACATCTTCAAATGAAATTATTTATAGT<br>GCTCATTGCCATGACGATTTAGGAATGGCTGTTTCAAATAGTTTAGCTGC<br>AATTGAAGGCGGTGCGAGACGAATTGAAGGCACTGTAAATGGTATTGGTG<br>AACGAGCAGGTAATGCAGCACTTGAAGAAGTCGCGCTTGCACTATACGTT<br>CGAAATGATCATTATGGTGCTCAAACTGCCCTTAATCTCGAAGAAACTAA<br>AAAAACATCGGATTTAATTTCAAGATATGCAGGTATTCGAGTGCCTAGAA<br>ATAAAGCAATTGTTGGCCAAAATGCATTTAGTCATGAATCAGGTATTCAC<br>CAAGATGGCGTATTAAAACATCGTGAAACATATGAAATTATGACACCTCA<br>ACTTGTTGGTGTAAGCACGACTGAACTTCCATTAGGAAAATTATCTGGTA<br>AACACGCCTTCTCAGAGAAGTTAAAAGCATTAGGTTATAACATTGATAAA<br>GAAGCGCAAATAGATTTATTTAAACAATTCAAGACCATTGCGGACAAAAA<br>GAAATCTGTTTCAGATAGAGATATTCATGCGATTATTCAAGGTTCTGAGC<br>ATGAGCATCAAGCACTTTATAAATTGGAAACACTACAACTACAATATGTC<br>TCTAGCGGCCTTCAAAGTGCTGTTGTTGTTGTTAAAGATAAAGAGGGTCA<br>TATTTACCAGGATTCAAGTATTGGTACTGGTTCAATCGTAGCAATTTACA<br>ATGCAGTTGATCGTATTTTCCAGAAAGAAACAGAATTAATTGATTATCGT<br>ATTAATTCTGTCACTGAAGGTACTGATGCCCAAGCAGAAGTACATGTAAA<br>TTTATTGATTGAAGGTAAGACTGTCAATGGCTTTGGTATTGATCATGATA<br>TTTTACAAGCCTCTTGTAAAGCATACGTAGAAGCACATGCTAAATTTGCA<br>GCTGAAAATGTTGAGAAGGTAGGTAAT<br>SEQ ID NO: 6 |

As discussed herein below, the synthetic microorganism may include an expression clamp molecular modification that prevents expression of the cell death gene, wherein the expression clamp comprises an antitoxin gene specific for the cell death gene operably associated with a second promoter which is active upon dermal or mucosal colonization or in TSB media, and is preferably downregulated in blood, serum or plasma, for example, the second promoter may comprise a clfB gene (clumping factor B), for example as shown in Table 3.

TABLE 3

| Other Sequences Used for Design of Real time PCR probes | |
|---|---|
| clfB ORF of 502a (to drive antitoxin for "expression clamp") | ATGAAAAAAAGAATTGATTATTTGTCGAATAAGCAGAATAAGTATTCGAT<br>TAGACGTTTTACAGTAGGTACCACATCAGTAATAGTAGGGGCAACTATAC<br>TATTTGGGATAGGCAATCATCAAGCACAAGCTTCAGAACAATCGAACGAT<br>ACAACGCAATCTTCGAAAAATAATGCAAGTGCAGATTCCGAAAAAAACAA<br>TATGATAGAAACACCTCAATTAAATACAACGGCTAATGATACATCTGATA<br>TTAGTGCAAACACAAACAGTGCGAATGTAGATAGCACAACAAAACCAATG<br>TCTACACAAACGAGCAATACCACTACAACAGAGCCAGCTTCAACAAATGA<br>AACACCTCAACCGACGGCAATTAAAAATCAAGCAACTGCTGCAAAAATGC<br>AAGATCAAACTGTTCCTCAAGAAGCAAATTCTCAAGTAGATAATAAAACA<br>ACGAATGATGCTAATAGCATAGCAACAAACAGTGAGCTTAAAAATTCTCA<br>AACATTAGATTTACCACAATCATCACCACAAACGATTTCCAATGCGCAAG<br>GAACTAGTAAACCAAGTGTTAGAACGAGAGCTGTACGTAGTTTAGCTGTT<br>GCTGAACCGGTAGTAAATGCTGCTGATGCTAAAGGTACAAATGTAAATGA |

TABLE 3-continued

| Other Sequences Used for Design of Real time PCR probes | |
|---|---|
| | TAAAGTTACGGCAAGTAATTTCAAGTTAGAAAAGACTACATTTGACCCTA<br>ATCAAAGTGGTAACACATTTATGGCGGCAAATTTTACAGTGACAGATAAA<br>GTGAAATCAGGGGATTATTTTACAGCGAAGTTACCAGATAGTTTAACTGG<br>TAATGGAGACGTGGATTATTCTAATTCAAATAATACGATGCCAATTGCAG<br>ACATTAAAAGTACGAATGGCGATGTTGTAGCTAAAGCAACATATGATATC<br>TTGACTAAGACGTATACATTTGTCTTTACAGATTATGTAAATAATAAAGA<br>AAATATTAACGGACAATTTTCATTACCTTTATTTACAGACCGAGCAAAGG<br>CACCTAAATCAGGAACATATGATGCGAATATTAATATTGCGGATGAAATG<br>TTTAATAATAAAATTACTTATAACTATAGTTCGCCAATTGCAGGAATTGA<br>TAAACCAAATGGCGCGAACATTTCTTCTCAAATTATTGGTGTAGATACAG<br>CTTCAGGTCAAAACACATACAAGCAAACAGTATTTGTTAACCCTAAGCAA<br>CGAGTTTTAGGTAATACGTGGGTGTATATTAAAGGCTACCAAGATAAAAT<br>CGAAGAAAGTAGCGGTAAAGTAAGTGCTACAGATACAAAACTGAGAATTT<br>TTGAAGTGAATGATACATCTAAATTATCAGATAGCTACTATGCAGATCCA<br>AATGACTCTAACCTTAAAGAAGTAACAGACCAATTTAAAAATAGAATCTA<br>TTATGAGCATCCAAATGTAGCTAGTATTAAATTTGGTGATATTACTAAAA<br>CATATGTAGTATTAGTAGAAGGGCATTACGACAATACAGGTAAGAACTTA<br>AAAACTCAGGTTATTCAAGAAAATGTTGATCCTGTAACAAATAGAGACTA<br>CAGTATTTTCGGTTGGAATAATGAGAATGTTGTACGTTATGGTGGTGGAA<br>GTGCTGATGGTGATTCAGCAGTAAATCCGAAAGACCCAACTCCAGGGCCG<br>CCGGTTGACCCAGAACCAAGTCCAGACCCAGAACCAGAACCAACGCCAGA<br>TCCAGAACCAAGTCCAGACCCAGAACCGGAACCAAGCCCAGACCCGGATC<br>CGGATTCGGATTCAGACAGTGACTCAGGCTCAGACAGCGACTCAGGTTCA<br>GATAGCGACTCAGAATCAGATAGCGATTCGGATTCAGACAGTGATTCAGA<br>TTCAGACAGCGACTCAGAATCAGATAGCGATTCAGAATCAGATAGCGACT<br>CAGATTCAGATAGCGATTCAGATTCAGATAGCGATTCAGAATCAGATAGC<br>GATTCGGATTCAGACAGTGATTCAGATTCAGACAGCGACTCAGAATCAGA<br>TAGCGACTCAGAATCAGATAGTGAGTCAGATTCAGACAGTGACTCGGACT<br>CAGACAGTGATTCAGACTCAGATAGCGATTCAGACTCAGATAGCGATTCA<br>GACTCAGACAGCGATTCAGATTCAGACAGCGACTCAGAATCAGACAGCGA<br>CTCAGACTCAGATAGCGACTCAGACTCAGACAGCGACTCAGATTCAGATA<br>GCGATTCAGACTCAGACAGCGACTCAGACTCAGACAGCGACTCAGACTCA<br>GATAGCGATTCAGACTCAGACAGCGACTCAGATTCAGATAGCGATTCGGA<br>CTCAGACAGCGATTCAGATTCAGACAGCGACTCAGACTCGGATAGCGATT<br>CAGATTCAGACAGCGACTCAGACTCGGATAGCGACTCGGATTCAGATAGT<br>GACTCCGATTCAAGAGTTACACCACCAAATAATGAACAGAAAGCACCATC<br>AAATCCTAAAGGTGAAGTAAACCATTCTAATAAGGTATCAAAACAACACA<br>AAACTGATGCTTTACCAGAAACAGGAGATAAGAGCGAAAACACAAATGCA<br>ACTTTATTTGGTGCAATGATGGCATTATTAGGATCATTACTATTGTTTAG<br>AAAACGCAAGCAAGATCATAAAGAAAAAGCGTAAATACTTTTTTAGGCCG<br>AATACATTTGTATTCGGTTTTTTTGTTGAAAATGATTTTAAAGTGAATTG<br>SEQ ID NO: 7 |
| gyrA ORF of 502a (internal housekeeping gene) | ATGGCTGAATTACCTCAATCAAGAATAAATGAACGAAATATTACCAGTGA<br>AATGCGTGAATCATTTTTAGATTATGCGATGAGTGTTATCGTTGCTCGTG<br>CATTGCCAGATGTTCGTGACGGTTTAAAACCAGTACATCGTCGTATACTA<br>TATGGATTAAATGAACAAGGTATGACACCGGATAAATCATATAAAAAATC<br>AGCACGTATCGTTGGTGACGTAATGGGTAAATATCACCCTCATGGTGACT<br>CATCTATTTATGAAGCAATGGTACGTATGGCTCAAGATTTCAGTTATCGT<br>TATCCGCTTGTTGATGGCCAAGGTAACTTTGGTTCAATGGATGGAGATGG<br>CGCAGCAGCAATGCGTTATACTGAAGCGCGTATGACTAAAATCACACTTG<br>AACTGTTACGTGATATTAATAAAGATACAATAGATTTTATCGATAACTAT<br>GATGGTAATGAAAGAGAGCCGTCAGTCTTACCTGCTCGATTCCCTAACTT<br>GTTAGCCAATGGAGCATCAGGTATAGCGGTAGGTATGGCAACGAATATTC<br>CACCACATAACTTAACAGAATTAATCAATGGTGTACTTAGCTTAAGTAAG<br>AACCCTGATATTTCAATTGCTGAGTTAATGGAGGATATTGAAGGTCCTGA<br>TTTCCCAACTGCTGGACTTATTTTAGGTAAGAGTGGTATTAGACGTGCAT<br>ATGAAACAGGTCGTGGTTCAATTCAAATGCGTTCTCGTGCAGTTATTGAA<br>GAACGTGGAGGCGGACGTCAACGTATTGTTGTCACTGAAATTCCTTTCCA<br>AGTGAATAAGGCTCGTATGATTGAAAAAATTGCAGAGCTCGTTCGTGACA<br>AGAAAATTGACGGTATCACTGATTTACGTGATGAAACAAGTTTACGTACT<br>GGTGTGCGTGTCGTTATTGATGTGCGTAAGGATGCAAATGCTAGTGTCAT<br>TTTAAATAACTTATACAAACAAACACCTCTTCAAACATCATTTGGTGTGA<br>ATATGATTGCACTTGTAAATGGTAGACCGAAGCTTATTAATTTAAAAGAA<br>GCGTTGGTACATTATTTAGAGCATCAAAAGACAGTTGTTAGAAGACGTAC<br>GCAATACAACTTACGTAAAGCTAAAGATCGTGCCCACATTTTAGAAGGAT<br>TACGTATCGCACTTGACCATATCGATGAAATTATTTCAACGATTCGTGAG<br>TCAGATACAGATAAAGTTGCAATGGAAAGCTTGCAACAACGCTTCAAACT<br>TTCTGAAAAACAAGCTCAAGCTATTTTAGACATGCGTTTAAGACGTCTAA<br>CAGGTTTAGAGAGAGACAAAATTGAAGCTGAATATAATGAGTTATTAAAT<br>TATATTAGTGAATTAGAAACAATCTTAGCTGATGAAGAAGTATTACTACA<br>ATTAGTTAGAGATGAATTAACAGAAATTCGAGATCGTTTCGGTGATGATC<br>GTCGTACTGAAATCCAATTAGGTGGATTTGAAGATTTAGAAGATGAAGAT<br>CTCATTCCAGAAGAACAAATTGTAATTACACTAAGCCATAATAACTACAT<br>TAAACGTTTGCCGGTATCTACATATCGTGCTCAAAACCGTGGTGGTCGTG<br>GTGTTCAAGGTATGAATACATTGGAAGAAGATTTTGTCAGTCAATTGGTA<br>ACTTTAAGTACACATGACCATGTATTGTTCTTTACTAACAAAGGTCGTGT<br>ATACAAACTTAAAGGTTATGAAGTGCCTGAGTTATCAAGACAGTCTAAAG |

TABLE 3-continued

| Other Sequences Used for Design of Real time PCR probes |
|---|
| GTATTCCTGTAGTGAATGCTATTGAACTTGAAAATGATGAAGTCATTAGT<br>ACAATGATTGCTGTTAAAGACCTTGAAAGTGAAGACAACTTCTTAGTGTT<br>TGCAACTAAACGTGGTGTCGTTAAACGTTCAGCATTAAGTAACTTCTCAA<br>GAATAAATAGAAATGGTAAGATTGCGATTTCGTTCAGAGAAGATGATGAG<br>TTAATTGCAGTTCGCTTAACAAGTGGTCAAGAAGATATCTTGATTGGTAC<br>ATCACATGCATCATTAATTCGATTCCCTGAATCAACATTACGTCCTTTAG<br>GCCGTACAGCAACGGGTGTGAAAGGTATTACACTTCGTGAAGGTGACGAA<br>GTTGTAGGGCTTGATGTAGCTCATGCAAACAGTGTTGATGAAGTATTAGT<br>AGTTACTGAAAATGGTTATGGTAAACGTACGCCAGTTAATGACTATCGTT<br>TATCAAATCGTGGTGGTAAAGGTATTAAAACAGCTACGATTACTGAGCGT<br>AATGGTAATGTTGTATGTATCACTACAGTAACTGGTGAAGAAGATTTAAT<br>GATTGTTACTAATGCAGGTGTCATTATTCGACTAGATGTTGCAGATATTT<br>CTCAAAATGGTCGTGCAGCACAAGGTGTTCGCTTAATTCGCTTAGGTGAT<br>GATCAATTTGTTTCAACGGTTGCTAAAGTAAAAGAAGATGCAGAAGATGA<br>AACGAATGAAGATGAGCAATCTACTTCAACTGTATCTGAAGATGGTACTG<br>AACAACAACGTGAAGCGGTTGTAAATGATGAAACACCAGGAAATGCAATT<br>CATACTGAAGTGATTGATTCAGAAGAAAATGATGAAGATGGACGTATTGA<br>AGTAAGACAAGATTTCATGGATCGTGTTGAAGAAGATATACAACAATCAT<br>CAGATGAAGATGAAGAATAATAA<br>SEQ ID NO: 8 |

Additional oligonucleotides used in the recombinant approach to preparing the synthetic microorganism molecularly modified *Staphylococcus aureus* 502a are shown in Table 4A shown in FIG. 3A-C, and promoter sequences are shown below.

Cell Death Genes

The synthetic microorganism may contain a kill switch molecular modification comprising cell death gene operably associated with an inducible first promoter, as described herein. The cell death gene may be selected from any gene, that upon overexpression results in cell death or significant reduction in the growth of the synthetic microorganism within a predefined period of time, preferably within 15 minutes, 30 minutes, 60 minutes, 90 minutes, 120 minutes, 240 minutes, or 360 minutes of induction.

Cell death genes, toxin genes, or kill switch genes, have been developed in other contexts.

WO 2016/210373, Jonathan Kotula et al., assigned to Synlogic, Inc. discloses a recombinant bacterial cell that is an auxotroph engineered for biosafety, for example, that comprises a repression based kill switch gene that comprises a toxin, an anti-toxin and an arabinose inducible promoter and depends on the presence of an inducer (e.g., arabinose) to keep cells alive.

U.S. Pat. No. 8,975,061, Bielinski, discloses regulation of toxin and antitoxin genes for biological containment for preventing unintentional and/or uncontrolled spread of the microorganisms in the environment.

WO 1999/058652, Gerdes, discloses cytotoxin based biological containment and kill systems including *E. coli* relBE locus and similar systems found in Gram-negative and Gram-positive bacteria and Archae.

US20150050253, Gabant, discloses controlled growth of microorganisms and controlling the growth/spread of other exogenous recombinant or other microbes.

WO 2017/023818 and WO 2016/210384, Falb, disclose bacteria engineered to treat disorders involving propionate metabolism.

US20160333326, Falb, discloses bacteria engineered to treat diseases associated with hyperammonemia.

U.S. Pat. No. 9,101,597, Garry, discloses immunoprotective primary mesenchymal stem cells and methods and a proaptoptotic kill switch is described for use in mesenchymal stem cells.

US20160206666, Falb, discloses bacteria engineered to treat diseases that benefit from reduced gut inflammation and/or tighten gut mucosal barrier.

In some embodiments, synthetic microorganisms are provided that comprise one or more of SprA1 (*Staphylococcus aureus*), Sma1 (*Serratia marcescens*), RelF (*E. coli*), KpnI (*K. pneumoniae*) and/or RsaE (*Staphylococcus aureus*) toxin genes.

In the present disclosure, various cell death toxin genes were tested in combinations with previously identified optimal control regions: i) a 30 amino acid peptide (PepA1) that forms pores in the cell membrane, impairing its function; if) a restriction enzyme (Kpn1 or other) that rapidly digests the bacterial chromosome; iii) a small RNA (RsaE) that impairs central biochemical metabolism by inhibiting translation of 2 essential genes; iv) a restriction endonuclease (Sma1) derived from *Serratia marcescens*; and v) a toxin gene derived from *E. coli* (RelF). Some toxins are more potent than others and the ideal combination of control region induction strength and toxin potency may result in a strain that is healthy at baseline and that rapidly dies in the circulatory system.

sprA1 (*Staphylococcus aureus*) toxin gene (encoding PepA1 peptide) is described in WO 2013/050590, Felden, B, and Sayed, N, disclosing use of PepA1 as an antimicrobial, but the focus is on using the peptide as purified exogenous therapeutic to be delivered into the body.

relF (*E. coli*) toxin gene is described in EP 20090168998, Gerdes, disclosing kill switches for the purpose of biocontainment and focuses on revolve around killing of Gram-negative bacteria.

relF toxin gene is described in U.S. Pat. No. 8,852,916, Hyde and Roderick, disclosing mechanisms of triggering cell death of microorganisms (programmed cell death). The main application is to use RelF in environmental biocontainment.

relF is described in U.S. Pat. No. 8,682,619, Amodei, prophetically discloses RelF to regulate bacterial population growth.

The synthetic microorganism may be derived from a *Staphylococcus aureus* target microorganism by insertion of a kill switch molecular modification comprising a regulatory region comprising an inducible promoter operably linked to a cell death gene which may be a toxin gene.

The cell death gene may be selected from or derived from a sprA1 gene (encoding a peptide toxin that forms pores in cell membrane), sprA2 gene, sprG gene, sma1 gene (a restriction endonuclease), kpn1 gene (restriction enzyme that rapidly digests bacterial chromosome), rsaE gene (a small RNA that impairs central metabolism by inhibiting translation of 2 essential genes), a relF gene (*E. coli*), yoeB gene, mazF gene, yefM gene, or lysostaphin toxin gene. The synthetic *Staphylococcus aureus* may include a kill switch molecular modification comprising a cell death gene having a nucleotide sequence selected from SEQ ID NOs: 122, 124, 125, 126, 127, 128, 274, 275, 284, 286, 288, 290, 315, or 317, or a substantially identical nucleotide sequence.

In a specific embodiment, a synthetic *Staphylococcus aureus* is provided having a molecular modification comprising a blood or serum inducible first promoter operably associated with a cell death gene comprising or derived from a SprA1 gene.

Multiple Kill Switches

One KS may be sufficient to equip the synthetic microorganism with the desired characteristics, but more than one KS may further enhance the strain by: i) dramatically reducing the rate of KS-inactivating mutations, and; ii) killing the cell by more than one pathway, which could cause faster cell death (a product-enhancing feature). The cell death gene may comprise one or more of the DNA sequences (7) downstream of promoters that are shown below. Base pair numbers correspond to pCN51 vector location.

1. The sprA1 gene sequence between restriction sites PstI and EcoRI is shown below. The sequence was synthesized by DNA 2.0(Atum) and ligated into a vector, which can be transformed into *E. coli* cells for replication. The sprAI gene was restriction cut at PstI and EcoRI sites and isolated by gel electrophoresis. Full sequence between restriction sites with possible start and stop sites italicized.

```
                                          SEQ ID NO: 122
                    PstI
                    CTGCAGGG TACCGCAGAG AGGAGGTGTA

6101   TAAGGTGATG CTTATTTTCG TTCACATCAT AGCACCAGTC ATCAGTGGCT

6151   GTGCCATTGC GTTTTTTTCT TATTGGCTAA GTAGACGCAA TACAAAATAG

6201   GTGACATATA GCCGCACCAA TAAAAATCCC CTCACTACCG CAAATAGTGA

6251   GGGGATTGGT GTATAAGTAA ATACTTATTT TCGTTGTGGA TCCTTGACTG

6301   AATTC
       EcoRI
```

2. The DNA sequence for the regulatory RNA sprAIsprAI$_{AS}$ (sprAIsprAI antisense) under the ClfB promoter (which is cloned in reverse behind the sprA1 gene, including the antisense regulatory RNA). This DNA sequence produces a non-coding antisense regulatory RNA, which acts as an antitoxin by regulating the translation of sprA1 outside of the environmental factors of serum and/or blood. Below is the sprA1sprA1$_{AS}$ DNA sequence.

```
                                          SEQ ID NO: 123
EcoRI
GAATTCAGTCAAGGATCCACAACGAAAATAAGTATTTACTTATACACCAATCCCCTCACTATTTGCGGTAGTGAGGG

GATTTTTATTGGTGCGGCTATATGTCACCTATTTTGTATTGCGTCTACTTAGCCAATAAGAAAAAAACGCAATGGCA

CAGCCACTGATGACTGGTGCTATGATGTGAACGAAAATAAGCATCACCTTATACACCTCCTCTCTGCGGTACCCTGC

AG
PstI
```

3. The SmaI DNA sequence between restriction sites PstI and EcoRI. Sequence was synthesized by DNA 2.0(Atum) and ligated into a vector that can be transformed into *E. coli* cells for replication. SmaI gene was restriction cut at PstI and EcoRI sites and isolated by gel electrophoresis. Full sequence between restriction sites with start and stop sites italicized.

```
                                          SEQ ID NO: 124
                                          C TGCAGATGAG

5751   CAGGGATGAC CAACTCTTTA CACTTTGGGG AAAGCTTAAC GATCGTCAGA

5801   AGGATAATTT TCTAAAATGG ATGAAAGCTT TTGATGTAGA GAAAACTTAC

5851   CAAAAAACAA GTGGGGATAT TTTCAATGAT GATTTTTTCG ATATATTTGG
```

-continued

```
5901   TGATAGATTA ATTACTCATC ATTTCAGTAG CACGCAAGCT TTAACAAAAA
5951   CTTTATTCGA ACATGCTTTT AATGACTCCT TAAATGAATC TGGAGTTATA
6001   TCCTCTCTTG CGGAAAGTAG AACAAACCCT GGGCATGACA TAACAATCGA
6051   TAGCATAAAG GTTGCTTTAA AAACAGAAGC AGCTAAAAAT ATTAGCAAAT
6101   CATATATTCA TGTAAGTAAG TGGATGGAGT TAGGCAAGGG GGAGTGGATT
6151   CTAGAATTAT TATTAGAACG GTTTTTAGAG CATCTAGAGA ATTATGAACG
6201   TATTTTCACA CTCAGATATT TTAAAATATC CGAGTATAAA TTTAGCTACC
6251   AGCTTGTAGA AATACCCAAG AGTCTTTTGT TGGAAGCAAA AAATGCGAAA
6301   TTAGAAATAA TGTCGGGAAG CAAACAAAGC CCTAAGCCCG GCTATGGATA
6351   TGTGTTAGAT GAAAATGAAA ATAAGAAGTT TTCTCTATAC TTTGATGGTG
6401   GTGCCGAGAG AAAACTTCAA ATAAAACATT TAAATTTAGA ACATTGCATT
6451   GTTCATGGAG TTTGGGATTT TATTCTACCG CCGCCTTAAG AATTC
```

4. The rsaE DNA sequence between restriction sites PstI and EcoRI. Sequence was synthesized by DNA 2.0(Atum) and ligated into a vector that can be transformed into *E. coli* cells for replication. RsaE small regulatory RNA (sRNA) was restriction cut at PstI and EcoRI sites and isolated by gel electrophoresis. This contains a 5' run-in and the mature RNA is processed out starting at the bold GAAATTAA and ending at the stretch of Ts after the ACG.

SEQ ID NO: 125

```
                         CTGCAGAT GGTAGAGATA GCATGTTATA
6101   TTATGAACAT GAAATTAATC ACATAACAAA CATACCCCTT TGTTTGAAGT
6151   GAAAAATTTC TCCCATCCCC TTTGTTTAGC GTCGTGTATT CAGACACGAC
6201   GTTTTTTTGA ATTC
```

5. A variant can be used for RsaE sRNA which may express the sRNA more highly which may work more effectively. This variant would start with the GAAATTAA at the 5' end.

SEQ ID NO: 126

```
6110   GAAATTAATC ACATAACAAA CATACCCCTT TGTTTGAAGT
6151   GAAAAATTTC TCCCATCCCC TTTGTTTAGC GTCGTGTATT CAGACACGAC
6201   GTTTTTTTGA ATTC
```

6. The relF (*E. coli*) DNA sequence. This potential kill gene will be tested and cloned.

SEQ ID NO: 127

```
ATGAAGCAGC AAAAGGCGAT GTTAATCGCC CTGATCGTCA
TCTGTTTAAC CGTCATAGTG ACGGCACTGG TAACGAGGAA
AGACCTCTGC GAGGTACGAA TCCGAACCGG CCAGACGGAG
GTCGCTGTCT TCACAGCTTA CGAACCTGAG GAGTAA
```

7. The KpuI (restriction enzyme from *K. pneumoniae*) DNA sequence will be tested and cloned.

SEQ ID NO: 128

```
atggatgtctttgataaagtttatagtgatgataataatagttatgacca
aaaaactgtaagtcagcgtattgaagccctatttcttaataaccttggca
aagttgtaactcgtcagcaaatcattagggcggcaactgatccaaaaaca
```

-continued

```
gggaaacaaccagaaaattggcatcagagactttcagaactacgaactga
taaaggatatactattttatcctggegggatatgaaggttttagctccgc
```

-continued

```
aagagtatataatgccacacgcaacaagacgcccaaaggcagcaaagcgt
gtattaccgacaaaagaaacctgggaacaggttttggatagagctaatta
ctcttgcgagtggcaggaagatggtcaacactgtgggttagttgaaggtg
atattgatcctatagggggaggcacggtcaaactaacaccagaccatatg
acacctcattcaatagatcccgcaactgatgtaaatgatcctaaaatgtg
gcaagcattgtgtggacgtcatcaagttatgaaaaaaaaattattgggatt
```

-continued

```
caaataatgggaaaataaatgtcattggtatattgcagtcagtaaatgag

aaacaaaagaatgatgctttagagtttcttttgaattattatggattgaa

aagataa
```

A synthetic *Staphylococcus aureus* 502a is provided herein comprising at least one molecular modification (kill switch) comprising a first cell death gene operably linked to a first regulatory region comprising a first promoter, optionally wherein the first cell death gene comprises a nucleotide sequence selected from SEQ ID NO; 122, 124, 125, 126, 127, 128, 274, 275, 284, 286, 288, 290, 315, and 317, or a substantially identical nucleotide sequence Although kill switches (KSs) have been described for other purposes, the present KS has the unique features: i) it responds to being exposed to blood or serum; ii) it is endogenously regulated, meaning that the addition or removal of small molecules is not needed to activate or tune the KS (not an auxotroph); and iii) useful combinations of control region/toxin, and of multiple such cassettes may be used to achieve superior performance.

Expression Clamp

A synthetic microorganism is provided which comprises kill switch molecular modification comprising (i) a cell death gene operatively associated with (ii) a first regulatory region comprising a first inducible promoter which is induced by exposure to blood or serum. In order for the synthetic microorganism to durably occupy a dermal or mucosal niche in the subject, the kill switch preferably should be silent (not expressed) in the absence of blood or serum.

In order to avoid "leaky expression" of the cell death gene, the synthetic microorganism may further comprise at least a second molecular modification (expression clamp) comprising (iii) an antitoxin gene specific for the cell death gene, wherein the antitoxin gene is operably associated with (iv) a second regulatory region comprising a second promoter which is active (e.g., constitutive) upon dermal or mucosal colonization or in a media (e.g., TSB), and preferably is downregulated by exposure to blood, serum or plasma.

The basal level of gene expression (the expression observed when cells are not exposed to blood or serum, e.g., in TSB (tryptic soy broth) in the KS strain should ideally be very low because producing the toxin prior to contact with serum would kill or weaken the strain prematurely. Even moderate cell health impairment is unacceptable because: 1) escape mutations in the KS would accumulate (KS instability)—a known phenomenon that must be avoided, and/or; 2) the natural efficacy observed with our strain in preliminary trials could be reduced or lost. To understand if leaky expression is a problem, both the absolute level of baseline expression and the fold change in serum are being measured and closely considered in the selection of the optimal control region to drive the KS.

Awareness of leaky expression does not fix the problem and the reality is that even widely used "tightly controlled" rheostatic promoters such as $P_{CUP1}$ and $P_{Gal7}$, and $P_{Tet}$-on/off variants produce measurable mRNA transcription in the absence of specific induction. In some embodiments, an "expression clamp" is employed in which the KS cassette contains not only the serum-responsive control region that drives toxin expression, but also encodes a "translation blocking" RNA under control of a *Staphylococcus aureus* promoter ($P_{clfB}$ etc) that is normally strongly active in *Staphylococcus aureus* during colonization of the skin, and in downregulated in blood.

The ci/B gene promoter ($P_{clfB}$) will be cloned to drive expression of the sprA1sprA1$_{AS}$ RNA and the cassette will be incorporated into the same expression module as is used for expression of the sprA1 toxin from a serum-responsive promoter (eg, $P_{isdB}$, $P_{hlgA}$ etc). In this strain, serum/blood exposure activates the toxin (e.g., up to 350-fold or more) but not the antitoxin, and growth in TSB or on the skin activates antitoxin but not toxin. A representative diagram of an exemplary molecular modification of a synthetic strain is shown in FIG. 1.

An Alternate Approach to a Synthetic Microorganism: KO Method

An alternative way to create a kill-switch-like phenotype in the synthetic microorganism is to disrupt ("knock-out") one or more genes that are required for survival in blood and/or for infection of organs but that are not required (or important) for growth in media or on the skin. In some embodiments, one or more, or two or more, of the 6 genes shown in Table 5 may be employed in the KO method.

TABLE 5

Candidates for gene knockout to create an attenuated strain:

| Reference | Type of mutagenesis | Genes required for survival in blood or infection of organs | Reported gene function |
|---|---|---|---|
| Benton et al (2004) Large-Scale Identification of Genes Required for Full Virulence of *Staphylococcus aureus*. J. bact. 186(24): 8478-8489. DOI 10.1128/JB.186.24.8478-8489.2004 | Transposon insertion | PycA; AspB; GabP. Mutation of these causes up to 1000-fold reduction in rate of organ infection in vivo | PycA: Pyruvate carboxylase AspB: Aspartate aminotransferase GabP: Gamma-aminobutyrate permease |
| Valentino et al (2014). Genes Contributing to *Staphylococcus aureus* Fitness in Abscess- and Infection-Related Ecologies. mBio5(5): e01729-14.doi: 10.1128/mBio.01729-14. | Transposon insertion | Genes essential for in vitro survival in blood but not needed for growth in BHI liquid or agar: SAOUHSC_01216 SAOUHSC_00686 SAOUHSC_00378 | SAOUHSC_01216: succinyl CoA-synthetase subunit b. SAOUHSC_00686: Unknown hypothetical protein SAOUHSC_00378: Unknown hypothetical protein |

In one embodiment; a synthetic microorganism is provided comprising replacement of one or more of the genes in Table 5 with unmodified or expression-clamped KS, using allelic exchange. This may further enhance the death rate of the synthetic microorganism in blood. Alternatively, the need to integrate two KSs is diminished by having one KO and one KS. In a further embodiment, a synthetic microorganism may comprise a combination of more than one KO that may have synergistic effects.

Kill Switch Regulatory Region

A synthetic microorganism comprising a kill switch is provided. The kill switch comprises a cell death gene operably linked to a regulatory region (RR) comprising an inducible promoter, as described herein.

Development of a synthetic microorganism involves identification and characterization of optimal regulatory regions (RRs) in order to drive kill switch genes; a list of serum responsive loci are chosen; RRs are identified; and Serum activation response is verified, and basal expression is investigated.

Identification and Characterization of Optimal Regulatory Regions to Drive Kill Switch Candidates.

This important phase of KS strain construction involves identifying genes that are strongly upregulated in response to human serum and/or whole heparinized blood. Once the genes are identified, their RRs, which contain the promoter and other upstream elements, are identified and annotated. In one approach, any known serum- and blood-responsive gene in *Staphylococcus aureus* may be employed that is known in the literature.

A RR includes the upstream regulatory sequences needed for activation (or repression) of mRNA transcription in response to stimuli. The motifs include "up" elements, −35, and −10 consensus elements, ribosome binding sites ("shine-dalgarno sequence") and "operator" sequences which bind protein factors that strongly influence transcription. In practice for eubacteria, harnessing a 200 bp region of DNA sequence upstream of the start codon is usually adequate to capture all of these elements. However, it is preferred to deliberately identify these sequences to ensure their inclusion.

Six *Staphylococcus aureus* genes that are strongly upregulated by exposure to human blood or serum are shown in Table 6.

TABLE 6

Identification of candidate RRs and serum or blood inducible promoters to drive kill switch components for driving the toxin.

| Gene | Function | First author, year | Fold change in serum or blood | Time of exposure to blood or serum | SA strain used in study | Comments |
|---|---|---|---|---|---|---|
| spa | Staphyloccocal Protein A; Ig binding; monocistronic gene | Malachowa 2011 | ~45 fold | 90 min | USA300 and mu50 | Wang 2004 predicts the monocistronic gene structure. Both experi-mental& computational evidence of this structure exist |
| sir | Sir ABC; iron transport | Malachowa 2011 and Wang 2004 | 81 fold in serum; 68-fold in blood (sirA; first ORF in operon) | 30 to 120 minutes | USA300 and mu50 | High induction at earliest timepoint. Experimental and predicted operon structure match |
| sst | SstABCD operon; Iron transport | Malachowa 2011 and Wang 2004 | 25-fold in serum; 15 fold in blood; | 30 to 120 minute | USA300 and mu50 | High induction at earliest timepoint. Experimental and predicted operon structure match |
| Gamma hemolysin hlgA | rbc lysis | Malachowa 2011; | ~350-fold (FIG. 4b) | 90 min | USA300 | Operon structure characterized by Cooney 1993 |
| sai-1 (seg 7 surface protein). Also called isdA | 29 kd cell surface protein; heme transporter; | Wiltshire 2001 | 50-fold in serum; 24-fold in blood. IsdB from the same operon is upregulated240-fold in serum and 140-fold in blood | 16 h (O/N plating assay) | 8325-4 | Serum agar and solution phase assays, separate pubs. Serum was sufficient for induction in Wiltshire 2001 & Malachowa 2011. |

TABLE 6-continued

Identification of candidate RRs and serum or blood inducible promoters to drive kill switch components for driving the toxin.

| Gene | Function | First author, year | Fold change in serum or blood | Time of exposure to blood or serum | SA strain used in study | Comments |
|---|---|---|---|---|---|---|
| leuA | 2-isopropyl malate synthase | Malachowa 2011 | −6 fold downreg. in TSB; 15 fold upreg in serum; 12 fold upreg in blood | 30 to 120 min | USA300 | Attractive b/c of downreg. in TSB but the fold upreg. in serum might be insufficient |
| SAUSA300_0119 | Ornithine cyclo-deaminase family protein | Malachowa 2011 | 50 fold upreg. in serum, 27 fold in blood; no upreg in TSB compared to time 0 in TSB | 30 to 120 min | USA300 | Different category of gene than above and also seemingly tightly regulated in TSB |
| IrgA | Murein hydrolase transporter | Malachowa 2011 | −3.3 fold downreg in TSB; 12 fold upreg in serum; 17 fold upreg in blood | 30 to 120 min | USA300 | Attractive b/c it is down-regulated in TSB |
| bioA | Adenosyl methionine-8-amino-7-oxononanoate aminotrans-ferase | Malachowa 2011 | 107 fold upreg in serum; 56 fold upreg in blood; no reg in TSB | 30 to 120 min | USA300 | Attractive b/c very strong upreg and a lesser known metabolic gene |

The full genes in each operon and the flanking sequences from strain BioPlx-01 are obtained from Genbank and annotated based on the literature plus known motif-identifying algorithms. Transcription terminators have been identified through a combination of published experiments and predictive tools.

Additional Literature evidence of expression of serum responsive promoters in TSB (or similar media) was investigated. For example, spa gene and isdA gene are disclosed in Ythier et al 2012, Molecular & Cellular Proteomics, 11:1123-1139, 2012. The sirA gene is disclosed in Dale et al, 2004 J Bacteriol 186(24) 8356-8362. The sst gene is disclosed in Morrissey et al. 2000. The hlgA gene is disclosed in Flack et al 2014, PNAS E2037-E2045, www.pnas.org/cgi/doi/10.1073/pnas.1322125111. The leuA gene is disclosed in Lei et al 2015, Virulence 6:1, 75-84.

Since these data come from many different strains and experimental systems, the entire collection may be assessed for expression in a single standardized assay system with quantitative gene expression measurements made by using real time PCR. Importantly, the basal "leaky" level of gene expression (the expression observed when cells are not exposed to blood or serum, e.g., in TSB) should be very low because producing the toxin prior to contact with serum would kill/weaken the BioPlx-XX strain (synthetic microorganism comprising a kill switch) prematurely. Even moderate cell health impairment is unacceptable because: 1) escape mutations in the KS would accumulate (KS instability)—a known phenomenon that must be avoided, and/or 2) the natural efficacy observed with BioPlx-01 could be reduced or lost. Thus, both the absolute level of baseline expression and the fold change in serum may be measured and closely considered in the selection of the optimal RRs to drive the KS. It is noted that leuA is downregulated in TSB (6-fold) and upregulated in serum (IS-fold) making its RR particularly interesting candidate to control KS expression.

In some embodiments, the synthetic microorganism having a kill switch may further comprise an "expression clamp" in which the KS cassette contains not only the serum-responsive RR that drives toxin expression, but also encodes a "translation blocking" RNA antitoxin under control of a promoter that is normally active on the skin or nasal mucosa during colonization. The kill switch may encode an antitoxin that is capable of suppressing the negative effects of the cell death toxin gene.

In some embodiments, the synthetic microorganism is a *Staphylococcus aureus* having a molecular modification comprising a kill switch which further comprises an "expression clamp" in which the KS cassette contains not only the serum-responsive RR that drives toxin expression, but also encodes a "translation blocking" RNA antitoxin under control of a *Staphylococcus aureus* promoter (Pam etc.) that is normally active on the skin during colonization, for example, as shown in Table 7.

From those promoters listed on Table 6 plus real time PCR data, two or more RRs with the best mix of low basal expression and high response to serum/blood may be selected to drive KS expression. These RRs may be paired with 3 different KS genes as described herein, generating a panel of KS candidate strains for testing. The panel will include an "expression clamp" candidate as described next.

Expression Clamp to Block Toxin Expression when the KS Strain is on the Skin or Nasal Epithelia The synthetic microorganism may comprise an expression clamp. Genes involved in *Staphylococcus aureus* colonization of human nares are shown in Table 7 may be employed as a second promoter for use in an expression clamp further comprising an antitoxin gene to block leaky toxin expression when the synthetic strain is colonized on skin or mucosal environments. The second promoter may be a constitutive promoter, such as a housekeeping gene. The second promoter or may be preferably downregulated in the presence of blood or serum.

TABLE 7

Genes involved in *Staphylococcus aureus* colonization of human nares

| Gene | Known or Putative role | Reference | Comments |
|---|---|---|---|
| clfB (Clumping factor B) (ClfB) | Adhesion | Wertheim H F, Walsh 2008; also Burian 2010 | 10 fold higher than Gyr in vivo; same high expression as gyr in vitro. Also, expression in rodent models and in humans is important for nasal colonization. It is expressed in exponential phase in vitro. Gene is downregulated 3-fold in human serum (Malachowa 2011) |
| autolysin (sceD) (exoprotein D) | Lytic transglycosylase | Stapleton M R, Horsburgh M J 2007 | expressed in exponential phase in vitro |
| walKR (virulence regulator) | essential master regulator of virulence | Burian 2010 | In vivo expression at time zero and at year 1 is on par with gyrA |
| atlA (Major autolysin) | major autolysin; Bifunctional peptidoglycan hydrolase | Burian 2010 | Similar characteristics as walKR but expression is higher (5 fold above gyr) |
| oatA (O-acetyltransferase A) | O-acetylation of peptidoglycan; renders *Staphylococcus aureus* cells resistant to lysozyme | Burian 2010 | Similar to WalKR |

or more second promoter candidate genes in the target microorganism, growing the microorganism in a media, obtaining samples of the microorganism at t=0 min, adding serum or blood to the media, obtaining samples at t=n minutes, where n=1-240 min or more, 15-180 min, or 30-120 min, performing RNA sequencing of the samples, and comparing RNA sequencing read numbers for candidate first promoter in samples obtained at obtained at t=0 min, and t=n minutes after exposure to blood or serum for the candidate first promoter gene. Alternatively, samples obtained after t=n minutes after exposure to blood or serum may be compared to t=n minutes in media without blood or serum for the candidate second promoter. Candidate second promoters may be selected from those that exhibit down-regulation by RNA sequencing after target cell growth at t=n min in blood or serum, when compared to the candidate promoter in the target cell at t=0, or when compared to the candidate promoter in the target cell at t=n in media without serum or blood.

In some embodiment, a synthetic microorganism is provided having a molecular modification comprising a kill switch and further comprising an expression clamp comprising an antitoxin gene driven by a second promoter that is normally active on the skin or nasal mucosa during colonization, optionally wherein the second promoter is selected from a gene selected from or derived from clumping factor B (clfB), autolysin (sceD; exoprotein D), walKR (virulence regulator), atlA (Major autolysin), and oatA (O-acetyltransferase A), as shown in Table 7. The constitutive second promoter may alternatively be selected from or derived from a housekeeping gene, for example, gyrB, sigB, or rho, optionally wherein the second promoter comprises a nucleotide sequence of SEQ ID NO: 324, 325, or 326, respectively, or a substantially identical sequence.

The second promoter for use in the expression clamp may be selected from a gene identified in the target microorganism that has been recognized as being downregulated upon exposure to blood or serum.

The second promoter for use in an expression clamp molecular modification should be a constitutive promoter that is preferably downregulated upon exposure to blood or serum after a period of time, e.g., after 15 minutes, 30 minutes, 45 minutes, 90 minutes, 120 minutes, 180 minutes, 240 minutes, 360 minutes, or any time point in between, to decrease transcription and/or expression of the cell death gene, by at least 2-fold, 3-fold, 4-fold, S-fold, or at least 10-fold, compared to transcription and/or expression in the absence of blood or serum.

The second promoter may be selected by a process comprising selecting a target microorganism, selecting one The second promoter may be selected from or derived from a promoter candidate gene identified herein for potential use in an expression clamp in *Staphylococcus aureus* 502a that were found to be downregulated by at least 2-fold after exposure to serum for 30 minutes as determined by RNA sequencing as compared to t=0 including phosphoribosylglycinamide formyltransferase gene CH52_00525 (−4.30 fold), phosphoribosylaminoimidazole synthetase gene CH52_00530 (−4.27 fold), amidophosphoribosyltransferase gene CH52_00535 (−4.13 fold), phosphoribosylformylglycinamidine synthase gene CH52_00540 (−4.04 fold), phosphoribosylformylglycinamidine synthase gene CH52_00545 (−3.49 fold), phosphoribosylaminoimidazole-succinocarboxamide gene CH52_00555 (−3.34 fold), trehalose permease IIC gene CH52_03480 (−3.33 fold), DeoR family transcriptional regulator gene CH52_02275 (−2.5S fold), phosphofructokinase gene CH52_02270 (−2.46 fold), and PTS fructose transporter subunit IIC gene CH52_02265 (−2.04 fold).

The second promoter may be selected from or derived from phosphoribosylglycinamide formyltransferase gene CH52_00525, trehalose permease IIC gene CH52_03480, DeoR family transcriptional regulator gene CH52_02275, phosphofructokinase gene CH52_02270, or PTS fructose transporter subunit IIC gene CH52_02265.

The second promoter may be a $P_{clfB}$ (clumping factor B) gene; optionally wherein the second promoter comprises a nucleotide sequence of SEQ ID NO: 7, 117, 118, 129 or 130, or a substantially identical sequence.

In one specific example, one of the KS constructs (sprA1) is equipped with an expression clamp comprising an antitoxin (sprA1$_{AS}$) driven from the Clamping factor B (clfB) promoter. This promoter is one choice to drive the clamp because it is strongly expressed in TSB and during nasal/skin colonization (10 fold higher than the abundant housekeeping gene gyrA) (Burian 2010). This is directly relevant to manufacturing and use of the product, respectively. The Clamping factor B (clfB) promoter is also downregulated 3 fold in blood (Malachowa 2011), favoring clamp inactivity when. Complete inactivity in blood may not be needed because the serum-responsive promoters driving is so robustly activated in the blood.

The Clumping factor B (clfB) promoter is also stably expressed over at least 12 months during nasal colonization in humans and was also identified in rodent and in vitro models of colonization (Burian 2010).

In one example of an expression clamp, clfB is selected as a constitutive promoter for use in an expression clamp after confirmation of strong expression in TSB, and lower levels of expression in blood or serum (real time PCR), to determine its characteristics in target strain *Staphylococcus aureus* 502a. The clfB regulatory region is cloned to drive expression of the sprA1 antisense (antitoxin) RNA (see Table 3, first entry), and the cassette is incorporated into the same expression shuttle vector as is used for expression of the sprA1 toxin gene from a serum-responsive promoter. It is desirable that the serum/blood exposure may strongly activate the toxin but not the antitoxin, and TSB or skin/nasal epithelial exposure activates antitoxin but not toxin. This concept may be applied to the other KS genes in Table 3 below. An alternative possibility for using the clamp is for the restriction enzyme KpnI (toxin) approach for which the antitoxin may be an RNA aptamer that was recently developed as a potent inhibitor of this enzyme (Mondragon, 2015) as a means of imparting metabolic stability to the aptamer.

Awareness of leaky expression does not fix the problem and the reality is that even widely used “tightly controlled” rheostatic promoters such as $P_{CUP1}$ and $P_{Gal7}$, and $P_{Tet}$-on/off variants produce measurable mRNA transcription in the absence of specific induction.

The expression clamp comprises a second promoter operably linked to an antitoxin gene. For example, the antitoxin gene is specific for the cell death toxin gene in the kill switch in order to be effective. Under normal physiological conditions, the expression clamp acts to prevent leaky expression of the cell death gene. When exposed to blood or serum, the second promoter operably linked to the antitoxin is downregulated, allowing expression of the cell death gene.

The synthetic microorganism may contain an expression clamp comprising an antitoxin gene which is specific for silencing the cell death gene. The antitoxin may be selected or derived from any antitoxin specific for the cell death gene in the kill switch molecular modification that is known in the art. The antitoxin gene may encode an antisense RNA specific for the cell death gene or an antitoxin protein specific for the cell death gene.

The antitoxin gene may be a sprA1 antitoxin gene, or sprA1(AS). The sprA1 antitoxin gene may comprise a nucleotide sequence of TATAATTGAGATAA CGAAAATAAGTATTTACTTATACACCAATCCCCTCACTATTTGCGGTAGTGAGGGGA TTT (SEQ ID NO: 311), or a substantially identical sequence, or CCCCTCACTA CCGCAAATAGTGAGGGGATTGGTGTATAAGTAAATACTTATTTTCGTTGT (SEQ ID NO: 273), or a substantially identical sequence.

The antitoxin gene may be a sprA2 antitoxin, or sprA2 (AS), and may comprise a nucleotide sequence of TATAATTAATTACATAATAAATTGAACATCTAAATACA CCAAATCCCCTCACTACTGCCATAGTGAGGGGATTTATT (SEQ ID NO: 306), or a substantially identical sequence; or TATAATTAATTACATAATAAATTGAACATCTAAAT ACACCAAATCCCCTCACTACTGCCATAGTGAGGGGATTTATTTAGGTGTTGGTTA (SEQ ID NO: 312), or a substantially identical sequence.

The antitoxin gene may be a sprG antitoxin gene, also known as sprF, and may comprise a nucleotide sequence of (5'-3') ATATATAGAAAAAGGG CAACATGCOCAAACATOTTACCCTAATGAG CCCGTTAAAAAGACGGTGGCTATTTTAGATTAAAGATTAAATTAATAACCATTTAAC CATCGAAACCAGCCAAAGTTAGCGATGGTTATTTTTT (SEQ ID NO: 307), or a substantially identical sequence. Pinel-Marie, Marie-Laure, Régine Brielle, and Brice Felden. “Dual toxic-peptide-coding *Staphylococcus aureus* RNA under antisense regulation targets host cells and bacterial rivals unequally.” *Cell reports* 7.2 (2014): 424-435.

The antitoxin gene may be a yefM antitoxin gene which is specific for silencing yoeB toxin gene. The yefM antitoxin gene may comprise a nucleotide sequence of MIITSPTEARKDFYQLLKNVNNNHEPIYISGNNAENNAVIIGLEDWKSIQETIYLESTGTM DKVREREKDNSGTTNIDDIDWDNL (SEQ ID NO: 314), or a substantially identical nucleotide.

The antitoxin gene may be a lysostaphin antitoxin gene specific for a lysostaphin toxin gene. The lysostaphin antitoxin may comprise a nucleotide sequence of TATAATTGAGATATOTTCATGTGTTATTTACTTATACACCAATCCCCTCACTATTTGC GGTAGTGAGGGGATTTTT (SEQ ID NO: 319), or a substantially identical nucleotide sequence.

The antitoxin gene may be a mazE antitoxin gene that targets mazF. The mazE toxin gene may comprise a nucleotide sequence of ATGTTATCTTTTAGTCAAAAT AGAAGTCATAGCTTAGAACAATCTTTAAAAGAAGGATATTCACAAATGGCTGATTTA AATCTCTCCCTAGCGAACGAAGCTTTTCCGATAGAGTGTGAAGCATGCGATTGCAAC GAAACATATTTATCTTCTAATTC (SEQ ID NO; 322), or a substantially identical sequence.

The antitoxin gene may alternatively be designed as follows. In *Staphylococcus aureus*, there are two main methods used for gene silencing. In one style of gene silencing, which is exemplified by sprA1, antisense RNA binds to the 5' UTR of the targeted gene, blocking translation of the gene and causing premature mRNA degradation. Another style of gene silencing is used for genes that do not have a transcriptional terminator located close to the stop codon. Translation can be controlled for these genes by an antisense RNA that is complementary (~3-10 bases) to the 3' end of the targeted gene. The antisense RNA will bind to the mRNA transcript covering the sequence coding for the last couple codons and creating double stranded RNA which is then targeted for degradation by RNaseIII.

Since there are many examples of RNA silencing in *Staphylococcus aureus* that have been identified with demonstrated ability to control their target genes, these regions and sequences may be used as a base for designing the toxin/antitoxin cassettes. This approach requires only small changes in the DNA sequences.

In the present disclosure, the antitoxin for a cell death gene may be designed to involve antisense binding to 5'UTR of targeted gene. The toxin gene may be inserted into the PepA1 reading frame, and the 12 bp in the endogenous sprA1 antisense is swapped out for a sequence homologous to 12 bp towards the beginning of the heterologous toxin gene.

In one example, Holin inserted into the sprA1 location can be controlled by the antisense RNA fragment encoded by (12 bp Holin targeting sequence in BOLD)=TATA ATTGAGAT AGTTTCATTAGCTATTTACTTATACACCAATCCCCTCA CTATTT GCGGTAGTGA GGGGATTTTT (SEQ ID NO: 308).

In another example, 187-lysK inserted into the sprA1 location can be controlled by the antisense RNA fragment encoded by (12 bp 187-lysK targeting sequence in BOLD) TATAATTGAGAT TTTAGGCAGTGC TATTTACTTATACACCAA TCCCCTCA CTATTTGCGOT AGTGAGGGGATTTTT (SEQ ID NO: 309).

The antitoxin specific for the cell death gene may involve antisense binding to the 3° UTR of the toxin gene. This method involves inserting the heterologous toxin in the place of sprG in the genome of *Staphylococcus aureus*, and adding an additional lysine codon (AAA) before the final stop codon. The last 6 bases of the coding region (AAAAAA) plus the stop codon (TAA) overlap with the 3' region of the endogenous sprF antitoxin. When the sprF RNA is transcribed at a rate of 2.5 times greater than the heterologous toxin gene, it will form a duplex with the 3'UTR region of the toxin transcript, initiating degradation by RNaseIII and blocking the formation of a functional peptide. Since the 3' end of both of the heterologous toxins were manipulated in the same manner to overlap with the sprF sequence (adding the codon AAA in front of the TAA stop codon), which is also the same as the endogenous sprG'3' end, the sequence of the antitoxin will remain the same for all three of these toxin genes. For example, the sprG antitoxin gene (sprF) may comprise the nucleotide sequence ATATATAGAAAAA GGGCAACATGCGCAAACATGTTACCCTAATGAGCCC GTTAAAAAGACGGTGGCTATTTTAGATTAAAGATTAAATTAATAACCATTTAACCAT CGAAACCAGCCAAAGTTAGCGATGGTTATTTTTT (SEQ ID NO: 310).

The antitoxin gene may comprise a nucleotide sequence selected from any of SEQ ID NOs: 273, 306, 307, 308, 309, 310, 311, 312, 314, 319, or 322, or a substantially identical sequence thereof.

The antitoxin gene may or may not encode an antitoxin peptide. Wherein the synthetic microorganism is derived from a *Staphylococcus aureus* strain, the antitoxin peptide may be specific for the toxin peptide encoded by the cell death gene. For example, when the toxin gene is a yoeB toxin gene, e.g., encoding a toxin peptide comprising an amino acid sequence of SEQ ID NO: 316, the antitoxin gene may encode a yefM antitoxin protein comprising the amino acid sequence of MIITSPTEARKDFYQLLKNVNNNHEPI YISGNNAENNA VIIGLEDWKSIQETIYLESTGTMDKVREREKDNSGTTNIDDIDWDNL (SEQ ID NO: 314), or a substantially similar sequence. As another example, wherein the antitoxin gene is a mazF toxin gene, e.g., encoding a toxin peptide comprising an amino acid sequence of SEQ ID NO: 321, the antitoxin gene may be an mazE antitoxin gene, e.g., encoding an antitoxin protein comprising an amino acid sequence of MLSFSQNRSHSLEQSLKEGYSQ MADLNLSLANEAFPIECEACDCNETYLSSNSTNE (SEQ ID NO: 323), or a substantially similar sequence.

Three KS candidate genes were selected as being of particular interest because they elicit cell death in 3 disparate ways. In some embodiments, the synthetic microorganism comprises one or more, two or more or each of sprA1, kpnI or rsaE to achieve maximal death rates as early data instruct. The sprA1 mechanism of action is a loss of plasma membrane integrity/function by expression of a pore-forming peptide, the kpuI mechanism of action involves destruction of the *Staphylococcus aureus* genome with a restriction enzyme. The rsaE mechanism of action involves impairment of central metabolism including TCA cycle and tetrahydrfolate biosynthesis.

In some embodiments, the synthetic microorganism comprises regulatory region comprising a first promoter operably linked to a cell death gene, wherein the cell death gene encodes a toxin peptide or protein, and wherein the first promoter is upregulated upon exposure to blood or serum. The cell death gene may be a sprA1 gene. SprA1 encodes toxin peptide PepA1 as described in Sayed et al., 2012 JBC VOL. 287, NO. 52, pp. 43454-43463. Dec. 21, 2012. PepA1 induces cell death by membrane permeabilization. PepA1 has amino acid sequence: MLIFVHIIAPVISGCAIAFFSYWLSRRNTK SEQ ID NO: 104. Related antimicrobial peptides include MMLIFVHIIAPVISGCAIAFFSYWLSRRNIK (SEQ ID NO: 105). AIAFFSYWLSRRNTK (SEQ ID NO: 106), IAFFSYWLSRRNTK (SEQ ID NO: 107), AFFSYWLSRRNIK (SEQ ID NO: 108), FFSYWLSRRNTK (SEQ ID NO: 109), FSYWLSRRNIK (SEQ ID NO: 110), SYWLSRRNTK (SEQ ID NO: 111), or YWLSRRNTK (SEQ ID NO: 112), as described in WO 2013/050590, which is incorporated herein by reference. The cell death gene may be an sprA2 gene. The sprA2 gene may encode a toxin MFNLLINIMTSALSGCLVAFFAHWLRTRNNKKGDK (SEQ ID NO: 305). The cell death gene may be a *Staphylococcus aureus* yoeB gene which may encode a yoeB toxin having the amino acid sequence of MSNYTVKIKNSAKSDLRKIKHSYLKKSFLEIVETLKND PYKITQSFEKLEPKYLERYSRRINHQHRVVYTVDDRNKEVLILSAWSHYD (SEQ ID NO: 316), or a substantially similar sequence. The cell death gene may be a *Staphylococcus simulans* gene which may encode a metallopeptidase toxin gene having an amino acid sequence of MTHEHSAQWLNNYKKGYGYGPYPLGINGGMHYGVDFFMNIGTPVKAISSGKIVEAGW SNYGGGNQIGLIENDGVHRQWYMHLSKYNVKVGDYVKAGQHIGWSGSTGYSTAPHLH FORMVNSFSNSTAQDPMPFLKSAGYGKAGGTVTPTPNTGWKINKYGTLYKSESASFTP NTDIITRTTGPFRSMPQSGVLKAGQTIHYDEVMKQDGHVWVGYTONSGORIYLPVRTW NKSTNTLGVLWGTIK (SEQ ID NO: 318), or a substantially similar sequence. The cell death gene may be a mazF toxin gene that encodes a mazF toxin comprising an amino acid sequence of MIRRGDVYLADLSPVQGSEQGGVRPVVIIQNDTONKYSPTVIVAAITGRINKAKIPTHVEI EKKKYKLDKDSVILLEQIRTLDKKRLKEKL- TYLSDDKMKEVDNALMISLGLNAVAHQK N (SEQ ID NO: 321), or a substantially similar sequence.

The cell death gene may encode a toxin peptide or protein comprising an amino acid sequence of SEQ ID NO: 104, 105, 106, 107, 108, 109, 110, 111, 112, 285, 287, 289, 291, 305, 316, 318, or 321, or a substantially similar amino acid sequence. Preferably, the first promoter is silent, is not active, or is minimally active, in the absence of blood or serum.

PepA1 is a toxic pore forming peptide that causes *Staphylococcus aureus* death by altering essential cell membrane functions. Its natural role is unknown but speculated to be altruistic assistance to the *Staphylococcus aureus* population/culture by killing of cells that are adversely affected by environmental conditions. By over-expressing this gene a rapid and complete cell death occurs in the presence of serum. Of note, sprA1 mRNA translation is repressed by an antisense RNA called sprA11 (SprA1 antisense). The cis-encoded SprA1$_{AS}$ RNA operates in trans to downregulate the sprA1-encoded peptide expression in vivo, as described in WO 2013/050590, which is incorporated herein by reference. The antisense RNA may in fact be a convenient safeguard to minimize "leaky" toxicity. It will be driven from a promoter that is expressed in *Staphylococcus aureus* on the human skin and nasal epithelia during colonization. Advantages of sprA1 include the expression of a small peptide, having known structure and activity.

In a particular embodiment, a synthetic microorganism is provided comprising a first cell death gene sprA1 operably linked to a first regulatory region comprising a blood and/or serum inducible first promoter comprising a nucleotide sequence of any one of SEQ ID NOs: 1, 2, 3, 4, 5, 6, 114, 115, 119, 120, 121, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, or 163. The first promoter may be upregulated greater than 5-fold, greater than 10-fold, greater than 50-fold, greater than 100-fold, greater than 300-fold, or greater than 600-fold after 15, 30, 45, 60, 90, 120, 180 or 240 minutes of incubation in blood or serum. The first promoter may be upregulated greater than 5-fold after 90 minutes of incubation in serum and may be selected from fhuA, fhuB, isdI, isdA, srtB, isdG, sbnE, sbnA, sbnC, and isdB. The first promoter may be upregulated greater than 100-fold after 90 minutes of incubation in serum and may be selected from isdA, srtB, isdG, sbnE, sbnA, sbnC, and isdB.

The cell death gene may encode an antimicrobial peptide comprising an amino acid sequence of SEQ ID NO: 104, 105, 106, 107, 108, 109, 110, 111, 112, 285, 287, 289, 291, 305, 316, 318, or 321, or a substantially similar amino acid sequence thereof.

The cell death gene may be selected from any known *Staphylococcus* spp. toxin gene. The cell death gene may be selected from a sprA1 toxin gene, sprA2 toxin gene, 187-lysK toxin gene, holin toxin gene, sprG toxin gene, yoeB toxin gene, lysostaphin toxin gene, metallopeptidase toxin gene, or mazF toxin gene, or a substantially identical toxin gene. The toxin gene may comprise a nucleotide sequence of SEQ ID NO: 274, 275, 284, 286, 288, 290, 304, 315, 317, or 320, or a substantially identical nucleotide sequence thereof.

The cell death gene may be sprA1 which encodes the antimicrobial peptide PepA1. In some embodiments, the synthetic microorganism further comprises an antitoxin gene SprA1-AS operably linked to a second regulatory region comprising a second promoter comprising a nucleotide sequence of clfB comprising a nucleotide sequence of SEQ ID NO: 7, 117, 118, 129 or 130, or a substantially identical sequence.

In some embodiments, the synthetic microorganism comprises a restriction enzyme KpnI (*Klebsiella pnemonlae*) gene. KpnI protects bacterial genomes against invasion by foreign DNA. High-level expression of (eg) 6-bp recognition restriction enzyme KpnI will efficiently cleave the *Staphylococcus aureus* genome. In some embodiments, the expression vector (below) will be engineered to lack cleavage recognition sites by (eg) adjustment of codon usage. The 6-base recognition sequence occurs once every 4096 bp, cutting the 2.8 MB genome of *Staphylococcus aureus* into ~684 fragments. KpnI has the advantage of rapid activity. In some embodiments, "leaky" expression problem may be managed by expressing an RNA aptamer as the clamp as described above for sprA1.

In some embodiments, the synthetic microorganism comprises a rsaE gene. The rsaE gene is a small RNA (93 nt) that coordinately inhibits 2 different metabolic pathways by targeting translation initiation of certain housekeeping mRNAs encoding enzymes of THE biosynthesis pathway and citric acid cycle; high-level expression is toxic. By over-expressing RseE growth impairment occurs due to inhibition of essential housekeeping enzymes. This occurs by binding to the Opp3A and OppB mRNAs in the ribosome-binding site and start codon region, preventing translation. Both genes encode components of the ABC peptide transporter system and affect the supply of essential nitrogen/amino acids in the cell, impairing central biochemical metabolism directly and indirectly. Advantages include severe growth inhibition (10,000 fold over empty vector controls), and efficient multifunctionality because a single sRNA impairs expression of multiple essential biochemical pathways. Geissman et al. 2009 and Bohn et al. 2010 report on the natural function of RsaE.

Creation of a panel of serum-activated kill switch (KS) plasmid candidates for expression in *Staphylococcus aureus* is performed wherein serum responsive RRs are sub-cloned to *Staphylococcus aureus* shuttle vectors; cell death genes are inserted downstream of RRs, and sequenced; feasibility of leaky expression repressor "expression clamp" is tested; and candidate strains are completed and evaluated to select lead candidate(s) that exhibit rapid and complete death, and good baseline viability.

Chromosomal integration of optimal kill switch candidates is important for long-term stable expression. In addition, comparison of death rate extent and stability of strains in vitro is performed. Insertion of up to 3 optimal kill switch cassettes alone and in 3 combinations of two, for a total of up to 6 strains is performed. This achievement may require a multistep cloning in *E. coli* to build the constructs. For example, *E. coli* strain DC10B may be employed. DC10B is an *E. coli* strain that is only DCM minus (BEI product number NR-49804). This is one way to generate DNA that can be readily transfected into most *Staphylococcus aureus* strains. To this end, stable integrants are obtained, and plasmid vector is excised during counter selection. The rate and extent of serum-induced cell death is confirmed and characterized, and genetic stability is determined for all 6 strains. A non-human functional test of preferred KS strain candidates is performed including a functional test of strain death in vivo; and a functional test of colonization-skin discs.

In some embodiments, a method for preparing a synthetic *Staphylococcus aureus* strain from BioPlx-01 is provided comprising (1) producing a shuttle vector pCN51 in mid-scale in *E. coli*, (2) cloning cell death genes into pCN51 in *E. coli* under Cd-inducible promoter $P_{cad}$, (3) replacing $P_{cad}$ with serum-responsive promoters and optionally inserting expression clamp, (4) verifying constructs by sequencing KS cassettes, (5) electroporating into *Staphylococcus aureus* RN4220 and selecting transformants on erythromycin plates (this strain is restriction minus and generates the right methylation pattern to survive in BioPlx-01), (6) preparing plasmid from RN4220 and restriction digest to confirm identification, (7) electroporating plasmids into BioPlx-01 and select on erythromycin plates, and (8) isolating strains. Stains produced in this fashion are ready for performance testing and serum experimentation. The method is further described in detail herein.

In some embodiments, a method for performance testing a synthetic *Staphylococcus aureus* strain from BioPlx-01 is provided comprising (1) growing in TSB plus antibiotic as selective pressure for plasmid, (2) comparing growth to WT BioPlx-01 optionally generating a growth curve, (3a) for Cd-promoter variants, washing and shifting cells to Cd-medium (control is BioPlx-01 containing empty vector with no cell death gene)—or—(3b) for KS variants, washing and shifting cells to serum (control is WT BioPlx-01 containing empty vector with no cell death gene), and (4) monitoring growth using $OD_{630\ nm}$ with plate reader, optionally for extended period with monitoring for escape mutants. For whole blood test, the method is only performed on preferred candidates and using colony forming units (CFUs) on TSA as death readout. If colonies form on kill switch bearing strains after they have been exposed to blood, the plasmid should be sequenced to check for mutations. If there are escape mutants, shuttle plasmid out to *E. coli* and sequence whole plasmid.

Method for Creation of Serum-Activated Kill Switch (KS) Plasmid Candidates for Expression in *Staphylococcus aureus* (SA)

Methods are provided for evaluation of cell death induction comprises recombinant construction of the synthetic microorganism comprising cloning the genes into an *E. coli*-SA shuttle vector and transfecting this vector into BioPlx-01 for evaluation.

Step 1: Request Shuttle Vector PCN51

A commercially available shuttle vector is obtained such as PCN51 (available through BEI) is one excellent choice as it contains: ij a cadmium-inducible promoter that can be used in positive control strains to prove the toxins are expressed and functional; ii) a universal Transcription terminator (TT) that will apply to all of our constructs; and, iii) well-established replicons for *E. coli* and *Staphylococcus aureus*. A schematic of commercially available shuttle vector pCN51 (BEI cat #NR-46149) is shown in FIG. 2. Genetic elements shown of pCN51 shuttle plasmid are shown in Table 8.

TABLE 8

Elements of pCN51 Shuttle Vector
Shuttle Plasmid pCN51 (BEI cat # NR-46149)

| Element | Purpose |
| --- | --- |
| pT181cop-WT repC | SA replication machinery |
| ermC | erythromycin resistance |
| Amp | beta-lactamase; confers resistance to ampicillin in *E coli* |
| ColE1 Ori | Origin of replication for *E coli* |
| Pcad-cadC | Cadmium-inducible promoter |
| MCS (black box) | Multiple Cloning Site; unique sites for cloning our KS. |
| TT | blaZ transcription terminator |

Promoter sequences (7) used in development are shown below, the base pair numbers in leuA, hlgA and Cadmium promoters correspond to pCN51 vector location.

1. leuA promoter (Par) sequence between restriction sites SphI and PstI (underlined) amplified from genomic BioPix-01 (502a) DNA.

```
                                          SEQ ID NO: 114
                                SphI
                                GCATGCGAAA CAGATTATCT

5501 ATTCAAAGTT AATTGTAAGA AAATTTAAAA TATTTGTTGA CATACTAAAG

5551 CAGATATAGT AAATTAAATT TATCAAATTT TTAGACAATT CTAACTATTA

5601 AAGTGATATA TACCATTCAC GGAAGGAGTA TAATAAAATG CTTAATCAAT

5651 ATACTGAACA TCAACCGACA ACTTCAAATA TTATTATTTT ATTATACTCT

5701 TTAGGACTCG AACGTTAGTA AATATTTACT AAACGCTTTA AGTCCTATTT

5751 CTGTTTGAAT GGGACTTGTA AACGTCCCAA TAATATTGGG ACGTTTTTTT

5801 ATGTTTTATC TTTCAATTAC TTATTTTTAT TACTATAAAA CATGATTAAT

5851 CATTAAAATT TACGGGGGAA TTTACTCTGC AG
                                  PstI
```

2. hlgA promoter ($P_{hlgA}$) sequence between restriction sites SphI and PstI amplified from genomic BioPlx-01 (502a) DNA.

```
                                    SEQ ID NO: 115
                                SphI
                                GCATGC AAACTATTGC

5501 GAAATCCATT CCTCTTCCAC TACAAGCACC ATAATTAAAC AACAATTCAA

5551 TAGAATAAGA CTTGCAAAAC ATAGTTATGT CGCTATATAA ACGCCTGCGA

5601 CCAATAAATC TTTTAAACAT AACATAATGC AAAAACATCA TTTAACAATG

5651 CTAAAAATGT CTCTTCAATA CATGTTGATA GTAATTAACT TTTAACGAAC

5701 AGTTAATTCG AAAACGCTTA CAAATGGATT ATTATATATA TGAACTTAAA

5751 ATTAAATAGA AAGAAAGTGA TTTCTCTGCA G
                              PstI
```

3. Cadmium promoter (Par) sequence between restriction sites SphI and PstI. This promoter is used for controls and is part of the original pCN51 vector from BEI Resources (https://www.beiresources.org/).

```
                                    SEQ ID NO: 116
                              SphI
                              GCATGCGCAC TTATTCAAGT

5501 GTATTTTTTA ATAAATTATT TTACTTATTG AAATGTATTA TTTTCTAATG

5551 TCATACCCTG GTCAAAACCG TTCGTTTTTG AGACTAGAAT TTTATGCCCT

5601 ACTTACTTCT TTTATTTTCA TTCAAATATT TGCTTGCATG ATGAGTCGAA

5651 AATGGTTATA ATACACTCAA ATAAATATTT GAATGAAGAT GGGATGATAA

5701 TATGAAAAAG AAAGATACTT GTGAAATTTT TTGTTATGAC GAAGAAAAGG

5751 TTAATCGAAT ACAAGGGGAT TTACAAACAG TTGATATTTC TGGTGTTAGC

5801 CAAATTTTAA AGGCTATTGC CGATGAAAAT AGAGCAAAAA TTACTTACGC

5851 TCTGTGTCAG GATGAAGAGT TGTGTGTTTG TGATATAGCA AATATCTTAG

5901 GTGTTACGAT AGCAAATGCA TCTCATCATT TACGTACGCT TTATAAGCAA

5951 GGGGTGGTCA ACTTTAGAAA AGAAGGAAAA CTAGCTTTAT ATTCTTTAGG

6001 TGATGAACAT ATCAGGCAGA TAATGATGAT CGCCCTAGCA CATAAGAAAG

6051 AAGTGAAGGT CAATGTCTGA ACCTGCAG
                            PstI
```

4. clfB promoter ($P_{clfB}$) to drive the antisense regulatory RNA sprA1$_{AS}$. This is the forward sequence with EcoRI and BamHI sites. This sequence is put in reverse to drive the sprA1$_{AS}$ to potentially act as a clamp to keep the sprAI gene regulated in the absence of blood. Underlined represents EcoRI and BamHI sites, respectively.

```
EcoRI
                                           SEQ ID NO: 117
GAATTCAGGTGATGAAAAATTTAGAACTTCTAAGTTTTTGAAAAGTAAAA

AATTTGTAATAGTGTAAAAATAGTATATTGATTTTTGCTAGTTAACAGAA

AATTTTAAGTTATATAAATAGGAAGAAAACAAATTTTACGTAATTTTTTT

CGAAAAGCAATTGATATAATTCTTATTTCATTATACAATTTAGACTAATC

TAGAAATTGAAATGGAGTAATATTTGGATCC
```

$P_{clfB}$ as it is cloned in pCN51 vector with EcoRI and BamHI reversed.

```
BamHI
                                           SEQ ID NO: 118
GGATCCAAATATTACTCCATTTCAATTTCTAGATTAGTCTAAATTGTATA

ATGAAATAAGAATTATATCAATTGCTTTTCGAAAAAAATTACGTAAAATT

TGTTTTCTTCCTATTTATATAACTTAAAATTTTCTGTTAACTAGCAAAAA

TCAATATACTATTTTTACACTATTACAAATTTTTTACTTTTCAAAAACTT

AGAAGTTCTAAATTTTTCATCACCTGAATTC
```

5. The sirA promoter ($P_{strA}$) as found in the NCBI 502a complete genome. This sequence was taken 300 base pairs upstream of the sir 4 start codon as shown underlined below.

SEQ ID NO: 119 ttagaaagatttacttttatatatgaagagactggattaaatacttttat tgacgtaaaaattcacttttgaaccgttcaatatcttgccgatttttata taacagctacaaataaaatataacagtttgattttacagcctcggtaaat cgtatgacaaacaaaaattttgtgctatcacaacatttgcaacgtcttaa caagtcatctataaacatttctaaatatttaacattacttatgcgtcatt tattgctaaaattattgtattaaaatatacatagaattgatgggatatcA

TG

6. The sstA promoter ($P_{sstA}$) as found in the NCBI 502a complete genome. This sequence was taken 300 base pairs upstream of the sstA start codon as shown underlined below.

SEQ ID NO: 120 acgaaaaattaattaacatcgcattgtttattactgcaactattacagca ttggtagtggtgactgttggaacattaccgttcttaggactagtaatacc aaatattatttcaatttatcgaggtgatcatttgaaaaatgctatccctc atacgatgatgttaggtgccatctttgtattattttctgatatagttggc agaattgttgtttatccatatgaaataaatattggtttaacaataggtgt atttggaacaatcattttccttatcttgcttatgaaaggtaggaaaaatt

ATG

7. The isdA promoter ($P_{isdA}$). This sequence was taken 300 base pairs upstream of the SstA start site as shown underlined below from the NCBI 502a complete genome.

SEQ ID NO: 121

CTATCTGCGGCATTTGCAGAATTACTGAATGTCGCGATGATGATAATTAA

CGCTAAAATCGTTGTATTAAAAACTTTTAAAATATTTTTCAAAACATAAT

CCTCCTTTTTATGATTGCTTTTAAGTCTTTAGTAAAATCATAAATAATAA

TGATTATCATTGTCAATATTTATTTTATAATCAATTTATTATTGTTATAC

GGAAATAGATGTGCTAGTATAATTGATAACCATTATCAATTGCAATGGTT

AATCATCTCATATAACAACACATAATTTGTATCCTTAGGAGGAAAACAAC

ATG.

In some embodiments, a plasmid, vector, or synthetic microorganism is provided comprising a molecular modification comprising a cell death gene operably linked to an inducible blood or serum responsive first promoter comprising a nucleotide sequence selected from the group consisting of SEQ ID NO: 114, 115, 119, 120, 121, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, and 163, or a substantially identical nucleotide sequence. In some embodiments, the molecular modification further comprises an expression clamp comprising an antitoxin gene operably linked to a second promoter comprising a nucleotide sequence selected from SEQ ID NO: 7, 117, 118, 129 or 130.

Step 2: Cloning Best Two Serum-Responsive RRs into the Shuttle Vector (*E. coli* Host)

Cloning of candidate serum-responsive RRs into the shuttle vector (*E. coli* host) comprises: (a) PCR amplification of the best two preferred serum-responsive RRs from BioPlx-01 genomic DNA (gDNA); and (b) replacing the Cadmium-inducible promoter with these RR fragments in pCN51 to create two new plasmids (RR1 and RR2), and (3) selecting clones in *E. coli* DH10B (or DH5 alpha) and sequencing of insertions.

The following KS genes are obtained from *Staphylococcus aureus* gDNA or by de novo synthesis: (1) sprAI/sprAI$_{AS}$: synthetic; (ii) RsaE: *Staphylococcus aureus* genomic DNA. And (iii) KpnI: synthetic. For genes amplified from gDNA, PCR primers are used with relevant restriction enzymes for cloning. For synthetic genes, the cloning sites will be included at synthesis and any undesirable sites removed during construction. For example, KpnI sites will be removed from the kpnI cassette to prevent auto-digestion. The KS genes are inserted downstream of serum-responsive RRs in plasmids RR1 and RR2, generating all constructs listed below. Insert the KS genes downstream of Cd-inducible promoter in pCN51 to create positive control constructs. See additional relevant sequences and primer sequences provided herein useful for these steps, for example, Tables 2, 3 and 4. Sequencing of promoters and inserts of all constructs is performed to ensure that mutations have not accumulated in the construction process A list of Plasmid constructs to be produced is shown below. All but 2, 4, 8 and 11 will be transfected into *Staphylococcus aureus*.

1. Cd-inducible promoter-sprA1
2. Cd-inducible promoter-reverse orientation sprA1
3. Serum responsive RR1-sprA1
4. Serum responsive RR1-reverse orientation sprA1
5. Serum responsive RR1-sprA1+$P_{clfB}$-sprAI$_{AS}$
6. Serum responsive RR2-sprA1
7. Serum responsive RR1-rsaE
8. Serum responsive RR1-rsaE-reverse orientation
9. Serum responsive RR2-rsaE
10. Serum responsive RR1-kpnI
11. Serum responsive RR1-kpnI reverse orientation
12. Serum responsive RR2-kpnI The reverse orientation constructs are being created in the process, because if a cell death gene has some basal toxicity even in growth medium, it may not be possible to obtain the forward orientation construct. Such a negative result is not conclusive unless the reverse orientation construct is readily obtained in side-by-side fashion.

Step 3: Transfect Plasmids into Intermediate *Staphylococcus aureus* RN4220 (to Obtain Correct DNA Methylation Pattern).

There is no need to transfect reverse orientation constructs; but transfection of pCN51 empty vector is performed as follows:

A. Electroporate into RN4220;

B. Select transformants on plates containing erythromycin; and

C. Isolate and confirm plasmid ID with restriction digests.

Step 4: Transfect into BioPlx-01

A. Electroporate plasmids from step 3C into competent BioPlx-01;

B. Select transformants by erythromycin resistance; and

C. Isolate and confirm plasmid ID with restriction digests, save stocks of 9 strains.

Step 5: Test KS Expression and Extent and Rate of Death in Response to Serum and Blood Exposure A. Qualitative test of expression of kill genes with real time PCR pre- and post-blood/serum exposure. This will: i) confirm the strain construction; ii) correlate onset of toxin production with onset of death, and iii) determine promoter "leakiness" in the context of the KS;

B. Cell death induction curves in serum/blood compared to TSB (killing extent and kinetics by CFU); and C. Simple growth rate comparison of BioPlx-01 containing empty vector vs. BioPlx-01 with the KS plasmids.

Step 6: Measure the Rate of KS Mutation

Count colonies that grow on serum or blood agar plates and/or in serum containing liquid media over several hundred generations via serial passaging. Determine if mutation rate is acceptable. It has been reported that the rate of functional KS loss is $10^{-6}$ for one copy of a KS gene, but as low as $10^{-10}$ for two copies of the same or different KS genes from two different promoters (Knudsen 1995; reporting on actual mutation rate assay measurements).

Step 7: Analysis and Interpretation

The best KS strain(s) are those with unaffected growth rates (and colonization potential); and that show rapid and complete death in response to blood and/or serum; and that have stable molecular modifications.

Step 8: Determine Need for Inserting Multiple KS Cassettes

If the molecular stability of one KS is deemed inadequate, a second and different functional KS from the list of 9 candidates (if another functional one exists) will be added to the plasmid and a re-test of killing and stability will be performed. A dramatic improvement in KS stability is anticipated on the basis of Knudsen 1995 and theoretical calculations.

Method for Chromosomal Integration of Optimal Kill Switch(es), for Long-Term Stable Expression The optimal serum/blood responsive KS construct(s) will be integrated into the chromosome precisely at a pre-selected location known to tolerate insertions without notably altering the cell's biology Step 1: Obtain an Integrative Vector for Use in *Staphylococcus aureus*.

Figures 5A, 5B:
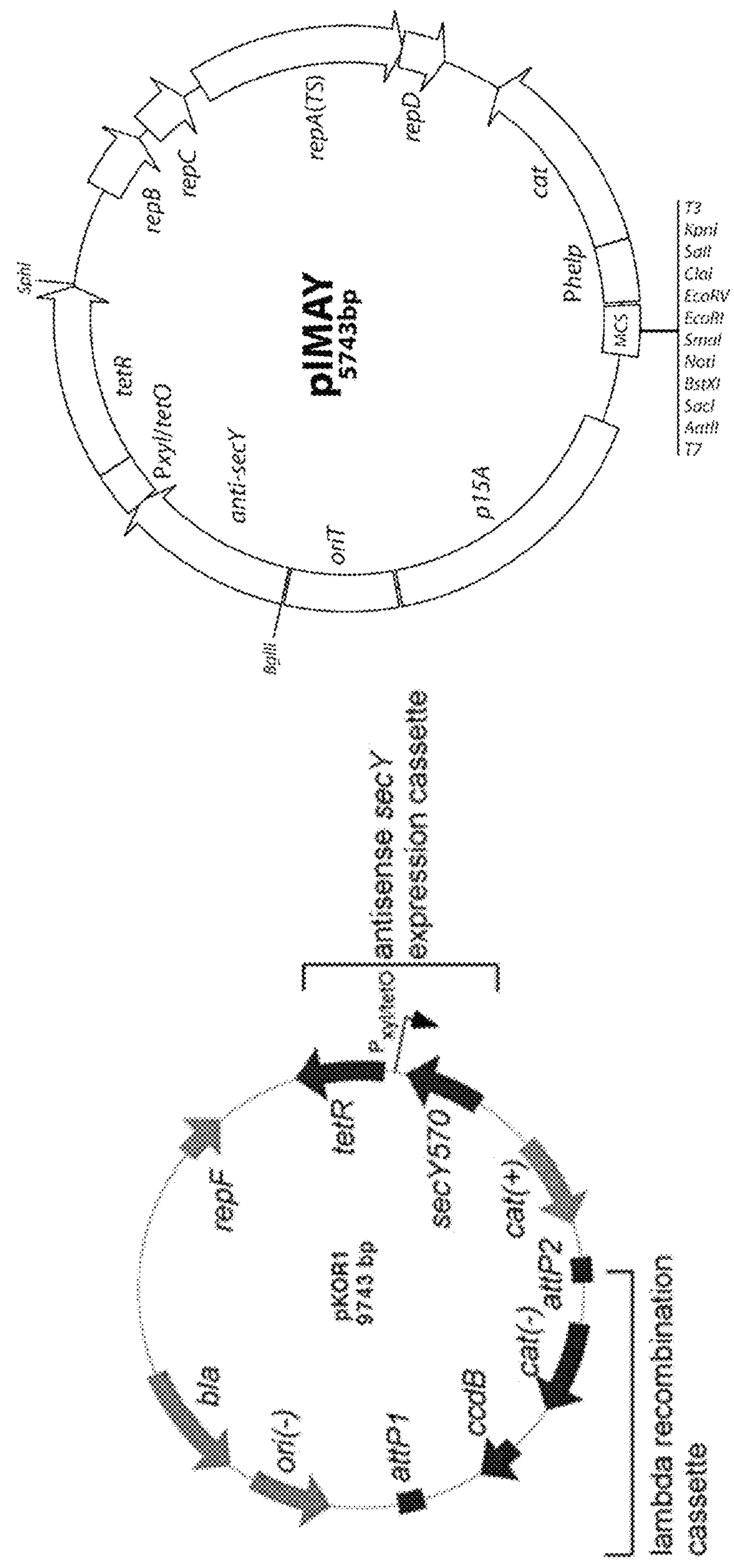
FIG. 5A shows a genetic map of a pKOR1 Integrative Plasmid depicting the repF (replication gene of pE194ts), secY570 (N-terminal 570 nucleotides of secY including ribosome binding site), cat (chloramphenicol acetyltransferase), attP (page lambda attachment site), ori(−) (ColE1 plasmid replication origin), and bla (b-lactamase), (+) or (−) indicates functions in gram positive (+) or gram negative (−) bacteria. The Pxyl/tetO promoter and the transcription direction of the promoter are indicated by an arrow.
FIG. 5B shows a genetic map of a pIMAY Integrative Plasmid. (accession number JQ62198).

After careful consideration to the optimal integrative vector, plasmids pKOR1 or pIMAY may be employed because they provide the ability to choose the integration site, allowing us to avoid perturbing biologically critical regions of the genome that can occur with other methods. Both vectors possess a convenient means for counter-selection (secY) so that the plasmid backbone and its markers can be excised from the genome after the KS has been integrated. A genetic map of pKOR1 is shown in FIG. 5A and the features are described in Bae et al. 2006 Plasmid 55, pp. 58-63, and briefly described in Table 9. An advantage of pKOR is the ability to clone inserts without the limits of specific restriction enzymes.

TABLE 9

Purpose of elements in pKOR integrative plasmid
Integrative Plasmid pKOR

| Element | Purpose |
|---|---|
| AmpR | beta-lactamase; confers resistance to ampicillin in *E. coli* (but not in *Staphylococcus aureus*) |
| Ori (—) | *E. coli* origin of replication |
| Attp1 and 2 | Recombine with AttB elements of DNA inserts |
| CcdB | *E. coli* gyrase inhibitor protein; growth of cells containing non-recombinant plasmid are inhibited by this protein |
| Cat− and Cat+ | Chloramphenicol resistance genes for use in gram neg and gram + bacteria respectively |
| SecY570 | 570 nt encoding essential N terminus of secY; its antisense is expressed from the ATc-indicible pxyl/tetO promoter; growth in the presence of Atc means the plasmid backbone has been lost |
| RepF | Replication gene for *Staphylococcus aureus* |

A Genetic map of pIMAY is shown in FIG. 5B from Monk, I R et al., mBio 2012; doi: 10.1128/mBio.00277-11. FIG. 12A-12C shows nucleotide sequence (SEQ ID NO: 131) of pIMAY Integrative Plasmid. (accession number JQ62198). The *E. coli*/staphylococcal temperature-sensitive plasmid pIMAYz comprises the low-copy-number *E. coli* origin of replication (p15A), an origin of transfer for conjugation (oriT), the pBluescript multiple cloning site (MCS), and the highly expressed cat gene (Phelp-cat) derived from pIMC. The temperature-sensitive replicon for Gram-positive bacteria (repBCAD) and the anhydrotetracycline-inducible antisense secY region (anti-secY) may be amplified from pVE6007 and pKOR1, respectively. The restriction sites listed are unique. Primers (IM151/152) bind external to the MCS of pIMAY and are used to screen clones in *E. coli* (amplify 283 bp without a cloned insert) and to determine the presence of a replicating plasmid in staphylococci. Advantages of pIMAYz are smaller size, blue white screening, and a lower nonpermissive temperature, which has been reported to avoid mutations that can occur in the integration process. Thus, the plasmid may be made by de novo gene synthesis at a contract vendor firm.

Step 2. Review Selectable Markers in BioPlx-01.

BioPlx-01 is sensitive to ampicillin (50 μg/mL and 100 μg/mL), chloramphenicol (10 μg/mL), and erythromycin (Drury 1965). In one embodiment, the chloramphenicol (cat+) gene is used to select for transformants on chloramphenicol plates during the integration process.

Step 3. Generate the DNA Fragment to be Integrated.

Prepare a plasmid in shuttle vector pTKI that contains the following elements in tandem: [aTTB2]-[1 Kb of sequence upstream of target region to be replaced]-[KS cassette-AmpR]-[1 Kb of sequence downstream of target region] ATTB1 according to a modification of Bae et al., 2006. Drop the fragment out of this plasmid with restriction enzymes and isolate it. The "KS cassette" may actually be one or two copies of a KS, pending the outcome of genetic stability testing.

Step 4. Insert KS Cassette(s) to pKOR Plasmid

Perform in vitro recombination of the fragment from step 3 with the plasmid PKOR1 and then transfect the recombination mixture into DH5 alpha and obtain desired plasmid construct by standard screening methods in *E. coli*, using restriction mapping to verify construction.

Step 5. Obtain the KS Strain-Containing Integration Plasmid, in BioPlx-01

Electroporate the plasmid into RN4220; isolate plasmid DNA from the thus transfected RN4220, and electroporate this DNA into BioPlx-01 and select transformants on TSA plates containing chloramphenicol (10 μg/mL).

Step 6. Plasmid Integration to Chromosome.

Shift the strains to the non-permissive temperature (43° C.) to promote plasmid integration to the target site, and select a colony on a chloramphenicol plate (10 μg/mL).

Step 7. Counter Selection to Evict Plasmid Backbone

Grow the colony isolate from step 6 at the permissive temperature (30° C.) to favor plasmid excision and plate on 2 μg/ml and 3 ng/mL anhydrotetracycline (aTc) agar to obtain colonies in which the target gene has integrated and the plasmid has been excised and lost (the counterselection step). Any colonies that grow on plates containing ≥2 μg/mL aTc do not contain the plasmid because the plasmid backbone contains the lethal a Tc-derepressible SecY antisense gene.

Step 8. Confirm Integrated Allele Sequence

Isolate genomic DNA from the KS strain and confirm the knock-in cassette and flanking structure by PCR (and sequencing of the PCR amplicon).

Step 9. Check Serum-Induced Cell Death

Once confirmed, conduct cell death rate assays by growing the cells first in TSB, then shifting to human blood or serum and determining the rate of death by CFU plating assays in TSA (10 days).

Step 10. Verify Expression of KS mRNA

Confirm expression changes of the target gene in blood, serum, and in TSB.

Step 11. Prepare Frozen Banks

Animal studies may be performed with synthetic microorganisms BioPlx-XX created by these methods. In vivo functional studies to test kill switch strain function may be performed. Possible studies include a mouse study to show difference in pathogenicity of intravenous or intraperitoneal injection of wt BioPlx-01 vs. KS strain. An in vitro skin colonization test may also be performed. Additional tests may include, in mouse: LDso test, BioPlx-01 vs. BioPlx-XX is performed. As another example, in rat or other: colonization test, BioPlx-01 vs. BioPlx-XX is performed.

CRISPR-Cas Induced Homology Directed Repair to Direct Insertion of Optimal Kill Switch Candidates for Long Term Stable Expression In some embodiments, a method for preparing a synthetic *Staphylococcus aureus* strain from BioPlx-01 is provided comprising use of CRISPR-Cas induced homology directed repair to direct insertion of optimal KS candidates for long-term stable expression. In some embodiments, a method for preparing a synthetic *Staphylococcus aureus* strain from BioPlx-01 is provided comprising (1) obtaining competent cells, (2) design and testing of CRISPR guide RNA (gRNA) sequences and simultaneously testing pCasSA, (3) designing and testing homology dependent repair templates using a fluorescent reporter controlled by a constitutive reporter. (4) checking KS promoters with fluorescent reporter. (S) inserting KS into BioPlx-01 and verifying incorporation, and (6) testing for efficacy and longevity. Optionally, inserting additional KS cassettes in alternative locations within BioPlx-01 genome is performed.

Figure 10:
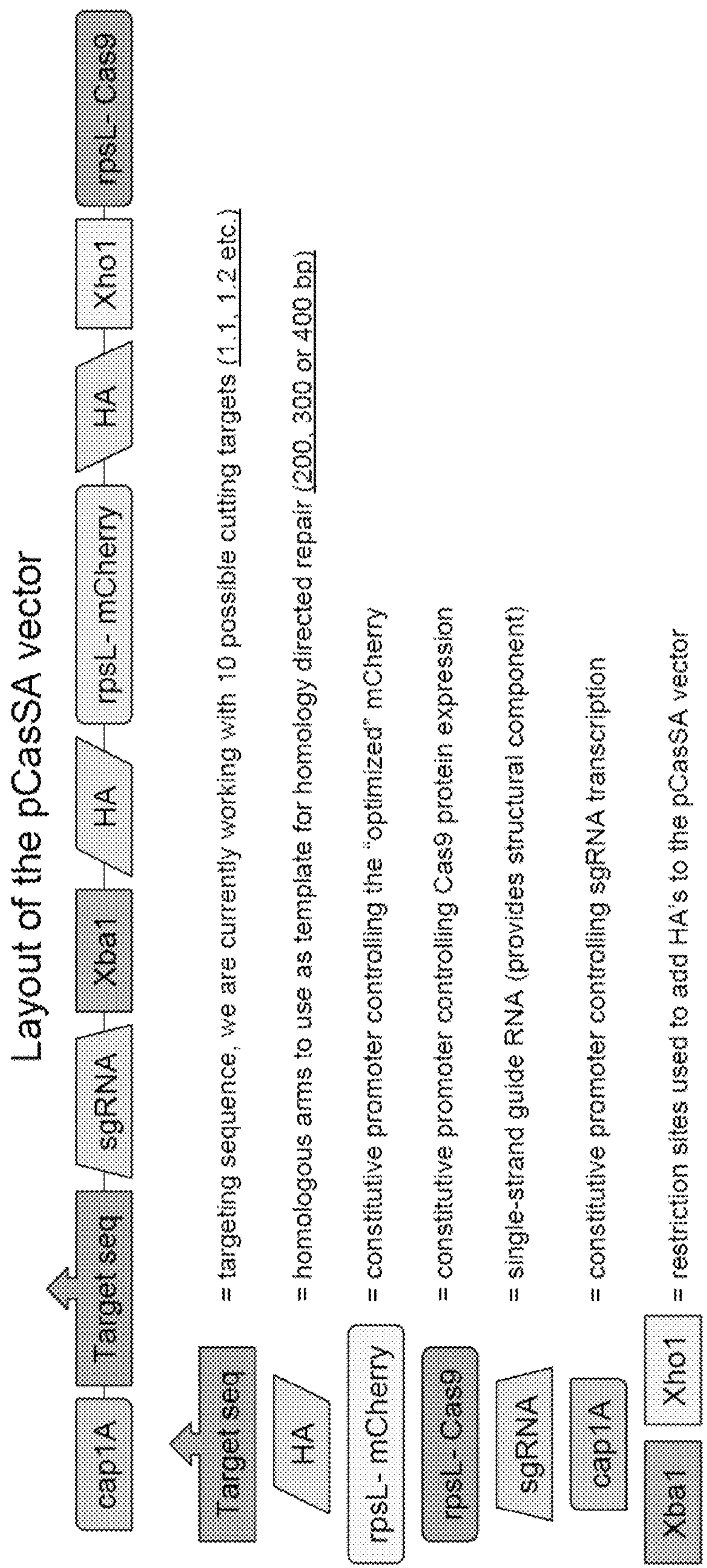
FIG. 10 shows cassette for integration via CRISPR and layout of the pCasSA vector, Cap1A is a constitutive promoter controlling gRNA transcription. Target seq is targeting sequence, for example, with 10 possible cutting targets (1.1, 1.2 etc.). sgRNA is single-strand guide RNA (provides structural component). Xba1 and Xho1 are two restriction sites used to add the HA's to the pCasSA vector. HAs are homologous arms to use as templates for homology directed repair (typically 200-1000 bp). P*rpsL*-mCherry is a constitutive promoter controlling the "optimized" mCherry. $P_{rpsL}$-Cas9 is a constitutive promoter controlling Cas9 protein expression.

FIG. 10 shows cassette for integration via CRISPR and layout of the pCasSA vector. Pcap1A is a constitutive promoter controlling gRNA transcription. Target seq is targeting sequence, for example, with 10 possible cutting targets (1.1, 1.2 etc.). gRNA is single-strand guide RNA (provides structural component). Xba1 and Xho1 are two restriction sites used to add the homology arms (HAs) to the pCasSA vector. HAs are homology arms to use as templates for homology directed repair (200-1000 bp). $P_{rpsL}$-mCherry is a constitutive promoter controlling the "optimized" mCherry, $P_{rpsL}$-Cas9 is a constitutive promoter controlling Cas9 protein expression.

FIG. 11 shows vectors for various uses in the present disclosure. A is a vector used for promoter screen with fluorescence using pCN51. B is a vector for promoter screen with cell death gene. C is a vector for chromosomal integration using CRISPR. D is a vector for chromosomal integration using homologous recombination. L & R HA: homology arms to genomic target locus, CRISPR targeting: RNA guide to genomic locus, mCherry: fluorescent reporter protein, Cas9 protein: CRISPR endonuclease, kanR: kanamycin resistance, oriT: origin of transfer (for integration), and Sma1: representative kill gene (restriction endonuclease).

Administration and Compositions

In some embodiments, compositions are provided comprising a synthetic microorganism and an excipient, or carrier. The compositions can be administered in any method suitable to their particular immunogenic or biologically or immunologically reactive characteristics, including oral, intravenous, buccal, nasal, mucosal, dermal or other method, within an appropriate carrier matrix. In one embodiment, compositions are provided for topical administration to a dermal site, and/or a mucosal site in a subject. Another specific embodiment involves the oral administration of the composition of the disclosure.

In some embodiments, the replacing step comprises topically administering of the synthetic strain to the dermal or mucosal at least one host subject site and optionally adjacent areas in the subject no more than one, no more than two, or no more than three times. The administration may include initial topical application of a composition comprising at least $10^6$, at least $10^7$, at least $10^8$, at least $10^9$, or at least $10^{10}$ CFU of the synthetic strain and a pharmaceutically acceptable carrier to the at least one host site in the subject. The initial replacing step may be performed within 12 hours, 24 hours, 36 hours, 48 hours, 72 hours, 4 days, 5 days, 6 days, 7 days, 8 days, or 9 days of the final suppressing step.

The composition comprising a synthetic microorganism may be administered to the dermal and/or mucosal at least one site in the subject, and optionally adjacent sites at least once, for example, from one to 30 times, one to 20 times, one to ten times, one to six times, one to five times, one to four times, one to three times, or one to two times, or no more than once, twice, three times, 4 times, 5 times, 6 times, 8 times per month, 10 times, or no more than 12 times per month. Subsequent administration of the composition may occur after a period of, for example, one to 30 days, two to 20 days, three to 15 days, or four to 10 days after the first administration.

Colonization of the synthetic microorganism may be promoted in the subject by administering a composition comprising a promoting agent selected from a nutrient, prebiotic, stabilizing agent, humectant, and/or probiotic bacterial species. The promoting agent may be administered to a subject in a separate promoting agent composition or may be added to the microbial composition.

In some embodiments, the promoting agent may be a nutrient, for example, selected from sodium chloride, lithium chloride, sodium glycerophosphate, phenylethanol, mannitol, tryptone, and yeast extract. In some embodiments, the prebiotic is selected from the group consisting of short-chain fatty acids (acetic acid, propionic acid, butyric acid, isobutyric acid, valeric acid, isovaleric acid), glycerol, pectin-derived oligosaccharides from agricultural by-products, fructo-oligosaccarides (e.g., inulin-like prebiotics), galacto-oligosaccharides (e.g., raffinose), succinic acid, lactic acid, and mannan-oligosaccharides.

In some embodiments, the promoting agent may be a probiotic. The probiotic may be any known probiotic known in the art. Probiotics are live microorganisms that provide a health benefit to the host. In methods provided herein, probiotics may be applied topically to dermal and mucosal microbiomes, and/or probiotics may be orally administered to provide dermal and mucosal health benefits to the subject. Several strains of *Lactobacillus* have been shown to have Systemic anti-inflammatory effects. Studies have shown that certain strains of *Lactobacillus reuteri* induce systemic anti-inflammatory cytokines, such as interleukin (IL)-10. Soluble factors from *Lactobacillus reuteri* inhibit production of pro-inflammatory cytokines. *Lactobacillus paracasei* strains have been shown to inhibit neutrogenic inflammation in a skin model Kober at al., 2015, Int J Women's Dermatol 1(2015) 85-89. In human dermal fibroblasts and hairless mice models, *Lactobacillus Plantarum* has been shown to inhibit UVB-induced matrix metalloproteinase 1 (MMP-1) expression to preserve procollagen expression in human fibroblasts. Oral administration of *L. plantarum* in hairless mice histologic samples demonstrated that *L. plantarum* inhibited MMP-13, MMP-2, and MMP-9 expression in dermal tissue, Clinically, the topical application of probiotics has also been shown to modify the barrier function of the skin with a secondary increase in antimicrobial properties of the skin. *Streptococcus thermophiles* when applied topically has been shown to modify the barrier function of the skin with a secondary increase in antimicrobial properties of the skin. *Streptococcus thermophiles* when applied topically has been shown to increase ceramide production both in vitro and in vivo. Ceramides trap moisture in the skin, and certain ceramide sphingolipids, such as phytosphingosine (PS), exhibit direct antimicrobial activity against *P. acnes*. Kober at al., 2015, Int J Women's Dermatol 1 (2015) 85-89.

Two clinical trials of topical preparations of probiotics have assessed their effect on acne. *Enterococcus fecalis* lotion applied to the face for 8 weeks resulted in a 50% reduction of inflammatory lesions was noted compared to placebo. A reduction in acne count, size, and associated erythema was noted during a clinical study of *Lactobacillus plantarum* topical extract. Kober at al., 2015, Int J Women's Dermatol 1 (2015) 85-89.

Clinical trials of topical probiotics have evaluated their effect on mucosal systems. In one study, *Streptococcus salivarius* was administered by nasal spray for the prevention of acute otitis media (AOM). If the nasopharynx was successfully colonized, there was significant effect on reducing AOM. Marchisio et al. (2015). Eur. J. Clin, Microbiol, Infect. Dis. 34, 2377~2383. In another trial, sprayed application of *S. sanguinis* and L. *Rhamnosus* decreased middle car fluid in children with secretory otitis media. Skovbjerg et al. (2008). Arch. Dis. Child. 94, 92-98.

The probiotic may be a topical probiotic or an oral probiotic. The probiotic may be, for example, a different genus and species than the undesirable microorganism, or of the same genus but different species, than the undesirable microorganism. The probiotic species may be a different genus and species than the target microorganism. The probiotic may or may not be modified to comprise a kill switch molecular modification. The probiotic may be selected from a *Lactobacillus* spp, *Bifidobacterium* spp. *Streptococcus* spp., or *Enterococcus* spp. The probiotic may be selected from *Bifidobacterium breve, Bifidobacterium bifidum, Bifidobacterium lactis, Bifidobacterium infantis, Bifidobacterium breve, Bifidobacterium longum, Lactobacillus reuteri, Lactobacillus paracasei, Lactobacillus plantarum, Lactobacillus johnsonii, Lactobacillus rhamnosus, Lactobacillus acidophilus, Lactobacillus salivarius, Lactobacillus casei, Lactobacillus planetarium, Lactococcus lactis, Streptococcus thermophiles, Streptococcus salivarius*, or *Enterococcus fecalis*.

The promoting agent may include a protein stabilizing agent such as those disclosed in an incorporated by reference from U.S. Pat. No. 5,525,336 is included in the composition. Non-limiting examples include glycerol, trehelose, ethylenediaminetetraacetic acid, cysteine, a cyclodextrin such as an alpha-, beta-, or gamma-cyclodextrin, or a derivative thereof, such as a 2-hydroxypropyl beta-cyclodextrin, and proteinase inhibitors such as leupeptin, pepstatin, antipain, and cystatin.

The promoting agent may include a humectant. Non-limiting examples of humectants include glycerin, sorbitol, sodium 2-pyrrolidone-5-carboxylate, soluble collagen, and dibutylphthalate.

Compositions

Compositions are provided comprising a synthetic microorganism and a pharmaceutically acceptable carrier, diluent, emollient, binder, excipient, lubricant, sweetening agent, flavoring agent, buffer, thickener, wetting agent, or absorbent.

Pharmaceutically acceptable diluents or carriers for formulating the composition are selected from the group consisting of water, saline, phosphate buffered saline, or a solvent. The solvent may be selected from, for example, ethyl alcohol, toluene, isopropanol, n-butyl alcohol, castor oil, ethylene glycol monoethyl ether, diethylene glycol monobutyl ether, diethylene glycol monoethyl ether, dimethyl sulphoxide, dimethyl formamide and tetrahydrofuran. The carrier or diluent may further comprise one or more surfactants such as i) Anionic surfactants, such as metallic or alkanolamine salts of fatty acids for example sodium laurate and triethanolamine oleate; alkyl benzene sulphones, for example triethanolamine dodecyl benzene sulphonate; alkyl sulphates, for example sodium lauryl sulphate; alkyl ether sulphates, for example sodium lauryl ether sulphate (2 to 8 EO); sulphosuccinates, for example sodium dioctyl sulphosuccinate; monoglyceride sulphates, for example sodium glyceryl monostearate monosulphate; isothionates, for example sodium isothionate; methyl taurides, for example Igepon T; acylsarcosinates, for example sodium myristyl sarcosinate; acyl peptides, for example Maypons and lamepons; acyl lactylates, polyalkoxylated ether glycollates, for example trideceth-7 carboxylic acid; phosphates, for example sodium dilauryl phosphate; Cationic surfactants, such as amine salts, for example sapamin hydrochloride; quartenary ammonium salts, for example Quaternium 5, Quaternium 31 and Quaternium 18; Amphoteric surfactants, such as imidazol compounds, for example Miranol; N-alkyl amino acids, such as sodium cocaminopropionate and asparagine derivatives; betaines, for example cocamidopropylebetaine; Nonionic surfactants, such as fatty acid alkanolamides, for example oleic ethanolamide, esters or polyalcohols, for example Span; polyglycerol esters, for example that esterified with fatty acids and one or several OH groups; Polyalkoxylated derivatives, for example polyoxy: polyoxyethylene stearate; ethers, for example polyoxyethe lauryl ether; ester ethers, for example Tween; amine oxides, for example coconut and dodecyl dimethyl amine oxides. In some embodiments, more than one surfactant or solvent is included.

The composition may include a buffer component to help stabilize the pH. In some embodiments, the pH is between 4.5-8.5. For example, the pH can be approximately 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0, including any value in between. In some embodiments, the pH is from 5.0 to 8.0, 6.0 to 7.5, 6.8 to 7.4, or about 7.0. Non-limiting examples of buffers can include ACES, acetate, ADA, ammonium hydroxide, AMP (2-amino-2-methyl-1-propanol), AMPD (2-amino-2-methyl-1,3-propanediol), AMPSO, BES, BICINE, bis-tris, BIS-TRIS propane, borate, CABS, cacodylate, CAPS, CAPSO, carbonate (pK1), carbonate (pK2), CHES, citrate (pK1), citrate (pK2), citrate (pK3), DIPSO, EPPS, HEPPS, ethanolamine, formate, glycine (pK1), glycine (pK2), glycylglycine (pK1), glycylglycine (pK2), HEPBS, HEPES, HEPPSO, histidine, hydrazine, imidazole, malate (pK1), malate (pK2), maleate (pK1), maleate (pK2), MES, methylamine, MOBS, MOPS, MOPSO, phosphate (pK1), phosphate (pK2), phosphate (pK3), piperazine (pK1), piperazine (pK2), piperidine, PIPES, POPSO, propionate, pyridine, pyrophosphate, succinate (pK1), succinate (pK2), TABS, TAPS, TAPSO, taurine (AES), TES, tricine, triethanolamine (TEA), and Trizma (tris). Excipients may include a lactose, mannitol, sorbitol, microcrystalline cellulose, sucrose, sodium citrate, dicalcium phosphate, phosphate buffer, or any other ingredient of the similar nature alone or in a suitable combination thereof.

The microbial composition may include a binder may, for example, a gum tragacanth, gum acacia, methyl cellulose, gelatin, polyvinyl pyrrolidone, starch or any other ingredient of the similar nature alone or in a suitable combination thereof; excipients selected from the group consisting of agar-agar, calcium carbonate, sodium carbonate, silicates, alginic acid, corn starch, potato tapioca starch, primogel or any other ingredient of the similar nature alone or in a suitable combination thereof; lubricants selected from the group consisting of a magnesium stearate, calcium stearate, talc, solid polyethylene glycols, sodium lauryl sulfate or any other ingredient of the similar nature alone; glidants selected from the group consisting of colloidal silicon dioxide or any other ingredient of the similar nature alone or in a suitable combination thereof; a stabilizer selected from the group consisting of such as mannitol, sucrose, trehalose, glycine, arginine, dextran, or combinations thereof; an odorant agent or flavoring selected from the group consisting of peppermint, methyl salicylate, orange flavor, vanilla flavor, or any other pharmaceutically acceptable odorant or flavor alone or in a suitable combination thereof; wetting agents selected from the group consisting of acetyl alcohol, glyceryl monostearate or any other pharmaceutically acceptable wetting agent alone or in a suitable combination thereof; absorbents selected from the group consisting of kaolin, bentonite clay or any other pharmaceutically acceptable absorbents alone or in a suitable combination thereof; retarding agents selected from the group consisting of wax, paraffin, or any other pharmaceutically acceptable retarding agent alone or in a suitable combination thereof.

The microbial composition may comprise one or more emollients. Non-limiting examples of emollients include stearyl alcohol, glyceryl monoricinoleate, glyceryl mono stearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, sesame oil, coconut oil, arrachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate.

The microbial composition may include a thickener, for example, where the thickener may be selected from hydroxyethylcelluloses (e.g. Natrosol), starch, gums such as gum arabic, kaolin or other clays, hydrated aluminum silicate, fumed silica, carboxyvinyl polymer, sodium carboxymethyl cellulose or other cellulose derivatives, ethylene glycol monostearate and sodium alginates. The microbial composition may include preservatives, antiseptics, pigments or colorants, fragrances, masking agents, and carriers, such as water and lower alkyl, alcohols, such as those disclosed in an incorporated by reference from U.S. Pat. No. 5,525,336 are included in compositions.

The microbial compositions for topical administration may be provided in liquid, solution, suspension, cream, lotion, ointment, gel, or in a solid form such as a powder, tablet, of troche for suspension immediately prior to administration. The compositions for topical use may also be provided as hard capsules, or soft gelatin capsules, wherein the benign and/or synthetic microorganism is mixed with water or an oil medium, for example, peanut oil, liquid paraffin, or olive oil. Powders and granulates may be prepared using the ingredients mentioned above under tablets and capsules for dissolution in a conventional manner using, e.g., a mixer, a fluid bed apparatus, lyophilization or a spray drying equipment. A dried microbial composition may administered directly or may be for suspension in a carrier. When the composition is in a powder form, the powders may include chalk, talc, fullers earth, colloidal silicon dioxide, sodium polyacrylate, tetra alkyl and/or trialkyl aryl ammonium smectites and chemically modified magnesium aluminum silicate in a carrier. When the composition is in a powder form, the powders may include chalk, talc, fullers earth, colloidal silicon dioxide, sodium polyacrylate, tetra alkyl and/or trialkyl aryl ammonium smectites and chemically modified magnesium aluminum silicate The microbial composition may exhibit a stable CFU losing less than 30%, 20%, 10% or 5% cfu over at least one, two, three months, six months, 12 months 18 months, or 24 months when stored at frozen, refrigerated or preferably at room temperature.

Kits

Any of the above-mentioned compositions or synthetic microorganisms may be provided in the form of a kit. In some embodiments, a kit comprises a container housing live bacteria or a container housing freeze-dried live bacteria. Kits can include a second container including media. Kits may also include one or more decolonizing agents. Kits can also include instructions for administering the composition. In certain embodiments, instructions are provided for mixing the bacterial strains with other components of the composition. In some embodiments, a kit further includes an applicator to apply the microbial composition to a subject.

Dose

In certain embodiments, a composition is provided for topical administration that is a solution composition, or for reconstitution to a solution composition. In one embodiment, composition may include from about $1\times10^5$ to $1\times10^{12}$ cfu/ml, $1\times10^6$ to $1\times10^{10}$ cfu/ml, or $1.2\times10^7$ to $1.2\times10^9$ CFU/mL of the synthetic microorganism in an aqueous solution, such as phosphate buffered saline (PBS). Lower doses may be employed for preliminary irritation studies in a subject.

Preferably, the subject does not exhibit recurrence of the undesirable microorganism as evidenced by swabbing the subject at the at least one site after at least 2, 3, 4, 6, 10, 35, 22, 26, 30 or 52 weeks after performing the initial administering step.

Nanofactory

In some embodiments, methods are provided to create production of a desired substance at the site of the microbiome (nanofactory). Synthetic microorganisms are provided that may comprise a nanofactory molecular modification. The term "nanofactory" refers to a molecular modification of a target microorganism that results in the production of a product-either a primary product such as a protein, enzyme, polypeptide, amino acid or nucleic acid, or a secondary product such as a small molecule to produce a beneficial effect. The product may be secreted from the synthetic microorganism or may be in the form of an inclusion body. Such nanofactory bacterial strains have the potential to provide to the host subject a wide range of durable benefits including: (i) the acquisition of cellular products and enzymes for which the host was previously deficient and; (ii) the acquisition of a delivery system of a microbially manufactured small molecule, polypeptide or protein pharmaceuticals for diverse therapeutic and prophylactic benefit. Such nanofactory bacterial strains when durably integrated into the biome as described herein would provide a useful durable alternative steady state production of product than direct product application.

Methods and synthetic microorganisms are provided herein to replace existing colonization by an undesirable microorganism with a synthetic bacterial strain comprising a nanofactory molecular modification for the production or consumption of a primary or secondary product, where the target microorganism may be a strain of *Acinetobacter johnsonii, Acinetobacter baumannii, Staphylococcus aureus, Staphylococcus epidermidis, Staphylococcus lugdunensis, Staphylococcus warneri, Staphylococcus saprophyticus, Corynebacterium acnes, Corynebacterium striatum, Corynebacterium diphtheriae, Corynebacterium minutissimum, Cutibacterium acnes, Propionibacterium acnes, Propionibacterium granulosum, Streptococcus pyogenes, Streptococcus aureus. Streptococcus agalactiae, Streptococcus mitis, Streptococcus viridans, Streptococcus pneumoniae, Streptococcus anginosis, Streptococcus constellatus, Streptococcal intermedius, Streptococcus agalactiae, Pseudomonas aeruginosa, Pseudomonas oryzihabitans, Pseudomonas stutzeri, Pseudomonas maida*, and *Pseudomonas fluorescens, Lactobacillus crispatus, Lactobacillus gasseri, Lactobacillus jensenii* and *Lactobacillus iners*.

The nanofactory molecular modification in a synthetic microorganism may be used to assist its host subject, i.e., a patient with a deficit of some primary (anabolic or catabolic) or secondary metabolic pathway or any other ailment stemming from the over or under abundance of some small molecule or macromolecule such as an enzyme. The nanofactory molecular modification may encode an enzyme, amino acid, metabolic intermediate, or small molecule. The nanofactory molecular modification may confer a new production (synthesis) or metabolic function into the host microbiome, such as the ability to endogenously synthesize or metabolize specific compounds, or synthesize enzymes or other active molecules to operate within the exogenous microbiome.

The microorganism will carry a nanofactory selected from a biosynthetic gene, biosynthetic gene cluster, or gene(s) coding for one or multiple enzymes under the control of a differentially regulated, inducible or constitutively regulated promoter. The synthetic microorganism comprising a nanofactory is to be administered to at the at least one site of the body be it dermal, mucosal, or other site as a singular agent or in conjunction with a second, third or fourth synthetic microorganism that help the first synthetic microorganism restore the loss of function on or in the host subject.

In one example, a synthetic microorganism comprising a nanofactory may be used for restoration of function by the production of intracellularly active factors, for example, microbial supplementation of digestive enzymes in patients with exocrine pancreatic insufficiency by secreted recombinant enzymes in the small intestine. The pancreas is a vital organ and plays a key role in digestion. Exocrine pancreatic insufficiency (EPI) is caused by prolonged damage to the pancreas, which leads to the reduction or absence of quintessential digestive enzymes in the small intestine that primarily breakdown fats and carbohydrates. The loss of these enzymes can lead to a wide breadth or symptoms and depends on the severity of the EPI. The small intestine's pH level in the proximal small intestine (duodenum) is lower than that of the distal region. This shift in environment leads to microbial niche occupation that is pH dependent. This pH dependency has naturally selected for duodenum commensal bacteria that could be molecularly modified to become synthetic microorganisms, which would intrinsically localize themselves to that region of the gastrointestinal tract. The stomach and upper two-thirds of the small intestine contain acid tolerant *Lactobacilli* and Streptococci (Hao, W I, Lee Y K. Microflora of the gastrointestinal tract: a review. Methods Mol. Biol. 2004, 268, 491-502) and could be isolated from healthy donors. By knocking in recombinant lipases, amylases and/or proteases with secretory signaling sequences, the colonization of the duodenum by the synthetic microorganisms could restore digestive function in patients suffering from EPI.

In another example of a nanofactory, a synthetic microorganism comprising a nanofactory may be used for restoration of function by the production of intracellularly active factors. For example, protecting a subject suffering from phenylketonuria (PKU) by eliminating phenylalanine in the gastrointestinal tract. Phenylalanine is an essential amino acid, meaning that the human body cannot produce it and must acquire it through nourishment. Once in the body, the breakdown of phenylalanine is carried out by one protein, phenylalanine hydroxylase (PAH). The inheritable genetic disorder known as phenylketonuria (PKU) is caused by mutations in the gene coding for PAH, which results in the build up of phenylalanine in the body. One of the most common approaches to circumvent this accumulation is to avoid phenylalanine rich foods. Alternatively, a synthetic microorganism that has been molecularly modified to breakdown phenyalanine intracellularly can be introduced into the gastrointestinal tract. This synthetic microorganism constitutes a PAH nanofactory, breaking down phenyalanine before it has a chance to enter the body of the host with PKU.

In another example of a nanofactory, a synthetic bacteria may be derived from a target commensal bacteria from the skin microbiota may comprising a nanofactory molecular modification. The target commensal skin or mucosal bacterium may be, e.g., a *Staphylococcus* spp., *Streptococcus* spp., or a Cutibacterium spp. For example, *Staphylococcus epidermidis* may be the target microorganism because it is found in multiple dermal or mucosal environmental types. Engineering a synthetic *S. epidermidis*, given its ability to persist in different environments, would allow for the development and optimization of multiple kinds of delivery techniques and locations.

In one example, a synthetic *S. epidermidis* strain may comprise a nanofactory molecular modification to produce testosterone for men suffering from male hypogonadism. The production of testosterone could be accomplished by: (i)

introduction of the entire sterol biosynthetic pathway with the additional enzymes necessary to generate testosterone, or (ii) introduction of the partial sterol biosynthetic pathway and having the necessary precursor molecules in the carrying medium, i.e., farnysel, squalene, cholesterol etc, so that testosterone could be assembled in the synthetic bacterium. In another example, a synthetic *S. epidermidis* strain could comprise a nanofactory molecular modification for production of nicotine; this synthetic strain could be applied as a transdermal therapy to help with smoking cessation. This synthetic strain may include a molecular modification to include one or more biosynthetic pathways found in the Solanaceae family of plants, and optionally further include a molecular modification for the enhancement of intrinsic pathways of precursor molecules, i.e., aspartic acid, ornithine etc.

In a further example of a nanofactory, a synthetic *S. epidermidis* strain may comprise a nanofactory molecular modification for the production of scopolamine. Scopolamine is currently delivered via an extended release transdermal patch for treatment of motion sickness and postoperative prophylaxis. This strain would need to carry the biosynthetic pathways found in the Solanaceae family of plants and possibly the enhancement of intrinsic pathways of precursor molecules.

As another example, a synthetic *S. epidermidis* strain may comprise a nanofactory molecular modification for the production of capsaicin to alleviate pain stemming from postherpetic neuralgia, psoriasis or other skin related disorders.

In another example, the target microorganism is a *Streptococcus mutans* strain, which may have one or more of a kill switch, V-block, or nanofactory molecular modification. Dental caries and dental plaque are among the most common diseases worldwide, and are caused by a mixture of microorganisms and food debris. Specific types of acid-producing bacteria, especially *Streptococcus mutans*, colonize the dental surface and cause damage to the hard tooth structure in the presence of fermentable carbohydrates e.g., sucrose and fructose. Dental caries and dental plaque are among the most common diseases worldwide, and are caused by a mixture of microorganisms and food debris. Specific types of acid-producing bacteria, especially *Streptococcus mutans*, colonize the dental surface and cause damage to the hard tooth structure in the presence of fermentable carbohydrates e.g., sucrose and fructose. Forrsten et al, Nutrients, 2010 March; 2(3): 290-298. In some embodiments, the target microorganism is *S. mutans* having a KS and/or a nanofactory knock out for reducing acid production in presence of sucrose, fructose, or other fermentable carbohydrates.

Further examples of nanofactory molecular modifications in a synthetic microorganism to address dermatological and cosmetic uses include: (i) hyaluronic acid production in *Staphylococcus epidermidis* for atopic dermatitis or dry skin, (ii) alpha-hydroxy acid production in *Staphylococcus epidermidis* to reduce fine lines and wrinkles as well as lessen irregular pigmentation, (iii) salicylic acid production in Cutibacterium *acnes* to reduce acne, (iv) arbutin production in *Staphylococcus epidermidis* (arbutin and its metabolite hydroquinone function as skin lightening agents by melanin suppression, (v) Kojic acid (produced by several fungi including *Aspergillus oryzae*) in *Staphylococcus epidermidis* to lighten skin pigmentation, (vi) Retinoid production by *Staphylococcus epidermidis* for the reduction of fine lines and wrinkles, (vii) L-ascorbic acid (Vitamin C) production in *Staphylococcus epidermidis* for the stimulation of collagen and antioxidant effects on the skin, (viii) copper peptide (GHK-Cu) production in *Staphylococcus epidermidis* for stimulation of collagen and elastin production and reduction of scar formation, (ix) alpha lipoic acid production in *Staphylococcus epidermidis* for beneficial antioxidant effects on the skin., and (x) dimethylaminoethanol production in *Staphylococcus epidermis* for reducing fine lines and wrinkles.

Cutibacterium *acnes* is a dominant bacteria living on the skin, and has been associated with both healthy skin and various diseases. This is another organism and niche available for enhancing and strengthening with modern molecular biology techniques. Studies have shown that the levels of *C. acnes* are similar between healthy skin and skin laden with acne. Dréno, B., et al. "*Cutibacterium acnes* (*Propionibacterium acnes*) and acne vulgaris: a brief look at the latest updates." Journal of the European Academy of Dermatology and Venereology 32 (2018): 5-14. This indicates that just lowering the number of viable *C. acnes* on a person's skin will not help to alleviate the disease or symptoms. Instead, other strains of *C. acnes* or other members of the dermal and subcutaneous microbiome can be altered to mitigate the mechanisms that certain *C. acnes* strains use to cause disease. The isolates that showed to have the greatest association with increased acne severity also have been shown to produce higher quantities of propionic and butyric acid. Beylot, C., et al. "*Propionibacterium acnes*: an update on its role in the pathogenesis of acne." *Journal of the European Academy of Dermatology and Venereology* 28.3 (2014): 271-278.

Another example of a nanofactory molecular modification includes another strain of *C. acnes* that is modified to have an increased appetite for short chain fatty acids, such as propionic and butyric acid, thereby removing the inflammatory chemical secretions from the virulent strain rendering it less toxic. The carbon rich fatty acids could be used to induce a heterologous pathway and used as precursors for vitamin synthesis or other organic compounds beneficial for the skin or microbiome that inhabits that location.

In another example, in *S. epidermidis* lipoteichoic acid has shown to help mitigate the inflammatory response of *Propionibacterium acnes* (i.e., *Cutibacterium acnes*) by inducing miR-143. Xia, Xiaoli, et al. "Staphylococcal LTA-induced miR-143 inhibits *Propionibacterium acnes*-mediated inflammatory response in skin." *Journal of Investigative Dermatology* 136.3 (2016): 621-630. A synthetic microorganism comprising a nanofactory molecular modification producing lipoteichoic acid which inhibits *C. acnes*-induced inflammation via induction of miR-143 may be employed. The nanofactory may be used to modulate inflammatory responses by *S. epidermidis* at the site of acne vulgaris for management of *C. acnes*-induced inflammation. This pathway is just one example of a useful product that could be made from short chain fatty acids that when left alone cause inflammation and skin irritation.

In another example, inflammation and an increase in temperature are factors involved in the disease caused by (*acnes*, they could be used as signals to induce previously silent heterologous pathways in an engineered strain. A temperature increase (signalling a sealed pore and progressing localized disease state) could induce in the virulent strain or another commensal microbe, the transcription and translation of a non-immune stimulating lipase (or other enzyme) that is capable of degrading the sebum to the point of reopening a clogged pore allowing the location to resume its normal growth conditions.

In a further example, a synthetic *Lactobacillus* spp. such as *Lactobacillus crispatus, Lactobacillus gasseri, Lactobacillus jensen* or *Lactobacillus iners*-which are common dominant species present in the female vaginal vault may be engineered to comprises a nanocatory molecular modification that produces estradiol in the vaginal vault of post-menopausal women.

Methods and synthetic microorganisms are provided herein to replace existing colonization by an undesirable microorganism with a synthetic bacterial strain comprising a nanofactory molecular modification for the production or consumption of a primary or secondary product, for example, selected from an enzyme, nicotine, aspartic acid, ornithine, propionic acid, butyric acid, hyaluronic acid, an alpha-hydroxy acid, L-ascorbic acid, a copper peptide, alpha-lipoic acid, salicylic acid, arbutin, Kojic acid, scopolamine, capsaicin, a retinoid, dimethylaminoethanol, lipoteichoic acid, testosterone, estradiol, and progesterone.

The durable integration of a synthetic bacterial strain that is able to produce by means of a nanofactory molecular modification or synthetic addition to its genome, a substance, material, or product, or products, that are beneficial to the host at the site of the microbiome integration or at distant sites in the host following absorption may be tailored to the desired indication. Depending upon whether the synthetic nucleotide change is incorporated directly into the bacterial genome, or whether it was introduced into plasmids, the duration of the effect of the nanofactory production could range from short term (with non-replicating plasmids for the bacterial species) to medium term (with replicating plasmids without addiction dependency) to long term (with direct bacterial genomic manipulation).

Virulence Block

In some embodiments, methods are provided to replace existing colonization with a synthetic bacterial strain which cannot accept genetic transfer of undesired virulence or antibiotic resistance genes. Synthetic microorganisms are provided that may comprise a “virulence block” or “V-block”. The term “virulence block”, or “V-block” refers to a molecular modification of a microorganism that results in the organism have decreased ability to accept foreign DNA from other strains or species effectively resulting in the organism having decreased ability to acquire exogenous virulence or antibiotic resistance genes.

Methods are provided herein to replace existing colonization by an undesirable microorganism with a synthetic bacterial strain comprising a V-block molecular modification which cannot accept genetic transfer of undesired virulence or antibiotic resistance genes, where the target microorganism may be a strain of *Acinetobacter johnsonii, Acinetobacter boumannii, Staphylococcus aureus, Staphylococcus epidermidis, Staphylococcus lugdunensis, Staphylococcus warneri, Staphylococcus saprophyticus, Corynebacterium acnes, Corynebacterium striatum, Corynebacterium diphtheriae, Corynebacterium minutissimum, Cutibacterium acnes, Propionibacterium acnes, Propionibacterium granulosum, Streptococcus pyogenes, Streptococcus aureus, Streptococcus agalactiae, Streptococcus mitis, Streptococcus viridans, Streptococcus pneumoniae, Streptococcus anginasis, Streptococcus constellatus, Streptococcal intermedius, Streptococcus agalactiae, Pseudomonas aeruginosa, Pseudomonas oryzihabitans, Pseudomonas stutzeri, Pseudomonas puntida*, and *Pseudomonas fluorescens.*

One of the major concerns with regard to infectious diseases is commonly called “horizontal gene transfer” with potential bacterial pathogens acquiring either exogenous virulence protein genes or antimicrobial resistance genes. The acquisition may result from transfer of these genes from other bacteria strains or species in the local microbiome environment. As it is common for invasive bacterial pathogens to initially be a part of the colonizing bacterial microbiome on skin or mucosal surfaces prior to causing disease, it would be of great practical benefit to be able to imbue these colonizing strains with the inability to accept foreign bacterial DNA into the bacterial genome. The process to accomplish this in a durably integrated synthetic bacterial strain has been termed called “virulence block.” Such a “virulence block” manipulated strain would be able to be integrated into the microbiome after a decolonization event and then through the process of competitive exclusion, remain for a time as the dominant strain within that particular niche without reacquiring undesired virulence or antibiotic resistance characteristics. Such a concept carried out on potential pathogens within the microbiome would result in a stable microbiome which could acquire neither virulence nor antimicrobial resistance genes in the horizontal transfer manner, rendering the totality of the microbiome more robust and with lowered conversion potential.

The V-block is a molecular modification that may be employed in a synthetic microorganism in order to suppress virulence or horizontal gene transfer from an undesirable microorganism. The V-block molecular modification may be created in a target microorganism by: (i) gene knockout (excise or remove) of one or more known virulence genes, (ii) frameshifi of a virulence region (adding or subtracting base pairs to ‘break’ the coding frame), (iii) exogenous silencing of vinilence regions using inducible promoter or constitutive promoter (embedded in the DNA genome, but functions in RNA)—like antitoxin strategy, production of CRISPR-CAS9 or other editing proteins to digest incoming virulence genes using guide RNA which may be linked to an inducible promoter or constitutive promoter, or (iv) by a restriction modification (RM) such as a methylation system to turn the organism’s ‘innate immune system’ to recognize and destroy incoming virulence genes by class of molecule. Any of these methods may be employed to in order to increase resistance to horizontal gene transfer. Gene editing methods for constructing a V-block may include NgAgo, mini-Cas9, CRISPR-Cpf1, CRISPR-C2c2, Target-AID, Lambda Red, Integrases, Recombinases, or use of Phage. The virulence block may be operably linked to a constitutive promoter in the synthetic microorganism. The virulence block molecular modification may prevent horizontal gene transfer of genetic material from a virulent microorganism.

The gene cassette conferring antibiotic resistance to strains of *Staphylococcus aureus* (SA) may be integrated into the recipient cell’s genome at a particular site. This site could be deleted or changed in a cells genome, making the landing site no longer available for the incoming DNA sequence. This has been shown not to interfere with SA’s ability to grow, and would make the acquisition of the resistance cassette by the organism much less likely to occur The V-block molecular modifications may cause the removal or neutralization of virulence factors, resistance loci or cassettes, toxins or toxigenic functions, or other undesired attributes of the binomially integrated microorganism.

A virulence block in the form of Cas9 recognition system for sequences consistent with known virulence factors or antibiotic resistance genes in *Staphylococcus aureus* may be used to protect strains of *Staphylococcus aureus* Live Biotherapeutic Products from acquiring additional virulence factors and resistances to antibiotic classes, thus rendering them as safe as initially approved and manufactured.

CRISPR is a native adaptive immune system for prokaryotic cells that has evolved over time to help defend against phage attacks. The system uses short DNA sequences complementary to phage DNA (or any target DNA) sequences to target incoming DNA and digest the strand before it can be incorporated into the genome of the living cell. This same technology may be engineered to target DNA sequences that are non-threatening to the bacterial cell, but once acquired allow the organism to cause disease and persist in environments that were previously less habitable. Through integrating the Cas-9 enzyme into the genome, or harnessing the endogenous Cas-9 if available, it is possible to introduce into the genome constitutively expressed guide RNAs that target antibiotic resistance genes. If the targeted sequences are ever introduced to the cell through horizontal gene transfer or otherwise, the incoming DNA will be cut up and unable to integrate into the genome or produce a functional peptide. If the genes become integrated into the genome before the CRISPR-Cas system can target it, the engineered CRISPR-Cas system will find it in the genome and cut the sequences at the targeted location, thus producing a non-viable cell and stopping the spread of antibiotic resistance cassettes.

The CRISPR system can also be used to target RNA sequences with the result of silencing gene expression. Instead of recognition sequences targeting the DNA sequence of antibiotic resistance or virulence genes, the recognition sequences can be designed to target mRNA. If Cas9 and the targeting guide RNAs are constitutively expressed in a cell that receives the abxR or virulence genes, the translation will be interrupted by the engineered CRISPR system impeding protein formation and the ability of the cell to use the targeted genes.

Yet another method of gene silencing in prokaryotes that may be used to target the expression of virulence or antibiotic resistant genes is to design and constitutively express regulatory RNAs that target the mRNA transcript, usually at the RBS. These would be integrated into and constitutively expressed from the genome to create a synthetic organism. The regulatory RNA is a short sequence (>100 bp) and is complementary to the 5' untranslated region (UTR) of the mRNA transcript of the abxR or virulence gene. The constitutive expression of the short sequences should not be metabolically taxing for the organism, and will have the result of blocking translation of the targeted mRNA into a protein. The engineered RNA will sufficiently block the cells ability to utilize the targeted antibiotic resistance gene if and when it is received through horizontal gene transfer.

DNA methylation plays many important roles in prokaryotes and eukaryotes. One feature of DNA methylation allows a cell to distinguish its own DNA from foreign DNA. This makes editing and studying many wild type strains very difficult, because the organism's methylase systems recognize transformed plasmid DNA as foreign, and chew it up before it can be transcribed or integrated. Horizontal gene transfer can occur between organisms that have very similar methylation patterns because the incoming DNA looks very similar to the recipient's own DNA and it is not digested. Since the mechanism and genes responsible for adding methyl groups to specific sequences, and those that look for and cut improperly methylated DNA are known in a variety of bacterial strains, it is possible to create a synthetic organism that is capable of having a unique methylation pattern. This would serve to make all incoming DNA appear foreign to the synthetic organism and get digested before the organism can acquire the new traits. This would serve to render the horizontal gene transfer of virulence or antibiotic resistance genes into our synthetic organism a non-issue.

A V-Block in the form of a molecular disruption of one or more bacterial genomic cassette insertion sites in the synthetic microorganism can render the synthetic microorganism unable to acquire antibiotic class resistance genes from resident bacteria species that are cohabitating the biome. Such manipulation will also prevent the acquisition of virulence genes that could increase the possibility of invasive events across the bowel wall. The gene cassette conferring antibiotic resistance to strains of *Staph aureus* (SA) may be integrated into the recipient cell's genome at a particular site. This site could be deleted or changed in a cells genome, making the landing site no longer available for the incoming DNA sequence. So long as the V-block is shown not to interfere with the synthetic microorganisms ability to grow, and would make the acquisition of the resistance cassette by the organism much less likely to occur.

EXAMPLES

Example 1. Field Studies-Exclusionary Niche using Benign Microorganism

Clinical Studies-Suppress and Replace

A clinical study was designed to identify MRSA positive subjects, suppress the MRSA strain, replace the MRSA by administering Bioplx-01 (i.e., MSSA 502a), and periodically retesting subjects for recurrence of MRSA. The study population was largely drawn from Meerut area Medical Personnel and Medical Students. No symptomatic subjects were enrolled in the study.

This is a "proof of principle" study, being performed with largely unimproved materials and methods ~ any result greater that 55% non-recurrence will be considered an indication of the potential efficacy of these methods. Any result at 80% or greater non-recurrence would be considered a strong indication of the current technical strength of this approach.

Study purpose and primary endpoints:

1) To determine the rate of asymptomatic *Staphylococcus aureus* and MRSA occurrence in the general population—Meerut, UP (North India)—and to qualify participants for further phases of this study;

2) Determine the rate of MRSA recurrence in BioPlx decolonized participants;

3) Determine the rate of MRSA recurrence in BioPlx01-WT recolonized participants;

4) Determine the durability of BioPlx01-WT in preventing MRSA recurrence (to 8 & 12 wks);

5) Acceptable study recurrence level=40%, Target recurrence level=20%.

The study results are evaluated against the published recurrence rates from peer-reviewed sources, averaging 45% recurrence, 55% non-recurrence.

Identification and solicitation of potential participants was performed with total participants enrolled and tested: n=766. Patients were drawn from the Medical Staff and Medical Students of Meerut University Medical College—LLRM Medical College (MUMC Hospital), Harish Chandra Hospital, Murti Hospital, Silver Cross Hospital, JP Hospital, and Lokpriya Hospital, Dhanvantri Hospital, Jaswantrai Hospital. A paper disclosure, informed consent, and sign up document signed by all participants.

All 765 potential participants were swabbed (Nasal) by lab personnel. All swabs were plated onto a *Staphylococcus aureus* and a MRSA chromagar plate by lab personnel. All plates were incubated for 24 hours at 37° C., read and scored by the study supervisor personally. Photographs were taken of all plates at reading and labeled results.

The total *Staphylococcus aureus* nasal swab positive (MSSA and MRSA) participants was 162 or 21.18%, at the low end of expected rate for nasal swab only. The number of MSSA only (non-MRSA) participants was 97 or 12.68%.

The number of MRSA positive participants was 65 or 8.50% of total tested population.

The MRSA positive participants (n=65) were selected for the Efficacy Study by the study supervisor. The *Staphylococcus aureus* positive participants were selected for the irritation study by the study supervisor.

Efficacy Study was performed using BioPlx01-WT (10~8) in PBS.

Confirmed MRSA positive participants (n=65) were advised as to the 12 week duration and commitment to the process. Study duration was extended to 6 months. Subjects for the Efficacy Study were divided as shown in Table 10.

TABLE 10

| Efficacy Study | |
|---|---|
| MRSA Positives Identified | n = 65 |
| MRSA positive used in treatment groups - Decol/Recol | n = 34 |
| MRSA positive used in negative controls - Decol only | n = 15 |
| MRSA lost from study (Antibiotic use/drop-out) | n = 04 |
| MRSA positive not used | n = 12 |

Decolonization/Recolonization Process

Decolonization.

A complete decolonization is performed on participants first. Following is confirmation of MRSA eradication in key sites. The total body decolonization is done with chlorhexidine, nasal decolonization is done with mupirocin, and gargling with Listerine original antiseptic as per the "Decolonization Protocol" section. After complete course of decolonization procedure (five days), a confirmation MRSA test will be administered to verify that no MRSA is present in key areas, and an *Staphylococcus aureus* test will be administered to gather information about post-colonization *Staphylococcus aureus* levels, Participants underwent five-day decolonization process, which was administered and observed by study personnel. Dermal decolonization was performed by study personnel and included (1) full body spray application of chlorhexadine (4%), (2) nasal (mucosal) decolonization with mupriocine (2%), and (3) throat (mucosal) decolonization by application of Listerine, each once per day over 5 days. Participants undergo five-day decolonization process, administered and observed by BioPlx Pvt Ltd personnel.

Dermal—Chlorhexadine

Nasal (Mucosal)—Mupriocine

Throat (Mucosal)—Listerine

The participants undergo one full-body chlorhexidine bath that fully decolonizes the skin and hair. It is also true that chlorhexidine has a residual antibiotic activity that lasts as long as the outer layer of skin is present. A five-day waiting period ensures that the outer layer of skin has sloughed off and that when the subject is recolonized, BioPlx-01 is not being killed in the process.

Nasal Decolonization. To decolonize the nose and throat, the participants must use a five-day course of mupirocin antibiotics. This fully decolonizes the nares (nose).

Throat Decolonization. To decolonize the throat, the participants must gargle for 30 seconds every day with Original Listerine. This fully decolonizes the throat.

Successful decolonization is characterized by a negative MRSA result for nose, throat, and axilla (armpit). With successful decolonization only nasal follow-up testing is required at downstream timepoints. MRSA positive in nose or throat require second full round of decolonization procedure. Patients in this category do not proceed to next phase of study until decolonized. MRSA positive in axilla does not require second full round of decolonization and may proceed to next phase of study. Axilla site must now be included in all downstream MRSA testing.

Post-Decolonization Qualification Test N-T-H-A-*Staphylococcus aureus* and MRSA for each study Group (1,2,3). Swabs taken by Garg lab personnel. All swabs were plated onto a *Staphylococcus aureus* and a MRSA chromagar plate by Gard lab personnel. All plates were incubated in Dr. Garg's lab for 24 hours. All plates were read and scored by Dr. Garg personally. Photographs were taken of all plates at reading and labeled with Dr. Garg results. All data were recorded by BioPlx Pvt Ltd in paper and digital form. All digital data are transmitted to BioPlx, Inc. for filing and entry into the records system. This procedure was used for all steps in Efficacy Study.

Recolonization was performed with application of $1.2\times10^8$ cfu/mL. Bioplx-01 in phosphate buffered saline (PBS), as described below, about 15 mL once per day for two consecutive days per the following schedule:

1.2 ×10ˆ8 RECOLONIZATION AND QC TESTING was performed two days back-to-back;

POST 1.2×10ˆ8 RECOLONIZATION TESTING-one day;

POST 1.2×10ˆ8 RECOLONIZATION TESTING-one week; and

Weekly Observation—week 2 and thereafter.

Post-Decolonization Qualification Test N-T-H-A—*Staphylococcus aureus* and MRSA was performed for each study Group (1, 2, 3).

Weekly observations included swabs of the subjects were taken by lab personnel. Anatomical sites sampled included nares, throat, axilla, hand.

All swabs were plated onto a *Staphylococcus aureus* and a MRSA chromagar plate by lab personnel. All plates were incubated for 24 hours at 37° C. All plates were read and scored by the study director personally. Photographs were taken of all plates at reading and labeled with results.

Negative controls. Post decolonization negative controls n=15; ID #s: 0021, 0022, 0060, 0512, 0704, 0724, 0731, 0218, 0234, 0239, 0249, 0302, 0327, 0037, 0221. Post decolonization MRSA recurrence n=15: Initial negative control run (sheet week 4-Post-Decolonization average week 6) included MRSA positive n=08; MRSA negative n=07, resulting in Recurrence=53%. A Final Negative Control run (sheet week 12-Post-Decolonization average week 16) resulted in MRSA positive n=09; and MRSA negative n=06, with a recurrence=60%.

Treatment Groups 1, 2, 3, Decolonized/Recolonized (8/10 cell concentration): 34. The Decolonized/Recolonized was divided into three groups for the study: GROUP 1 BioPlx01-WT (10ˆ8) in PBS n=10; ID #s: 0015, 0086, 0146, 0147, 0149, 0155, 0178, 0625, 0657, 0667. GROUP 2 BioPlx01-WT (10/8) in PBS n=10; ID #s: 0063, 0075, 0124, 0138, 0172, 0325, 0444, 0478, 0483, 0538; and GROUP 3 BioPlx01-WT (10ˆ8) in PBS n=14 ID #s: 0064, 0112, 0158, 0232, 0336, 0488, 0497, 0498, 0499, 0552, 0574, 0692, 0725, 0735.

Post Decolonization/Recolonization MRSA Recurrence: 0; GROUP 1=0; GROUP 2=0; GROUP 3=0. Duration of post decolonization MRSA negative: 18 weeks=16 cases: 0 recurrence; and 17 weeks=18 cases: 0 recurrence.

Detectable Recolonization Performance

Subjects in the efficacy study were tested for *Staphylococcus aureus* positive results to detect presence of replacement BioPlx 01 WT using penicillinase disks. Results are shown in Table 11.

TABLE 11

| *Staphylococcus aureus* Positives (NvTvHvA) | |
|---|---|
| SA positives | Day/Week Post Colonization; +/total |
| 97.1% (Group 1 & 2 & 3) | 01 day; 33/34 |
| 91.2% (Group 1 & 2 & 3) | 01 week; 31/34 |
| 100% (Group 1 & 2 & 3) | 02 week; 34/34 |
| 97.1% (Group 1 & 2 & 3) | 03 week; 33/34 |
| 91.2% (Group 1 & 2 & 3) | 04 week; 31/34 |
| 100% (Group 1 & 2 & 3) | 05 week; 34/34 |
| 88.2% (Group 1 & 2 & 3) | 06 week; 30/34 |
| 79.5% (Group 1 & 2 & 3) | 08 week; 27/34 |
| 67.7% (Group 1 & 2 & 3) | 10 week; 23/34 |
| 85.3% (Group 1 & 2 & 3) | 12 week; 29/34 |
| 100% (Group 1 & 2& 3) | 14 week; 20/20 |

The study duration was extended to six months. At the conclusion of the study, *Staphylococcus aureus* positives were 100% showing a greater than 26 week total exclusionary effect of the BioPlx-01 MRSA decolonization/recolonization process with the BioPlx product as opposed to prior literature demonstrating 45% recurrence of *Staphylococcus aureus* nasal colonization at 4 weeks and 60% at 12 weeks with the standard decolonization method alone.

Irritation Studies

As described above, MRSA positive participants were selected for the Efficacy

Study by the study supervisor (Dr. Garg). *Staphylococcus aureus* positive participants were selected for the Irritation Study by the study supervisor. MRSA patients require a lot of effort to screen for, so an attempt was made to preserve them for the main efficacy evaluation of the study. Non-MRSA positive colonization rates are about 33%-66% of all screened participants, so there was a more plentiful supply of them. Because MRSA is an antibiotic resistant strain of *Staphylococcus aureus*, testing for irritation in *Staphylococcus aureus* positive participants is equivalent to testing for irritation in MRSA positive participants.

Irritation studies were performed on 55 *Staphylococcus aureus* positive subjects by topically administering about 5 mL of BioPlx-01 (502a), at 1.2× 10 CFU/mL in PBS, to the right forearm. The left arm served as a negative control. Forearms were observed and photographed by study personnel at day 1, day 4 and day 7 post-application for redness or pustule development. No suppression step was performed during the irritation study. No irritation or adverse events were observed.

Culture conditions

The efficacy studies used BioPlx-01 (1.2× 104 CFU/mL) in PBS (Fisher) BP2944100 phosphate buffered saline tablets dissolved in water to provide 100 mM phosphate buffer, 2.7 mM KCl and 137 mM NaCl, pH 7.4 at 25° C., Master stocks were prepared as follows. BioPlx-01 strain was streaked onto tryptic soy agar (TSA) plates in quad streak fashion. After 20 h at 37° C., a fresh bolus of cells was used to aseptically inoculate a flask of sterile tryptic soy broth (TSB). This culture was incubated at 37° C. with agitation at 250 rpm for 18 h. Sterile 50% glycerol was added to the culture to 5% (v/v) final and the batch was aliquoted into sterile 50 mL polypropylene screwcap tubes. The aliquots were frozen at −20° C. For quality control, one aliquot was thawed, fully resuspended by vigorous shake-mixing, and diluted for the determination of colony forming units (CFU) per mL by incubation on Brain Heart Infusion (BHI) agar plates for 18 h at 37° C. CFU values were calculated from dilution-corrected colony counts. A batch of the concentrated BioPlx-01 master stock produced in this way contained $8\times10_9$ CFU/mL of BioPlx-01. The phenotypic identity of the strain was confirmed by incubation on HiChrom staphylococcal chromogenic indicator medium for 18 h at 37° C., which produced only the expected green colonies. The material did not produce colonies when incubated on MRSA chromogenic indicator plates.

Preparation of Working Stock for the Efficacy Study $1.2\times10^8$ CFU/mL

One 10 mL aliquot of concentrated BioPlx-01 stock that is at $8\times10^9$ CFU/mL was completely thawed and then shaken for a full I minute to mix. 8.5 ml of this solution were added to 275 ml of sterile (room temperature) PBS, generating a $2.4\times10^8$ CFU/mL stock. This was mixed well by inversion and stored at 4° C. until use. As used in the efficacy studies, to provide PBS matrix $1.2\times10^8$ working solution-BioPlx-01, a vial of the "$2.4\times10^8$ CFU/mL" solution was mixed by vigorous inversion and 200 mL of it was added to 200 mL PBS to create a "$1.2\times10^8$ CFU/mL working solution-BioPlx-01". This latter solution was the material applied to subjects in efficacy studies. The bottle was tightly capped, mixed by shaking, and stored at 4 C until use Example 2. Selection of One or More Inducible Promoters In this example, promoter candidates were evaluated. The fold-induction and basal expression of 6 promoter candidates in a MSSA strain BioPlx-01 were evaluated by incubation with human whole blood and serum. Expression was normalized to a housekeeping gene (gyrB) and was compared with that in cells growing logarithmically in liquid tryptic soy broth (TSB) media.

The BioPlx-01 was grown to mid log phase (2 OD/mL) and then washed in large volume and shifted to freshly collected serum and heparinized blood from donor TK.

The samples were incubated in slowly agitating vented flask at 125 rpm; and samples were removed for RNA isolation at 15, 45, or 75 min at 37° C. The collected bacteria were washed, and RNA was extracted using Qiagen Allprep kit, eluted and the RNA frozen. Coding DNA (cDNA) was prepared from RNA and target gene expression evaluated by real time PCR (Taqman) in an ABI 7500 Fast instrument.

Relative RNA levels were determined by interpolation against a standard curve run on a common cDNA sample that was serially diluted and tested with primer/probes specific for ORFs driven by each of 5 putative serum-responsive promoters ($P_{hlgA}$, $P_{leuA}$, $P_{sstA}$, $P_{strA}$, $P_{tsdA}$) and one probe for a candidate gene that is upregulated in *Staphylococcus aureus* on the skin during colonization, but not reported to be upregulated in blood, for use in an expression clamp strategy ($P_{clfB}$).

Expression of all genes was normalized to the housekeeping gene gyrB (a gyrase subunit) widely used for this purpose in *Staphylococcus aureus*. Ct was determined by rt PCR. Ct, PCR threshold cycle, is the cycle number at a given fluorescence; the higher the gene (mRNA) quantity, the lower the Ct.

Preliminary results using serum of a single donor are shown in Table 12.

TABLE 12

| Effect of Serum exposure on activation of KS promoter candidates in BioPlx-01 and basal expression levels in TSB | | |
|---|---|---|
| Gene | Fold-induction increase in expression in serum treated samples by real time PCR | Basal Expression LeuA/GyrB ratio in TSB |
| hlgA (gamma hemolysin) | 30 | 0.19 |
| leuA (AA biosynthetic enzyme) | 7.7 | 0.75 |
| sstA (iron transport) | 12.8 | 0.33 |
| sirA (iron transport) | 1.2 | 0.95 |
| isdA (heme transporter) | 1.7 | 0.59 |
| clfB (clumping factor B) | 1.3 | 0.78 |

Figure 6:
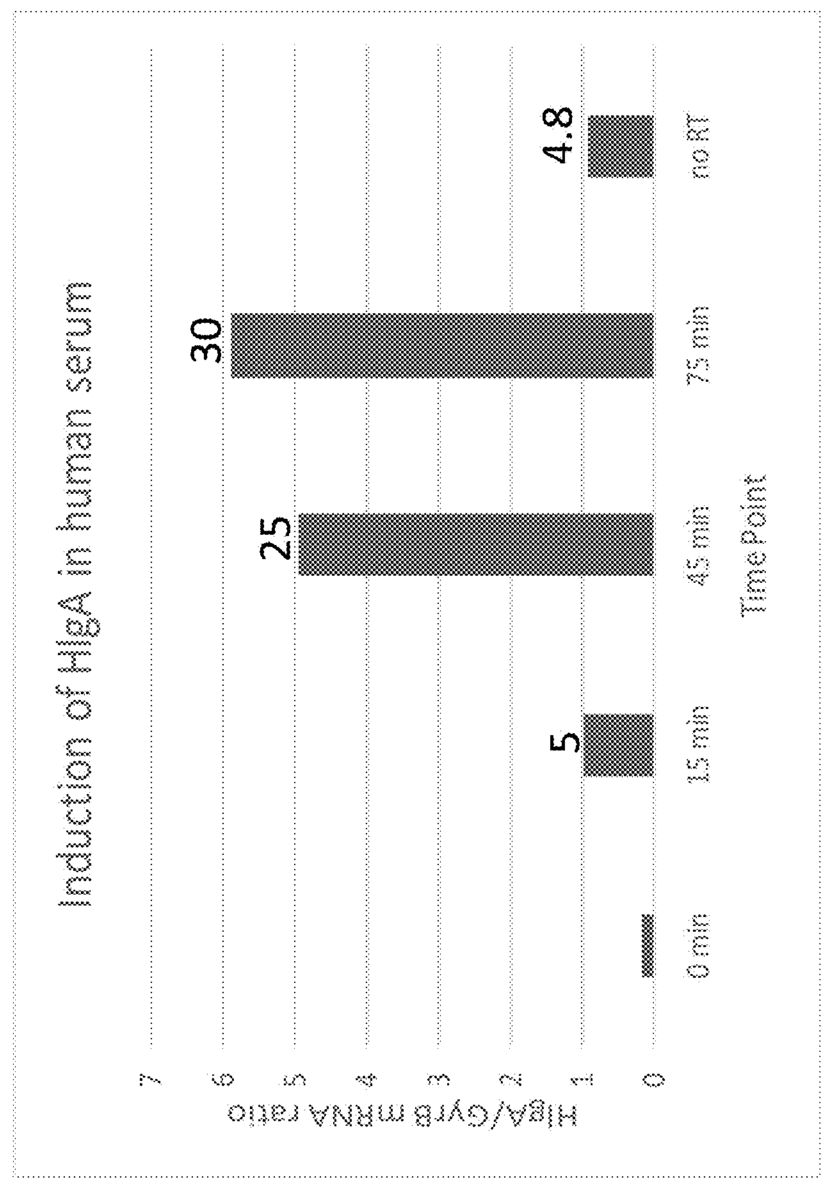
FIG. 6 shows fold-induction of the HigA (gamma hemolysin) promoter candidate in a methicillin-susceptible *Staphylococcus aureus* strain BioPlx-01 by incubation with human serum. Expression was normalized to a housekeeping gene (gyrB) and was compared with that in cells growing logarithmically in liquid TSB media.
Figure 7:
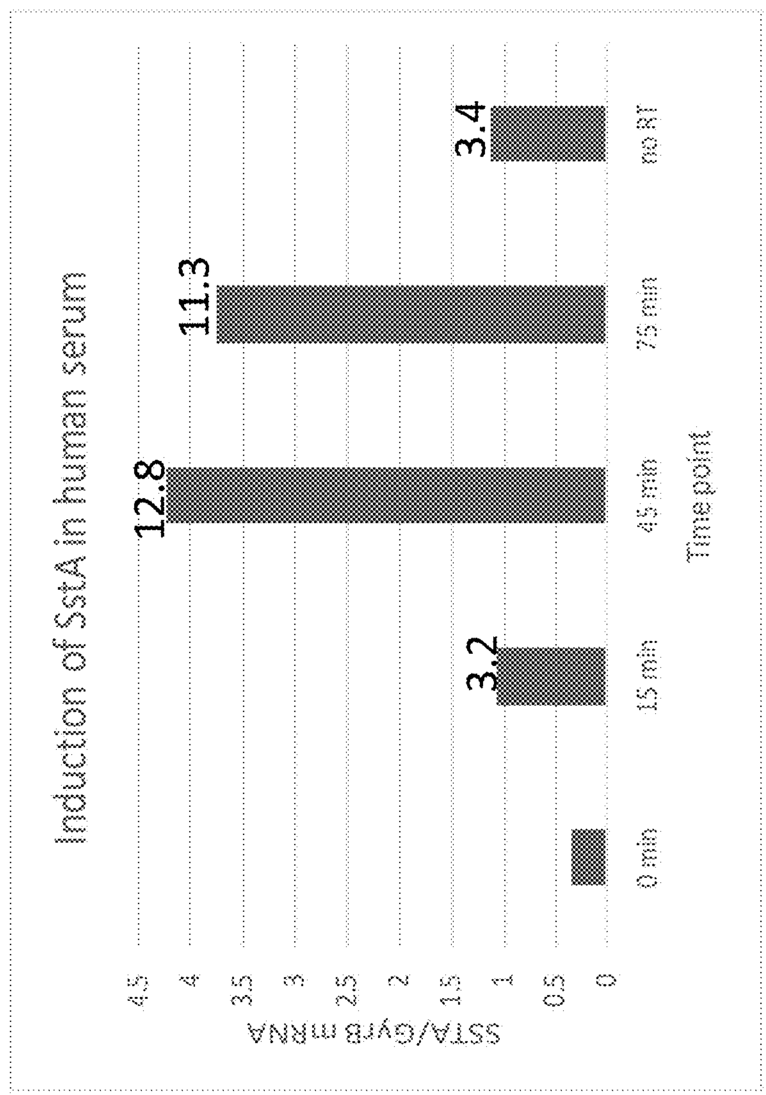
FIG. 7 shows fold-induction of the SstA (iron transport) promoter candidate in a methicillin-susceptible *Staphylococcus aureus* strain BioPlx-01 by incubation with human serum. Expression was normalized to a housekeeping gene (GyrB) and was compared with that in cells growing logarithmically in liquid TSB media.

The time course of induction of promoter candidate Piigs in human serum is shown in FIG. 6 showing a hlgB/gyrB ratio in TSB of 0.19, favorable for use in kill switch construct. "no RT": cDNA made from 75 min timepoint RNA was diluted into a reaction at same dilution as all other samples; if RNA preparation is devoid of gDNA, no signal should be visible. The time course of sstA in human serum is shown in FIG. 7 showing sst/gyrB ratio in TSB was 0.33. $P_{hlgA}$ and $P_{sstA}$ were selected as preliminary preferred candidates for further evaluation. hlgA levels in TSB were only $1/5^{th}$ of housekeeping gene gyrB, or lower, in TSB so this promoter became a lead candidate.

The experiment was repeated using serum and whole blood from two donors with analysis of total RNA, except that cDNAs were treated with DNaseI to remove contaminating genomic DNA. Specifically, RNA Samples were treated with the turbo DNAse kit following the kit protocol for treatment with and inactivation of Dnase. The "No Reverse Transcription" control (No RT control)—with DNAse was at bkg/baseline level, thus acceptable.

The treated RNA was then used to produce cDNA (and a no RT control was again run). The cDNA was analyzed (starting with hlgA and sstA) by Taqman in with technical triplicates. Results are shown in Table 13.

TABLE 13

Promoter Selection- Effect of Serum and Blood exposure on activation of KS promoter Candidates in BioPlx-01 and Basal expression levels in TSB.

| | Fold Induction at 15 min | | | "Leaky"expression | Serum induction >3 |
|---|---|---|---|---|---|
| Promoter | Serum (donor 1) | Serum (donor 2) | Blood (donor 2) | Target/GyrB (TSB) | fold through 75 min? |
| ISDA | 83 | 15 | 4.1 | 0.002, 0.022 | yes |
| SSTA | 9 | 6.7 | 0.3 | 0.16, 0.333 | yes |
| LEUA | 1393 | 1601 | 990 | 0.0013, 0.000017 | yes |
| HLGA | 27 | 6 | 35 | 0.23, 0.26 | yes |
| SIRA | 5.5 | 2.6 | 0.08 | 0.25, 1.1 | no |

$P_{isdA}$, $P_{sstA}$, $P_{strA}$ were eliminated based on date shown in Table 13. $P_{sstA}$ was eliminated because of significant basal expression, and it was not induced in whole blood. $P_{strA}$ was also eliminated because of significant basal expression, and low magnitude induction in serum, and was not induced in whole blood, as well as exhibiting induction that was not sustained.

Based on this experiment, $P_{leuA}$ was selected as one preferred promoter because it exhibited very high upregulation in serum, very low basal expression in TSB, and was not upregulated during colonization. An expression clamp may be employed, but may be optional when using $P_{leuA}$ as a promoter. $P_{leuA}$ also exhibited strong activation by blood or serum exposure in Malachawa 2011 (microarrays) and in the present example. leuA is part of a nine-gene Operon: ilvDBHC, leuABCD, ilvA. A factor called Cody binds the RR to repress transcription when it is bound to branched chain amino acids (leucine, isoleucine and valine), so when free amino acid levels are above a threshold, the promoter is silent. In porcine ex vivo nasal colonization assays with MRSA, amino acid biosynthetic operons including fen were not upregulated, and the authors propose that amino acids are present in sufficient quantity during colonization to prevent upregulation of these pathways (Tulinski et al., 2014).

The gene leuA is activated very strongly in blood and serum and has low basal expression, so further understanding is important, leuA is within the second of two cassettes in a nine-gene operon; the regulatory region driving it may be immediately upstream of ilvD or upstream of leuA. One way to understand is to test and compare both variants. ilvDBHC-leuABCD-ilvA $P_{hlgA}$ was selected as another preferred promoter because it exhibited high upregulation in serum and blood, and downregulation during nasal colonization. One drawback of $P_{hlg}$ is basal expression in TSB; which may be addressed by including an expression clamp for hlgA. The peptide HlgA is a subunit of a secreted, pore-forming toxin that lyses host red blood cells and leukocytes. HlgA (class S) associates with HlgB (class F) thus forming an AB toxin in strains producing both gamma-hemolysins and leukocidins (HlgA and LukF-PV can also form a complex).

Transcription of the HlgA operon is upregulated in TSB by quorum sensing agr activation, but agr is downregulated in serum while hlgA is upregulated, so hlgA upregulation is independent of the agr pathway in serum. In one paper, the hemolysins were downregulated 5.7 fold compared with TSB during colonization, specifically, porcine nasal explants colonized with MRSA ST398; see Tulinski et al 2014. However, in these experiments, no evidence of expression of hlgA was seen during colonization. The regulator sarT represses transcription of the hemolysin operon and may be a useful "expression clamp" if $P_{hlgA}$ is used to drive the KS, for example by overexpression of sarT from a colonization promoter.

In another embodiment, a synthetic microorganism comprises at least one molecular modification comprising a first cell death gene operably linked to a first regulatory region comprising a multiplicity of promoters that are activated by serum or blood, but exhibits little to no expression in human skin, mucosa, or in TSB. There is more certainty of lower expression on skin for hlgA, because it is downregulated in colonization. There is more certainly of lower expression in TSB for leuA.

Example 3. Selection of One or More Death Genes

In this example, cell death gene candidates are evaluated for preparing a synthetic microorganism having at least one molecular modification comprising a first cell death gene operably linked to a first regulatory region comprising a first indocible promoter, Relative potencies of death genes are unknown. What appears to be the best death gene is not necessarily the most potent one because of leaky expression. Diversity of mechanism of action could result in killing synergy for two or more death gene combinations. Death gene candidates include: SprA1: membrane disruption; sma1: genome destruction; and rsaE: blocks central metabolism. Various combinations of death genes are shown in Table 14. These plasmids are created and sequenced plasmids for testing of $P_{leuA}$ and $P_{hlgA}$-driven KS variants.

TABLE 14

Death Gene KS Constructs

| Strain # | Plasmid name | Promoter | Kill gene (PCD) | Purpose | Comments |
|---|---|---|---|---|---|
| 1 | pTK1 | Cadmium inducible | SprA1 | +control shows sprA1SprA1 is a functional kill gene | Cells in TSB treated with Cd should rapidly die |
| 1A | pTK2 | Cadmium inducible | sprA1SprA1 reversed | Neg control | Cells in TSB treated with Cd should NOT rapidly die |
| 2 | pTK3 | LeuA | sprA1SprA1 | KS | Cells shifted to serum or blood should rapidly die |
| 3 | pTK4 | LeuA | sprA1SprA1 reverse | plasmid more readily obtainable than # 2 | Compare Insertion frequency to # 2 |
| 4 | pTK5 | LeuA | sprA1SprA1 + CLFB:: sprA1SprA1 as | KS | Expression clamp variant of # 2 |
| 5 | pTK6 | HlgA | sprA1SprA1 | KS | Might not be healthy or even obtainable-basal exp |
| 6 | pTK7 | HlgA | SprA1 + CLFB::SprA 1 as | KS | Likely healthier than # 5 |
| 7 | pTK8 | Cadmium inducible | sma1 restriction enzyme | +control | Cells in TSB treated with Cd should rapidly die |
| 8 | pTK9 | HlgA | sma1 restriction enzyme | KS | expression clamp made using antisense |
| 9 | pTK10 | LeuA | sma1 restriction enzyme | KS | expression clamp made using antisense |
| 10 | pTK11 | Cadmium inducible | rsaE sRNA | +control | Cells in TSB treated with Cd should rapidly die |
| 11 | pTK12 | HlgA | rsaE sRNA | KS | expression clamp made using antisense |
| 12 | pTK13 | LeuA | rsaE sRNA | KS | expression clamp does not exist but could be made using antisense |

Death genes may be obtained commercially (Atum) and vector may also be obtained commeecially (BEI). Combinations comprisinig two death genes are constructed after results of single death genes are obtained. Synthetic plasmids, vectors and synthetic microorganism med based on Table 14.

Steps in creating a synthetic strain comprising a cell death gene are as follows.

1. Produce shuttle vector pCN51 in mid-scale in *E. coli.*

2. Clone death genes into pCN51 in *E coli* (under Cd-inducible $P_{cad}$).

3. Replace $P_{cad}$ with serum-responsive promoters; and insert expression clamp where applicable.

4. Verify constructions by sequencing the KS cassettes.

5. Electroporate into *Staphylococcus aureus* RN4220 and select transformants on erythromycin plates (this strain is restriction minus and generates the right methylation pattern to survive in BioPlx-01). RN4220 is and *Staphylococcus aureus* strain used as an intermediate; restriction minus, methylation +; BEI product number NR-45946.

6, Prepare plasmid from RN4220 and restriction digest to confirm ID.

7. Electroporate plasmids into BioPlx-01 and select on erythromycin plates.

8. Synthetic microorganism strains ready for serum experiment.

Steps in testing a synthetic microorganism strains having at least one molecular modification comprising a first cell death gene operably linked to a first regulatory region comprising a first promoter are as follows.

1. Growth in TSB plus antibiotic as selective pressure for plasmid.

2. How does growth compare with WT Bioplx-01? Prepare growth curve.

3. Cd-promoter variants: Wash and shift cells to Cd medium (control is WT Bioplx-01 containing empty vector with no death gene).

4. KS variants: Wash and shift cells to serum (control is WT Bioplx-01 containing empty vector with no death gene).

5. Monitor growth using $OD_{630\ nm}$ with plate reader (extended period, monitor for appearance of escape mutants).

6. For whole blood test, only perform on winning candidates and use CFU on TSB agar as death readout.

7. If there are apparent escape mutants, shuttle plasmid out to *E. coli* and sequence the whole plasmid.

Plasmids may be prepared from commercially available products. In one embodiment, pCN51 (6430 bp) is the commercial plasmid for modification. pCN51 is an *E. coli*-SA shuttle vector, with ampR for *E. coli* selection and ermC for *Staphylococcus aureus* selection. This is a pT181 based low copy rolling circle plasmid, containing a Cadmium inducible promoter and BLA terminator. BEI product number NR-46149. Combinations of KS variants are possible in one plasmid. It is possible to insert more than one KS into the MCS of a shuttle vector plasmid.

1. The 3 constructs encoding the 3 kill genes are ordered from Atum/DNA2.0, with restriction suites placed strategically at ends of each gene for directional cloning.

2. pCN51 shuttle vector (BEI NR-46149), RN4220 *Staphylococcus aureus* (BEI NR-45946), and DC10B *E. coli* (BEI NR-49804) are ordered from BEI Resources.

3. The DNA oligonucleotides shown in Table 15 are ordered from for: i) PCR amplification of RRs from BioPlx-01 gDNA, with restriction enzymes at ends for directional cloning, and, ii) DNA sequencing of KS constructs.

TABLE 15

Oligonucleotides used for sequencing KS constructs

| Oligo Name | Sequence (5' to 3') | Purpose |
|---|---|---|
| TKO1 | gatgcGCATGCGAAACAGATTATCTATTC (SEQ ID NO: 9) | $P_{leuA}$ PCR Amplification with Sph1 (upstream pr) |
| TKO2 | gatgcGCATGCCAGATTATCTATTCAAAG (SEQ ID NO: 10) | $P_{leuA}$ PCR Amplification with Sph1 (upstream pr-alternate) |
| TKO3 | catgatCTGCAGAGTAAATTCCCCCGTAAATT (SEQ ID NO: 11) | $P_{leuA}$ PCR Amplification with Pst1 (downstream pr) |
| TKO4 | cacgtgatCTGCAGAGTAAATTCCCCCGTAAA (SEQ ID NO: 12) | $P_{leuA}$ PCR Amplification with Pst1 (downstream pr-alternate) |
| TKO5 | gactacGAATTC AGGTGATGAA AAATTTAGAA (SEQ ID NO: 13) | upstream primer to amplify $P_{clfB}$ with EcoRI |
| TKO6 | gactacGAATTCTGATGAA AAATTTAGAACTT (SEQ ID NO: 14) | backup to TKO5 |
| TKO7 | cttagctGGATCCAAATATTACTCCATTTCAA (SEQ ID NO: 15) | downstream primer to amplify $P_{clfB}$ with BamHI |
| TKO8 | cttagctGGATCCAAATATTACTCCATTTCAAT TTC (SEQ ID NO: 16) | backup to TKO7 |
| TKO9 | gatgcGCATGCTCACAAACTA TTGCGAAATC (SEQ ID NO: 17) | upstream primer to amplify the $P_{hlgA}$; contains Sph1 |
| TKO10 | gatgcGCATGCAAACTA TTGCGAAATC CATTC (SEQ ID NO: 18) | backup to TKO9 |
| TKO11 | catgatCTGCAG ATATATAATAATCCATTTGT (SEQ ID NO: 19) | downstream primer to amplify $P_{hlgA}$; contains PstI |
| TKO12 | catgatCTGCAGATATATAATAATCCATTTGT AAGCG (SEQ ID NO: 20) | backup to TKO11 |

TABLE 15-continued

Oligonucleotides used for sequencing KS constructs

| Oligo Name | Sequence (5' to 3') | Purpose |
|---|---|---|
| TKO13 | GTGTTACGATAGCAAATGCA (SEQ ID NO: 21) | First sense primer for sequencing constructs containing $P_{cad}$ |
| TKO14 | TTATTGGCTAAGTAGACGCA (SEQ ID NO: 22) | second sense sequencing primer anneals roughly in the middle of the sprA1 gene |
| TKO15 | CACATGTTCTTTCCTGCGTT (SEQ ID NO: 23) | primer to anneal just upstream of the serum responsive $P_{leuA}$ and $P_{hlgA}$. Anneals in the pCN51 vector about 75 nt upstream of the Sph1 site |
| TKO16 | ACGCGGCCTTTTTACGGTTC (SEQ ID NO: 24) | backup for TKO15 |
| TKO17 | GAATGGGACTTGTAAACGTC (SEQ ID NO: 25) | primer to anneal near the downstream one third of the $P_{leuA}$ because its a fairly large segment and TKO15 may not read all the way through |
| TKO18 | GAATGGGACTTGTAAACG (SEQ ID NO: 26) | backup for TKO17 |
| TKO19 | ATAAACGCCTGCGACCAATA (SEQ ID NO: 27) | primer to anneal near the downstream one third of the $P_{hlgA}$ because its a fairly large segment and TKO15 may not read all the way through |
| TKO20 | GCGACCAATAAATCTTTTAA (SEQ ID NO: 28) | Backup for TKO19 |

Cloning

All gel-electrophoresis agarose gels are 1.0-2.0% agarose in IX TAE buffer and midori green (Nippon Genetics Europe GmbH) added per the manufacturer's instructions.

Example 3A. Constructing pTK1 and pTK2

1. Prepare Miniprep Quantities of pCN51 and of sprA1, sma1, and rsaE plasmids as follows A. Streak the strains on LB+ carbenicillin (100 μg/mL) plates and incubate 15-18 h at 37° C., B. Inoculate LB+ carbenicillin (100 μg/mL) liquid with single colony of each and incubate with agitation (240 rpm) for 15-18 h at 37° C.

C. Prepare 5× replicate minipreps of each strain with Qiagen spin miniprep kit per manufacturer's instructions, elute DNA from each column with 30 μL, and pool the replicate plasmid preps together (freeze DNA at −20° C.).

2. Digests, Ligation, Plating 2.1. Cut pCN51 with PstI and EcoRI to linearize (37° C., 30 mins). Expected size is ~6400 bp (a 35 bp fragment from the multiple cloning site (MCS) is dropped out/not visible on gel).

2.2. Cut pCN51 plasmid with Kpn1 and BamHI to linearize (37° C., 30 mins), Expected size is 6400 bp (a 35 bp fragment from the MCS is dropped out).

2.3 Cut sprA1 plasmid from DNA2.0 with PstI and EcoRI to liberate the desired 233 bp sprA1 insert.

2.4 Cut sprA1 plasmid from DNA2.0 with KpaI and BamHI to liberate the desired 233 bp sprA1 insert.

2.5. During DNA digestion pour a gel that is 1.5% agarose gel for electrophoresis as described.

2.6. Add 8 μL of 6× loading dye to all 4 reactions and to the 1 kb plus DNA size ladder (3 μL in 30 μL).

2.7. Run gel at 100 V for 1.5 h.

2.8. Excise the bands of interest mentioned above with a clean razor blade.

2.9. Melt the slices in 3 volumes of buffer QG from Qiagen gel extraction kit (56° C.), vortexing occasionally.

2.10. Isolate the paired vector and insert together on one column and elute the material into 30 μl of Qiagen's elution buffer.

A. Pst1+EcoRI insert plus pCN51 Pst1/EcoRI vector,

B. Kpn1+BamHI insert plus pCN51 Kpn1/BamHI.

2.11 Set up a waterbath by adding some ice to 500 ml RT water in a styrofoam box; add just enough ice to reach 16° C.

2.12. Add 3.4 μL of 10× T4 DNA ligase buffer and mix. Add 1 μL of T4 DNA ligase ($4\times10^5$ U/mL stock from NEB) and incubate for 2 h at 16° C.

2.13 Set electroporation unit to 1500 V/200 ohms/25 μF.

2.14. Thaw 2 vials of DH5α *E. coli* and add 40 μL into each into 2 Eppendorf tubes. Chill 2 electroporation cuvettes on ice.

2.15. Add 1 μL of undiluted ligation to 40 μL of the thawed DH5α *E. coli* and transfer to an ice-cold 1 mm gap electroporation cuvette.

2.16. Have ready: 1 mL of SOC medium in a 1 mL pipet, sterile 1 mL tips, and 2 sterile 14 ml culture tubes 2.17. Electroporate the cells (ligation A first) and then ASAP add 1 mL SOC to the cuvette, pipet up and down 6×, and transfer the whole volume to a fresh 14 mL culture tube for recovery. Repeat this process for electroporation of ligation B. Place the two recovering samples in the shaking water bath at 37° C. for 1 h.

2.18. Place 2 LB+cabenicillin (100 μg/mL) agar plates inverted with their lids slightly off in the 37° C. incubator (not humidified) while the cells recover 2.19. After the 1 h recovery period, remove and label the LB+cabenicillin (1050 μg/mL) agar plates accordingly and remove the 14 mL tubes from the waterbath.

2.20. Using a sterile glass beads, spread 150 μL of each 1 mL recovery mix onto a plate.

2.21 Place the plates in the 37° C. incubator for 16-18 h.

2.22. Record colony counts for

Ligation A ($P_{cad}$::sprA1 forward) and

Ligation B ($P_{cad}$::SprA1 reverse).

3. Screening for Positives:

3.1 Pick 6 colonies for screening 3.2 Inoculate 6 colonies of ligation A and 6 of ligation B, each into 3 mL of liquid LB+cabenicillin (1050 μg/mL) in a 14 mL culture tube.

3.3 Shake for 16 h at 37° C.

3.4 Isolate plasmid DNAs using Qiagen spin mini kit per manufacturer's instructions, and elute DNA into 40 μL elution buffer.

3.5 Digest 5 μL of each of the 12 plasmid DNAs with

A. PST1 plus ECORI

B. Kpn1+BamHI

C. Xmn1 alone

Mix for 7 reactions if Pst1+EcoRI. Add 5 μL of DNA solution to 15 μL of digestion mixture and incubate 2 h at 37° C. Do the same for KpnI+BamHI and Xml digestions.

Compare to expected gel patterns: Correct pattern for pTK1 digests: i) EcoRI and Pst1; ii) KpnI and BamHI; iii) Xmn1, Correct pattern for pTK2 digests: i) EcoRI and PstI; ii) Kpn1 and BamHI; (ii) Xmn1.

Example 3B. Making pTK3 ($P_{leuA}$::sprA1) and pTK6 ($P_{hlgA}$::sprA1) and pTK4 ($P_{leuA}$::sprA1 reversed)

1. Extract gDNA from a log-phase culture of BioPlx-01 using the Qiagen "All prep" kit.

2. Digest pTK1 SprA1 with Sph1 and Pst1 to drop out the cadmium-inducible promoter ($P_{cad}$).

3. PCR amplify the leuA regulatory region ($P_{leuA}$) from Bioplx-01 gDNA using PCR primers that contain the SphI restriction sequence upstream and Pst-1 restriction sequence downstream. (TKO1 and TKO3 Sequences below; or back-ups TKO2+TKO4). Verify the restriction with gel electrophoresis as previously described.

PCR Mixture:

| |
|---|
| 1.0 μL of gDNA from BioPlx-01 50 ng/μL |
| 25.0 μL dI water |
| 10.0 μL 5X HF buffer |
| 5.0 μL 2 mM dTNP mix |
| 4.0 μL primer TKO1 (5 pmol/μL stock) |
| 4.0 μL TKO3 (5 pmol/μL stock) |
| 1.0 μL phusion polymerase NEB |
| 50.0 μL total |

Cycles:

98° C. for 2 min 20 cycles of: 98° C. 15 sec—64° C. 30 sec—72° C. 1 min 15 cycles of: 98° C. for 15 sec—55° C. for 30 sec—72° C. for 1 min Hold: 4° C., indefinitely 4. PCR amplify the hlgA regulatory region ($P_{hlgA}$) from Bioplx-01 gDNA using PCR primers that contain the Sph1 restriction sequence upstream and Pst-1 restriction sequence downstream. (TKO9 and TKO11 or backup set TKO10 or TKO12). PCR conditions are as above for Paws except for the identity of the primers.

5. Using the Qiagen PCR cleanup kit, clean the PCR reactions and elute into 43 μL of elation buffer 6. Cut the $P_{leuA}$ PCR product from step 3 and the Para PCR product from step 4 with Sph1 and Pst1. Do this by adding 5 μL of 10×CutSmart (NEB) and 1 μL each of Sph1 and Pst1 and incubating for 2 h at 37° C.

7. Digest pTK1 with Sph1/Pst1.

8. Fractionate the pTK1 Sph/Pst digest and the Sph/Pst digested $P_{leuA}$ and $P_{hlgA}$ on a 1.5% agarose gel and excise the ~6000 pTK1 backbone and the $P_{leuA}$ (390 bp) and $P_{hlgA}$ (253 bp) fragments with a clean razor blade.

9. Divide the pTK1 backbone slice in two and combine one half with the LeuA slice and the other half with the HlgA slice. Melt together and isolate together using the Qiagen gel extraction kit. Elute each into 30 uL EB.

10. Add 3.4 μL of 10× T4 DNA ligase buffer and 1 μL of T4 DNA ligase and incubate at 16° C. for at least 1 h.

11. Follow steps in section 2.13-2.22 for electroporation, recovery, and colony plating.

12. The two ligations aim to generate $P_{leuA}$::sprA1 wt in the forward orientation (pTK3) and $P_{hlgA}$::sprA1 wt in the forward orientation (pTK6).

Example 3C. Making pTK4 (Conduct Steps Concurrently with pTK3)

1. Extract gDNA from a log-phase culture of BioPlx-01 using gDNA isolation kit.

2. Digest pTK2 (sense sprA1) with Sph1 and Pst1 to drop out the Paws (see above for digestion conditions).

3. Insert the Sph1/Pst1 digested $P_{leuA}$ fragment from above into the Sph1/Pst1 digested pTK2 to generate Pic: sprA/wt in the reverse orientation (pTK4). Details of the gel extraction, ligation and electroporation processes are the same as in Section 2 of cloning above.

Screening pTK3, pTK4 and pTK6:

3.1 Pick 6 colonies of each ligation for screening 3.2 Inoculate 6 colonies of pTK3 and 6 of pTK4 and 6 of pTK6 each into 3 mL LB+cabenicillin (100 μg/mL) in 14 mL culture tubes.

3.3 Incubate with agitation for 16 h (37° C., 240 rpm).

3.4 Isolate plasmid DNA using a mini prep kit and elute DNA with 40 μL elution buffer.

3.5 Digest 5 μL of each of the 18 plasmid DNAs as follows (prepare enough digestion reaction mixture for 20 reactions to account for pipetting errors):

A. Sph1 plus Pst1

B. Xmn1.

Add 5 μL DNA to 15 μL digestion reaction mixture and incubate 2 h at 37° C.

3.6 Verify digestion with gel electrophoresis, compare to expected gel patterns for pTK3, pTK4, and pTK6.

Making pTK5 and pTK7

1. Use gDNA of BioPlx-01 prepared above.

2. PCR amplify the clfB RR ($P_{clfB}$) from BioPlx-01 genomic DNA using primers with a EcoRI restriction sequence upstream and BamHI restriction sequence downstream (primers: TKO5 and TKO7)

PCR Mixture (50 μL total volume)

1.0 μL of gDNA from BioPlx-01 50 ng/μL.

25.0 μL dI water 10.0 μL 5× HF buffer (NEB)

5.0 μL 2 mM dTNP mix 4.0 μL primer TKO5 (5 pmol/μL stock)

4.0 μL TKO7 (5 pmol/μL stock)

1.0 μL phusion polymerase (NEB)

Cycles:

98° C. for 2 min 20 cycles of: 98° C. 15 sec—64° C. 30 sec—72° C. 1 min 15 cycles of: 98° C. for 15 sec—55° C. for 30 sec—72° C. for 1 min Hold: 4° C., indefinitely 3. Use 5 μL of the PCR reactions for gel electrophoresis as previously described.

4, Using the PCR cleanup kit, clean the PCR reaction and elute with 30 μL of elution buffer.

5. Digest the Pare PCR product with BamH1 and EcoR1 and insert it into the EcoR1/BamH1 digested pTK3 backbone to generate pTK5. This plasmid will contain spr4/ regulated by Picas and the sprA1$_{AS}$ regulated by $P_{clfB}$. Using the same $P_{clfB}$ fragment, insert it into the EcoRI/BamHI digested pTK6 to generate pTK7. This plasmid will contain sprA1 regulated by $P_{hlgA}$ and the sprA1$_{AS}$ regulated by $P_{clfB}$SprA1.

Details of the gel extraction, ligation and electroporation processes are the same as in section 2 of cloning above.

Screening for pTK5 and pTK7

3.1 Inoculate 6 colonies of ligation pTK5 and 6 colonies of ligation pTK7 into 3 mL LB+cabenicillin (100 μg/mL) in 14 mL culture tubes.

3.3 Incubate with agitation for 16 h (37° C., 240 rpm)

3.3 Isolate plasmid DNA using a mini prep kit and elute DNA into 40 μL elution buffer.

3.5 Digest 5 μL of each of the 12 plasmid DNAs with:

A. BamHI+EcoRI

B. Xma1 alone

Prepare digestion reaction mixture with BamHI/EcoRI and Xmn1 following the manufacturer's suggestions.

Add 5 μL of plasmid solution to 15 μL of digestion reaction mixture and incubate for 2 h at 37° C. Verify the digestion with gel electrophoresis as previously described.

Example 3D. Constructing pTK8, pTK9 and pTK10 ($P_{cad}$-smaI, $P_{hlgA}$-sma1 and $P_{leuA}$-smaI respectively)

The smaI gene was ordered from DNA2.0 with a Pst1 restriction site upstream and EcoRI restriction site downstream to allow for insertion into the following:

pCN51 to make $P_{cad}$::smaI resulting in pTK8 pTK6 from which sprA1 has been removed with Pst1/EcoR1 to make $P_{hlgA}$-sma1 resulting in pTK9 pTK3 from which sprA1 has been removed with Pst1/EcoR1 to make $P_{leuA}$-sma1 resulting in pTK10

1. Digest pCN51, pTK6 and pTK3 with Pst1 and EcoR1 by sprA1, incubating each for 2 h at 37° C.

2. Generate the sma1 fragment by digesting the ordered plasmid containing the gene with Pst1 and EcoR1 (2 h at 37° C.). Verify the digestion with gel electrophoresis (expected fragment size is 757 bp).

3. Follow steps 2.5 to 2.22 for gel extraction, ligation, electroporation, recovery, and antibiotic selection.

Screening for pTK8, pTK9, and pTK10

3.1 Inoculate 6 colonies of ligation pTK9 and 6 colonies of ligation pTK9 and 6 colonies of ligation pTK10 into 3 mL LB+cabenicillin (100 μg/mL) in 14 mL culture tubes.

3.3 Incubate with agitation for 16 h (37° C., 240 rpm)

3.3 Isolate plasmid DNA using a mini prep kit and elute DNA into 40 μL of elution buffer 3.5 Digest 5 μL of each of the 12 plasmid DNAs with A. Pst1 and EcoR1

B. Sph1 and Xcm1

C. Xmn1 alone

Follow previously described restriction reaction and gel electrophoresis procedures.

Example 3E. Making pTK11, pTK12 and pTK13 ($P_{cad}$-rsaE, $P_{hlgA}$-rsaE and $P_{leuA}$-rsaE respectively)

The rsaE gene was ordered from DNA2.0 with an upstream PstI restriction site and a downstream EcoR1 restriction site to allow for insertion into the following plasmids:

pCN51 to make Pro-rsaE resulting in pTK11 pTK6 from which sprA1 has been removed with Pst1/EcoRI restriction to make $P_{hlgA}$-rsaE resulting in pTK12 pTK3 from which sprA1SprA1 has been removed with Pst1/EcoR1 restriction to make Picas-rsaE resulting in pTK13

1. Digest pCN51, pTK6 and pTK3 with Pst1 and EcoRI sprA1 as described in previous sections.

2. Digest ordered DNA containing rsaE Pst1 and EcoR1 following manufacturer's suggestions. Verify digestion with gel electrophoresis (rsaE fragment should be 142 bp).

3. Follow steps 2.5 to 2.22 for gel isolation, ligation, electroporation, recovery, and antibiotic selection.

Example 4. Production of sprA1 Clamp and No Clamp Constructs Using DNA2.0 to Make Inserts Here pCN51 is employed as the vector backbone because it has cadmium inducible promoter ($P_{cad}$), Bla terminator, ampicillin resistance for *E. coli* and erythromycin resistance for *Staphylococcus aureus*. In Drutz 1965, 502a was shown to be sensitive to 2 μg/mL erythromycin.

Plasmid pTK1: Positive control cassette to prove that sprA1, when induced, causes death.

1. Order the following insert from DNA2.0. It is cut out of the ordered vector with Pst1 and EcoRI restriction enzymes, and inserted into Pst1/EcoR1-digested pCN51. It is just the open reading frame and a little flanking downstream to capture sprA1-essentially as in Sayed et al. 2012, except that the $P_{cad}$ feature is used instead of the aTe promoter ($P_{tet}$). This sequence was verified in pDRAW, to assure strategy will work.

SEQ ID NO: 122

```
CTGCAGggtaccgcagagaggaggtgtataaggtg
ATGCTTATTTTCGTTCACATCATAGCACCAGTCATCAGTGGCTGTGC
CATTGCGTTTTTTTCTTATTGGCTAAGTAGACGCAATACAAAATAGGTGA
CATATAGCCGCACCAATAAAAATCCCCTCACTACCGCAAATAGTGAGGGG
ATTGGTGTataagtaaatacttattttcgttgt
ggatccttgactGAATTC
```

Resulting plasmid: pTKXXX

Underlined upper case: start codon

Italicized: stop codon

BOLD; PstI site upstream

UPPERCASE BOLD ITALICIZED: EcoRI site lower case bold italicized: KpnI site

Rust color: shine-delgarno (naturally used for SprA1)

Lower case underlined: BamHI site

Produce pTK2: Reverse the insert in pTK1

1. Cut the insert of pTK1 out with Kpn1 and BamHI and insert it into Kpn1 and BamH1-digested pCN51. This creates the antisense orientation of the toxin gene and toxin should not be expressed at all, whether it is induced with cadmium or not. Product is pTK2.

PTK3 and PTK4: $P_{hlgA}$ regulating sprA1 toxin to prove that sprA1, when induced by serum or blood, causes cell death (forward and reverse constructs, respectively).

$sprA1_{AS}$ is present but has only its natural promoter, so the expression clamp should be inactive—and also if $P_{hlgA}$ is leaky, some cell toxicity may occur because the expression clamp is not present.

pTK3:

1. Digest pTK1 (sense sprA1) with Sph1 and Pst1 to drop out $P_{cad}$.

2. PCR amplify the hlgA regulatory region ($P_{hlgA}$) from strain 502a using PCR primers that contain an upstream Sph1 restriction site and Pst1 downstream restriction site. (Primers: TKO1 and TKO2)

3. Cut the $P_{hlgA}$ PCR product with Sph1 and Pst1 and insert it into the Sph1/Pst1 digested pTK1 to generate $P_{hlgA}$::sprA1 wt in the forward orientation generating pTK3.

```
  1 TTGCGAAATC CATTCCTCTT CCACTACAAG CACCATAATT AAACAACAAT
    AACGCTTTAG GTAAGGAGAA GGTGATGTTC GTGGTATTAA TTTGTTGTTA

 51 TCAATAGAAT AAGACTTGCA AAACATAGTT ATGTCGCTAT ATAAACGCCT
    AGTTATCTTA TTCTGAACGT TTTGTATCAA TACAGCGATA TATTTGCGGA

101 GCGACCAATA AATCTTTTAA ACATAACATA ATGCAAAAAC ATCATTTAAC
    CGCTGGTTAT TTAGAAAATT TGTATTGTAT TACGTTTTTG TAGTAAATTG

151 AATGCTAAAA ATGTCTCTTC AATACATGTT GATAGTAATT AACTTTTAAC
    TTACGATTTT TACAGAGAAG TTATGTACAA CTATCATTAA TTGAAAATTG

201 GAACAGTTAATTCGAAAACGCTTACAAATGGATTATTATATAT          SEQ ID NO: 327
    CTTGTCAATT AAGCTTTTGC GAATGTTTAC CTAATAATATATA       SEQ ID NO: 328
```

TKO1:

SEQ ID NO: 329

5'-gatgcGCATGCTTGC GAAATC CATTCCTCTT-3' (contains SphI)

TKO2:

SEQ ID NO: 20

5'-catgatCTGCAGATATATAATAATCCATTTGTAAGCG-3' (contains PstI)

pTK4:

1. Digest pTK2 (reverse sprA1) with Sph1 and Pst1 to drop out the cadmium promoter.

2. Insert the same Sph1/Pst1 digested $P_{hlgA}$ PCR product. This provides the reverse orientation SprA1.

pTK5: Expression clamp for pTK3, using $P_{clfB}$ to drive $SprA1_{AS}$

1. PCR amplify the $P_{clfB}$ from 502a gDNA using with primers to generate an upstream EcoR1 restriction site and a BamHI downstream restriction site.

2. Digest pTK3 with EcoRI and BamHI and insert the EcoR1/BamHI-digested $P_{clfB}$.

The resulting plasmid is called pTK5 and will contain the SprAl sense regulated by the serum responsive $P_{hlgA}$ (upregulated) and the $sprA1_{AS}$ SprA1 regulated by serum responsive $P_{clfB}$ (downregulated).

The sequence below is the $P_{clfB}$ (219 nucleotides immediately upstream of TTG start codon).

```
  1 AGGTGATGAA AAATTTAGAA CTTCTAAGTT TTTGAAAAGT AAAAAATTTG
    TCCACTACTT TTTAAATCTT GAAGATTCAA AAACTTTTCA TTTTTTAAAC

 51 TAATAGTGTA AAAATAGTAT ATTGATTTTT GCTAGTTAAC AGAAAATTTT
    ATTATCACAT TTTTATCATA TAACTAAAAA CGATCAATTG TCTTTTAAAA

101 AAGTTATATA AATAGGAAGA AAACAAATTT TACGTAATTT TTTTCGAAAA
    TTCAATATAT TTATCCTTCT TTTGTTTAAA ATGCATTAAA AAAAGCTTTT
```

-continued

```
151     GCAATTGATA TAATTCTTAT TTCATTATAC AATTTAGACT AATCTAGAAA
        CGTTAACTAT ATTAAGAATA AAGTAATATG TTAAATCTGA TTAGATCTTT

201     TTGAAATGGA GTAATATTT                              SEQ ID NO: 129
        AACTTTACCT CATTATAAA                              SEQ ID NO: 130

Primer:     5'--gactacGAATTC AGGTGATGAA AAATTTAGAA-3'     SEQ ID NO: 13
Primer:     5' cttagctGGATCCAAATATTACTCCATTTCAA-3'        SEQ ID NO: 15
PepA1       MQGFKEKHQELKKALCQIGLMRSISEVKQLNIA             SEQ ID NO: 113
(SA newman)
```

pTK6. serum responsive promoter 2-SprA1

In this construct, the responsive promoter 2 is $P_{leuA}$.

1. Digest pTK1 (containing sense sprA1) with Sph1 and Pst1 to drop out $P_{cad}$.

2. PCR amplify $P_{leuA}$ from *Staphylococcus aureus* 502a gDNA using PCR primers that contain an upstream Sph1 restriction site and a downstream Pst1 restriction site (Primers: TKO5 and TKO6).

3. Digest the $P_{leuA}$ PCR product with Sph1 and Pst1 and insert it into the Sph1/Pst1 digested pTK1 to generate $P_{leuA}$::SprA1 wt in the forward orientation generating pTK6.

In *Staphylococcus aureus*, the ilvleu operon consists of ilvDBHC-leuABCD-ilvA (9 genes). It is the BCAA biosynthetic operon.

Example 5. Preparation of Electrocompetent DC10B

Electrocompetent bacteria are prepared by harvesting log-phase cells and washing the cells extensively in sterile de-ionized water to lower the conductivity and to render the cells into an appropriate osmotic state for the electroporation process.

1. From freshly streaked antibiotic free plates, inoculate 250 ml LB media with each strain and incubate with agitation (37° C., 240 rpm).

2. Turn on centrifuge and cool rotor to 4° C. well in advance of harvesting cells. Place 1 L of sterile filtered 10% glycerol on ice well in advance of harvesting cells.

3. Monitor growth by $OD_{630}$ and when the cells are at 1.0 $OD_{630}$ units per mL, place flask immediately on wet ice for 10 minutes. From this point on the cultures must be kept ice cold. Pour each 250 mL culture into chilled 500 mL sterile centrifuge bottles.

4. Centrifuge (15 mins, 3500 rpm, 4° C.). Pour off the supernatant and aspirate any residual broth.

5. Add 250 ml of sterile 10% glycerol to each of the centrifuge bottles and completely suspend the cells by pipetting up and down.

6. Repeat 4 and 5 two more times.

7. Pour off the supernatant and suspend the cells in 2 mL 10% glycerol by pipetting up and down.

8. To freeze, aliquot 100 μL of the culture to microcentrifuge tubes on wet ice. Once you have used all of the culture, transfer the tubes to a dry ice/ethanol bath for 10 minutes. Once the cultures are frozen, transfer cells to a −80° C. freezer for storage.

To confirm cell's efficiency—transform cells with 1 μL of pUC19 (10 pM).

Electroporation conditions for *E. coli* are 1500 V, 25 μF, 200 ohmns. Use 1 μL of plasmid miniprep from DH5α and electroporate it into 50 μL of the electrocompetent DC10B.

1. Electrocompetent *E. coli* are thawed on ice, and 1 μl of plasmid is added to 50 μl of cells in an ice cold 0.1 cm gap electroporation cuvette.

2. Electroporate as above and add recovery medium immediately (1 mL, SOC medium).

3. Agitate at 37° C. for 1 h at 250 rpm and plate 100 μL onto LB+100 μg/mL carbenicillin. Incubate plates for 16 h at 37° C.

Example 6. SATransformation

Techniques for transformation are adapted from Chen, W., et al. 2017, Rapid and Efficient Genome Editing in *Staphylococcus aureus* by Using an Engineered CRISPR/Cas9 System. J Am Chem Soc 139, 3790-3795. Materials to have on hand: LB agar plate containing 50 μg/ml kanamycin; sequencing primers for PCR screening of 12 clones; TSB broth with kanamicyn, sterile tubes for bacterial growth; PCR reagents to do colony PCR (master mix for 500 μl) and PCR grade $H_2O$.

10 μL product of Golden Gate assembly is transformed into 100 μL *E. coli* DH10B competent cells. The successful colonies are selected on a LB agar plate containing 50 μg/mL kanamycin. The success for the construction of the pCasSA-NN spacer plasmid was verified by PCR or sequencing,

Example 7. Purification Plasmids from *E. coli* DH10B to Confirm Sequence

1. DNA Sequencing of Inserts

Primers TKO13 through TKO20 are used variously to sequence the inserts of these 13 plasmids. The primers to use for each plasmid are indicated in Table 15. The kill gene inserts are obtained from DNA2.0. PCR amplified $P_{leuA}$ and $P_{hlgA}$ promoters to evaluate any possible polymerase errors for these fragments.

2. Assembly and Confirmation of Sequences 2.1 Raw chromatograms are inspected and only high quality regions (very high signal/noise and good peak separation) are chosen to use in assembly process.

2.2 Overlap regions of sequence reads from successive primers are identified and removed; unique reads are strung head to tail in Microsoft word with color coding of the text.

2.3 Clustal W is used to generate sequence alignments of theoretical sequences to the actual. Any discrepancies are confirmed by manual inspection of chromatograms.

Example 8. Preparation of Electrocompetent BioPlx-01 and RN4220

Electrocompetent bacteria are prepared by harvesting log phase cells and washing the cells extensively in sterile de-ionized water to lower the conductivity and to render the cells into an appropriate osmotic state for the electroporation process.

Materials to have on hand:

1. 500 mL orange capped y-bottom coming centrifuge bottles 2. 50 mL falcon tubes
3. 1.5 ml sterile microcentrifuge tubes
4. 96 well plate for A630 measurements
5. 10 and 25 mL sterile pipets and sterile pipet tips all sizes
6. TSB broth (need 600 mL total)
7. IL of Sterile 500 mM sucrose on wet ice well in advance of harvesting cells Protocol 1. From freshly streaked antibiotic free plates, inoculate 250 mL TSB media with each strain and incubate with agitation (37° C., 250 rpm).

2. Turn on centrifuge and cool rotor to 4° C. well in advance of harvesting cells, Place 1 L of 10% glycerol on ice well in advance of harvesting cells.

3. Monitor growth by $OD_{630}$ and when the cells are at 1.0 $OD_{630}$ units per mL, place flask immediately on wet ice for 15 min. From this point on the cultures must be kept ice cold. Pour each 250 ml culture into chilled 500 ml sterile centrifuge bottles.

4. Centrifuge at 2900 rpm for 15 min. Pour off the supernatant and aspirate any residual broth.

5. Add 250 ml of 10% glycerol to each of the centrifuge bottles and completely suspend the cells by pipetting up and down.

6. Centrifuge at 2900 rpm for 15 min. Pour off the supernatant, it is not necessary to aspirate. Completely suspend the cells in 250 ml glycerol and re-centrifuge.

7. Pour off the supernatant and suspend the cells in the residual glycerol by pipetting up and down.

8. To freeze, add 100 microliters of the culture to microcentrifuge tubes on wet ice. Once you have used all of the culture, transfer the tubes to a dry ice/ethanol bath for 10 minutes. Once the cultures are frozen, transfer them to a −80° C. freezer.

Example 9. Design and Test CRISPR gRNA Sequences and Test pCasSA Simultaneously In this example a CRISPR-Cas system is obtained that is effective in *Staphylococcus aureus* (pCasSA) from Addgene (Addgene plasmid repository, Cambridge, MA), identify an intergenic region to target from prior experiments, and finally, design and test gRNA aimed for the intergenic region.

1. Order verified CRISPR components from Addgene as shown in Table 16.

TABLE 16

| CRISPR Plasmids | | | |
|---|---|---|---|
| ID | Plasmid | Gene/Insert | Vector Type |
| 42876 | pCas9 | tracr/Cas9 | Bacterial Expression, CRISPR; *E. coli* |
| 42875 | pCRISPR | CRISPR-BsaI | Bacterial Expression, CRISPR; *E. coli* |
| 65770 | BPK2101 | CRISPR-Cas9 | Bacterial expression plasmid for *Staphylococcus aureus* Cas9 & sgRNA (need to clone in spacer into BsaI sites): T7-humanSaCas9-NLS-3xFLAG-T7-BsaIcassette-Sa-sgRNA |
| 98211 | pCasSA | CRISPR-Cas9 | Sa-specific CRISPR |

Figure 8:
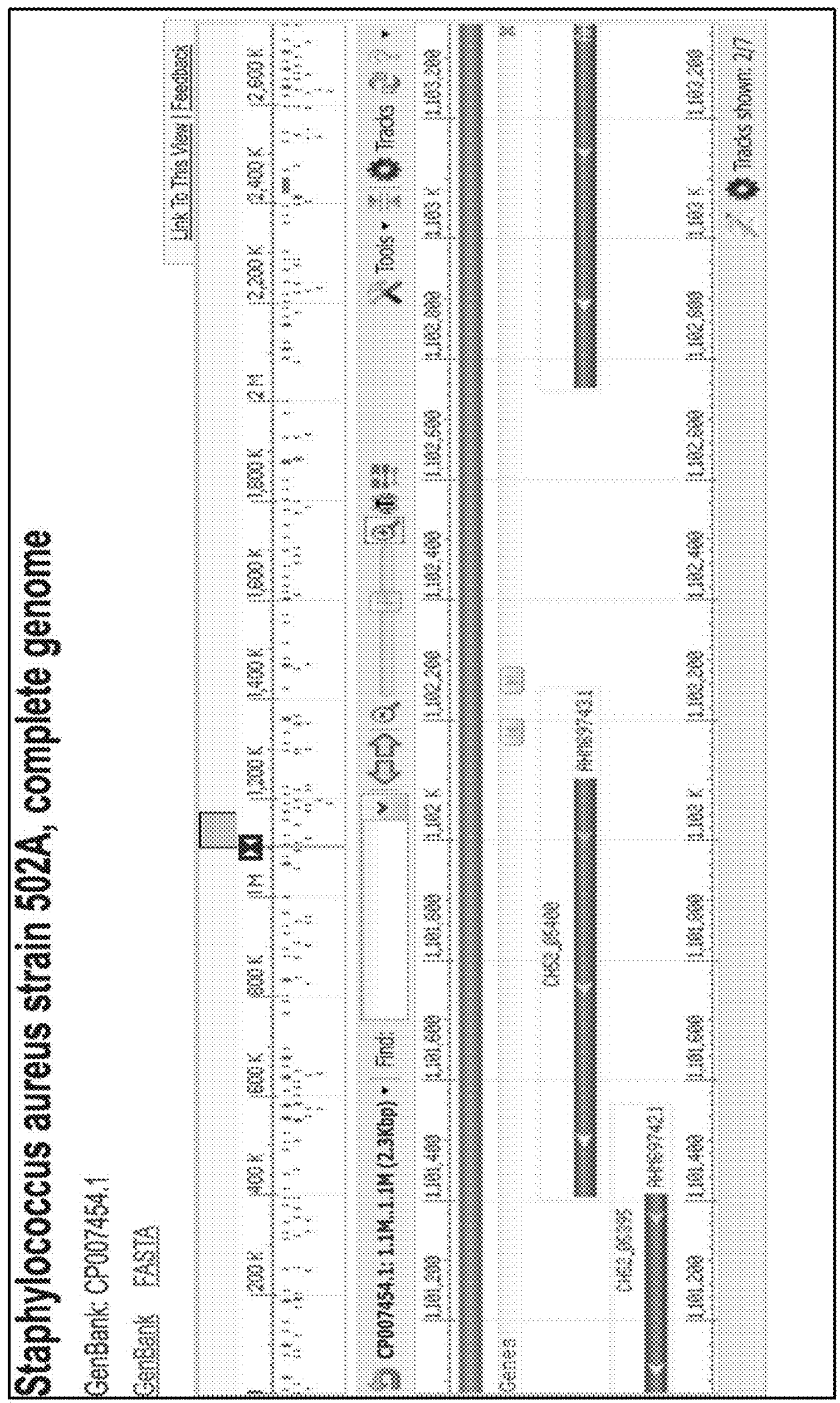
FIG. 8 shows CRISPR gRNA target site intergenic region identified between 1,102,100 and 1,102,700 bp in the *Staphylococcus aureus* 502a genome, GenBank: CP007454.1.

2. Select CRISPR gRNA target sites. Find where to target, this should be in an intergenic region so as not to disrupt viability. Currently, one such region has been identified between 1,102,100 and 1,102,700 bp in the 502a genome, GenBank: CP007454.1, as shown in FIG. 8. This region aligns with the region previously identified in the recombinant approach.

3. Once region has been chosen, use CRISPRScan (http://www.crisprscan.org/) Moreno-Mateos et al., 2012, Nature Methods 12, 982-988, to find putative gRNAs as shown in FIG. 9; note that the usable sequence is in all caps.

4. Check for possible off-target binding using BLAST (https://blast.nchi.nim.nih.gov/Blast.cgi?PAGE_TYPE=BlastSearch&PROG_DEF=blastn&BLAST_PROG_DEF=megaBlast&BLAST_SPEC=MicrobialGenomes_1280&DB_GR or searching the sequence directly (APE or similar). Note: gRNA marked as non-canonical will often have a single mismatched base pair, these will likely still work but may cause additional off target effects 5. Modify and order oligos as shown in Table 4B, FIG. 4A-4D. Name of oligos is shown in the format=oligo #, BPC (BioPlx CRISPR), Target #, direction (FOR or REV), followed by the target sequence.

6. Add each of the CRISPR targeting sequences into the pCasSA plasmid as per protocol shown below, adapted from Chen, W. et al. 2017. *Rapid and Efficient Genome Editing in Staphylococcus aureus by Using an Engineered CRISPR/Cas9 System*. J Am Chem Soc 139, 3790-3795.

a. Oligo Design

Select a 20 bp-spacer sequence before NGG (NGG is not included in the spacer) in the target gene of *Staphylococcus aureus* (40%~60% GC ratio is the best). Synthesize the two oligos in the following form (described above):

Note: FOR primer should be immediately upstream of the NGG in the target sequence.

```
5'-GAAANNNNNNNNNNNNNNNNNNNN-3'

3'-NNNNNNNNNNNNNNNNNNNNCAAA-5'
```

b. Phosphorylation

Prepare phosphorylation mixture as shown in Table 17.

TABLE 17

| Phosphorylation mixture | |
|---|---|
| 2 μl | oligo I (50 μM) |
| 2 μl | oligo II (50 μM) |
| 5 μl | 10x T4 DNA ligase buffer (NEB) |
| 1 μl | T4 polynucleotide kinase (Takara) |
| 40 μl | ddH2O |
| 50 μl | total |

Incubate at 37° C. for 1 hour.

c. Annealing

Add 2.5 μl of 1 M NaCl to the phosphorylated oligo pairs. Incubate at 95° C. for 3 min and slowly cool down to room temperature (use a thermocycler). (Alternatively, use a heat block and take the block out of the heater and let it cool naturally for 2 hours.) Dilute the annealed oligos 20 times using $ddH_2O$.

d. Vector Digestion

Digest 1-2 ug of pCas9 with BsaI (NEB) as shown I Table 18.

TABLE 18

| Vector digestion mixture | |
|---|---|
| x ul (1-2 ug) | pCas9 |
| 1 ul | BsaI (NEB) |
| 5 ul | 10 x NEB Buffer |
| 0.5 ul | 100X BSA |
| y ul (to 50 ul) | $ddH_2O$ |
| 50 ul | total |

Gel purify digested pCas9 (important for successful cloning).

e. Ligation

Prepare ligation mixture as shown in Table 19.

TABLE 19

| Ligation mixture | |
|---|---|
| 1 ul (possibly more) | Gel purified, BsaI digested Cas9 |
| 2 ul | Diluted oligos |
| 2 ul | 10x T4 ligase buffer |
| 1 ul | T4 ligase |
| x ul (to 20 ul) | $ddH_2O$ |
| 20 ul | total |

Incubate at RT for 2 h or 16 C for O/N.

8| Transform into *E. coli* cells (DH5a, DH10B or DC10B).

f. Select for Plasmid Uptake

Select for plasmid uptake by plating cells on LB-agar plates with Kanamycin (50 ug/mL). Note: The pCasSA plasmid causes the *E. coli* to grow very slowly at 30° C. and plates may need to be incubated for 24-36 hours in order to see colonies.

Once colonies are visible select a few for liquid grow up in LB broth with Kanamycin (50 ug/mL). Save an aliquot of liquid culture for easier grow up at a later date.

In a cryotube, add 50% sterile glycerol to liquid culture mix by inverting, then place at −80° C. for long term storage.

Extract the plasmids using Qiagen kit, spec and store and −20° C.

7. Verification of Inclusion by PCR and/or Sequencing a. PCR Testing

Test using 21BPC FOR (SEQ ID NO: 63) and 22BPC REV (SEQ ID NO: 64) on the templates generated above in step 6.

Perform PCR of constructs. The PCR products will be ~275 bp in the uncut pCasSA vector (positive control=intact pCasSA vector). PCR using the digested pCasSA vector should not produce any products (negative control=Bsa1 digested pCasSA vector).

A small portion of the digested product should be tested to ensure 100% efficacy. Testing can be by PCR or gel electrophoresis directly on the digested plasmid. PCR on the pCasSA vector with the gRNA sequences will produce ~278 bp amplicons. Note: these will not be visibly different when compared to the intact pCasSA vector. As such, the Bsa1 digestion needs to be 100%.

b. Sequencing Method

Prepare the PCR products generated above for sequencing. Clean up PCR reaction using spin column clean up kit per manufacturers protocol.

Measure concentration of purified PCR product using NanoDrop.

Mix sample with either forward or reverse primer (21BPC FOR and 22BPC REV, respectively) for sequencing with Quintara Biosciences.

PCR product at 5 ng/ul and primer at 5 pmol/ul (5 uM), PCR products from the intact pCasSA vector should be sequenced alongside the other products to provide a baseline.

8. Testing CRISPR-Cas Efficacy/Targeting

Introduction of any plasmid with the inserted gRNA sequences should cause a double-strand break at the targeted CRISPR site. Additionally, the lack of a homologous sequence for homology directed repair (HDR) will cause double strand break induced lethality. Therefore, transforming the targeting plasmids with the targeted plasmid should result in a death rate corresponding to the CRISPR targeting efficacy Transform each of the 10 (assuming all targeting combinations worked) into separate aliquots of electrocompetent RN4220 *Staphylococcus aureus* cells.

In this case targets 1, 4, and 6-10 should show activity in the RN4220 cells (the sequences are similar enough to allow CRISPR gRNA binding).

Example 10. Design and Test Homology Dependent Repair Templates and Efficacy Using a Fluorescent Reporter Controlled by a Constitutive Promoter a. Homologous arms are designed of varying length (200, 300 and 400 bp) corresponding to the ~600 bp intergenic region identified above. For proof of viability, a fluorescent reporter gene (e.g., mCherry) is inserted under control of a constitutive promoter (rspL). The promoter and reporter will be flanked with restriction sites (NotI and XmaI) to allow transgene swapping. The current design contains a single stop codon. Optionally additional stop codons may be added. Constructs are designed and ordered through ATUM (formerly DNA2.0). This entire sequence (homologous arms+promoter+mCherry) is placed into the pCasSA vector using the XhoI and XbaI restriction sites.

b. Checking for mCherry Incorporation/Expression

Once the full pCasSA-XX-XXX vector is assembled and transformed into an *Staphylococcus aureus* strain, verify: 1) mCherry expression, and 2) genomic incorporation of the mCherry sequence. We currently have a few viable methods to check for these. Note: mCherry expression should occur in bacteria that maintain the plasmid as well as those with successful incorporation. To differentiate these, the plasmid must be cured (removed), except in the case of PCR which may be able to differentiate between the two.

For Plasmid curing (with repF cassette):

Grow a liquid culture at 30° C. wish antibiotic as previous;

Dilute 3-5 ul of this culture 1000-fold in fresh TSB (no antibiotic);

Place at 42-43° C. until growth is apparent (e.g., overnight).

Streak the liquid culture on TSA plates with and without chloramphenicol and grow at 37° C.

Cultures should grow on − chlor plate and should not on + chlor plate at 37° C., if so, the plasmid has been removed For Fluorescence Microscopy:

The mCherry fluorophore is excited by ~587 nm light and emits ~610 nm.

For PCR:

PCR across the inserted region to confirm incorporation. Primers designed to amplify: Across the insertion region (41/42 and 43/44). To test for the presence of mCherry (51/45). To verify the presence of genomic DNA (TKO 1/3). Mixing and matching insertion and mCherry primers can also serve to test for mCherry incorporation.

Incorporation may also be confirmed by Western blot analysis.

Employ western blot equipment gel box and iBlot transfer system, Employ Primary anti-mCherry antibody, Secondary colorimetric antibody, Precast gels (or gel casting equipment and reagents), iBlot transfer kits, Protease inhibitors, Protein extraction solutions (e.g., RIPA), Protein markers (ladders), and Buffers (TBS, tween etc.) as known in the art.

Example 11. Analysis of KS Promoters with Fluorescent Reporters

The fluorescent reporter is under control of the promoters identified in the recombinant approach (PleuA, PhlgA etc). This combination allows testing of the efficacy of the chosen promoter with a measurable (positive) outcome. Preferably, the mCherry would be placed in the constructs based on the pCN51 backbone. The combination is used to test for multiple possible issues:

If the plasmid containing cells are exposed to blood/serum mCherry should be expressed. This can be verified either with fluorescence microscopy (Ex 587 nm, Em 610 nm) or by western blotting for the mCherry protein.

If the mCherry protein is created in "normal" conditions (no blood/serum activation) then the promoter is "leaky". Leaky activation could explain some of the issues obtaining KS plasmids with certain promoters (i.e. Plus) as even low levels of KS expression could cause a loss of viability.

What is the rate and conformity of the upregulation caused by a specific primer?

Cells are viewed in real time (fluorescence microscopy) or through time course sampling (western blot) to observe the rate of fluorescence generation upon exposure to blood and/or serum.

Example 12. Insertion of KS into BioPlx-01, Verify Incorporation, Test for Efficacy and Longevity A KS of choice is inserted in a pCasSA vector using Not1 and Xma1 restriction sites flanking each sequence. The pTK is amplified using primer BP-40 which adds the Xma1 restriction site. The KS is inserted into *Staphylococcus aureus* 502a cells and genomic incorporation verified. The incorporated cells are cured of the plasmid and tested for KS activity when exposed to blood/serum. The KS cells named "BioPlx-XX" are then passaged as described herein to analyze longevity and viability.

Example 13. Confirm/Characterize the Rate and Extent of Serum-Induced Cell Death The KS cells BioPlx-XX having the KS are grown side-by-side with BioPlx-01 (*Staphylococcus aureus* 502a WT) in TSB, and then washed and shifted to fresh human serum. The KS strain will "flatline" soon after the shift whereas the WT strain will begin to grow in the serum.

Example 14. Evaluate the Stability of the KS Strain BioPlx-XX

This experiment is performed to demonstrate that the KS in BioPlx-XX is phenotypically and genotypically stable during in vitro propagation.

Phenotypic stability (in this case, KS performance) will be assessed by determining the rate of cell death in serum after passaging the strain for X, Y and Z generations, where X is the number of doublings experienced in strain manufacturing to produce a single clinical lot of material sufficient to treat 200 patients, and Y and Z are the number of generations experienced after up to 41 total culture doublings. We are aiming for 4×10 cells per patient×200 patients=$8\times10^8$ total cells.

A dose of $4\times10^9$ cells per patient×200 patients=$8\times10_{11}$ total cells.

1. Inoculate 5 mL of TSB with a single large colony of BioPlx-01 and a second 5 mL of BioPlx-02-both have been streaked from the frozen master cell banks. (approximate density is 0.05 A630/mL).

2. Allow the 2 strains to grow to 1.6 A630 units per mL (monitor in the Biotek plate reader; 5 doublings). This is ~ mid exponential phase. (remember that the linear range of the instrument is between 0.1 and 0.9—you must dilute samples in TSB to stay in this linear range). Keep detailed notes on growth rates. We are assuming for the sake of this calculation that about 4 A630 units/mL=$8\times10^9$ CFU/mL. Volume of saturated culture needed to obtain $8\times10^{11}$ CFU total=($8\times10^{11}$ CFU/$8\times10^9$ CFU/mL)=100 mL 3. Use the starter cultures from (2) to inoculate 100 mL "final" cultures of each to a density of 0.05 A630 units per mL. 1.6 mL starter is added to 98.4 ml TSB.

4. Allow the two strains to grow at 37 C/250 rpm. Monitor the density until an A630 of 3.2 is reached. (6 doublings). Create a new culture of each strain-100 mL initiated at 0.05 A630 units/mL (this is "round 2"). Return the flasks to the shaker 250 rpm/37 C.

5. Harvest a 1 mL volume of cells from step 4 into 50 mL PBS for each strain.

5A. Snap freeze a second 1 mL of culture and place at −80 C for later genetic tests (see genotypic stability below).

6. Centrifuge 2900 rpm for 15 min.

7. Aspirate the supernatant and vortex the cell pellet to resuspend.

8. Bring volume again to 50 mL in PBS and harvest as in step 6.

9. Resuspend the pellets of each strain (BioPlx-01, BioPlx-02) in pre-warmed fresh human serum 20 ml each.

10. Shake at 250 rpm/37 C, monitoring growth. Expected outcome is that BioPlx-01 grows and BioPlx-02 (KS) does not. Collect enough data-points that the slopes of each can be calculated from semilog plots and ratioed. This ratio will be a measure of KS performance. Kill ratio (KR) slope of BioPlx-01 growth in serum/slope of BioPlx-02 growth in serum. This KR is a measure of KS performance at 11 total doublings was reached in TSB.

11. The "round 2" culture from step 4A will be monitored until an A630 of 3.2 is reached (6 doublings). Use this to seed a "round 3" culture to 0.0S A630/mL, then follow steps 5-10 using the Round 2 saturated culture. The KR is a measure of KS performance at 17 total doublings.

12. The "round 3" culture from step 11 will be monitored until an A630 of 3.2 is reached (6 doublings), then split back again to 0.05 A630/mL. This process of growth to 3.2 followed by splitting to 0.05 was performed 4 times as follows: Round 3: was 23 doublings; Round 4:29 doublings; Round 5:35 doublings; Round 6:41 doublings. Follow steps 5-10. The KR is a measure of KS performance at 41 doublings.

Plot KR as a function of culture doubling #.

Genotypic Stability:

1. Find the samples of BioPlx-02 cells from each time point 11, 17 and 41 doublings, see step 5A.

2. Conduct NextGen sequencing to determine the sequence homogeneity of this sample. Single molecule sequencing may be used to determine the % of mutations occurring in a population of cells at a given time point.

Example 15. Candidate Serum and Blood Responsive Promoters screened by fluorescence to detect up-regulation Overview. In this example, potential *Staphylococcus aureus* promoters were tested for activity in blood and/or serum. Candidate promoters were selected from the literature based on the upregulation of gene expression after exposure to blood or serum. These promoters were then cloned upstream of a reporter molecule, green fluorescent protein (GFP), which fluoresces when the promoter is activated, After several growth steps, *Staphylococcus aureus* cells containing this promoter-GFP cassette were exposed to blood or serum, and the activity of GFP was viewed with fluorescent microscopy. The results of this screen show several promoters with varying degrees of activity in blood and/or serum, which may be used to regulate a molecular modification such as a kill switch, virulence block or nanofactory.

In example 1, a non-pathogenic strain of *Staphylococcus aureus*, denoted 502a, was used to exclude methicillin-resistant *Staphylococcus aureus* (MRSA) from the human skin microbiome. While the application of 502a has shown no adverse side effects in this trial, a kill switch was designed as an additional measure of safety. The kill switch molecular modification disclosed herein may be incorporated to target microorganisms such as *Staphylococcus aureus* 502a or RN4220 cells, and will function to inhibit cell growth, either by slowing cell growth, or promoting cell death, upon exposure to blood or serum. As such, the possibility of systemic infection in patients will be reduced or eliminated. The kill switch comprises two key elements a kill gene to slow or stop cell growth, and a blood or serum responsive promoter to control the kill gene expression. In this example, candidate *Staphylococcus aureus* promoters were tested for increased activity in blood or serum. Candidate promoter sequences derived from *Staphylococcus aureus* strain 502a genome (NCBI CP007454.1), including about 300 bp upstream and including start codon are shown in Table 20.

TABLE 20

Candidate Promoter Sequences

| Gene/Description | Nucleotide sequence |
|---|---|
| leuA | Atttttagacaattctaactattaaagtgatatataccattcacggaaggagtataataaaatgcttaatcaatatactgaacatcaaccgacaacttcaaatattattattttattatactctttaggactcgaacgttagtaaatatttactaaacgctttaagtcctatttctgtttgaatgggacttgtaaacgteccaataatattgggacgtttttttatgttttatctttcaattacttatttttattactataaaacatgattaatcattaaaatttacgggggaatttactatg (SEQ ID NO: 132) |
| hlgA2 | Acttcaaattttcacaaactattgcgaaatccattcctcttccactacaagcaccataattaaacaacaattcaatagaataagacttgcaaaacatagttatgtcgctatataaacgcctgcgaccaataaatcttttaaacataacataatgcaaaaacatcatttaacaatgctaaaaatgtctcttcaatacatgttgatagtaattaacttttaacgaacagttaattcgaaaacgcttacaaatggattattatatatatgaacttaaaattaaatagaaagaaagtgatttctatg (SEQ ID NO: 133) |
| hrtAB | Gttcatattgagttcatatttcaaccttatactgacgctaaagaagaaatagggagaagtgaatcgatatg (SEQ ID NO: 134) |
| hlb | Ttcaggctatcaataatgctttgaaatcagcctgtagagtcaataatataccaattattacatcgcacgcattaagacac (SEQ ID NO: 135) |
| sbnC | Actcattgttcttatttactagcaaaaggtgtatctatacattacatttctaaaagattaggtcataaaaatatagcaat (SEQ ID NO: 136) |
| isdI | Aactacatccgtgtattcgcatttgttagaagaaaaatttaatgaagaggacaaaaaaacaactaaaattttagaaagta (SEQ ID NO: 137) |
| isdG | Tgtaatttagggacccattagggactccaaacccaataaatactgttgttacaaggtttctatg (SEQ ID NO: 138) |
| sbnE | Gaatacttcaaggattaacatatagtgcattgattcaaagtgtcatgtttgttgtcgtgaatgcgtgtcatcaacaacttaaaggcacatttgttggaacgacgaacagtatgttagttgttggtcaaattattggcagtcttagtggcgctgccattacaagttatactacaccagctactacgtttatcgttatgggcgtagtatttgcagtaagtagtttatttttaatttgttcaaccatcactaatcaaatcaacgatcacacattaatgaaattatgggagttgaaacaaaaaagtg (SEQ ID NO: 139) |
| lrgA | Atgaaaaacgattgaatcccacttattttatacgtattcatcgttcatatattattaacacgaaacacattaaagaagtgcaacaatggtttaactacacttatatggtaatattgacaaatggtgtcaagatgcaagttggacgttcatttatgaaagattttaaagcgtcgataggattactttaacagtaatcctttttttttatgcattttacctatgatattttgtatttcggactaaaaatcacgcaaatcgaagtgagccatctatactttagttaaatcaaacgtaggaggcaatg (SEQ ID NO: 140) |
| lrgB | Gtttagtattattatttgtattattatgtactggtgctgttaagttaggcgaagtcgaaaaagtaggaacgacactaacaaataacattggcttactatcgtaccagccggtatctcagttgttaactctttaggtgtcattagccaagcaccatttttaatcattggactaataatcgtctcaacaatactattacttatttgtactggctatgtcacacaaattattatgaaagttacttcgagatctaaaggtgacaaagtcacaaaaaagatcaaaatagaggaggcacaagctcatg (SEQ ID NO: 141) |
| hlgB | Aagatcctagagattatttcgttccagacagtgagttacctcctatgtacaaagtggatttaacccttcatttatcgccacagtatctcatgaaaaaggttcaagcgatacaagcgaatttgaaattacttacggaagaaacatggatgtcactcatgccattaaaagatcaacgcattatggcaacagttatttagacggacatagagtccataatgcattcgtaaatagaaactatactgttaaatacgaggtcaattggaagactcatgaaatcaaggtgaaaggacagaattgatatg (SEQ ID NO: 142) |

TABLE 20-continued

| Candidate Promoter Sequences | |
|---|---|
| Gene/ Descrip- tion | Nucleotide sequence |
| fhuB | Tcaaaatgtaacaatgatcagaggcatatgtttaattattgctatgattctagcaggtattgcagttgctatcgctggacaag<br>ttgcatttgtaggtttgatggtacctcatatagcaagatttttaattggaactgattatgctaaaattctaccattaacagccttgt<br>taggtgggatactcgtgcttgttgccgatgtgatagcacgatatttaggagaagcgcctgttggtgcaatcatttcatttatc<br>ggtgttccttactttttatatttagttaaaaaaggaggacgctcaatatg (SEQ ID NO: 143) |
| splF | Gttcacctatattaaatagtaagcgagaagcaattggtgttatgtatgctagtgataaaccaacaggtgaaagtacaaggt<br>catttgctgtttatttctctcctgaaattaagaaatttattgcagataatttagataaataaatcatccatccatacattgataaatg<br>atttttagaaattaacaacaaaatcaacaattttaaacatctctgtgattctatttattcgaaatgatttaaaaaataaaacttcaa<br>aaacctaaccttatatttatacgaatacttagaggagcacaaaaatg (SEQ ID NO: 144) |
| SAUS A300_ 2268 | Gatgatgtatgtttcgaatttatcaattaacatgtgaggacctcccgaggaatacatggcattaaatacacgtttaatatttat<br>aaaggtgacttaattttgttcaagttgattttaccacgctttttttctttattcactaagacttttgaatgaagtttaaaataattgttt<br>atcagtgataaaatatttgcaataagaagagaatggctaaataatcttaattttcagaaaagtaattgtaaccttactggtctta<br>tggtaatatttttcaatattatcgacgaggatgtgttaacaatg (SEQ ID NO: 145) |
| SAUS A300_ 2616 | Ctatcattataatgagataatgtcatttttaattgagctaaacagacagggaaagacgattattatgattacgcatgatatgca<br>tttattgtctgagtatagttcaagaacagttgtattatcaaaaggacaagtcgttgctgataccacgccagtattgatattaaat<br>gataaaaaaatctgtgagattgcatcattgagacaaacatcgctatttgaaatggccgaatatatagggattagcgagcca<br>cagaaattagtacaattatttattaaccatgataggaaggtgagacgccaatg (SEQ ID NO: 146) |
| SAUS A300_ 2617 | Caggcctattttctaggaaatcgatgatttattttaatatcggtcaaattattgcgaatattatttgctgggcacttattgcacca<br>acattagatattttgatttataacgaaccggctaacaaggtttatacacaaggtgttatctctgcagtattaaatattatttcagtt<br>ggtattattgggacaatattattaaaagcatatgcttcatctcaaataaaaaaaggtagtttacgtaaagaataatcattttgtt<br>gaatcagatatgtaaatgaatgtagaaaggtaatgatatatcatg (SEQ ID NO: 147) |
| isdA | CTATCTGCGGCATTTGCAGAATTACTGAATGTCGCGATGATGATAATTAA<br>CGCTAAAATCGTTGTATTAAAAACTTTTAAAATATTTTTCAAAACATAAT<br>CCTCCTTTTTATGATTGCTTTTAAGTCTTTAGTAAAATCATAAATAATAAT<br>GATTATCATTGTCAATATTTATTTTATAATCAATTTATTATTGTTATACGG<br>AAATAGATGTGCTAGTATAATTGATAACCATTATCAATTGCAATGGTTAA<br>TCATCTCATATAACAACACATAATTTGTATCCTTAGGAGGAAAACAACA<br>TG (SEQ ID NO: 148) |
| isdB | CTTCAGTTGATAACTTTATTAGCACAGTTGCCTTCGCAACACTTGCCCTTT<br>TAGGTTCATTATCTTTATTACTTTTCAAAAGAAAAGAATCTAAATAAATC<br>ATCGTCACACTCATAACTTAATATATTTTTTATTTTAAATTTTATTTAACC<br>TATGTCATAGATATTTCATAATCTATAACATAGGTTATTTTTTTATAAAAT<br>AATGTTGCAATTAACTACCATTTCAATGTACAATACAAGTAATCAATTGA<br>TAATGATTATCAGTTGATAATATACAATTAGGAGTTGTTTCTACAACATG<br>(SEQ ID NO: 149) |
| fhuA/C | Ctttcttgcagatgaataaataaatggtatgagcacacatacttaaatagaagtccacggacaagtttttgaactatgaaga<br>cttatctgtgggcgtttttatttttataaaagtaatatacaagacatgacaaatcgagctatccaatttaaaaagtaatgttagtc<br>aataagattgaaaaatgttataatgatgttcatgataatcattatcaattgggatgcctttgaaaattgataatttaaaaatagaa<br>attatttttataaacagaaagaattttattgaaagtagggaaattatg (SEQ ID NO: 150) |
| ear | Tgacacctgctaattcaaacattatttgagacattcttttcaaattaattataaatttttacctatagactagtttgatatttatctac<br>atctcaaaattctcatcaacaatctttcacatccaacatttttactttagtttttataattcaaaacaacaaaacgatgttaaaaaa<br>ttattctattattagttaatagatagttaatacattttttgatatttagttaattgttcttttaaaaaaatattattatattttcattgta<br>aacgtttacaatataaaaaaaggagcaattaaaatg (SEQ ID NO: 151) |
| fnb | Tgtacaggcgataattatgaaacacttagtatattgttttaaattagataatgatgaatttaatttgaaaaataagtataaaaaa<br>tacaagccttgtgtgacaagggtttatgatgacttgaatacaatttataggtatatttcaaataataaaattatcaattaacataa<br>aattaatgacaatcttaacttttcattaactcgctttttttgtattgatttaaaaaccgaacaatatagacttgcatttattaagttta<br>aaaaaattaatgaattttgcatttaaagggagatattatagtg (SEQ ID NO: 152) |
| splD | Attttaaattttgatgcatacattgaacccgggaattcaggatcaccagttctaaattctaacaatgaggtcataggtgtggt<br>gtatggcggtattggaaaaattggttctgaatataatggtgccgtatactttacgcctcaaatcaaagattttattcaaaagca<br>cattgaacaataaacaaatttaaatatacaccatgagcatgtgttcaataattttaatgaaaaacatcggtcgaatataacata<br>aaaaaacgtctatatcaaaagcatcatgaataaacagaggagcacaaaaatg (SEQ ID NO: 153) |
| dps | Ataatagaaatagaatgtggaaaacaacatggcaccaaccaaatgattatgaaaaatcgttctttttagatgataatgcga<br>aagtaaaacttactgattgataaaacatacttgctaattgataatggatatactagatgatgaattaaaatttagacatttaaaa<br>ageggaacaccttacatttagattagaataattataaaaaagagagtaaaaacactttacagattagaatcattataatataat<br>aattaatataaacaagcaagacgtagacaattttaaggagtgtattaaatatg (SEQ ID NO: 154) |
| CH52_ 00360 | GAATTCTTTATAGCGCGTGCAATCACACCACAAGATAAAAGATTAAAAA<br>GTGACAAAGCATTTATTGCATTTTTAGAAGAAACCTTCGATCAGTTCTTA<br>CCATTTTATTCTGCATAAATAACTTTGTTTAAATAATAGAGCACGTAATC<br>ACATCCATGATTTCGTGCTCTTTTTTCTTAATATTAAATCGAACGTTCAAC<br>ATAATAATTCATACTTTTAAAAAAATTAAAATAAATTTAGGTTGACCTAA<br>ACATTTTATTAGGTTATTATATTGTCCATAAGAAGTAGAGGTGAGTCAAA<br>(SEQ ID NO: 155) |

TABLE 20-continued

Candidate Promoter Sequences

| Gene/ Descrip- tion | Nucleotide sequence |
|---|---|
| CH52_ 00305 | CATAATCCCCCTCCTTAAATTTGTTCATATAAGATTATGATATCTTAGATT<br>GCATAAAAAGACTAGGTTTAATAAAATTAAAATGTGACAAATTAACGAC<br>AAGAGAAAATGTCAATTTTGTGACACAAATAACATTTAATTTATTGCTAT<br>AATGTATATGTTAGAAAATTTTAATAAGTAGAATCATGCATCTAAAAGA<br>GATTAATATTTAAGCTTCAAATTTGAGTAAACGTGGATTACATAATTATC<br>CCAATAAAAAAATCATTACGATTAAGTTCTTTTTATGTCGTCCACATACA<br>ATAC (SEQ ID NO: 156) |
| CH52_ 01670 | CATTTTATATTCCCTCCGTAAAATATAAAGTTTTCTTAACTAGTTTATAAT<br>AATTTTAATTTGTAGTCAAAAAGACTTTGTAATAATGCGTTCAGTTAATT<br>ATAACTTACTTATACCTTAATATAAACAACTTAAACCCTTTTTATTATTTT<br>TAATAACTCTAAAGTACAACTCTAATCCGCTCTCTTTAAAAATATAAATG<br>ATAATAAGTGCACATAATTTCTCAATGGATTTTATGAATTTAAAATATGT<br>TATCATTTCACTAGGACATTTGTAATATGGTATGATGCTATTTATGATTTT<br>(SEQ ID NO: 157) |
| srtB | CATAAAAATCCTCTTTTATTAACGACGTTTCTTCAGTCATCACTAAACCA<br>GTTGTTGTACCGTTTTAGATTCGATTTCGTTGACTTTGACAAATTAAGTA<br>AATTAGCATTGGACCACCGACAATCATTAAAATAGCATTGGCTGGAATT<br>TCTAAAGGAGGCTGTATCACTCGTCCTAATAAATCAGCCACTAACAATA<br>GCCATGCACCAATAACTGTAGAAAACGGAATAAGTACTCTGTAATTGCC<br>CCCAACTAGCTTTCTAACCACATGTGGCACAATAATACCTAAAAAGGCT<br>AGTTGT (SEQ ID NO: 158) |
| sbnA | CAAAAGCGCTTCCTCCTCAAATTTAAAATTCTATAATATTGTGTGTTACC<br>TAATTGATAATGATTCTCACTATCAAGTAATTAGGATTATATTTTTTATG<br>CATTTATATGTCAAATAATTATAAGTTGCATGTAAATCATAAATATTTTA<br>TTGACTTAGGAAAAAATTTAATTCATACTAAATCGTGATAATGATTCTCA<br>TTGTCATACATCACGAAGGAGGCTAATTAGTCAATGAATAAAGTAATTA<br>AAATGCTTGTTGTTACGCTTGCTTTCCTACTTGTTTTAGCAGGATGTAGTG<br>GGA (SEQ ID NO: 159) |
| clfA | CATTTTATTCCCTCTTTTTAAAAAGTCATTTTATATTAACTATATACCCTT<br>TAAAGATATATTTAATCTCTGTTAATGGAATTATACACTAAAATTGCATT<br>ATAGCAATTAATTTGTATCGATATTTTATTATCCACAATAATACTTTACT<br>AACAAACATTTTATTTATTGCTATTTTAAGAATTACAAACGACAACGTAC<br>GATTTGATTGCAAACATTTTTTATTATTAATATGAACTCTACCTAATGTA<br>ATC CTAGCTTTAAATCATATTTTTTCAAAAGCAGATGTGTAATTTATGGT<br>AC (SEQ ID NO: 160) |
| emp homolog | CATCTGTTATTTCTCCTTTATATAGACTCAATATTATAACCAATATAATTT<br>CCCTGTTATATTCACTAACAGCATTATATACCAGAATTTTCAGTATAATA<br>ATTAACTTGAAGTAAACGTTGTCTTAACATTTTTATTGTTTTTCAGCTTAA<br>AATTAATTATTGATATTGATAGTTAAGCATAATAATTTTTTCGTAATATA<br>AAGTGAAAAAAGTAATAGTCCACACCTGTTTAGAATGTGGACTATACTA<br>GATTGCATCATTGAAATGATGACTTTGATATTATTTATTGCTAGTTTAAA<br>AT (SEQ ID NO: 161) |
| rsaC | CACGCTGTGTTTTAATGAAGTAAGATGAATTGATGTTGATGCAACCTAA<br>AATATTGGTATCTCCAATATTTTAGGCTACACATCAACATAACAAAGTCG<br>AAGGCTAATAGTCCCATATCGTGCGTTAAATATATATTACCCTCCTATTA<br>ATATATATACCGTTCCCGATCGCACGATATGGTGGTATTAGAACTTCTCT<br>TTGAACGAAAGAGAAAAGCTAGAACTTATGCAGTTTTAATTAAACTGTA<br>AACATTTGTCACTCTTTAAATCAAAGAGTAAAGTT (SEQ ID NO: 162) |
| hlgA1 | Aacaatttgtattttacaaacattaattaaaaataaaagcaagacattcgtgcaatcggttaccttaaattgtttacaactgtca<br>acaataccaaggttttattaactatatttctcacaaaattagcttttagcattccaaacaaaaaaggttaaattgaacggaatta<br>tggcattttttaacttaattgtaaaaaagttgataatggtcaattgttaatgaacagttaattataataacgtccaaaatatattatt<br>atttaattaagttaaataaaattatagaaagaaagtgaaacttatg (SEQ ID NO: 163) |

Initially, 21 promoter candidates were selected from literature reporting gene expression changes when *Staphylococcus aureus* cells were cultured with blood or serum. The following genes are described by Malachowa N., et al. (2011). Global changes in *Staphylococcus aureus* gene expression in human blood. PLOS ONE 6: e18617. 10.1371/journal.pone.0018617: isdA, isdB, isdG, isdI, sbnC, sbnE, fhuA, fhuB, SAUSA300_2268, SAUSA300_2616, SAUSA300_2617, hlgB, lrgA, lrgB, ear, splD, and splF. The following genes are described by Palazzolo-Ballance A. M. et al. (2008). Neutrophil microbicides induce a pathogen survival response in community-associated methicillin-resistant *Staphylococcus aureus*. J Immunol 180(1): 500-509; fnb, hlb, hlgB, isdA, isdB, isdG, fhuA, fhuB, dps. Finally, Stauff D. L. et al., (2007). Signaling and DNA-binding activities of the *Staphylococcus aureus* HssR-HssS two-component system required for heme sensing. J Biol Chem September 7; 282(36): 26111-21, describes hrtAB. In order to capture all of the relevant regulatory elements of these genes, we selected 300 base pairs upstream of the start codon of each gene as the promoter region. Each promoter region was then cloned upstream of Green Fluorescent Protein (GFP) to visualize promoter activity in media, blood, and serum. The promoters were cloned in front of GFPmut2 (a GFP variant) such that when the promoter is activated, GFP is transcribed and translated into a fluorescent protein. High fluorescence correlates with high promoter activity.

Materials and Methods

Cloning. For each blood or serum-responsive gene selected from the literature, 300 base pairs of sequence immediately upstream from the start codon was selected as the promoter region. Promoters were amplified from the 502a *Staphylococcus aureus* genome and cloned in front of GFP using either Gibson assembly (GA) or restriction enzyme (RE) digest. For Gibson assembly, promoters were amplified using primers with homology to the vector backbone. In the table below, primer sequence that matches the promoter is uppercase, while primer sequence that is homologous to the vector backbone is lowercase. For restriction enzyme digest, promoters were amplified using primers with SphI or PstI restriction sites. In the table below, primer sequence containing restriction sites is bold. The vector backbone, plasmid pCN56 (BEI Resources), was amplified using PCR for Gibson assembly, or simply digested with restriction enzymes for restriction enzyme cloning. Note that the dps promoter was never successfully cloned with GFP. After multiple attempts, the dps-GFP cassette was dropped. Final plasmid cassettes for screening are: pCN56-promoter-GFP. Primers used for amplification of promoters are shown in Table 21. Primers used for amplification of vector backbone are shown in Table 22.

TABLE 21

Primers used for amplification of promoters

| Promoter Method | Cloning | Forward Primer (BPC#: Sequence) | Reverse Primer (BPC#: Sequence) |
|---|---|---|---|
| isdA | RE | 366: TATAT**GCATGC**CTATCTGCGGCATTTGCAG (SEQ ID NO: 164) | 367: GATAC**CTGCAG**GTTGTTTTCCTCCTAAGGATA (SEQ ID NO: 165) |
| isdB | RE | 368: GATGC**GCATGC**CTTCAGTTGATAACTTTATTA (SEQ ID NO: 166) | 369: GATGC**CTGCAG**GTTGTAGAAACAACTCCTAAT (SEQ ID NO: 167) |
| isdI | RE | 379: GATAC**GCATGC**TTACTCGTAGCAGTTTTTTGT (SEQ ID NO: 168) | 380: GATAG**CTGCAG**GGGCAATTCACTCCTCTATTTT (SEQ ID NO: 169) |
| isdG | RE | 377: GATGC**GCATGC**AAACACAAGATAATTGAATTT (SEQ ID NO: 170) | 378: GATGC**CTGCAG**AATTATCCTCTTTTCTGTTTAA (SEQ ID NO: 171) |
| sbnC | RE | 381: GAATC**GCATGC**CTTTATTAAAGCTGACAAAGTCGTA (SEQ ID NO: 172) | 382: GAAATC**CTGCAG**TGTTCAGACACCTCGCATTC (SEQ ID NO: 173) |
| sbnE | GA | 305: taactgactaggcggccgcGAATACTTCAAGGATTAACATATAGTGCATTG (SEQ ID NO: 174) | 306: ccagtgaaaagttcttctcctttactcatTTTTTGTTTCAACTCCCATAATTTCATTAATG (SEQ ID NO: 175) |
| lrgA | GA | 307: taactgactaggcggccgcATGAAAAACGATTGAATCCCACTTATTTTATACG (SEQ ID NO: 176) | 308: ccagtgaaaagttcttctcctttactcatTGCCTCCTACGTTTGATTTAACTAAAG (SEQ ID NO: 177) |
| lrgB | GA | 309: taactgactaggcggccgcGTTTAGTATTATTATTTGTATTATTATGTACTGGTGCTG (SEQ ID NO: 178) | 310: ccagtgaaaagttcttctcctttactcatGAGCTTGTGCCTCCTCTATTTTG (SEQ ID NO: 179) |
| hlgB | GA | 311: taactgactaggcggccgcAAGATCCTAGAGATTATTTCGTTCCAG (SEQ ID NO: 180) | 312: ccagtgaaaagttcttctcctttactcatATCAATTCTGTCCTTTCACCTTGATTTC (SEQ ID NO: 181) |
| fhuA | GA | 313: taactgactaggcggccgcCTTTCTTGCAGATGAATAAATAAATGGTATGAGC (SEQ ID NO: 182) | 314: ccagtgaaaagttcttctcctttactcatAATTTCCCTACTTTCAATAAAATTCTTTCTG (SEQ ID NO: 183) |
| fhuB | GA | 315: taactgactaggcggccgcTCAAAATGTAACAATGATCAGAGGC (SEQ ID NO: 184) | 316: ccagtgaaaagttcttctcctttactcatATTGAGCGTCCTCCTTTTTTAACTAAATATAAAAAG (SEQ ID NO: 185) |

TABLE 21-continued

| Primers used for amplification of promoters | | | |
|---|---|---|---|
| Promoter | Cloning Method | Forward Primer (BPC#: Sequence) | Reverse Primer (BPC#: Sequence) |
| ear | GA | 317: taactgactaggcggccgcTGACACCTGCTAATTCAAACATTATTTG (SEQ ID NO: 186) | 318: ccagtgaaaagttcttctcctttactcatTTTAATTGCTCCTTTTTTATATTGTAAACGTTTAC (SEQ ID NO: 187) |
| fnb | GA | 319: taactgactaggcggccgcTGTACAGGCGATAATTATGAAACACTTAG (SEQ ID NO: 188) | 320: ccagtgaaaagttcttctcctttactcatTATAATATCTCCCTTTAAATGCAAAATTCATTAATTTTTTTAAAC (SEQ ID NO: 189) |
| hlb | GA | 321: taactgactaggcggccgcTTCAGGCTATCAATAATGCTTTGAAATC (SEQ ID NO: 190) | 322: ccagtgaaaagttcttctcctttactcatAGAAACCTTGTAACAACAGTATTTATTGGG (SEQ ID NO: 191) |
| splF | GA | 323: taactgactaggcggccgcGTTCACCTATATTAAATAGTAAGCGAGAAGC (SEQ ID NO: 192) | 324: ccagtgaaaagttcttctcctttactcatTTTTGTGCTCCTCTAAGTATTCGTATAAATATAAGG (SEQ ID NO: 193) |
| splD | GA | 325: taactgactaggcggccgcATTTTAAATTTTGATGCATACATTGAACCCGG (SEQ ID NO: 194) | 326: ccagtgaaaagttcttctcctttactcatTTTTGTGCTCCTCTGTTTATTCATGATGC (SEQ ID NO: 195) |
| dps | GA | 327: taactgactaggcggccgcATAATAGAAATAGAATGTGGAAAACAACATGGC (SEQ ID NO: 196) | 328: ccagtgaaaagttcttctcctttactcatATTTAATACACTCCTTAAAATTGTCTACGTC (SEQ ID NO: 197) |
| SAUSA 300_2268 | GA | 329: taactgactaggcggccgcGATGATGTATGTTTCGAATTTATCAATTAACATGTG (SEQ ID NO: 198) | 330: ccagtgaaaagttcttctcctttactcatTGTTAACACATCCTCGTCGATAATATTG (SEQ ID NO: 199) |
| SAUSA 300_2616 | GA | 331: taactgactaggcggccgcCTATCATTATAATGAGATAATGTCATTTTTAATTGAGC (SEQ ID NO: 200) | 332: ccagtgaaaagttcttctcctttactcatTGGCGTCTCACCTTCCTATC (SEQ ID NO: 201) |
| SAUSA 300_2617 | GA | 333: taactgactaggcggccgcCAGGCCTATTTTCTAGGAAATCGATG (SEQ ID NO: 202) | 334: ccagtgaaaagttcttctcctttactcatGATATATCATTACCTTTCTACATTCATTTACATATC (SEQ ID NO: 203) |
| hlgA2 | GA | 201: cgttaactaattaatttaagaaggagatatacatACTTCAAATTTTCACAAACTATTGCG (SEQ ID NO: 204) | 185: ccagtgaaaagttcttctcctttactcatAGAAATCACTTTCTTTCTATTTAATTTTAAGTTCATATATA (SEQ ID NO: 205) |
| hrtAB | GA | 205: cgttaactaattaatttaagaaggagatatacatGTTCATATTGAGTTCATATTTCAACC (SEQ ID NO: 206) | 188: ccagtgaaaagttcttctcctttactcatATCGATTCACTTCTCCCTATTTCTTC (SEQ ID NO: 207) |

TABLE 22

| Primers used for amplification of vector backbone | | | |
|---|---|---|---|
| Plasmid | Cloning Method | Forward Primer | Reverse Primer |
| pCN56 | GA (hlgA2, hrtAB) | 197: ATGAGTAAAGGAGAAGAACTTTTCACTGG (SEQ ID NO: 208) | 198: ATGTATATCTCCTTCTTAAATTAATTAGTTAACGAATTCG (SEQ ID NO: 209) |
| pCN56 | GA (all other promoters) | 197: ATGAGTAAAGGAGAAGAACTTTTCACTGG (SEQ ID NO: 210) | 265: gcggccgcctagtcagttaACTCAAAGGCGGTAATACGG (SEQ ID NO: 211) |

Blood and Serum Samples. For blood samples, 4-8 ml of human blood was drawn into heparinized tubes and frozen. For serum samples, 4-8 ml of human blood was drawn into non-heparinized tubes, rested at room temperature for 15-30 minutes until fully clotted, and centrifuged at 3,000 rpm for 15 minutes. The serum supernatant was carefully removed, transferred to a new tube, and frozen.

Construction of Cell Lines, RN4220 *Staphylococcus aureus* cells were transformed with pCN56-promoter-GFP plasmids using electroporation. Glycerol stocks of each cell line were preserved as a starting material for the following blood/serum induction assay. Final cell lines for screening are: RN4220+pCN56-promoter-GFP.

Blood and Serum Induction. For each cell line, 1-3 ml tryptic soy broth (TSB) media with 10 μg/ml erythromycin was inoculated with a small scoop of glycerol stock. The culture was grown at 37° C. overnight shaking at 240 rpm. In the morning, the optical density (OD) of the culture was measured and the culture was used to inoculate 1 ml of fresh TSB+erythromycin to an OD of 0.1. This 0.1 OD culture was grown at 37° C. shaking at 240 rpm for 2-3 hours until the OD reached 1-2. The culture was then used to inoculate three separate cultures of 500 μl of freshly thawed blood, serum, or TSB, all with erythromycin, to an OD of 0.1. These three cultures were grown at 37° C. shaking at 240 rpm for 1.5-2 hours. 10 μl of each culture was dropped onto a microscope slide, covered with a coverslip, and viewed with fluorescent microscopy.

Microscopy. Images were taken with an iPhone through the eyepiece of a fluorescent microscope.

Results and Conclusions. The fluorescent images of each *Staphylococcus aureus* RN4220+pCN56-promoter-GFP cell line cultured in either media (negative control), blood, or serum were read and fluorescence level was scored as summarized in Table 23.

TABLE 23

Relative promoter GFP fluorescence levels in TSB, Blood or Serum

| | Fluorescence Level | | |
|---|---|---|---|
| Promoter | TSB Media | Blood | Serum |
| isdA | high | high | high |
| isdB | high | (no sample) | high |
| isdI | low | high | high |
| isdG | very low | high | high |
| sbnC | very low | medium | medium |
| sbnE | very low | low | low |
| lrgA | very low | low | low |
| lrgB | very low | low | none |
| hlgB | very low/none | medium | medium |
| fhuA | high | high | high |
| fhuB | very low | low | low |
| ear | high | high | high |
| fnb | medium | medium | medium |
| hlb | very low/none | medium | medium |
| splF | very low/none | low | low |
| splD | very low/none | very low/none | very low/none |
| SAUSA 300_2268 | low | high | medium |
| SAUSA 300_2616 | very low/none | low | low |
| SAUSA 300_2617 | very low/none | low | low |
| hlgA2 | low | high | medium |
| hrtAB | very low/none | medium | medium |

The promoter for the kill switch requires two essential characteristics. First, the promoter must turn on, or be upregulated, when the cells are exposed to blood or serum. This screen clearly shows a spectrum of promoter activity in the presence of blood or serum; some promoters are very active in blood or serum, and others less so. Depending on the mechanism of activity, different kill genes will likely require promoters with different levels of activity. For example, a kill gene that is extremely lethal, rather than toxic, may require a promoter with very low strength. As various kill genes are tested, it will be possible to return to this list of promoters and rationally build kill switches.

The second requirement is that the candidate promoter must have little or no activity when the cells are not exposed to blood or serum. As the primary purpose of 502a is to colonize the skin before exposure to MRSA, it is critical that the cells grow normally in their intended niche and kill switch activity not interfere with this function. The most desirable kill switch candidate promoters in this screen exhibited very low activity in TSB and medium/high activity in blood or serum including isdG, sbnC, sbnE, hlgB, hlb, SAUSA300_2268, hlgA2, and hrtAB. However, isd1, lrgA, lrgB, fhuB, splF, dps, SAUSA300_2616, SAUSA300_2617 may also be useful promoter candidates for further evaluation. This screen shows several candidate promoters (isdA, isdB, fhuA, ear, and fnb) were active before exposure to blood and serum, so these were deprioritized from the list of potential kill switch promoters.

Additional candidate promoters were selected from the literature for future screening including lukG, lukH, chs, efb, icaB, SAUSA300_1059, SAUSA300_0370, aur, and SAUSA300_0169, as described in Malachowa N, 2011 and Palazzolo-Ballance AM, 2008.

Example 16. qRT PCR for Genomic Expression of Blood and Serum-Responsive Promoters In this example, qRT PCR was performed for 20 endogenous *Staphylococcus aureus* genes found in the literature to be blood and/or serum responsive. The screen was used to help identify candidate blood and/or serum responsive promoters for use in construction of a kill switch molecular modification comprising a cell death gene. Briefly, 502a cells were grown in TSB media, blood, or serum, and RNA was extracted at various time points. In addition, several *Staphylococcus aureus* genes were tested that are predicted to be unresponsive in blood or serum. These are considered to be candidates for a second promoter to be operably linked to an antitoxin specific for the cell death gene. The results show several genes that are upregulated in blood or serum and a few that are stable in blood or serum.

Growth Procedure. A growth experiment was performed as follows. 4 ml overnight culture of' 502a cells was inoculated with a small scoop of competent cells. In the morning, a 125 ml disposable sterile shake flask was inoculated with 50 ml of overnight culture to an optical density (OD) of 0.1. Cells were grown to an OD of 2 (several hours), At OD 2, 500 ul was removed for a T=0 RNA sample. 3×7 ml of the remaining cells were transferred to triplicate 50 ml conical tubes. The tubes were spun, supernatant decanted, washed with PBS, spun again, supernatant removed, and cells resuspended in 7 ml TSB, serum, or blood. Tubes were placed at 37° C. with shaking at 240 rpm. Additional RNA samples were collected at Tel (tubes were sampled immediately and did not shake at 37° C.), T=15 and T=45 minutes after exposure to serum or blood. RNA sampling method for TSB and serum cultures consisted of 500 ul transferred to a 1.5 ml tube, cells spun at 13,200 rpm for 1 minute, supernatant decanted, and 100 ul of RNALater added. Sampling for blood cultures was the same, except the supernatant was aspirated, and 200 ul of RNALater was added. All samples were stored at −20° C. until further processing (10 months of storage).

qPCR. Sample Processing and Data Analysis. RNA extraction and cDNA synthesis was performed. Frozen RNA pellets stored in RNALater were washed once in PBS, extracted using Ambion RiboPure Bacteria kit and eluted in 2×25 ul. RNA samples were DNased using Ambion Turbo DNase kit. Samples with a final concentration less than 50 ng/ul were ethanol precipitated to concentrate DNA. 10 ul of DNased RNA was used in Applied Biosystems High-Capacity cDNA Reverse Transcription kit. qPCR was performed with Applied Biosystems PowerUp SYBR Green Master Mix (10 ul reaction with 1 ul of cDNA). Samples were probed to look for changes in gene expression over time and in different media, and normalized to housekeeping gene, gyrB, using the ΔΔCt method. Ct (cycles to threshold) values for gyrB transcripts were subtracted from Ct values for gene transcripts for each RNA sample. These ΔCt values were then normalized to the initial time point. Primers for qRT PCR screening of candidate serum and/or blood responsive genes are shown in Table 24.

TABLE 24

Primers for qRT PCR screening of candidate serum and/or blood responsive genes

| Gene | qRT PCR Primers (BPC#-sequence) | |
|---|---|---|
| | Forward | Reverse |
| gyrB | BPC802-TTGGTACAGGAATCGGTGGC (SEQ ID NO: 212) | BPC803-TCCATCCACATCGGCATCAG (SEQ ID NO: 213) |
| isdA | BPC114-GCAACAGAAGCTACGAACGC (SEQ ID NO: 214) | BPC115-AGAGCCATCTTTTTGCACTTGG (SEQ ID NO: 215) |
| isdB | BPC116-GCAACAATTTTATCATTATGCCAGC (SEQ ID NO: 216) | BPC117-TGGCAACTTTTTGTCACCTTCA (SEQ ID NO: 217) |
| isdI | BPC764-ACCGAGGATACAGACGAAGTT (SEQ ID NO: 218) | BPC765-TGCTGTCCATCGTCATCACTT (SEQ ID NO: 219) |
| isdG | BPC120-AACCAATCCGTAAAAGCTTGC (SEQ ID NO: 220) | BPC121-AGGCTTTGATGGCATGTTTG (SEQ ID NO: 221) |
| sbnC | BPC768- AGGGAAGGGTGTCTAAGCAAC (SEQ ID NO: 222) | BPC769-TCAGTCCTTCTTCAACGCGA (SEQ ID NO: 223) |
| sbnE | BPC124-ATTCGCTTTAGCCGCAATGG (SEQ ID NO: 224) | BPC125-GCAACTTGTAGCGCATCGTC (SEQ ID NO: 225) |
| lrgA | BPC126-GATACCGGCTGGTACGAAGAG (SEQ ID NO: 226) | BPC127-TGGTGCTGTTAAGTTAGGCGA (SEQ ID NO: 227) |
| lrgB | BPC128-ACAAAGACAGGCACAACTGC (SEQ ID NO: 228) | BPC129-GGTGTAGCACCAGCCAAAGA (SEQ ID NO: 229) |
| hlgB | BPC760-TGGTTGGGGACCTTATGGAAG (SEQ ID NO: 230) | BPC761-GGCATTTGGTGTTGCGCTAT (SEQ ID NO: 231) |
| fhuA | BPC132-CACGTTGTCTTTGACCACCAC (SEQ ID NO: 232) | BPC133-TGGGCAATGGAAGTTACAGGA (SEQ ID NO: 233) |
| fhuB | BPC134-CAATACCTGCTGGAACCCCA (SEQ ID NO: 234) | BPC135-GGGTCCGCATATTGCCAAAC (SEQ. ID NO: 235) |
| ear | BPC136-CCACTTGTCAGATCTGCTCCT (SEQ ID NO: 236) | BPC137-GGTTTGGTTACAGATGGACAAACA (SEQ ID NO: 237) |
| fnb | BPC772-CGCAGTGAGCGACCATACA (SEQ ID NO: 238) | BPC773-TTGGTCCTTGTGCTTGACCA (SEQ ID NO: 239) |
| hlb | BPC140-CTACGCCACCATCTTCAGCA (SEQ ID NO: 240) | BPC141-ACACCTGTACTCGGTCGTTC (SEQ ID NO: 241) |
| splF | BPC142-TGCAATTATTCAGCCTGGTAGC (SEQ ID NO: 242) | BPC143-CCTGATGGCTTATTACCGGCAT (SEQ ID NO: 243) |
| splD | BPC144-AGTGACATCTGATGCGGTTG (SEQ ID NO: 244) | BPC145-AACACCAATTGCTTCTCGCTT (SEQ ID NO: 245) |

TABLE 24-continued

| Primers for qRT PCR screening of candidate serum and/or blood responsive genes | | |
|---|---|---|
| | qRT PCR Primers (BPC#-sequence) | |
| Gene | Forward | Reverse |
| dps | BPC146-AGCGGTAGGAGGAAACCCTG (SEQ ID NO: 246) | BPC147-GTTCTGCAGAGTAACCTTTCGC (SEQ ID NO: 247) |
| srtB | BPC846-TGAGCGAGAACATCGACGTAA (SEQ ID NO: 248) | BPC847-CCGACATGGTGCCCGTATAA (SEQ ID NO: 249) |
| emp | BPC854-TCGCGTGAATGTAGCAACAAA (SEQ ID NO: 250) | BPC855-ACTTCTGGGCCTTTAGCAACA (SEQ ID NO: 251) |
| sbnA | BPC858-CCTGGAGGCAGCATGAAAGA (SEQ ID NO: 252) | BPC859-CATTGCCAACGCAATGCCTA (SEQ ID NO: 253) |
| CH52_ 360 | BPC834-TTCAACTCGAACGCTGACGA (SEQ ID NO: 254) | BPC835-TTGCACCCATTGTTGCACCT (SEQ ID NO: 255) |
| CH52_ 305 | BPC838-TTCCTGGAGCAGTACCACCA (SEQ ID NO: 256) | BPC839-CAGCGCAATCGCTGTTAAACTA (SEQ ID NO: 257) |
| CH521670 | BPC842-GCGATTATGGGACCAAACGG (SEQ ID NO: 258) | BPC843-ACTTCATAGCTTGGGTGTCCC (SEQ ID NO: 259) |
| clfA | BPC850-TCCAGCACAACAGGAAACGA (SEQ ID NO: 260) | BPC851-TAGCTTCACCAGTTACCGGC (SEQ ID NO: 261) |
| SAUSA300_ 2268 | BPC778-GCTTCTACAGCTTTGCCGAT (SEQ ID NO: 262) | BPC779-GATTTGGTGCTTACTGCCACC (SEQ ID NO: 263) |
| SAUSA300_ 2616 | BPC774-ACAAGCGCAACAAGCAAGAG (SEQ ID NO: 264) | BPC775-TGCGTTTGATACCTTTAACACGG (SEQ. ID NO: 265) |
| SAUSA300_ 2617 | BPC152-GGGCTGAAAAAGTTGGCATGA (SEQ ID NO: 266 ) | BPC153-ACCGCGTTGTTTTTGACCTCC (SEQ ID NO: 267) |
| hlgA2 | BPC179-TGATTTCTGCACCTTGACCGA (SEQ ID NO: 268) | BPC180-AGCCCCTTTAGCCAATCCAT (SEQ ID NO: 269) |
| hrtAB | BPC713-ACACAACAACAACGTGATGAGC (SEQ ID NO: 270) | BPC714-TAACGGTGCTTGCTCTGCTT (SEQ ID NO: 271) |

Figure 13A:
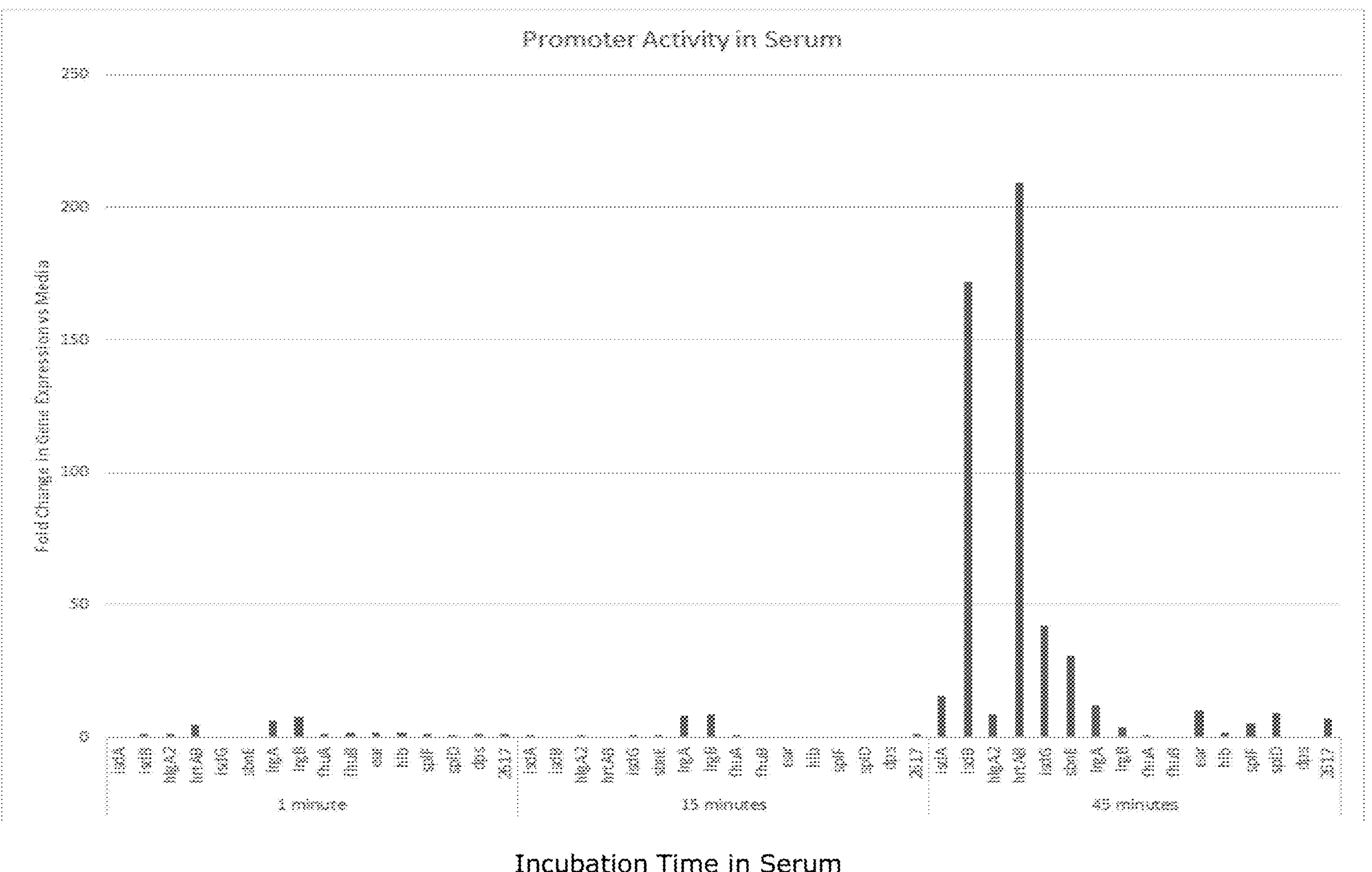
FIG. 13A shows activity of promoter candidates isdA, isdB, hlgA2, hrtAB, isdG, sbnE, lrgA, lrgB, fhuA, fhuA, fhuB, hlb, splF, splD, dps, and SAUSA300_2617 at 1 min, 15 min and 45 min in serum and fold changes in gene expression vs. media by qPCR.
Figure 13B:
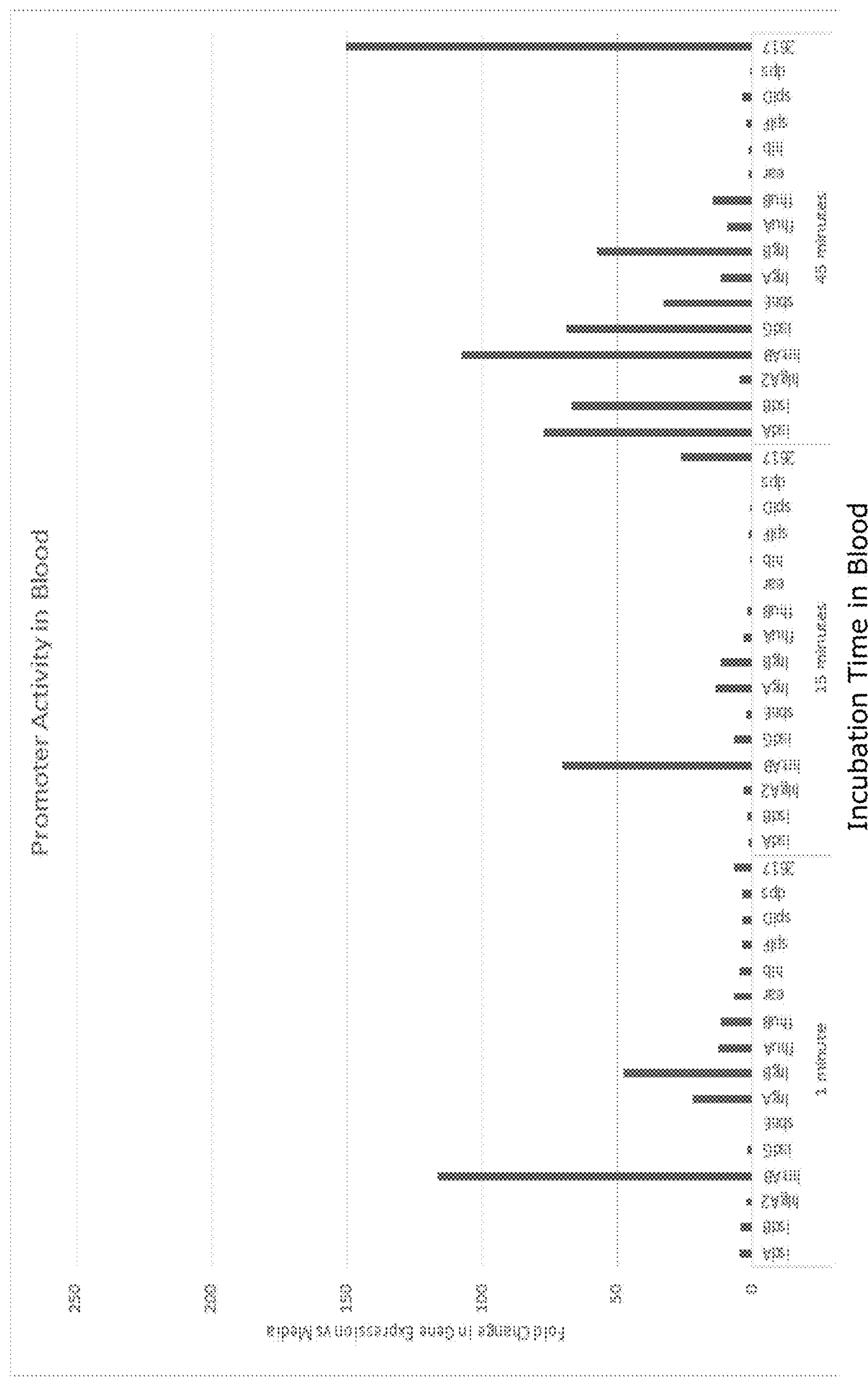
FIG. 13B shows activity of promoter candidates isdA, isdB, hlgA2, hrtAB, isdG, sbnE, lrgA, lrgB, fhuA, fhuB, ear, hlb, splF, splD, dps, and SAUSA300_2617 at 1 min, 15 min and 45 min in blood and fold changes in gene expression vs. media by qPCR.

The qPCR results are shown in FIGS. 13A and 13B showing several genes that are upregulated in blood and/or serum. FIG. 13A shows promoter candidates isdA, isdB, hlgA2, hrtAB, isdG, sbnE, lrgA, lrgB, fhuA, fhuB, ear, hlb, splF, splD, dps, and SAUSA300_2617 at 1 min, 15 min and 45 min in serum and fold changes in gene expression vs. media. Preferred serum responsive promoter candidates in this screen include hlgA2, hrtAB, isdA, isdB, isdG, sbnE, ear, and splD, as shown in Table 25 because they exhibit at least a 9-fold increase in gene expression when exposed to serum after 45 min, a slightly delayed response to serum, and are not significantly upregulated at T=1 min.

TABLE 25

| Preferred promoter candidates for serum-responsive genes by qPCR | |
|---|---|
| Upregulated Gene | Fold Change in Serum at T = 45 min |
| hlgA2 | 9 |
| hrtAB | 209 |
| isdA | 15 |
| isdB | 172 |
| isdG | 42 |
| sbnE | 30 |
| ear | 10 |
| splD | 9 |

FIG. 13B shows candidate promoter activity when exposed to blood of promoter candidates isdA, isdB, hlgA2, hrtAB, isdG, sbnE, lrgA, lrgB, fhuA, fhuB, ear, hlb, splF, splD, dps, and SAUSA300_2617 at 1 min, 15 min and 45 min in serum and fold changes in gene expression vs. media by qPCR. Preferred promoter candidates exhibited a slightly delayed gene expression response at 1 minute, but were significantly upregulated at least 30-fold the 15 and 45 min time points. Preferred promoter candidates for blood-responsive genes by qPCR included isdA, isdB, isdG, sbnE, and SAUSA300_2617, as shown in Table 26.

TABLE 26

| Preferred promoter candidates for blood-responsive genes by qPCR | |
|---|---|
| Upregulated Gene | Fold Change in Blood at T = 45 |
| isdA | 77 |
| isdB | 66 |
| isdG | 69 |
| sbnE | 33 |
| SAUSA300_2617 | 150 |

Another qRT PCR for Genomic Expression of Serum-Responsive Promoters In this example, qRT PCR is also performed for screening further *Staphylococcus aureus* genes found in the literature to be blood and/or serum responsive. Briefly, 502a cells were grown in TSB media or serum, and RNA was extracted at various time points. The results show several genes that are highly upregulated in serum. Essentially, the experimental protocol was similar to the example above, except RNA samples were normalized before conversion to cDNA, and samples were collected at T=90 min.

Growth Procedure. The growth experiment was performed as follows. 502a glycerol stock was struck onto a fresh bacterial plate and grown overnight. 3-5 single colonies from the plate were inoculated into a 4 ml culture of BHI media and grown overnight at 37° C. with shaking at 240 rpm. In the morning, the culture was dilated to an optical density (OD) of 0.05 in 5 ml fresh BHI media. Cells were grown at 37° C. with shaking at 150 rpm for several hours to an OD of approximately 1. At this time, samples for RNA were collected for a T=0 time point (1 ml was transferred to a 1.5 ml microcentrifuge tube, centrifuged at 16,000 rpm for 1 minute, supernatant dumped, cells resuspended in 1 ml sterile PBS, centrifuged at 16,000 rpm for 1 minute, supernatant aspirated, cells resuspended in 200 ul RNALater, and stored at −20° C.). The remaining culture was rediluted to an OD of 0.05 in 3 replicate heparinized tubes of 10 ml fresh BHI media or thawed human serum, and incubated at 37° C. with shaking at 150 rpm. Additional samples for RNA were collected at T=90 minutes, and T=180 minutes. For these later samples, one 10 ml tube was centrifuged at 3,000 rpm for 10 minutes, supernatant dumped, cells resuspended in 1 ml PBS, transferred to a 1.5 ml microcentrifuge tube, centrifuged at 16,000 rpm for 1 minute, supernatant aspirated, cells resuspended in 200 ul RNALater, and stored at −20° C.

qPCR Sample Processing and Data Analysis. RNA extraction and cDNA synthesis was performed as follows. Frozen RNA pellets stored in RNALater were washed once in PBS, extracted using Ambion RiboPure Bacteria kit and eluted in 2×50 ul. RNA samples were DNased using Ambion Turbo DNase kit. Samples with a final concentration less than 50 ng/ul were ethanol precipitated to concentrate DNA. 500 ng of DNased RNA was used in Applied Biosystems High-Capacity cDNA Reverse Transcription kit. qPCR was performed with Applied Biosystems PowerUp SYBR Green Master Mix (10 ul reaction with 1 ul of cDNA).

Samples were probed to look for changes in gene expression over time and in different media, and normalized to housekeeping genes, gyrB, sigB, rho, or an average of the three, using the ΔΔCt method. Ct (cycles to threshold) values for housekeeping gene transcripts were subtracted from Ct values for gene transcripts for each RNA sample. These ΔCt values were then normalized to the initial time point. Gene expression at 90 minutes in both TSB and serum were normalized to values at T=0.

Figure 13C:
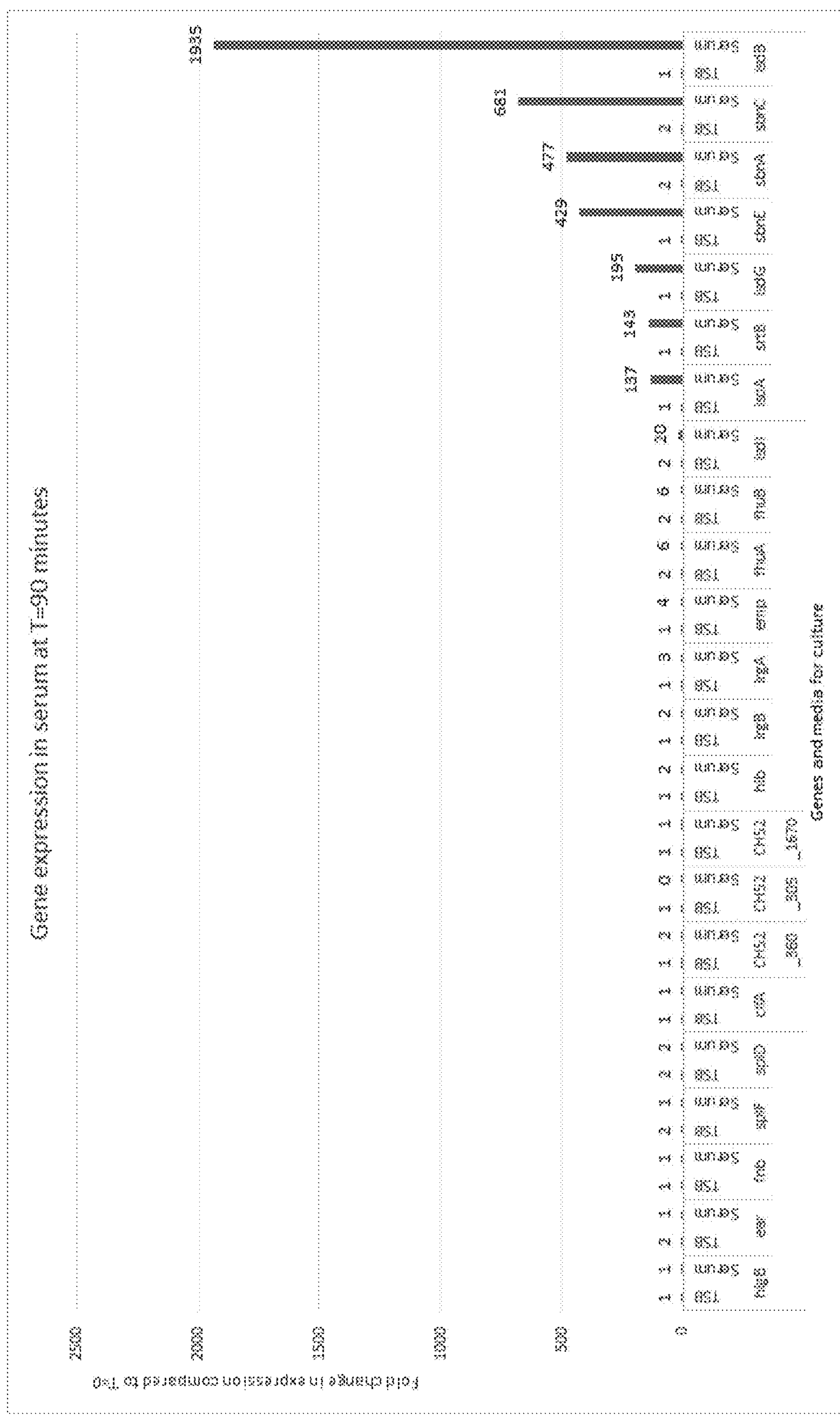

Results are shown in FIG. 13C which shows gene expression in serum at T=90 min for promoter candidates hlgB, ear, fnb, splF, splD, clfA, CH52_360, CH52_305, CH52_1670, hlb, lrgB, lrgA, emp, fhuA, fhuB, isdI, isdA, srtB, isdG, sbnE, sbnA, sbnC, and isdB by qPCR compared to TSB. FIG. 13C shows genes upregulated greater than 5-fold in serum include fhuA, fhuB, isdI, isdA, srtB, isdG, sbnE, sbnA, sbnC, and isdB. FIG. 13C shows several genes are upregulated greater than 100-fold after 90 minutes of incubation in serum including isdA, srtB, isdG, sbnE, sbnA, sbnC, and isdB. Specifically, genes in the isd, sbn, and fhu families are upregulated to varying degrees. All of the genes surveyed here have stable expression from T=0 to T=90 minutes in TSB. Several genes from this experiment show high upregulation in serum, while others show stable expression in serum. Both of these characteristics may be useful in construction of a kill switch. For example, a cell death gene may be controlled with a promoter that will upregulate in serum and/or blood, and an antitoxin gene specific for the cell death gene may be controlled with a promoter that will downregulate or remain stable in serum.

Example 17. Sprat as a Candidate Cell Death Gene Toxin Using Plasmid Based Induction Systems In this example, candidate cell death gene sprA1 was evaluated using two different plasmid based induction systems in two *Staphylococcus aureus* strains.

Example 17A. Initial testing of sprA1 as an inhibitor of cell growth of Staph *aureus* cells (RN4220) was performed using a cadmium inducible promoter. A spra1 toxin gene was cloned behind the cadmium promoter in pCN51 (pTK1). pCN51 vector is a low copy plasmid containing a cadmium inducible promoter.

This version of spra1 contains an antisense which regulates spra1. The full sequence of the sprA1-sprA1AS which is downstream of the cadmium promoter is shown below. This construct is called pTK1.

pTK1: sprA1-sprA1AS: sprA1 toxin gene and ribosome binding site, and antitoxin gene (pTK1 or p001). pTK1 was used in experiments with Cadmium promoter.

(SEQ ID NO: 272)

CGCAGAGAGGAGGTGTATAAGGTGATGCTTATTTTCGTTCACATCATAGC

ACCAGTCATCAGTGGCTGTGCCATTGCGTTTTTTTCTTATTGGCTAAGTA

GACGCAATACAAAATAGGTGACATATAGCCGCACCAATAAAAATCCCCTC

ACTACCGCAAATAGTGAGGGGATTGGTGTATAAGTAAATACTTATTTTCG

TTGT

Ribosome Binding Site Region
sprA1 Toxin Gene
sprA1 Antitoxin Gene (SEQ ID NO: 273)

CCCCTCACTACCGCAAATAGTGAGGGGATTGGTGTATAAGTAAATACTTA

TTTTCGTTGT sprA1 antitoxin gene

Cadmium is a toxic compound so the first step was to find the sub-inhibitory concentration in which the cadmium has enough of a minimal effect on growth to see a marked delta if sprA1 is having a negative on growth of RN4220. RN4220's were grown overnight in TSB media and diluted down to 0.5 ODs and separated into eight 14 ml culture tubes each containing 3 ml of diluted RN4220 cells. Four concentrations of cadmium were inoculated into 4 tubes with each having no cadmium control. 10 nM, 100 nM, 1 uM and 10 uM were the final cadmium concentrations. The results were evaluated at 2 and 22 hours of growth at 30° C. with 240 RPM shaking (data not shown). After 22 hours the 10 uM Cadmium showed the greatest negative effect. The experiment of determining the minimal sub-inhibitory concentration of cadmium was repeated in duplicate using 10 nM, 100 nM and 1 uM cadmium using *Staphylococcus aureus* RN4220 cells. After 2 hours, cell growth results from the cadmium test show good tolerance up to 1 uM (data not shown).

Next, 500 nM and 1 uM cadmium was tested using RN4220 cells transformed with pCN54 which has a cadmium inducible promoter was used as an additional control. RN4220 cells were diluted to 0.5 ODs (630 nm) and aliquoted to 4 culture tubes each with 3 ml. Two of the tubes were inoculated with 500 nM and 1 uM cadmium. RN4220 cells containing pCN54 were diluted to 0.5 ODs (630 nm) and aliquoted to 4 culture tubes each with 3 ml. Two of the tubes were inoculated with 500 nM and 1 uM cadmium. All pCN54 growths contained erythromycin 10 as an antibiotic selection. After 2 hours of growth at 30° C., ODs (630 nm) were measured. Results showed good tolerance at 500 nM and 1 uM cadmium. (data not shown). It was concluded that the 4220 cells exhibited good cadmium tolerance at the levels tested except for 10 uM which was too high of a concentration to potentially see a difference between cadmium effects only and an induced toxin. The next experiments included a toxin (sprA1) behind a cadmium promoter on a pCN51 plasmid (pTK1) which had been transformed into RN4220 cells. Both 500 nM and 1 uM concentrations were tested with 2 pTK1 clone picks and RN4220 cells (wt). Overnight cultures of wt RN4220 cells and two clones of pTK1 in RN4220 cells were diluted to 0.5 ODs. Wild-type (WT) RN4220 cells were divided into 3 culture tubes at 3 ml/tube. Two tubes were inoculated with 500 nM and 1 uM cadmium and ODs were read after 2 hours post induction. Each pTK1 clone was divided into 3 culture tubes at 3 ml/tube (6 tubes total). Each pTK1 clone was induced with 500 nm and 1 uM with one being a control. ODs were read after 2 hours post induction. Results are shown in the Table 27 and FIG. 14.

Figure 14:
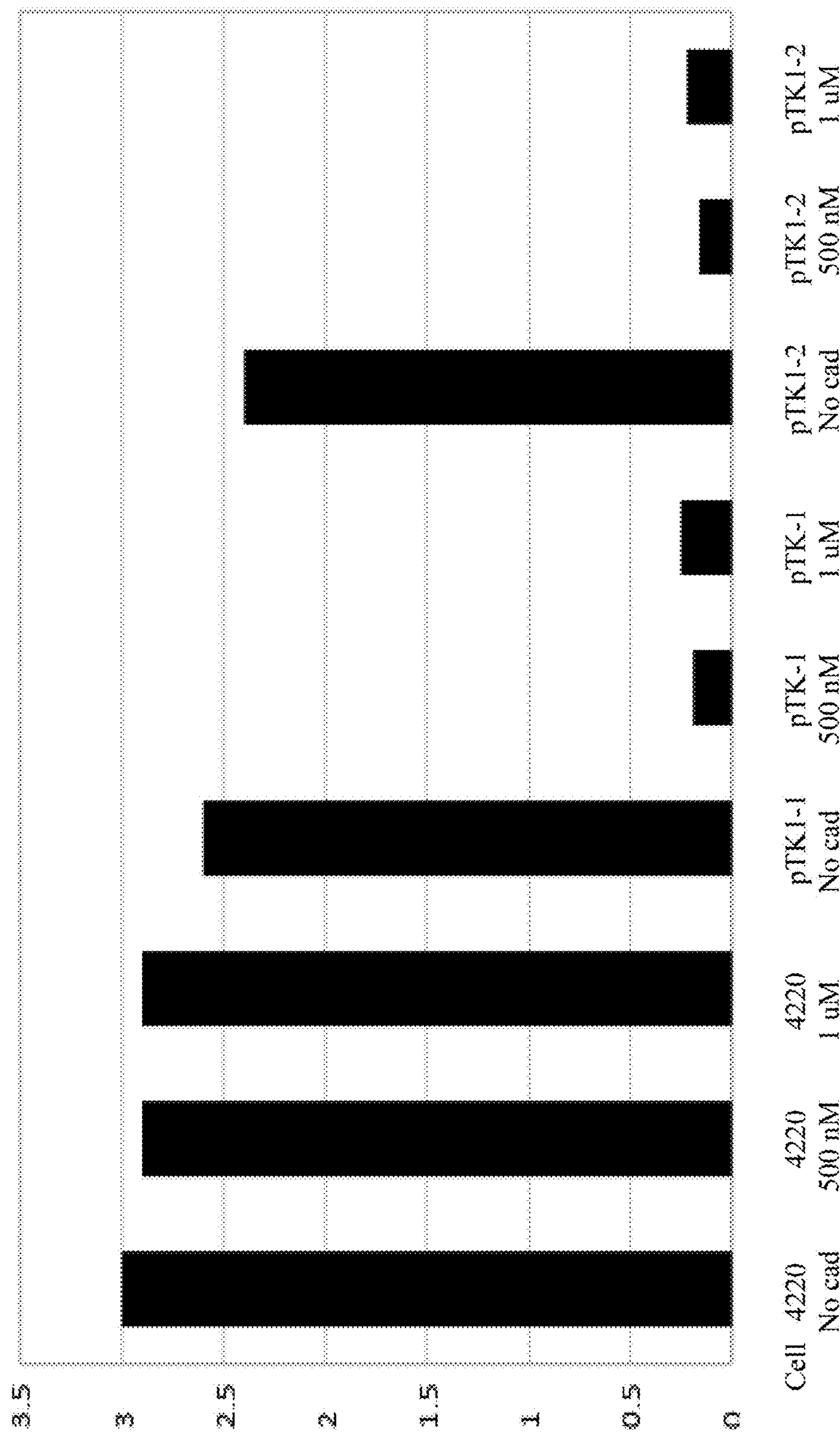
FIG. 14 shows inducible inhibition of cell growth of synthetic microorganism pTK1 cells comprising a cell death toxin gene (sprA1) behind a cadmium promoter on a pCN51 plasmid (pTK1) which had been transformed into *Staphylococcus aureus* RN4220 cells. OD (630 nm) read at 2 hrs post induction. Wild-type 4220 cells showed good cell growth both in the absence of cadmium and in the presence of 500 nM and 1 uM cadmium. pTK1-1 and pTK1-2 cells showed good growth in the absence of cadmium, but cell growth was significantly inhibited in presence of 500 nM and 1 uM cadmium at 2 hours post induction.

FIG. 14 shows inducible inhibition of cell growth of synthetic microorganism pTK1 cells comprising a cell death toxin gene (sprA1) behind a cadmium promoter on a pCN51 plasmid (pTK1) which had been transformed into *Staphylococcus aureus* RN4220 cells. OD (630 mm) read at 2 hrs post induction, as shown in Table 27. Wild-type 4220 cells showed good cell growth both in the absence of cadmium and in the presence of 500 nM and 1 uM cadmium. pTK1-1 and pTK1-2 cells showed good growth in the absence of cadmium, but cell growth was significantly inhibited in presence of 500 nM and 1 uM cadmium at 2 hours post induction.

TABLE 27

*Staphylococcus aureus* RN4220 cells Optical Density (630 nm) 2 hours post-induction

| Cells | 2 Hr Post OD (630 nm) |
|---|---|
| WT4220 Cad− | 3.0 |
| WT 4220 Cad+ 500 nM | 2.9 |
| WT 4220 Cad+ 1 uM | 2.9 |
| ptK1-1 Cad− | 2.6 |
| pTK1-1 Cad+ 500 nM | 0.19 |
| pTK1-1 Cad+ 1 uM | 0.25 |
| ptK1-2 Cad− | 2.4 |
| pTK1-2 Cad+ 500 nM | 0.16 |
| pTK1-2 Cad+ 1 uM | 0.22 |

The experiment was reproduced and each sample exhibited similar OD (630 nm) results at 2 hrs post-induction (data not shown). In summary, a cadmium tolerance test was performed on wt RN4220 cells and 500 nM-1 uM cadmium showed minimal negative on RN4220 cells. This example shows induction of pTK1 showed suppression of cell growth when induced with cadmium.

Figure 15A:
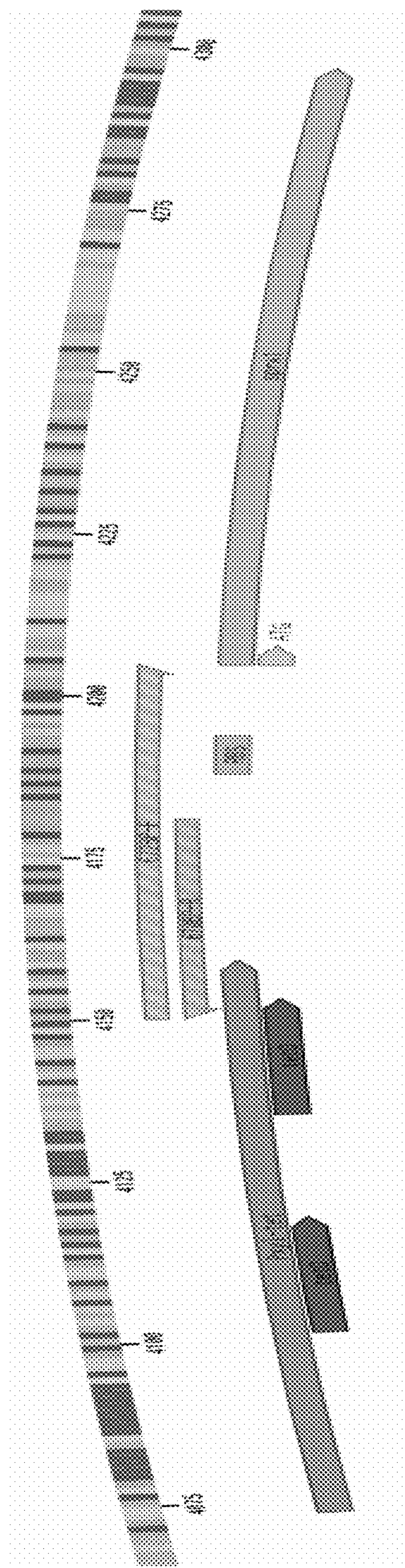
FIG. 15A shows a plasmid map of p174 (pRAB11_Ptet-sprA1) zoomed view of the region of the plasmid containing the Ptet-sprA cassette.
Figure 15B:
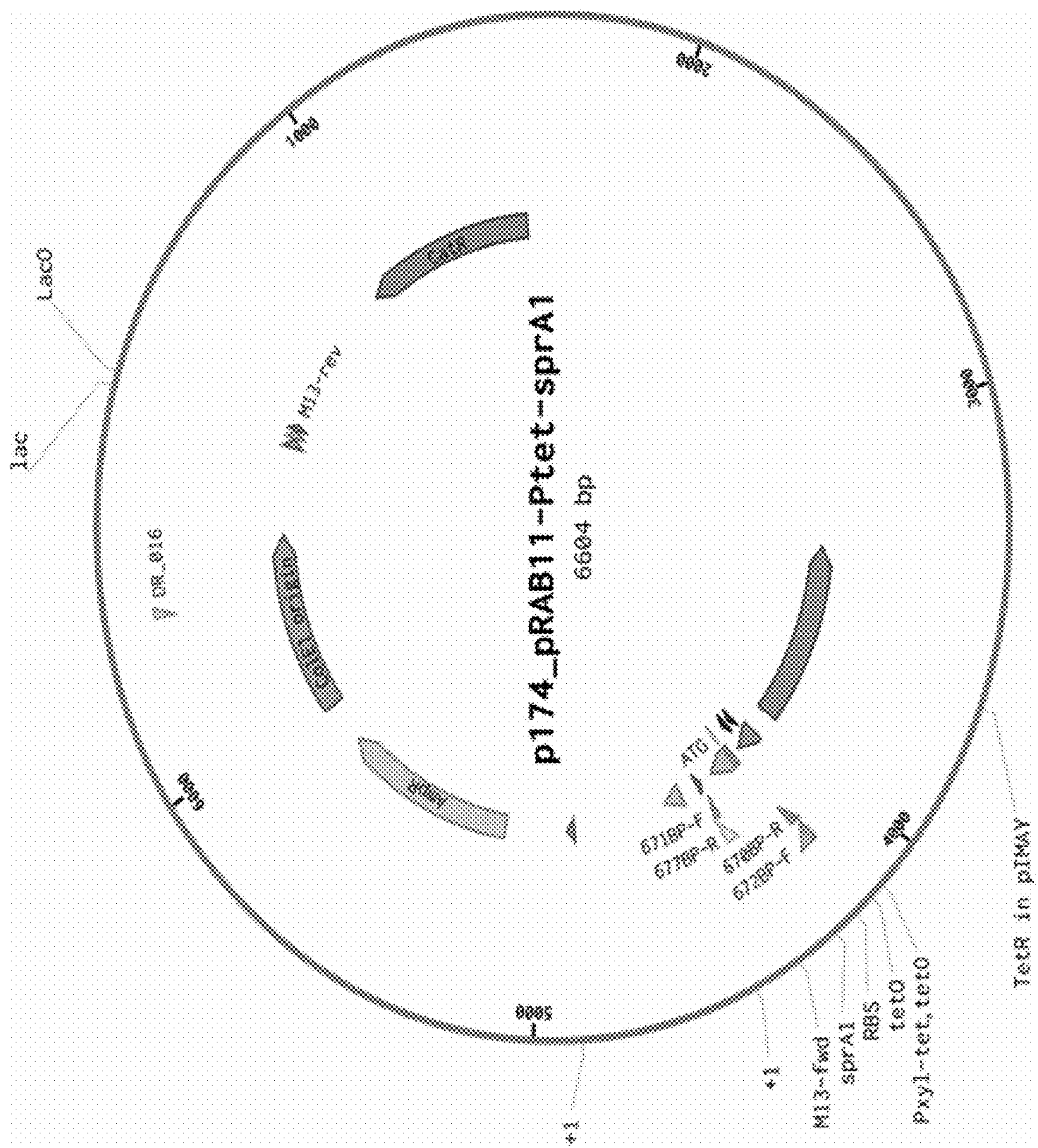
FIG. 15B shows the p174 (pRAB11_Ptet-sprA1) whole plasmid in its native circular form.

Example 17B. Candidate cell death gene SprA1 was evaluated as an inhibitor of cell growth of *Staph aureus* cells (502a) using an anhydrotetracycline (ATc) inducible promoter: pRAB11 which is a high copy plasmid containing a tetracycline inducible promoter. Two versions of the sprA1 toxin were cloned behind the tet promoter in pRAB11-2. Clones tested were p174 plasmid containing a deleted spra1 antisense (Das) and p175 plasmid which contains a deleted spra1 antisense plus a missing RBS site. A plasmid map of p174(pRAB11_Ptet-sprA1) is shown in FIGS. 15A and 15B. FIG. 15A shows a zoomed view of the region of the plasmid containing the Ptet-sprA cassette, FIG. 15B shows the p174 whole plasmid in its native circular form.

Sequences employed in p174 and p175 are shown below. Both p174 and p175 were used in experiments using a tetracycline promoter

```
p174 sprA1: sprA1 toxin gene and ribosome binding
site (p174):
                                      (SEQ ID NO: 274)
CGCAGAGAGGAGGTGTATAAGGTGATGCTTATTTTCGTTCACATCATAGC

ACCAGTCATCAGTGGCTGTGCCATTGCGTTTTTTTCTTATTGGCTAAGTA

GACGCAATACAAAATAGGTGACATATAGCCGCACCAATAAAAAT

p175 sprA1(ATG): sprA1 toxin gene beginning at
start codon (ribosome binding site removed)
(p175):
                                      (SEQ ID NO: 275)
ATGCTTATTTTCGTTCACATCATAGCACCAGTCATCAGTGGCTGTGCCAT

TGCGTTTTTTTCTTATTGGCTAAGTAGACGCAATACAAAATAGGTGACAT

ATAGCCGCACCAATAAAAAT
```

Cell growth. Specifically, tet inducible genes on the pRAB11 vector in 502a cells were grown overnight growths in BHI. The p174 pRAB11-pro-tet-spra1Das exhibited 5.4 OD. The p175 pRAB11-pro-tet-spra1Das(ATG) exhibited 6.2 OD. All 5 overnight cultures were diluted to 0.5 ODs in 1 ml final (14 ml tubes) of BHI-chlor10 (502a wt just BHI). Each cell line was divided into 2 tubes for non-induced and induced anhydrotetracycline (ATc)-10 total. Induction. Literature shows induction at 100 ng/ml of ATc is effective, so this concentration was selected for induction in these experiments. One tube from each set was induced with 100 ng/ml final concentration. A 1 mg/ml ATc stock in Ethanol was diluted to 100 ug/ml in EtOH. One microliter was added to the appropriate tubes for a final of 100 ng/ml.

The OD's at 630 nm were taken at 2, 4 and 6 hours. The ODs were at 2 and 4 hours were read at a 1/10 dilation while the 6 hour OD was taken at a 1/100 dilution to make sure readings were staying in the linear range.

The 502a's (non-induced and induced) and p174 (pRAB11-pro-tet-spra1Das) tubes were serially diluted to 10e−5 and 10e−6 for dilution plating onto BHI and BHI-chlor10 respectively.

Figure 15C:
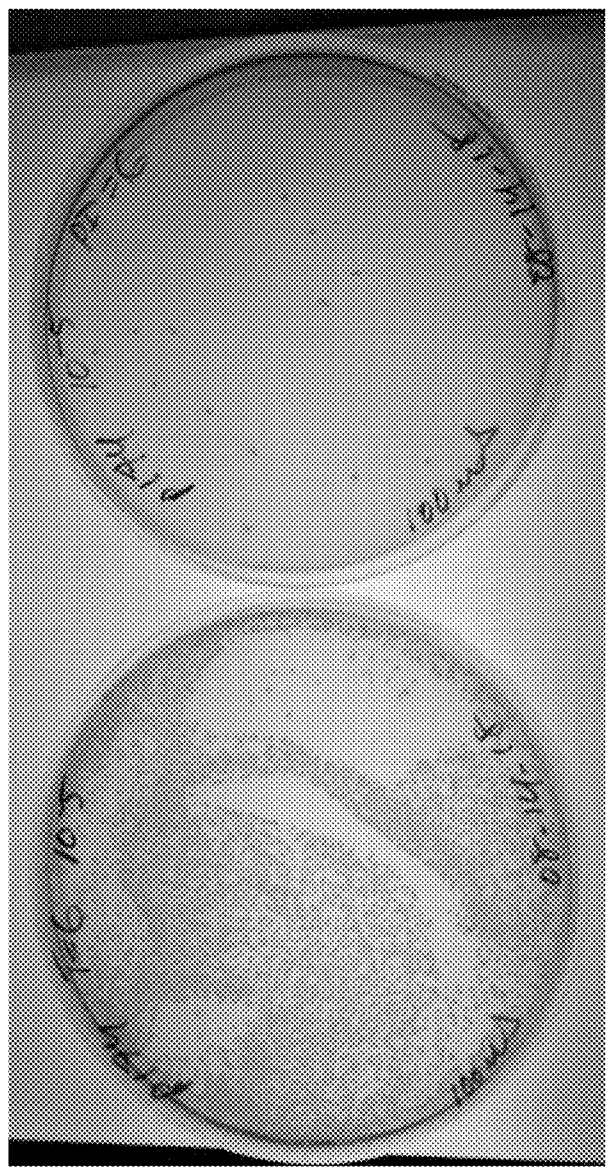
FIG. 15C shows photographs of plate dilutions at 6 hours synthetic microorganism *Staphylococcus aureus* 502a p174 cells comprising a cell death toxin gene (sprA1) behind an anhydrotetracycline promoter on a pRAB11-2 plasmid (p174) which had been transformed into *Staphylococcus aureus* 502a cells. The p174 plasmid containing a deleted spra1 antisense (Das). Plate dilutions at 10e−5 are shown after 6 hours of induction for uninduced (left) and induced (right) 502a p174 (tet-spra1Das) cells on BHI chlor10. The plate on the left (Uninduced) was uncountable at 10e−5 but at 10e−6 counted ~720 colonies. The induced plate on the right at 10e−5 produced 16 colonies. The survival percentage of induced cells at 6 hours post induction was 0.22%.

Results are shown in Tables 28 and 29 for ODs, and a plate comparison picture is shown in FIG. 15C.

TABLE 28

| Calculations Table for Induction growth curves. | | | | | |
|---|---|---|---|---|---|
| Sample Name | O/N OD | ul O/N culture | BHI | # of tubes | conditions |
| 502a wt | 4.7 | 106 | 1 ml | 2 | Un-ind. & Induced |
| 502a p174 pRAB11-ptet-sp a1Das | 5.4 | 93 | 1 ml | 2 | Un-ind. & Induced |
| 502a p175 pRAB11-ptet-spa1Das(ATG) | 6.2 | 81 | 1 ml | 2 | Un-ind. & Induced |

TABLE 29

| 502a pRAB11 tet induction experiment | | | | | | | |
|---|---|---|---|---|---|---|---|
| | $OD_{630}$ readings at time point (hours) | | | | | | |
| Sample Name | 0.0 | 1.0 | 2.0 | 3.0 | 4.0 | 5.0 | 6.0 |
| 502a wt | 0.5 | | 4.8 | | 8.0 | | 14 |
| 502a wt + 100 ng ATc | 0.5 | | 4.4 | | 7.1 | | 11 |
| 502a p174 pRAB11-ptet-spa1Das | 0.5 | | 4.5 | | 7.7 | | 13 |
| 502a p174 pRAB11-ptet-spa1Das + 100 ng ATc | 0.5 | | 0.7 | | 0.3 | | 0 |
| 502a p175 pRAB11-ptet-spa1Das(ATG) | 0.5 | | 4.3 | | 7.7 | | 7 |
| 502a p175 pRAB11-ptet-spa1Das(ATG) + 100 ng ATc | 0.5 | | 3.8 | | 8.1 | | 13 |

FIG. 15C shows plate dilutions at 10e−5 after 6 hours of induction for uninduced (left) and induced (right) 502a p174 (tet-spra1Das). The Plate on the left=uninduced p174 (tet-spra1Das) at 10e−5 dilution on BHI chlor10. Plate on the right is the induced p174 (tet-spra1Das) at 10e−5 on BHI chlor10. Both plates are samples from post-induction time point of 6 hrs. The plate on the left (Uninduced) was uncountable at 10e−5 but at 10e−6 counted~720 colonies. The induced plate on the right at 10e−5 produced 16 colonies as shown in Table 30.

TABLE 30

| Survival percentage of induced *Staphylococcus aureus* 502a p174 (tet-spra1Das) cells at 6 hours post-induction | | | | |
|---|---|---|---|---|
| Condition | Colonies | Countable Dilution | Calculation for 0.1 mls plated | CFU's/ml |
| Uninduced | 720 | 10e−6 | (720*10e6)/0.1 | 7.2* 10e9 |
| Induced | 16 | 10e−5 | (16*10e5)/0.1 | 1.6* 10e7 |

As shown in Table 30, the survival percentage of induced cells at 6 hours post-induction was calculated as 1.6*10e7/7.2*10e9=0.00222×100=0.222%. The survival percentage of induced *Staphylococcus aureus* 502a p174 (tet-spra1Das) cells at 6 hours post-induction was only 0.222% compared to uninduced cells. Therefore, the *Staphylococcus aureus* 502a p174 cells exhibited 100%−0.222%=99.78% measurable average cell death at 6 hours post-induction compared to uninduced cells.

In summary, induction with 100 ng/ml ATc showed good suppression of growth of p174 in 502a cells up to 6 hours post induction of less than 1%, less than 0.5%, or less than 0.25%. Specifically, CFU counts at the end of 6 hours showed a survival percentage of only 0.22% when compared to the uninduced sample and 502a wild type. Induction of p175 control with the deleted RBS site for spra1 showed no negative effects on growth up to 6 hours. In summary, induction of p174 showed suppression of cell growth when induced with ATc. However, induction of p175 control lacking RBS showed no suppression of cell growth when induced with ATc, comparable to 502a wild type cells.

Example 18. 502a Inducible Plasmid Based Expression of Various Toxin Genes

This example shows the effectiveness of various candidate cell death toxin genes that may be used for a kill switch in *Staphylococcus aureus* 502a. A plasmid based inducible toxin expression was used for this experiment. pRAB11 is a high copy plasmid in Staph *aureus Staphylococcus aureus*, and the Ptet promoter is derepressed by the addition of 100 ng/mL of AtC (anhydrotetracycline), allowing for high transcription rates. pRAB11 is described in Helle, Leonie, et al. "Vectors for improved Tet repressor-dependent gradual gene induction or silencing in *Staphylococcus aureus*." Microbiology 157.12 (2011): 3314-3323. Four candidate cell death toxin genes were selected for evaluation: sprA1, 187-lysK, Holin, and sprG.

sprA1 (PepA1). The gene srpA1 found in *Staphylococcus aureus* strains has been shown to code for a small membrane toxin PepA1. Sayed, Nour et al. "Functional and Structural Insights of A *Staphylococcus Aureus* Apoptotic-like Membrane Peptide from a Toxin-Antitoxin Module." *Journal of Biological Chemistry*, vol. 287, no. 52, 2012, pp. 43454-43463. doi: 10.1074/jbc.m112.402693. Sayed et al. described how the sprA1 gene codes for the toxin protein called PepA1, which localizes at the bacterial membrane and causes cell death. This is part of a type I toxin antitoxin system in *Staphylococcus aureus*, and has been evolutionarily preserved in their genome.

187-lysK. This is an engineered phage lysin protein from the *Staphylococcus aureus* phage K. Horgan, Marianne, et al. "Phage lysin LysK can be truncated to its CHAP domain and retain lytic activity against live antibiotic-resistant staphylococci." *Applied and environmental microbiology* 75.3 (2009): 872-874. O'Flaherty et al. designed and truncated this peptide and determined it to still retain is lytic activity for many *Staphylococcus aureus* strains. O'Flaherty, S., et al. "The recombinant phage lysin LysK has a broad spectrum of lytic activity against clinically relevant staphylococci, including methicillin-resistant *Staphylococcus aureus." Journal of bacteriology* 187.20 (2005): 7161-7164.

holin. The holin toxin we tested in this experiment is part of the genome of many lytic phages that target *Staphylococcus aureus*. It has been shown to disrupt cell growth in *E. coli* when induced from a plasmid expression vector by forming lesions in the cellular membrane. Song, Jun, et al. *Journal of General Virology* 97.5 (2016): 1272-1281.

sprG. The coding region termed sprG is part of another type I toxin antitoxin system in *Staphylococcus aureus*. Two peptides are coded for in the same reading frame of sprG, and both have been shown to cause cell death when induced. Pinel-Marie et al. Cell reports 7.2 (2014): 424-435.

Materials. Various synthetic strains were prepared as shown below and 502a wt was also employed. Strains include:

BP_068(502a pRAB11-Ptet-sprA1)

BP_069 (502a pRAB11-Ptet-187lysK)

BP_070 (502a pRAB11-Ptet-holin)

BP_071 (502a pRAB11-Ptet-sprG1)

BP_001 (502a wt).

Growth Media used in this example included BHI broth media (37 g/L) (Alpha Biosciences), BHI agar plates, BHI Chloramphenicol (10 ng/ml. (Teknova)) agar plates, and BHI Chlor (10 µg/mL (Teknova))+AtC (100 ng/ml. (Alfa Aesar)) agar plates. Table 31 below shows a list of oligonucleotide sequences used for constructing the plasmids.

TABLE 31

List of oligos and their sequences used for constructing plasmids

| Oligo Name | DNA sequence (5' - 3') |
|---|---|
| BPC_670 | GCTCAGATCTGTTAACGGTACCATCATACTC (SEQ ID NO: 276) |
| BPC_671 | CACTGGCCGTCGTTTTACAAC (SEQ ID NO: 277) |
| BPC_672 | gagtatgatggtaccgttaacagatctgagcCGCAGAGAGGAGGTGTATAAGGTG (SEQ ID NO: 278) |
| BPC_674 | gagtatgatggtaccgttaacagatctgagcATGGTGGCATTACTGAAATCTTTAGA AAG (SEQ ID NO: 279) |
| BPC_675 | gagtatgatggtaccgttaacagatctgagcATGGCACTGCCTAAAACGGG (SEQ ID NO: 280) |
| BPC_676 | gagtatgatggtaccgttaacagatctgagcATGGCTAATGAAACTAAACAACCTA AAGTT (SEQ ID NO: 281) |
| BPC_677 | gttgtaaaacgacggccagtgCCCGGGCTCAGCTATTATCA (SEQ ID NO: 282) |
| BPC_678 | gttgtaaaacgacggccagtgGCGGCCGCCCATGCATGC (SEQ ID NO: 283) |

Table 32 shows the DNA sequence and amino acid sequence for toxin genes. sprA1, 187-lysK, holin, and sprG) were tested in this experiment: The toxin gene sprG has two reading frames which have both been shown to have toxin activity in *Staphylococcus aureus*. The shorter sequence is in bold.

TABLE 32

DNA and amino acid sequences for toxins

| Toxin | DNA Sequence | Protein Sequence |
|---|---|---|
| sprA1 | ATGCTTATTTTCGTTCACATCATAGCACCAGT CATCAGTGGCTGTGCCATTGCGTTTTTTTCTT ATTGGCTAAGTAGACGCAATACAAAATAG (SEQ ID NO: 284) | LIFVHIIAPVISGCAIAFFSY WLSRRNTK (SEQ ID NO: 285) |
| 187-lysK | Atggcactgcctaaaacgggtaaaccaacggcaaaacaggtggttgact gggcaatcaatttaatcggcagtggtgtcgatgttgatggttattatggtcgg caatgttgggatttacctaactatatttttaatagatactggaactttaagacac caggcaacgcaagagatatggcatggtatagatatcctgaagggtttaaag tgtttagaaacacttctgattttgtccctaaaccaggtgatatagcagtgtgga caggtggtaattacaattggaacacttggggacacactggtattgttgtagg tccatcaactaaaagttacttttatagtgtagatcagaattggaataactctaa ctcttacgttggtagtcctgcagcaaagataaaacatagttatttggtgtaac tcatttgttagacccgcatacaaagcagaaccgaaacctacaccaccact ggacagtacaccggcaactagaccagttacaggttcttggaaaaagaacc agtacggaacttggtataaaccggaaaatgcaacatttgtcaatggtaacca acctatagtaactagaataggttctccattcttaaatgctccagtaggcggta acttaccggcaggggctacaattgtatatgacgaagtttgtatccaagcagg tcacatttggataggttataatgcttacaacggtaacagagtatattgccctgt tagaacttgtcaaggtgttccacctaatcaaatacctggcgttgcctgggga gtattcaaa (SEQ ID NO: 286) | MALPKTGKPTAKQVVDW AINLIGSGVDVDGYYGRQ CWDLPNYIFNRWNFKTP GNARDMAWYRYPEGFKV FRNTSDFVPKPGDIAVWT GGNYNWNTWGHTGIVVG PSTKSYFYSVDQNWNNSN SYVGSPAAKIKHSYFGVT HFVRPAYKAEPKPTPPLD STPATRPVTGSWKKNQY GTWYKPENATFVNGNQPI VTRIGSPFLNAPVGGNLPA GATIVYDEVCIQAGHIWIG YNAYNGNRVYCPVRTCQ GVPPNQIPGVAWGVFK (SEQ ID NO: 287) |
| Holin | Atggctaatgaaactaaacaacctaaagttgttggaggaataaactttagc acaagaactaagagtaaaacattttgggtagcaattatatcagcagtagcag tatttgctaatcaaattacaggtgcttttggtttagactactcagctcaaattga gcaaggtgtaaatatcataggttctatactaacattattagcaggtttaggtatt attgttgataataatactaaaggtcttaaagatagtgatattgttcaaacagatt atataaaacctcgtgatagtaaagaccctaatgaatttgttcaatggcaagca | MANETKQPKVVGGINFST RTKSKTFWVAIISAVAVF ANQITGAFGLDYSAQIEQ GVNIIGSILTLLAGLGIIVD NNTKGLKDSDIVQTDYIK PRDSKDPNEFVQWQANA |

TABLE 32-continued

DNA and amino acid sequences for toxins

| Toxin | DNA Sequence | Protein Sequence |
|---|---|---|
| | aatgcaaacacagctagcactttcgaattagacaactatgaaaacaatgca gaacctgatacagatgatagtgatgaagtacctgctattgaagatgaaattg atggcggttcagcaccttctcaagatgaagaagataccgaggaacacggt aaagtatttgcagaggaggaagttaagtag (SEQ ID NO: 288) | NTASTFELDNYENNAEPD TDDSDEVPAIEDEIDGGSA PSQDEEDTEEHGKVFAEE EVK (SEQ ID NO: 289) |
| sprG | ATGGTGGCATTACTGAAATCTTTAGAAAGGA GACGCCTA**ATGATTACAATTAGTACCATGT TGCAGTTTGGTTTATTCCTTATTGCATTGA TAGGTCTAGTAATCAAGCTTATTGAATTAA GCAATAAAAAATAA** (SEQ ID NO: 290) | MVALLKSLERRRL**MITIS TMLQFGLFLIALIGLVIK LIELSNKK** (SEQ ID NO: 291) |
| sprA2 | ATGTTCAATTTATTAATTAACATCATGACTTC AGCTTTAAGCGGCTGTCTTGTTGCGTTTTTTG CACATTGGTTACGAACGCGCAACAATAAAAA AGGTGACAAATAA (SEQ ID NO: 304) | MFNLLINIMTSALSGCLV AFFAHWLRTRNNKKGDK (SEQ ID NO: 305) |

Methods

Plasmid Construction was performed as follows.

1) PCR amplify pRAB11 backbone using primers BPC_670 and BPC_671 using an empty vector as a template.
2) PCR amplify toxin genes from synthesized plasmid DNA (Genscript). This allows for designing a primer that binds to the plasmid backbone downstream of the target gene, negating the need to design and order unique primers for both ends of each gene.
3) Primer pairs
   a) sprA—BPC_672/BPC_677
   b) 187-lysK-BPC_675/BPC_678
   c) Holin—BPC_676/BPC_678
   d) sprG-BPC_674/BPC 678
4) Run PCR products to check for correct size, digest the template DNA with DpnI (NEB), and clean up the reactions with a Zymo spin column.
5) Assemble the cleaned up PCR products by Gibson Assembly and transform into electrocompetent IM08B *E. coli* cells using the manufacturers protocol (NEB).
6) Verify correct sequences for the promoter and toxins on the plasmids.
7) Transform sequence verified plasmids into electrocompetent *Staphylococcus aureus.*

Growth Experiments were performed as follows.

1) Start overnight cultures of each strain in 5 mL BHI broth media. Add 10 ug/mL. Chloramphenicol to the media for strains BP_068-BP_071.
2) Perform a 1:100 dilution of the overnight culture into fresh BHI. Add 10 ug/mL chloramphenicol to the media for strains BP_068-BP_071. Incubate at 37° C. shaking at 250 rpm for 2 hours. Streak a plate of each strain and incubate overnight at 37° C. to confirm cultures are good.
3) Take OD600 readings of 2 hr cultures and dilute the cultures to an OD of 0.05
   a) Each strain gets (4) 5 mL tubes with BHI broth
   b) The following table shows the recorded OD readings, and the calculated amounts of each culture used to inoculate fresh cultures to an OD of 0.05. Table 33

TABLE 33

Starting $OD_{600}$ readings.

| Strain | OD600 | uL inoculum | Calculated starting OD |
|---|---|---|---|
| BP_068 | 2.1 | 119 | 0.0499 |
| BP_069 | 1.7 | 147 | 0.0498 |
| BP_070 | 2.0 | 125 | 0.05 |
| BP_071 | 1.8 | 139 | 0.05 |
| BP_001 | 1.7 | 147 | 0.0498 |

4) Save 100 uL sample of each culture for dilution plating. (3 plates/culture)
5) Incubate cultures at 37° C. until the OD reaches 0.5. Add 150 ng/mL anhydrotetracycline (AtC) to 2 tubes for each strain and label them with a+to indicate they received the inducer (derepressor). Continue to grow the cells for another 4 hours taking samples as described below.
6) Take OD600 readings at T=30 min, 60 min, 120 min, and 240 min. Record values in the table below
   a) Perform dilution plating at T=0, 60 min, and 240 min, and plate the correct dilution on the following plates (BHI, BHI Chlor10, BHI Chlor10+AtC 0.1)

Cfu investigation was performed as follows.

1) Identify BHI (Chlor 10, AtC 0.1) agar plates with colonies growing on them from strains containing plasmids with toxin genes present. Plates from T240 would be best.
2) If possible, pick 8 colonies per strain. Patch colonies to new BHI (Chlor 10, AtC 1) agar plate, and perform *Staphylococcus aureus* lysis procedure. Use 5 uL of the lysis reaction as the template for colony PCR using primer DR_215/DR_216 using a HF polymerase, such as Q5/Phusion.
   a) Reactions that produce a good band, perform DpnI digest for 1 hr, and column purify PCR reaction. Send purified product for sequencing using primers DR_215/DR_216.

Figure 16:
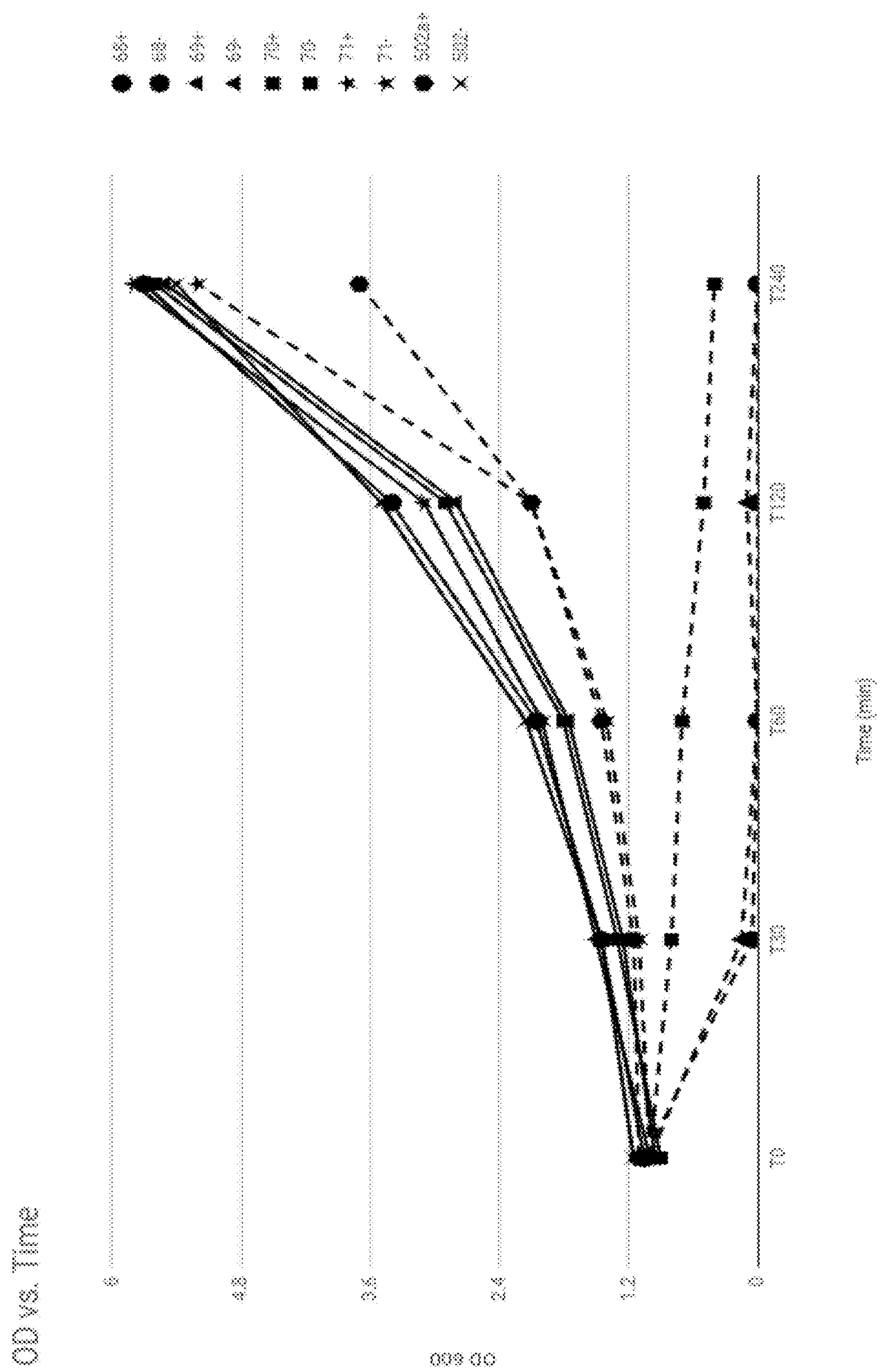

Calculated OD600 readings were taken at T=0, 30, 60, 120, and 240 min after induction. All values after TO are the average of 2 tubes. Results are shown in Table 34 and FIG. 16. The + indicates the cultures that received AtC, and the – indicates the cultures that did not receive any additional factors. FIG. 16 shows calculated OD600 values vs. time. The dashed lines represent the cultures that received 150 ng/ml AtC at T=0. FIG. 16 shows the sprA gene that codes for the PepA1 toxin protein showed the largest reduction in viable 502a *Staphylococcus aureus* cells after 4 hours of growth post induction.

Specifically, FIG. 16 shows cell growth pre- and post-induction of four synthetic strains derived from *Staphylococcus aureus* 502a having a plasmid based inducible expression system comprising four different cell death gene candidates sprA1, 187-lysK, Holin, and sprG. The candidate cell death genes had been cloned behind an tetracycline inducible promoter on pRAB11 plasmids and transformed into *Staphylococcus aureus* 502a cells. Calculated OD600 readings were taken at T=0, 30, 60, 120, and 240 min after induction of AtC induced (+) strains illustrated by dashed lines (- - - - - -) and uninduced (–) strains indicated by solid lines (. . . . . . . . . . . . . .) for BP_068 (502a pRAB11-Ptet-sprA1), BP_069 (502a pRAB11-Ptet-187lysK), BP_070 (502a pRAB11-Ptet-holin), and BP_071 (502a pRAB11-Ptet-sprG1) and compared to BP_001 (502a wt) in BHI media. Each of the induced (+) strains BP_068 (sprA1), BP_069 (187lysK) and BP_070 (holin) exhibited both (i) good cell growth pre-induction and (ii) significant inhibition of cell growth post-induction. BP_068 (+) exhibited the best inhibition of cell growth at each time point T=30, T=60, T=60, T=120 and T=240 min post-induction, so the sprA1 gene was selected for initial further development of a kill switch in *Staphylococcus aureus* 502a.

TABLE 34

Calculated OD600 at T = 0, 30, 60, 120, and 240 min after induction as shown in FIG. 16

| | Average OD600 Readings | | | | |
|---|---|---|---|---|---|
| Strain +/– ind. | T0 | T30 min | T60 min | T120 min | T240 min |
| 68+ | 1.05 | 0.05 | 0 | 0 | 0 |
| 68– | 1.05 | 1.45 | 2.05 | 3.4 | 5.7 |
| 69+ | 1 | 0.15 | 0 | 0.1 | 0 |
| 69– | 0.95 | 1.25 | 1.75 | 2.8 | 5.5 |
| 70+ | 1 | 0.8 | 0.7 | 0.5 | 0.4 |
| 70– | 0.9 | 1.3 | 1.8 | 2.9 | 5.6 |
| 71+ | 1 | 1.1 | 1.4 | 2.1 | 5.2 |
| 71– | 1 | 1.5 | 2 | 3.1 | 5.8 |
| 502a+ | 1.1 | 1.15 | 1.45 | 2.1 | 3.7 |
| 502– | 1.15 | 1.45 | 2.15 | 3.5 | 5.4 |

Figure 17:
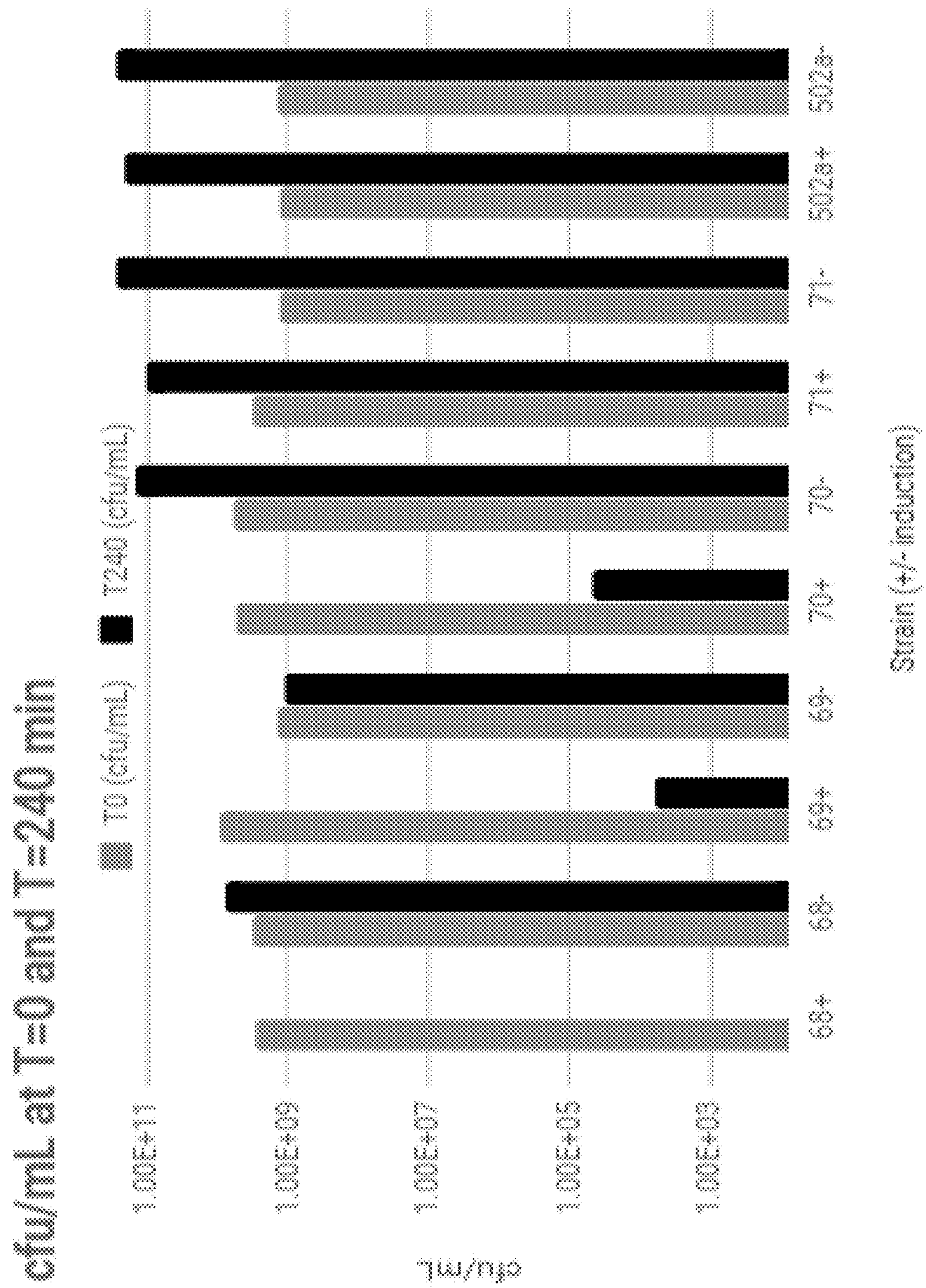

Table 35 below and FIG. 17 show colony forming units calculated from plate counts of diluted liquid culture samples. FIG. 17 shows a bar graph showing difference in the colony forming units/mL between T=0) (gray) and 240 min (black).

TABLE 35

CFUs calculated from plate counts of diluted liquid culture samples.

| | AtC | T0 (cfu/mL) | T240 (cfu/mL) |
|---|---|---|---|
| 68 | 68+ | 2.85E+09 | 7.50E+01 |
| | 68– | 3.12E+09 | 7.75E+09 |
| 69 | 69+ | 8.75E+09 | 6.30E+03 |
| | 69– | 1.40E+09 | 1.10E+09 |
| 70 | 70+ | 5.25E+09 | 4.75E+04 |
| | 70– | 6.05E+09 | 1.41E+11 |

TABLE 35-continued

CFUs calculated from plate counts of diluted liquid culture samples.

| | AtC | T0 (cfu/mL) | T240 (cfu/mL) |
|---|---|---|---|
| 71 | 71+ | 3.00E+09 | 1.04E+11 |
| | 71– | 1.34E+09 | 2.69E+11 |
| 502 | 502a+ | 1.29E+09 | 2.07E+11 |
| | 502a– | 1.45E+09 | 2.62E+11 |

This example investigated the effectiveness of multiple toxin genes when operably linked to an inducible promoter at disrupting cell viability when grown in complex rich media. Two native Staph toxins sprA and sprG, one chimeric phage toxin we have termed 187lysK, and one more phage holin toxin were tested using a plasmid based inducible expression system. The sprA1 gene that codes for the PepA1 toxin protein showed the largest reduction in viable 502a *Staphylococcus aureus* cells after 4 hours of growth post induction. The sprA1 gene was selected for initial further development of a kill switch in *Staphylococcus aureus* 502a.

Example 19. Induced Expression of GFP from the Genome in Strain BP_076 (502a Δspr1::A):: $P_{tet}$~gfp)

Overview. In this example the expression of green fluorescent protein (GFP) from the genome of a *Staphylococcus aureus* 502a variant strain (BP_076) was confirmed with quantitative polymerase chain reaction (qPCR), The gfp gene was integrated into the genome along with a tetracycline-inducible promoter ($P_{tet}$) and tetracycline repressor protein gene (tetR). The $P_{tet}$~gfp expression system was introduced into the genome via the suicide plasmid pIMAYz to allow for controllable expression of a recombinant gene. The wild-type strain (BP_001) served as the negative control and a strain carrying a high-copy plasmid with the same $P_{tet}$-gfp expression system served as the positive control. Due to its lower toxicity than tetracycline, anhydrotetracycline (aTc) was used to induce expression at 100 ng/mL.

Summarized Results. When comparing the t=0 min samples of BP_055 and BP_076 to BP_001, the qPCR data shows minor GFP expression before induction (indicating that $P_{tet}$ is leaky); however, the expression fold change after induction is still clearly evident. Different expression patterns are seen between plasmid-based and integrated gfp. Integrated gfp shows a sustained increase in expression throughout the assay, whereas plasmid-based gfp shows a high upregulation at 30 minutes and nearly no expression at 90 minutes. The difference in expression between BP_076 and BP_055 is due to the copy number of tetR per cell in each strain. BP_076 has one copy per cell, whereas BP_055 has 300-500 copies depending on the number of plasmids in each cell. The high amount of total TetR protein present in the BP_055 culture clearly exceeded the amount of aTc used for induction by the end of the assay, which lead to repression of gfp expression.

Bacteria Strains and Materials.

Strains

BP_001 (*Staphylococcus aureus* 502a)

BP_055 (SA 502a, p229_pRAB11-Ptet-GFP)

BP_076 (SA 502a, ΔsprA1::Ptet-GFP)

Brain Heart Infusion (BHI) media, BHI+Chloramphenicol (10 μg/mL) agar plates. Anhydrotetracycline (aTc) were employed.

Samples were RNA (1 mL culture): t=0, 30 and 90 minutes.

Methods-Strain Construction

1. In order to make a modification in the genome of Staph *aureus Staphylococcus aureus*, we must first add the required genetic elements to a plasmid capable of making those modifications.
2. The plasmid backbone is an *E. coli-Staphylococcus aureus* shuttle vector called pIMAYz, and has chloramphenicol resistance, a low copy *E. coli* origin of replication, a low copy temperature sensitive *Staphylococcus aureus* origin of replication (permissible replication at 30° C., but not at 37° C.), the see Y toxin under the control of a Ptet promoter, and a lacZ gene for blue/white screening during integration into *Staphylococcus aureus.*
3. The plasmid was constructed using linear PCR products that were assembled into a circular construct using Gibson Assembly
   a. Use primers DR_022/DR_023 to PCR amplify the backbone of the pIMAYz vector to linearize it for use in downstream assemblies. The background template DNA must be enzymatically digested with DpnI (NEB) per manufacturer's instructions prior to further use
   b. Use primers DR_255/DR_241 to PCR amplify the tetR-Ptet-GFP region using the pRAB11 plasmid as the template.
   c. Use primers DR_256/DR_257, and DR_240/DR_236 to PCR amplify 1 kb regions from the *Staphylococcus aureus* 502a genome. These will be used as homology arms to target the region for integration into the *Staphylococcus aureus* genome.
   d. These linear fragments are then assembled into a circular plasmid with the Gibson Assembly Master mix (NEB) per manufacturer's instructions and transformed into IM08B cells.
4. Once the sequence of the new plasmid DNA can be confirmed, 50 mL cultures are started to obtain a sufficient amount for transformation into *Staphylococcus aureus* 502a by electroporation.
5. Integration into *Staphylococcus aureus* by homologous recombination
   a. Use between 1 and 5 micrograms of plasmid DNA to electroporate into *Staphylococcus aureus*. Recover at 37° C. for 1 hour, and plate on BHI+10 ug/mL chloramphenicol and 100 ug/mL x-Gal, and incubate overnight at 37° C.
   b. The following day pick multiple blue colonies and start 5 mL BHI broth cultures at room temp, and allow them to grow in a rotary shaking unit for 12-20 hours.
   c. Perform and plate serial dilutions (usually $10^{-4}$-$10^{-6}$) on BHI+1 ug/mL anhydrotetracycline (AtC) and 100 ug/mL X-gal. Incubate overnight at 37° C.
   d. The following day, pick and screen white colonies by patching onto BHI, BHI+1 ug/mL anhydrotetracycline (AtC) and 100 ug/mL X-gal, and BHI+10 ng/ml chloramphenicol and 100 ug/mL x-Gal agar plates to confirm chlor sensitivity and AtC resistance.
   e. Colonies showing the desired phenotypes should be screened by PCR with primers DR_237/DR_238. Colonies that have taken the new genes should produce a 4.4 kb band, and colonies that have reverted back to wild type should have a 2.86 kb band. Several positive clones should be sequenced to verify the correct sequences, and one of the sequence verified clones to be picked for use in downstream experiments.

Cell Growth Procedure

1. Start overnight cultures of each strain in BHI broth media (5 mL) and incubate with agitation (37° C., 240 rpm). Add chloramphenicol (final concentration 10 μg/mL) to the media for BP_055.
2. Measure optical density (OD) of overnight culture and record.

The optical density (OD) of the cultures was measured at 630 nm, fresh media served as the blank The OD of the overnight cultures is denoted as the initial OD. The inoculum transferred to 5 ml of fresh media reduced the OD to 0.05 so that the new cultures would be in the exponential growth phase two hours after inoculation, as shown in Table 36.

TABLE 36

OD of cultures for P__001, BP__055 and BP__076

| Strain | Initial OD | Inoculum for 5 mL [μL] | OD at 2 hr |
|---|---|---|---|
| BP__001 | 8.2 | 30.5 | 1.01 |
| BP__055 | 9.1 | 27.5 | 0.88 |
| BP__076 | 8.7 | 28.7 | 1.01 |

3. Dilute overnight cultures to 0.05 OD in fresh BHI (5 ml) in 2× 14 mL culture tubes per culture; again add chloramphenicol to the BP_055 cultures.
4. Incubate with agitation (37° C., 240 rpm) until OD reaches 0.5 ~ 1("2 hr culture").
5. Remove 1 ml of culture for t=0 min RNA samples and transfer them to 1.5 ml microtubes. Spin down the samples (16,000×g, 1 min, RT), aspirate off supernatant and resuspend the pellet in 200 AL RNAlater. Allow them to incubate for a few minutes at room temperature (RT) and then store at −20° C.
6. Add aTc (4 μL, 100 μg/mL) to first 14 mL culture tube for each strain. Add 4 μL 100% ethanol to second tube for each strain as induction controls (the a Tc was solvated in 100% ethanol).
7. Incubate the cultures with agitation (37° C., 240 rpm) until other sampling timepoints.
8, Repeat RNA sampling at t=30 and 90 mins, measure OD at t=90 mins.

qPCR Sample Processing and Data Analysis

RNA was extracted from frozen cell pellets stored in RNALater using Ambion RiboPure Bacteria Kit per protocols in example above. The gfp expression level was normalized to the housekeeping gene gyrB and quantitated using the ΔΔCt method, see the primer sequences in Table 37.

TABLE 37

Sequences of qPCR primers.

| Target | Database Number | Sequence |
|---|---|---|
| gyrB | BP 802 | 5'-TTGGTACAGGAATCGGTGGC (SEQ ID NO: 212) |
| gyrB | BP 803 | 5'-TCCATCCACATCGGCATCAG (SEQ ID NO: 213) |
| gfP | BP 195 | 5'-CTGTCCACACAATCTGCCCT (SEQ ID NO: 292) |

TABLE 37-continued

| Sequences of qPCR primers. | | |
|---|---|---|
| Target | Database Number | Sequence |
| gfP | BP 196 | 5'-TGCCATGTGTAATCCCAGCA (SEQ ID NO: 293) |

Primer sequences used for plasmid and strain construction are shown in Table 38.

TABLE 38

| Primers used for plasmid and strain construction | |
|---|---|
| Primer Name | ssDNA sequence (5'-3') |
| DR_022 | Caagcttatcgataccgtcgacctc (SEQ ID NO: 294) |
| DR_023 | Gggatccactagttctagagcgg (SEQ. ID NO: 295) |
| DR_237 | GCAACTGGTACATCACAATTGGTACTCTCAC (SEQ. ID NO: 296) |
| DR_238 | GACCACGCATACCTATCTATAAACGGACAATG (SEQ. ID NO: 297) |
| DR_255 | GTCCAATTAGATGGCATGTAACTGGGCAGTGTCTTAAAAAATCG (SEQ. ID NO: 298) |
| DR_241 | CAGGCCAATTTGGCATAGAGCCGGATGTGCTGCAAGGCGATTAAGTTGGGTAACG (SEQ ID NO: 299) |
| DR_256 | GTTACATGCCATCTAATTGGACAAATTCTATGAGAGTAGATTTTG (SEQ ID NO: 300) |
| DR_257 | GCCAAATCGCTTTCGTGTATACGATTCCCAGTC (SEQ ID NO: 301) |
| DR_240 | GGCTCTATGCCAAATTGGCCTGATGAGTTC (SEQ ID NO: 302) |
| DR_236 | gactagaactagtggatcccGGCGATTTTATTGTGACAAGAGACTGAAGAGC (SEQ ID NO: 303) |

Figure 19:
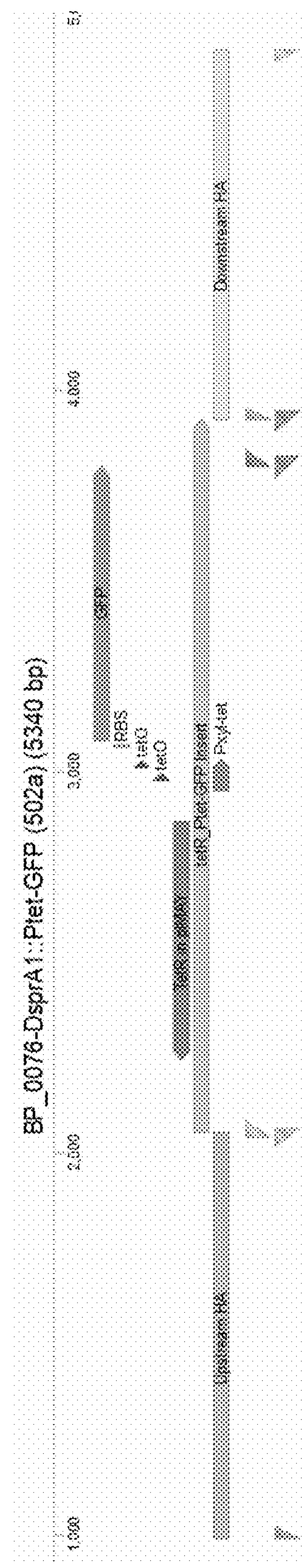
FIG. 19 shows a map of the genome for Strain BP_076 (SA 502a, ΔsprA1::Ptet-GFP).

FIG. 19 shows a map of the genome for Strain BP_076 (SA 502a, ΔsprA1::Ptet-GFP).

Figure 20:
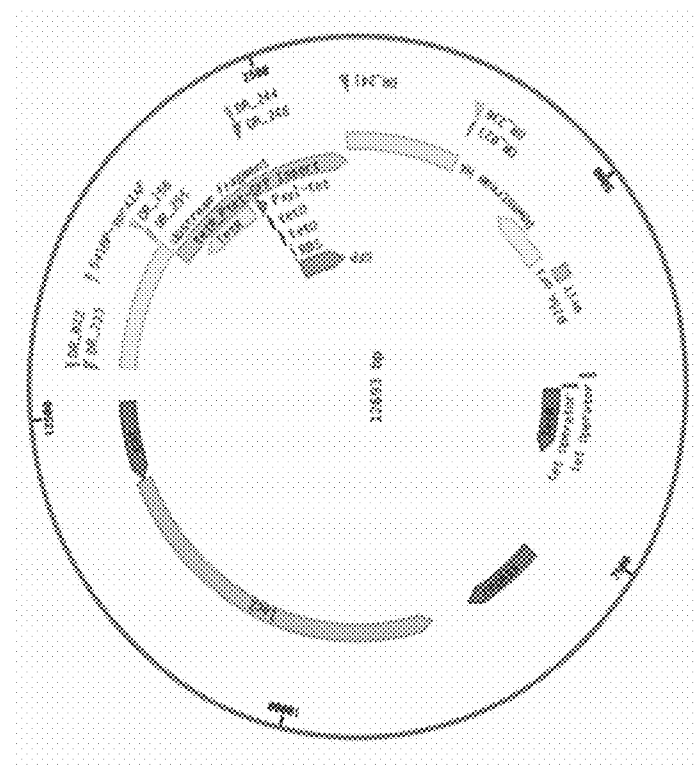
FIG. 20 shows a map of plasmid constructed for making genomic integration in *Staphylococcus aureus.*

FIG. 20 shows a map of plasmid constructed for making genomic integration in *Staphylococcus aureus.*

Results. The t=0 samples of both strains carrying the $P_{tet}$-gfp system showed some GFP expression before induction, Table 2 shows the Ct values of the three investigated strains at t=0. The wild-type strain BP_001 amplification curve crossed the threshold (0.4) after 30 cycles, which may be attributed to some form of unspecific amplification or primer dimer formation. Table 39 shows the Cycles to Threshold (Ct) values prior to expression induction for the wild-type strain BP_001, plasmid based $P_{tet}$-g/p BP_055 carry strain and $P_{tet}$-gfp genetically modified strain BP_076 are shown. The threshold was set to 0.4.

TABLE 39

| Cycles to Threshold (Ct) values prior to induction for BP_001, BP_055 and BP_076 | | | |
|---|---|---|---|
| Strain | BP_001 | BP_055 | BP_076 |
| Ct Value | 33.65 ± 0.61 | 22.99 ± 0.06 | 23.09 ± 0.10 |

Figure 18:
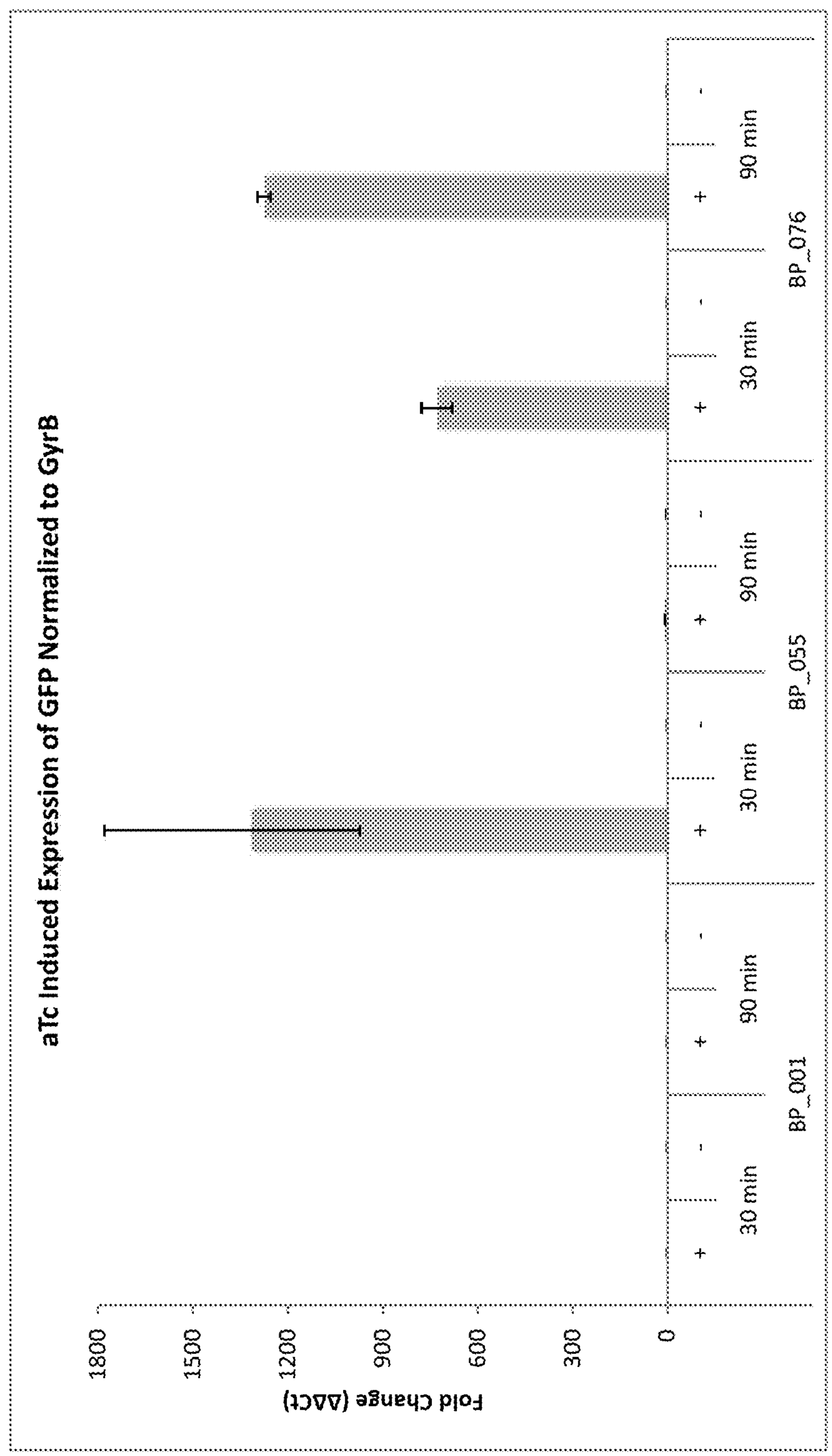
FIG. 18 shows GFP expression fold change of induced (+) and uninduced (−) subcultures of *Staphylococcus aureus* strains BP_001, BP_055 and BP_076.

The basal expression level of GFP was accounted for in the ΔΔCt calculations by normalizing the experimental timepoints (t=30 min, 90 min) to the control timepoint (t=0) for each strain individually. The expression levels of GFP determined by qPCR are displayed below in FIG. 18. FIG. 18 shows GFP expression fold change of induced (+) and uninduced (−) subcultures of *Staphylococcus aureus* strains BP_001, BP_055 and BP_076. Different expression patterns are seen between plasmid-based and integrated gfp. Integrated gfp shows a sustained increase in expression throughout the assay, whereas plasmid-based gfp shows a high upregulation at 30 minutes and nearly no expression at 90 minutes The induced subculture (+) and uninduced subculture (−) for all three strains show expression induction dependency on the presence of a Tc and the Per-gfp expression system. As expected, BP_001 showed no expression throughout the experiment. The expression of GFP in BP_076 increased throughout the experiment, demonstrating expression from the genome of *Staphylococcus aureus* 502a. The expression pattern determined for BP_055 can be attributed to less than ideal experimental design, however, it did fulfill its purpose as a positive control for induction. BP OSS carries the $P_{tet}$-gfp expression system on the plasmid pRAB11, a high-copy plasmid. Each plasmid has two TetR protein binding sites, which repress expression of GFP in the absence of aTc. Within 30 minutes of induction the high number of plasmids multiplied by cell count resulted in a ca. 1300 fold upregulation in GFP expression, confirming aTc was in an active form during the assay. One might expect that the expression level of GFP would be even higher at 90 minutes, but the data shows nearly no expression (ca. 7 fold upregulation compared to t=0). This is not surprising given the total number of TetR proteins present in the culture a t=90 minutes. The amount of aTc was not enough to inhibit repression by TetR at the 90-minute timepoint, resulting in nearly no expression, Gene expression from a molecularly modified strain of *Staphylococcus aureus* 502a was confirmed by qPCR analysis of tetracycline induced GFP expression.

Example 20. Candidate Serum Responsive Promoters Screened by RNA Seq to Detect Up-Regulation In this experiment, RNA sequencing of 502a *Staphylococcus aureus* variant strain BP_001 WT when grown in human serum compared to TSB was performed in order to gain a holistic understanding of the transcriptional changes that occur within the microorganism upon entry into the circulatory system. RNA sequencing was performed on samples collected from laboratory growth medium and human serum.

A culturing (growth assay) in TSB with or without human serum was performed as follows. *S. aureus* 502a cells were struck out from a cryo stock on a tryptic soy broth (TSB) agar plate with 5% sheep's blood and grown overnight (37° C.). The following day five single colonies were used to inoculate 5 mL of TSB in a 14 mL culture tube and grown overnight with agitation (37° C., 240 rpm). The next morning 50 mL of TSB were transferred to a 250 mL flask and warmed to 37° C. The $OD_{600}$ of the overnight culture was measured ($OD_{600}$=6.0) and used to inoculate (416 μL) the warmed TSB to an $OD_{600}$ of 0.05. This culture grew for ca. two hours (37° C., 100 rpm) and reached an $OD_{600}$ of 1.24. During this time a 50 mL aliquot of human serum was placed in the 37° C. incubator to thaw and warm, fresh TSB was also warmed. Using a serological pipette, 15 mL of culture were transferred to a 15 mL. Falcon tube and centrifuged (RT, 2000× g, 10 min). The supernatant was decanted, the pellet was resuspended in sterile PBS (15 mL) and centrifuged (RT, 2000× g. 10 min). The supernatant from the wash step was decanted and the pellet was resuspended in sterile PBS (7.5 mL), doubling the $OD_{600}$ of the inoculum to 2.48. The PBS suspension was used to inoculate the TSB and serum culture samples at an $OD_{600}$ of 0.05 (202 μL per 10 mL medium).

RNA sequencing sample preparation was performed as follows.

The t=0 min samples (3×) were each 1 mL of the original 50 mL starter culture prior to washing. At the allotted timepoint, the culture tubes were removed from the incubator and placed in an ice water bath for 5 minutes and then centrifuged (4° C., 2000 g, 10 min). The supernatant was decanted, the pellet was resuspended in 1 mL ice-cold sterile PBS and transferred to microtubes. The suspensions were centrifuged (4° C., 6000×g, 3 min), the supernatant was aspirated off and the pellets were resuspended in RNAlater. The RNAlater suspensions were stored at −20° C.

The samples were removed from the −20° C. freezer for RNA extraction and allowed to thaw at RT. The cells were pelleted (RT, 16000×g, 1 min), the supernatant was aspirated off and the cells were then washed with PBS-washing helped remove carryover from the serum. To wash the cells, the pellets were resuspended in PBS and centrifuged (RT, 16000× g, 1 min), the supernatant was discarded. The RNA was extracted using Invitrogen's RiboPure Bacteria Kit following the manufacturer's instructions. The extracted RNA was then DNase I treated and ethanol precipitated. Per the sequencing firm's request the samples were sent as pellets in ethanol on dry ice.

From the total RNA samples, the ribosomal RNA molecules were depleted using the Ribo-Zero rRNA Removal Kit for Bacteria (Illumina). The quality of the RNA samples was analyzed on a Shimadzu MultiNA microchip electrophoresis system and then fragmented using ultrasound (4 pulses, 30 s, 4° C.). An adapter was ligated to the 3' end of the molecules to enable first strand cDNA synthesis with M-MLV reverse transcriptase. The cDNA was purified and a 5' Illumina TruSeq adapter ligated to the 3' end of the antisense cDNA. The cDNA was then amplified by PCR using a high fidelity polymerase, the concentration after amplification was 10-20 ng/μL. The cDNA samples were then barcoded according to the growth condition they represented, purified using a Agencourt AMPure XP kit (Beckman Coulter Genomics) and analyzed by capillary electrophoresis. The cDNA was then pooled, the pool covered 200 to 500 bp molecules.

For Illumina NextSeq the primers used for PCR amplification were designed for TruSeq sequencing following Illumina's instructions. The cDNA was sequenced on an Illumina NextSeq 500 system using 75 bp read length. The differential expression of genes was analyzed via DESeq2 using SARTools.

Results for upregulated genes by RNA sequencing are shown in the Table 40; t=time in minutes after exposure to human serum.

TABLE 40

Genes in *Staphylococcus aureus* 502a WT upregulated upon exposure to human serum by RNAseq

| Gene | | t = 30 Serum vs t = 0 | t = 30 Serum vs t = 30 TSB | t = 90 Serum vs t = 0 | t = 90 Serum vs t = 90 TSB |
|---|---|---|---|---|---|
| gene name | gene number | fold change | fold change | fold change | fold change |
| isdB | CH52_00245 | 479.653 | 471.648 | 2052.474 | 1240.112 |
| sbnB | CH52_05135 | 158.756 | 44.41 | 310.08 | 130.622 |
| isdC | CH52_00235 | 93.006 | 56.211 | 173.376 | 149.117 |
| sbnA | CH52_05140 | 88.832 | 37.808 | 143.558 | 93.474 |
| srtB | CH52_00215 | 73.135 | 47.421 | 143.059 | 170.578 |
| sbnE | CH52_05120 | 70.475 | 50.083 | 190.255 | 171.279 |
| sbnD | CH52_05125 | 66.84 | 52.434 | 187.025 | 224.017 |
| isdI | CH52_00210 | 65.951 | 53.426 | 115.302 | 118.724 |
| heme ABC transporter 2 | CH52_00225 | 65.024 | 43.415 | 117.603 | 135.956 |
| sbnC | CH52_05130 | 63.092 | 51.306 | 162.927 | 147.385 |
| heme ABC transporter | CH52_00230 | 60.967 | 40.137 | 125.227 | 196.142 |
| isd ORF3 | CH52_00220 | 51.262 | 35.978 | 97.439 | 119.584 |
| sbnF | CH52_05115 | 43.997 | 44.31 | 129.516 | 127.889 |
| alanine dehydrogenase | CH52_11875 | 43.589 | 20.237 | 304.444 | NA |
| HarA | CH52_10455 | 43.215 | 28.041 | 114.425 | 117.787 |
| sbnG | CH52_05110 | 42.446 | 34.095 | 133.373 | 120.433 |
| diaminopimelate decarboxylase | CH52_05105 | 32.541 | 25.864 | 102.838 | 141.629 |
| iron ABC transporter | CH52_05145 | 31.417 | 19.576 | 44.885 | 47.226 |
| threonine dehydratase | CH52_11880 | 24.559 | 20.237 | NA | NA |

TABLE 40-continued

Genes in *Staphylococcus aureus* 502a WT upregulated upon exposure to human serum by RNAseq

| Gene | | t = 30 Serum vs t = 0 | t = 30 Serum vs t = 30 TSB | t = 90 Serum vs t = 0 | t = 90 Serum vs t = 90 TSB |
|---|---|---|---|---|---|
| gene name | gene number | fold change | fold change | fold change | fold change |
| isdA | CH52_00240 | 21.471 | 40.712 | 44.477 | 115.432 |
| siderophore ABC transporter | CH52_05150 | NA | NA | 33.201 | 37.267 |
| sbnI | CH52_05100 | NA | 22.602 | 101.548 | 89.778 |
| SAM dep Metrans | CH52_04385 | NA | NA | 75.292 | 25.847 |

Several genes were found to be upregulated greater than 20-fold after exposure to human serum at t=30 min compared to t=0, or compared to t=30 in TSB, by RNA sequencing including isdB, sbnB, isdC, sbnA, srtB, sbnE, sbnD, isdI, heme ABC transporter 2, heme ABC transporter 2, heme ABC transporter, isd ORF3, sbnF, alanine dehydrogenase, HarA, sbnG, diaminopimelate decarboxylase, iron ABC transporter, threonine dehydratase, isdA, and sbnI.

Several genes were upregulated greater than 50-fold after exposure to human serum at (=30 min compared to t=0, or compared to t=30 in TSB, by RNA sequencing including isdB, sbnB, isdC, sbnA, srtB, sbnE, sbnD, isdI, heme ABC transporter 2, heme ABC transporter 2, heme ABC transporter, isd ORF3. Genes upregulated greater than 100-fold after exposure to human serum at t=30 min compared to t=0, or compared to t=30 in TSB, by RNA sequencing include isdB, and sbnB, Several genes were upregulated greater than 100-fold after exposure to human serum at t=90 min compared to t=0, or compared to (=90 in TSB, by RNA sequencing including isdB, sbnB, isdC, sbnA, srtB, sbnE, sbnD, isdI, heme ABC transporter 2, heme ABC transporter 2, heme ABC transporter, isd ORF3, sbnF, alanine dehydrogenase, HarA, sbnG, diaminopimelate decarboxylase, isdA.

Preferred upregulated genes in *Staphylococcus aureus* 502a when exposed to serum include isdB gene CH52_00245, srB gene CH52_00215, heme ABC transporter2 gene CH52_00215, and HarA gene CH52_00215.

Several *Staphylococcus aureus* 502aWT genes were found to be downregulated when exposed to human serum by RNA sequencing as shown in Table 41 and Table 42.

TABLE 41

Genes in *Staphylococcus aureus* 502a WT downregulated upon exposure to human serum at 30 min by RNAseq

| gene name | gene number | t = 30 Serum vs t = 0 fold change | t = 30 Serum vs t = 30 TSB fold change |
|---|---|---|---|
| phosphoribosylglycinamide formyltransferase | CH52_00525 | −4.307 | −2.001 |
| phosphoribosylaminoimidazole synthetase | CH52_00530 | −4.271 | −2.063 |
| amidophosphoribosyltransferase | CH52_00535 | −4.131 | −2.117 |
| phosphoribosylformyl-glycinamidine synthase | CH52_00540 | −4.046 | −2.244 |
| phosphoribosylformyl-glycinamidine synthase | CH52_00545 | −3.498 | −2.215 |

TABLE 41-continued

Genes in *Staphylococcus aureus* 502a WT downregulated upon exposure to human serum at 30 min by RNAseq

| gene name | gene number | t = 30 Serum vs t = 0 fold change | t = 30 Serum vs t = 30 TSB fold change |
|---|---|---|---|
| phosphoribosylaminoimidazole-succinocarboxamide | CH52_00555 | −3.345 | −2.134 |
| trehalose permease IIC | CH52_03480 | −3.338 | −2.401 |
| DeoR faimly transcriptional regulator | CH52_02275 | −2.55 | −2.171 |
| phosphofructokinase | CH52_02270 | −2.464 | −1.984 |
| PTS fructose transporter subunit IIC | CH52_02265 | −2.042 | −1.806 |
| galactose-6-phosphate isomerase | CH52_07975 | NA | −2.137 |

TABLE 42

Genes in *Staphylococcus aureus* 502a WT downregulated upon exposure to human serum at 90 min by RNAseq

| gene name | gene number | t = 90 Serum vs t = 0 fold change | t = 90 Serum vs t = 90 TSB fold change |
|---|---|---|---|
| NarZ | CH52_07000 | −5.012 | −3.989 |
| phosphoribosylglycinamide formyltransferase | CH52_00525 | −3.737 | −1.680 |
| trehalose permease IIC | CH52_03480 | −3.279 | −4.381 |
| NarH | CH52_07005 | −3.265 | NA |
| alkylhydroperoxidase | CH52_06615 | −3.211 | −3.573 |
| NarT | CH52_07045 | −3.108 | −3.680 |
| hypothetical protein | CH52_04875 | −2.911 | −3.396 |
| DeoR trans factor | CH52_02275 | −2.245 | −3.322 |
| PTS fructose transporter subunit IIC | CH52_02265 | −2.211 | −4.474 |
| lysophospholipase | CH52_02680 | −1.837 | −3.000 |
| protein disaggregation chaperon | CH52_01005 | −0.009 | −2.989 |
| alkylhydroperoxidase | CH52_06615 | NA | −3.573 |
| phosphofructokinase | CH52_02270 | NA | −3.878 |

Several genes in *Staphylococcus aureus* 502a were downregulated at least 2 fold after t=30 or t=90 minutes in serum compared to t=0 or in TSB including phosphoribosylglycinamide formyltransferase gene CH52_00525, trehalose permease IIC gene CH52_03480, DeoR family transcriptional regulator gene CH52_02275, phosphofructokinase gene CH52_02270, and PTS fructose transporter subunit IIC gene CH52_02265.

Example 21. Kill Switch Construction

For this experiment, a serum responsive kill switch cassette was designed and constructed for the purpose of making a strain of *Staphylococcus aureus* (SA) 502a that is unable to grow in serum or blood. We based this cassette around the endogenous sprAI toxin antitoxin system in SA. This is a type I T/AT system where the toxin is a small membrane porin peptide (PepA1) that is translationally repressed by an antisense RNA. The antisense RNA binds to the 5' UTR of sprA1 covering the RBS and blocking its ability to bind to the single stranded mRNA and synthesize the protein.

The design of this kill switch changes the promoter region that drives the expression of the PepA1 toxin from its endogenous system to one that is highly upregulated when the organism is cultured in human serum. This construct was made with the sbnA promoter from SA 502a. For this kill switch, the promoter region was not changed for the antisense RNA, but additional versions of kill switches are in progress that will have this region changed as well to promoters that have been identified to be highly upregulated during growth in normal complex media, but highly repressed or down regulated when the organism is grown in blood or serum. This should make it even easier to overcome the antitoxin suppression of sprA1 in blood or serum conditions.

Figures 21, 22:
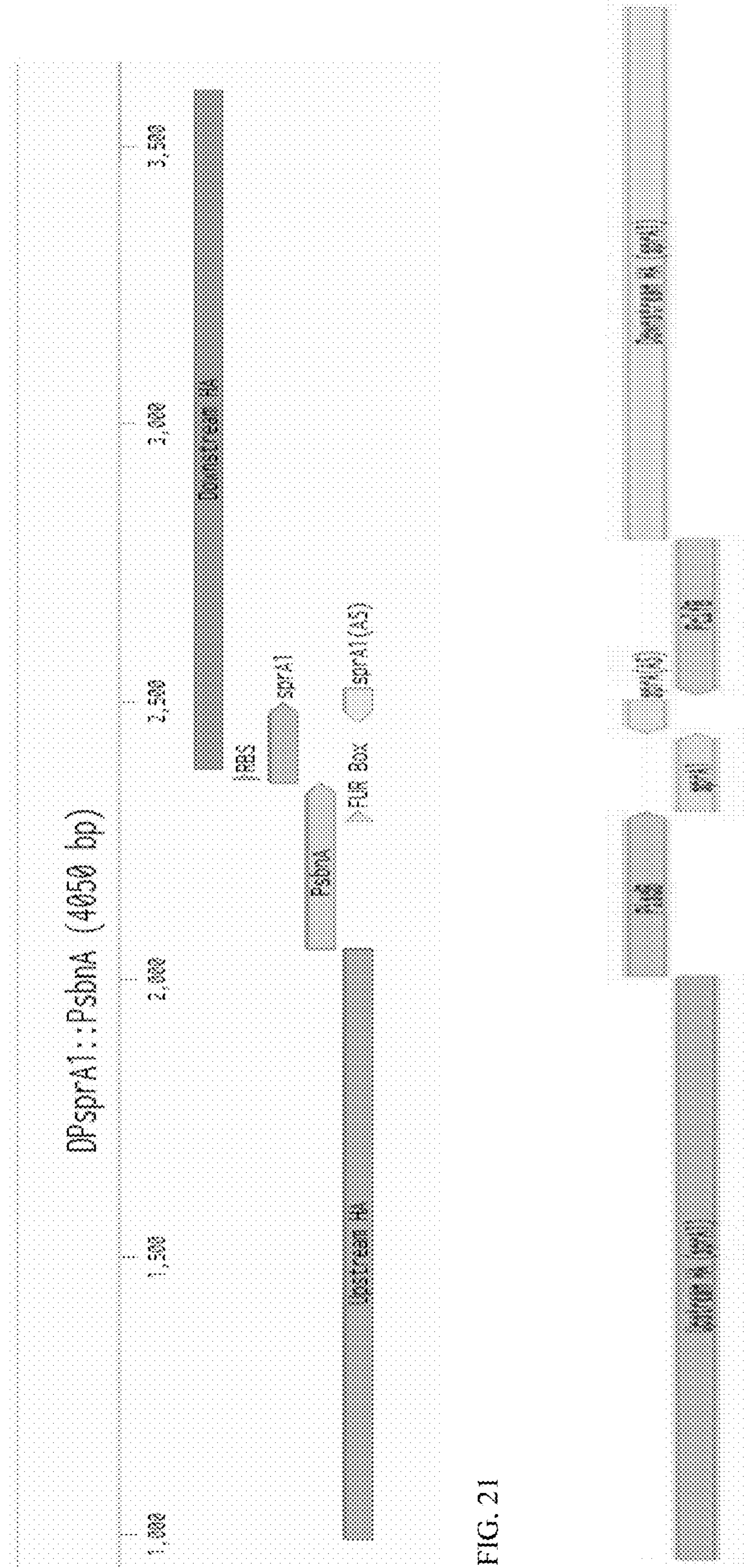
FIG. 21 shows a map of PsbnA-sprA1 kill switch in *Staphylococcus aureus* 502a genome. Serum and blood responsive promoter PisdB is operably linked to sprA1 toxin cell death gene.
FIG. 22 shows a map of a kill switch construction using serum and blood responsive promoter PisdB operably linked to sprA1 toxin cell death gene and an expression clamp comprising a second promoter clfB operably linked to sprA AS to prevent leaky expression of the toxin in the absence of blood or serum. The kill switch is incorporated to the *Staphylococcus aureus* 502a genome.

To test the functionality of the kill switch, the expression of the PepA1 toxin was induced by taking a culture that was growing at early exponential phase in complex media, tryptic soy broth (TSB), and changing the growth media to human serum. The OD was monitored and serial dilutions to plate were performed and CFUs were counted to monitor the number of viable cells in the culture and compare it to wild type SA 502a grown under the same conditions. FIG. 21 shows a map of PsbnA-sprA1 Kill Switch in *Staphylococcus aureus* 502a genome.

The methods used for plasmid construction, oligos, protocol for making changes in *Staphylococcus aureus* 502a genome using homologous recombination, and Kill Assay are shown below.

Strains

502a—*Staphylococcus aureus* wild type

BP_011—502a ΔsprA1-sprA1 (AS)

BP_084-502a ΔPsprA::PsbnA

In this experiment BP_011 has both the sprA1 toxin gene and sprA1 antitoxin region knocked out, because it was considered to be easier to "cure" the KO by integrating the kill switch into that site than to do the integration directly into the wild type 502a. This is because the system used for integrations, i.e. homologous recombination, relies on segments of homology between the inserted gene and the chromosomal target to dictate the location of the integration, and it was felt the endogenous sprA1 toxin/antitoxin might interfere with the integration if present in the genome. The BP_011 strain is the parent of the kill switch strain BP_084. The BP-011 strain was included in this experiment as a control.

Plasmid Construction

1) PCR amplify homology regions from SA 502a genome
   a. Upstream Homology Arm—DR_233/DR_296
   b. Downstream Homology Arm—DR_280/DR_236
2) PCR amplify PsbnA-sprA1 from synthesized linear DNA fragment from IDT
   a. PsbnA-sprA1—DR_297/DR_228
3) PCR amplify pIMAYz backbone vector
   a. DR_022/DR_023
4) Gel purify all fragments with Qiagen kit per manufactures instructions
5) Assemble linear DNA fragments into circular plasmid and transform into electrocompetent IM08B *E. coli* cells per the manufacturer's instructions
6) Perform colony PCR to screen colonies for fully assembled plasmid
   a. DR_117/DR_228 (1571 bp fragment)
7) Pick multiple positive colonies, grow culture overnight and sequence the plasmid to confirm there are no mutations in the newly assembled plasmid
8) Transform sequence confirmed plasmid into electrocompetent SA 502a and follow protocol for making edits in SA genome using homologous recombination
9) Screen final colonies by PCR for integrant with the primer pair DR_303/DR_304
   a. Send PCR product for sequence confirmation if correct band size is observed.

TABLE 43

Oligo Sequences used in plasmid construction

| Primer Name | 5'-3' DNA sequence |
|---|---|
| DR_233 | cgacggtatcgataagcttgGCCACTGGCGTCAAATACTGTAATGAAGAATG (SEQ ID NO: 330) |
| DR_296 | CATCTAATTGGACAAATTCTATGAGAGTAGATTTTGTTAATTTAAG (SEQ ID NO: 331) |
| DR_280 | GTAGACGCAATACAAAATAGGTGACATATAGCCGCACC (SEQ ID NO: 332) |
| DR_236 | gctctagaactagtggatcccGGCGATTTTATTGTGACAAGAGACTGAAGAGC (SEQ ID NO: 333) |
| DR_297 | CATAGAATTTGTCCAATTAGATGTCCCACTACATCCTGCTAAAACAAGTAGGAAAGC (SEQ ID NO: 334) |
| DR_228 | CTATTTTGTATTGCGTCTACTTAGCCAATAAG (SEQ ID NO: 335) |
| DR_022 | Caagcttatcgataccgtcgacctc (SEQ ID NO: 336) |
| DR_023 | Gggatccactagttctagagcgg (SEQ ID NO: 337) |
| DR_303 | CAAGCCACCAAAGCACGTGCCTATTTGCC (SEQ ID NO: 338) |
| DR_304 | CAGTGAAATAGATAGATTGGTTGAAAAACAATCTTCAAAAGTCGGACG (SEQ ID NO: 339) |

The protocol used for making changes in *Staphylococcus aureus* 502a genome using homologous recombination is shown below, Materials BHI agar (Chloramphenicol 10 ug/mL) (X-Gal 100 ug/mL)

BHI agar (AnhydroTet 1 ug/mL) (X-Gal 100 ug/mL)

BHI agar

BHI broth.

Primers to screen colonies after primary and secondary recombination events

Protocol

1. Prepare a highly concentrated pIMAYz integration plasmid. ~25 mL overnight culture spun down into (4) 2× volumes of the miniprep protocol. This can be purified through 2 columns if desired, and performed to maximize yield of DNA. Elutions should be pooled and concentrated using the Zymo concentrator kit performed to maximize concentration.
2. Use up to 5 uL of concentrated plasmid from above to transform 502a using the labs optimized electroporation protocol.
3. Recover cells for 1 hr at 30° C. in shaker
4. Plate entire recovery mixture between 3-4 BHI (Chlor 10, X-Gal 100) agar plates. Incubate 1 plate at 30° C. and the rest at 37° C. overnight (make sure incubator is at 37 C or above)
5. Screen blue colonies on the plates for the presence of circular plasmid using primers DR_116/DR_117. The primers are flanking the multiple cloning site in pIMAYz, and for the 30 C plates will produce a band the same size as the homology arms plus any region being integrated. The 37° C. plates should not produce any band.
6. The blue colonies on the 37° C. plates should be screened for the integrated plasmid into the genome using primers that bind outside the homology arms. Each primer should be paired with either DR_116 or DR_117. This will confirm that the plasmid is integrated into the proper location in the genome.
7. If no colonies on the 37° C. plates produce bands indicating the plasmid has been integrated, colonies showing a plasmid band on the 30° C. plates can be diluted and plated on BHI agar (Chlor 10, X-Gal 100) and incubated at 37° C. Repeat steps 5-6 to rescreen the new colonies for integration.
8. If PCR shows integrated plasmid, pick a couple colonies, if possible pick clones that have integrated each way. Grow overnight (~16 hr) in 5 mL. BHI broth in room temp shaker.
9. Dilute to 10^−5 and 10^−6 and plate 50 uL on BHI agar (AnhydroTet 1 ug/mL, X-Gal 100 ug/mL). Incubate plates overnight at 37° C.
10. Patch white colonies to BHI agar (Chlor 10 uG/mL, X-Gal 100), BHI agar (AnhydroTet 1 ug/mL, X-Gal 100 ug/mL), BHI agar to screen for resistance to anhydrotet and sensitivity to chloramphenicol. Colonies with both phenotypes should be picked from the BHI agar plate and screened for the knock out or knock in. At least one of the primers used to screen the final genotype should bind outside the regions used as homology ans.
11. Streak plate from patch plate of several positive clones, perform HF PCR using primers that bind outside the homology arms, and send for sequencing. Incubate plates overnight at 37° C.
12. Pick at least 3 colonies from struck out plates and perform colony PCR to confirm genotype. If PCR's are all positive, the plate is used to create strain stocks and a new strain number is assigned.

The kill assay used for preliminary evaluation of the synthetic PsbnA-sprAI Kill Switch in *Staphylococcus aureus* 502a genome is shown below.

Kill Assay

1) Start 5 mL TSB cultures of strains to be tested and wild type control strain and grow overnight at 37° C. in an incubator with orbital shaking at 250 RPM 2) The following day perform 1:100 dilutions into fresh TSB media and allow the cultures to grow for 2 hours.

3) Take an OD600 reading and record the values. Calculate the volume of cell culture required to inoculate 5 ml, cultures to an OD of 0.05. Inoculate new cultures with calculated volume into prewarmed media (TSB/serum)

4) Continue to grow cultures at 37° C. Perform serial dilutions and plate several cell dilutions on BHI or TSB agar plates. Incubate the plates overnight at 37° C. and count the colonies on each plate after they appear (>16 hr).

Preliminary results using PsbnA-sprA1 Kill Switch in *Staphylococcus aureus* 502a genome showed there was no difference in growth curves between KS and wild-type under normal growth conditions in TSB, as desired. Recorded colony counts are shown in Table 44 and FIG. 23.

TABLE 44

Recorded colony counts after 180 min when exposed to human serum

| Strain | t = min | Recorded Colony Count | | | |
|---|---|---|---|---|---|
| | | t = 0 min | t = 45 min | t = 90 min | t = 180 min |
| BP_011 | TSB | 188*10^4 | 409*10^4 | 30*10^6 | 68*10^7 |
| | Serum | 560*10^3 | 76 * 10^4 | 63*10^5 | 5*10^7 |
| 502a | TSB | | 305*10^4 | 199*10^5 | 89*10^6 |
| | Serum | | 305*10^4 | 35*10^5 | 6*10^7 |
| BP_084 | TSB | 220*10^4 | 75*10^5 | 77*10^5 | 135*10^6 |
| | Serum | 62*10^4 | 180*10^4 | 34*10^5 | 157*10^4 |

Figure 23:
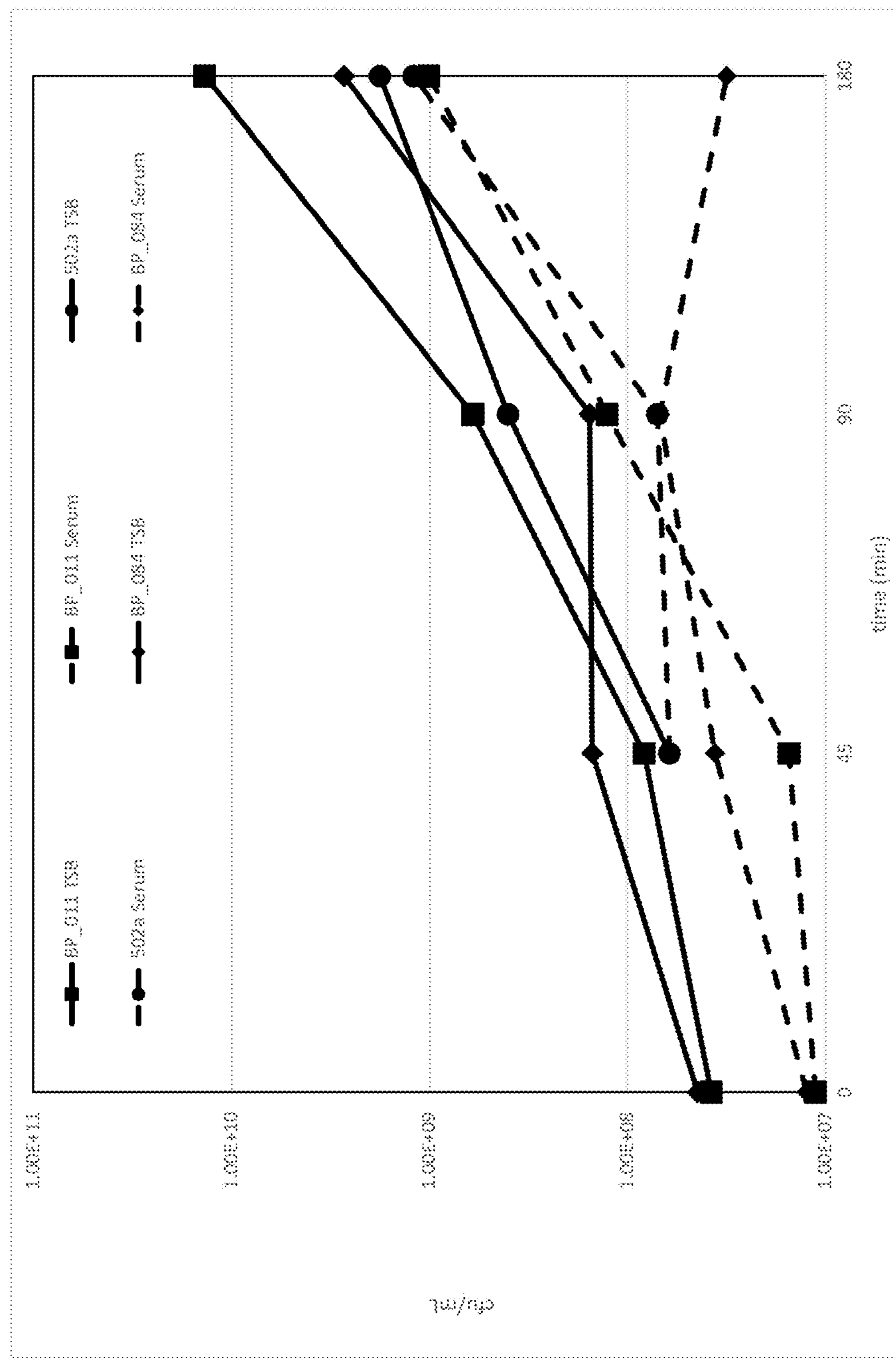
FIG. 23 shows a growth curve of three strains when exposed to human serum compared to TSB: 502a—*Staphylococcus aureus* wild type, *Staphylococcus aureus* BP_011—502a ΔsprA1-sprA1(AS), and *Staphylococcus aureus* BP_084—502a ΔPsprA::PsbnA in which the kill switch is integrated to the genome of *Staphylococcus aureus* 502a. The dashed lines represent the strains grown in serum, and the solid lines represent the strains grown in TSB. After 180 minutes, the strain BP_084 with the integrated kill switch shows a growth curve that is significantly reduced compared to the wild type in serum and the kill switch in complex media. After 3 hours of exposure to human serum, the *Staphylococcus aureus* BP_084 (502a ΔPsprA::PsbnA) cells exhibited 98.84% measurable average cell death compared to the same BP_084 cells in TSB.

As shown in Table 44 and FIG. 23, after three hours of exposure to human serum, the *Staphylococcus aureus* KS strain BP. 084 having the kill switch incorporated to the genome had fewer colonies than the wild-type strain by a factor of about 1000.

The calculated cfu/ml was found by taking the number of colonies counted*dilution factor*20 (to account for 50 uL being plated from each dilution) as shown in Table 45.

TABLE 45

Calculated cfu/mL in Human Serum and TSB

| Strain | t = min | Calculated CFU/mL | | | |
|---|---|---|---|---|---|
| | | 0 | 45 | 90 | 180 |
| BP_011 | TSB | 37600000 | 81800000 | 600000000 | 13600000000 |
| | Serum | 11200000 | 15200000 | 126000000 | 1000000000 |

TABLE 45-continued

| Calculated cfu/mL in Human Serum and TSB | | | | | |
|---|---|---|---|---|---|
| | | Calculated CFU/mL | | | |
| Strain | t = min | 0 | 45 | 90 | 180 |
| 502a | TSB | | 61000000 | 398000000 | 1780000000 |
| | Serum | | 61000000 | 70000000 | 1200000000 |
| BP_084 | TSB | 44000000 | 150000000 | 154000000 | 2700000000 |
| | Serum | 12400000 | 36000000 | 68000000 | 31400000 |

Using the data in Table 45, the cfu/mL of the kill switch strain was compared to wild type 502a. After 3 hours post serum induction, the strain harboring the integrated kill switch *Staphylococcus aureus* KS strain BP_084 (502a ΔPsprA::PsbnA) showed a survival rate of 2.61%, which corresponds to a 97.39% reduction in viable cells compared to the wild type in serum.

Also as shown in Table 45 after three hours of exposure to human serum, the *Staphylococcus aureus* KS strain BP_084 having the kill switch incorporated to the genome exhibited the survival percentage of BP_084 (serum)/BP_084 (TSB)*100=1.16% survival percentage. Therefore, when exposed to human serum the *Staphylococcus aureus* KS strain BP_084 (502a ΔPsprA::PsbnA) cells at 3 hours post-induction exhibited 100%-1.16%=98.84% measurable average cell death compared to the same BP_084 cells in TSB.

The synthetic microorganism BP_084 comprising the kill switch molecular modification incorporated to the genome exhibited desired growth properties under normal conditions, but significantly reduced cell growth when exposed to human serum.

Example 22. Kill Switch Construction with Expression Clamp

Kill switch construction with expression clamp will be performed as follows. In prior examples, certain genes were identified that are up or down regulated in *Staphylococcus aureus* when exposed to human serum and blood. For example, isdB is selected as a promoter that is significantly upregulated a blood and serum responsive promoter. Also, clfB is selected as a second promoter for use in an expression clamp that is active in the absence of serum or blood, but is downregulated in the presence of serum or blood.

In prior examples, an endogenous toxin in Staph *aureus* was identified that when significantly upregulated, kill the cell. For example, sprAI toxin is selected as a cell death gene.

By using stitch PCR and Gibson assembly, operons are constructed that use the promoter region responsible for upregulating serum/blood genes in *Staphylococcus aureus* to drive the expression of the sprAI toxin, and using the promoter regions responsible for downregulating serum/blood genes in *Staphylococcus aureus* to drive the expression of the sprAI$_{AS}$. FIG. 22 shows a cartoon of kill switch construction using serum and blood responsive promoter isdB operably linked to sprA1 cell death gene and a second promoter clfB operably linked to sprA AS to prevent leaky expression of the toxin in the absence of blood or serum. This cassette will be integrated into the native sprA1 location in the genome of *Staphylococcus aureus* 502a by homologous recombination, using the same technique described in previous examples.

To confirm utility, kill assay experiments will be performed using synthetic *Staphylococcus aureus* 502a to determine functionality of Kill Switch under various culture conditions and dermal assays in the absence and presence of blood or serum. The synthetic *Staphylococcus aureus* 502a will exhibit good growth under dermal or mucosal conditions, but will exhibit significantly reduced growth or cell death when exposed to blood or serum. It is contemplated that the colonized synthetic *Staphylococcus aureus* 502a will thus be safe to administer to a subject because it will be unable to survive or reproduce under systemic conditions. It is also contemplated that the synthetic *Staphylococcus aureus* 502a will be able to durably occupy a vacated niche in a host microbiome created by decolonization of a *Staphylococcus aureus* strain such as MRSA.

SEQUENCE LISTING

```
<160> NUMBER OF SEQ ID NOS: 350

<210> SEQ ID NO 1
<211> LENGTH: 1536
<212> TYPE: DNA
<213> ORGANISM: Staphylococcus aureus

<400> SEQUENCE: 1

atgactttac aaatacatac agggggtatt aatttgaaaa agaaaaacat ttattcaatt      60

cgtaaactag gtgtaggtat tgcatctgta actttaggta cattacttat atctggtggc     120

gtaacacctg ctgcaaatgc tgcgcaacac gatgaagctc aacaaaatgc tttttatcaa     180

gtgttaaata tgcctaactt aaacgctgat caacgtaatg gttttatcca aagccttaaa     240

gatgatccaa gccaaagtgc taacgtttta ggtgaagctc aaaaacttaa tgactctcaa     300
```

```
gctccaaaag ctgatgcgca acaaaataac ttcaacaaag atcaacaaag cgccttctat    360
gaaatcttga acatgcctaa cttaaacgaa gcgcaacgta acggcttcat tcaaagtctt    420
aaagacgacc caagccaaag cactaatgtt ttaggtgaag ctaaaaaatt aaacgaatct    480
caagcaccga aagctgataa caatttcaac aaagaacaac aaaatgcttt ctatgaaatc    540
ttgaatatgc ctaacttaaa cgaagaacaa cgcaatggtt tcatccaaag cttaaaagat    600
gacccaagcc aaagtgctaa cctattgtca gaagctaaaa agttaaatga atctcaagca    660
ccgaaagcgg ataacaaatt caacaaagaa caacaaaatg ctttctatga aatcttacat    720
ttacctaact taaacgaaga acaacgcaat ggtttcatcc aaagcttaaa agatgaccca    780
agccaaagcg ctaacctttt agcagaagct aaaaagctaa atgatgcaca agcaccaaaa    840
gctgacaaca aattcaacaa agaacaacaa aatgctttct atgaaatttt acatttacct    900
aacttaactg aagaacaacg taacggcttc atccaaagcc ttaaagacga tccttcagtg    960
agcaaagaaa ttttagcaga agctaaaaag ctaaacgatg ctcaagcacc aaaagaggaa   1020
gacaacaaaa aacctggtaa agaagacggc aacaagcctg gtaaagaaga caacaaaaaa   1080
cctggtaaag aagacggcaa caagcctggt aaagaagaca acaacaaacc tggcaaagaa   1140
gacggcaaca agcctggtaa agaagacaac aacaagcctg gtaaagaaga cggcaacaag   1200
cctggtaaag aagacggcaa caaacctggt aaagaagacg gcaacggagt acatgtcgtt   1260
aaacctggtg atacagtaaa tgacattgca aaagcaaacg gcactactgc tgacaaaatt   1320
gctgcagata acaaattagc tgataaaaac atgatcaaac ctggtcaaga acttgttgtt   1380
gataagaagc aaccagcaaa ccatgcagat gctaacaaag ctcaagcatt accagaaact   1440
ggtgaagaaa atccattcat cggtacaact gtatttggtg gattatcatt agccttaggt   1500
gcagcgttat tagctggacg tcgtcgcgaa ctataa                              1536
```

```
<210> SEQ ID NO 2
<211> LENGTH: 993
<212> TYPE: DNA
<213> ORGANISM: Staphylococcus aureus

<400> SEQUENCE: 2

atgaataaag taattaaaat gcttgttgtt acgcttgctt tcctacttgt tttagcagga     60
tgtagtggga attcaaataa acaatcatct gataacaaag ataaggaaac aacttcaatt    120
aaacatgcaa tgggtacaac tgaaattaaa gggaaaccaa agcgtgttgt tacgctatat    180
caaggtgcca ctgacgtcgc tgtatcttta ggtgttaaac ctgtaggtgc tgtagaatca    240
tggacacaaa aaccgaaatt cgaatacata aaaaatgatt taaaagatac taagattgta    300
ggtcaagaac ctgcacctaa cttagaggaa atctctaaat taaaaccgga cttaattgtc    360
gcgtcaaaag ttagaaatga aaaagtttac gatcaattat ctaaaatcgc accaacagtt    420
tctactgata cagttttcaa attcaaagat acaactaagt taatggggaa agctttaggg    480
aaagaaaaag aagctgaaga tttacttaaa aagtacgatg ataaagtagc tgcattccaa    540
aaagatgcaa aagcaaagta taaagatgca tggccattga aagcttcagt tgttaacttc    600
cgtgctgatc atacaagaat ttatgctggt ggatatgctg gtgaaatctt aaatgattta    660
ggattcaaac gtaataaaga cttacaaaaa caagttgata atggtaaaga tattatccaa    720
cttacatcta aagaaagcat tccattaatg aacgctgatc atatttttgt agtaaaatca    780
gatccaaatg cgaaagatgc tgcattagtt aaaaagactg aaagcgaatg gacttcaagt    840
```

aaagagtgga aaaatttaga cgcagttaaa aacaaccaag tatctgatga tttagatgaa 900
atcacttgga acttagctgg cggatataaa tcttcattaa aacttattga cgatttatat 960
gaaaagttaa atattgaaaa acaatcaaaa taa 993

<210> SEQ ID NO 3
<211> LENGTH: 1014
<212> TYPE: DNA
<213> ORGANISM: Staphylococcus aureus

<400> SEQUENCE: 3
atgataatga ttatcattaa tttaaaggga gaaaaatttg taatgaagta tttattaaag 60
ggaaatattt tgcttctatt actaatattg ttgacaatta tttcgttgtt cataggtgtg 120
agtgaactat caattaaaga tttactacat ttaactgaat cacagcggaa tattttattc 180
tcaagccgaa taccaaggac gatgagtatt ttaattgctg gaagttcgtt ggctttagca 240
ggcttgataa tgcaacaaat gatgcaaaat aagtttgtta gtccgactac agctggaacg 300
atggaatggg ctaaactagg tattttaatt gctttattgt tctttccaac cggtcatatt 360
ttattaaaac tagtatttgc tgttatttgc agtatttgcg gtacgttttt atttgttaaa 420
atcattgatt ttataaaagt gaaagatgtc atttttgtac cgcttttagg aattatgatg 480
ggtgggattg ttgcaagttt cacaaccttc atctcattgc gcacgaatgc tgttcaaagc 540
attggtaact ggcttaacgg gaactttgcc attatcacaa gtggacgcta tgaaatttta 600
tatttaagta ttcctctttt agcattgaca tatctttttg ctaatcattt cacgattgta 660
ggaatgggta aagactttac taataattta ggtttgagtt acgaaaaatt aattaacatc 720
gcattgttta ttactgcaac tattacagca ttggtagtgg tgactgttgg aacattaccg 780
ttcttaggac tagtaatacc aaatattatt tcaatttatc gaggtgatca tttgaaaaat 840
gctatccctc atacgatgat gttaggtgcc atctttgtat tattttctga tatagttggc 900
agaattgttg tttatccata tgaaataaat attggtttaa caataggtgt atttggaaca 960
atcattttcc ttatcttgct tatgaaaggt aggaaaaatt atgcgcaaca ataa 1014

<210> SEQ ID NO 4
<211> LENGTH: 909
<212> TYPE: DNA
<213> ORGANISM: Staphylococcus aureus

<400> SEQUENCE: 4
acagcaactt tagcagttgg tttaatagcc cctttagcca atccatttat agaaatttct 60
aaagcagaaa ataagataga agatatcggt caaggtgcag aaatcatcaa aagaacacaa 120
gacattacta gcaaacgatt agctataact caaaacattc aatttgattt tgtaaaagat 180
aaaaaatata acaaagatgc cctagttgtt aagatgcaag gcttcatcag ctctagaaca 240
acatattcag acttaaaaaa atatccatat attaaaagaa tgatatggcc atttcaatat 300
aatatcagtt tgaaaacgaa agactctaat gttgatttaa tcaattatct tcctaaaaat 360
aaaattgatt cagcagatgt tagtcagaaa ttaggctata atatcggcgg aaacttccaa 420
tcagcgccat caatcggagg cagtggctca ttcaactact ctaaaacaat tagttataat 480
caaaaaaact atgttactga agtagaaagt cagaactcta aaggtgttaa atggggagtg 540
aaagcaaatt catttgttac accgaatggt caagtatctg catatgatca atacttattt 600
gcacaagacc caactggtcc agcagcaaga gactatttcg tcccagataa tcaattacct 660
cctttaattc aaagtggctt taatccatca tttattacaa cattgtcaca cgaaagaggt 720

```
aaaggtgata aaagcgagtt tgaaatcact tacggcagaa acatggatgc tacatatgct    780

tacgtgacaa gacatcgttt agccgttgat agaaaacatg atgcttttaa aaaccgaaac    840

gttacagtta aatatgaagt gaactggaaa acacatgaag taaaaattaa aagcatcaca    900

cctaagtaa                                                            909
```

<210> SEQ ID NO 5
<211> LENGTH: 1053
<212> TYPE: DNA
<213> ORGANISM: Staphylococcus aureus

<400> SEQUENCE: 5

```
atgacaaaac attatttaaa cagtaagtat caatcagaac aacgttcatc agctatgaaa     60

aagattacaa tgggtacagc atctatcatt ttaggttccc ttgtatacat aggcgcagac    120

agccaacaag tcaatgcggc aacagaagct acgaacgcaa ctaataatca aagcacacaa    180

gtttctcaag caacatcaca accaattaat ttccaagtgc aaaaagatgg ctcttcagag    240

aagtcacaca tggatgacta tatgcaacac cctggtaaag taattaaaca aaataataaa    300

tattatttcc aaaccgtgtt aaacaatgca tcattctgga aagaatacaa attttacaat    360

gcaaacaatc aagaattagc aacaactgtt gttaacgata ataaaaaagc ggatactaga    420

acaatcaatg ttgcagttga acctggatat aagagcttaa ctactaaagt acatattgtc    480

gtgccacaaa ttaattacaa tcatagatat actacgcatt tggaatttga aaaagcaatt    540

cctacattag ctgacgcagc aaaaccaaac aatgttaaac cggttcaacc aaaaccagct    600

caacctaaaa cacctactga gcaaactaaa ccagttcaac ctaaagttga aaaagttaaa    660

cctactgtaa ctacaacaag caaagttgaa gacaatcact ctactaaagt tgtaagtact    720

gacacaacaa aagatcaaac taaaacacaa actgctcata cagttaaaac agcacaaact    780

gctcaagaac aaaataaagt tcaaacacct gttaaagatg ttgcaacagc gaaatctgaa    840

agcaacaatc aagctgtaag tgataataaa tcacaacaaa ctaacaaagt tacaaaacat    900

aacgaaacgc ctaaacaagc atctaaagct aaagaattac caaaaactgg tttaacttca    960

gttgataact ttattagcac agttgccttc gcaacacttg cccttttagg ttcattatct   1020

ttattacttt tcaaaagaaa agaatctaaa taa                                1053
```

<210> SEQ ID NO 6
<211> LENGTH: 1527
<212> TYPE: DNA
<213> ORGANISM: Staphylococcus aureus

<400> SEQUENCE: 6

```
atgagtagtc atattcaaat ttttgatacg acactaagag acggtgaaca aacaccagga     60

gtgaatttta cttttgatga acgcttgcgt attgcattgc aattagaaaa atggggtgta    120

gatgttattg aagctggatt tcctgcttca agtacaggta gctttaaatc tgttcaagca    180

attgcacaaa cattaacaac aacggctgta tgtggtttag ctagatgtaa aaaatctgac    240

atcgatgctg tatatgaagc aacaaaagat gcagcgaagc cggtcgtgca tgtttttata    300

gcaacatcac ctattcatct tgaacataaa cttaaaatgt ctcaagaaga cgttttagca    360

tctattaaag aacatgtcac atacgcgaaa caattatttg acgttgttca attttcacct    420

gaagatgcaa cgcgtactga attaccattc ttagtgaaat gtgtacaaac tgccgttgac    480

gctggagcta cagttattaa tattcctgat acagtcggct acagttacca tgatgaatat    540
```

```
gcacatattt tcaaaacctt aacagaatct gtaacatctt caaatgaaat tatttatagt    600

gctcattgcc atgacgattt aggaatggct gtttcaaata gtttagctgc aattgaaggc    660

ggtgcgagac gaattgaagg cactgtaaat ggtattggtg aacgagcagg taatgcagca    720

cttgaagaag tcgcgcttgc actatacgtt cgaaatgatc attatggtgc tcaaactgcc    780

cttaatctcg aagaaactaa aaaaacatcg gatttaattt caagatatgc aggtattcga    840

gtgcctagaa ataaagcaat tgttggccaa aatgcattta gtcatgaatc aggtattcac    900

caagatggcg tattaaaaca tcgtgaaaca tatgaaatta tgacacctca acttgttggt    960

gtaagcacga ctgaacttcc attaggaaaa ttatctggta aacacgcctt ctcagagaag   1020

ttaaaagcat taggttataa cattgataaa gaagcgcaaa tagatttatt taaacaattc   1080

aagaccattg cggacaaaaa gaaatctgtt tcagatagag atattcatgc gattattcaa   1140

ggttctgagc atgagcatca agcactttat aaattggaaa cactacaact acaatatgtc   1200

tctagcggcc ttcaaagtgc tgttgttgtt gttaaagata aagagggtca tatttaccag   1260

gattcaagta ttggtactgg ttcaatcgta gcaatttaca atgcagttga tcgtattttc   1320

cagaaagaaa cagaattaat tgattatcgt attaattctg tcactgaagg tactgatgcc   1380

caagcagaag tacatgtaaa tttattgatt gaaggtaaga ctgtcaatgg ctttggtatt   1440

gatcatgata ttttacaagc ctcttgtaaa gcatacgtag aagcacatgc taaatttgca   1500

gctgaaaatg ttgagaaggt aggtaat                                       1527
```

```
<210> SEQ ID NO 7
<211> LENGTH: 2700
<212> TYPE: DNA
<213> ORGANISM: Staphylococcus aureus

<400> SEQUENCE: 7

atgaaaaaaa gaattgatta tttgtcgaat aagcagaata agtattcgat tagacgtttt     60

acagtaggta ccacatcagt aatagtaggg gcaactatac tatttgggat aggcaatcat    120

caagcacaag cttcagaaca atcgaacgat acaacgcaat cttcgaaaaa taatgcaagt    180

gcagattccg aaaaaaacaa tatgatagaa acacctcaat taaatacaac ggctaatgat    240

acatctgata ttagtgcaaa cacaaacagt gcgaatgtag atagcacaac aaaaccaatg    300

tctacacaaa cgagcaatac cactacaaca gagccagctt caacaaatga aacacctcaa    360

ccgacggcaa ttaaaaatca agcaactgct gcaaaaatgc aagatcaaac tgttcctcaa    420

gaagcaaatt ctcaagtaga taataaaaca acgaatgatg ctaatagcat agcaacaaac    480

agtgagctta aaaattctca aacattagat ttaccacaat catcaccaca aacgatttcc    540

aatgcgcaag gaactagtaa accaagtgtt agaacgagag ctgtacgtag tttagctgtt    600

gctgaaccgg tagtaaatgc tgctgatgct aaaggtacaa atgtaaatga taaagttacg    660

gcaagtaatt tcaagttaga aaagactaca tttgacccta atcaaagtgg taacacattt    720

atggcggcaa attttacagt gacagataaa gtgaaatcag gggattattt tacagcgaag    780

ttaccagata gtttaactgg taatggagac gtggattatt ctaattcaaa taatacgatg    840

ccaattgcag acattaaaag tacgaatggc gatgttgtag ctaaagcaac atatgatatc    900

ttgactaaga cgtatacatt tgtctttaca gattatgtaa ataataaaga aaatattaac    960

ggacaatttt cattaccttt atttacagac cgagcaaagg cacctaaatc aggaacatat   1020

gatgcgaata ttaatattgc ggatgaaatg tttaataata aaattactta taactatagt   1080

tcgccaattg caggaattga taaaccaaat ggcgcgaaca tttcttctca aattattggt   1140
```

```
gtagatacag cttcaggtca aaacacatac aagcaaacag tatttgttaa ccctaagcaa   1200

cgagttttag gtaatacgtg ggtgtatatt aaaggctacc aagataaaat cgaagaaagt   1260

agcggtaaag taagtgctac agatacaaaa ctgagaattt ttgaagtgaa tgatacatct   1320

aaattatcag atagctacta tgcagatcca aatgactcta accttaaaga agtaacagac   1380

caatttaaaa atagaatcta ttatgagcat ccaaatgtag ctagtattaa atttggtgat   1440

attactaaaa catatgtagt attagtagaa gggcattacg acaatacagg taagaactta   1500

aaaactcagg ttattcaaga aaatgttgat cctgtaacaa atagagacta cagtattttc   1560

ggttggaata atgagaatgt tgtacgttat ggtggtggaa gtgctgatgg tgattcagca   1620

gtaaatccga aagacccaac tccagggccg ccggttgacc cagaaccaag tccagaccca   1680

gaaccagaac caacgccaga tccagaacca agtccagacc cagaaccgga accaagccca   1740

gacccggatc cggattcgga ttcagacagt gactcaggct cagacagcga ctcaggttca   1800

gatagcgact cagaatcaga tagcgattcg gattcagaca gtgattcaga ttcagacagc   1860

gactcagaat cagatagcga ttcagaatca gatagcgact cagattcaga tagcgattca   1920

gattcagata gcgattcaga atcagatagc gattcggatt cagacagtga ttcagattca   1980

gacagcgact cagaatcaga tagcgactca gaatcagata gtgagtcaga ttcagacagt   2040

gactcggact cagacagtga ttcagactca gatagcgatt cagactcaga tagcgattca   2100

gactcagaca gcgattcaga ttcagacagc gactcagaat cagacagcga ctcagactca   2160

gatagcgact cagactcaga cagcgactca gattcagata gcgattcaga ctcagacagc   2220

gactcagact cagacagcga ctcagactca gatagcgatt cagactcaga cagcgactca   2280

gattcagata gcgattcgga ctcagacagc gattcagatt cagacagcga ctcagactcg   2340

gatagcgatt cagattcaga cagcgactca gactcggata gcgactcgga ttcagatagt   2400

gactccgatt caagagttac accaccaaat aatgaacaga aagcaccatc aaatcctaaa   2460

ggtgaagtaa accattctaa taaggtatca aaacaacaca aaactgatgc tttaccagaa   2520

acaggagata agagcgaaaa cacaaatgca actttatttg gtgcaatgat ggcattatta   2580

ggatcattac tattgtttag aaaacgcaag caagatcata aagaaaaagc gtaaatactt   2640

ttttaggccg aatacatttg tattcggttt ttttgttgaa aatgatttta aagtgaattg   2700
```

```
<210> SEQ ID NO 8
<211> LENGTH: 2673
<212> TYPE: DNA
<213> ORGANISM: Staphylococcus aureus

<400> SEQUENCE: 8

atggctgaat tacctcaatc aagaataaat gaacgaaata ttaccagtga aatgcgtgaa     60

tcatttttag attatgcgat gagtgttatc gttgctcgtg cattgccaga tgttcgtgac    120

ggtttaaaac cagtacatcg tcgtatacta tatggattaa atgaacaagg tatgacaccg    180

gataaatcat ataaaaaatc agcacgtatc gttggtgacg taatgggtaa atatcaccct    240

catggtgact catctattta tgaagcaatg gtacgtatgg ctcaagattt cagttatcgt    300

tatccgcttg ttgatggcca aggtaacttt ggttcaatgg atggagatgg cgcagcagca    360

atgcgttata ctgaagcgcg tatgactaaa atcacacttg aactgttacg tgatattaat    420

aaagatacaa tagattttat cgataactat gatggtaatg aaagagagcc gtcagtctta    480

cctgctcgat tccctaactt gttagccaat ggagcatcag gtatagcggt aggtatggca    540
```

```
acgaatattc caccacataa cttaacagaa ttaatcaatg gtgtacttag cttaagtaag    600

aaccctgata tttcaattgc tgagttaatg gaggatattg aaggtcctga tttcccaact    660

gctggactta ttttaggtaa gagtggtatt agacgtgcat atgaaacagg tcgtggttca    720

attcaaatgc gttctcgtgc agttattgaa gaacgtggag gcggacgtca acgtattgtt    780

gtcactgaaa ttcctttcca agtgaataag gctcgtatga ttgaaaaaat tgcagagctc    840

gttcgtgaca agaaaattga cggtatcact gatttacgtg atgaaacaag tttacgtact    900

ggtgtgcgtg tcgttattga tgtgcgtaag gatgcaaatg ctagtgtcat tttaaataac    960

ttatacaaac aaacacctct tcaaacatca tttggtgtga atatgattgc acttgtaaat   1020

ggtagaccga agcttattaa tttaaaagaa gcgttggtac attatttaga gcatcaaaag   1080

acagttgtta gaagacgtac gcaatacaac ttacgtaaag ctaaagatcg tgcccacatt   1140

ttagaaggat tacgtatcgc acttgaccat atcgatgaaa ttatttcaac gattcgtgag   1200

tcagatacag ataaagttgc aatggaaagc ttgcaacaac gcttcaaact ttctgaaaaa   1260

caagctcaag ctattttaga catgcgttta agacgtctaa caggtttaga gagagacaaa   1320

attgaagctg aatataatga gttattaaat tatattagtg aattagaaac aatcttagct   1380

gatgaagaag tattactaca attagttaga gatgaattaa cagaaattcg agatcgtttc   1440

ggtgatgatc gtcgtactga aatccaatta ggtggatttg aagatttaga agatgaagat   1500

ctcattccag aagaacaaat tgtaattaca ctaagccata ataactacat taaacgtttg   1560

ccggtatcta catatcgtgc tcaaaaccgt ggtggtcgtg gtgttcaagg tatgaataca   1620

ttggaagaag attttgtcag tcaattggta actttaagta cacatgacca tgtattgttc   1680

tttactaaca aaggtcgtgt atacaaactt aaaggttatg aagtgcctga gttatcaaga   1740

cagtctaaag gtattcctgt agtgaatgct attgaacttg aaaatgatga agtcattagt   1800

acaatgattg ctgttaaaga ccttgaaagt gaagacaact tcttagtgtt tgcaactaaa   1860

cgtggtgtcg ttaaacgttc agcattaagt aacttctcaa gaataaatag aaatggtaag   1920

attgcgattt cgttcagaga agatgatgag ttaattgcag ttcgcttaac aagtggtcaa   1980

gaagatatct tgattggtac atcacatgca tcattaattc gattccctga atcaacatta   2040

cgtcctttag gccgtacagc aacgggtgtg aaaggtatta cacttcgtga aggtgacgaa   2100

gttgtagggc ttgatgtagc tcatgcaaac agtgttgatg aagtattagt agttactgaa   2160

aatggttatg gtaaacgtac gccagttaat gactatcgtt tatcaaatcg tggtggtaaa   2220

ggtattaaaa cagctacgat tactgagcgt aatggtaatg ttgtatgtat cactacagta   2280

actggtgaag aagatttaat gattgttact aatgcaggtg tcattattcg actagatgtt   2340

gcagatattt ctcaaaatgg tcgtgcagca caaggtgttc gcttaattcg cttaggtgat   2400

gatcaatttg tttcaacggt tgctaaagta aaagaagatg cagaagatga aacgaatgaa   2460

gatgagcaat ctacttcaac tgtatctgaa gatggtactg aacaacaacg tgaagcggtt   2520

gtaaatgatg aaacaccagg aaatgcaatt catactgaag tgattgattc agaagaaaat   2580

gatgaagatg gacgtattga agtaagacaa gatttcatgg atcgtgttga agaagatata   2640

caacaatcat cagatgaaga tgaagaataa taa                                2673
```

<210> SEQ ID NO 9
<211> LENGTH: 29
<212> TYPE: DNA
<213> ORGANISM: Artificial Sequence
<220> FEATURE:
<223> OTHER INFORMATION: Primer; TKO1; leuA PCR Amplification with Sph1;

upstream pr

<400> SEQUENCE: 9
gatgcgcatg cgaaacagat tatctattc 29

<210> SEQ ID NO 10
<211> LENGTH: 29
<212> TYPE: DNA
<213> ORGANISM: Artificial Sequence
<220> FEATURE:
<223> OTHER INFORMATION: Primer; TKO2; LeuA PCR Amplification with Sph1 (upstream pr-alternate)

<400> SEQUENCE: 10
gatgcgcatg ccagattatc tattcaaag 29

<210> SEQ ID NO 11
<211> LENGTH: 32
<212> TYPE: DNA
<213> ORGANISM: Artificial Sequence
<220> FEATURE:
<223> OTHER INFORMATION: Primer; TKO3; LeuA PCR Amplification with Pst1 (downstream pr)

<400> SEQUENCE: 11
catgatctgc agagtaaatt cccccgtaaa tt 32

<210> SEQ ID NO 12
<211> LENGTH: 32
<212> TYPE: DNA
<213> ORGANISM: Artificial Sequence
<220> FEATURE:
<223> OTHER INFORMATION: Primer; TKO4; LeuA PCR Amplification with Pst1 (downstream pr-alternate)

<400> SEQUENCE: 12
cacgtgatct gcagagtaaa ttcccccgta aa 32

<210> SEQ ID NO 13
<211> LENGTH: 32
<212> TYPE: DNA
<213> ORGANISM: Artificial Sequence
<220> FEATURE:
<223> OTHER INFORMATION: Primer; TKO5; upstream primer to amplify ClfB promoter with EcoRI

<400> SEQUENCE: 13
gactacgaat tcaggtgatg aaaaatttag aa 32

<210> SEQ ID NO 14
<211> LENGTH: 32
<212> TYPE: DNA
<213> ORGANISM: Artificial Sequence
<220> FEATURE:
<223> OTHER INFORMATION: Primer; TKO6; backup upstream primer to amplify ClfB promoter with EcoRI

<400> SEQUENCE: 14
gactacgaat tctgatgaaa aatttagaac tt 32

<210> SEQ ID NO 15
<211> LENGTH: 32
<212> TYPE: DNA
<213> ORGANISM: Artificial Sequence
<220> FEATURE:
<223> OTHER INFORMATION: Primer; TKO7; downstream primer to amplify ClfB promoter with BamHI

<400> SEQUENCE: 15
cttagctgga tccaaatatt actccatttc aa 32

<210> SEQ ID NO 16
<211> LENGTH: 36
<212> TYPE: DNA
<213> ORGANISM: Artificial Sequence
<220> FEATURE:
<223> OTHER INFORMATION: Primer; TKO8; backup downstream primer to amplify ClfB promoter with BamHI

<400> SEQUENCE: 16
cttagctgga tccaaatatt actccatttc aatttc 36

<210> SEQ ID NO 17
<211> LENGTH: 31
<212> TYPE: DNA
<213> ORGANISM: Artificial Sequence
<220> FEATURE:
<223> OTHER INFORMATION: Primer; TKO9; upstream primer to amplify the hlgA RR; contains Sph1

<400> SEQUENCE: 17
gatgcgcatg ctcacaaact attgcgaaat c 31

<210> SEQ ID NO 18
<211> LENGTH: 32
<212> TYPE: DNA
<213> ORGANISM: Artificial Sequence
<220> FEATURE:
<223> OTHER INFORMATION: Primer; TKO10; backup upstream primer to amplify the hlgA RR

<400> SEQUENCE: 18
gatgcgcatg caaactattg cgaaatccat tc 32

<210> SEQ ID NO 19
<211> LENGTH: 32
<212> TYPE: DNA
<213> ORGANISM: Artificial Sequence
<220> FEATURE:
<223> OTHER INFORMATION: Primer; TKO11; downstream primer to amplify hlgA RR; contains pstI

<400> SEQUENCE: 19
catgatctgc agatatataa taatccattt gt 32

<210> SEQ ID NO 20
<211> LENGTH: 37
<212> TYPE: DNA
<213> ORGANISM: Artificial Sequence
<220> FEATURE:
<223> OTHER INFORMATION: Primer; TKO12; backup downstream primer to amplify hlgA RR

<400> SEQUENCE: 20
catgatctgc agatatataa taatccattt gtaagcg 37

<210> SEQ ID NO 21
<211> LENGTH: 20
<212> TYPE: DNA
<213> ORGANISM: Artificial Sequence
<220> FEATURE:
<223> OTHER INFORMATION: Primer; TKO13; First sense primer for sequencing constructs containing pCAD promoter

```
<400> SEQUENCE: 21

gtgttacgat agcaaatgca                                              20


<210> SEQ ID NO 22
<211> LENGTH: 20
<212> TYPE: DNA
<213> ORGANISM: Artificial Sequence
<220> FEATURE:
<223> OTHER INFORMATION: Primer; TKO14; second sense sequencing primer
      anneals roughly in the middle of the SprA1 gene

<400> SEQUENCE: 22

ttattggcta agtagacgca                                              20


<210> SEQ ID NO 23
<211> LENGTH: 20
<212> TYPE: DNA
<213> ORGANISM: Artificial Sequence
<220> FEATURE:
<223> OTHER INFORMATION: Primer; TKO15; primer to anneal just upstream
      of the serum responsive RRs for leuA and hlgA. Anneals in the
      PCN51 vector about 75 nt upstream of the Sph1 site

<400> SEQUENCE: 23

cacatgttct ttcctgcgtt                                              20


<210> SEQ ID NO 24
<211> LENGTH: 20
<212> TYPE: DNA
<213> ORGANISM: Artificial Sequence
<220> FEATURE:
<223> OTHER INFORMATION: Primer; TKO16; backup primer to anneal just
      upstream of the serum responsive RRs for leuA and hlgA

<400> SEQUENCE: 24

acgcggcctt tttacggttc                                              20


<210> SEQ ID NO 25
<211> LENGTH: 20
<212> TYPE: DNA
<213> ORGANISM: Artificial Sequence
<220> FEATURE:
<223> OTHER INFORMATION: Primer; TKO17; primer to anneal near the
      downstream one third of the leuA promoter/RR

<400> SEQUENCE: 25

gaatgggact tgtaaacgtc                                              20


<210> SEQ ID NO 26
<211> LENGTH: 18
<212> TYPE: DNA
<213> ORGANISM: Artificial Sequence
<220> FEATURE:
<223> OTHER INFORMATION: Primer; TKO18; backup primer to anneal near the
      downstream one third of the leuA promoter/RR

<400> SEQUENCE: 26

gaatgggact tgtaaacg                                                18


<210> SEQ ID NO 27
<211> LENGTH: 20
<212> TYPE: DNA
<213> ORGANISM: Artificial Sequence
<220> FEATURE:
<223> OTHER INFORMATION: Primer; TKO19; primer to anneal near the
      downstream one third of the hlgA promoter/RR
```

<400> SEQUENCE: 27
ataaacgcct gcgaccaata 20

<210> SEQ ID NO 28
<211> LENGTH: 20
<212> TYPE: DNA
<213> ORGANISM: Artificial Sequence
<220> FEATURE:
<223> OTHER INFORMATION: Primer; TKO20; backup primer to anneal near the downstream one third of the hlgA promoter/RR

<400> SEQUENCE: 28
gcgaccaata aatcttttaa 20

<210> SEQ ID NO 29
<211> LENGTH: 40
<212> TYPE: DNA
<213> ORGANISM: Artificial Sequence
<220> FEATURE:
<223> OTHER INFORMATION: Primer; TKO21; pTK1 vector with leuA pro homology R

<400> SEQUENCE: 29
ttgaatagat aatctgtttc gcatgcagcg gccgccagct 40

<210> SEQ ID NO 30
<211> LENGTH: 40
<212> TYPE: DNA
<213> ORGANISM: Artificial Sequence
<220> FEATURE:
<223> OTHER INFORMATION: Primer; TKO22; pTK1 vector with leuA pro homology F

<400> SEQUENCE: 30
aatttacggg ggaatttact ctgcagggta ccgcagagag 40

<210> SEQ ID NO 31
<211> LENGTH: 49
<212> TYPE: DNA
<213> ORGANISM: Artificial Sequence
<220> FEATURE:
<223> OTHER INFORMATION: Primer; TKO23; leuA insert with pTK1 homology F

<400> SEQUENCE: 31
agctggcggc cgctgcatgc gaaacagatt atctattcaa agttaattg 49

<210> SEQ ID NO 32
<211> LENGTH: 46
<212> TYPE: DNA
<213> ORGANISM: Artificial Sequence
<220> FEATURE:
<223> OTHER INFORMATION: Primer; TKO24; leuA insert with pTK1 homology R

<400> SEQUENCE: 32
ctctctgcgg taccctgcag agtaaattcc cccgtaaatt ttaatg 46

<210> SEQ ID NO 33
<211> LENGTH: 46
<212> TYPE: DNA
<213> ORGANISM: Artificial Sequence
<220> FEATURE:
<223> OTHER INFORMATION: Primer; TKO25; pTK9 vector with leuA pro homology F

<400> SEQUENCE: 33
cattaaaatt tacgggggaa tttactctgc agatgagcag ggatga 46

<210> SEQ ID NO 34
<211> LENGTH: 49
<212> TYPE: DNA
<213> ORGANISM: Artificial Sequence
<220> FEATURE:
<223> OTHER INFORMATION: Primer; TKO26; pTK9 vector with leuA pro homology R

<400> SEQUENCE: 34
caattaactt tgaatagata atctgtttcg catgcagcgg ccgccagct 49

<210> SEQ ID NO 35
<211> LENGTH: 46
<212> TYPE: DNA
<213> ORGANISM: Artificial Sequence
<220> FEATURE:
<223> OTHER INFORMATION: Primer; TKO27; pTK12 vector with leuA pro homology F

<400> SEQUENCE: 35
cattaaaatt tacgggggaa tttactctgc agatggtaga gatagc 46

<210> SEQ ID NO 36
<211> LENGTH: 46
<212> TYPE: DNA
<213> ORGANISM: Artificial Sequence
<220> FEATURE:
<223> OTHER INFORMATION: Primer; TKO28; leuA insert with pTK12 homology R

<400> SEQUENCE: 36
gctatctcta ccatctgcag agtaaattcc cccgtaaatt ttaatg 46

<210> SEQ ID NO 37
<211> LENGTH: 49
<212> TYPE: DNA
<213> ORGANISM: Artificial Sequence
<220> FEATURE:
<223> OTHER INFORMATION: Primer; TKO29; pTKvector R with kanR homology

<400> SEQUENCE: 37
gcaatccatc ttgttcaatc attataaccc tctttaattt ggttatatg 49

<210> SEQ ID NO 38
<211> LENGTH: 44
<212> TYPE: DNA
<213> ORGANISM: Artificial Sequence
<220> FEATURE:
<223> OTHER INFORMATION: Primer; TKO30; pTKvector F with kanR homology

<400> SEQUENCE: 38
ccttcttgac gagttcttct gagttaaggg atgcataaac tgca 44

<210> SEQ ID NO 39
<211> LENGTH: 49
<212> TYPE: DNA
<213> ORGANISM: Artificial Sequence
<220> FEATURE:
<223> OTHER INFORMATION: Primer; TKO31; pCASSA kanR F with pTK homology

<400> SEQUENCE: 39
catataacca aattaaagag ggttataatg attgaacaag atggattgc 49

<210> SEQ ID NO 40
<211> LENGTH: 44

```
<212> TYPE: DNA
<213> ORGANISM: Artificial Sequence
<220> FEATURE:
<223> OTHER INFORMATION: Primer; TKO32; pCASSA kanR R with pTK homology

<400> SEQUENCE: 40

tgcagtttat gcatccctta actcagaaga actcgtcaag aagg                 44


<210> SEQ ID NO 41
<211> LENGTH: 22
<212> TYPE: DNA
<213> ORGANISM: Artificial Sequence
<220> FEATURE:
<223> OTHER INFORMATION: Primer; TKO33; leuA colony screen PCR F

<400> SEQUENCE: 41

gaatgggact tgtaaacgtc cc                                         22


<210> SEQ ID NO 42
<211> LENGTH: 22
<212> TYPE: DNA
<213> ORGANISM: Artificial Sequence
<220> FEATURE:
<223> OTHER INFORMATION: Primer; TKO34; leuA colony screen PCR R

<400> SEQUENCE: 42

gggacgttta caagtcccat tc                                         22


<210> SEQ ID NO 43
<211> LENGTH: 24
<212> TYPE: DNA
<213> ORGANISM: Artificial Sequence
<220> FEATURE:
<223> OTHER INFORMATION: Primer; BPC - T1.1  - FOR; gRNA insertion for
      pCasSA

<400> SEQUENCE: 43

gaaaggagta atatcgatgg agta                                       24


<210> SEQ ID NO 44
<211> LENGTH: 24
<212> TYPE: DNA
<213> ORGANISM: Artificial Sequence
<220> FEATURE:
<223> OTHER INFORMATION: Primer; BPC - T1.1  - REV; gRNA insertion for
      pCasSA

<400> SEQUENCE: 44

caaatactcc atcgatatta ctcc                                       24


<210> SEQ ID NO 45
<211> LENGTH: 24
<212> TYPE: DNA
<213> ORGANISM: Artificial Sequence
<220> FEATURE:
<223> OTHER INFORMATION: Primer; gRNA insertion for pCasSA

<400> SEQUENCE: 45

gaaaggagag gatgatgatt ataa                                       24


<210> SEQ ID NO 46
<211> LENGTH: 24
<212> TYPE: DNA
<213> ORGANISM: Artificial Sequence
<220> FEATURE:
<223> OTHER INFORMATION: Primer; BPC - T1.2 - REV; gRNA insertion for
      pCasSA
```

<400> SEQUENCE: 46
caaattataa tcatcatcct ctcc 24

<210> SEQ ID NO 47
<211> LENGTH: 24
<212> TYPE: DNA
<213> ORGANISM: Artificial Sequence
<220> FEATURE:
<223> OTHER INFORMATION: Primer; BPC - T1.3 - FOR; gRNA insertion for pCasSA

<400> SEQUENCE: 47
gaaagggaga ggatgatgat tata 24

<210> SEQ ID NO 48
<211> LENGTH: 24
<212> TYPE: DNA
<213> ORGANISM: Artificial Sequence
<220> FEATURE:
<223> OTHER INFORMATION: Primer; BPC - T1.3 - REV; gRNA insertion for pCasSA

<400> SEQUENCE: 48
caaatataat catcatcctc tccc 24

<210> SEQ ID NO 49
<211> LENGTH: 24
<212> TYPE: DNA
<213> ORGANISM: Artificial Sequence
<220> FEATURE:
<223> OTHER INFORMATION: Primer; BPC - T1.4 - FOR; gRNA insertion for pCasSA

<400> SEQUENCE: 49
gaaagggtct aatgttattg ctta 24

<210> SEQ ID NO 50
<211> LENGTH: 24
<212> TYPE: DNA
<213> ORGANISM: Artificial Sequence
<220> FEATURE:
<223> OTHER INFORMATION: Primer; BPC - T1.4 - REV; gRNA insertion for pCasSA

<400> SEQUENCE: 50
caaataagca ataacattag accc 24

<210> SEQ ID NO 51
<211> LENGTH: 23
<212> TYPE: DNA
<213> ORGANISM: Artificial Sequence
<220> FEATURE:
<223> OTHER INFORMATION: Primer; BPC - T1.5 - FOR; gRNA insertion for pCasSA

<400> SEQUENCE: 51
gaaaggagag gatgatgatt ata 23

<210> SEQ ID NO 52
<211> LENGTH: 23
<212> TYPE: DNA
<213> ORGANISM: Artificial Sequence
<220> FEATURE:
<223> OTHER INFORMATION: Primer; BPC - T1.5 - REV; gRNA insertion for pCasSA

<400> SEQUENCE: 52
caaatataat catcatcctc tcc 23

<210> SEQ ID NO 53
<211> LENGTH: 24
<212> TYPE: DNA
<213> ORGANISM: Artificial Sequence
<220> FEATURE:
<223> OTHER INFORMATION: Primer; BPC - T1.6 - FOR; gRNA insertion for pCasSA

<400> SEQUENCE: 53
gaaaggtagt atgagtaata tcga 24

<210> SEQ ID NO 54
<211> LENGTH: 24
<212> TYPE: DNA
<213> ORGANISM: Artificial Sequence
<220> FEATURE:
<223> OTHER INFORMATION: Primer; BPC - T1.6 - REV; gRNA insertion for pCasSA

<400> SEQUENCE: 54
caaatcgata ttactcatac tacc 24

<210> SEQ ID NO 55
<211> LENGTH: 24
<212> TYPE: DNA
<213> ORGANISM: Artificial Sequence
<220> FEATURE:
<223> OTHER INFORMATION: Primer; BPC - T1.7 - FOR; gRNA insertion for pCasSA

<400> SEQUENCE: 55
gaaaggaatt atataaatat aaag 24

<210> SEQ ID NO 56
<211> LENGTH: 24
<212> TYPE: DNA
<213> ORGANISM: Artificial Sequence
<220> FEATURE:
<223> OTHER INFORMATION: Primer; BPC - T1.7 - REV; gRNA insertion for pCasSA

<400> SEQUENCE: 56
caaactttat atttatataa ttcc 24

<210> SEQ ID NO 57
<211> LENGTH: 24
<212> TYPE: DNA
<213> ORGANISM: Artificial Sequence
<220> FEATURE:
<223> OTHER INFORMATION: Primer; BPC - T1.8 - FOR; gRNA insertion for pCasSA

<400> SEQUENCE: 57
gaaaggctac ctccatattt tcta 24

<210> SEQ ID NO 58
<211> LENGTH: 24
<212> TYPE: DNA
<213> ORGANISM: Artificial Sequence
<220> FEATURE:
<223> OTHER INFORMATION: Primer; BPC - T1.8 - REV; gRNA insertion for pCasSA

<400> SEQUENCE: 58
caaatagaaa atatggaggt agcc 24

<210> SEQ ID NO 59
<211> LENGTH: 24
<212> TYPE: DNA
<213> ORGANISM: Artificial Sequence
<220> FEATURE:
<223> OTHER INFORMATION: Primer; BPC - T1.9 - FOR; gRNA insertion for pCasSA

<400> SEQUENCE: 59
gaaaggatag aactgtatta gact 24

<210> SEQ ID NO 60
<211> LENGTH: 24
<212> TYPE: DNA
<213> ORGANISM: Artificial Sequence
<220> FEATURE:
<223> OTHER INFORMATION: Primer; BPC - T1.9 - REV; gRNA insertion for pCasSA

<400> SEQUENCE: 60
caaaagtcta atacagttct atcc 24

<210> SEQ ID NO 61
<211> LENGTH: 24
<212> TYPE: DNA
<213> ORGANISM: Artificial Sequence
<220> FEATURE:
<223> OTHER INFORMATION: Primer BPC - T1.10 - FOR; gRNA insertion for pCasSA

<400> SEQUENCE: 61
gaaaggtgtc taatgttatt gctt 24

<210> SEQ ID NO 62
<211> LENGTH: 24
<212> TYPE: DNA
<213> ORGANISM: Artificial Sequence
<220> FEATURE:
<223> OTHER INFORMATION: Primer; BPC - T1.10 - REV; gRNA insertion for pCasSA

<400> SEQUENCE: 62
caaaaagcaa taacattaga cacc 24

<210> SEQ ID NO 63
<211> LENGTH: 20
<212> TYPE: DNA
<213> ORGANISM: Artificial Sequence
<220> FEATURE:
<223> OTHER INFORMATION: Primer; BPC - gRNA - FOR; sequencing primer for gRNA insertion into the pCasSA vector

<400> SEQUENCE: 63
tgttctttcc tgcgttgtcg 20

<210> SEQ ID NO 64
<211> LENGTH: 24
<212> TYPE: DNA
<213> ORGANISM: Artificial Sequence
<220> FEATURE:
<223> OTHER INFORMATION: Primer; BPC - gRNA - REV; sequencing primer for gRNA insertion into the pCasSA vector

<400> SEQUENCE: 64
tcgcattgac gttaatacct acat 24

<210> SEQ ID NO 65
<211> LENGTH: 24
<212> TYPE: DNA
<213> ORGANISM: Artificial Sequence
<220> FEATURE:
<223> OTHER INFORMATION: Primer; BPC - T1.1.2 - REV; reverse primer for gRNA

<400> SEQUENCE: 65
aaactactcc atcgatatta ctcc 24

<210> SEQ ID NO 66
<211> LENGTH: 24
<212> TYPE: DNA
<213> ORGANISM: Artificial Sequence
<220> FEATURE:
<223> OTHER INFORMATION: Primer; BPC - T1.2.2 - REV; reverse primer for gRNA

<400> SEQUENCE: 66
aaacttataa tcatcatcct ctcc 24

<210> SEQ ID NO 67
<211> LENGTH: 24
<212> TYPE: DNA
<213> ORGANISM: Artificial Sequence
<220> FEATURE:
<223> OTHER INFORMATION: Primer BPC - T1.3.2 - REV; reverse primer for gRNA

<400> SEQUENCE: 67
aaactataat catcatcctc tccc 24

<210> SEQ ID NO 68
<211> LENGTH: 24
<212> TYPE: DNA
<213> ORGANISM: Artificial Sequence
<220> FEATURE:
<223> OTHER INFORMATION: Primer; BPC - T1.4.2 - REV; reverse primer for gRNA

<400> SEQUENCE: 68
aaactaagca ataacattag accc 24

<210> SEQ ID NO 69
<211> LENGTH: 23
<212> TYPE: DNA
<213> ORGANISM: Artificial Sequence
<220> FEATURE:
<223> OTHER INFORMATION: Primer; BPC - T1.5.2 - REV; reverse primer for gRNA

<400> SEQUENCE: 69
aaactataat catcatcctc tcc 23

<210> SEQ ID NO 70
<211> LENGTH: 24
<212> TYPE: DNA
<213> ORGANISM: Artificial Sequence
<220> FEATURE:
<223> OTHER INFORMATION: Primer; BPC - T1.6.2 - REV; reverse primer for gRNA

<400> SEQUENCE: 70
aaactcgata ttactcatac tacc 24

<210> SEQ ID NO 71
<211> LENGTH: 24
<212> TYPE: DNA
<213> ORGANISM: Artificial Sequence
<220> FEATURE:
<223> OTHER INFORMATION: Primer; BPC - T1.7.2 - REV; reverse primer for gRNA

<400> SEQUENCE: 71
aaacctttat atttatataa ttcc 24

<210> SEQ ID NO 72
<211> LENGTH: 24
<212> TYPE: DNA
<213> ORGANISM: Artificial Sequence
<220> FEATURE:
<223> OTHER INFORMATION: Primer; BPC - T1.8.2 - REV; reverse primer for gRNA

<400> SEQUENCE: 72
aaactagaaa atatggaggt agcc 24

<210> SEQ ID NO 73
<211> LENGTH: 24
<212> TYPE: DNA
<213> ORGANISM: Artificial Sequence
<220> FEATURE:
<223> OTHER INFORMATION: Primer; BPC - T1.9.2 - REV; reverse primer for gRNA

<400> SEQUENCE: 73
aaacagtcta atacagttct atcc 24

<210> SEQ ID NO 74
<211> LENGTH: 24
<212> TYPE: DNA
<213> ORGANISM: Artificial Sequence
<220> FEATURE:
<223> OTHER INFORMATION: Primer; BPC - T1.10.2 - REV; reverse primer for gRNA

<400> SEQUENCE: 74
aaacaagcaa taacattaga cacc 24

<210> SEQ ID NO 75
<211> LENGTH: 20
<212> TYPE: DNA
<213> ORGANISM: Artificial Sequence
<220> FEATURE:
<223> OTHER INFORMATION: Primer; BPC - pCN51-1 - FOR; Primer to check insertion into pCN51

<400> SEQUENCE: 75
tttgctggcc ttttgctcac 20

<210> SEQ ID NO 76
<211> LENGTH: 24
<212> TYPE: DNA
<213> ORGANISM: Artificial Sequence
<220> FEATURE:
<223> OTHER INFORMATION: Primer; BPC - pCN51-1 - REV; Primer to check insertion into pCN51

<400> SEQUENCE: 76
tgctttttcg attgatgaac acct 24

```
<210> SEQ ID NO 77
<211> LENGTH: 20
<212> TYPE: DNA
<213> ORGANISM: Artificial Sequence
<220> FEATURE:
<223> OTHER INFORMATION: Primer; BPC - pCN51-2 - FOR; Primer to check
      insertion into pCN51

<400> SEQUENCE: 77

cggccttttt acggttcctg                                               20


<210> SEQ ID NO 78
<211> LENGTH: 24
<212> TYPE: DNA
<213> ORGANISM: Artificial Sequence
<220> FEATURE:
<223> OTHER INFORMATION: Primer; BPC - pCN51-2 - REV; Primer to check
      insertion into pCN51

<400> SEQUENCE: 78

acgttgcttt ttcgattgat gaac                                          24


<210> SEQ ID NO 79
<211> LENGTH: 33
<212> TYPE: DNA
<213> ORGANISM: Artificial Sequence
<220> FEATURE:
<223> OTHER INFORMATION: Primer; BPC - mChr-1 - FOR; mCherry mRNA with
      Pst1

<400> SEQUENCE: 79

cacgtgatct gcagtcacat ggtgagcaag ggc                                33


<210> SEQ ID NO 80
<211> LENGTH: 33
<212> TYPE: DNA
<213> ORGANISM: Artificial Sequence
<220> FEATURE:
<223> OTHER INFORMATION: Primer; BPC - mChr-1 - REV; mCherry mRNA with
      EcoR1

<400> SEQUENCE: 80

gactacgaat tcaaaactga tttcgttgac ccg                                33


<210> SEQ ID NO 81
<211> LENGTH: 34
<212> TYPE: DNA
<213> ORGANISM: Artificial Sequence
<220> FEATURE:
<223> OTHER INFORMATION: Primer; BPC - mChr-2 - REV; mCherry mRNA with
      BamH1

<400> SEQUENCE: 81

cttagctgga tccaaaactg atttcgttga cccg                               34


<210> SEQ ID NO 82
<211> LENGTH: 37
<212> TYPE: DNA
<213> ORGANISM: Artificial Sequence
<220> FEATURE:
<223> OTHER INFORMATION: Primer; BPC - pCN51-hdr - REV; 34BPC-REV with
      Xma1, use with TKO15 to add homologous arms

<400> SEQUENCE: 82

cttagctccc gggtgctttt tcgattgatg aacacct                            37
```

```
<210> SEQ ID NO 83
<211> LENGTH: 20
<212> TYPE: DNA
<213> ORGANISM: Artificial Sequence
<220> FEATURE:
<223> OTHER INFORMATION: Primer; BPC - 2a - FOR; 502a Target 1 genomic
      incorp check

<400> SEQUENCE: 83

cgccaaacgt ttcgtcagtt                                                   20


<210> SEQ ID NO 84
<211> LENGTH: 20
<212> TYPE: DNA
<213> ORGANISM: Artificial Sequence
<220> FEATURE:
<223> OTHER INFORMATION: Primer; BPC - 2a - REV; 502a Target 1 genomic
      incorp check

<400> SEQUENCE: 84

ttcaagcgtg acaaagcagc                                                   20


<210> SEQ ID NO 85
<211> LENGTH: 20
<212> TYPE: DNA
<213> ORGANISM: Artificial Sequence
<220> FEATURE:
<223> OTHER INFORMATION: Primer; BPC - 2a - FOR; 502a Target 1 genomic
      incorp check

<400> SEQUENCE: 85

tgcgcaatgg ccaaaaagat                                                   20


<210> SEQ ID NO 86
<211> LENGTH: 20
<212> TYPE: DNA
<213> ORGANISM: Artificial Sequence
<220> FEATURE:
<223> OTHER INFORMATION: Primer; BPC - 2a - REV; 502a Target 1 genomic
      incorp check

<400> SEQUENCE: 86

cgtgctaaca tccgcttcaa                                                   20


<210> SEQ ID NO 87
<211> LENGTH: 21
<212> TYPE: DNA
<213> ORGANISM: Artificial Sequence
<220> FEATURE:
<223> OTHER INFORMATION: Primer; BPC - mChr-1 - REV; mCherry

<400> SEQUENCE: 87

aaaactgatt tcgttgaccc g                                                 21


<210> SEQ ID NO 88
<211> LENGTH: 33
<212> TYPE: DNA
<213> ORGANISM: Artificial Sequence
<220> FEATURE:
<223> OTHER INFORMATION: Primer; BPC - mChr-1 - FOR; mCherry with Pst1

<400> SEQUENCE: 88

cacgtgatct gcagtcacat ggtttctaaa ggt                                    33


<210> SEQ ID NO 89
<211> LENGTH: 22
<212> TYPE: DNA
```

<213> ORGANISM: Artificial Sequence
<220> FEATURE:
<223> OTHER INFORMATION: Primer; BPC - pJ204-1 - FOR; Checking for insertion btwn HAs in pJ204

<400> SEQUENCE: 89
acgttgcttt ttcgattgat ga 22

<210> SEQ ID NO 90
<211> LENGTH: 19
<212> TYPE: DNA
<213> ORGANISM: Artificial Sequence
<220> FEATURE:
<223> OTHER INFORMATION: Primer; Checking for insertion btwn HAs in pJ204; Checking for insertion btwn HAs in pJ204

<400> SEQUENCE: 90
tccccatgcg agagtaggg 19

<210> SEQ ID NO 91
<211> LENGTH: 23
<212> TYPE: DNA
<213> ORGANISM: Artificial Sequence
<220> FEATURE:
<223> OTHER INFORMATION: Primer; BPC - pJ204-2 - FOR; Checking for insertion btwn HAs in pJ204

<400> SEQUENCE: 91
gaatatttaa gggcgcctgt cac 23

<210> SEQ ID NO 92
<211> LENGTH: 18
<212> TYPE: DNA
<213> ORGANISM: Artificial Sequence
<220> FEATURE:
<223> OTHER INFORMATION: Primer; BPC - pJ204-2 - REV; Checking for insertion btwn HAs in pJ204

<400> SEQUENCE: 92
tatggggtgt cgcccttt 18

<210> SEQ ID NO 93
<211> LENGTH: 19
<212> TYPE: DNA
<213> ORGANISM: Artificial Sequence
<220> FEATURE:
<223> OTHER INFORMATION: Primer; BPC - mChr-1 - FOR; mCherry codon opt seq in pJ204: 300995

<400> SEQUENCE: 93
tcacatggtt tctaaaggt 19

<210> SEQ ID NO 94
<211> LENGTH: 20
<212> TYPE: DNA
<213> ORGANISM: Artificial Sequence
<220> FEATURE:
<223> OTHER INFORMATION: Primer; BP - repF-1 - F; Checking for repF removal

<400> SEQUENCE: 94
catgcctgca gaacggattg 20

<210> SEQ ID NO 95
<211> LENGTH: 20
<212> TYPE: DNA
<213> ORGANISM: Artificial Sequence

```
<220> FEATURE:
<223> OTHER INFORMATION: Primer; BP - repF-1 - R; Checking for repF
      removal

<400> SEQUENCE: 95

gcgcgggaat atgatgctaa                                                   20


<210> SEQ ID NO 96
<211> LENGTH: 20
<212> TYPE: DNA
<213> ORGANISM: Artificial Sequence
<220> FEATURE:
<223> OTHER INFORMATION: Primer; BP - repF-2 - F; Checking for repF
      removal

<400> SEQUENCE: 96

aggtgactga tggctggttg                                                   20


<210> SEQ ID NO 97
<211> LENGTH: 20
<212> TYPE: DNA
<213> ORGANISM: Artificial Sequence
<220> FEATURE:
<223> OTHER INFORMATION: Primer; BP - repF-2 - R; Checking for repF
      removal

<400> SEQUENCE: 97

tatgtctttt gcgcagtcgg                                                   20


<210> SEQ ID NO 98
<211> LENGTH: 24
<212> TYPE: DNA
<213> ORGANISM: Artificial Sequence
<220> FEATURE:
<223> OTHER INFORMATION: Primer; BP - srtA - F; srtA CRISPR targeting
      from Dong et al.

<400> SEQUENCE: 98

gaaacaaaca aatatgctgc cact                                              24


<210> SEQ ID NO 99
<211> LENGTH: 24
<212> TYPE: DNA
<213> ORGANISM: Artificial Sequence
<220> FEATURE:
<223> OTHER INFORMATION: Primer; BP - srtA - R; srtA CRISPR targeting

<400> SEQUENCE: 99

aaacagtggc agcatatttg tttg                                              24


<210> SEQ ID NO 100
<211> LENGTH: 24
<212> TYPE: DNA
<213> ORGANISM: Artificial Sequence
<220> FEATURE:
<223> OTHER INFORMATION: Primer; BP - hla - F; hla CRISPR targeting from
      Dong et al.

<400> SEQUENCE: 100

gaaagcttcc aatatctgta gtac                                              24


<210> SEQ ID NO 101
<211> LENGTH: 24
<212> TYPE: DNA
<213> ORGANISM: Artificial Sequence
<220> FEATURE:
<223> OTHER INFORMATION: Primer; BP - hla - R; BP - hla - R
```

<400> SEQUENCE: 101
aaacgtacta cagatattgg aagc 24

<210> SEQ ID NO 102
<211> LENGTH: 24
<212> TYPE: DNA
<213> ORGANISM: Artificial Sequence
<220> FEATURE:
<223> OTHER INFORMATION: Primer; BP - coa - F; coa CRISPR targeting from Dong et al.

<400> SEQUENCE: 102
gaaagccatt tttaaatctg tacg 24

<210> SEQ ID NO 103
<211> LENGTH: 24
<212> TYPE: DNA
<213> ORGANISM: Artificial Sequence
<220> FEATURE:
<223> OTHER INFORMATION: Primer; BP - coa - R; coa CRISPR targeting

<400> SEQUENCE: 103
aaaccgtaca gatttaaaaa tggc 24

<210> SEQ ID NO 104
<211> LENGTH: 30
<212> TYPE: PRT
<213> ORGANISM: Staphylococcus aureus

<400> SEQUENCE: 104

Met Leu Ile Phe Val His Ile Ile Ala Pro Val Ile Ser Gly Cys Ala
1 5 10 15

Ile Ala Phe Phe Ser Tyr Trp Leu Ser Arg Arg Asn Thr Lys
20 25 30

<210> SEQ ID NO 105
<211> LENGTH: 31
<212> TYPE: PRT
<213> ORGANISM: Artificial Sequence
<220> FEATURE:
<223> OTHER INFORMATION: pepA1- related antimicrobial peptide; WO 2013/050590

<400> SEQUENCE: 105

Met Met Leu Ile Phe Val His Ile Ile Ala Pro Val Ile Ser Gly Cys
1 5 10 15

Ala Ile Ala Phe Phe Ser Tyr Trp Leu Ser Arg Arg Asn Thr Lys
20 25 30

<210> SEQ ID NO 106
<211> LENGTH: 15
<212> TYPE: PRT
<213> ORGANISM: Artificial Sequence
<220> FEATURE:
<223> OTHER INFORMATION: pepA1- related antimicrobial peptide; WO 2013/050590

<400> SEQUENCE: 106

Ala Ile Ala Phe Phe Ser Tyr Trp Leu Ser Arg Arg Asn Thr Lys
1 5 10 15

<210> SEQ ID NO 107
<211> LENGTH: 14
<212> TYPE: PRT

```
<213> ORGANISM: Artificial Sequence
<220> FEATURE:
<223> OTHER INFORMATION: pepA1- related antimicrobial peptide; WO
      2013/050590

<400> SEQUENCE: 107

Ile Ala Phe Phe Ser Tyr Trp Leu Ser Arg Arg Asn Thr Lys
1               5                   10


<210> SEQ ID NO 108
<211> LENGTH: 13
<212> TYPE: PRT
<213> ORGANISM: Artificial Sequence
<220> FEATURE:
<223> OTHER INFORMATION: pepA1- related antimicrobial peptide; WO
      2013/050590

<400> SEQUENCE: 108

Ala Phe Phe Ser Tyr Trp Leu Ser Arg Arg Asn Thr Lys
1               5                   10


<210> SEQ ID NO 109
<211> LENGTH: 12
<212> TYPE: PRT
<213> ORGANISM: Artificial Sequence
<220> FEATURE:
<223> OTHER INFORMATION: pepA1- related antimicrobial peptide; WO
      2013/050590

<400> SEQUENCE: 109

Phe Phe Ser Tyr Trp Leu Ser Arg Arg Asn Thr Lys
1               5                   10


<210> SEQ ID NO 110
<211> LENGTH: 11
<212> TYPE: PRT
<213> ORGANISM: Artificial Sequence
<220> FEATURE:
<223> OTHER INFORMATION: pepA1- related antimicrobial peptide; WO
      2013/050590

<400> SEQUENCE: 110

Phe Ser Tyr Trp Leu Ser Arg Arg Asn Thr Lys
1               5                   10


<210> SEQ ID NO 111
<211> LENGTH: 10
<212> TYPE: PRT
<213> ORGANISM: Artificial Sequence
<220> FEATURE:
<223> OTHER INFORMATION: pepA1- related antimicrobial peptide; WO
      2013/050590

<400> SEQUENCE: 111

Ser Tyr Trp Leu Ser Arg Arg Asn Thr Lys
1               5                   10


<210> SEQ ID NO 112
<211> LENGTH: 9
<212> TYPE: PRT
<213> ORGANISM: Artificial Sequence
<220> FEATURE:
<223> OTHER INFORMATION: pepA1- related antimicrobial peptide; WO
      2013/050590

<400> SEQUENCE: 112

Tyr Trp Leu Ser Arg Arg Asn Thr Lys
1               5
```

<210> SEQ ID NO 113
<211> LENGTH: 33
<212> TYPE: PRT
<213> ORGANISM: Staphylococcus aureus

<400> SEQUENCE: 113

```
Met Gln Gly Phe Lys Glu Lys His Gln Glu Leu Lys Lys Ala Leu Cys
1               5                   10                  15

Gln Ile Gly Leu Met Arg Ser Ile Ser Glu Val Lys Gln Leu Asn Ile
            20                  25                  30

Ala
```

<210> SEQ ID NO 114
<211> LENGTH: 402
<212> TYPE: DNA
<213> ORGANISM: Staphylococcus aureus

<400> SEQUENCE: 114

```
gcatgcgaaa cagattatct attcaaagtt aattgtaaga aaatttaaaa tatttgttga     60

catactaaag cagatatagt aaattaaatt tatcaaattt ttagacaatt ctaactatta    120

aagtgatata taccattcac ggaaggagta taataaaatg cttaatcaat atactgaaca    180

tcaaccgaca acttcaaata ttattatttt attatactct ttaggactcg aacgttagta    240

aatatttact aaacgcttta agtcctattt ctgtttgaat gggacttgta aacgtcccaa    300

taatattggg acgttttttt atgttttatc tttcaattac ttatttttat tactataaaa    360

catgattaat cattaaaatt tacgggggaa tttactctgc ag                       402
```

<210> SEQ ID NO 115
<211> LENGTH: 297
<212> TYPE: DNA
<213> ORGANISM: Staphylococcus aureus

<400> SEQUENCE: 115

```
gcatgcaaac tattgcgaaa tccattcctc ttccactaca agcaccataa ttaaacaaca     60

attcaataga ataagacttg caaaacatag ttatgtcgct atataaacgc ctgcgaccaa    120

taaatctttt aaacataaca taatgcaaaa acatcattta acaatgctaa aaatgtctct    180

tcaatacatg ttgatagtaa ttaactttta acgaacagtt aattcgaaaa cgcttacaaa    240

tggattatta tatatatgaa cttaaaatta aatagaaaga aagtgatttc tctgcag       297
```

<210> SEQ ID NO 116
<211> LENGTH: 598
<212> TYPE: DNA
<213> ORGANISM: Artificial Sequence
<220> FEATURE:
<223> OTHER INFORMATION: Promoter; Cadmium promoter sequence between
      restriction sites SphI and PstI

<400> SEQUENCE: 116

```
gcatgcgcac ttattcaagt gtattttta ataaattatt ttacttattg aaatgtatta     60

ttttctaatg tcataccctg gtcaaaaccg ttcgtttttg agactagaat tttatgccct    120

acttacttct tttattttca ttcaaatatt tgcttgcatg atgagtcgaa aatggttata    180

atacactcaa ataaatattt gaatgaagat gggatgataa tatgaaaaag aaagatactt    240

gtgaaatttt ttgttatgac gaagaaaagg ttaatcgaat acaaggggat ttacaaacag    300

ttgatatttc tggtgttagc caaattttaa aggctattgc cgatgaaaat agagcaaaaa    360
```

ttacttacgc tctgtgtcag gatgaagagt tgtgtgtttg tgatatagca aatatcttag 420
gtgttacgat agcaaatgca tctcatcatt tacgtacgct ttataagcaa ggggtggtca 480
actttagaaa agaaggaaaa ctagctttat attctttagg tgatgaacat atcaggcaga 540
taatgatgat cgccctagca cataagaaag aagtgaaggt caatgtctga acctgcag 598

<210> SEQ ID NO 117
<211> LENGTH: 231
<212> TYPE: DNA
<213> ORGANISM: Artificial Sequence
<220> FEATURE:
<223> OTHER INFORMATION: Promoter; clfB promoter forward sequence with EcoRI and BamHI sites

<400> SEQUENCE: 117
gaattcaggt gatgaaaaat ttagaacttc taagtttttg aaaagtaaaa aatttgtaat 60
agtgtaaaaa tagtatattg atttttgcta gttaacagaa aattttaagt tatataaata 120
ggaagaaaac aaattttacg taattttttt cgaaaagcaa ttgatataat tcttatttca 180
ttatacaatt tagactaatc tagaaattga aatggagtaa tatttggatc c 231

<210> SEQ ID NO 118
<211> LENGTH: 231
<212> TYPE: DNA
<213> ORGANISM: Artificial Sequence
<220> FEATURE:
<223> OTHER INFORMATION: Promoter; clfB promoter as it is cloned in pCN51 vector with EcoRI and BamHI reversed

<400> SEQUENCE: 118
ggatccaaat attactccat ttcaatttct agattagtct aaattgtata atgaaataag 60
aattatatca attgcttttc gaaaaaaatt acgtaaaatt tgttttcttc ctatttatat 120
aacttaaaat tttctgttaa ctagcaaaaa tcaatatact atttttacac tattacaaat 180
tttttacttt tcaaaaactt agaagttcta aatttttcat cacctgaatt c 231

<210> SEQ ID NO 119
<211> LENGTH: 303
<212> TYPE: DNA
<213> ORGANISM: Staphylococcus aureus

<400> SEQUENCE: 119
ttagaaagat ttacttttat atatgaagag actggattaa atacttttat tgacgtaaaa 60
attcactttt gaaccgttca atatcttgcc gatttttata taacagctac aaataaaata 120
taacagtttg attttacagc ctcggtaaat cgtcttgaca aacaaaaatt ttgtgctatc 180
acaacatttg caacgtctta acaagtcatc tataaacatt tctaaatatt taacattact 240
tatgcgtcat ttattgctaa aattattgta ttaaaatata catagaattg atgggatatc 300
atg 303

<210> SEQ ID NO 120
<211> LENGTH: 303
<212> TYPE: DNA
<213> ORGANISM: Staphylococcus aureus

<400> SEQUENCE: 120
acgaaaaatt aattaacatc gcattgttta ttactgcaac tattacagca ttggtagtgg 60
tgactgttgg aacattaccg ttcttaggac tagtaatacc aaatattatt tcaatttatc 120

```
gaggtgatca tttgaaaaat gctatccctc atacgatgat gttaggtgcc atctttgtat    180

tattttctga tatagttggc agaattgttg tttatccata tgaaataaat attggtttaa    240

caataggtgt atttggaaca atcattttcc ttatcttgct tatgaaaggt aggaaaaatt    300

atg                                                                  303
```

<210> SEQ ID NO 121
<211> LENGTH: 303
<212> TYPE: DNA
<213> ORGANISM: Staphylococcus aureus

<400> SEQUENCE: 121

```
ctatctgcgg catttgcaga attactgaat gtcgcgatga tgataattaa cgctaaaatc     60

gttgtattaa aaacttttaa aatatttttc aaaacataat cctccttttt atgattgctt    120

ttaagtcttt agtaaaatca taaataataa tgattatcat tgtcaatatt tattttataa    180

tcaatttatt attgttatac ggaaatagat gtgctagtat aattgataac cattatcaat    240

tgcaatggtt aatcatctca tataacaaca cataatttgt atccttagga ggaaaacaac    300

atg                                                                  303
```

<210> SEQ ID NO 122
<211> LENGTH: 233
<212> TYPE: DNA
<213> ORGANISM: Artificial Sequence
<220> FEATURE:
<223> OTHER INFORMATION: ORF for sprA1 for plasmid construction

<400> SEQUENCE: 122

```
ctgcagggta ccgcagagag gaggtgtata aggtgatgct tattttcgtt cacatcatag     60

caccagtcat cagtggctgt gccattgcgt ttttttctta ttggctaagt agacgcaata    120

caaaataggt gacatatagc cgcaccaata aaaatcccct cactaccgca aatagtgagg    180

ggattggtgt ataagtaaat acttattttc gttgtggatc cttgactgaa ttc           233
```

<210> SEQ ID NO 123
<211> LENGTH: 233
<212> TYPE: DNA
<213> ORGANISM: Artificial Sequence
<220> FEATURE:
<223> OTHER INFORMATION: DNA sequence for the regulatory RNA sprA1sprA1AS (sprA1sprA1 antisense) under the ClfB promoter which is cloned in reverse behind the sprA1 gene, including the antisense regulatory RNA

<400> SEQUENCE: 123

```
gaattcagtc aaggatccac aacgaaaata agtatttact tatacaccaa tcccctcact     60

atttgcggta gtgaggggat ttttattggt gcggctatat gtcacctatt ttgtattgcg    120

tctacttagc caataagaaa aaaacgcaat ggcacagcca ctgatgactg gtgctatgat    180

gtgaacgaaa ataagcatca ccttatacac ctcctctctg cggtaccctg cag           233
```

<210> SEQ ID NO 124
<211> LENGTH: 756
<212> TYPE: DNA
<213> ORGANISM: Artificial Sequence
<220> FEATURE:
<223> OTHER INFORMATION: SmaI DNA sequence between restriction sites PstI and EcoRI

<400> SEQUENCE: 124

```
ctgcagatga gcagggatga ccaactcttt acactttggg gaaagcttaa cgatcgtcag     60
```

```
aaggataatt ttctaaaatg gatgaaagct tttgatgtag agaaaactta ccaaaaaaca    120

agtggggata ttttcaatga tgattttttc gatatatttg gtgatagatt aattactcat    180

catttcagta gcacgcaagc tttaacaaaa actttattcg aacatgcttt taatgactcc    240

ttaaatgaat ctggagttat atcctctctt gcggaaagta gaacaaaccc tgggcatgac    300

ataacaatcg atagcataaa ggttgcttta aaaacagaag cagctaaaaa tattagcaaa    360

tcatatattc atgtaagtaa gtggatggag ttaggcaagg gggagtggat tctagaatta    420

ttattagaac ggtttttaga gcatctagag aattatgaac gtattttcac actcagatat    480

tttaaaatat ccgagtataa atttagctac cagcttgtag aaatacccaa gagtcttttg    540

ttggaagcaa aaaatgcgaa attagaaata atgtcgggaa gcaaacaaag ccctaagccc    600

ggctatggat atgtgttaga tgaaaatgaa aataagaagt tttctctata ctttgatggt    660

ggtgccgaga gaaaacttca aataaaacat ttaaatttag aacattgcat tgttcatgga    720

gtttgggatt ttattctacc gccgccttaa gaattc                              756
```

```
<210> SEQ ID NO 125
<211> LENGTH: 142
<212> TYPE: DNA
<213> ORGANISM: Artificial Sequence
<220> FEATURE:
<223> OTHER INFORMATION: rsaE DNA sequence between restriction sites
      PstI and EcoRI

<400> SEQUENCE: 125

ctgcagatgg tagagatagc atgttatatt atgaacatga aattaatcac ataacaaaca     60

taccccttg tttgaagtga aaaatttctc ccatcccctt tgtttagcgt cgtgtattca    120

gacacgacgt ttttttgaat tc                                             142


<210> SEQ ID NO 126
<211> LENGTH: 104
<212> TYPE: DNA
<213> ORGANISM: Artificial Sequence
<220> FEATURE:
<223> OTHER INFORMATION: Variant can be used for RsaE sRNA which may
      express the sRNA

<400> SEQUENCE: 126

gaaattaatc acataacaaa catacccctt tgtttgaagt gaaaaatttc tcccatcccc     60

tttgtttagc gtcgtgtatt cagacacgac gtttttttga attc                     104


<210> SEQ ID NO 127
<211> LENGTH: 156
<212> TYPE: DNA
<213> ORGANISM: Escherichia coli

<400> SEQUENCE: 127

atgaagcagc aaaaggcgat gttaatcgcc ctgatcgtca tctgtttaac cgtcatagtg     60

acggcactgg taacgaggaa agacctctgc gaggtacgaa tccgaaccgg ccagacggag    120

gtcgctgtct tcacagctta cgaacctgag gagtaa                              156


<210> SEQ ID NO 128
<211> LENGTH: 657
<212> TYPE: DNA
<213> ORGANISM: Klebsiella pneumoniae

<400> SEQUENCE: 128
```

```
atggatgtct ttgataaagt ttatagtgat gataataata gttatgacca aaaaactgta     60

agtcagcgta ttgaagccct atttcttaat aaccttggca aagttgtaac tcgtcagcaa    120

atcattaggg cggcaactga tccaaaaaca gggaaacaac cagaaaattg gcatcagaga    180

ctttcagaac tacgaactga taaaggatat actattttat cctggcggga tatgaaggtt    240

ttagctccgc aagagtatat aatgccacac gcaacaagac gcccaaaggc agcaaagcgt    300

gtattaccga caaaagaaac ctgggaacag gttttggata gagctaatta ctcttgcgag    360

tggcaggaag atggtcaaca ctgtgggtta gttgaaggtg atattgatcc tataggggga    420

ggcacggtca aactaacacc agaccatatg acacctcatt caatagatcc cgcaactgat    480

gtaaatgatc ctaaaatgtg gcaagcattg tgtggacgtc atcaagttat gaaaaaaaat    540

tattgggatt caaataatgg gaaaataaat gtcattggta tattgcagtc agtaaatgag    600

aaacaaaaga atgatgcttt agagtttctt ttgaattatt atggattgaa aagataa       657
```

<210> SEQ ID NO 129
<211> LENGTH: 219
<212> TYPE: DNA
<213> ORGANISM: Artificial Sequence
<220> FEATURE:
<223> OTHER INFORMATION: Promoter; clfB promoter F downregulated in serum

<400> SEQUENCE: 129

```
aggtgatgaa aaatttagaa cttctaagtt tttgaaaagt aaaaaatttg taatagtgta     60

aaaatagtat attgattttt gctagttaac agaaaatttt aagttatata aataggaaga    120

aaacaaattt tacgtaattt ttttcgaaaa gcaattgata taattcttat ttcattatac    180

aatttagact aatctagaaa ttgaaatgga gtaatattt                           219
```

<210> SEQ ID NO 130
<211> LENGTH: 219
<212> TYPE: DNA
<213> ORGANISM: Artificial Sequence
<220> FEATURE:
<223> OTHER INFORMATION: Promoter; clfB promoter R downregulated in serum

<400> SEQUENCE: 130

```
tccactactt tttaaatctt gaagattcaa aaacttttca ttttttaaac attatcacat     60

ttttatcata taactaaaaa cgatcaattg tcttttaaaa ttcaatatat ttatccttct    120

tttgtttaaa atgcattaaa aaaagctttt cgttaactat attaagaata aagtaatatg    180

ttaaatctga ttagatcttt aactttacct cattataaa                           219
```

<210> SEQ ID NO 131
<211> LENGTH: 5743
<212> TYPE: DNA
<213> ORGANISM: Artificial Sequence
<220> FEATURE:
<223> OTHER INFORMATION: Plasmid; pIMAY Integrative Plasmid accession number JQ62198

<400> SEQUENCE: 131

```
gcatgcgttt tagcgtttat ttcgtttagt tatcggcata atcgttaaaa caggcgttat     60

cgtagcgtaa aagcccttga gcgtagcgtg gctttgcagc gaagatgttg tctgttagat    120

tatgaaagcc gatgactgaa tgaaataata agcgcagcgc ccttctattt cggttggagg    180

aggctcaagg gagtatgagg gaatgaaatt ccctcatggg tttgatttta aaaattgctt    240
```

-continued

```
gcaattttgc cgagcggtag cgctggaaaa tttttgaaaa aaatttggaa tttggaaaaa    300
aatgggggga aaggaagcga attttgcttc cgtactacga ccccccatta agtgccgagt    360
gccaattttt gtgccaaaaa cgctctatcc caactggctc aagggtttaa ggggtttttc    420
aatcgccaac gaatcgccaa cgttttcgcc aacgtttttt ataaatctat atttaagtag    480
ctttattgtt gtttttatga ttacaaagtg atacactaac tttataaaat tatttgattg    540
gagtttttta aatggtgatt tcagaatcga aaaaaagagt tatgatttct ctgacaaaag    600
agcaagataa aaaattaaca gatatggcga aacaaaaagg tttttcaaaa tctgcggttg    660
cggcgttagc tatagaagaa tatgcaagaa aggaatcaga acaaaaaaaa taagcgaaag    720
ctcgcgtttt tagaaggata cgagttttcg ctacttgttt ttgataaggt aattatatca    780
tggctattaa aaatactaaa gctagaaatt ttggattttt attatatcct gactcaattc    840
ctaatgattg gaaagaaaaa ttagagagtt tgggcgtatc tatggctgtc agtcctttac    900
acgatatgga cgaaaaaaaa gataaagata catggaataa tagtaatatt atacaaaatg    960
gaaagcacta taaaaaacca cactatcacg ttatatatat tgcacgaaat cctgtaacaa   1020
tagaaagcgt taggaacaag attaagcgaa aattggggaa tagttcagtt gctcatgttg   1080
agatacttga ttatatcaaa ggttcatatg aatatttgac tcatgaatca aaggacgcta   1140
ttgctaagaa taaacatata tacgacaaaa aagatatttt gaacattaat gattttgata   1200
ttgaccgcta tataacactt gatgaaagcc aaaaaagaga attgaagaat ttacttttag   1260
atatagtgga tgactataat ttggtaaata caaaagattt aatggctttt attcgcctta   1320
ggggagcgga gtttggaatt ttaaatacga atgatgtaaa agatattgtt tcaacaaact   1380
ctagcgcctt tagattatgg tttgagggca attatcagtg tggatataga gcaagttatg   1440
caaaggttct tgatgctgaa acgggggaaa taaaatgaca aacaaagaaa aagagttatt   1500
tgctgaaaat gaggaattaa aaaaagaaat taaggactta aaagagcgta ttgaaagata   1560
cagagaaatg gaagttgaat taagtacaac aatagattta ttgagaggag ggattattga   1620
ataaataaaa gccccctgac gaaagtcgaa gggggttttt attttggttt gatgttgcga   1680
ttaatagcaa tacattctat aatagaaggt atggaggatg ttatataatg agacagaatt   1740
atgatgatca tatgtcaact aacggggcag gttagtgaca ttagaaaacc gactgtaaaa   1800
agtacagtcg gcattatctc atattataaa agccagtcat taggcctatc tgacaattcc   1860
tgaatagagt tcataaacaa tcctgcatga taaccatcac aaacagaatg atgtacctgt   1920
aaagatagcg gtaaatatat tgaattacct ttattaatga attttcctgc tgtaataatg   1980
ggtagaaggt aattactatt attattgata tttaagttaa acccagtaaa tgaagtccat   2040
ggaataatag aaagagaaaa agcattttca ggtataggtg ttttgggaaa caatttcccc   2100
gaaccattat atttctctac atcagaaagg tataaatcat aaaactcttt gaagtcattc   2160
tttacaggag tccaaatacc agagaatgtt ttagatacac catcaaaaat tgtataaagt   2220
ggctctaact tatcccaata acctaactct ccgtcgctat tgtaaccagt tctaaaagct   2280
gtatttgagt ttatcaccct tgtcactaag aaaataaatg cagggtaaaa tttatatcct   2340
tcttgtttta tgtttcggta taaaacacta atatcaattt ctgtggttat actaaaagtc   2400
gtttgttggt tcaaataatg attaaatatc tcttttctct tccaattgtc taaatcaatt   2460
ttattaaagt tcatgggttt cactctcctt ctacattttt taacctaata atgccaaata   2520
ccgtttgcca cccctctctt tgataattat aatattggcg aaattcgctt ctaaagatga   2580
aacgcaatat tatatgcttg ctttatcggc cgtatgtgat tataccagcc ccctcactac   2640
```

```
atgtcaagaa taaactgcca aagcataatg ggataattaa ccctcactaa agggaacaaa   2700
agctgggtac cgggcccccc ctcgaggtcg acggtatcga taagcttgat atcgaattcc   2760
tgcagcccgg gggatccact agttctagag cggccgccac cgcggtggag ctccaattcg   2820
ccctatagtg agtcgtatta cgacgtccca gggcttcccg gtatcaacag ggacaccagg   2880
atttatttat tctgcgaagt gatcttccgt cacaggtatt tattcggcgc aaagtgcgtc   2940
gggtgatgct gccaacttac tgatttagtg tatgatggtg tttttgaggt gctccagtgg   3000
cttctgtttc tatcagctgt ccctcctgtt cagctactga cggggtggtg cgtaacggca   3060
aaagcaccgc cggacatcag cgctagcgga gtgtatactg gcttactatg ttggcactga   3120
tgagggtgtc agtgaagtgc ttcatgtggc aggagaaaaa aggctgcacc ggtgcgtcag   3180
cagaatatgt gatacaggat atattccgct tcctcgctca ctgactcgct acgctcggtc   3240
gttcgactgc ggcgagcgga aatggcttac gaacggggcg gagatttcct ggaagatgcc   3300
aggaagatac ttaacaggga agtgagaggg ccgcggcaaa gccgtttttc cataggctcc   3360
gcccccctga caagcatcac gaaatctgac gctcaaatca gtggtggcga aacccgacag   3420
gactataaag ataccaggcg tttcccccctg gcggctccct cgtgcgctct cctgttcctg   3480
cctttcggtt taccggtgtc attccgctgt tatggccgcg tttgtctcat tccacgcctg   3540
acactcagtt ccgggtaggc agttcgctcc aagctggact gtatgcacga accccccgtt   3600
cagtccgacc gctgcgcctt atccggtaac tatcgtcttg agtccaaccc ggaaagacat   3660
gcaaaagcac cactggcagc agccactggt aattgattta gaggagttag tcttgaagtc   3720
atgcgccggt taaggctaaa ctgaaaggac aagttttggt gactgcgctc ctccaagcca   3780
gttacctcgg ttcaaagagt tggtagctca gagaaccttc gaaaaaccgc cctgcaaggc   3840
ggtttttttcg ttttcagagc aagagattac gcgcagacca aaacgatctc aagaagatca   3900
tcttattaat cagataaaat atttctagat ttcagtgcaa tttatctctt caaatgtagc   3960
acctgaagtc agccccatac gatataagtt gtaattctcc gccgcttgcc ctcatctgtt   4020
acgccggcgg tagccggcca gcctcgcaga gcaggattcc cgttgagcac cgccaggtgc   4080
gaataaggga cagtgaagaa ggaacacccg ctcgcgggtg ggcctacttc acctatcctg   4140
cccggctgac gccgttggat acaccaagga aagtctacac gaaccctttg gcaaaatcct   4200
gtatatcgtg cgaaaaagga tggatatacc gaaaaaatcg ctataatgac cccgaagcag   4260
ggttatgcag cggaaaagcg ctgcttccct gctgttttgt ggaatatcta ccgactggaa   4320
acaggcaaat gcaggaaatt actgaactga ggggacaggc gagaggagat cttgatctaa   4380
tgattcaaac ccttgtgaac ttctttagaa caaaagaggt tcgtaacaag attttcttca   4440
cactagcaat gttagtaatt tttaaaatag ggacttatat accagctcca ggagtaaatc   4500
ctgcagcttt tgataatccc caaggttctc aaggtgccac tgagttatta aatacttttg   4560
gtggcggagc cttgaaacga ttttctattt ttgcaatggg tattgtaccc tacatcactg   4620
catcaatcgt aatgcaatta ttacaaatgg atattgtccc taaattctca gaatgggcaa   4680
aacaaggtga agtaggtaga agaaagttaa ataacgttac tcgttattta gcaatttctt   4740
tagcatttat ccaatctata ggtatggcat tccaatttaa taattatctc aaaggtgcgc   4800
tgattatcaa tcagtcaatt atgagttatt tattaatagc actagttttg acagcaggaa   4860
ctgctttctt aatatggctt ggtgatcaaa tcactcagtt cggtgttggt aatggtattt   4920
ctattatcat attcccatca agcttatttt aattatactc tatcaatgat agagtgtcaa   4980
```

```
tattttttt agtttttcat gaactcgagg ggatccaaat aaaaaactag tttgacaaat   5040

aactctatca atgatagagt gtcaacaaaa aggaggaatt aatgatgtct agattagata   5100

aaagtaaagt gattaacagc gcattagagc tgcttaatga ggtcggaatc gaaggtttaa   5160

caacccgtaa actcgcccag aagctaggtg tagagcagcc tacattgtat tggcatgtaa   5220

aaaataagcg ggctttgctc gacgccttag ccattgagat gttagatagg caccatactc   5280

acttttgccc tttagaaggg gaaagctggc aagatttttt acgtaataac gctaaaagtt   5340

ttagatgtgc tttactaagt catcgcgatg gagcaaaagt acatttaggt acacggccta   5400

cagaaaaaca gtatgaaact ctcgaaaatc aattagcctt tttatgccaa caaggttttt   5460

cactagagaa tgcattatat gcactcagcg ctgtggggca ttttacttta ggttgcgtat   5520

tggaagatca agagcatcaa gtcgctaaag aagaaaggga aacacctact actgatagta   5580

tgccgccatt attacgacaa gctatcgaat tatttgatca ccaaggtgca gagccagcct   5640

tcttattcgg ccttgaattg atcatatgcg gattagaaaa acaacttaaa tgtgaaagtg   5700

ggtcttaaaa gcagcataac ctttttccgt gatggtaact tca                     5743
```

```
<210> SEQ ID NO 132
<211> LENGTH: 303
<212> TYPE: DNA
<213> ORGANISM: Artificial Sequence
<220> FEATURE:
<223> OTHER INFORMATION: Promoter; promoter leuA

<400> SEQUENCE: 132

atttttagac aattctaact attaaagtga tatataccat tcacggaagg agtataataa     60

aatgcttaat caatatactg aacatcaacc gacaacttca aatattatta ttttattata    120

ctctttagga ctcgaacgtt agtaaatatt tactaaacgc tttaagtcct atttctgttt    180

gaatgggact tgtaaacgtc ccaataatat tgggacgttt ttttatgttt tatctttcaa    240

ttacttattt ttattactat aaaacatgat taatcattaa aatttacggg ggaatttact    300

atg                                                                  303
```

```
<210> SEQ ID NO 133
<211> LENGTH: 303
<212> TYPE: DNA
<213> ORGANISM: Artificial Sequence
<220> FEATURE:
<223> OTHER INFORMATION: Promoter; promoter hlgA2

<400> SEQUENCE: 133

acttcaaatt ttcacaaact attgcgaaat ccattcctct tccactacaa gcaccataat     60

taaacaacaa ttcaatagaa taagacttgc aaaacatagt tatgtcgcta tataaacgcc    120

tgcgaccaat aaatctttta aacataacat aatgcaaaaa catcatttaa caatgctaaa    180

aatgtctctt caatacatgt tgatagtaat taacttttaa cgaacagtta attcgaaaac    240

gcttacaaat ggattattat atatatgaac ttaaaattaa atagaaagaa agtgatttct    300

atg                                                                  303
```

```
<210> SEQ ID NO 134
<211> LENGTH: 71
<212> TYPE: DNA
<213> ORGANISM: Artificial Sequence
<220> FEATURE:
<223> OTHER INFORMATION: Promoter; promoter hrtAB

<400> SEQUENCE: 134
```

gttcatattg agttcatatt tcaaccttat actgacgcta aagaagaaat agggagaagt 60
gaatcgatat g 71

<210> SEQ ID NO 135
<211> LENGTH: 80
<212> TYPE: DNA
<213> ORGANISM: Artificial Sequence
<220> FEATURE:
<223> OTHER INFORMATION: Promoter; promoter hlb

<400> SEQUENCE: 135
ttcaggctat caataatgct ttgaaatcag cctgtagagt caataatata ccaattatta 60
catcgcacgc attaagacac 80

<210> SEQ ID NO 136
<211> LENGTH: 80
<212> TYPE: DNA
<213> ORGANISM: Artificial Sequence
<220> FEATURE:
<223> OTHER INFORMATION: Promoter; promoter sbnC

<400> SEQUENCE: 136
actcattgtt cttatttact agcaaaaggt gtatctatac attacatttc taaaagatta 60
ggtcataaaa atatagcaat 80

<210> SEQ ID NO 137
<211> LENGTH: 80
<212> TYPE: DNA
<213> ORGANISM: Artificial Sequence
<220> FEATURE:
<223> OTHER INFORMATION: Promoter; promoter isdI

<400> SEQUENCE: 137
aactacatcc gtgtattcgc atttgttaga agaaaaattt aatgaagagg acaaaaaaac 60
aactaaaatt ttagaaagta 80

<210> SEQ ID NO 138
<211> LENGTH: 64
<212> TYPE: DNA
<213> ORGANISM: Artificial Sequence
<220> FEATURE:
<223> OTHER INFORMATION: Promoter; promoter isdG

<400> SEQUENCE: 138
tgtaatttag ggacccatta gggactccaa acccaataaa tactgttgtt acaaggtttc 60
tatg 64

<210> SEQ ID NO 139
<211> LENGTH: 303
<212> TYPE: DNA
<213> ORGANISM: Artificial Sequence
<220> FEATURE:
<223> OTHER INFORMATION: Promoter; promoter sbnE

<400> SEQUENCE: 139
gaatacttca aggattaaca tatagtgcat tgattcaaag tgtcatgttt gttgtcgtga 60
atgcgtgtca tcaacaactt aaaggcacat ttgttggaac gacgaacagt atgttagttg 120
ttggtcaaat tattggcagt cttagtggcg ctgccattac aagttatact acaccagcta 180
ctacgtttat cgttatgggc gtagtatttg cagtaagtag tttattttta atttgttcaa 240

```
ccatcactaa tcaaatcaac gatcacacat taatgaaatt atgggagttg aaacaaaaaa    300

gtg                                                                  303


<210> SEQ ID NO 140
<211> LENGTH: 303
<212> TYPE: DNA
<213> ORGANISM: Artificial Sequence
<220> FEATURE:
<223> OTHER INFORMATION: Promoter; promoter lrgA

<400> SEQUENCE: 140

atgaaaaacg attgaatccc acttatttta tacgtattca tcgttcatat attattaaca     60

cgaaacacat taaagaagtg caacaatggt ttaactacac ttatatggta atattgacaa    120

atggtgtcaa gatgcaagtt ggacgttcat ttatgaaaga ttttaaagcg tcgataggat    180

tactttaaca gtaatccttt tttttatgca ttttacctat gatattttgt atttcggact    240

aaaaatcacg caaatcgaag tgagccatct atactttagt taaatcaaac gtaggaggca    300

atg                                                                  303


<210> SEQ ID NO 141
<211> LENGTH: 303
<212> TYPE: DNA
<213> ORGANISM: Artificial Sequence
<220> FEATURE:
<223> OTHER INFORMATION: Promoter; promoter lrgB

<400> SEQUENCE: 141

gtttagtatt attatttgta ttattatgta ctggtgctgt taagttaggc gaagtcgaaa     60

aagtaggaac gacactaaca aataacattg gcttactctt cgtaccagcc ggtatctcag    120

ttgttaactc tttaggtgtc attagccaag caccattttt aatcattgga ctaataatcg    180

tctcaacaat actattactt atttgtactg gctatgtcac acaaattatt atgaaagtta    240

cttcgagatc taaaggtgac aaagtcacaa aaaagatcaa aatagaggag gcacaagctc    300

atg                                                                  303


<210> SEQ ID NO 142
<211> LENGTH: 303
<212> TYPE: DNA
<213> ORGANISM: Artificial Sequence
<220> FEATURE:
<223> OTHER INFORMATION: Promoter; promoter hlgB

<400> SEQUENCE: 142

aagatcctag agattatttc gttccagaca gtgagttacc tcctcttgta caaagtggat     60

ttaacccttc atttatcgcc acagtatctc atgaaaaagg ttcaagcgat acaagcgaat    120

ttgaaattac ttacggaaga aacatggatg tcactcatgc cattaaaaga tcaacgcatt    180

atggcaacag ttatttagac ggacatagag tccataatgc attcgtaaat agaaactata    240

ctgttaaata cgaggtcaat tggaagactc atgaaatcaa ggtgaaagga cagaattgat    300

atg                                                                  303


<210> SEQ ID NO 143
<211> LENGTH: 303
<212> TYPE: DNA
<213> ORGANISM: Artificial Sequence
<220> FEATURE:
<223> OTHER INFORMATION: Promoter; promoter fhuB

<400> SEQUENCE: 143
```

```
tcaaaatgta acaatgatca gaggcatatg tttaattatt gctatgattc tagcaggtat     60

tgcagttgct atcgctggac aagttgcatt tgtaggtttg atggtacctc atatagcaag    120

atttttaatt ggaactgatt atgctaaaat tctaccatta acagccttgt taggtgggat    180

actcgtgctt gttgccgatg tgatagcacg atatttagga gaagcgcctg ttggtgcaat    240

catttcattt atcggtgttc cttacttttt atatttagtt aaaaaaggag gacgctcaat    300

atg                                                                  303


<210> SEQ ID NO 144
<211> LENGTH: 303
<212> TYPE: DNA
<213> ORGANISM: Artificial Sequence
<220> FEATURE:
<223> OTHER INFORMATION: Promoter; promoter splF

<400> SEQUENCE: 144

gttcacctat attaaatagt aagcgagaag caattggtgt tatgtatgct agtgataaac     60

caacaggtga aagtacaagg tcatttgctg tttatttctc tcctgaaatt aagaaattta    120

ttgcagataa tttagataaa taaatcatcc atccatacat tgataaatga tttttagaaa    180

ttaacaacaa aatcaacaat tttaaacatc tctgtgattc tatttattcg aaatgattta    240

aaaaataaaa cttcaaaaac ctaaccttat atttatacga atacttagag gagcacaaaa    300

atg                                                                  303


<210> SEQ ID NO 145
<211> LENGTH: 303
<212> TYPE: DNA
<213> ORGANISM: Artificial Sequence
<220> FEATURE:
<223> OTHER INFORMATION: Promoter; promoter SAUSA300_2268

<400> SEQUENCE: 145

gatgatgtat gtttcgaatt tatcaattaa catgtgagga cctcccgagg aatacatggc     60

attaaataca cgtttaatat ttataaaggt gacttaattt tgttcaagtt gattttacca    120

cgcttttttt ctttattcac taagactttt gaatgaagtt taaaataatt gtttatcagt    180

gataaaatat ttgcaataag aagagaatgg ctaaataatc ttaattttca gaaaagtaat    240

tgtaacctta ctggtcttat ggtaatattt ttcaatatta tcgacgagga tgtgttaaca    300

atg                                                                  303


<210> SEQ ID NO 146
<211> LENGTH: 303
<212> TYPE: DNA
<213> ORGANISM: Artificial Sequence
<220> FEATURE:
<223> OTHER INFORMATION: Promoter; promoter SAUSA300_2616

<400> SEQUENCE: 146

ctatcattat aatgagataa tgtcattttt aattgagcta aacagacagg gaaagacgat     60

tattatgatt acgcatgata tgcatttatt gtctgagtat agttcaagaa cagttgtatt    120

atcaaaagga caagtcgttg ctgataccac gccagtattg atattaaatg ataaaaaaat    180

ctgtgagatt gcatcattga gacaaacatc gctatttgaa atggccgaat atatagggat    240

tagcgagcca cagaaattag tacaattatt tattaaccat gataggaagg tgagacgcca    300

atg                                                                  303
```

<210> SEQ ID NO 147
<211> LENGTH: 303
<212> TYPE: DNA
<213> ORGANISM: Artificial Sequence
<220> FEATURE:
<223> OTHER INFORMATION: Promoter; promoter SAUSA300_2617

<400> SEQUENCE: 147
caggcctatt ttctaggaaa tcgatgattt attttaatat cggtcaaatt attgcgaata 60
ttatttgctg ggcacttatt gcaccaacat tagatatttt gatttataac gaaccggcta 120
acaaggttta tacacaaggt gttatctctg cagtattaaa tattatttca gttggtatta 180
ttgggacaat attattaaaa gcatatgctt catctcaaat aaaaaaaggt agtttacgta 240
aagaataatc attttgttga atcagatatg taaatgaatg tagaaaggta atgatatatc 300
atg 303

<210> SEQ ID NO 148
<211> LENGTH: 303
<212> TYPE: DNA
<213> ORGANISM: Artificial Sequence
<220> FEATURE:
<223> OTHER INFORMATION: Promoter; promoter isdA

<400> SEQUENCE: 148
ctatctgcgg catttgcaga attactgaat gtcgcgatga tgataattaa cgctaaaatc 60
gttgtattaa aaacttttaa aatatttttc aaaacataat cctccttttt atgattgctt 120
ttaagtcttt agtaaaatca taaataataa tgattatcat tgtcaatatt tattttataa 180
tcaatttatt attgttatac ggaaatagat gtgctagtat aattgataac cattatcaat 240
tgcaatggtt aatcatctca tataacaaca cataatttgt atccttagga ggaaaacaac 300
atg 303

<210> SEQ ID NO 149
<211> LENGTH: 303
<212> TYPE: DNA
<213> ORGANISM: Artificial Sequence
<220> FEATURE:
<223> OTHER INFORMATION: Promoter; promoter isdB

<400> SEQUENCE: 149
cttcagttga taactttatt agcacagttg ccttcgcaac acttgccctt ttaggttcat 60
tatctttatt actttcaaa agaaaagaat ctaaataaat catcgtcaca ctcataactt 120
aatatatttt ttattttaaa ttttatttaa cctatgtcat agatatttca taatctataa 180
cataggttat ttttttataa aataatgttg caattaacta ccatttcaat gtacaataca 240
agtaatcaat tgataatgat tatcagttga taatatacaa ttaggagttg tttctacaac 300
atg 303

<210> SEQ ID NO 150
<211> LENGTH: 303
<212> TYPE: DNA
<213> ORGANISM: Artificial Sequence
<220> FEATURE:
<223> OTHER INFORMATION: Promoter; promoter fhuA/C

<400> SEQUENCE: 150
ctttcttgca gatgaataaa taaatggtat gagcacacat acttaaatag aagtccacgg 60
acaagttttt gaactatgaa gacttatctg tgggcgtttt ttattttata aaagtaatat 120
acaagacatg acaaatcgag ctatccaatt taaaaagtaa tgttagtcaa taagattgaa 180
aaatgttata atgatgttca tgataatcat tatcaattgg gatgcctttg aaaattgata 240
atttaaaaat agaaattatt ttttataaac agaaagaatt ttattgaaag tagggaaatt 300
atg 303

<210> SEQ ID NO 151
<211> LENGTH: 303
<212> TYPE: DNA
<213> ORGANISM: Artificial Sequence
<220> FEATURE:
<223> OTHER INFORMATION: Promoter; promoter ear

<400> SEQUENCE: 151
tgacacctgc taattcaaac attatttgag acattctttt caaattaatt ataaattttt 60
acctatagac tagtttgata tttatctaca tctcaaaatt ctcatcaaca atctttcaca 120
tccaacattt ttactttagt ttttataatt caaaacaaca aaacgatgtt aaaaaattat 180
tctatttttt agttaataga tagttaatac atttttgata tttagttaat tgttctttta 240
aaaaaatatt attatatttt cattgtaaac gtttacaata taaaaaaagg agcaattaaa 300
atg 303

<210> SEQ ID NO 152
<211> LENGTH: 303
<212> TYPE: DNA
<213> ORGANISM: Artificial Sequence
<220> FEATURE:
<223> OTHER INFORMATION: Promoter; promoter fnb

<400> SEQUENCE: 152
tgtacaggcg ataattatga aacacttagt atattgtttt aaattagata atgatgaatt 60
taatttgaaa aataagtata aaaaatacaa gccttgtgtg acaagggttt atgatgactt 120
gaatacaatt tataggtata tttcaaataa taaaattatc aattaacata aaattaatga 180
caatcttaac ttttcattaa ctcgcttttt tgtattgctt ttaaaaaccg aacaatatag 240
acttgcattt attaagttta aaaaaattaa tgaattttgc atttaaaggg agatattata 300
gtg 303

<210> SEQ ID NO 153
<211> LENGTH: 303
<212> TYPE: DNA
<213> ORGANISM: Artificial Sequence
<220> FEATURE:
<223> OTHER INFORMATION: Promoter; promoter splD

<400> SEQUENCE: 153
attttaaatt ttgatgcata cattgaaccc gggaattcag gatcaccagt tctaaattct 60
aacaatgagg tcataggtgt ggtgtatggc ggtattggaa aaattggttc tgaatataat 120
ggtgccgtat actttacgcc tcaaatcaaa gattttattc aaaagcacat tgaacaataa 180
acaaatttaa atatacacca tgagcatgtg ttcaataatt ttaatgaaaa acatcggtcg 240
aatataacat aaaaaaacgt ctatatcaaa agcatcatga ataaacagag gagcacaaaa 300
atg 303

<210> SEQ ID NO 154
<211> LENGTH: 303
<212> TYPE: DNA

<213> ORGANISM: Artificial Sequence
<220> FEATURE:
<223> OTHER INFORMATION: Promoter; promoter dps

<400> SEQUENCE: 154
ataatagaaa tagaatgtgg aaaacaacat ggcaccaacc aaatgattat gaaaaatcgt 60
tctttttaga tgataatgcg aaagtaaaac ttactgattg ataaaacata cttgctaatt 120
gataatggat atactagatg atgaattaaa atttagacat ttaaaaagcg gaacacctta 180
catttagatt agaataatta taaaaaagag agtaaaaaca ctttacagat tagaatcatt 240
ataatataat aattaatata aacaagcaag acgtagacaa ttttaaggag tgtattaaat 300
atg 303

<210> SEQ ID NO 155
<211> LENGTH: 300
<212> TYPE: DNA
<213> ORGANISM: Artificial Sequence
<220> FEATURE:
<223> OTHER INFORMATION: Promoter; promoter CH52_00360

<400> SEQUENCE: 155
gaattcttta tagcgcgtgc aatcacacca caagataaaa gattaaaaag tgacaaagca 60
tttattgcat ttttagaaga aaccttcgat cagttcttac cattttattc tgcataaata 120
actttgttta aataatagag cacgtaatca catccatgat ttcgtgctct tttttcttaa 180
tattaaatcg aacgttcaac ataataattc atacttttaa aaaaattaaa ataaatttag 240
gttgacctaa acattttatt aggttattat attgtccata agaagtagag gtgagtcaaa 300

<210> SEQ ID NO 156
<211> LENGTH: 303
<212> TYPE: DNA
<213> ORGANISM: Artificial Sequence
<220> FEATURE:
<223> OTHER INFORMATION: Promoter; promoter CH52_00305

<400> SEQUENCE: 156
cataatcccc ctccttaaat ttgttcatat aagattatga tatcttagat tgcataaaaa 60
gactaggttt aataaaatta aaatgtgaca aattaacgac aagagaaaat gtcaattttg 120
tgacacaaat aacatttaat ttattgctat aatgtatatg ttagaaaatt ttaataagta 180
gaatcatgca tctaaaagag attaatattt aagcttcaaa tttgagtaaa cgtggattac 240
ataattatcc caataaaaaa atcattacga ttaagttctt tttatgtcgt ccacatacaa 300
tac 303

<210> SEQ ID NO 157
<211> LENGTH: 303
<212> TYPE: DNA
<213> ORGANISM: Artificial Sequence
<220> FEATURE:
<223> OTHER INFORMATION: Promoter; promoter CH52_01670

<400> SEQUENCE: 157
cattttatat tccctccgta aaatataaag ttttcttaac tagtttataa taattttaat 60
ttgtagtcaa aaagactttg taataatgcg ttcagttaat tataacttac ttataccttta 120 atataaacaa cttaaaccct ttttattatt tttaataact ctaaagtaca actctaatcc 180
gctctcttta aaaatataaa tgataataag tgcacataat ttctcaatgg attttatgaa 240
tttaaaatat gttatcattt cactaggaca tttgtaatat ggtatgatgc tatttatgat 300

```
ttt                                                              303


<210> SEQ ID NO 158
<211> LENGTH: 302
<212> TYPE: DNA
<213> ORGANISM: Artificial Sequence
<220> FEATURE:
<223> OTHER INFORMATION: Promoter; promoter srtB

<400> SEQUENCE: 158

cataaaaatc ctcttttatt aacgacgttt cttcagtcat cactaaacca gttgttgtac     60

cgttttagat tcgatttcgt tgactttgac aaattaagta aattagcatt ggaccaccga    120

caatcattaa aatagcattg gctggaattt ctaaaggagg ctgtatcact cgtcctaata    180

aatcagccac taacaatagc catgcaccaa taactgtaga aaacggaata agtactctgt    240

aattgccccc aactagcttt ctaaccacat gtggcacaat aatacctaaa aaggctagtt    300

gt                                                                   302


<210> SEQ ID NO 159
<211> LENGTH: 303
<212> TYPE: DNA
<213> ORGANISM: Artificial Sequence
<220> FEATURE:
<223> OTHER INFORMATION: Promoter; promoter sbnA

<400> SEQUENCE: 159

caaaagcgct tcctcctcaa atttaaaatt ctataatatt gtgtgttacc taattgataa     60

tgattctcac tatcaagtaa ttaggattat attttttatg catttatatg tcaaataatt    120

ataagttgca tgtaaatcat aaatatttta ttgacttagg aaaaaattta attcatacta    180

aatcgtgata atgattctca ttgtcataca tcacgaagga ggctaattag tcaatgaata    240

aagtaattaa aatgcttgtt gttacgcttg ctttcctact tgttttagca ggatgtagtg    300

gga                                                                  303


<210> SEQ ID NO 160
<211> LENGTH: 303
<212> TYPE: DNA
<213> ORGANISM: Artificial Sequence
<220> FEATURE:
<223> OTHER INFORMATION: Promoter; promoter clfA

<400> SEQUENCE: 160

cattttattc cctcttttta aaaagtcatt ttatattaac tatataccct ttaaagatat     60

atttaatctc tgttaatgga attatacact aaaattgcat tatagcaatt aatttgtatc    120

gatattttat tatccacaat aatactttac taacaaacat tttatttatt gctattttaa    180

gaattacaaa cgacaacgta cgatttgatt gcaaacattt tttattatta atatgaactc    240

tacctaatgt aatcctagct ttaaatcata ttttttcaaa agcagatgtg taatttatgg    300

tac                                                                  303


<210> SEQ ID NO 161
<211> LENGTH: 303
<212> TYPE: DNA
<213> ORGANISM: Artificial Sequence
<220> FEATURE:
<223> OTHER INFORMATION: Promoter; promoter emp homolog

<400> SEQUENCE: 161
```

```
catctgttat ttctccttta tatagactca atattataac caatataatt tccctgttat     60

attcactaac agcattatat accagaattt tcagtataat aattaacttg aagtaaacgt    120

tgtcttaaca tttttattgt ttttcagctt aaaattaatt attgatattg atagttaagc    180

ataataattt tttcgtaata taaagtgaaa aaagtaatag tccacacctg tttagaatgt    240

ggactatact agattgcatc attgaaatga tgactttgat attatttatt gctagtttaa    300

aat                                                                  303


<210> SEQ ID NO 162
<211> LENGTH: 283
<212> TYPE: DNA
<213> ORGANISM: Artificial Sequence
<220> FEATURE:
<223> OTHER INFORMATION: Promoter; promoter rsaC

<400> SEQUENCE: 162

cacgctgtgt tttaatgaag taagatgaat tgatgttgat gcaacctaaa atattggtat     60

ctccaatatt ttaggctaca catcaacata acaaagtcga aggctaatag tcccatatcg    120

tgcgttaaat atatattacc ctcctattaa tatatatacc gttcccgatc gcacgatatg    180

gtggtattag aacttctctt tgaacgaaag agaaaagcta gaacttatgc agttttaatt    240

aaactgtaaa catttgtcac tctttaaatc aaagagtaaa gtt                      283


<210> SEQ ID NO 163
<211> LENGTH: 303
<212> TYPE: DNA
<213> ORGANISM: Artificial Sequence
<220> FEATURE:
<223> OTHER INFORMATION: Promoter; promoter hlgA1

<400> SEQUENCE: 163

aacaatttgt attttacaaa cattaattaa aaataaaagc aagacattcg tgcaatcggt     60

taccttaaat tgtttacaac tgtcaacaat accaaggttt tattaactat atttctcaca    120

aaattagctt ttagcattcc aaacaaaaaa ggttaaattg aacggaatta tggcattttt    180

aacttaattg taaaaaagtt gataatggtc aattgttaat gaacagttaa ttataataac    240

gtccaaaata tattattatt taattaagtt aaataaaatt atagaaagaa agtgaaactt    300

atg                                                                  303


<210> SEQ ID NO 164
<211> LENGTH: 30
<212> TYPE: DNA
<213> ORGANISM: Artificial Sequence
<220> FEATURE:
<223> OTHER INFORMATION: Primer; forward primer isdA

<400> SEQUENCE: 164

tatatgcatg cctatctgcg gcatttgcag                                      30


<210> SEQ ID NO 165
<211> LENGTH: 32
<212> TYPE: DNA
<213> ORGANISM: Artificial Sequence
<220> FEATURE:
<223> OTHER INFORMATION: Primer; reverse primer isdA

<400> SEQUENCE: 165

gatacctgca ggttgttttc ctcctaagga ta                                   32
```

```
<210> SEQ ID NO 166
<211> LENGTH: 32
<212> TYPE: DNA
<213> ORGANISM: Artificial Sequence
<220> FEATURE:
<223> OTHER INFORMATION: Primer; forward primer isdB

<400> SEQUENCE: 166

gatgcgcatg ccttcagttg ataactttat ta                                  32


<210> SEQ ID NO 167
<211> LENGTH: 32
<212> TYPE: DNA
<213> ORGANISM: Artificial Sequence
<220> FEATURE:
<223> OTHER INFORMATION: Primer; reverse primer isdB

<400> SEQUENCE: 167

gatgcctgca ggttgtagaa acaactccta at                                  32


<210> SEQ ID NO 168
<211> LENGTH: 32
<212> TYPE: DNA
<213> ORGANISM: Artificial Sequence
<220> FEATURE:
<223> OTHER INFORMATION: Primer; forward primer isdI

<400> SEQUENCE: 168

gatacgcatg cttactcgta gcagtttttt gt                                  32


<210> SEQ ID NO 169
<211> LENGTH: 32
<212> TYPE: DNA
<213> ORGANISM: Artificial Sequence
<220> FEATURE:
<223> OTHER INFORMATION: Primer; reverse primer isdI

<400> SEQUENCE: 169

gatagctgca ggggcaatca ctcctctatt tt                                  32


<210> SEQ ID NO 170
<211> LENGTH: 32
<212> TYPE: DNA
<213> ORGANISM: Artificial Sequence
<220> FEATURE:
<223> OTHER INFORMATION: Primer; forward primer isdG

<400> SEQUENCE: 170

gatgcgcatg caaacacaag ataattgaat tt                                  32


<210> SEQ ID NO 171
<211> LENGTH: 33
<212> TYPE: DNA
<213> ORGANISM: Artificial Sequence
<220> FEATURE:
<223> OTHER INFORMATION: Primer; reverse primer isdG

<400> SEQUENCE: 171

gatgcctgca gaattatcct cttttctgtt taa                                 33


<210> SEQ ID NO 172
<211> LENGTH: 36
<212> TYPE: DNA
<213> ORGANISM: Artificial Sequence
<220> FEATURE:
<223> OTHER INFORMATION: Primer; forward primer sbnC
```

<400> SEQUENCE: 172
gaatcgcatg cctttattaa agctgacaaa gtcgta 36

<210> SEQ ID NO 173
<211> LENGTH: 32
<212> TYPE: DNA
<213> ORGANISM: Artificial Sequence
<220> FEATURE:
<223> OTHER INFORMATION: Primer; reverse primer sbnC

<400> SEQUENCE: 173
gaaatcctgc agtgttcaga cacctcgcat tc 32

<210> SEQ ID NO 174
<211> LENGTH: 51
<212> TYPE: DNA
<213> ORGANISM: Artificial Sequence
<220> FEATURE:
<223> OTHER INFORMATION: Primer; forward primer sbnE

<400> SEQUENCE: 174
taactgacta ggcggccgcg aatacttcaa ggattaacat atagtgcatt g 51

<210> SEQ ID NO 175
<211> LENGTH: 62
<212> TYPE: DNA
<213> ORGANISM: Artificial Sequence
<220> FEATURE:
<223> OTHER INFORMATION: Primer; reverse primer sbnE

<400> SEQUENCE: 175
ccagtgaaaa gttcttctcc tttactcatt tttttgtttc aactcccata atttcattaa 60
tg 62

<210> SEQ ID NO 176
<211> LENGTH: 53
<212> TYPE: DNA
<213> ORGANISM: Artificial Sequence
<220> FEATURE:
<223> OTHER INFORMATION: Primer; forward primer lrgA

<400> SEQUENCE: 176
taactgacta ggcggccgca tgaaaaacga ttgaatccca cttattttat acg 53

<210> SEQ ID NO 177
<211> LENGTH: 56
<212> TYPE: DNA
<213> ORGANISM: Artificial Sequence
<220> FEATURE:
<223> OTHER INFORMATION: Primer; reverse primer lrgA

<400> SEQUENCE: 177
ccagtgaaaa gttcttctcc tttactcatt gcctcctacg tttgatttaa ctaaag 56

<210> SEQ ID NO 178
<211> LENGTH: 58
<212> TYPE: DNA
<213> ORGANISM: Artificial Sequence
<220> FEATURE:
<223> OTHER INFORMATION: Primer; forward primer lrgB

<400> SEQUENCE: 178
taactgacta ggcggccgcg tttagtatta ttatttgtat tattatgtac tggtgctg 58

<210> SEQ ID NO 179
<211> LENGTH: 52
<212> TYPE: DNA
<213> ORGANISM: Artificial Sequence
<220> FEATURE:
<223> OTHER INFORMATION: Primer; reverse primer lrgB

<400> SEQUENCE: 179
ccagtgaaaa gttcttctcc tttactcatg agcttgtgcc tcctctattt tg 52

<210> SEQ ID NO 180
<211> LENGTH: 46
<212> TYPE: DNA
<213> ORGANISM: Artificial Sequence
<220> FEATURE:
<223> OTHER INFORMATION: Primer; forward primer hlgB

<400> SEQUENCE: 180
taactgacta ggcggccgca agatcctaga gattatttcg ttccag 46

<210> SEQ ID NO 181
<211> LENGTH: 57
<212> TYPE: DNA
<213> ORGANISM: Artificial Sequence
<220> FEATURE:
<223> OTHER INFORMATION: Primer; reverse primer hlgB

<400> SEQUENCE: 181
ccagtgaaaa gttcttctcc tttactcata tcaattctgt cctttcacct tgatttc 57

<210> SEQ ID NO 182
<211> LENGTH: 53
<212> TYPE: DNA
<213> ORGANISM: Artificial Sequence
<220> FEATURE:
<223> OTHER INFORMATION: Primer; forward primer fhuA

<400> SEQUENCE: 182
taactgacta ggcggccgcc tttcttgcag atgaataaat aaatggtatg agc 53

<210> SEQ ID NO 183
<211> LENGTH: 60
<212> TYPE: DNA
<213> ORGANISM: Artificial Sequence
<220> FEATURE:
<223> OTHER INFORMATION: Primer; reverse primer fhuA

<400> SEQUENCE: 183
ccagtgaaaa gttcttctcc tttactcata atttccctac tttcaataaa attctttctg 60

<210> SEQ ID NO 184
<211> LENGTH: 44
<212> TYPE: DNA
<213> ORGANISM: Artificial Sequence
<220> FEATURE:
<223> OTHER INFORMATION: Primer; forward primer fhuB

<400> SEQUENCE: 184
taactgacta ggcggccgct caaaatgtaa caatgatcag aggc 44

<210> SEQ ID NO 185
<211> LENGTH: 65
<212> TYPE: DNA
<213> ORGANISM: Artificial Sequence
<220> FEATURE:
<223> OTHER INFORMATION: Primer; reverse primer fhuB

<400> SEQUENCE: 185
ccagtgaaaa gttcttctcc tttactcata ttgagcgtcc tcctttttta actaaatata 60
aaaag 65

<210> SEQ ID NO 186
<211> LENGTH: 47
<212> TYPE: DNA
<213> ORGANISM: Artificial Sequence
<220> FEATURE:
<223> OTHER INFORMATION: Primer; forward primer ear

<400> SEQUENCE: 186
taactgacta ggcggccgct gacacctgct aattcaaaca ttatttg 47

<210> SEQ ID NO 187
<211> LENGTH: 65
<212> TYPE: DNA
<213> ORGANISM: Artificial Sequence
<220> FEATURE:
<223> OTHER INFORMATION: Primer; reverse primer ear

<400> SEQUENCE: 187
ccagtgaaaa gttcttctcc tttactcatt ttaattgctc ctttttttat attgtaaacg 60
tttac 65

<210> SEQ ID NO 188
<211> LENGTH: 48
<212> TYPE: DNA
<213> ORGANISM: Artificial Sequence
<220> FEATURE:
<223> OTHER INFORMATION: Primer; forward primer fnb

<400> SEQUENCE: 188
taactgacta ggcggccgct gtacaggcga taattatgaa acacttag 48

<210> SEQ ID NO 189
<211> LENGTH: 74
<212> TYPE: DNA
<213> ORGANISM: Artificial Sequence
<220> FEATURE:
<223> OTHER INFORMATION: Primer; reverse primer fnb

<400> SEQUENCE: 189
ccagtgaaaa gttcttctcc tttactcatt ataatatctc cctttaaatg caaaattcat 60
taattttttt aaac 74

<210> SEQ ID NO 190
<211> LENGTH: 47
<212> TYPE: DNA
<213> ORGANISM: Artificial Sequence
<220> FEATURE:
<223> OTHER INFORMATION: Primer; forward primer hlb

<400> SEQUENCE: 190
taactgacta ggcggccgct tcaggctatc aataatgctt tgaaatc 47

<210> SEQ ID NO 191
<211> LENGTH: 59
<212> TYPE: DNA
<213> ORGANISM: Artificial Sequence
<220> FEATURE:
<223> OTHER INFORMATION: Primer; reverse primer hlb

<400> SEQUENCE: 191
ccagtgaaaa gttcttctcc tttactcata gaaaccttgt aacaacagta tttattggg 59

<210> SEQ ID NO 192
<211> LENGTH: 50
<212> TYPE: DNA
<213> ORGANISM: Artificial Sequence
<220> FEATURE:
<223> OTHER INFORMATION: Primer; forward primer splF

<400> SEQUENCE: 192
taactgacta ggcggccgcg ttcacctata ttaaatagta agcgagaagc 50

<210> SEQ ID NO 193
<211> LENGTH: 65
<212> TYPE: DNA
<213> ORGANISM: Artificial Sequence
<220> FEATURE:
<223> OTHER INFORMATION: Primer; reverse primer splF

<400> SEQUENCE: 193
ccagtgaaaa gttcttctcc tttactcatt tttgtgctcc tctaagtatt cgtataaata 60
taagg 65

<210> SEQ ID NO 194
<211> LENGTH: 51
<212> TYPE: DNA
<213> ORGANISM: Artificial Sequence
<220> FEATURE:
<223> OTHER INFORMATION: Primer; forward primer splD

<400> SEQUENCE: 194
taactgacta ggcggccgca ttttaaattt tgatgcatac attgaacccg g 51

<210> SEQ ID NO 195
<211> LENGTH: 58
<212> TYPE: DNA
<213> ORGANISM: Artificial Sequence
<220> FEATURE:
<223> OTHER INFORMATION: Primer; reverse primer splD

<400> SEQUENCE: 195
ccagtgaaaa gttcttctcc tttactcatt tttgtgctcc tctgtttatt catgatgc 58

<210> SEQ ID NO 196
<211> LENGTH: 52
<212> TYPE: DNA
<213> ORGANISM: Artificial Sequence
<220> FEATURE:
<223> OTHER INFORMATION: Primer; forward primer dps

<400> SEQUENCE: 196
taactgacta ggcggccgca taatagaaat agaatgtgga aaacaacatg gc 52

<210> SEQ ID NO 197
<211> LENGTH: 60
<212> TYPE: DNA
<213> ORGANISM: Artificial Sequence
<220> FEATURE:
<223> OTHER INFORMATION: Primer; reverse primer dps

<400> SEQUENCE: 197
ccagtgaaaa gttcttctcc tttactcata tttaatacac tccttaaaat tgtctacgtc 60

<210> SEQ ID NO 198

<211> LENGTH: 55
<212> TYPE: DNA
<213> ORGANISM: Artificial Sequence
<220> FEATURE:
<223> OTHER INFORMATION: Primer; forward primer SAUSA 300_2268

<400> SEQUENCE: 198
taactgacta ggcggccgcg atgatgtatg tttcgaattt atcaattaac atgtg 55

<210> SEQ ID NO 199
<211> LENGTH: 57
<212> TYPE: DNA
<213> ORGANISM: Artificial Sequence
<220> FEATURE:
<223> OTHER INFORMATION: Primer; reverse primer SAUSA 300_2268

<400> SEQUENCE: 199
ccagtgaaaa gttcttctcc tttactcatt gttaacacat cctcgtcgat aatattg 57

<210> SEQ ID NO 200
<211> LENGTH: 57
<212> TYPE: DNA
<213> ORGANISM: Artificial Sequence
<220> FEATURE:
<223> OTHER INFORMATION: Primer; forward primer SAUSA 300_2616

<400> SEQUENCE: 200
taactgacta ggcggccgcc tatcattata atgagataat gtcattttta attgagc 57

<210> SEQ ID NO 201
<211> LENGTH: 49
<212> TYPE: DNA
<213> ORGANISM: Artificial Sequence
<220> FEATURE:
<223> OTHER INFORMATION: Primer; reverse primer SAUSA 300_2616

<400> SEQUENCE: 201
ccagtgaaaa gttcttctcc tttactcatt ggcgtctcac cttcctatc 49

<210> SEQ ID NO 202
<211> LENGTH: 45
<212> TYPE: DNA
<213> ORGANISM: Artificial Sequence
<220> FEATURE:
<223> OTHER INFORMATION: Primer; forward primer SAUSA 300_2617

<400> SEQUENCE: 202
taactgacta ggcggccgcc aggcctattt tctaggaaat cgatg 45

<210> SEQ ID NO 203
<211> LENGTH: 65
<212> TYPE: DNA
<213> ORGANISM: Artificial Sequence
<220> FEATURE:
<223> OTHER INFORMATION: Primer; reverse primer SAUSA 300_2617

<400> SEQUENCE: 203
ccagtgaaaa gttcttctcc tttactcatg atatatcatt acctttctac attcatttac 60
atatc 65

<210> SEQ ID NO 204
<211> LENGTH: 60
<212> TYPE: DNA
<213> ORGANISM: Artificial Sequence
<220> FEATURE:
<223> OTHER INFORMATION: Primer; forward primer hlgA2

<400> SEQUENCE: 204
cgttaactaa ttaatttaag aaggagatat acatacttca aattttcaca aactattgcg 60

<210> SEQ ID NO 205
<211> LENGTH: 70
<212> TYPE: DNA
<213> ORGANISM: Artificial Sequence
<220> FEATURE:
<223> OTHER INFORMATION: Primer; reverse primer hlgA2

<400> SEQUENCE: 205
ccagtgaaaa gttcttctcc tttactcata gaaatcactt tctttctatt taattttaag 60
ttcatatata 70

<210> SEQ ID NO 206
<211> LENGTH: 60
<212> TYPE: DNA
<213> ORGANISM: Artificial Sequence
<220> FEATURE:
<223> OTHER INFORMATION: Primer; forward primer hrtAB

<400> SEQUENCE: 206
cgttaactaa ttaatttaag aaggagatat acatgttcat attgagttca tatttcaacc 60

<210> SEQ ID NO 207
<211> LENGTH: 55
<212> TYPE: DNA
<213> ORGANISM: Artificial Sequence
<220> FEATURE:
<223> OTHER INFORMATION: Primer; reverse primer hrtAB

<400> SEQUENCE: 207
ccagtgaaaa gttcttctcc tttactcata tcgattcact tctccctatt tcttc 55

<210> SEQ ID NO 208
<211> LENGTH: 29
<212> TYPE: DNA
<213> ORGANISM: Artificial Sequence
<220> FEATURE:
<223> OTHER INFORMATION: Primer; forward primer for pCN56 plasmid with
hlgA2, hrtAB promoters

<400> SEQUENCE: 208
atgagtaaag gagaagaact tttcactgg 29

<210> SEQ ID NO 209
<211> LENGTH: 40
<212> TYPE: DNA
<213> ORGANISM: Artificial Sequence
<220> FEATURE:
<223> OTHER INFORMATION: Primer; reverse primer for pCN56 plasmid with
hlgA2, hrtAB promoters

<400> SEQUENCE: 209
atgtatatct ccttcttaaa ttaattagtt aacgaattcg 40

<210> SEQ ID NO 210
<211> LENGTH: 29
<212> TYPE: DNA
<213> ORGANISM: Artificial Sequence
<220> FEATURE:
<223> OTHER INFORMATION: Primer; forward primer for pCN56 plasmid

<400> SEQUENCE: 210
atgagtaaag gagaagaact tttcactgg 29

<210> SEQ ID NO 211
<211> LENGTH: 39
<212> TYPE: DNA
<213> ORGANISM: Artificial Sequence
<220> FEATURE:
<223> OTHER INFORMATION: Primer; reverse primer for pCN56 plasmid

<400> SEQUENCE: 211
gcggccgcct agtcagttaa ctcaaaggcg gtaatacgg 39

<210> SEQ ID NO 212
<211> LENGTH: 20
<212> TYPE: DNA
<213> ORGANISM: Artificial Sequence
<220> FEATURE:
<223> OTHER INFORMATION: Primer; forward qRT PCR primer for gyrB housekeeping

<400> SEQUENCE: 212
ttggtacagg aatcggtggc 20

<210> SEQ ID NO 213
<211> LENGTH: 20
<212> TYPE: DNA
<213> ORGANISM: Artificial Sequence
<220> FEATURE:
<223> OTHER INFORMATION: Primer; reverse qRT PCR primer for gyrB housekeeping

<400> SEQUENCE: 213
tccatccaca tcggcatcag 20

<210> SEQ ID NO 214
<211> LENGTH: 20
<212> TYPE: DNA
<213> ORGANISM: Artificial Sequence
<220> FEATURE:
<223> OTHER INFORMATION: Primer; isdA forward qRT PCR primer

<400> SEQUENCE: 214
gcaacagaag ctacgaacgc 20

<210> SEQ ID NO 215
<211> LENGTH: 22
<212> TYPE: DNA
<213> ORGANISM: Artificial Sequence
<220> FEATURE:
<223> OTHER INFORMATION: Primer; isdA reverse qRT PCR primer

<400> SEQUENCE: 215
agagccatct ttttgcactt gg 22

<210> SEQ ID NO 216
<211> LENGTH: 25
<212> TYPE: DNA
<213> ORGANISM: Artificial Sequence
<220> FEATURE:
<223> OTHER INFORMATION: Primer; isdB forward qRT PCR primer

<400> SEQUENCE: 216
gcaacaattt tatcattatg ccagc 25

<210> SEQ ID NO 217
<211> LENGTH: 22

<212> TYPE: DNA
<213> ORGANISM: Artificial Sequence
<220> FEATURE:
<223> OTHER INFORMATION: Primer; isdB reverse qRT PCR primer

<400> SEQUENCE: 217
tggcaacttt ttgtcacctt ca 22

<210> SEQ ID NO 218
<211> LENGTH: 21
<212> TYPE: DNA
<213> ORGANISM: Artificial Sequence
<220> FEATURE:
<223> OTHER INFORMATION: Primer; isdI forward qRT PCR primer

<400> SEQUENCE: 218
accgaggata cagacgaagt t 21

<210> SEQ ID NO 219
<211> LENGTH: 21
<212> TYPE: DNA
<213> ORGANISM: Artificial Sequence
<220> FEATURE:
<223> OTHER INFORMATION: Primer; isdI reverse qRT PCR primer

<400> SEQUENCE: 219
tgctgtccat cgtcatcact t 21

<210> SEQ ID NO 220
<211> LENGTH: 21
<212> TYPE: DNA
<213> ORGANISM: Artificial Sequence
<220> FEATURE:
<223> OTHER INFORMATION: Primer; isdG forward primer

<400> SEQUENCE: 220
aaccaatccg taaaagcttg c 21

<210> SEQ ID NO 221
<211> LENGTH: 20
<212> TYPE: DNA
<213> ORGANISM: Artificial Sequence
<220> FEATURE:
<223> OTHER INFORMATION: Primer; isdG reverse qRT PCR primer

<400> SEQUENCE: 221
aggctttgat ggcatgtttg 20

<210> SEQ ID NO 222
<211> LENGTH: 21
<212> TYPE: DNA
<213> ORGANISM: Artificial Sequence
<220> FEATURE:
<223> OTHER INFORMATION: Primer; sbnC forward qRT PCR primer

<400> SEQUENCE: 222
agggaagggt gtctaagcaa c 21

<210> SEQ ID NO 223
<211> LENGTH: 20
<212> TYPE: DNA
<213> ORGANISM: Artificial Sequence
<220> FEATURE:
<223> OTHER INFORMATION: Primer; sbnC reverse qRT PCR primer

<400> SEQUENCE: 223
tcagtccttc ttcaacgcga 20

<210> SEQ ID NO 224
<211> LENGTH: 20
<212> TYPE: DNA
<213> ORGANISM: Artificial Sequence
<220> FEATURE:
<223> OTHER INFORMATION: Primer; sbnE forward qRT PCR primer

<400> SEQUENCE: 224
attcgcttta gccgcaatgg 20

<210> SEQ ID NO 225
<211> LENGTH: 20
<212> TYPE: DNA
<213> ORGANISM: Artificial Sequence
<220> FEATURE:
<223> OTHER INFORMATION: Primer; sbnE reverse qRT PCR primer

<400> SEQUENCE: 225
gcaacttgta gcgcatcgtc 20

<210> SEQ ID NO 226
<211> LENGTH: 21
<212> TYPE: DNA
<213> ORGANISM: Artificial Sequence
<220> FEATURE:
<223> OTHER INFORMATION: Primer; lrgA forward qRT PCR primer

<400> SEQUENCE: 226
gataccggct ggtacgaaga g 21

<210> SEQ ID NO 227
<211> LENGTH: 21
<212> TYPE: DNA
<213> ORGANISM: Artificial Sequence
<220> FEATURE:
<223> OTHER INFORMATION: Primer; lrgA reverse qRT PCR primer

<400> SEQUENCE: 227
tggtgctgtt aagttaggcg a 21

<210> SEQ ID NO 228
<211> LENGTH: 20
<212> TYPE: DNA
<213> ORGANISM: Artificial Sequence
<220> FEATURE:
<223> OTHER INFORMATION: Primer; lrgB forward qRT PCR primer

<400> SEQUENCE: 228
acaaagacag gcacaactgc 20

<210> SEQ ID NO 229
<211> LENGTH: 20
<212> TYPE: DNA
<213> ORGANISM: Artificial Sequence
<220> FEATURE:
<223> OTHER INFORMATION: Primer; lrgB reverse qRT PCR primer

<400> SEQUENCE: 229
ggtgtagcac cagccaaaga 20

<210> SEQ ID NO 230
<211> LENGTH: 21
<212> TYPE: DNA
<213> ORGANISM: Artificial Sequence
<220> FEATURE:
<223> OTHER INFORMATION: Primer; hlgB forward qRT PCR primer

<400> SEQUENCE: 230
tggttgggga ccttatggaa g 21

<210> SEQ ID NO 231
<211> LENGTH: 20
<212> TYPE: DNA
<213> ORGANISM: Artificial Sequence
<220> FEATURE:
<223> OTHER INFORMATION: Primer; hlgB reverse qRT PCR primer

<400> SEQUENCE: 231
ggcatttggt gttgcgctat 20

<210> SEQ ID NO 232
<211> LENGTH: 21
<212> TYPE: DNA
<213> ORGANISM: Artificial Sequence
<220> FEATURE:
<223> OTHER INFORMATION: Primer; fhuA forward qRT PCR primer

<400> SEQUENCE: 232
cacgttgtct ttgaccacca c 21

<210> SEQ ID NO 233
<211> LENGTH: 21
<212> TYPE: DNA
<213> ORGANISM: Artificial Sequence
<220> FEATURE:
<223> OTHER INFORMATION: Primer; fhuA reverse qRT PCR primer

<400> SEQUENCE: 233
tgggcaatgg aagttacagg a 21

<210> SEQ ID NO 234
<211> LENGTH: 20
<212> TYPE: DNA
<213> ORGANISM: Artificial Sequence
<220> FEATURE:
<223> OTHER INFORMATION: Primer; fhuB forward qRT PCR primer

<400> SEQUENCE: 234
caatacctgc tggaacccca 20

<210> SEQ ID NO 235
<211> LENGTH: 20
<212> TYPE: DNA
<213> ORGANISM: Artificial Sequence
<220> FEATURE:
<223> OTHER INFORMATION: Primer; fhuB reverse qRT PCR primer

<400> SEQUENCE: 235
gggtccgcat attgccaaac 20

<210> SEQ ID NO 236
<211> LENGTH: 21
<212> TYPE: DNA
<213> ORGANISM: Artificial Sequence
<220> FEATURE:
<223> OTHER INFORMATION: Primer; ear forward qRT PCR primer

<400> SEQUENCE: 236
ccacttgtca gatctgctcc t 21

<210> SEQ ID NO 237
<211> LENGTH: 24
<212> TYPE: DNA
<213> ORGANISM: Artificial Sequence
<220> FEATURE:
<223> OTHER INFORMATION: Primer; ear reverse qRT PCR primer

<400> SEQUENCE: 237
ggtttggtta cagatggaca aaca 24

<210> SEQ ID NO 238
<211> LENGTH: 19
<212> TYPE: DNA
<213> ORGANISM: Artificial Sequence
<220> FEATURE:
<223> OTHER INFORMATION: Primer; fnb forward qRT PCR primer

<400> SEQUENCE: 238
cgcagtgagc gaccataca 19

<210> SEQ ID NO 239
<211> LENGTH: 20
<212> TYPE: DNA
<213> ORGANISM: Artificial Sequence
<220> FEATURE:
<223> OTHER INFORMATION: Primer; fnb reverse qRT PCR primer

<400> SEQUENCE: 239
ttggtccttg tgcttgacca 20

<210> SEQ ID NO 240
<211> LENGTH: 20
<212> TYPE: DNA
<213> ORGANISM: Artificial Sequence
<220> FEATURE:
<223> OTHER INFORMATION: Primer; hlb forward qRT PCR primer

<400> SEQUENCE: 240
ctacgccacc atcttcagca 20

<210> SEQ ID NO 241
<211> LENGTH: 20
<212> TYPE: DNA
<213> ORGANISM: Artificial Sequence
<220> FEATURE:
<223> OTHER INFORMATION: Primer; hlb reverse qRT PCR primer

<400> SEQUENCE: 241
acacctgtac tcggtcgttc 20

<210> SEQ ID NO 242
<211> LENGTH: 22
<212> TYPE: DNA
<213> ORGANISM: Artificial Sequence
<220> FEATURE:
<223> OTHER INFORMATION: Primer; splF forward qRT PCR primer

<400> SEQUENCE: 242
tgcaattatt cagcctggta gc 22

<210> SEQ ID NO 243
<211> LENGTH: 22
<212> TYPE: DNA
<213> ORGANISM: Artificial Sequence
<220> FEATURE:
<223> OTHER INFORMATION: Primer; splF reverse qRT PCR primer

<400> SEQUENCE: 243
cctgatggct tattaccggc at 22

<210> SEQ ID NO 244
<211> LENGTH: 20
<212> TYPE: DNA
<213> ORGANISM: Artificial Sequence
<220> FEATURE:
<223> OTHER INFORMATION: Primer; splD forward qRT PCR primer

<400> SEQUENCE: 244
agtgacatct gatgcggttg 20

<210> SEQ ID NO 245
<211> LENGTH: 21
<212> TYPE: DNA
<213> ORGANISM: Artificial Sequence
<220> FEATURE:
<223> OTHER INFORMATION: Primer; splD reverse qRT PCR primer

<400> SEQUENCE: 245
aacaccaatt gcttctcgct t 21

<210> SEQ ID NO 246
<211> LENGTH: 20
<212> TYPE: DNA
<213> ORGANISM: Artificial Sequence
<220> FEATURE:
<223> OTHER INFORMATION: Primer; dps forward qRT PCR primer

<400> SEQUENCE: 246
agcggtagga ggaaaccctg 20

<210> SEQ ID NO 247
<211> LENGTH: 22
<212> TYPE: DNA
<213> ORGANISM: Artificial Sequence
<220> FEATURE:
<223> OTHER INFORMATION: Primer; dps reverse qRT PCR primer

<400> SEQUENCE: 247
gttctgcaga gtaacctttc gc 22

<210> SEQ ID NO 248
<211> LENGTH: 21
<212> TYPE: DNA
<213> ORGANISM: Artificial Sequence
<220> FEATURE:
<223> OTHER INFORMATION: Primer; srtB forward qRT PCR primer

<400> SEQUENCE: 248
tgagcgagaa catcgacgta a 21

<210> SEQ ID NO 249
<211> LENGTH: 20
<212> TYPE: DNA
<213> ORGANISM: Artificial Sequence
<220> FEATURE:
<223> OTHER INFORMATION: Primer; srtB reverse qRT PCR primer

<400> SEQUENCE: 249
ccgacatggt gcccgtataa 20

<210> SEQ ID NO 250

<211> LENGTH: 21
<212> TYPE: DNA
<213> ORGANISM: Artificial Sequence
<220> FEATURE:
<223> OTHER INFORMATION: Primer; emp forward qRT PCR primer

<400> SEQUENCE: 250
tcgcgtgaat gtagcaacaa a 21

<210> SEQ ID NO 251
<211> LENGTH: 21
<212> TYPE: DNA
<213> ORGANISM: Artificial Sequence
<220> FEATURE:
<223> OTHER INFORMATION: Primer; emp reverse qRT PCR primer

<400> SEQUENCE: 251
acttctgggc ctttagcaac a 21

<210> SEQ ID NO 252
<211> LENGTH: 20
<212> TYPE: DNA
<213> ORGANISM: Artificial Sequence
<220> FEATURE:
<223> OTHER INFORMATION: Primer; sbnA forward qRT PCR primer

<400> SEQUENCE: 252
cctggaggca gcatgaaaga 20

<210> SEQ ID NO 253
<211> LENGTH: 20
<212> TYPE: DNA
<213> ORGANISM: Artificial Sequence
<220> FEATURE:
<223> OTHER INFORMATION: Primer; sbnA reverse qRT PCR primer

<400> SEQUENCE: 253
cattgccaac gcaatgccta 20

<210> SEQ ID NO 254
<211> LENGTH: 20
<212> TYPE: DNA
<213> ORGANISM: Artificial Sequence
<220> FEATURE:
<223> OTHER INFORMATION: Primer; CH52_360 forward qRT PCR primer

<400> SEQUENCE: 254
ttcaactcga acgctgacga 20

<210> SEQ ID NO 255
<211> LENGTH: 20
<212> TYPE: DNA
<213> ORGANISM: Artificial Sequence
<220> FEATURE:
<223> OTHER INFORMATION: Primer; CH52_360 reverse qRT PCR primer

<400> SEQUENCE: 255
ttgcacccat tgttgcacct 20

<210> SEQ ID NO 256
<211> LENGTH: 20
<212> TYPE: DNA
<213> ORGANISM: Artificial Sequence
<220> FEATURE:
<223> OTHER INFORMATION: Primer; CH52_305 forward qRT PCR primer

<400> SEQUENCE: 256
ttcctggagc agtaccacca 20

<210> SEQ ID NO 257
<211> LENGTH: 22
<212> TYPE: DNA
<213> ORGANISM: Artificial Sequence
<220> FEATURE:
<223> OTHER INFORMATION: Primer; CH52_305 reverse qRT PCR primer

<400> SEQUENCE: 257
cagcgcaatc gctgttaaac ta 22

<210> SEQ ID NO 258
<211> LENGTH: 20
<212> TYPE: DNA
<213> ORGANISM: Artificial Sequence
<220> FEATURE:
<223> OTHER INFORMATION: Primer; CH521670 forward qRT PCR primer

<400> SEQUENCE: 258
gcgattatgg gaccaaacgg 20

<210> SEQ ID NO 259
<211> LENGTH: 21
<212> TYPE: DNA
<213> ORGANISM: Artificial Sequence
<220> FEATURE:
<223> OTHER INFORMATION: Primer; CH521670 reverse qRT PCR primer

<400> SEQUENCE: 259
acttcatagc ttgggtgtcc c 21

<210> SEQ ID NO 260
<211> LENGTH: 20
<212> TYPE: DNA
<213> ORGANISM: Artificial Sequence
<220> FEATURE:
<223> OTHER INFORMATION: Primer; clfA forward qRT PCR primer

<400> SEQUENCE: 260
tccagcacaa caggaaacga 20

<210> SEQ ID NO 261
<211> LENGTH: 20
<212> TYPE: DNA
<213> ORGANISM: Artificial Sequence
<220> FEATURE:
<223> OTHER INFORMATION: Primer; clfA reverse qRT PCR primer

<400> SEQUENCE: 261
tagcttcacc agttaccggc 20

<210> SEQ ID NO 262
<211> LENGTH: 20
<212> TYPE: DNA
<213> ORGANISM: Artificial Sequence
<220> FEATURE:
<223> OTHER INFORMATION: Primer; SAUSA300_2268 forward qRT PCR primer

<400> SEQUENCE: 262
gcttctacag ctttgccgat 20

<210> SEQ ID NO 263
<211> LENGTH: 21
<212> TYPE: DNA

<213> ORGANISM: Artificial Sequence
<220> FEATURE:
<223> OTHER INFORMATION: Primer; SAUSA300_2268 reverse qRT PCR primer

<400> SEQUENCE: 263
gatttggtgc ttactgccac c 21

<210> SEQ ID NO 264
<211> LENGTH: 20
<212> TYPE: DNA
<213> ORGANISM: Artificial Sequence
<220> FEATURE:
<223> OTHER INFORMATION: Primer; SAUSA300_2616 forward qRT PCR primer

<400> SEQUENCE: 264
acaagcgcaa caagcaagag 20

<210> SEQ ID NO 265
<211> LENGTH: 23
<212> TYPE: DNA
<213> ORGANISM: Artificial Sequence
<220> FEATURE:
<223> OTHER INFORMATION: Primer; SAUSA300_2616 reverse qRT PCR primer

<400> SEQUENCE: 265
tgcgtttgat acctttaaca cgg 23

<210> SEQ ID NO 266
<211> LENGTH: 21
<212> TYPE: DNA
<213> ORGANISM: Artificial Sequence
<220> FEATURE:
<223> OTHER INFORMATION: Primer; SAUSA300_2617 forward qRT PCR primer

<400> SEQUENCE: 266
gggctgaaaa agttggcatg a 21

<210> SEQ ID NO 267
<211> LENGTH: 20
<212> TYPE: DNA
<213> ORGANISM: Artificial Sequence
<220> FEATURE:
<223> OTHER INFORMATION: Primer; SAUSA300_2617 reverse qRT PCR primer

<400> SEQUENCE: 267
acgcgttgtt tttgacctcc 20

<210> SEQ ID NO 268
<211> LENGTH: 21
<212> TYPE: DNA
<213> ORGANISM: Artificial Sequence
<220> FEATURE:
<223> OTHER INFORMATION: Primer; hlgA2 forward qRT PCR primer

<400> SEQUENCE: 268
tgatttctgc accttgaccg a 21

<210> SEQ ID NO 269
<211> LENGTH: 20
<212> TYPE: DNA
<213> ORGANISM: Artificial Sequence
<220> FEATURE:
<223> OTHER INFORMATION: Primer; hlgA2 reverse qRT PCR primer

<400> SEQUENCE: 269
agccccttta gccaatccat 20

<210> SEQ ID NO 270
<211> LENGTH: 22
<212> TYPE: DNA
<213> ORGANISM: Artificial Sequence
<220> FEATURE:
<223> OTHER INFORMATION: Primer; hrtAB forward qRT PCR primer

<400> SEQUENCE: 270
acacaacaac aacgtgatga gc 22

<210> SEQ ID NO 271
<211> LENGTH: 20
<212> TYPE: DNA
<213> ORGANISM: Artificial Sequence
<220> FEATURE:
<223> OTHER INFORMATION: Primer; hrtAB reverse qRT PCR primer

<400> SEQUENCE: 271
taacggtgct tgctctgctt 20

<210> SEQ ID NO 272
<211> LENGTH: 204
<212> TYPE: DNA
<213> ORGANISM: Staphylococcus aureus

<400> SEQUENCE: 272
cgcagagagg aggtgtataa ggtgatgctt attttcgttc acatcatagc accagtcatc 60
agtggctgtg ccattgcgtt tttttcttat tggctaagta gacgcaatac aaaataggtg 120
acatatagcc gcaccaataa aaatcccctc actaccgcaa atagtgaggg gattggtgta 180
taagtaaata cttattttcg ttgt 204

<210> SEQ ID NO 273
<211> LENGTH: 60
<212> TYPE: DNA
<213> ORGANISM: Staphylococcus aureus

<400> SEQUENCE: 273
cccctcacta ccgcaaatag tgaggggatt ggtgtataag taaatactta ttttcgttgt 60

<210> SEQ ID NO 274
<211> LENGTH: 144
<212> TYPE: DNA
<213> ORGANISM: Staphylococcus aureus

<400> SEQUENCE: 274
cgcagagagg aggtgtataa ggtgatgctt attttcgttc acatcatagc accagtcatc 60
agtggctgtg ccattgcgtt tttttcttat tggctaagta gacgcaatac aaaataggtg 120
acatatagcc gcaccaataa aaat 144

<210> SEQ ID NO 275
<211> LENGTH: 120
<212> TYPE: DNA
<213> ORGANISM: Staphylococcus aureus

<400> SEQUENCE: 275
atgcttattt tcgttcacat catagcacca gtcatcagtg gctgtgccat tgcgtttttt 60
tcttattggc taagtagacg caatacaaaa taggtgacat atagccgcac caataaaaat 120

<210> SEQ ID NO 276

<211> LENGTH: 31
<212> TYPE: DNA
<213> ORGANISM: Artificial Sequence
<220> FEATURE:
<223> OTHER INFORMATION: BPC_670 oligo for plasmid construction

<400> SEQUENCE: 276
gctcagatct gttaacggta ccatcatact c 31

<210> SEQ ID NO 277
<211> LENGTH: 21
<212> TYPE: DNA
<213> ORGANISM: Artificial Sequence
<220> FEATURE:
<223> OTHER INFORMATION: BPC_671 oligo for plasmid construction

<400> SEQUENCE: 277
cactggccgt cgttttacaa c 21

<210> SEQ ID NO 278
<211> LENGTH: 55
<212> TYPE: DNA
<213> ORGANISM: Artificial Sequence
<220> FEATURE:
<223> OTHER INFORMATION: BPC_672 oligo for plasmid construction

<400> SEQUENCE: 278
gagtatgatg gtaccgttaa cagatctgag ccgcagagag gaggtgtata aggtg 55

<210> SEQ ID NO 279
<211> LENGTH: 60
<212> TYPE: DNA
<213> ORGANISM: Artificial Sequence
<220> FEATURE:
<223> OTHER INFORMATION: BPC_674 oligo for plasmid construction

<400> SEQUENCE: 279
gagtatgatg gtaccgttaa cagatctgag catggtggca ttactgaaat ctttagaaag 60

<210> SEQ ID NO 280
<211> LENGTH: 51
<212> TYPE: DNA
<213> ORGANISM: Artificial Sequence
<220> FEATURE:
<223> OTHER INFORMATION: BPC_675 oligo for plasmid construction

<400> SEQUENCE: 280
gagtatgatg gtaccgttaa cagatctgag catggcactg cctaaaacgg g 51

<210> SEQ ID NO 281
<211> LENGTH: 61
<212> TYPE: DNA
<213> ORGANISM: Artificial Sequence
<220> FEATURE:
<223> OTHER INFORMATION: BPC_676 oligo for plasmid construction

<400> SEQUENCE: 281
gagtatgatg gtaccgttaa cagatctgag catggctaat gaaactaaac aacctaaagt 60
t 61

<210> SEQ ID NO 282
<211> LENGTH: 41
<212> TYPE: DNA
<213> ORGANISM: Artificial Sequence
<220> FEATURE:
<223> OTHER INFORMATION: BPC_677 oligo for plasmid construction

<400> SEQUENCE: 282
gttgtaaaac gacggccagt gcccgggctc agctattatc a 41

<210> SEQ ID NO 283
<211> LENGTH: 39
<212> TYPE: DNA
<213> ORGANISM: Artificial Sequence
<220> FEATURE:
<223> OTHER INFORMATION: BPC_678 oligo for plasmid construction

<400> SEQUENCE: 283
gttgtaaaac gacggccagt ggcggccgcc catgcatgc 39

<210> SEQ ID NO 284
<211> LENGTH: 93
<212> TYPE: DNA
<213> ORGANISM: Staphylococcus aureus

<400> SEQUENCE: 284
atgcttattt tcgttcacat catagcacca gtcatcagtg gctgtgccat tgcgtttttt 60
tcttattggc taagtagacg caatacaaaa tag 93

<210> SEQ ID NO 285
<211> LENGTH: 29
<212> TYPE: PRT
<213> ORGANISM: Staphylococcus aureus

<400> SEQUENCE: 285

Leu Ile Phe Val His Ile Ile Ala Pro Val Ile Ser Gly Cys Ala Ile
1 5 10 15

Ala Phe Phe Ser Tyr Trp Leu Ser Arg Arg Asn Thr Lys
20 25

<210> SEQ ID NO 286
<211> LENGTH: 795
<212> TYPE: DNA
<213> ORGANISM: Artificial Sequence
<220> FEATURE:
<223> OTHER INFORMATION: 187-lysK toxin gene encodes engineered phage lysin protein from the Staphylococcus aureus phage

<400> SEQUENCE: 286
atggcactgc ctaaaacggg taaaccaacg gcaaaacagg tggttgactg ggcaatcaat 60
ttaatcggca gtggtgtcga tgttgatggt tattatggtc ggcaatgttg ggatttacct 120
aactatattt ttaatagata ctggaacttt aagacaccag gcaacgcaag agatatggca 180
tggtatagat atcctgaagg gtttaaagtg tttagaaaca cttctgattt tgtccctaaa 240
ccaggtgata tagcagtgtg gacaggtggt aattacaatt ggaacacttg ggacacact 300 ggtattgttg taggtccatc aactaaaagt tacttttata gtgtagatca gaattggaat 360
aactctaact cttacgttgg tagtcctgca gcaaagataa aacatagtta ttttggtgta 420
actcattttg ttagacccgc atacaaagca gaaccgaaac ctacaccacc actggacagt 480
acaccggcaa ctagaccagt tacaggttct tggaaaaaga accagtacgg aacttggtat 540
aaaccggaaa atgcaacatt tgtcaatggt aaccaaccta tagtaactag aataggttct 600
ccattcttaa atgctccagt aggcggtaac ttaccggcag ggctacaat tgtatatgac 660 gaagtttgta tccaagcagg tcacatttgg ataggttata atgcttacaa cggtaacaga 720
gtatattgcc ctgttagaac ttgtcaaggt gttccaccta atcaaatacc tggcgttgcc 780

```
tggggagtat tcaaa                                                    795


<210> SEQ ID NO 287
<211> LENGTH: 265
<212> TYPE: PRT
<213> ORGANISM: Artificial Sequence
<220> FEATURE:
<223> OTHER INFORMATION: recombinant phage lysin LysK toxin

<400> SEQUENCE: 287

Met Ala Leu Pro Lys Thr Gly Lys Pro Thr Ala Lys Gln Val Val Asp
1               5                   10                  15

Trp Ala Ile Asn Leu Ile Gly Ser Gly Val Asp Val Asp Gly Tyr Tyr
            20                  25                  30

Gly Arg Gln Cys Trp Asp Leu Pro Asn Tyr Ile Phe Asn Arg Tyr Trp
        35                  40                  45

Asn Phe Lys Thr Pro Gly Asn Ala Arg Asp Met Ala Trp Tyr Arg Tyr
    50                  55                  60

Pro Glu Gly Phe Lys Val Phe Arg Asn Thr Ser Asp Phe Val Pro Lys
65                  70                  75                  80

Pro Gly Asp Ile Ala Val Trp Thr Gly Gly Asn Tyr Asn Trp Asn Thr
                85                  90                  95

Trp Gly His Thr Gly Ile Val Val Gly Pro Ser Thr Lys Ser Tyr Phe
            100                 105                 110

Tyr Ser Val Asp Gln Asn Trp Asn Asn Ser Asn Ser Tyr Val Gly Ser
        115                 120                 125

Pro Ala Ala Lys Ile Lys His Ser Tyr Phe Gly Val Thr His Phe Val
    130                 135                 140

Arg Pro Ala Tyr Lys Ala Glu Pro Lys Pro Thr Pro Pro Leu Asp Ser
145                 150                 155                 160

Thr Pro Ala Thr Arg Pro Val Thr Gly Ser Trp Lys Lys Asn Gln Tyr
                165                 170                 175

Gly Thr Trp Tyr Lys Pro Glu Asn Ala Thr Phe Val Asn Gly Asn Gln
            180                 185                 190

Pro Ile Val Thr Arg Ile Gly Ser Pro Phe Leu Asn Ala Pro Val Gly
        195                 200                 205

Gly Asn Leu Pro Ala Gly Ala Thr Ile Val Tyr Asp Glu Val Cys Ile
    210                 215                 220

Gln Ala Gly His Ile Trp Ile Gly Tyr Asn Ala Tyr Asn Gly Asn Arg
225                 230                 235                 240

Val Tyr Cys Pro Val Arg Thr Cys Gln Gly Val Pro Pro Asn Gln Ile
                245                 250                 255

Pro Gly Val Ala Trp Gly Val Phe Lys
            260                 265


<210> SEQ ID NO 288
<211> LENGTH: 504
<212> TYPE: DNA
<213> ORGANISM: Staphylococcus aureus

<400> SEQUENCE: 288

atggctaatg aaactaaaca acctaaagtt gttggaggaa taaactttag cacaagaact      60

aagagtaaaa cattttgggt agcaattata tcagcagtag cagtatttgc taatcaaatt     120

acaggtgctt ttggtttaga ctactcagct caaattgagc aaggtgtaaa tatcataggt     180

tctatactaa cattattagc aggtttaggt attattgttg ataataatac taaaggtctt     240
```

```
aaagatagtg atattgttca aacagattat ataaaacctc gtgatagtaa agaccctaat    300

gaatttgttc aatggcaagc aaatgcaaac acagctagca ctttcgaatt agacaactat    360

gaaaacaatg cagaacctga tacagatgat agtgatgaag tacctgctat tgaagatgaa    420

attgatggcg gttcagcacc ttctcaagat gaagaagata ccgaggaaca cggtaaagta    480

tttgcagagg aggaagttaa gtag                                           504


<210> SEQ ID NO 289
<211> LENGTH: 167
<212> TYPE: PRT
<213> ORGANISM: Staphylococcus aureus

<400> SEQUENCE: 289

Met Ala Asn Glu Thr Lys Gln Pro Lys Val Val Gly Gly Ile Asn Phe
1               5                   10                  15

Ser Thr Arg Thr Lys Ser Lys Thr Phe Trp Val Ala Ile Ile Ser Ala
            20                  25                  30

Val Ala Val Phe Ala Asn Gln Ile Thr Gly Ala Phe Gly Leu Asp Tyr
        35                  40                  45

Ser Ala Gln Ile Glu Gln Gly Val Asn Ile Ile Gly Ser Ile Leu Thr
    50                  55                  60

Leu Leu Ala Gly Leu Gly Ile Ile Val Asp Asn Asn Thr Lys Gly Leu
65                  70                  75                  80

Lys Asp Ser Asp Ile Val Gln Thr Asp Tyr Ile Lys Pro Arg Asp Ser
                85                  90                  95

Lys Asp Pro Asn Glu Phe Val Gln Trp Gln Ala Asn Ala Asn Thr Ala
            100                 105                 110

Ser Thr Phe Glu Leu Asp Asn Tyr Glu Asn Asn Ala Glu Pro Asp Thr
        115                 120                 125

Asp Asp Ser Asp Glu Val Pro Ala Ile Glu Asp Glu Ile Asp Gly Gly
    130                 135                 140

Ser Ala Pro Ser Gln Asp Glu Glu Asp Thr Glu Glu His Gly Lys Val
145                 150                 155                 160

Phe Ala Glu Glu Glu Val Lys
                165


<210> SEQ ID NO 290
<211> LENGTH: 135
<212> TYPE: DNA
<213> ORGANISM: Staphylococcus aureus

<400> SEQUENCE: 290

atggtggcat tactgaaatc tttagaaagg agacgcctaa tgattacaat tagtaccatg     60

ttgcagtttg gtttattcct tattgcattg ataggtctag taatcaagct tattgaatta    120

agcaataaaa aataa                                                     135


<210> SEQ ID NO 291
<211> LENGTH: 44
<212> TYPE: PRT
<213> ORGANISM: Staphylococcus aureus

<400> SEQUENCE: 291

Met Val Ala Leu Leu Lys Ser Leu Glu Arg Arg Arg Leu Met Ile Thr
1               5                   10                  15

Ile Ser Thr Met Leu Gln Phe Gly Leu Phe Leu Ile Ala Leu Ile Gly
            20                  25                  30
```

```
Leu Val Ile Lys Leu Ile Glu Leu Ser Asn Lys Lys
        35                  40


<210> SEQ ID NO 292
<211> LENGTH: 20
<212> TYPE: DNA
<213> ORGANISM: Artificial Sequence
<220> FEATURE:
<223> OTHER INFORMATION: Primer; gfp primer

<400> SEQUENCE: 292

ctgtccacac aatctgccct                                                    20


<210> SEQ ID NO 293
<211> LENGTH: 20
<212> TYPE: DNA
<213> ORGANISM: Artificial Sequence
<220> FEATURE:
<223> OTHER INFORMATION: Primer; gfp primer

<400> SEQUENCE: 293

tgccatgtgt aatcccagca                                                    20


<210> SEQ ID NO 294
<211> LENGTH: 25
<212> TYPE: DNA
<213> ORGANISM: Artificial Sequence
<220> FEATURE:
<223> OTHER INFORMATION: Primer; DR_022 primer

<400> SEQUENCE: 294

caagcttatc gataccgtcg acctc                                              25


<210> SEQ ID NO 295
<211> LENGTH: 23
<212> TYPE: DNA
<213> ORGANISM: Artificial Sequence
<220> FEATURE:
<223> OTHER INFORMATION: Primer; DR_023 primer

<400> SEQUENCE: 295

gggatccact agttctagag cgg                                                23


<210> SEQ ID NO 296
<211> LENGTH: 31
<212> TYPE: DNA
<213> ORGANISM: Artificial Sequence
<220> FEATURE:
<223> OTHER INFORMATION: Primerr; DR_237 primer

<400> SEQUENCE: 296

gcaactggta catcacaatt ggtactctca c                                       31


<210> SEQ ID NO 297
<211> LENGTH: 32
<212> TYPE: DNA
<213> ORGANISM: Artificial Sequence
<220> FEATURE:
<223> OTHER INFORMATION: Primer; DR_238 primer

<400> SEQUENCE: 297

gaccacgcat acctatctat aaacggacaa tg                                      32


<210> SEQ ID NO 298
<211> LENGTH: 44
```

<212> TYPE: DNA
<213> ORGANISM: Artificial Sequence
<220> FEATURE:
<223> OTHER INFORMATION: Primer; DR_255 primer

<400> SEQUENCE: 298
gtccaattag atggcatgta actgggcagt gtcttaaaaa atcg 44

<210> SEQ ID NO 299
<211> LENGTH: 55
<212> TYPE: DNA
<213> ORGANISM: Artificial Sequence
<220> FEATURE:
<223> OTHER INFORMATION: Primer; DR_241 primer

<400> SEQUENCE: 299
caggccaatt tggcatagag ccggatgtgc tgcaaggcga ttaagttggg taacg 55

<210> SEQ ID NO 300
<211> LENGTH: 45
<212> TYPE: DNA
<213> ORGANISM: Artificial Sequence
<220> FEATURE:
<223> OTHER INFORMATION: Primer; DR_256 primer

<400> SEQUENCE: 300
gttacatgcc atctaattgg acaaattcta tgagagtaga ttttg 45

<210> SEQ ID NO 301
<211> LENGTH: 33
<212> TYPE: DNA
<213> ORGANISM: Artificial Sequence
<220> FEATURE:
<223> OTHER INFORMATION: Primer; DR_257 primer

<400> SEQUENCE: 301
gccaaatcgc tttcgtgtat acgattccca gtc 33

<210> SEQ ID NO 302
<211> LENGTH: 30
<212> TYPE: DNA
<213> ORGANISM: Artificial Sequence
<220> FEATURE:
<223> OTHER INFORMATION: Primer; DR_240 primer

<400> SEQUENCE: 302
ggctctatgc caaattggcc tgatgagttc 30

<210> SEQ ID NO 303
<211> LENGTH: 53
<212> TYPE: DNA
<213> ORGANISM: Artificial Sequence
<220> FEATURE:
<223> OTHER INFORMATION: Primer; DR_236 primer

<400> SEQUENCE: 303
gctctagaac tagtggatcc cggcgatttt attgtgacaa gagactgaag agc 53

<210> SEQ ID NO 304
<211> LENGTH: 108
<212> TYPE: DNA
<213> ORGANISM: Staphylococcus aureus

<400> SEQUENCE: 304
atgttcaatt tattaattaa catcatgact tcagctttaa gcggctgtct tgttgcgttt 60
tttgcacatt ggttacgaac gcgcaacaat aaaaaaggtg acaaataa 108

<210> SEQ ID NO 305
<211> LENGTH: 35
<212> TYPE: PRT
<213> ORGANISM: Staphylococcus aureus

<400> SEQUENCE: 305

Met Phe Asn Leu Leu Ile Asn Ile Met Thr Ser Ala Leu Ser Gly Cys
1 5 10 15

Leu Val Ala Phe Phe Ala His Trp Leu Arg Thr Arg Asn Asn Lys Lys
20 25 30

Gly Asp Lys
35

<210> SEQ ID NO 306
<211> LENGTH: 77
<212> TYPE: DNA
<213> ORGANISM: Staphylococcus aureus

<400> SEQUENCE: 306
tataattaat tacataataa attgaacatc taaatacacc aaatcccctc actactgcca 60
tagtgagggg atttatt 77

<210> SEQ ID NO 307
<211> LENGTH: 140
<212> TYPE: DNA
<213> ORGANISM: Staphylococcus aureus

<400> SEQUENCE: 307
atatatagaa aaagggcaac atgcgcaaac atgttaccct aatgagcccg ttaaaaagac 60
ggtggctatt ttagattaaa gattaaatta ataaccattt aaccatcgaa accagccaaa 120
gttagcgatg gttatttttt 140

<210> SEQ ID NO 308
<211> LENGTH: 76
<212> TYPE: DNA
<213> ORGANISM: Artificial Sequence
<220> FEATURE:
<223> OTHER INFORMATION: holin antitoxin gene

<400> SEQUENCE: 308
tataattgag atagtttcat tagctattta cttatacacc aatcccctca ctatttgcgg 60
tagtgagggg attttt 76

<210> SEQ ID NO 309
<211> LENGTH: 76
<212> TYPE: DNA
<213> ORGANISM: Artificial Sequence
<220> FEATURE:
<223> OTHER INFORMATION: 187-lysK antitoxin gene

<400> SEQUENCE: 309
tataattgag attttaggca gtgctattta cttatacacc aatcccctca ctatttgcgg 60
tagtgagggg attttt 76

<210> SEQ ID NO 310
<211> LENGTH: 140
<212> TYPE: DNA
<213> ORGANISM: Artificial Sequence
<220> FEATURE:

<223> OTHER INFORMATION: sprG antitoxin gene (sprF)

<400> SEQUENCE: 310

```
atatatagaa aaagggcaac atgcgcaaac atgttaccct aatgagcccg ttaaaaagac     60

ggtggctatt ttagattaaa gattaaatta ataaccattt aaccatcgaa accagccaaa    120

gttagcgatg gttatttttt                                                140
```

<210> SEQ ID NO 311
<211> LENGTH: 74
<212> TYPE: DNA
<213> ORGANISM: Staphylococcus aureus

<400> SEQUENCE: 311

```
tataattgag ataacgaaaa taagtattta cttatacacc aatcccctca ctatttgcgg     60

tagtgagggg attt                                                       74
```

<210> SEQ ID NO 312
<211> LENGTH: 90
<212> TYPE: DNA
<213> ORGANISM: Staphylococcus aureus

<400> SEQUENCE: 312

```
tataattaat tacataataa attgaacatc taaatacacc aaatcccctc actactgcca     60

tagtgagggg atttatttag gtgttggtta                                      90
```

<210> SEQ ID NO 313
<211> LENGTH: 158
<212> TYPE: DNA
<213> ORGANISM: Staphylococcus aureus

<400> SEQUENCE: 313

```
atgattatca ctagccctac agaagcgaga aaagattttt atcaattact aaaaaatgtt     60

aataataatc acgaaccaat ttatattagt ggcaataatg ccgaaaataa tgctgtgatt    120

ataggtttag aagattggaa aagtatacaa gagacaat                            158
```

<210> SEQ ID NO 314
<211> LENGTH: 85
<212> TYPE: PRT
<213> ORGANISM: Staphylococcus aureus

<400> SEQUENCE: 314

```
Met Ile Ile Thr Ser Pro Thr Glu Ala Arg Lys Asp Phe Tyr Gln Leu
1               5                   10                  15

Leu Lys Asn Val Asn Asn Asn His Glu Pro Ile Tyr Ile Ser Gly Asn
            20                  25                  30

Asn Ala Glu Asn Asn Ala Val Ile Ile Gly Leu Glu Asp Trp Lys Ser
        35                  40                  45

Ile Gln Glu Thr Ile Tyr Leu Glu Ser Thr Gly Thr Met Asp Lys Val
    50                  55                  60

Arg Glu Arg Glu Lys Asp Asn Ser Gly Thr Thr Asn Ile Asp Asp Ile
65                  70                  75                  80

Asp Trp Asp Asn Leu
                85
```

<210> SEQ ID NO 315
<211> LENGTH: 159
<212> TYPE: DNA
<213> ORGANISM: Staphylococcus aureus

<400> SEQUENCE: 315

```
atgagcaatt acacggttaa gattaaaaat tcagcgaaat cagatttaag gaaaataaaa      60

cattcttatt taaagaagtc atttttagaa attgttgaga ctttaaaaaa tgatccgtat     120

aaaataacac aatcttttga aaaattagag cctaaatat                            159
```

<210> SEQ ID NO 316
<211> LENGTH: 88
<212> TYPE: PRT
<213> ORGANISM: Staphylococcus aureus

<400> SEQUENCE: 316

```
Met Ser Asn Tyr Thr Val Lys Ile Lys Asn Ser Ala Lys Ser Asp Leu
1               5                   10                  15

Arg Lys Ile Lys His Ser Tyr Leu Lys Lys Ser Phe Leu Glu Ile Val
            20                  25                  30

Glu Thr Leu Lys Asn Asp Pro Tyr Lys Ile Thr Gln Ser Phe Glu Lys
        35                  40                  45

Leu Glu Pro Lys Tyr Leu Glu Arg Tyr Ser Arg Arg Ile Asn His Gln
    50                  55                  60

His Arg Val Val Tyr Thr Val Asp Asp Arg Asn Lys Glu Val Leu Ile
65                  70                  75                  80

Leu Ser Ala Trp Ser His Tyr Asp
                85
```

<210> SEQ ID NO 317
<211> LENGTH: 738
<212> TYPE: DNA
<213> ORGANISM: Staphylococcus simulans

<400> SEQUENCE: 317

```
atgacacatg aacattcagc acaatggttg aataattaca aaaaaggata tggttacggt      60

ccttatccat taggtataaa tggcggtatg cactacggag ttgatttttt tatgaatatt     120

ggaacaccag taaaagctat ttcaagcgga aaaatagttg aagctggttg gagtaattac     180

ggaggaggta atcaaatagg tcttattgaa aatgatggag tgcatagaca atggtatatg     240

catctaagta aatataatgt taaagtagga gattatgtca aagctggtca aataatcggt     300

tggtctggaa gcactggtta ttctacagca ccacatttac acttccaaag aatggttaat     360

tcattttcaa attcaactgc ccaagatcca atgcctttct taaagagcgc aggatatgga     420

aaagcaggtg gtacagtaac tccaacgccg aatacaggtt ggaaaacaaa caaatatggc     480

acactatata aatcagagtc agctagcttc acacctaata cagatataat aacaagaacg     540

actggtccat ttagaagcat gccgcagtca ggagtcttaa aagcaggtca aacaattcat     600

tatgatgaag tgatgaaaca agacggtcat gtttgggtag gttatacagg taacagtggc     660

caacgtattt acttgcctgt aagaacatgg aataaatcta ctaatacttt aggtgttctt     720

tggggaacta taaagtga                                                   738
```

<210> SEQ ID NO 318
<211> LENGTH: 245
<212> TYPE: PRT
<213> ORGANISM: Staphylococcus simulans

<400> SEQUENCE: 318

```
Met Thr His Glu His Ser Ala Gln Trp Leu Asn Asn Tyr Lys Lys Gly
1               5                   10                  15
```

```
Tyr Gly Tyr Gly Pro Tyr Pro Leu Gly Ile Asn Gly Gly Met His Tyr
            20                  25                  30

Gly Val Asp Phe Phe Met Asn Ile Gly Thr Pro Val Lys Ala Ile Ser
        35                  40                  45

Ser Gly Lys Ile Val Glu Ala Gly Trp Ser Asn Tyr Gly Gly Gly Asn
    50                  55                  60

Gln Ile Gly Leu Ile Glu Asn Asp Gly Val His Arg Gln Trp Tyr Met
65                  70                  75                  80

His Leu Ser Lys Tyr Asn Val Lys Val Gly Asp Tyr Val Lys Ala Gly
                85                  90                  95

Gln Ile Ile Gly Trp Ser Gly Ser Thr Gly Tyr Ser Thr Ala Pro His
            100                 105                 110

Leu His Phe Gln Arg Met Val Asn Ser Phe Ser Asn Ser Thr Ala Gln
        115                 120                 125

Asp Pro Met Pro Phe Leu Lys Ser Ala Gly Tyr Gly Lys Ala Gly Gly
    130                 135                 140

Thr Val Thr Pro Thr Pro Asn Thr Gly Trp Lys Thr Asn Lys Tyr Gly
145                 150                 155                 160

Thr Leu Tyr Lys Ser Glu Ser Ala Ser Phe Thr Pro Asn Thr Asp Ile
                165                 170                 175

Ile Thr Arg Thr Thr Gly Pro Phe Arg Ser Met Pro Gln Ser Gly Val
            180                 185                 190

Leu Lys Ala Gly Gln Thr Ile His Tyr Asp Glu Val Met Lys Gln Asp
        195                 200                 205

Gly His Val Trp Val Gly Tyr Thr Gly Asn Ser Gly Gln Arg Ile Tyr
    210                 215                 220

Leu Pro Val Arg Thr Trp Asn Lys Ser Thr Asn Thr Leu Gly Val Leu
225                 230                 235                 240

Trp Gly Thr Ile Lys
                245
```

<210> SEQ ID NO 319
<211> LENGTH: 76
<212> TYPE: DNA
<213> ORGANISM: Artificial Sequence
<220> FEATURE:
<223> OTHER INFORMATION: proposed lysostaphin antitoxin gene; encodes RNA antitoxin for lysostaphin

<400> SEQUENCE: 319

```
tataattgag atatgttcat gtgttattta cttatacacc aatcccctca ctatttgcgg     60

tagtgagggg attttt                                                     76
```

<210> SEQ ID NO 320
<211> LENGTH: 157
<212> TYPE: DNA
<213> ORGANISM: Staphylococcus aureus

<400> SEQUENCE: 320

```
atgattagac gaggagatgt ttatttagca gatttatcac cagtacaggg atctgaacaa     60

gggggagtca gacctgtagt cataattcaa aatgatactg gtaataaata tagtcctaca    120

gttattgttg cggcaataac tggtaggatt aataaag                             157
```

<210> SEQ ID NO 321
<211> LENGTH: 120
<212> TYPE: PRT

<213> ORGANISM: Staphylococcus aureus

<400> SEQUENCE: 321

```
Met Ile Arg Arg Gly Asp Val Tyr Leu Ala Asp Leu Ser Pro Val Gln
1               5                   10                  15

Gly Ser Glu Gln Gly Gly Val Arg Pro Val Val Ile Ile Gln Asn Asp
            20                  25                  30

Thr Gly Asn Lys Tyr Ser Pro Thr Val Ile Val Ala Ala Ile Thr Gly
        35                  40                  45

Arg Ile Asn Lys Ala Lys Ile Pro Thr His Val Glu Ile Glu Lys Lys
    50                  55                  60

Lys Tyr Lys Leu Asp Lys Asp Ser Val Ile Leu Leu Glu Gln Ile Arg
65                  70                  75                  80

Thr Leu Asp Lys Lys Arg Leu Lys Glu Lys Leu Thr Tyr Leu Ser Asp
                85                  90                  95

Asp Lys Met Lys Glu Val Asp Asn Ala Leu Met Ile Ser Leu Gly Leu
            100                 105                 110

Asn Ala Val Ala His Gln Lys Asn
        115                 120
```

<210> SEQ ID NO 322
<211> LENGTH: 158
<212> TYPE: DNA
<213> ORGANISM: Staphylococcus aureus

<400> SEQUENCE: 322

```
atgttatctt ttagtcaaaa tagaagtcat agcttagaac aatctttaaa agaaggatat     60

tcacaaatgg ctgatttaaa tctctcccta gcgaacgaag cttttccgat agagtgtgaa    120

gcatgcgatt gcaacgaaac atatttatct tctaattc                            158
```

<210> SEQ ID NO 323
<211> LENGTH: 56
<212> TYPE: PRT
<213> ORGANISM: Staphylococcus aureus

<400> SEQUENCE: 323

```
Met Leu Ser Phe Ser Gln Asn Arg Ser His Ser Leu Glu Gln Ser Leu
1               5                   10                  15

Lys Glu Gly Tyr Ser Gln Met Ala Asp Leu Asn Leu Ser Leu Ala Asn
            20                  25                  30

Glu Ala Phe Pro Ile Glu Cys Glu Ala Cys Asp Cys Asn Glu Thr Tyr
        35                  40                  45

Leu Ser Ser Asn Ser Thr Asn Glu
    50                  55
```

<210> SEQ ID NO 324
<211> LENGTH: 300
<212> TYPE: DNA
<213> ORGANISM: Staphylococcus aureus

<400> SEQUENCE: 324

```
aatggcatgg atgctcaaac atatggttct caaggacagc aacgtacaac ggctttgtcc     60

attaaattag ctgaaattga gttaatgaat atcgaagttg gggaatatcc catcttatta    120

ttagacgatg tactcagtga attagatgat tcgcgtcaaa cgcatttatt aagtacgatt    180

cagcataaag tacaaacatt tgtcactacg acatctgtag atggtattga tcatgaaatc    240

atgaataacg ctaaattgta tcgtattaat caaggtgaaa ttataaagta acagaaagcg    300
```

<210> SEQ ID NO 325
<211> LENGTH: 300
<212> TYPE: DNA
<213> ORGANISM: Staphylococcus aureus

<400> SEQUENCE: 325
caaatgcagt taaacatgca tacaaagaaa ataacaatgt gggcattatt aacatatatt 60
ttgaaatttt agaagataaa attaaaattg ttatttctga taaaggtgac agttttgatt 120
atgaaacaac taaatcaaaa ataggtcctt acgataaaga cgaaaatata gactttttac 180
gcgaaggtgg cctaggttta tttttaatcg aatctttaat ggatgaagtc acagtatata 240
aagaatctgg tgtgacaatc agtatgacta agtatataaa aaaagagcag gtgcgaaata 300

<210> SEQ ID NO 326
<211> LENGTH: 300
<212> TYPE: DNA
<213> ORGANISM: Staphylococcus aureus

<400> SEQUENCE: 326
tatggtattg aagagttctt agaagtgaaa tctatagctg gatattttaa ataaatttga 60
tttttgaatt aaaaatcgca ataaaacagt gcacatgact aattaagttt tgtgtactgt 120
tttaattttg caatttttat aaatagattt tgtaattaaa ataaaaattt gctatagtta 180
ttcatgtatt taaaaggttg gggattagca taatgggatt gtgctagcac agttatttat 240
gcattgtcat gcctatctat tacttactaa ctaaaaaata atgaaatggg tgtaaactat 300

<210> SEQ ID NO 327
<211> LENGTH: 243
<212> TYPE: DNA
<213> ORGANISM: Artificial Sequence
<220> FEATURE:
<223> OTHER INFORMATION: Promoter pTK3 forward

<400> SEQUENCE: 327
ttgcgaaatc cattcctctt ccactacaag caccataatt aaacaacaat tcaatagaat 60
aagacttgca aaacatagtt atgtcgctat ataaacgcct gcgaccaata aatcttttaa 120
acataacata atgcaaaaac atcatttaac aatgctaaaa atgtctcttc aatacatgtt 180
gatagtaatt aacttttaac gaacagttaa ttcgaaaacg cttacaaatg gattattata 240
tat 243

<210> SEQ ID NO 328
<211> LENGTH: 243
<212> TYPE: DNA
<213> ORGANISM: Artificial Sequence
<220> FEATURE:
<223> OTHER INFORMATION: Promoter pTK3 reverse

<400> SEQUENCE: 328
aacgctttag gtaaggagaa ggtgatgttc gtggtattaa tttgttgtta agttatctta 60
ttctgaacgt tttgtatcaa tacagcgata tatttgcgga cgctggttat ttagaaaatt 120
tgtattgtat tacgtttttg tagtaaattg ttacgatttt tacagagaag ttatgtacaa 180
ctatcattaa ttgaaaattg cttgtcaatt aagcttttgc gaatgtttac ctaataatat 240
ata 243

<210> SEQ ID NO 329

<211> LENGTH: 31
<212> TYPE: DNA
<213> ORGANISM: Artificial Sequence
<220> FEATURE:
<223> OTHER INFORMATION: Primer TKO1

<400> SEQUENCE: 329
gatgcgcatg cttgcgaaat ccattcctct t 31

<210> SEQ ID NO 330
<211> LENGTH: 52
<212> TYPE: DNA
<213> ORGANISM: Artificial Sequence
<220> FEATURE:
<223> OTHER INFORMATION: Primer DR_233

<400> SEQUENCE: 330
cgacggtatc gataagcttg gccactggcg tcaaatactg taatgaagaa tg 52

<210> SEQ ID NO 331
<211> LENGTH: 46
<212> TYPE: DNA
<213> ORGANISM: Artificial Sequence
<220> FEATURE:
<223> OTHER INFORMATION: Primer DR_296

<400> SEQUENCE: 331
catctaattg gacaaattct atgagagtag attttgttaa tttaag 46

<210> SEQ ID NO 332
<211> LENGTH: 38
<212> TYPE: DNA
<213> ORGANISM: Artificial Sequence
<220> FEATURE:
<223> OTHER INFORMATION: Primer DR_280

<400> SEQUENCE: 332
gtagacgcaa tacaaaatag gtgacatata gccgcacc 38

<210> SEQ ID NO 333
<211> LENGTH: 53
<212> TYPE: DNA
<213> ORGANISM: Artificial Sequence
<220> FEATURE:
<223> OTHER INFORMATION: Primer DR_236

<400> SEQUENCE: 333
gctctagaac tagtggatcc cggcgatttt attgtgacaa gagactgaag agc 53

<210> SEQ ID NO 334
<211> LENGTH: 57
<212> TYPE: DNA
<213> ORGANISM: Artificial Sequence
<220> FEATURE:
<223> OTHER INFORMATION: Primer DR_297

<400> SEQUENCE: 334
catagaattt gtccaattag atgtcccact acatcctgct aaaacaagta ggaaagc 57

<210> SEQ ID NO 335
<211> LENGTH: 32
<212> TYPE: DNA
<213> ORGANISM: Artificial Sequence
<220> FEATURE:
<223> OTHER INFORMATION: Primer DR_228

<400> SEQUENCE: 335
ctattttgta ttgcgtctac ttagccaata ag 32

<210> SEQ ID NO 336
<211> LENGTH: 25
<212> TYPE: DNA
<213> ORGANISM: Artificial Sequence
<220> FEATURE:
<223> OTHER INFORMATION: Primer DR_022

<400> SEQUENCE: 336
caagcttatc gataccgtcg acctc 25

<210> SEQ ID NO 337
<211> LENGTH: 23
<212> TYPE: DNA
<213> ORGANISM: Artificial Sequence
<220> FEATURE:
<223> OTHER INFORMATION: Primer DR_023

<400> SEQUENCE: 337
gggatccact agttctagag cgg 23

<210> SEQ ID NO 338
<211> LENGTH: 29
<212> TYPE: DNA
<213> ORGANISM: Artificial Sequence
<220> FEATURE:
<223> OTHER INFORMATION: Primer DR_303

<400> SEQUENCE: 338
caagccacca aagcacgtgc ctatttgcc 29

<210> SEQ ID NO 339
<211> LENGTH: 48
<212> TYPE: DNA
<213> ORGANISM: Artificial Sequence
<220> FEATURE:
<223> OTHER INFORMATION: Primer DR_304

<400> SEQUENCE: 339
cagtgaaata gatagattgg ttgaaaaaca atcttcaaaa gtcggacg 48

<210> SEQ ID NO 340
<211> LENGTH: 322
<212> TYPE: DNA
<213> ORGANISM: Artificial Sequence
<220> FEATURE:
<223> OTHER INFORMATION: Oligo

<400> SEQUENCE: 340
catgtaacac tcccttataa tcatcatcct ctccccctac cctactccat cgatattact 60
catactacat caacgaaatc agttttttat cacttaattt cctataatag tgatgctcaa 120
aattgttacg ttttagattg ttttagttca tcataattat cccgtattgt tgctataatg 180
aaatgcgttc accccattaa accacaaact taatttattg ttgttatgtg cattggctca 240
ctattatact tttacagcac aaaaaaagtg gcgacagctt cgtcaccact ttttaaaata 300
ttatttaaag tatcttgccc tt 322

<210> SEQ ID NO 341
<211> LENGTH: 52
<212> TYPE: DNA
<213> ORGANISM: Artificial Sequence
<220> FEATURE:

<223> OTHER INFORMATION: Oligo

<400> SEQUENCE: 341
taatacgact cactatagga gtaatatcga tggagtagtt ttagagctag aa 52

<210> SEQ ID NO 342
<211> LENGTH: 52
<212> TYPE: DNA
<213> ORGANISM: Artificial Sequence
<220> FEATURE:
<223> OTHER INFORMATION: Oligo

<400> SEQUENCE: 342
taatacgact cactatagga gaggatgatg attataagtt ttagagctag aa 52

<210> SEQ ID NO 343
<211> LENGTH: 52
<212> TYPE: DNA
<213> ORGANISM: Artificial Sequence
<220> FEATURE:
<223> OTHER INFORMATION: Oligo

<400> SEQUENCE: 343
taatacgact cactataggg agaggatgat gattatagtt ttagagctag aa 52

<210> SEQ ID NO 344
<211> LENGTH: 52
<212> TYPE: DNA
<213> ORGANISM: Artificial Sequence
<220> FEATURE:
<223> OTHER INFORMATION: Oligo

<400> SEQUENCE: 344
taatacgact cactataggg tctaatgtta ttgcttagtt ttagagctag aa 52

<210> SEQ ID NO 345
<211> LENGTH: 51
<212> TYPE: DNA
<213> ORGANISM: Artificial Sequence
<220> FEATURE:
<223> OTHER INFORMATION: Oligo

<400> SEQUENCE: 345
taatacgact cactatagga gaggatgatg attatagttt tagagctaga a 51

<210> SEQ ID NO 346
<211> LENGTH: 52
<212> TYPE: DNA
<213> ORGANISM: Artificial Sequence
<220> FEATURE:
<223> OTHER INFORMATION: Oligo

<400> SEQUENCE: 346
taatacgact cactataggt agtatgagta atatcgagtt ttagagctag aa 52

<210> SEQ ID NO 347
<211> LENGTH: 52
<212> TYPE: DNA
<213> ORGANISM: Artificial Sequence
<220> FEATURE:
<223> OTHER INFORMATION: Oligo

<400> SEQUENCE: 347
taatacgact cactatagga attatataaa tataaaggtt ttagagctag aa 52

-continued

```
<210> SEQ ID NO 348
<211> LENGTH: 52
<212> TYPE: DNA
<213> ORGANISM: Artificial Sequence
<220> FEATURE:
<223> OTHER INFORMATION: Oligo

<400> SEQUENCE: 348

taatacgact cactataggc tacctccata ttttctagtt ttagagctag aa           52


<210> SEQ ID NO 349
<211> LENGTH: 52
<212> TYPE: DNA
<213> ORGANISM: Artificial Sequence
<220> FEATURE:
<223> OTHER INFORMATION: Oligo

<400> SEQUENCE: 349

taatacgact cactatagga tagaactgta ttagactgtt ttagagctag aa           52


<210> SEQ ID NO 350
<211> LENGTH: 52
<212> TYPE: DNA
<213> ORGANISM: Artificial Sequence
<220> FEATURE:
<223> OTHER INFORMATION: Oligo

<400> SEQUENCE: 350

taatacgact cactataggt gtctaatgtt attgcttgtt ttagagctag aa           52
```

What is claimed is:

1. A synthetic organism comprising a recombinant nucleotide comprising at least one kill switch molecular modification comprising a first cell death gene operatively associated with a first regulatory region comprising an inducible first promoter, wherein the inducible first promoter exhibits conditionally high level gene expression of the recombinant nucleotide in response to exposure to blood, serum, or plasma of at least three fold increase of basal productivity as determined before and from 30 minutes to 180 minutes after the exposure to blood, serum, or plasma by quantitative polymerase chain reaction (qPCR) or RNA sequencing (RNAseq), wherein the synthetic microorganism is derived from a *Staphylococcus aureus* strain, wherein the at least one kill switch molecular modification is integrated to a chromosome of the synthetic microorganism, and wherein the first cell death gene comprises an sprA1 gene comprising the nucleotide sequence of SEQ ID NO: 284.

2. The synthetic microorganism of claim 1, wherein the synthetic microorganism further comprises at least a second molecular modification comprising an antitoxin gene specific for the first cell death gene, wherein the antitoxin gene is operably associated with a second regulatory region comprising a second promoter which is active upon dermal or mucosal colonization or in a complete media, but is not induced, induced less than 1.5-fold, or is repressed after exposure to blood, serum or plasma for at least 30 minutes.

3. The synthetic microorganism of claim 2, wherein the second regulatory region comprising a second promoter is active upon dermal or mucosal colonization or in TSB media, but is repressed at least 2 fold upon exposure to blood, serum or plasma after a period of time selected from the group consisting of the group consisting of at least 30 min, 60 min, 90 min, 120 min, and 180 min.

4. The synthetic microorganism of claim 2, wherein the antitoxin gene encodes an antisense RNA sequence capable of hybridizing with at least a portion of the first cell death gene.

5. The synthetic microorganism of claim 4, wherein the antitoxin gene is a sprA1 antitoxin gene, or a fragment thereof.

6. The synthetic microorganism of claim 5, wherein the antitoxin gene comprises a nucleotide sequence of SEQ ID NO: 273.

7. The synthetic microorganism of claim 5, wherein the second promoter comprises or is derived from a gene selected from the group consisting of clfB (Clumping factor B), sceD (autolysin, exoprotein D), walKR (virulence regulator), atlA (Major autolysin), oatA (O-acetyltransferase A); phosphoribosylglycinamide formyltransferase gene, phosphoribosylaminoimidazole synthetase gene, amidophosphoribosyltransferase gene, phosphoribosylformylglycinamidine synthase gene, phosphoribosylformylglycinamidine synthase gene, phosphoribosylaminoimidazole-succinocarboxamide gene, trehalose permease IIC gen, DeoR family transcriptional regulator gene, phosphofructokinase gene, PTS fructose transporter subunit IIC gene, galactose-6-phosphate isomerase gene, NarZ, NarH, NarT, alkylhydroperoxidase gene, hypothetical protein gene, DeoR trans factor gene, lysophospholipase gene, protein disaggregation chaperon gene, alkylhydroperoxidase gene, phosphofructokinase gene, gyrB, sigB, and rho.

8. The synthetic microorganism of claim 7, wherein the second promoter is a clumping factor B ($P_{clfB}$) and comprises a nucleotide sequence of SEQ ID NO: 117, 118, 129 or 130.

9. The synthetic microorganism of claim 1, wherein the synthetic microorganism is derived from a target microorganism having the same genus and species as an undesirable microorganism, wherein the undesirable microorganism is a pathogenic microorganism, drug-resistant microorganism, antibiotic-resistant microorganism, irritation-causing microorganism, odor-causing microorganism and/or a microorganism comprising an undesirable virulence factor.

10. The synthetic microorganism of claim 9, wherein the target microorganism is susceptible to at least one antimicrobial agent.

11. The synthetic microorganism of claim 1, wherein the first promoter is upregulated by at least 5-fold, at least 10-fold, at least 20-fold, at least 50-fold, or at least 100-fold within at least 30 min, 60 min, 90 min, 120 min, or 180 min following exposure to blood, serum, or plasma.

12. The synthetic microorganism of claim 1, wherein the first promoter is not induced, induced less than 1.5 fold, or is repressed in the absence of blood, serum, or plasma.

13. The synthetic microorganism of claim 1, wherein measurable average cell death of the synthetic microorganism occurs within at least a preset period of time following induction of the first promoter.

14. The synthetic microorganism of claim 13, wherein the measurable average cell death occurs within at least a preset period of time selected from the group consisting of within at least 1, 5, 15, 30, 60, 90, 120, or 180 minutes following exposure to blood, serum, or plasma.

15. The synthetic microorganism of claim 14, wherein the measurable average cell death is at least a 50% cfu, at least 70%, at least 80%, at least 90%, at least 95%, at least 99%, at least 99.5%, at least 99.8%, or at least 99.9% cfu count reduction following the preset period of time.

16. The synthetic microorganism of claim 1, wherein the kill switch molecular modification reduces or prevents infectious growth of the synthetic microorganism under systemic conditions in a subject.

17. The synthetic microorganism of claim 1, wherein the synthetic microorganism is capable of colonizing a dermal and/or mucosal niche.

18. The synthetic microorganism of claim 1, wherein the synthetic microorganism further comprises an additional cell death gene selected from the group consisting of sprA2, kpn1, sma1, sprG, relF, rsaE, yoeB, mazF, yefM, and lysostaphin toxin gene.

19. The synthetic microorganism of claim 18, wherein the additional cell death gene comprises a nucleotide sequence selected from the group consisting of SEQ ID NOs: 122, 124, 125, 126, 127, 128, 274, 275, 286, 288, 290, 315, and 317.

20. The synthetic microorganism of claim 1, wherein the inducible first promoter comprises or is derived from a gene selected from the group consisting of isdA (iron-regulated surface determinant protein A), isdB (iron-regulated surface determinant protein B), isdG (heme-degrading monooxygenase), hlgA (gamma-hemolysin component A), hlgA1 (gamma-hemolysin), hlgA2(gamma-hemolysin), hlgB (gamma-hemolysin component B), hrtAB (heme-regulated transporter), sbn (' (luc C family siderophore biosyntheis protein), sbnD, sbnI, sbnE (lucA/lucC family siderophore biosynthesis protein), isdI, lrgA (murein hydrolase regulator A), lrgB (murein hydrolase regulator B), ear (Ear protein), fhuA (ferrichrome transport ATP-binding protein fhuA), fhuB (ferrichrome transport permease), heme ABC transporter 2 gene, heme ABC transporter gene, isd ORF3, sbnF, alanine dehydrogenase gene, diaminopimelate decarboxylase gene, iron ABC transporter gene, threonine dehydratase gene, siderophore ABC transporter gene, SAM dep Metrans gene, HarA, splF (serine protease SplF), splD (serine protease SplD), SAUSA300_2617 (putative cobalt ABC transporter, ATP-binding protein), SAUSA300_2268 (sodium/bile acid symporter family protein), SAUSA300_2616 (cobalt family transport protein), srtB (Sortase B), sbnA (probable siderophore biosynthesis protein sbnA), sbnB, sbnG, leuA (2-isopropylmalate synthase amino acid biosynthetic enzyme), sstA (iron transport membrane protein), sirA (iron ABC transporter substrate-binding protein), isdA (heme transporter), and spa (Staphyloccocal protein A).

21. The synthetic microorganism of claim 20, wherein the first promoter comprises a nucleotide sequence selected from the group consisting of SEQ ID NO:

114, 115, 119, 120, 121, 132, 133, 134, 136, 137, 138, 139, 140, 141, 142, 143, 144, 145, 146, 147, 148, 149, 150, 151, 152, 153, 155, 156, 157, 158, 159, 160, 161, 162, and 163.

22. The synthetic microorganism according to claim 1, further comprising a molecular modification selected from the group consisting of a virulence block molecular modification, and nanofactory molecular modification.

23. The synthetic microorganism of claim 22, wherein the virulence block molecular modification prevents horizontal gene transfer of genetic material from an undesirable microorganism.

24. The synthetic microorganism of claim 22, wherein the nanofactory molecular modification comprises an insertion of a gene that encodes, a knock out of a gene that encodes, or a genetic modification of a gene that encodes a product selected from the group consisting of an enzyme, amino acid, metabolic intermediate, and a small molecule.

25. A composition comprising an effective amount of the synthetic microorganism of claim 1, and a pharmaceutically acceptable carrier, diluent, emollient, binder, excipient, lubricant, sweetening agent, flavoring agent, wetting agent, preservative, buffer, or absorbent, or a combination thereof.

26. The composition of claim 25, further comprising a nutrient, prebiotic, commensal, and/or probiotic bacterial species.

27. A single dose unit comprising the composition of claim 25.

28. The single dose unit of claim 27, comprising at least $10^5$, at least $10^6$, at least $10^7$, at least $10^8$, at least $10^9$, at least $10^{10}$ CFU, or at least $10^{11}$ of the synthetic strain and a pharmaceutically acceptable carrier.

29. The single dose unit of claim 28 formulated for topical administration.

30. A kit comprising in at least one container, the composition according to claim 25 and optionally at least a second container comprising a decolonizing agent, a sheet of instructions, at least a third container comprising a promoting agent, and/or an applicator.

* * * * *